US012709756B2

(12) United States Patent
Niu et al.

(10) Patent No.: US 12,709,756 B2
(45) **Date of Patent: *Aug. 18, 2026**

(54) PLANT CELLS, PLANTS, AND SEEDS HAVING TARGETED ENHANCER ELEMENT INSERTIONS

(71) Applicant: INARI AGRICULTURE TECHNOLOGY, INC., Cambridge, MA (US)

(72) Inventors: Yajie Niu, Lexington, MA (US); Randall William Shultz, Acton, MA (US); Maria Margarita D. Unson, Pawcatuck, CT (US); Michael Andreas Kock, Rheinfelden (DE); John Patrick Casey, Jr., Boston, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 93 days.

This patent is subject to a terminal disclaimer.

(21) Appl. No.: 18/167,581

(22) Filed: Feb. 10, 2023

(65) Prior Publication Data

US 2023/0242927 A1 Aug. 3, 2023

Related U.S. Application Data

(62) Division of application No. 16/480,992, filed as application No. PCT/US2018/015793 on Jan. 29, 2018, now Pat. No. 11,624,071.

(60) Provisional application No. 62/451,708, filed on Jan. 28, 2017, provisional application No. 62/451,710, filed on Jan. 28, 2017, provisional application No. 62/452,610, filed on Jan. 31, 2017, provisional application No. 62/477,244, filed on Mar. 27, 2017, provisional application No. 62/480,989, filed on Apr. 3, 2017, provisional application No. 62/510,645, filed on May 24, 2017, provisional application No. 62/523,675, filed on Jun. 22, 2017, provisional application No. 62/530,495, filed on Jul. 10, 2017, provisional application No. 62/530,839, filed on Jul. 10, 2017, provisional application No. 62/531,305, filed on Jul. 11, 2017.

(51) Int. Cl.
*C12N 15/82* (2006.01)

(52) U.S. Cl.
CPC ................................ *C12N 15/8213* (2013.01)

(58) Field of Classification Search
CPC ........................ C12N 15/8213; C12N 2310/20
See application file for complete search history.

(56) References Cited

U.S. PATENT DOCUMENTS 5,573,932 A * 11/1996 Ellis ........................ C12N 15/67 536/23.6
6,453,242 B1 9/2002 Eisenberg et al.
6,534,261 B1 3/2003 Cox, III
7,422,889 B2 9/2008 Sauer
7,605,300 B2 10/2009 Gan et al.
7,691,995 B2 4/2010 Zamore
7,786,350 B2 8/2010 Allen
7,816,581 B2 10/2010 Gilbertson
8,030,473 B2 10/2011 Carrington
8,314,290 B2 11/2012 Allen
8,334,430 B2 12/2012 Allen
8,395,023 B2 3/2013 Gilbertson
8,404,928 B2 3/2013 Allen
8,410,334 B2 4/2013 Allen
8,697,359 B1 4/2014 Zhang
8,771,945 B1 7/2014 Zhang
8,795,965 B2 8/2014 Zhang
8,816,153 B2 8/2014 Gilbertson
8,865,406 B2 10/2014 Zhang
8,871,445 B2 10/2014 Cong
8,889,356 B2 11/2014 Zhang
8,889,418 B2 11/2014 Zhang
8,895,308 B1 11/2014 Zhang
8,906,616 B2 12/2014 Zhang
8,932,814 B2 1/2015 Cong
8,945,839 B2 2/2015 Zhang
8,946,511 B2 2/2015 Allen
8,993,233 B2 3/2015 Zhang
8,999,641 B2 4/2015 Zhang
9,040,774 B2 5/2015 Ivashuta
9,139,838 B2 9/2015 Huang
9,192,112 B2 11/2015 Allen
11,220,694 B1 1/2022 Cermak et al.
11,603,536 B2 * 3/2023 Flavell ..................... C12N 9/22

(Continued)

FOREIGN PATENT DOCUMENTS

AU 2011204287 A1 * 8/2012 ............. C12N 15/52
CN 104450745 A 3/2015

(Continued)

OTHER PUBLICATIONS

Svitashev et al (Genome editing in maize directed by CRISPR-Cas9 ribonucleoprotein complexes. Nature communications, 1-7, 2016) (Year: 2016).*

(Continued)

*Primary Examiner* — Wayne Zhong

(74) *Attorney, Agent, or Firm* — McKee, Voorhees & Sease, PLC

(57) ABSTRACT

The invention relates to novel plants, seeds and compositions, as well as improvements to plant breeding and methods for creating modifications in plant genomes.

13 Claims, 18 Drawing Sheets

Specification includes a Sequence Listing.

(56) References Cited

U.S. PATENT DOCUMENTS

| | | | | |
|---|---|---|---|---|
| 2007/0011761 | A1 | 1/2007 | Thai | |
| 2009/0293148 | A1 | 11/2009 | Ren | |
| 2013/0326645 | A1 | 12/2013 | Cost | |
| 2015/0047074 | A1 | 2/2015 | Strano | |
| 2015/0059010 | A1 | 2/2015 | Cigan | |
| 2015/0082478 | A1 | 3/2015 | Cigan | |
| 2015/0307889 | A1 | 10/2015 | Petolino et al. | |
| 2015/0344912 | A1 | 12/2015 | Kim | |
| 2016/0017348 | A1 | 1/2016 | Jacobsen | |
| 2016/0138008 | A1 | 5/2016 | Doudna | |
| 2016/0194653 | A1 | 7/2016 | Cutler | |
| 2016/0208243 | A1 | 7/2016 | Zhang | |
| 2016/0264981 | A1 | 9/2016 | Yang | |
| 2016/0304891 | A1 | 10/2016 | Brower-Toland | |
| 2017/0037432 | A1 | 2/2017 | Donohoue | |
| 2017/0166912 | A1 | 6/2017 | Brower-Toland | |
| 2017/0175140 | A1 | 6/2017 | Hummel et al. | |
| 2019/0264218 | A1 | 8/2019 | Shultz | |
| 2019/0352655 | A1 | 11/2019 | Niu | |
| 2021/0324401 | A1 * | 10/2021 | Abbitt | C12N 15/8286 |

FOREIGN PATENT DOCUMENTS

| | | | | |
|---|---|---|---|---|
| DE | 4222407 | C1 * | 10/1993 | C12N 15/8216 |
| WO | WO-0127297 | A2 * | 4/2001 | C12N 15/8237 |
| WO | 2015006294 | A2 | 1/2015 | |
| WO | 2015131101 | A1 | 9/2015 | |
| WO | 2016007347 | A1 | 1/2016 | |
| WO | 2016007948 | A1 | 1/2016 | |
| WO | 2016044698 | A1 | 3/2016 | |
| WO | 2016123514 | A1 | 8/2016 | |

OTHER PUBLICATIONS

Jacobs et al (Targeted genome modifications in soybean with CRISPR/Cas9. BMC Biotechnology. 1-10, 2015) (Year: 2015).*

UniProt Sequence Accession B9TSW5 for Maize; retrieved from the internet site <https://uniprot.org/uniprot/> on Oct. 4, 2020.

UniProt Sequence Accession Q1HFQ1 for Maize; retrieved from the internet site <https://uniprot.org/uniprot/> on Oct. 4, 2020.

UniProt Sequence Accession Q53CL7 for Maize; retrieved from the internet site <https://uniprot.org/uniprot/> on Oct. 4, 2020.

UniProt Sequence Accession Q9FDY4 for Maize; retrieved from the internet site <https://uniprot.org/uniprot/> on Oct. 4, 2020.

UniProtKB—P00333 (ADH1_MAIZE); retrieved from www.uniprot.org/uniprot/P00333 <http://www.uniprot.org/uniprot/P00333> on Oct. 29, 2020.

UniProtKB—P13526 (ARLC_MAIZE); retrieved from www.uniprot.org/uniprot/P13526 <http://www.uniprot.org/uniprot/P13526> on Oct. 29, 2020.

UniProtKB—W8E7P1 (W8E7P1_SOYBN); retrieved from the internet site <http://www.uniprot.org/uniprot/W8E7P1 > on Nov. 12, 2020.

Van De Wiel et al., "New Traits in Crops Produced by Genome Editing Techniques Based on Deletions", Plant Biotechnology Reports, 2017, pp. 1-8, vol. 11.

Walker et al., "Molecular Mechanisms of Auxin Action", Current Opinion in Plant Biology, 1998, pp. 434-439, vol. 1.

Williams et al., "Sequences Flanking the Hexameric G-Box Core CACGTG Affect the Specificity of Protein Binding", The Plant Cell, Apr. 1992, pp. 485-496, vol. 4.

Wong et al., "Lipid Exchange Envelope Penetration (LEEP) of Nanoparticles for Plant Engineering: A Universal Localization Mechanism", Nano Letters, 2016, pp. 1161-1172, vol. 16.

Xu et al, "Global translational reprogramming is a fundamental layer of immune regulation in plants", Nature, May 25, 2017, pp. 487-490, vol. 545, No. 7655.

Xu et al., "uORF-mediated translation allows engineered plant disease resistance without fitness costs", Nature, May 25, 2017, pp. 491-494, vol. 545, No. 7655.

Xu et al., "The Soybean-Specific Maturity Gene E1 Family of Floral Repressors Controls Night-Break Responses Through Down-Regulation of Flowering Locus T Orthologs", Plant Physiology, Aug. 2015, pp. 1735-1746, vol. 168.

Yadava et al., "Advances in Maize Transformation Technologies and Development of Transgenic Maize", Frontiers in Plant Science, Jan. 2017, pp. 1-12, vol. 7, Article 1949.

Yang et al, "PAM-Dependent Target DNA Recognition and Cleavage by C2c1 CRISPR-Cas Endonuclease", Cell, Dec. 15, 2016, pp. 1814-1828, vol. 167, Elsevier Inc.

Ye et al., "Tuber-Specific Silencing of the Acid Invertase Gene Substantially Lowers the Acrylamide-Forming Potential of Potato", Journal of Agricultural and Food Chemistry, 2010, pp. 12162-12167, vol. 58, No. 23.

You et al., "Design of LNA probes that improve mismatch discrimination", Nucleic Acids Research, 2006, 11 pages, vol. 34, No. 8.

Zetsche et al, "Cpf1 Is a Single RNA-Guided Endonuclease of a Class 2 CRISPR-Cas System" Oct. 22, 2015, Cell, pp. 759-771, vol. 163, Elsevier Inc.

Zhang et al, "Genetic transformation of commercial cultivars of oat (*Avena sativa* L.) and barley (*Hordeum vulgare* L.) using in vitro shoot meristematic cultures derived from germinated seedlings", Plant Cell Reports, Jan. 14, 1999, pp. 959-966, vol. 18, Springer-Verlag.

Zhang et al., "Molecular Recognition Using Corona Phase Complexes Made of Synthetic Polymers Adsorbed on Carbon Nanotubes", Nature Nanotechnology, Nov. 24, 2013, pp. 959-968, vol. 8.

Zhu et al., "Silencing of Vacuolar Invertase and Asparagine Synthetase Genes and Its Impact on Acrylamide Formation of Fried Potato Products", Plant Biotechnology Journal, 2016, pp. 709-718, vol. 14.

Zhu et al., "Vacuolar Invertase Gene Silencing in Potato (*Solanum tuberosum* L.) Improves Processing Quality by Decreasing the Frequency of Sugar-End Defects", PLOS ONE, Apr. 2014, pp. 1-11, vol. 9, No. 4, e93381.

Andersson et al., "Efficient Targeted Multiallelic Mutagenesis in Tetraploid Potato (*Solanum tuberosum*) by Transient CRISPR-Cas9 Expression in Protoplasts", Plant Cell Rep., 2017, pp. 117-128, vol. 36.

Bartlett et al., "Mapping Genome-Wide Transcription Factor Binding Sites Using DAP-Seq", Nat. Protoc., 2017, pp. 1659-1672, vol. 12, No. 8.

Office Action for U.S. Appl. No. 16/261,233 dated Jun. 12, 2020.

Office Action for U.S. Appl. No. 16/261,243 dated Jun. 26, 2020.

O'Malley et al., "Cistrome and Epicistrome Features Shape the Regulatory DNA Landscape", Cell, 2016, pp. 1280-1292, vol. 165.

Pnueli et al., "The Self-Pruning Gene of Tomato Regulates Vegetative to Reproductive Switching of Sympodial Meristems and is the Ortholog of CEN and TFL1", Development, 1998, pp. 1979-1989, vol. 123, No. 11.

Schaeffer et al., "CRISPR/Cas9-Mediated Genome Editing and Gene Replacement in Plants: Transitioning from Lab to Field", Plant Science, 2015, pp. 130-142, vol. 240.

Soyk et al., "Bypassing Negative Epistasis on Yield in Tomato Imposed by a Domestication Gene", Cell, 2017, pp. 1142-1155, vol. 169.

Stroud et al, "Plants regenerated from tissue culture contain stable epigenome changes in rice", eLife, Mar. 19, 2013, pp. 1-14.

Svitashev et al., "Targeted Mutagenesis, Precise Gene Editing, and Site-Specific Gene Insertion in Maize using Cas9 and Guide RNA", Plant Physiology, 2015, pp. 931-945, vol. 169.

Szczesniak et al., "ERISdb: A Database of Plant Splice Sites and Splicing Signals", Plant Cell Physiol., 2013, 8 pages, vol. 54, No. 2.

Tomato Genome Consortium, "The Tomato Genome Sequence Provides Insight into Fleshy Fruit Evolution", Nature, 2012, pp. 635-641, vol. 485, No. 7400.

UniProt Sequence Accession ADH1 for Maize; retrieved from the internet site <https://uniprot.org/uniprot/> on Oct. 4, 2020.

UniProt Sequence Accession ARLC for Maize; retrieved from the internet site <https://uniprot.org/uniprot/> on Oct. 4, 2020.

(56) References Cited

OTHER PUBLICATIONS

Wang et al, "Simultaneous Editing of Three Homoeoalleles in Hexaploid in Hexaploid Bread Wheat Confers Heritable Resistance to Powdery Mildew", Nature Biotechnology, Sep. 2014, pp. 947-952, vol. 32, No. 9.
Weinthal et al., "Plant Genome Editing and Its Applications in Cereals", Intech Open, 2016, Chapter 4, pp. 63-73.
Wielgoss et al., "Mutation Rate Inferred From Synonymous Substitutions in a Long-Term Evolution Experiment in *Escherichia coli*",G3 (Bethesda), Aug. 1, 2011, pp. 183-186, vol. 1.
Zhang, et al, "Efficient and Transgene-Free Genome Editing in Wheat Through Transient Expression of CRISPR/Cas9 DNA or RNA", Nature Communication, 7:12617, Aug. 25, 2016, pp. 1-8.
Bortesi et al., "The CRISPR/Cas9 System for Plant Genome Editing and Beyond", Biotechnology Advances, 2015, pp. 41-52, vol. 33, No. 1.
Burgess et al., "Advances in Understanding Cis Regulation of the Plant Gene with Emphasis on Comparative Genomics", Current Opinion in Plant Biology, 2015, pp. 141-147, vol. 27.
Chakarov et al., "DNA Damage and Mutation: Types of DNA Damage", BioDiscovery, Feb. 23, 2014, pp. 1-43, vol. 11, e8957.
ERISdb: a Database of Plant Splice Sites downloaded from <http://lemur.amu.edu.pl/share/ERISdb/home.html> on Mar. 2, 2020.
Extended European Search Report for EP Application 18744149.8 dated Jul. 31, 2020.
Gil-Humanes et al., "High-Efficiency Gene Targeting in Hexaploid Wheat Using DNA Replicons and CRISPR/Cas9", The Plant Journal, 2017, pp. 1251-1262, vol. 89.
He et al., "Improved Regulatory Element Prediction Based on Tissue-Specific Local Epigenomic Signatures", PNAS, 2017, pp. 1633-1640.
Liang et al., "Efficient DNA-free Genome Editing of Bread Wheatusing CRISPR/Cas9 Ribonucleoprotein Complexes", Nature Communications, Oct. 6, 2016, pp. 1-5, vol. 8.
Lynch, "Evolution of the Mutation Rate", Trends in Genetics, Jun. 30, 2010, pp. 345-352, vol. 26, No. 8.
MaizeGDB Gene Record Page: Zm0000 1d045450, <<https://www.maizegdb.org/gene_center/gene/Zm00001d045450>>, retrieved Oct. 26, 2020, 3 pages.
Office Action for U.S. Appl. No. 16/146,871 dated Mar. 20, 2020.
Svitashev et al (Targeted Mutagenesis, Precise Gene Editing, and Site-Specific Gene Insertion in Maize Using Cas9 and Guide RNA. Plant Physiology, vol. 169, pp. 931-945. 2015.
Richardson et al (Enhancing homology-directed genome editing by catalytically active and inactive CRISPR-Cas9 using asymmetric donor DNA. Nature Biotechnology, 339-344, published on-line Jan. 20, 2016.
Zhang et al (The CRISPR/Cas9 system produces specific and homozygous targeted gene editing in rice in one generation. Plant Biotechnology Journal 12, pp. 797-807. 2014.
Lieber et al (The Mechanism of Double-Strand DNA Break Repair by the Nonhomologous DNA End Joining Pathway. Annu Rev Biochem, p. 1-34. 2010.
Collonnier et al., "Towards mastering CRISPR-induced gene knock-in in plants: Survey of key features and focus on the model Physcomitrella patens", Methods, vols. 121-122, pp. 103-117, 2017.
Lyznik et al., "Double-Strand Break-Induced Targeted Mutagenesis in Plants", Methods in Molecular Biology, vol. 347, pp. 399-416, 2012.
Ma, et al., "A Robust CRISPR/Cas9 System for Convenient, High-Efficiency Multiplex Genome Editing in Monocot and Dicot Plants", Molecular Plant, vol. 8, pp. 1274-1284, Aug. 2015.
Intellectual Property Office of Singapore, "Second Written Opinion" in connection with Application No. 11201906795S, Application Filing Date Jan. 29, 2018, Date of Second Written Opinion Apr. 22, 2021, 8 pages.
Intellectual Property Office of Singapore, "Search Report" in connection with Application No. 112019067955, Application Filing Date Jan. 29, 2018, Date of Search Report Oct. 22, 2020, 3 pages.
Intellectual Property Office of Singapore, "Written Opinion" in connection with Application No. 112019067955, Application Filing Date Jan. 29, 2018, Date of Written Opinion Oct. 22, 2020, 10 pages.
AGRIS *Arabidopsis* Gene Regulatory Information Server, AGRIS Binding Sites List, <<https://agris-knowledgebase.org/AtcisDB/bindingsites.html>>, retrieved Oct. 6, 2020, 13 pages.
Buchanan et al., "Phylogenetic Analysis of 5'-Noncoding Regions From the ABA-Responsive rab16/17 Gene Family of Sorghum, Maize and Rice Provides Insight Into the Composition, Organization and Function of cis-Regulatory Modules", Genetics, Nov. 2004, pp. 1639-1654, vol. 168.
Burstein et al., "New CRISPR-Cas Systems from Uncultivated Microbes", Nature, Feb. 9, 2017, pp. 237-241, vol. 542, No. 7640.
Clasen et al., "Improving Cold Storage and Processing Traits in Potato Through Targeted Gene Knockout", Plant Biotechnology Journal, 2015, pp. 169-176, vol. 14.
Cong et al., "Multiplex Genome Engineering Using CRISPR/Cas Systems", Science, Feb. 15, 2013, pp. 819-823, vol. 339, No. 6121.
Dong et al., "Pod Shattering Resistance Associated with Domestication is Mediated by a NAC Gene in Soybean", Nature Communications, 2014, pp. 1-11, vol. 5, No. 3352.
Fattash et al., "Miniature Inverted-Repeat Transposable Elements: Discovery, Distribution, and Activity", Genome, 2013, pp. 475-486, vol. 56.
Fauser et al., "Both CRISPR/Cas-Based Nucleases and Nickases Can Be Used Efficiently for Genome Engineering in *Arabidoposis thaliana*", The Plant Journal, 2014, pp. 348-359, vol. 79.
Ferré-D'-Amaré et al., "Small Self-Cleaving Ribozymes", 2010, Cold Spring Harbor Perspectives Biol., pp. 1-10.
Giraldo et al., "Plant Nanobionics Approach to Augment Photosynthesis and Biochemical Sensing", Nature Materials, 2014, pp. 1-20, doi:10.1038/NMAT3890.
Hendel et al, "Chemically modified guide RNAs enhance CRISPR-Cas genome editing in human primary cells", Nat Biotechnol., Sep. 2015, pp. 985-989, vol. 33, No. 9.
Ishige et al., "A G-box Motif (GCCACGTGCC) Tetramer Confers High-Level Constitutive Expression in Dicot and Monocot Plants", The Plant Journal, 1999, pp. 443-448, vol. 18, No. 4.
Je et al., "Signaling from Maize Organ Primordia Via Fasciated EAR3 Regulates Stem Cell Proliferation and Yield Traits", Nature Genetics, Jul. 2016, pp. 785-791, vol. 48, No. 7.
Kagale et al., "EAR Motif-Mediated Transcriptional Repression in Plants", Epigenetics, 2011, pp. 141-146, vol. 6, No. 2.
Kim et al., "Genome Sequence of the Hot Pepper Provides Insights into the Evolution of Pungency in *Capsicum* Species", Nature Genetics, Mar. 2014, pp. 270-279, vol. 46, No. 3.
Komorl et al, "Programmable editing of a target base in genomic DNA without double-stranded DNA cleavage", Nature, Oct. 20, 2016, pp. 420-424, vol. 533, No. 7603.
Kurai et al., "Introduction of the ZmDof1 Gene Into Rice Enhances Carbon and Nitrogen Assimilation Under Low-Nitrogen Conditions", Plant Biotechnology Journal, 2011, pp. 826-837, vol. 9.
Liu et al, "C2c1-sgRNA Complex Structure Reveals RNA-Guided DNA Cleavage Mechanism", Molecular Cell, Jan. 19, 2017, pp. 310-322, vol. 65, Elsevier Inc.
Mahfouz et al, "TALE nucleases and next generation GM Crops", GM Crops, Jun. 2011, pp. 99-103, vol. 2, No. 2, Landes Bioscience.
Mahfouz et al., "De Novo-Engineered Transcription Activator-Like Effector (TALE) Hybrid Nuclease with Novel DNA Binding Specificity Creates Double-Strand Breaks", PNAS, Feb. 8, 2011, pp. 2623-2628, vol. 108, No. 6.
Maizegdb, Maize B73 RefGen_v4, <<https://www.maizegdb.org/gbrowse?name=GRMZM2G118950>>, retrieved Oct. 26, 2020, 3 pages.
Maruthachalam et al., "How to Make Haploid *Arabidopsis thaliana*", Department of Plant Biology, UC Davis, 7 pages 2010.
Medrano et al., "From Leaf to Whole-Plant Water Use Efficiency (WUE) in Complex Canopies: Limitations of Leaf WUE as a Selection Target", The Crop Journal, 2015, pp. 220-228, vol. 3.
Molla et al., "Tissue-Specific Expression of Arabidopsis NPR1 Gene in Rice for Sheath Blight Resistance without Compromising Phenotypic Cost", Plant Science, 2016, pp. 105-114, vol. 250.

(56) References Cited

OTHER PUBLICATIONS

Mout et al., "Direct Cytosolic Delivery of CRISPR/Cas9-Ribonucleoprotein for Efficient Gene Editing", ACS Nano, 2017, pp. 2452-2458, vol. 11.

Newman et al., "DST Sequences, Highly Conserved Among Plant SAUR Genes, Target Reporter Transcripts for Rapid Decay in Tobacco", The Plant Cell, Jun. 1993, pp. 701-714, vol. 5.

Oka et al., "Genome-Wide Mapping of Transcriptional Enhancer Candidates Using DNA and Chromatin Features in Maize", Genome Biology, 2017, pp. 1-24, vol. 18, No. 137.

Oliveira et al., "Overexpression of Cytosolic Glutamine Synthetase. Relation to Nitrogen, Light, and Photorespiration", Plant Physiology, 2002, pp. 1170-1180, vol. 129.

Pajerowska-Mukhtar et al, "The HSF-like Transcription Factor TBF1 Is a Major Molecular Switch for Plant Growth-to-Defense Transition", Jan. 24, 2012, pp. 103-112, vol. 22, No. 2, Elsevier Ltd.

Quilis et al., "The *Arabidopsis* AtNPR1 Inversely Modulates Defense Responses Against Fungal, Bacterial, or Viral Pathogens While Conferring Hypersensitivity to Abiotic Stresses in Transgenic Rice", Molecular Plant-Microbe Interactions, 2008, pp. 1215-1231, vol. 21, No. 9.

Ran et al, "Genome engineering using the CRISPR-Cas 9 system", Nat Protoc., Nov. 2013, pp. 2281-2308, vol. 8, No. 11.

Ravi et al, "A haploid genetics toolbox for *Arabidopsis thaliana*", Nature Communications, Oct. 31, 2014, pp. 1-8, Macmillan Publishers Limited.

RiceGE: Rice Functional Genomic Express Database, Rice (*Oryza sativa jap*.), <<https://signal.salk.edu/cgi-bin/RiceGE?GENE=Os09g28340>>, retrieved Oct. 26, 2020, 2 pages.

Shmakov et al, "Discovery and functional characterization of diverse Class 2 CRISPR-Cas systems", Mol. Cell., Nov. 5, 2015, pp. 385-397, vol. 60, No. 3.

Sun et al., "Silencing of DND1 in Potato and Tomato Impedes Conidial Germination, Attachment and Hyphal Growth in Botrytis Cinerea", BMC Plant Biology, 2017, pp. 1-12, vol. 17, No. 235.

Sun et al., "Silencing of Six Susceptibility Genes Results in Potato Late Blight Resistance", Transgenic Research, 2016, pp. 731-742, vol. 25.

Ulmasov et al., "Aux/IAA Proteins Repress Expression of Reporter Genes Containing Natural and Highly Active Synthetic Auxin Response Elements", The Plant Cell, 1997, pp. 1963-1971, vol. 9.

UniProt Sequence Accession A0A1D6HA42 for Maize; retrieved from the internet site <https://uniprot.org/uniprot/> on Oct. 4, 2020.

UniProt Sequence Accession B4FIM5 for Maize; retrieved from the internet site <https://uniprot.org/uniprot/> on Oct. 4, 2020.

UniProt Sequence Accession B4FV06 for Maize; retrieved from the internet site <https://uniprot.org/uniprot/> on Oct. 4, 2020.

Extended European Search Report in EP21873582.7, mailed Jul. 26, 2024, 7 pages.

United States Utility Patent eGrant in U.S. Pat. No. 12,188,031, patented Jan. 7, 2025, 29 pages.

* cited by examiner

Figure 1A

```
NCBI gi 22123 230     ACTATGCGATTGCTTTCCTGGACCCGTGCAGCTGCGGTGGCATGGGAGGC
CONTIG 230 p1-62.1%   ACTATGCGATTGCTTTCCTGGACCCGTGCAGCTGCGGTGGCATGGGAGGC
CONTIG 229 p2-7.43%   ACTATGCGATTGCTTTCCTGGACCCGTGCAGCTGCGGTGGCATGGGAGGC
CONTIG 228 p3-3.91%   ACTATGCGATTGCTTTCCTGGACCCGTGCAGCTGCGGTGGCATGGGAGGC
CONTIG 229 p4-3.9%    ACTATGCGATTGCTTTCCTGGACCCGTGCAGCTGCGGTGGCATGGGAGGC
CONTIG 227 p5-3.63%   ACTATGCGATTGCTTTCCTGGACCCGTGCAGCTGCGGTGGCATGGGAGGC
CONTIG 226 p6-3.32%   ACTATGCGATTGCTTTCCTGGACCCGTGCAGCTGCGGTGGCATGGGAGGC
CONTIG 225 p7-2.93%   ACTATGCGATTGCTTTCCTGGACCCGTGCAGCTGCGGTGGCATGGGAGGC
CONTIG 224 p8-2.68%   ACTATGCGATTGCTTTCCTGGACCCGTGCAGCTGCGGTGGCATGGGAGGC
CONTIG 231 p9-2.57%   ACTATGCGATTGCTTTCCTGGACCCGTGCAGCTGCGGTGGCATGGGAGGC
CONTIG 231 p10-1.01%  ACTATGCGATTGCTTTCCTGGACCCGTGCAGCTGCGGTGGCATGGGAGGC
CONTIG 224 p11-0.87%  ACTATGCGATTGCTTTCCTGGACCCGTGCAGCTGCGGTGGCATGGGAGGC
CONTIG 227 p12-0.65%  ACTATGCGATTGCTTTCCTGGACCCGTGCAGCTGCGGTGGCATGGGAGGC
CONTIG 222 p13-0.55%  ACTATGCGATTGCTTTCCTGGACCCGTGCAGCTGCGGTGGCATGGGAGGC
CONTIG 226 p14-0.51%  ACTATGCGATTGCTTTCCTGGACCCGTGCAGCTGCGGTGGCATGGGAGGC
CONTIG 223 p15-0.5%   ACTATGCGATTGCTTTCCTGGACCCGTGCAGCTGCGGTGGCATGGGAGGC
CONTIG 220 p16-0.36%  ACTATGCGATTGCTTTCCTGGACCCGTGCAGCTGCGGTGGCATGGGAGGC
CONTIG 229 p17-0.33%  -ATATGCGATTGCTTTCCTGGACCCGTGCAGCTGCGGTGGCATGGGAGGC
CONTIG 228 p18-0.32%  ACTATGCGATTGCTTTCCTGGACCCGTGCAGCTGCGGTGGCATGGGAGGC
CONTIG 231 p19-0.31%  ACTATGCGATTGCTTTCCTGGACCCGTGCAGCTGCGGTGGCATGGGAGGC
CONTIG 221 p20-0.28%  ACTATGCGATTGCTTTCCTGGACCCGTGCAGCTGCGGTGGCATGGGAGGC
CONTIG 229 p21-0.27%  ACTATGCGATTGCTTTCCTGGACCCGTGCAGCTGCGGTGGCATGGGAGGC
CONTIG 221 p22-0.22%  ACTATGCGATTGCTTTCCTGGACCCGTGCAGCTGCGGTGGCATGGGAGGC
CONTIG 227 p23-0.22%  ACTATGCGATTGCTTTCCTGGACCCGTGCAGCTGCGGTGGCATGGGAGGC
CONTIG 228 p24-0.21%  ACTATGCGATTGCTTTCCTGGACCCGTGCAGCTGCGGTGGCATGGGAGGC
CONTIG 225 p25-0.21%  ACTATGCGATTGCTTTCCTGGACCCGTGCAGCTGCGGTGGCATGGGAGGC
CONTIG 237 p26-0.2%   ACTATGCGATTGCTTTCCTGGACCCGTGCAGCTGCGGTGGCATGGGAGGC
CONTIG 263 p27-0.19%  ACTATGCGATTGCTTTCCTGGACCCGTGCAGCTGCGGTGGCATGGGAGGC
CONTIG 221 p28-0.18%  ACTATGCGATTGCTTTCCTGGACCCGTGCAGCTGCGGTGGCATGGGAGGC
                        ************************************************

NCBI gi 22123 230     CGGCAAGCCACTGTCGATCGAGGAGGTGGAGGTAGCGCCTCCGCAGGCCA
CONTIG 230 p1-62.1%   CGGCAAGCCACTGTCGATCGAGGAGGTGGAGGTAGCGCCTCCGCAGGCCA
CONTIG 229 p2-7.43%   CGGCAAGCCACTGTCGATCGAGGAGGTGGAGGTAGCGCCTCCGCAGGCCA
CONTIG 228 p3-3.91%   CGGCAAGCCACTGTCGATCGAGGAGGTGGAGGTAGCGCCTCCGCAGGCCA
CONTIG 229 p4-3.9%    CGGCAAGCCACTGTCGATCGAGGAGGTGGAGGTAGCGCCTCCGCAGGCCA
CONTIG 227 p5-3.63%   CGGCAAGCCACTGTCGATCGAGGAGGTGGAGGTAGCGCCTCCGCAGGCCA
CONTIG 226 p6-3.32%   CGGCAAGCCACTGTCGATCGAGGAGGTGGAGGTAGCGCCTCCGCAGGCCA
CONTIG 225 p7-2.93%   CGGCAAGCCACTGTCGATCGAGGAGGTGGAGGTAGCGCCTCCGCAGGCCA
CONTIG 224 p8-2.68%   CGGCAAGCCACTGTCGATCGAGGAGGTGGAGGTAGCGCCTCCGCAGGCCA
CONTIG 231 p9-2.57%   CGGCAAGCCACTGTCGATCGAGGAGGTGGAGGTAGCGCCTCCGCAGGCCA
CONTIG 231 p10-1.01%  CGGCAAGCCACTGTCGATCGAGGAGGTGGAGGTAGCGCCTCCGCAGGCCA
CONTIG 224 p11-0.87%  CGGCAAGCCACTGTCGATCGAGGAGGTGGAGGTAGCGCCTCCGCAGGCCA
CONTIG 227 p12-0.65%  CGGCAAGCCACTGTCGATCGAGGAGGTGGAGGTAGCGCCTCCGCAGGCCA
CONTIG 222 p13-0.55%  CGGCAAGCCACTGTCGATCGAGGAGGTGGAGGTAGCGCCTCCGCAGGCCA
CONTIG 226 p14-0.51%  CGGCAAGCCACTGTCGATCGAGGAGGTGGAGGTAGCGCCTCCGCAGGCCA
CONTIG 223 p15-0.5%   CGGCAAGCCACTGTCGATCGAGGAGGTGGAGGTAGCGCCTCCGCAGGCCA
CONTIG 220 p16-0.36%  CGGCAAGCCACTGTCGATCGAGGAGGTGGAGGTAGCGCCTCCGCAGGCCA
CONTIG 229 p17-0.33%  CGGCAAGCCACTGTCGATCGAGGAGGTGGAGGTAGCGCCTCCGCAGGCCA
CONTIG 228 p18-0.32%  CGGCAAGCCACTGTCGATCGAGGAGGTGGAGGTAGCGCCTCCGCAGGCCA
CONTIG 231 p19-0.31%  CGGCAAGCCACTGTCGATCGAGGAGGTGGAGGTAGCGCCTCCGCAGGCCA
CONTIG 221 p20-0.28%  CGGCAAGCCACTGTCGATCGAGGAGGTGGAGGTAGCGCCTCCGCAGGCCA
CONTIG 229 p21-0.27%  CGGCAAGCCACTGTCGATCGAGGAGGTGGAGGTAGCGCCTCCGCAGGCCA
CONTIG 221 p22-0.22%  CGGCAAGCCACTGTCGATCGAGGAGGTGGAGGTAGCGCCTCCGCAGGCCA
CONTIG 227 p23-0.22%  CGGCAAGCCACTGTCGATCGAGGAGGTGGAGGTAGCGCCTCCGCAGGCCA
CONTIG 228 p24-0.21%  CGGCAAGCCACTGTCGATCGAGGAGGTGGAGGTAGCGCCTCCGCAGGCCA
CONTIG 225 p25-0.21%  CGGCAAGCCACTGTCGATCGAGGAGGTGGAGGTAGCGCCTCCGCAGGCCA
CONTIG 237 p26-0.2%   CGGCAAGCCACTGTCGATCGAGGAGGTGGAGGTAGCGCCTCCGCAGGCCA
CONTIG 263 p27-0.19%  CGGCAAGCCACTGTCGATCGAGGAGGTGGAGGTAGCGCCTCCGCAGGCCA
CONTIG 221 p28-0.18%  CGGCAAGCCACTGTCGATCGAGGAGGTGGAGGTAGCGCCTCCGCAGGCCA
                      **************************************************
```

Figure 1B

```
NCBI gi 22123 230      TGGAGGTGCGCGTCAAGATCCTCTTCACCTCGCTCTGCCACACCGACGT-
CONTIG 230 p1-62.1%    TGGAGGTGCGCGTCAAGATCCTCTTCACCTCGCTCTGCCACACCGACGT-
CONTIG 229 p2-7.43%    TGGAGGTGCGCGTCAAGATCCTCTTCACCTCGCTCTGCCACACCGACG--
CONTIG 228 p3-3.91%    TGGAGGTGCGCGTCAAGATCCTCTTCACCTCGCTCTGCCACACCGACG--
CONTIG 229 p4-3.9%     TGGAGGTGCGCGTCAAGATCCTCTTCACCTCGCTCTGCCACACCGACT--
CONTIG 227 p5-3.63%    TGGAGGTGCGCGTCAAGATCCTCTTCACCTCGCTCTGCCACACCGACG--
CONTIG 226 p6-3.32%    TGGAGGTGCGCGTCAAGATCCTCTTCACCTCGCTCTGCCACACCGACG--
CONTIG 225 p7-2.93%    TGGAGGTGCGCGTCAAGATCCTCTTCACCTCGCTCTGCCACACCGACG--
CONTIG 224 p8-2.68%    TGGAGGTGCGCGTCAAGATCCTCTTCACCTCGCTCTGCCACACCGACG--
CONTIG 231 p9-2.57%    TGGAGGTGCGCGTCAAGATCCTCTTCACCTCGCTCTGCCACACCGACGTT
CONTIG 231 p10-1.01%   TGGAGGTGCGCGTCAAGATCCTCTTCACCTCGCTCTGCCACACCGACGCT
CONTIG 224 p11-0.87%   TGGAGGTGCGCGTCAAGATCCTCTTCACCTCGCTCTGCCACACCGAC---
CONTIG 227 p12-0.65%   TGGAGGTGCGCGTCAAGATCCTCTTCACCTCGCTCTGCCACACCGAC---
CONTIG 222 p13-0.55%   TGGAGGTGCGCGTCAAGATCCTCTTCACCTCGCTCTGCCACACCGACG--
CONTIG 226 p14-0.51%   TGGAGGTGCGCGTCAAGATCCTCTTCACCTCGCTCTGCCACACCGAC---
CONTIG 223 p15-0.5%    TGGAGGTGCGCGTCAAGATCCTCTTCACCTCGCTCTGCCACACCGACG--
CONTIG 220 p16-0.36%   TGGAGGTGCGCGTCAAGATCCTCTTCACCTCGCTCTGCCACACCGAC---
CONTIG 229 p17-0.33%   TGGAGGTGCGCGTCAAGATCCTCTTCACCTCGCTCTGCCACACCGACGT-
CONTIG 228 p18-0.32%   TGGAGGTGCGCGTCAAGATCCTCTTCACCTCGCTCTGCCACACCGACC--
CONTIG 231 p19-0.31%   TGGAGGTGCGCGTCAAGATCCTCTTCACCTCGCTCTGCCACACCGACGAT
CONTIG 221 p20-0.28%   TGGAGGTGCGCGTCAAGATCCTCTTCACCTCGCTCTGCCACACCGAC---
CONTIG 229 p21-0.27%   TGGAGGTGCGCGTCAAGATCCTCTTCACCTCGCTCTGCCACACCGACGT-
CONTIG 221 p22-0.22%   TGGAGGTGCGCGTCAAGATCCTCTTCACCTCGCTCTGCCACACCGACG--
CONTIG 227 p23-0.22%   TGGAGGTGCGCGTCAAGATCCTCTTCACCTCGCTCTGCCACACCGACGT-
CONTIG 228 p24-0.21%   TGGAGGTGCGCGTCAAGATCCTCTTCACCTCGCTCTGCCACACCGAT---
CONTIG 225 p25-0.21%   TGGAGGTGCGCGTCAAGATCCTCTTCACCTCGCTCTGCCACACCGAC---
CONTIG 237 p26-0.2%    TGGAGGTGCGCGTCAAGATCCTCTTCACCTCGCTCTGCCACACCGACGTT
CONTIG 263 p27-0.19%   TGGAGGTGCGCGTCAAGATCCTCTTCACCTCGCTCTGCCACACCGACGGA
CONTIG 221 p28-0.18%   TGGAGGTGCGCGTCAAGATCCTCTTCACCTCGCTCTGCCACACCG-----
                       *********************************************

NCBI gi 22123 230      -----------------CT-------ACT----TCTG----GGAGGCCAA
CONTIG 230 p1-62.1%    -----------------CT-------ACT----TCTG----GGAGGCCAA
CONTIG 229 p2-7.43%    -----------------CT-------ACT----TCTG----GGAGGCCAA
CONTIG 228 p3-3.91%    ------------------T-------ACT----TCTG----GGAGGCCAA
CONTIG 229 p4-3.9%     -----------------CT-------ACT----TCTG----GGAGGCCAA
CONTIG 227 p5-3.63%    --------------------------ACT----TCTG----GGAGGCCAA
CONTIG 226 p6-3.32%    ---------------------------CT----TCTG----GGAGGCCAA
CONTIG 225 p7-2.93%    ----------------------------T----TCTG----GGAGGCCAA
CONTIG 224 p8-2.68%    ---------------------------------TCTG----GGAGGCCAA
CONTIG 231 p9-2.57%    -----------------CT-------ACT----TCTG----GGAGGCCAA
CONTIG 231 p10-1.01%   -----------------CT-------ACT----TCTG----GGAGGCCAA
CONTIG 224 p11-0.87%   ----------------------------T----TCTG----GGAGGCCAA
CONTIG 227 p12-0.65%   ------------------T-------ACT----TCTG----GGAGGCCAA
CONTIG 222 p13-0.55%   -----------------------------------TG----GGAGGCCAA
CONTIG 226 p14-0.51%   --------------------------ACT----TCTG----GGAGGCCAA
CONTIG 223 p15-0.5%    ----------------------------------CTG----GGAGGCCAA
CONTIG 220 p16-0.36%   ------------------------------------G----GGAGGCCAA
CONTIG 229 p17-0.33%   -----------------CT-------ACT----TCTG----GGAGGCCAA
CONTIG 228 p18-0.32%   ------------------T-------ACT----TCTG----GGAGGCCAA
CONTIG 231 p19-0.31%   -----------------CT-------ACT----TCTG----GGAGGCCAA
CONTIG 221 p20-0.28%   -----------------------------------TG----GGAGGCCAA
CONTIG 229 p21-0.27%   ------------------T-------ACT----TCTG----GGAGGCCAA
CONTIG 221 p22-0.22%   ------------------------------------G----GGAGGCCAA
CONTIG 227 p23-0.22%   ---------------------------CT----TCTG----GGAGGCCAA
CONTIG 228 p24-0.21%   -----------------CT-------ACT----TCTG----GGAGGCCAA
CONTIG 225 p25-0.21%   ---------------------------CT----TCTG----GGAGGCCAA
CONTIG 237 p26-0.2%    TTTTTT-----------CT-------ACT----TCTG----GGAGGCCAA
CONTIG 263 p27-0.19%   AGAAAACCTGATGGAGTCTGCAAAAGACCTGAGACTGGGAGGGAGGCCAA
CONTIG 221 p28-0.18%   ---------------------------------TCTG----GGAGGCCAA
                                                           *    *********
```

Figure 1C

```
NCBI gi 22123 230      GGTATCTAATCAGCCATCCCATTTGTGATCTTTGTCAGTAGATATGATAC
CONTIG 230 p1-62.1%    GGTATCTAATCAGCCATCCCATTTGTGATCTTTGTCAGTAGATATGATAC
CONTIG 229 p2-7.43%    GGTATCTAATCAGCCATCCCATTTGTGATCTTTGTCAGTAGATATGATAC
CONTIG 228 p3-3.91%    GGTATCTAATCAGCCATCCCATTTGTGATCTTTGTCAGTAGATATGATAC
CONTIG 229 p4-3.9%     GGTATCTAATCAGCCATCCCATTTGTGATCTTTGTCAGTAGATATGATAC
CONTIG 227 p5-3.63%    GGTATCTAATCAGCCATCCCATTTGTGATCTTTGTCAGTAGATATGATAC
CONTIG 226 p6-3.32%    GGTATCTAATCAGCCATCCCATTTGTGATCTTTGTCAGTAGATATGATAC
CONTIG 225 p7-2.93%    GGTATCTAATCAGCCATCCCATTTGTGATCTTTGTCAGTAGATATGATAC
CONTIG 224 p8-2.68%    GGTATCTAATCAGCCATCCCATTTGTGATCTTTGTCAGTAGATATGATAC
CONTIG 231 p9-2.57%    GGTATCTAATCAGCCATCCCATTTGTGATCTTTGTCAGTAGATATGATAC
CONTIG 231 p10-1.01%   GGTATCTAATCAGCCATCCCATTTGTGATCTTTGTCAGTAGATATGATAC
CONTIG 224 p11-0.87%   GGTATCTAATCAGCCATCCCATTTGTGATCTTTGTCAGTAGATATGATAC
CONTIG 227 p12-0.65%   GGTATCTAATCAGCCATCCCATTTGTGATCTTTGTCAGTAGATATGATAC
CONTIG 222 p13-0.55%   GGTATCTAATCAGCCATCCCATTTGTGATCTTTGTCAGTAGATATGATAC
CONTIG 226 p14-0.51%   GGTATCTAATCAGCCATCCCATTTGTGATCTTTGTCAGTAGATATGATAC
CONTIG 223 p15-0.5%    GGTATCTAATCAGCCATCCCATTTGTGATCTTTGTCAGTAGATATGATAC
CONTIG 220 p16-0.36%   GGTATCTAATCAGCCATCCCATTTGTGATCTTTGTCAGTAGATATGATAC
CONTIG 229 p17-0.33%   GGTATCTAATCAGCCATCCCATTTGTGATCTTTGTCAGTAGATATGATAC
CONTIG 228 p18-0.32%   GGTATCTAATCAGCCATCCCATTTGTGATCTTTGTCAGTAGATATGATAC
CONTIG 231 p19-0.31%   GGTATCTAATCAGCCATCCCATTTGTGATCTTTGTCAGTAGATATGATAC
CONTIG 221 p20-0.28%   GGTATCTAATCAGCCATCCCATTTGTGATCTTTGTCAGTAGATATGATAC
CONTIG 229 p21-0.27%   GGTATCTAATCAGCCATCCCATTTGTGATCTTTGTCAGTAGATATGATAC
CONTIG 221 p22-0.22%   GGTATCTAATCAGCCATCCCATTTGTGATCTTTGTCAGTAGATATGATAC
CONTIG 227 p23-0.22%   GGTATCTAATCAGCCATCCCATTTGTGATCTTTGTCAGTAGATATGATAC
CONTIG 228 p24-0.21%   GGTATCTAATCAGCCATCCCATTTGTGATCTTTGTCAGTAGATATGATAC
CONTIG 225 p25-0.21%   GGTATCTAATCAGCCATCCCATTTGTGATCTTTGTCAGTAGATATGATAC
CONTIG 237 p26-0.2%    GGTATCTAATCAGCCATCCCATTTGTGATCTTTGTCAGTAGATATGATAC
CONTIG 263 p27-0.19%   GGTATCTAATCAGCCATCCCATTTGTGATCTTTGTCAGTAGATATGATAC
CONTIG 221 p28-0.18%   GGTATCTAATCAGCCATCCCATTTGTGATCTTTGTCAGTAGATATGATAC
                       **************************************************

NCBI gi 22123 230      AACAACTCGCGGT   (SEQ ID NO:47)
CONTIG 230 p1-62.1%    AACAACTCGCGGT   (SEQ ID NO:48)
CONTIG_229_p2-7.43%    AACAACTCGCGGT   (SEQ ID NO:49)
CONTIG 228 p3-3.91%    AACAACTCGCGGT   (SEQ ID NO:50)
CONTIG 229 p4-3.9%     AACAACTCGCGGT   (SEQ ID NO:51)
CONTIG_227_p5-3.63%    AACAACTCGCGGT   (SEQ ID NO:52)
CONTIG 226 p6-3.32%    AACAACTCGCGGT   (SEQ ID NO:53)
CONTIG 225 p7-2.93%    AACAACTCGCGGT   (SEQ ID NO:54)
CONTIG_224_p8-2.68%    AACAACTCGCGGT   (SEQ ID NO:55)
CONTIG 231 p9-2.57%    AACAACTCGCGGT   (SEQ ID NO:56)
CONTIG 231 p10-1.01%   AACAACTCGCGGT   (SEQ ID NO:57)
CONTIG 224 p11-0.87%   AACAACTCGCGGT   (SEQ ID NO:58)
CONTIG 227 p12-0.65%   AACAACTCGCGGT   (SEQ ID NO:59)
CONTIG 222 p13-0.55%   AACAACTCGCGGT   (SEQ ID NO:60)
CONTIG 226 p14-0.51%   AACAACTCGCGGT   (SEQ ID NO:61)
CONTIG 223 p15-0.5%    AACAACTCGCGGT   (SEQ ID NO:62)
CONTIG 220 p16-0.36%   AACAACTCGCGGT   (SEQ ID NO:63)
CONTIG 229 p17-0.33%   AACAACTCGCGGT   (SEQ ID NO:64)
CONTIG 228 p18-0.32%   AACAACTCGCGGT   (SEQ ID NO:65)
CONTIG 231 p19-0.31%   AACAACTCGCGGT   (SEQ ID NO:66)
CONTIG 221 p20-0.28%   AACAACTCGCGGT   (SEQ ID NO:67)
CONTIG 229 p21-0.27%   AACAACTCGCGGT   (SEQ ID NO:68)
CONTIG 221 p22-0.22%   AACAACTCGCGGT   (SEQ ID NO:69)
CONTIG 227 p23-0.22%   AACAACTCGCGGT   (SEQ ID NO:70)
CONTIG 228 p24-0.21%   AACAACTCGCGGT   (SEQ ID NO:71)
CONTIG_225_p25-0.21%   AACAACTCGCGGT   (SEQ ID NO:72)
CONTIG 237 p26-0.2%    AACAACTCGCGGT   (SEQ ID NO:73)
CONTIG 263 p27-0.19%   AACAACTCGCGGT   (SEQ ID NO:74)
CONTIG_221_p28-0.18%   AACAACTCGCGGT   (SEQ ID NO:75)
                       *************
```

Figure 2A

```
NCBI_gi_392931134_255 GAAACCTACCAGTCTCTCCTTTGAAGAAGACATGAACAAAATTAGCCACG
CONTIG_256_p1_55.02%  GAAACCTACCAGTCTCTCCTTTGAAGAAAACATGAACAAAATTAGCCACG
CONTIG_256_p2_23.68%  GAAACCTACCAGTCTCTCCTTTGAAGAAAACATGAACAAAATTAGCCACG
CONTIG_255_p3_5.63%   GAAACCTACCAGTCTCTCCTTTGAAGAAAACATGAACAAAATTAGCCACG
CONTIG_257_p4_4.3%    GAAACCTACCAGTCTCTCCTTTGAAGAAAACATGAACAAAATTAGCCACG
CONTIG_250_p5_2.36%   GAAACCTACCAGTCTCTCCTTTGAAGAAAACATGAACAAAATTAGCCACG
CONTIG_257_p6_1.43%   GAAACCTACCAGTCTCTCCTTTGAAGAAAACATGAACAAAATTAGCCACG
CONTIG_257_p7_1.03%   GAAACCTACCAGTCTCTCCTTTGAAGAAAACATGAACAAAATTAGCCACG
CONTIG_254_p8_0.73%   GAAACCTACCAGTCTCTCCTTTGAAGAAAACATGAACAAAATTAGCCACG
CONTIG_255_p9_0.64%   GAAACCTACCAGTCTCTCCTTTGAAGAAAACATGAACAAAATTAGCCACG
CONTIG_255_p10_0.61%  GAAACCTACCAGTCTCTCCTTTGAAGAAAACATGAACAAAATTAGCCACG
CONTIG_253_p11_0.52%  GAAACCTACCAGTCTCTCCTTTGAAGAAAACATGAACAAAATTAGCCACG
CONTIG_252_p12_0.45%  GAAACCTACCAGTCTCTCCTTTGAAGAAAACATGAACAAAATTAGCCACG
CONTIG_257_p13_0.39%  GAAACCTACCAGTCTCTCCTTTGAAGAAAACATGAACAAAATTAGCCACG
CONTIG_249_p14_0.33%  GAAACCTACCAGTCTCTCCTTTGAAGAAAACATGAACAAAATTAGCCACG
CONTIG_249_p15_0.31%  GAAACCTACCAGTCTCTCCTTTGAAGAAAACATGAACAAAATTAGCCACG
CONTIG_257_p16_0.29%  GAAACCTACCAGTCTCTCCTTTGAAGAAAACATGAACAAAATTAGCCACG
CONTIG_252_p17_0.25%  GAAACCTACCAGTCTCTCCTTTGAAGAAAACATGAACAAAATTAGCCACG
CONTIG_251_p18_0.2%   GAAACCTACCAGTCTCTCCTTTGAAGAAAACATGAACAAAATTAGCCACG
CONTIG_253_p19_0.17%  GAAACCTACCAGTCTCTCCTTTGAAGAAAACATGAACAAAATTAGCCACG
CONTIG_255_p20_0.16%  G-AACCTACCAGTCTCTCCTTTGAAGAAAACATGAACAAAATTAGCCACG
CONTIG_247_p21_0.15%  GAAACCTACCAGTCTCTCCTTTGAAGAAAACATGAACAAAATTAGCCACG
CONTIG_248_p22_0.15%  GAAACCTACCAGTCTCTCCTTTGAAGAAAACATGAACAAAATTAGCCACG
CONTIG_251_p23_0.15%  GAAACCTACCAGTCTCTCCTTTGAAGAAAACATGAACAAAATTAGCCACG
CONTIG_245_p24_0.14%  GAAACCTACCAGTCTCTCCTTTGAAGAAAACATGAACAAAATTAGCCACG
CONTIG_257_p25_0.14%  GAAACCTACCAGTCTCTCCTTTGAAGAAAACATGAACAAAATTAGCCACG
CONTIG_257_p26_0.13%  GAAACCTACCAGTCTCTCCTTTGAAGAAAACATGAACAAAATTAGCCACG
CONTIG_253_p27_0.11%  GAAACCTACCAGTCTCTCCTTTGAAGAAAACATGAACAAAATTAGCCACG
CONTIG_254_p28_0.1%   GAAACCTACCAGTCTCTCCTTTGAAGAAAACATGAACAAAATTAGCCACG
CONTIG_251_p29_0.1%   GAAACCTACCAGTCTCTCCTTTGAAGAAAACATGAACAAAATTAGCCACG
CONTIG_254_p30_0.09%  GAAACCTACCAGTCTCTCCTTTGAAGAAAACATGAACAAAATTAGCCACG
CONTIG_249_p31_0.09%  GAAACCTACCAGTCTCTCCTTTGAAGAAAACATGAACAAAATTAGCCACG
                      * ************************** *********************
```

Figure 2B

```
NCBI_gi_392931134_255 GCGCTCTA-TCTCGGCCTTCCG-GTAACGTTTCTTGTTCAATAT-TGTTG
CONTIG_256_p1_55.02%  GCGCTCTC-TCTCGGCCTTCCG-GTAACGTTTCTTGTTCAGTATTTGTTG
CONTIG_256_p2_23.68%  GCGCTCTC-TCTCGGCCTTCCG-GTAATGTTTCTTGTTCAGTATTTGTTG
CONTIG_255_p3_5.63%   GCGCTCTC-TCTCGGCCTTCCG--TAACGTTTCTTGTTCAGTATTTGTTG
CONTIG_257_p4_4.3%    GCGCTCTC-TCTCGGCCTTCCGGGTAACGTTTCTTGTTCAGTATTTGTTG
CONTIG_250_p5_2.36%   GCGCTCTC-TCTCGGCCTTCC-------GTTTCTTGTTCAGTATTTGTTG
CONTIG_257_p6_1.43%   GCGCTCTC-TCTCGGCCTTCCAGGTAACGTTTCTTGTTCAGTATTTGTTG
CONTIG_257_p7_1.03%   GCGCTCTC-TCTCGGCCTTCCGGGTAATGTTTCTTGTTCAGTATTTGTTG
CONTIG_254_p8_0.73%   GCGCTCTC-TCTCGGCCTTCC---TAACGTTTCTTGTTCAGTATTTGTTG
CONTIG_255_p9_0.64%   GCGCTCTC-TCTCGGCCTTCCG--TAATGTTTCTTGTTCAGTATTTGTTG
CONTIG_255_p10_0.61%  GCGCTCTC-TCTCGGCCTTCG--GTAACGTTTCTTGTTCAGTATTTGTTG
CONTIG_253_p11_0.52%  GCGCTCTC-TCTCGGCCTTCCG----ACGTTTCTTGTTCAGTATTTGTTG
CONTIG_252_p12_0.45%  GCGCTCTC-TCTCGGCCTTCCG-----CGTTTCTTGTTCAGTATTTGTTG
CONTIG_257_p13_0.39%  GCGCTCTC-TCTCGGCCTTCCTGGTAACGTTTCTTGTTCAGTATTTGTTG
CONTIG_249_p14_0.33%  GCGCTCTC-TCTCGGCCTTCCG--------TTCTTGTTCAGTATTTGTTG
CONTIG_249_p15_0.31%  GCGCTCTC-TCTCGGCCTTCC--------TTTCTTGTTCAGTATTTGTTG
CONTIG_257_p16_0.29%  GCGCTCTC-TCTCGGCCTTCCCGGTAACGTTTCTTGTTCAGTATTTGTTG
CONTIG_252_p17_0.25%  GCGCTCTC-TCTCGGCCTTCC-----ACGTTTCTTGTTCAGTATTTGTTG
CONTIG_251_p18_0.2%   GCGCTCTC-TCTCGGCCTTCC------CGTTTCTTGTTCAGTATTTGTTG
CONTIG_253_p19_0.17%  GCGCTCTC-TCTCGGCCTTCC----AACGTTTCTTGTTCAGTATTTGTTG
CONTIG_255_p20_0.16%  GCGCTCTC-TCTCGGCCTTCCG-GTAACGTTTCTTGTTCAGTATTTGTTG
CONTIG_247_p21_0.15%  GCGCTCTC-TCTCGGCCTTCC----------TCTTGTTCAGTATTTGTTG
CONTIG_248_p22_0.15%  GCGCTCTC-TCTCGGCCTTCC---------TTCTTGTTCAGTATTTGTTG
CONTIG_251_p23_0.15%  GCGCTCTC-TCTCGGCCTTCCG------GTTTCTTGTTCAGTATTTGTTG
CONTIG_245_p24_0.14%  GCGCTCTC-TCTCGGCCT------------TTCTTGTTCAGTATTTGTTG
CONTIG_257_p25_0.14%  GCGCTCTC-TCTCGGCCTTCCGTGTAACGTTTCTTGTTCAGTATTTGTTG
CONTIG_257_p26_0.13%  GCGCTCTCATCTCGGCCTTCCG-GTAATGTTTCTTGTTCAGTATTTGTTG
CONTIG_253_p27_0.11%  GCGCTCTC-TCTCGGCCTTCCG----ATGTTTCTTGTTCAGTATTTGTTG
CONTIG_254_p28_0.1%   GCGCTCTC-TCTCGGCCTTGG---TAATGTTTCTTGTTCAGTATTTGTTG
CONTIG_251_p29_0.1%   GCGCTCTCTTCTCGGCCTTCC-------GTTTCTTGTTCAGTATTTGTTG
CONTIG_254_p30_0.09%  GCGCTCTC-TCTCGGCCTTCCG---AACGTTTCTTGTTCAGTATTTGTTG
CONTIG_249_p31_0.09%  GCGCTCTC-TCTCGGCCTTCC--------CTTCTTGTTCAGTATTTGTTG
                      *******  *********             ********* *** *****
```

Figure 2C

```
NCBI_gi_392931134_255 TATTTGCTTTCATATGACCAAATTCTTCATAATTAAAGATCGGTATAGAA
CONTIG_256_p1_55.02%  TATTTGCTTTCATATGACCAAATTCTTCATAATTAAAGATCGGTATAGAA
CONTIG_256_p2_23.68%  TATTTGCTTTCATATGACCAAATTCTTCATAATTAAAGATCGGTATAGAA
CONTIG_255_p3_5.63%   TATTTGCTTTCATATGACCAAATTCTTCATAATTAAAGATCGGTATAGAA
CONTIG_257_p4_4.3%    TATTTGCTTTCATATGACCAAATTCTTCATAATTAAAGATCGGTATAGAA
CONTIG_250_p5_2.36%   TATTTGCTTTCATATGACCAAATTCTTCATAATTAAAGATCGGTATAGAA
CONTIG_257_p6_1.43%   TATTTGCTTTCATATGACCAAATTCTTCATAATTAAAGATCGGTATAGAA
CONTIG_257_p7_1.03%   TATTTGCTTTCATATGACCAAATTCTTCATAATTAAAGATCGGTATAGAA
CONTIG_254_p8_0.73%   TATTTGCTTTCATATGACCAAATTCTTCATAATTAAAGATCGGTATAGAA
CONTIG_255_p9_0.64%   TATTTGCTTTCATATGACCAAATTCTTCATAATTAAAGATCGGTATAGAA
CONTIG_255_p10_0.61%  TATTTGCTTTCATATGACCAAATTCTTCATAATTAAAGATCGGTATAGAA
CONTIG_253_p11_0.52%  TATTTGCTTTCATATGACCAAATTCTTCATAATTAAAGATCGGTATAGAA
CONTIG_252_p12_0.45%  TATTTGCTTTCATATGACCAAATTCTTCATAATTAAAGATCGGTATAGAA
CONTIG_257_p13_0.39%  TATTTGCTTTCATATGACCAAATTCTTCATAATTAAAGATCGGTATAGAA
CONTIG_249_p14_0.33%  TATTTGCTTTCATATGACCAAATTCTTCATAATTAAAGATCGGTATAGAA
CONTIG_249_p15_0.31%  TATTTGCTTTCATATGACCAAATTCTTCATAATTAAAGATCGGTATAGAA
CONTIG_257_p16_0.29%  TATTTGCTTTCATATGACCAAATTCTTCATAATTAAAGATCGGTATAGAA
CONTIG_252_p17_0.25%  TATTTGCTTTCATATGACCAAATTCTTCATAATTAAAGATCGGTATAGAA
CONTIG_251_p18_0.2%   TATTTGCTTTCATATGACCAAATTCTTCATAATTAAAGATCGGTATAGAA
CONTIG_253_p19_0.17%  TATTTGCTTTCATATGACCAAATTCTTCATAATTAAAGATCGGTATAGAA
CONTIG_255_p20_0.16%  TATTTGCTTTCATATGACCAAATTCTTCATAATTAAAGATCGGTATAGAA
CONTIG_247_p21_0.15%  TATTTGCTTTCATATGACCAAATTCTTCATAATTAAAGATCGGTATAGAA
CONTIG_248_p22_0.15%  TATTTGCTTTCATATGACCAAATTCTTCATAATTAAAGATCGGTATAGAA
CONTIG_251_p23_0.15%  TATTTGCTTTCATATGACCAAATTCTTCATAATTAAAGATCGGTATAGAA
CONTIG_245_p24_0.14%  TATTTGCTTTCATATGACCAAATTCTTCATAATTAAAGATCGGTATAGAA
CONTIG_257_p25_0.14%  TATTTGCTTTCATATGACCAAATTCTTCATAATTAAAGATCGGTATAGAA
CONTIG_257_p26_0.13%  TATTTGCTTTCATATGACCAAATTCTTCATAATTAAAGATCGGTATAGAA
CONTIG_253_p27_0.11%  TATTTGCTTTCATATGACCAAATTCTTCATAATTAAAGATCGGTATAGAA
CONTIG_254_p28_0.1%   TATTTGCTTTCATATGACCAAATTCTTCATAATTAAAGATCGGTATAGAA
CONTIG_251_p29_0.1%   TATTTGCTTTCATATGACCAAATTCTTCATAATTAAAGATCGGTATAGAA
CONTIG_254_p30_0.09%  TATTTGCTTTCATATGACCAAATTCTTCATAATTAAAGATCGGTATAGAA
CONTIG_249_p31_0.09%  TATTTGCTTTCATATGACCAAATTCTTCATAATTAAAGATCGGTATAGAA
                      **************************************************
```

Figure 2D

```
NCBI_gi_392931134_255 GTCATAGATTACATATATGTACATTTGCACGGGTGAGTTTGCAACAAATG
CONTIG_256_p1_55.02%  GTCATAGATTACATATATGTACATTTGCACGGGTGAGTTTGCAACAAATG
CONTIG_256_p2_23.68%  GTCATAGATTACATATATGTACATTTGCACGGGTGAGTTTGCAACAAATG
CONTIG_255_p3_5.63%   GTCATAGATTACATATATGTACATTTGCACGGGTGAGTTTGCAACAAATG
CONTIG_257_p4_4.3%    GTCATAGATTACATATATGTACATTTGCACGGGTGAGTTTGCAACAAATG
CONTIG_250_p5_2.36%   GTCATAGATTACATATATGTACATTTGCACGGGTGAGTTTGCAACAAATG
CONTIG_257_p6_1.43%   GTCATAGATTACATATATGTACATTTGCACGGGTGAGTTTGCAACAAATG
CONTIG_257_p7_1.03%   GTCATAGATTACATATATGTACATTTGCACGGGTGAGTTTGCAACAAATG
CONTIG_254_p8_0.73%   GTCATAGATTACATATATGTACATTTGCACGGGTGAGTTTGCAACAAATG
CONTIG_255_p9_0.64%   GTCATAGATTACATATATGTACATTTGCACGGGTGAGTTTGCAACAAATG
CONTIG_255_p10_0.61%  GTCATAGATTACATATATGTACATTTGCACGGGTGAGTTTGCAACAAATG
CONTIG_253_p11_0.52%  GTCATAGATTACATATATGTACATTTGCACGGGTGAGTTTGCAACAAATG
CONTIG_252_p12_0.45%  GTCATAGATTACATATATGTACATTTGCACGGGTGAGTTTGCAACAAATG
CONTIG_257_p13_0.39%  GTCATAGATTACATATATGTACATTTGCACGGGTGAGTTTGCAACAAATG
CONTIG_249_p14_0.33%  GTCATAGATTACATATATGTACATTTGCACGGGTGAGTTTGCAACAAATG
CONTIG_249_p15_0.31%  GTCATAGATTACATATATGTACATTTGCACGGGTGAGTTTGCAACAAATG
CONTIG_257_p16_0.29%  GTCATAGATTACATATATGTACATTTGCACGGGTGAGTTTGCAACAAATG
CONTIG_252_p17_0.25%  GTCATAGATTACATATATGTACATTTGCACGGGTGAGTTTGCAACAAATG
CONTIG_251_p18_0.2%   GTCATAGATTACATATATGTACATTTGCACGGGTGAGTTTGCAACAAATG
CONTIG_253_p19_0.17%  GTCATAGATTACATATATGTACATTTGCACGGGTGAGTTTGCAACAAATG
CONTIG_255_p20_0.16%  GTCATAGATTACATATATGTACATTTGCACGGGTGAGTTTGCAACAAATG
CONTIG_247_p21_0.15%  GTCATAGATTACATATATGTACATTTGCACGGGTGAGTTTGCAACAAATG
CONTIG_248_p22_0.15%  GTCATAGATTACATATATGTACATTTGCACGGGTGAGTTTGCAACAAATG
CONTIG_251_p23_0.15%  GTCATAGATTACATATATGTACATTTGCACGGGTGAGTTTGCAACAAATG
CONTIG_245_p24_0.14%  GTCATAGATTACATATATGTACATTTGCACGGGTGAGTTTGCAACAAATG
CONTIG_257_p25_0.14%  GTCATAGATTACATATATGTACATTTGCACGGGTGAGTTTGCAACAAATG
CONTIG_257_p26_0.13%  GTCATAGATTACATATATGTACATTTGCACGGGTGAGTTTGCAACAAATG
CONTIG_253_p27_0.11%  GTCATAGATTACATATATGTACATTTGCACGGGTGAGTTTGCAACAAATG
CONTIG_254_p28_0.1%   GTCATAGATTACATATATGTACATTTGCACGGGTGAGTTTGCAACAAATG
CONTIG_251_p29_0.1%   GTCATAGATTACATATATGTACATTTGCACGGGTGAGTTTGCAACAAATG
CONTIG_254_p30_0.09%  GTCATAGATTACATATATGTACATTTGCACGGGTGAGTTTGCAACAAATG
CONTIG_249_p31_0.09%  GTCATAGATTACATATATGTACATTTGCACGGGTGAGTTTGCAACAAATG
                      **************************************************
```

Figure 2E

```
NCBI_gi_392931134_255 TCGTTTTACTTTGTGAAATTTAATCCCTAATCATGTTTTAGGAATGCTGC
CONTIG_256_p1_55.02%  TCGTTTTACTTTGTGAAATTTAATCCCTAATCATGTTTTAGGAATGCTGC
CONTIG_256_p2_23.68%  TCGTTTTACTTTGTGAAATTTAATCCCTAATCATGTTTTAGGAATGCTGC
CONTIG_255_p3_5.63%   TCGTTTTACTTTGTGAAATTTAATCCCTAATCATGTTTTAGGAATGCTGC
CONTIG_257_p4_4.3%    TCGTTTTACTTTGTGAAATTTAATCCCTAATCATGTTTTAGGAATGCTGC
CONTIG_250_p5_2.36%   TCGTTTTACTTTGTGAAATTTAATCCCTAATCATGTTTTAGGAATGCTGC
CONTIG_257_p6_1.43%   TCGTTTTACTTTGTGAAATTTAATCCCTAATCATGTTTTAGGAATGCTGC
CONTIG_257_p7_1.03%   TCGTTTTACTTTGTGAAATTTAATCCCTAATCATGTTTTAGGAATGCTGC
CONTIG_254_p8_0.73%   TCGTTTTACTTTGTGAAATTTAATCCCTAATCATGTTTTAGGAATGCTGC
CONTIG_255_p9_0.64%   TCGTTTTACTTTGTGAAATTTAATCCCTAATCATGTTTTAGGAATGCTGC
CONTIG_255_p10_0.61%  TCGTTTTACTTTGTGAAATTTAATCCCTAATCATGTTTTAGGAATGCTGC
CONTIG_253_p11_0.52%  TCGTTTTACTTTGTGAAATTTAATCCCTAATCATGTTTTAGGAATGCTGC
CONTIG_252_p12_0.45%  TCGTTTTACTTTGTGAAATTTAATCCCTAATCATGTTTTAGGAATGCTGC
CONTIG_257_p13_0.39%  TCGTTTTACTTTGTGAAATTTAATCCCTAATCATGTTTTAGGAATGCTGC
CONTIG_249_p14_0.33%  TCGTTTTACTTTGTGAAATTTAATCCCTAATCATGTTTTAGGAATGCTGC
CONTIG_249_p15_0.31%  TCGTTTTACTTTGTGAAATTTAATCCCTAATCATGTTTTAGGAATGCTGC
CONTIG_257_p16_0.29%  TCGTTTTACTTTGTGAAATTTAATCCCTAATCATGTTTTAGGAATGCTGC
CONTIG_252_p17_0.25%  TCGTTTTACTTTGTGAAATTTAATCCCTAATCATGTTTTAGGAATGCTGC
CONTIG_251_p18_0.2%   TCGTTTTACTTTGTGAAATTTAATCCCTAATCATGTTTTAGGAATGCTGC
CONTIG_253_p19_0.17%  TCGTTTTACTTTGTGAAATTTAATCCCTAATCATGTTTTAGGAATGCTGC
CONTIG_255_p20_0.16%  TCGTTTTACTTTGTGAAATTTAATCCCTAATCATGTTTTAGGAATGCTGC
CONTIG_247_p21_0.15%  TCGTTTTACTTTGTGAAATTTAATCCCTAATCATGTTTTAGGAATGCTGC
CONTIG_248_p22_0.15%  TCGTTTTACTTTGTGAAATTTAATCCCTAATCATGTTTTAGGAATGCTGC
CONTIG_251_p23_0.15%  TCGTTTTACTTTGTGAAATTTAATCCCTAATCATGTTTTAGGAATGCTGC
CONTIG_245_p24_0.14%  TCGTTTTACTTTGTGAAATTTAATCCCTAATCATGTTTTAGGAATGCTGC
CONTIG_257_p25_0.14%  TCGTTTTACTTTGTGAAATTTAATCCCTAATCATGTTTTAGGAATGCTGC
CONTIG_257_p26_0.13%  TCGTTTTACTTTGTGAAATTTAATCCCTAATCATGTTTTAGGAATGCTGC
CONTIG_253_p27_0.11%  TCGTTTTACTTTGTGAAATTTAATCCCTAATCATGTTTTAGGAATGCTGC
CONTIG_254_p28_0.1%   TCGTTTTACTTTGTGAAATTTAATCCCTAATCATGTTTTAGGAATGCTGC
CONTIG_251_p29_0.1%   TCGTTTTACTTTGTGAAATTTAATCCCTAATCATGTTTTAGGAATGCTGC
CONTIG_254_p30_0.09%  TCGTTTTACTTTGTGAAATTTAATCCCTAATCATGTTTTAGGAATGCTGC
CONTIG_249_p31_0.09%  TCGTTTTACTTTGTGAAATTTAATCCCTAATCATGTTTTAGGAATGCTGC
                      **************************************************
```

Figure 2F

```
NCBI_gi_392931134_255 ACCGTGCC  (SEQ ID NO:76)
CONTIG_256_p1_55.02%  ACCGTGCC  (SEQ ID NO:77)
CONTIG_256_p2_23.68%  ACCGTGCC  (SEQ ID NO:78)
CONTIG_255_p3_5.63%   ACCGTGCC  (SEQ ID NO:79)
CONTIG_257_p4_4.3%    ACCGTGCC  (SEQ ID NO:80)
CONTIG_250_p5_2.36%   ACCGTGCC  (SEQ ID NO:81)
CONTIG_257_p6_1.43%   ACCGTGCC  (SEQ ID NO:82)
CONTIG_257_p7_1.03%   ACCGTGCC  (SEQ ID NO:83)
CONTIG_254_p8_0.73%   ACCGTGCC  (SEQ ID NO:84)
CONTIG_255_p9_0.64%   ACCGTGCC  (SEQ ID NO:85)
CONTIG_255_p10_0.61%  ACCGTGCC  (SEQ ID NO:86)
CONTIG_253_p11_0.52%  ACCGTGCC  (SEQ ID NO:87)
CONTIG_252_p12_0.45%  ACCGTGCC  (SEQ ID NO:88)
CONTIG_257_p13_0.39%  ACCGTGCC  (SEQ ID NO:89)
CONTIG_249_p14_0.33%  ACCGTGCC  (SEQ ID NO:90)
CONTIG_249_p15_0.31%  ACCGTGCC  (SEQ ID NO:91)
CONTIG_257_p16_0.29%  ACCGTGCC  (SEQ ID NO:92)
CONTIG_252_p17_0.25%  ACCGTGCC  (SEQ ID NO:93)
CONTIG_251_p18_0.2%   ACCGTGCC  (SEQ ID NO:94)
CONTIG_253_p19_0.17%  ACCGTGCC  (SEQ ID NO:95)
CONTIG_255_p20_0.16%  ACCGTGCC  (SEQ ID NO:96)
CONTIG_247_p21_0.15%  ACCGTGCC  (SEQ ID NO:97)
CONTIG_248_p22_0.15%  ACCGTGCC  (SEQ ID NO:98)
CONTIG_251_p23_0.15%  ACCGTGCC  (SEQ ID NO:99)
CONTIG_245_p24_0.14%  ACCGTGCC  (SEQ ID NO:100)
CONTIG_257_p25_0.14%  ACCGTGCC  (SEQ ID NO:101)
CONTIG_257_p26_0.13%  ACCGTGCC  (SEQ ID NO:102)
CONTIG_253_p27_0.11%  ACCGTGCC  (SEQ ID NO:103)
CONTIG_254_p28_0.1%   ACCGTGCC  (SEQ ID NO:104)
CONTIG_251_p29_0.1%   ACCGTGCC  (SEQ ID NO:105)
CONTIG_254_p30_0.09%  ACCGTGCC  (SEQ ID NO:106)
CONTIG_249_p31_0.09%  ACCGTGCC  (SEQ ID NO:107)
                      ********
```

Figure 3A

```
NCBI gi 199580303 202 CCGATGGTCTTCAGTTCTCTTCCTTGTT-ATGGTCTCCCCCACGTGACCC
CONTIG 207 p1 23.91%  CCGATGGTCTTCAGTTCTCTTCCTTGTT-ATGGTCTCCCCCACGTGACCC
CONTIG 205 p2 10.76%  CCGATGGTCTTCAGTTCTCTTCCTTGTT---GGTCTCCCCCACGTGACCC
CONTIG 204 p3 9.83%   CCGATGGTCTTCAGTTCTCTTCCTTGTG----GTCTCCCCCACGTGACCC
CONTIG 208 p4 8.98%   CCGATGGTCTTCAGTTCTCTTCCTTGTTTATGGTCTCCCCCACGTGACCC
CONTIG 206 p5 8.76%   CCGATGGTCTTCAGTTCTCTTCCTTGTA--TGGTCTCCCCCACGTGACCC
CONTIG 206 p6 5.77%   CCGATGGTCTTCAGTTCTCTTCCTTGTT-ATGGTCTCCCCCACGTGACCC
CONTIG 202 p7 5.69%   CCGATGGTCTTCAGTTCTCTTCCTTGT------TCTCCCCCACGTGACCC
CONTIG 201 p8 5.07%   CCGATGGTCTTCAGTTCTCTTCCTTG-------TCTCCCCCACGTGACCC
CONTIG 203 p9 2.64%   CCGATGGTCTTCAGTTCTCTTCCTTGTG----GTCTCCCCCACGTGACCC
CONTIG 204 p10 2.55%  CCGATGGTCTTCAGTTCTCTTCCTTGTT---GGTCTCCCCCACGTGACCC
CONTIG 205 p11 2.26%  CCGATGGTCTTCAGTTCTCTTCCTTGTA--TGGTCTCCCCCACGTGACCC
CONTIG 207 p12 2.25%  CCGATGGTCTTCAGTTCTCTTCCTTGTTTATGGTCTCCCCCACGTGACCC
CONTIG 203 p13 2.13%  CCGATGGTCTTCAGTTCTCTTCCTTGT-----GTCTCCCCCACGTGACCC
CONTIG 201 p14 1.46%  CCGATGGTCTTCAGTTCTCTTCCTTGT------TCTCCCCCACGTGACCC
CONTIG 200 p15 1.24%  CCGATGGTCTTCAGTTCTCTTCCTTG-------TCTCCCCCACGTGACCC
CONTIG 200 p16 1.21%  CCGATGGTCTTCAGTTCTCTTCCTTGT--------TCCCCCACGTGACCC
CONTIG 199 p17 1.2%   CCGATGGTCTTCAGTTCTCTTCCTTGT---------CCCCCACGTGACCC
CONTIG 204 p18 0.89%  CCGATGGTCTTCAGTTCTCTTCCTTGTT----GTCTCCCCCACGTGACCC
CONTIG 208 p19 0.66%  CCGATGGTCTTCAGTTCTCTTCCTTGTATATGGTCTCCCCCACGTGACCC
CONTIG 202 p20 0.46%  CCGATGGTCTTCAGTTCTCTTCCTTGT-----GTCTCCCCCACGTGACCC
CONTIG 203 p21 0.44%  CCGATGGTCTTCAGTTCTCTTCCTTGTT-----TCTCCCCCACGTGACCC
CONTIG 202 p22 0.38%  CCGATGGTCTTCAGTTCTCTTCCTTG------GTCTCCCCCACGTGACCC
CONTIG 206 p23 0.32%  CCGATGGTCTTCAGTTCTCTTCCTTGTT--TGGTCTCCCCCACGTGACCC
CONTIG 198 p24 0.28%  CCGATGGTCTTCAGTTCTCTTCCTTGT----------CCCCACGTGACCC
CONTIG 201 p25 0.28%  CCGATGGTCTTCAGTTCTCTTCCTTGT-------TTCCCCCACGTGACCC
CONTIG 203 p26 0.23%  CCGATGGTCTTCAGTTCTCTTCCTTGTT----GTCTCCCCCACGTGACCC
CONTIG 199 p27 0.21%  CCGATGGTCTTCAGTTCTCTTCCTTGT--------TCCCCCACGTGACCC
                      **************************           *************

NCBI gi 199580303 202 TCAACAACATAAGGTACTTAACCATA-----ATAAAGCTTCAGATGTTTC
CONTIG 207 p1 23.91%  TCAACAACATAAGGTACTTAACAATAAATAAATAAAGCCTCAGATGTCTC
CONTIG 205 p2 10.76%  TCAACAACATAAGGTACTTAACAATAAATAAATAAAGCCTCAGATGTCTC
CONTIG 204 p3 9.83%   TCAACAACATAAGGTACTTAACAATAAATAAATAAAGCCTCAGATGTCTC
CONTIG 208 p4 8.98%   TCAACAACATAAGGTACTTAACAATAAATAAATAAAGCCTCAGATGTCTC
CONTIG 206 p5 8.76%   TCAACAACATAAGGTACTTAACAATAAATAAATAAAGCCTCAGATGTCTC
CONTIG 206 p6 5.77%   TCAACAACATAAGGTACTTAACAATA-ATAAATAAAGCCTCAGATGTCTC
CONTIG 202 p7 5.69%   TCAACAACATAAGGTACTTAACAATAAATAAATAAAGCCTCAGATGTCTC
CONTIG 201 p8 5.07%   TCAACAACATAAGGTACTTAACAATAAATAAATAAAGCCTCAGATGTCTC
CONTIG 203 p9 2.64%   TCAACAACATAAGGTACTTAACAATA-ATAAATAAAGCCTCAGATGTCTC
CONTIG 204 p10 2.55%  TCAACAACATAAGGTACTTAACAATA-ATAAATAAAGCCTCAGATGTCTC
CONTIG 205 p11 2.26%  TCAACAACATAAGGTACTTAACAATA-ATAAATAAAGCCTCAGATGTCTC
CONTIG 207 p12 2.25%  TCAACAACATAAGGTACTTAACAATA-ATAAATAAAGCCTCAGATGTCTC
CONTIG 203 p13 2.13%  TCAACAACATAAGGTACTTAACAATAAATAAATAAAGCCTCAGATGTCTC
CONTIG 201 p14 1.46%  TCAACAACATAAGGTACTTAACAATA-ATAAATAAAGCCTCAGATGTCTC
CONTIG 200 p15 1.24%  TCAACAACATAAGGTACTTAACAATA-ATAAATAAAGCCTCAGATGTCTC
CONTIG 200 p16 1.21%  TCAACAACATAAGGTACTTAACAATAAATAAATAAAGCCTCAGATGTCTC
CONTIG 199 p17 1.2%   TCAACAACATAAGGTACTTAACAATAAATAAATAAAGCCTCAGATGTCTC
CONTIG 204 p18 0.89%  TCAACAACATAAGGTACTTAACAATAAATAAATAAAGCCTCAGATGTCTC
CONTIG 208 p19 0.66%  TCAACAACATAAGGTACTTAACAATAAATAAATAAAGCCTCAGATGTCTC
CONTIG 202 p20 0.46%  TCAACAACATAAGGTACTTAACAATA-ATAAATAAAGCCTCAGATGTCTC
CONTIG 203 p21 0.44%  TCAACAACATAAGGTACTTAACAATAAATAAATAAAGCCTCAGATGTCTC
CONTIG 202 p22 0.38%  TCAACAACATAAGGTACTTAACAATAAATAAATAAAGCCTCAGATGTCTC
CONTIG 206 p23 0.32%  TCAACAACATAAGGTACTTAACAATAAATAAATAAAGCCTCAGATGTCTC
CONTIG 198 p24 0.28%  TCAACAACATAAGGTACTTAACAATAAATAAATAAAGCCTCAGATGTCTC
CONTIG 201 p25 0.28%  TCAACAACATAAGGTACTTAACAATAAATAAATAAAGCCTCAGATGTCTC
CONTIG 203 p26 0.23%  TCAACAACATAAGGTACTTAACAATA-ATAAATAAAGCCTCAGATGTCTC
CONTIG 199 p27 0.21%  TCAACAACATAAGGTACTTAACAATA-ATAAATAAAGCCTCAGATGTCTC
                      ********************* ***     ******* ******** **
```

Figure 3B

```
NCBI gi 199580303 202  ATCCATGAACCGCTGCTGATTGTCTTTCTCCTTAGGATCAAGTCGTTGCT
CONTIG 207 p1 23.91%   ATCCATGAACCGGTGCTGATTGTCTTTCTCCTTAGGATCAAGTCGTTGCT
CONTIG 205 p2 10.76%   ATCCATGAACCGGTGCTGATTGTCTTTCTCCTTAGGATCAAGTCGTTGCT
CONTIG 204 p3 9.83%    ATCCATGAACCGGTGCTGATTGTCTTTCTCCTTAGGATCAAGTCGTTGCT
CONTIG 208 p4 8.98%    ATCCATGAACCGGTGCTGATTGTCTTTCTCCTTAGGATCAAGTCGTTGCT
CONTIG 206 p5 8.76%    ATCCATGAACCGGTGCTGATTGTCTTTCTCCTTAGGATCAAGTCGTTGCT
CONTIG 206 p6 5.77%    ATCCATGAACCGGTGCTGATTGTCTTTCTCCTTAGGATCAAGTCGTTGCT
CONTIG 202 p7 5.69%    ATCCATGAACCGGTGCTGATTGTCTTTCTCCTTAGGATCAAGTCGTTGCT
CONTIG 201 p8 5.07%    ATCCATGAACCGGTGCTGATTGTCTTTCTCCTTAGGATCAAGTCGTTGCT
CONTIG 203 p9 2.64%    ATCCATGAACCGGTGCTGATTGTCTTTCTCCTTAGGATCAAGTCGTTGCT
CONTIG 204 p10 2.55%   ATCCATGAACCGGTGCTGATTGTCTTTCTCCTTAGGATCAAGTCGTTGCT
CONTIG 205 p11 2.26%   ATCCATGAACCGGTGCTGATTGTCTTTCTCCTTAGGATCAAGTCGTTGCT
CONTIG 207 p12 2.25%   ATCCATGAACCGGTGCTGATTGTCTTTCTCCTTAGGATCAAGTCGTTGCT
CONTIG 203 p13 2.13%   ATCCATGAACCGGTGCTGATTGTCTTTCTCCTTAGGATCAAGTCGTTGCT
CONTIG 201 p14 1.46%   ATCCATGAACCGGTGCTGATTGTCTTTCTCCTTAGGATCAAGTCGTTGCT
CONTIG 200 p15 1.24%   ATCCATGAACCGGTGCTGATTGTCTTTCTCCTTAGGATCAAGTCGTTGCT
CONTIG 200 p16 1.21%   ATCCATGAACCGGTGCTGATTGTCTTTCTCCTTAGGATCAAGTCGTTGCT
CONTIG 199 p17 1.2%    ATCCATGAACCGGTGCTGATTGTCTTTCTCCTTAGGATCAAGTCGTTGCT
CONTIG 204 p18 0.89%   ATCCATGAACCGGTGCTGATTGTCTTTCTCCTTAGGATCAAGTCGTTGCT
CONTIG 208 p19 0.66%   ATCCATGAACCGGTGCTGATTGTCTTTCTCCTTAGGATCAAGTCGTTGCT
CONTIG 202 p20 0.46%   ATCCATGAACCGGTGCTGATTGTCTTTCTCCTTAGGATCAAGTCGTTGCT
CONTIG 203 p21 0.44%   ATCCATGAACCGGTGCTGATTGTCTTTCTCCTTAGGATCAAGTCGTTGCT
CONTIG 202 p22 0.38%   ATCCATGAACCGGTGCTGATTGTCTTTCTCCTTAGGATCAAGTCGTTGCT
CONTIG 206 p23 0.32%   ATCCATGAACCGGTGCTGATTGTCTTTCTCCTTAGGATCAAGTCGTTGCT
CONTIG 198 p24 0.28%   ATCCATGAACCGGTGCTGATTGTCTTTCTCCTTAGGATCAAGTCGTTGCT
CONTIG 201 p25 0.28%   ATCCATGAACCGGTGCTGATTGTCTTTCTCCTTAGGATCAAGTCGTTGCT
CONTIG 203 p26 0.23%   ATCCATGAACCGGTGCTGATTGTCTTTCTCCTTAGGATCAAGTCGTTGCT
CONTIG 199 p27 0.21%   ATCCATGAACCGGTGCTGATTGTCTTTCTCCTTAGGATCAAGTCGTTGCT
                       ************ *************************************

NCBI gi 199580303 202  TATGTCGAATACTTTGGTCAGTTCACATCAGAGCAATTCCCTGATGATAT
CONTIG 207 p1 23.91%   TATGTCGAATACTTTGGTCAGTTCACATCAGAGCAATTCCCTGATGATAT
CONTIG 205 p2 10.76%   TATGTCGAATACTTTGGTCAGTTCACATCAGAGCAATTCCCTGATGATAT
CONTIG 204 p3 9.83%    TATGTCGAATACTTTGGTCAGTTCACATCAGAGCAATTCCCTGATGATAT
CONTIG 208 p4 8.98%    TATGTCGAATACTTTGGTCAGTTCACATCAGAGCAATTCCCTGATGATAT
CONTIG 206 p5 8.76%    TATGTCGAATACTTTGGTCAGTTCACATCAGAGCAATTCCCTGATGATAT
CONTIG 206 p6 5.77%    TATGTCGAATACTTTGGTCAGTTCACATCAGAGCAATTCCCTGATGATAT
CONTIG 202 p7 5.69%    TATGTCGAATACTTTGGTCAGTTCACATCAGAGCAATTCCCTGATGATAT
CONTIG 201 p8 5.07%    TATGTCGAATACTTTGGTCAGTTCACATCAGAGCAATTCCCTGATGATAT
CONTIG 203 p9 2.64%    TATGTCGAATACTTTGGTCAGTTCACATCAGAGCAATTCCCTGATGATAT
CONTIG 204 p10 2.55%   TATGTCGAATACTTTGGTCAGTTCACATCAGAGCAATTCCCTGATGATAT
CONTIG 205 p11 2.26%   TATGTCGAATACTTTGGTCAGTTCACATCAGAGCAATTCCCTGATGATAT
CONTIG 207 p12 2.25%   TATGTCGAATACTTTGGTCAGTTCACATCAGAGCAATTCCCTGATGATAT
CONTIG 203 p13 2.13%   TATGTCGAATACTTTGGTCAGTTCACATCAGAGCAATTCCCTGATGATAT
CONTIG 201 p14 1.46%   TATGTCGAATACTTTGGTCAGTTCACATCAGAGCAATTCCCTGATGATAT
CONTIG 200 p15 1.24%   TATGTCGAATACTTTGGTCAGTTCACATCAGAGCAATTCCCTGATGATAT
CONTIG 200 p16 1.21%   TATGTCGAATACTTTGGTCAGTTCACATCAGAGCAATTCCCTGATGATAT
CONTIG 199 p17 1.2%    TATGTCGAATACTTTGGTCAGTTCACATCAGAGCAATTCCCTGATGATAT
CONTIG 204 p18 0.89%   TATGTCGAATACTTTGGTCAGTTCACATCAGAGCAATTCCCTGATGATAT
CONTIG 208 p19 0.66%   TATGTCGAATACTTTGGTCAGTTCACATCAGAGCAATTCCCTGATGATAT
CONTIG 202 p20 0.46%   TATGTCGAATACTTTGGTCAGTTCACATCAGAGCAATTCCCTGATGATAT
CONTIG 203 p21 0.44%   TATGTCGAATACTTTGGTCAGTTCACATCAGAGCAATTCCCTGATGATAT
CONTIG 202 p22 0.38%   TATGTCGAATACTTTGGTCAGTTCACATCAGAGCAATTCCCTGATGATAT
CONTIG 206 p23 0.32%   TATGTCGAATACTTTGGTCAGTTCACATCAGAGCAATTCCCTGATGATAT
CONTIG 198 p24 0.28%   TATGTCGAATACTTTGGTCAGTTCACATCAGAGCAATTCCCTGATGATAT
CONTIG 201 p25 0.28%   TATGTCGAATACTTTGGTCAGTTCACATCAGAGCAATTCCCTGATGATAT
CONTIG 203 p26 0.23%   TATGTCGAATACTTTGGTCAGTTCACATCAGAGCAATTCCCTGATGATAT
CONTIG 199 p27 0.21%   TATGTCGAATACTTTGGTCAGTTCACATCAGAGCAATTCCCTGATGATAT
                       **************************************************
```

Figure 3C

```
NCBI gi 199580303 202 TGCTGAGG  (SEQ ID NO:108)
CONTIG 207 p1 23.91%  TGCTGAGG  (SEQ ID NO:109)
CONTIG 205 p2 10.76%  TGCTGAGG  (SEQ ID NO:110)
CONTIG 204 p3 9.83%   TGCTGAGG  (SEQ ID NO:111)
CONTIG 208 p4 8.98%   TGCTGAGG  (SEQ ID NO:112)
CONTIG 206 p5 8.76%   TGCTGAGG  (SEQ ID NO:113)
CONTIG 206 p6 5.77%   TGCTGAGG  (SEQ ID NO:114)
CONTIG 202 p7 5.69%   TGCTGAGG  (SEQ ID NO:115)
CONTIG_201_p8_5.07%   TGCTGAGG  (SEQ ID NO:116)
CONTIG 203 p9 2.64%   TGCTGAGG  (SEQ ID NO:117)
CONTIG 204 p10 2.55%  TGCTGAGG  (SEQ ID NO:118)
CONTIG_205_p11_2.26%  TGCTGAGG  (SEQ ID NO:119)
CONTIG 207 p12 2.25%  TGCTGAGG  (SEQ ID NO:120)
CONTIG 203 p13 2.13%  TGCTGAGG  (SEQ ID NO:121)
CONTIG_201_p14_1.46%  TGCTGAGG  (SEQ ID NO:122)
CONTIG 200 p15 1.24%  TGCTGAGG  (SEQ ID NO:123)
CONTIG 200 p16 1.21%  TGCTGAGG  (SEQ ID NO:124)
CONTIG 199 p17 1.2%   TGCTGAGG  (SEQ ID NO:125)
CONTIG 204 p18 0.89%  TGCTGAGG  (SEQ ID NO:126)
CONTIG 208 p19 0.66%  TGCTGAGG  (SEQ ID NO:127)
CONTIG 202 p20 0.46%  TGCTGAGG  (SEQ ID NO:128)
CONTIG 203 p21 0.44%  TGCTGAGG  (SEQ ID NO:129)
CONTIG 202 p22 0.38%  TGCTGAGG  (SEQ ID NO:130)
CONTIG 206 p23 0.32%  TGCTGAGG  (SEQ ID NO:131)
CONTIG 198 p24 0.28%  TGCTGAGG  (SEQ ID NO:132)
CONTIG 201 p25 0.28%  TGCTGAGG  (SEQ ID NO:133)
CONTIG 203 p26 0.23%  TGCTGAGG  (SEQ ID NO:134)
CONTIG 199 p27 0.21%  TGCTGAGG  (SEQ ID NO:135)
                      ********
```

Figure 4A

```
NCBI_gi_22123_230        TGGAGGTGCGCGTCAAGATCCTCTTCACCTCGCTCTGCCACACCGACG--
CONTIG_230_p1_76.03%     TGGAGGTGCGCGTCAAGATCCTCTTCACCTCGCTCTGCCACACCGACG--
CONTIG_264_p2_4.18%      TGGAGGTGCGCGTCAAGATCCTCTTCACCTCGCTCTGCCACACCGACGA-
CONTIG_231_p3_1.21%      TGGAGGTGCGCGTCAAGATCCTCTTCACCTCGCTCTGCCACACCGACGT-
CONTIG_292_p4_1.2%       TGGAGGTGCGCGTCAAGATCCTCTTCACCTCGCTCTGCCACACCGNNNNN
CONTIG_262_p5_1%         TGGAGGTGCGCGTCAAGATCCTCTTCACCTCGCTCTGCCACACCGACGT-
CONTIG_229_p6_0.93%      TGGAGGTGCGCGTCAAGATCCTCTTCACCTCGCTCTGCCACACCGACG--
CONTIG_262_p7_0.92%      TGGAGGTGCGCGTCAAGATCCTCTTCACCTCGCTCTGCCACACCGACGA-
CONTIG_292_p8_0.92%      TGGAGGTGCGCGTCAAGATCCTCTTCACCTCGCTCTGCCACACCGNNNNN
CONTIG_225_p9_0.91%      TGGAGGTGCGCGTCAAGATCCTCTTCACCTCGCTCTGCCACACCGACGT-
CONTIG_292_p10_0.8%      TGGAGGTGCGCGTCAAGATCCTCTTCACCTCGCTCTGCCACACCGNNNNN
CONTIG_292_p11_0.74%     TGGAGGTGCGCGTCAAGATCCTCTTCACCTCGCTCTGCCACACCGNNNNN
CONTIG_292_p12_0.73%     TGGAGGTGCGCGTCAAGATCCTCTTCACCTCGCTCTGCCACACCGNNNNN
CONTIG_224_p13_0.63%     TGGAGGTGCGCGTCAAGATCCTCTTCACCTCGCTCTGCCACACCGA----
CONTIG_227_p14_0.62%     TGGAGGTGCGCGTCAAGATCCTCTTCACCTCGCTCTGCCACACCGACG--
CONTIG_231_p15_0.61%     TGGAGGTGCGCGTCAAGATCCTCTTCACCTCGCTCTGCCACACCGACGC-
CONTIG_292_p16_0.61%     TGGAGGTGCGCGTCAAGATCCTCTTCACCTCGCTCTGCCACACCGNNNNN
CONTIG_292_p17_0.6%      TGGAGGTGCGCGTCAAGATCCTCTTCACCTCGCTCTGCCACACCGNNNNN
CONTIG_292_p18_0.58%     TGGAGGTGCGCGTCAAGATCCTCTTCACCTCGCTCTGCCACACCGNNNNN
CONTIG_229_p19_0.54%     TGGAGGTGCGCGTCAAGATCCTCTTCACCTCGCTCTGCCACACCGAC---
CONTIG_260_p20_0.54%     TGGAGGTGCGCGTCAAGATCCTCTTCACCTCGCTCTGCCACACCGACGG-
CONTIG_259_p21_0.52%     TGGAGGTGCGCGTCAAGATCCTCTTCACCTCGCTCTGCCACACCGACGA-
CONTIG_258_p22_0.5%      TGGAGGTGCGCGTCAAGATCCTCTTCACCTCGCTCTGCCACACCGACGG-
CONTIG_261_p23_0.46%     TGGAGGTGCGCGTCAAGATCCTCTTCACCTCGCTCTGCCACACCGATA--
CONTIG_243_p24_0.42%     TGGAGGTGCGCGTCAAGATCCTCTTCACCTACC-----------------
CONTIG_221_p25_0.41%     TGGAGGTGCGCGTCAAGATCCTCTTCACCTCGCTCTGCCACACCGAC---
CONTIG_237_p26_0.36%     TGGAGGTGCGCGTCAAGATCCTCTTCACCTCGCTCTGCCACACCGACGG-
CONTIG_292_p27_0.36%     TGGAGGTGCGCGTCAAGATCCTCTTCACCTCGCTCTGCCACACCGNNNNN
CONTIG_263_p28_0.32%     TGGAGGTGCGCGTCAAGATCCTCTTCACCTCGCTCTGCCACACCGACGG-
CONTIG_227_p29_0.32%     TGGAGGTGCGCGTCAAGATCCTCTTCACCTCGCTCTGCCACACCGAC---
CONTIG_264_p30_0.32%     TGGAGGTGCGCGTCAAGATCCTCTTCACCTCGCTCTGCCACACCGACGA-
CONTIG_226_p31_0.32%     TGGAGGTGCGCGTCAAGATCCTCTTCACCTCGCTCTGCCACACCGAC---
CONTIG_264_p32_0.31%     TGGAGGTGCGCGTCAAGATCCTCTTCACCTCGCTCTGCCACACCGACGGT
CONTIG_292_p33_0.3%      TGGAGGTGCGCGTCAAGATCCTCTTCACCTCGCTCTGCCACACCGNNNNN
CONTIG_292_p34_0.3%      TGGAGGTGCGCGTCAAGATCCTCTTCACCTCGCTCTGCCACACCGNNNNN
CONTIG_229_p35_0.27%     TGGAGGTGCGCGTCAAGATCCTCTTCACCTCGCTCTGCCACACCGACG--
                         ******************************   *
```

Figure 4B

```
NCBI_gi_22123_230      --------------------------------------------------
CONTIG_230_p1_76.03%   --------------------------------------------------
CONTIG_264_p2_4.18%    --------------------------------------TACCGTT--ATT
CONTIG_231_p3_1.21%    --------------------------------------------------
CONTIG_292_p4_1.2%     ---------GA-GTTGTCATATGTTAATAACGGTATG-TTTAATTGAGTT
CONTIG_262_p5_1%       ---------------------------------------TTAATTGAGTT
CONTIG_229_p6_0.93%    --------------------------------------------------
CONTIG_262_p7_0.92%    --------------------------------------TACCGTT--ATT
CONTIG_292_p8_0.92%    --T------GA-GTTGTCATATGTTAATAACGGTATG--TTAATTGAGTT
CONTIG_225_p9_0.91%    --------------------------------------------------
CONTIG_292_p10_0.8%    --T---------ATTAACATATGACAACTCAATTAAACTACCGTT--ATT
CONTIG_292_p11_0.74%   GTT-TAATTGA-GTTGTCATATGTTAATAACGGTAT--TACCGTT--ATT
CONTIG_292_p12_0.73%   ---------G----------------------G-----TTTAATTGAGTT
CONTIG_224_p13_0.63%   --------------------------------------------------
CONTIG_227_p14_0.62%   --------------------------------------------------
CONTIG_231_p15_0.61%   --------------------------------------------------
CONTIG_292_p16_0.61%   ---------GA-GTTGTCATATGTTAATAACGGTATA-TACCGTT--ATT
CONTIG_292_p17_0.6%    --T-----TGA-GTTGTCATATGTTAATAACGGTA---TACCGTT--ATT
CONTIG_292_p18_0.58%   --T-TAATTGA-GTTGTCATATGTTAATAACGGTA---TACCGTT--ATT
CONTIG_229_p19_0.54%   --------------------------------------------------
CONTIG_260_p20_0.54%   --------------------------------------TTTAATTGAGTT
CONTIG_259_p21_0.52%   --------------------------------------TACCGTT--ATT
CONTIG_258_p22_0.5%    --------------------------------------TTTAATTGAGTT
CONTIG_261_p23_0.46%   ----------------------------------------CCGTT--ATT
CONTIG_243_p24_0.42%   ------------------------------------------GTT--ATT
CONTIG_221_p25_0.41%   --------------------------------------------------
CONTIG_237_p26_0.36%   --------------------------------------TTT---------
CONTIG_292_p27_0.36%   --C-----CGTTATTAACATATGACAACTCAATTA---TACCGTT--ATT
CONTIG_263_p28_0.32%   --------------------------------------TTTAATTGAGTT
CONTIG_227_p29_0.32%   --------------------------------------------------
CONTIG_264_p30_0.32%   --------------------------------------TACCGTT--ATT
CONTIG_226_p31_0.32%   --------------------------------------------------
CONTIG_264_p32_0.31%   --T-------------------------------------TAATTGAGTT
CONTIG_292_p33_0.3%    ----------A-GTTGTCATATGTTAATAACGGTATA-TACCGTT--ATT
CONTIG_292_p34_0.3%    --TATAATCCT------C--ATGTCAGCCATGGAGTA-TTTGGAA--ATA
CONTIG_229_p35_0.27%   --------------------------------------------------
```

Figure 4C

```
NCBI_gi_22123_230      -------------------------TCT----------------------
CONTIG_230_p1_76.03%   -------------------------TCT----------------------
CONTIG_264_p2_4.18%    AACATATGACAA-CTCAATTAAAC-TCT----------------------
CONTIG_231_p3_1.21%    -------------------------TCT----------------------
CONTIG_292_p4_1.2%     GTCATATGTTAA-T--AACGGTAT-TCT----------------------
CONTIG_262_p5_1%       GTCATATGTTAA-T--AACGGTA--TCT----------------------
CONTIG_229_p6_0.93%    -------------------------TCT----------------------
CONTIG_262_p7_0.92%    AACATATGACAA-CTCAATTAAA---CT----------------------
CONTIG_292_p8_0.92%    GTCATATGTTAA-T--AACGGTAT-TCT----------------------
CONTIG_225_p9_0.91%    --------------------------------------------------
CONTIG_292_p10_0.8%    AACATATGACAA-CTCAATTAAAC-TCT----------------------
CONTIG_292_p11_0.74%   AACATATGACAA-CTCAATTAA----------------------------
CONTIG_292_p12_0.73%   GTCATATGTTAA-T--AACGGTAG-TTTAATTGAGTTGTCATATGTTAAT
CONTIG_224_p13_0.63%   --------------------------------------------------
CONTIG_227_p14_0.62%   --------------------------------------------------
CONTIG_231_p15_0.61%   -------------------------TCT----------------------
CONTIG_292_p16_0.61%   AACATATGACAA-CTCAATTAAAC-TCT----------------------
CONTIG_292_p17_0.6%    AACATATGACAA-CTCAATTAAAC-TCT----------------------
CONTIG_292_p18_0.58%   AACATATGACAA-CTCAATTAA----------------------------
CONTIG_229_p19_0.54%   -------------------------TCT----------------------
CONTIG_260_p20_0.54%   GTCATATGTTAA-T--AACGGTA---------------------------
CONTIG_259_p21_0.52%   AACATATGACAA-CTCAATTAA----------------------------
CONTIG_258_p22_0.5%    GTCATATGTTAA-T--AACGGT----------------------------
CONTIG_261_p23_0.46%   AACATATGACAA-CTCAATTAAAC-TCT----------------------
CONTIG_243_p24_0.42%   AACATATGACAA-CTCAATTAAA--CCT----------------------
CONTIG_221_p25_0.41%   --------------------------------------------------
CONTIG_237_p26_0.36%   ----------A------A-----T-TCT----------------------
CONTIG_292_p27_0.36%   AACATATGACAA-CTCAATTAAA--CCT----------------------
CONTIG_263_p28_0.32%   GTCATATGTTAA-T--AACGGTA--TCT----------------------
CONTIG_227_p29_0.32%   ---------------------------T----------------------
CONTIG_264_p30_0.32%   AACATATGACAA-CTCAATTAAAC-TCT----------------------
CONTIG_226_p31_0.32%   --------------------------------------------------
CONTIG_264_p32_0.31%   GTCATATGTTAA-T--AACGGTAT-TCT----------------------
CONTIG_292_p33_0.3%    AACATATGACAA-CTCAATTAAACATCT----------------------
CONTIG_292_p34_0.3%    CAGAAATT-CATGGTTGGTGGA-CATCT----------------------
CONTIG_229_p35_0.27%   --------------------------CT----------------------
```

Figure 4D

```
NCBI_gi_22123_230       ---A-CTTCTGGGAGGCCAAGGTATCTAATCAGCCATCCCATTTGTGATC  (SEQ ID NO:269)
CONTIG_230_p1_76.03%    ---A-CTTCTGGGAGGCCAAGGTATCTAATCAGCCATCCCATTTGTGATC  (SEQ ID NO:270)
CONTIG_264_p2_4.18%     ---A-CTTCTGGGAGGCCAAGGTATCTAATCAGCCATCCCATTTGTGATC  (SEQ ID NO:271)
CONTIG_231_p3_1.21%     ---A-CTTCTGGGAGGCCAAGGTATCTAATCAGCCATCCCATTTGTGATC  (SEQ ID NO:272)
CONTIG_292_p4_1.2%      ---A-CTTCTGGGAGGCCAAGGTATCTAATCAGCCATCCCATTTGTGATC  (SEQ ID NO:273)
CONTIG_262_p5_1%        ---A-CTTCTGGGAGGCCAAGGTATCTAATCAGCCATCCCATTTGTGATC  (SEQ ID NO:274)
CONTIG_229_p6_0.93%     ---A-CTTCTGGGAGGCCAAGGTATCTAATCAGCCATCCCATTTGTGATC  (SEQ ID NO:275)
CONTIG_262_p7_0.92%     ---A-CTTCTGGGAGGCCAAGGTATCTAATCAGCCATCCCATTTGTGATC  (SEQ ID NO:276)
CONTIG_292_p8_0.92%     ---A-CTTCTGGGAGGCCAAGGTATCTAATCAGCCATCCCATTTGTGATC  (SEQ ID NO:277)
CONTIG_225_p9_0.91%     -------TCTGGGAGGCCAAGGTATCTAATCAGCCATCCCATTTGTGATC  (SEQ ID NO:278)
CONTIG_292_p10_0.8%     ---A-CTTCTGGGAGGCCAAGGTATCTAATCAGCCATCCCATTTGTGATC  (SEQ ID NO:279)
CONTIG_292_p11_0.74%    ------ACCTGGGAGGCCAAGGTATCTAATCAGCCATCCCATTTGTGATC  (SEQ ID NO:280)
CONTIG_292_p12_0.73%    AACG-GTATTGGGAGGCCAAGGTATCTAATCAGCCATCCCATTTGTGATC  (SEQ ID NO:281)
CONTIG_224_p13_0.63%    -----CTTCTGGGAGGCCAAGGTATCTAATCAGCCATCCCATTTGTGATC  (SEQ ID NO:282)
CONTIG_227_p14_0.62%    ---A-CTTCTGGGAGGCCAAGGTATCTAATCAGCCATCCCATTTGTGATC  (SEQ ID NO:283)
CONTIG_231_p15_0.61%    ---A-CTTCTGGGAGGCCAAGGTATCTAATCAGCCATCCCATTTGTGATC  (SEQ ID NO:284)
CONTIG_292_p16_0.61%    ---A-CTTCTGGGAGGCCAAGGTATCTAATCAGCCATCCCATTTGTGATC  (SEQ ID NO:285)
CONTIG_292_p17_0.6%     ---A-CTTCTGGGAGGCCAAGGTATCTAATCAGCCATCCCATTTGTGATC  (SEQ ID NO:286)
CONTIG_292_p18_0.58%    ---ACCTTCTGGGAGGCCAAGGTATCTAATCAGCCATCCCATTTGTGATC  (SEQ ID NO:287)
CONTIG_229_p19_0.54%    ---A-CTTCTGGGAGGCCAAGGTATCTAATCAGCCATCCCATTTGTGATC  (SEQ ID NO:288)
CONTIG_260_p20_0.54%    ---T-CTTCTGGGAGGCCAAGGTATCTAATCAGCCATCCCATTTGTGATC  (SEQ ID NO:289)
CONTIG_259_p21_0.52%    ---A-CTTCTGGGAGGCCAAGGTATCTAATTAGCCATCCCATTTGTGATC  (SEQ ID NO:290)
CONTIG_258_p22_0.5%     -----ATTCTGGGAGGCCAAGGTATCTAATCAGCCATCCCATTTGTGATC  (SEQ ID NO:291)
CONTIG_261_p23_0.46%    ---A-CTTCTGGGAGGCCAAGGTATCTAATCAGCCATCCCATTTGTGATC  (SEQ ID NO:292)
CONTIG_243_p24_0.42%    ---A-CTTCTGGGAGGCCAAGGTATCTAATCAGCCATCCCATTTGTGATC  (SEQ ID NO:293)
CONTIG_221_p25_0.41%    ---------GGGGAGGCCAAGGTATCTAATCAGCCATCCCATTTGTGATC  (SEQ ID NO:294)
CONTIG_237_p26_0.36%    ---A-CTTCTGGGAGGCCAAGGTATCTAATCAGCCATCCCATTTGTGATC  (SEQ ID NO:295)
CONTIG_292_p27_0.36%    ---A-CTTCTGGGAGGCCAAGGTATCTAATCAGCCATCCCATTTGTGATC  (SEQ ID NO:296)
CONTIG_263_p28_0.32%    ---A-CTTCTGGGAGGCCAAGGTATCTAATCAGCCATCCCATTTGTGATC  (SEQ ID NO:297)
CONTIG_227_p29_0.32%    ---A-CTTCTGGGAGGCCAAGGTATCTAATCAGCCATCCCATTTGTGATC  (SEQ ID NO:298)
CONTIG_264_p30_0.32%    ---A-CTTCTGGGAGGCCAAGGTATCTAATCAGCCATCCCATTTGTGATC  (SEQ ID NO:299)
CONTIG_226_p31_0.32%    ---A-CTTCTGGGAGGCCAAGGTATCTAATCAGCCATCCCATTTGTGATC  (SEQ ID NO:300)
CONTIG_264_p32_0.31%    ---A-CTTCTGGGAGGCCAAGGTATCTAATCAGCCATCCCATTTGTGATC  (SEQ ID NO:301)
CONTIG_292_p33_0.3%     ---A-CTTCTGGGAGGCCAAGGTATCTAATCAGCCATCCCATTTGTGATC  (SEQ ID NO:302)
CONTIG_292_p34_0.3%     ---A-CTTCTGGGAGGCCAAGGTATCTAATCAGCCATCCCATTTGTGATC  (SEQ ID NO:303)
CONTIG_229_p35_0.27%    ---A-CTTCTGGGAGGCCAAGGTATCTAATCAGCCATCCCATTTGTGATC  (SEQ ID NO:304)
                                  ******************** *******************
```

Figure 5
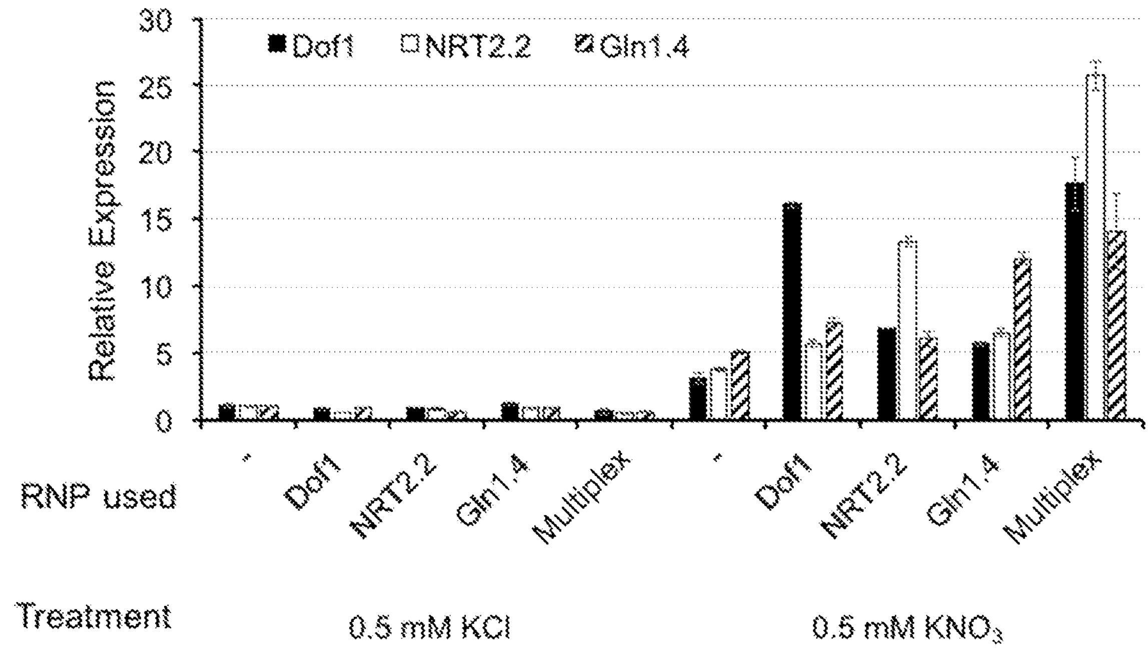
A
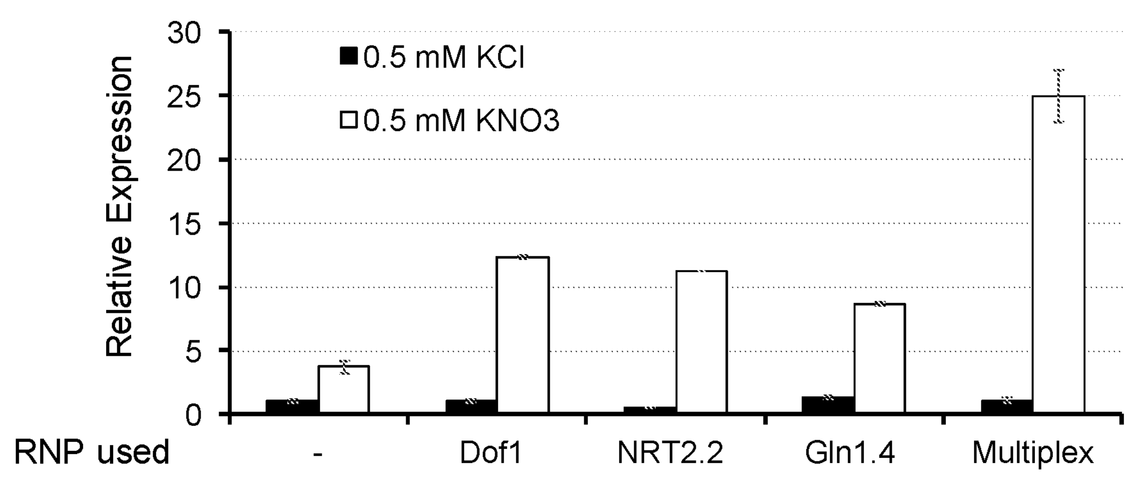
B

SEQUENCE LISTING

```
Sequence total quantity: 515
SEQ ID NO: 1             moltype = RNA  length = 36
FEATURE                  Location/Qualifiers
source                   1..36
                         mol_type = other RNA
                         organism = synthetic construct
SEQUENCE: 1
gcacttgatc accttccctg gttttagagc tatgct                          36

SEQ ID NO: 2             moltype = RNA  length = 36
FEATURE                  Location/Qualifiers
```

```
source                  1..36
                        mol_type = other RNA
                        organism = synthetic construct
SEQUENCE: 2
tccacctcct cgatcaccag gttttagagc tatgct                               36

SEQ ID NO: 3            moltype = RNA  length = 36
FEATURE                 Location/Qualifiers
source                  1..36
                        mol_type = other RNA
                        organism = synthetic construct
SEQUENCE: 3
ggcctcccag aagtagacgt gttttagagc tatgct                               36

SEQ ID NO: 4            moltype = RNA  length = 36
FEATURE                 Location/Qualifiers
source                  1..36
                        mol_type = other RNA
                        organism = synthetic construct
SEQUENCE: 4
gggaaggtga tcaagtgcaa gttttagagc tatgct                               36

SEQ ID NO: 5            moltype = RNA  length = 36
FEATURE                 Location/Qualifiers
source                  1..36
                        mol_type = other RNA
                        organism = synthetic construct
SEQUENCE: 5
gccaccgtcg aaccctttgg gttttagagc tatgct                               36

SEQ ID NO: 6            moltype = RNA  length = 36
FEATURE                 Location/Qualifiers
source                  1..36
                        mol_type = other RNA
                        organism = synthetic construct
SEQUENCE: 6
gtaaatgggc ttcccgttga gttttagagc tatgct                               36

SEQ ID NO: 7            moltype = RNA  length = 36
FEATURE                 Location/Qualifiers
source                  1..36
                        mol_type = other RNA
                        organism = synthetic construct
SEQUENCE: 7
gacagactcc cgtgttccct gttttagagc tatgct                               36

SEQ ID NO: 8            moltype = RNA  length = 36
FEATURE                 Location/Qualifiers
source                  1..36
                        mol_type = other RNA
                        organism = synthetic construct
SEQUENCE: 8
gtgaattcag gagctggagg gttttagagc tatgct                               36

SEQ ID NO: 9            moltype = RNA  length = 36
FEATURE                 Location/Qualifiers
source                  1..36
                        mol_type = other RNA
                        organism = synthetic construct
SEQUENCE: 9
gtacttgctg agatgaccaa gttttagagc tatgct                               36

SEQ ID NO: 10           moltype = RNA  length = 36
FEATURE                 Location/Qualifiers
source                  1..36
                        mol_type = other RNA
                        organism = synthetic construct
SEQUENCE: 10
gcaacatgtg tgatctgctc gttttagagc tatgct                               36

SEQ ID NO: 11           moltype = RNA  length = 36
FEATURE                 Location/Qualifiers
source                  1..36
                        mol_type = other RNA
                        organism = synthetic construct
SEQUENCE: 11
tggccgggag gattcccatg gttttagagc tatgct                               36

SEQ ID NO: 12           moltype = RNA  length = 36
```

```
FEATURE                 Location/Qualifiers
source                  1..36
                        mol_type = other RNA
                        organism = synthetic construct
SEQUENCE: 12
atggttcatg cagtgcacgg gttttagagc tatgct                        36

SEQ ID NO: 13           moltype = RNA  length = 36
FEATURE                 Location/Qualifiers
source                  1..36
                        mol_type = other RNA
                        organism = synthetic construct
SEQUENCE: 13
gctcgaggac gaactcggtg gttttagagc tatgct                        36

SEQ ID NO: 14           moltype = RNA  length = 36
FEATURE                 Location/Qualifiers
source                  1..36
                        mol_type = other RNA
                        organism = synthetic construct
SEQUENCE: 14
atgtactgga gggagctggg gttttagagc tatgct                        36

SEQ ID NO: 15           moltype = RNA  length = 36
FEATURE                 Location/Qualifiers
source                  1..36
                        mol_type = other RNA
                        organism = synthetic construct
SEQUENCE: 15
tagaatgtat aattacccgt gttttagagc tatgct                        36

SEQ ID NO: 16           moltype = RNA  length = 36
FEATURE                 Location/Qualifiers
source                  1..36
                        mol_type = other RNA
                        organism = synthetic construct
SEQUENCE: 16
cgggcctccc gggagccatc gttttagagc tatgct                        36

SEQ ID NO: 17           moltype = RNA  length = 36
FEATURE                 Location/Qualifiers
source                  1..36
                        mol_type = other RNA
                        organism = synthetic construct
SEQUENCE: 17
caagcacctg gggcgtctgc gttttagagc tatgct                        36

SEQ ID NO: 18           moltype = RNA  length = 36
FEATURE                 Location/Qualifiers
source                  1..36
                        mol_type = other RNA
                        organism = synthetic construct
SEQUENCE: 18
gagatcagat cttgccgatg gttttagagc tatgct                        36

SEQ ID NO: 19           moltype = RNA  length = 36
FEATURE                 Location/Qualifiers
source                  1..36
                        mol_type = other RNA
                        organism = synthetic construct
SEQUENCE: 19
gaaggtgatc ttgctattga gttttagagc tatgct                        36

SEQ ID NO: 20           moltype = RNA  length = 36
FEATURE                 Location/Qualifiers
source                  1..36
                        mol_type = other RNA
                        organism = synthetic construct
SEQUENCE: 20
gaagatgagt gagcttgcgt gttttagagc tatgct                        36

SEQ ID NO: 21           moltype = DNA  length = 720
FEATURE                 Location/Qualifiers
source                  1..720
                        mol_type = genomic DNA
                        organism = Zea mays
SEQUENCE: 21
gaacagtgcc gcagtggcgc tgatcttgta tgctatcctg caatcgtggt gaacttattt  60
cttttatatc ctttactccc atgaaaaggc tagtaatctt tctcgatgta acatcgtcca  120
```

```
gcactgctat taccgtgtgg tccatccgac agtctggctg aacacatcat acgatctatg  180
gagcaaaaat ctatcttccc tgttctttaa tgaaggacgt cattttcatt agtatgatct  240
aggaatgttg caacttgcaa ggaggcgttt ctttctttga atttaactaa ctcgttgagt  300
ggccctgttt ctcggacgta aggcctttgc tgctccacac atgtccattc gaattttacc  360
gtgtttagca agggcgaaaa gtttgcatct tgatgattta gcttgactat gcgattgctt  420
tcctggaccc gtgcagctgc ggtggcatgg gaggccggca agccactgtc gatcgaggag  480
gtggaggtag cgcctccgca ggccatggag gtgcgcgtca agatcctctt cacctcgctc  540
tgccacaccg acgtctactt ctgggaggcc aaggtatcta atcagccatc ccatttgtga  600
tctttgtcag tagatatgat acaacaactc gcggttgact tgcgccttct tggcggctta  660
tctgtcttag gggcagactc ccgtgttccc tcggatcttt ggccacgagg ctggagggta  720

SEQ ID NO: 22          moltype = DNA  length = 163
FEATURE                Location/Qualifiers
source                 1..163
                       mol_type = genomic DNA
                       organism = Zea mays
SEQUENCE: 22
atgcgattgc tttcctggac ccgtgcagct gcggtggcat gggaggccgg caagccactg  60
tcgatcgagg aggtggaggt agcgcctccg caggccatgg aggtgcgcgt caagatcctc  120
ttcacctcgc tctgccacac cgacgtctac ttctgggagg cca                    163

SEQ ID NO: 23          moltype = RNA  length = 36
FEATURE                Location/Qualifiers
source                 1..36
                       mol_type = other RNA
                       organism = synthetic construct
SEQUENCE: 23
ggcctcccag aagtagacgt gttttagagc tatgct                            36

SEQ ID NO: 24          moltype = DNA  length = 19
FEATURE                Location/Qualifiers
source                 1..19
                       mol_type = other DNA
                       organism = synthetic construct
SEQUENCE: 24
gaacagtgcc gcagtggcg                                               19

SEQ ID NO: 25          moltype = DNA  length = 19
FEATURE                Location/Qualifiers
source                 1..19
                       mol_type = other DNA
                       organism = synthetic construct
SEQUENCE: 25
taccctccag cctcgtggc                                               19

SEQ ID NO: 26          moltype = DNA  length = 23
FEATURE                Location/Qualifiers
source                 1..23
                       mol_type = other DNA
                       organism = synthetic construct
SEQUENCE: 26
actatgcgat tgctttcctg gac                                          23

SEQ ID NO: 27          moltype = DNA  length = 24
FEATURE                Location/Qualifiers
source                 1..24
                       mol_type = other DNA
                       organism = synthetic construct
SEQUENCE: 27
accgcgagtt gttgtatcat atct                                         24

SEQ ID NO: 28          moltype = DNA  length = 230
FEATURE                Location/Qualifiers
source                 1..230
                       mol_type = other DNA
                       organism = synthetic construct
SEQUENCE: 28
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 29          moltype = DNA  length = 606
FEATURE                Location/Qualifiers
source                 1..606
                       mol_type = genomic DNA
                       organism = Zea mays
SEQUENCE: 29
aaccggtgta atacatacta agggctagtt tgggaaccct ggttttctaa ggaattttat  60
```

```
ttttccaaaa aaaatagttt atttttcctt cggaaattag gaatctctta taaaattcga  120
gttcccaaac tattcctaat atatatatca tactctccat cagtctatat atagattaca  180
tatagtaagt atagagtatc tcgctatcac atagtgccac taatcttctg gagtgtacca  240
gttgtataaa tatctatcag tatcagcact actgtttgct gaatacccca aaactctctg  300
cttgacttct cttccctaac ctttgcactg tccaaaatgg cttcctgatc ccctcacttc  360
ctcgaatcat tctaagaaga aactcaagcc gctaccatta ggggcagatt aattgctgca  420
ctttcagata atctaccatg gccactgtga acaactggct cgctttctcc ctctccccgc  480
aggagctgcc gccctcccag acgacggact ccacgctcat ctcggccgcc accgccgacc  540
atgtctccgg cgatgtctgc ttcaacatcc cccaaggtag catctatcta tctggcgaca  600
tacgtg                                                             606

SEQ ID NO: 30          moltype = DNA  length = 254
FEATURE                Location/Qualifiers
source                 1..254
                       mol_type = genomic DNA
                       organism = Zea mays
SEQUENCE: 30
aaccggtgta atacatacta agggctagtt tgggaaccct ggttttctaa ggaattttat  60
ttttccaaaa aaaatagttt atttttcctt cggaaattag gaatctctta taaaattcga  120
gttcccaaac tattcctaat atatatatca tactctccat cagtctatat atagattaca  180
tatagtaagt atagagtatc tcgctatcac atagtgccac taatcttctg gagtgtacca  240
gttgtataaa tatc                                                    254

SEQ ID NO: 31          moltype = RNA  length = 36
FEATURE                Location/Qualifiers
source                 1..36
                       mol_type = other RNA
                       organism = synthetic construct
SEQUENCE: 31
aagagattcc taatttccga gttttagagc tatgct                            36

SEQ ID NO: 32          moltype = DNA  length = 20
FEATURE                Location/Qualifiers
source                 1..20
                       mol_type = other DNA
                       organism = synthetic construct
SEQUENCE: 32
gggaaccctg gttttctaag                                              20

SEQ ID NO: 33          moltype = DNA  length = 22
FEATURE                Location/Qualifiers
source                 1..22
                       mol_type = other DNA
                       organism = synthetic construct
SEQUENCE: 33
gcaaacagta gtgctgatac tg                                           22

SEQ ID NO: 34          moltype = DNA  length = 248
FEATURE                Location/Qualifiers
source                 1..248
                       mol_type = other DNA
                       organism = synthetic construct
SEQUENCE: 34
gggaaccctg gttttctaag gaattttatt tttccaaaaa aaatagttta tttttccttc  60
ggaaattagg aatctcttat aaaattcgag ttcccaaact attcctaata tatatatcat  120
actctccatc agtctatata tagattacat atagtaagta tagagtatct cgctatcaca  180
tagtgccact aatcttctgg agtgtaccag ttgtataaat atctatcagt atcagcacta  240
ctgtttgc                                                           248

SEQ ID NO: 35          moltype = DNA  length = 255
FEATURE                Location/Qualifiers
source                 1..255
                       mol_type = genomic DNA
                       organism = Brassica oleracea
SEQUENCE: 35
gaaacctacc agtctctcct ttgaagaaga catgaacaaa attagccacg gcgctctatc  60
tcggccttcc ggtaacgttt cttgttcaat attgttgtat tagctttcat atgaccaaat  120
tcttcataat taaagatcgg tatagaagtc atagattaca tatatgtaca tttgcacggg  180
tgagtttgca acaaatgtcg ttttactttg tgaaatttaa tccctaatca tgttttagga  240
atgctgcacc gtgcc                                                   255

SEQ ID NO: 36          moltype = DNA  length = 40
FEATURE                Location/Qualifiers
source                 1..40
                       mol_type = genomic DNA
                       organism = Brassica oleracea
SEQUENCE: 36
atgaacaaaa ttagccacgg cgctctatct cggccttccg                        40
```

```
SEQ ID NO: 37           moltype = DNA  length = 17
FEATURE                 Location/Qualifiers
source                  1..17
                        mol_type = genomic DNA
                        organism = Brassica oleracea
SEQUENCE: 37
gaatgctgca ccgtgcc                                                   17

SEQ ID NO: 38           moltype = RNA  length = 36
FEATURE                 Location/Qualifiers
source                  1..36
                        mol_type = other RNA
                        organism = synthetic construct
SEQUENCE: 38
gaacaagaaa cgttaccgga gttttagagc tatgct                              36

SEQ ID NO: 39           moltype = DNA  length = 23
FEATURE                 Location/Qualifiers
source                  1..23
                        mol_type = other DNA
                        organism = synthetic construct
SEQUENCE: 39
gaaacctacc agtctctcct ttg                                            23

SEQ ID NO: 40           moltype = DNA  length = 20
FEATURE                 Location/Qualifiers
source                  1..20
                        mol_type = other DNA
                        organism = synthetic construct
SEQUENCE: 40
ggcacggtgc agcattccta                                                20

SEQ ID NO: 41           moltype = DNA  length = 206
FEATURE                 Location/Qualifiers
source                  1..206
                        mol_type = genomic DNA
                        organism = Brassica oleracea
SEQUENCE: 41
ccgatggtct tcagttctct tccttgttat ggtctccccc acgagatcct caacaacata  60
aggtacttaa caataataaa taaagcctca gatgtctcat ccatgaaccg gtgctgattg  120
tctttctcct taggatcaag tcgttgctta tgtcgaatac tttggtcggt tcacatcaga  180
gcaattccct gatgatattg ctgagg                                         206

SEQ ID NO: 42           moltype = DNA  length = 60
FEATURE                 Location/Qualifiers
source                  1..60
                        mol_type = genomic DNA
                        organism = Brassica oleracea
SEQUENCE: 42
ccgatggtct tcagttctct tccttgttat ggtctccccc acgagatcct caacaacata  60

SEQ ID NO: 43           moltype = DNA  length = 72
FEATURE                 Location/Qualifiers
source                  1..72
                        mol_type = genomic DNA
                        organism = Brassica oleracea
SEQUENCE: 43
aggatcaagt cgttgcttat gtcgaatact ttggtcggtt cacatcagag caattccctg  60
atgatattgc tg                                                        72

SEQ ID NO: 44           moltype = RNA  length = 36
FEATURE                 Location/Qualifiers
source                  1..36
                        mol_type = other RNA
                        organism = synthetic construct
SEQUENCE: 44
tcgtggggga gaccataaca gttttagagc tatgct                              36

SEQ ID NO: 45           moltype = DNA  length = 20
FEATURE                 Location/Qualifiers
source                  1..20
                        mol_type = other DNA
                        organism = synthetic construct
SEQUENCE: 45
ccgatggtct tcagttctct                                                20

SEQ ID NO: 46           moltype = DNA  length = 20
FEATURE                 Location/Qualifiers
source                  1..20
```

```
                        mol_type = other DNA
                        organism = synthetic construct
SEQUENCE: 46
cctcagcaat atcatcaggg                                              20

SEQ ID NO: 47           moltype = DNA  length = 230
FEATURE                 Location/Qualifiers
source                  1..230
                        mol_type = other DNA
                        organism = synthetic construct
SEQUENCE: 47
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 48           moltype = DNA  length = 230
FEATURE                 Location/Qualifiers
source                  1..230
                        mol_type = other DNA
                        organism = synthetic construct
SEQUENCE: 48
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 49           moltype = DNA  length = 230
FEATURE                 Location/Qualifiers
source                  1..230
                        mol_type = other DNA
                        organism = synthetic construct
SEQUENCE: 49
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 50           moltype = DNA  length = 230
FEATURE                 Location/Qualifiers
source                  1..230
                        mol_type = other DNA
                        organism = synthetic construct
SEQUENCE: 50
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 51           moltype = DNA  length = 230
FEATURE                 Location/Qualifiers
source                  1..230
                        mol_type = other DNA
                        organism = synthetic construct
SEQUENCE: 51
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 52           moltype = DNA  length = 230
FEATURE                 Location/Qualifiers
source                  1..230
                        mol_type = other DNA
                        organism = synthetic construct
SEQUENCE: 52
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 53           moltype = DNA  length = 230
FEATURE                 Location/Qualifiers
source                  1..230
                        mol_type = other DNA
                        organism = synthetic construct
SEQUENCE: 53
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
```

```
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 54          moltype = DNA  length = 230
FEATURE                Location/Qualifiers
source                 1..230
                       mol_type = other DNA
                       organism = synthetic construct
SEQUENCE: 54
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 55          moltype = DNA  length = 230
FEATURE                Location/Qualifiers
source                 1..230
                       mol_type = other DNA
                       organism = synthetic construct
SEQUENCE: 55
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 56          moltype = DNA  length = 230
FEATURE                Location/Qualifiers
source                 1..230
                       mol_type = other DNA
                       organism = synthetic construct
SEQUENCE: 56
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 57          moltype = DNA  length = 230
FEATURE                Location/Qualifiers
source                 1..230
                       mol_type = other DNA
                       organism = synthetic construct
SEQUENCE: 57
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 58          moltype = DNA  length = 230
FEATURE                Location/Qualifiers
source                 1..230
                       mol_type = other DNA
                       organism = synthetic construct
SEQUENCE: 58
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 59          moltype = DNA  length = 230
FEATURE                Location/Qualifiers
source                 1..230
                       mol_type = other DNA
                       organism = synthetic construct
SEQUENCE: 59
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 60          moltype = DNA  length = 230
FEATURE                Location/Qualifiers
source                 1..230
                       mol_type = other DNA
                       organism = synthetic construct
SEQUENCE: 60
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230
```

```
SEQ ID NO: 61          moltype = DNA  length = 230
FEATURE                Location/Qualifiers
source                 1..230
                       mol_type = other DNA
                       organism = synthetic construct
SEQUENCE: 61
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 62          moltype = DNA  length = 230
FEATURE                Location/Qualifiers
source                 1..230
                       mol_type = other DNA
                       organism = synthetic construct
SEQUENCE: 62
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 63          moltype = DNA  length = 230
FEATURE                Location/Qualifiers
source                 1..230
                       mol_type = other DNA
                       organism = synthetic construct
SEQUENCE: 63
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 64          moltype = DNA  length = 230
FEATURE                Location/Qualifiers
source                 1..230
                       mol_type = other DNA
                       organism = synthetic construct
SEQUENCE: 64
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 65          moltype = DNA  length = 230
FEATURE                Location/Qualifiers
source                 1..230
                       mol_type = other DNA
                       organism = synthetic construct
SEQUENCE: 65
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 66          moltype = DNA  length = 230
FEATURE                Location/Qualifiers
source                 1..230
                       mol_type = other DNA
                       organism = synthetic construct
SEQUENCE: 66
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 67          moltype = DNA  length = 230
FEATURE                Location/Qualifiers
source                 1..230
                       mol_type = other DNA
                       organism = synthetic construct
SEQUENCE: 67
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 68          moltype = DNA  length = 230
```

```
FEATURE                Location/Qualifiers
source                 1..230
                       mol_type = other DNA
                       organism = synthetic construct
SEQUENCE: 68
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 69          moltype = DNA  length = 230
FEATURE                Location/Qualifiers
source                 1..230
                       mol_type = other DNA
                       organism = synthetic construct
SEQUENCE: 69
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 70          moltype = DNA  length = 230
FEATURE                Location/Qualifiers
source                 1..230
                       mol_type = other DNA
                       organism = synthetic construct
SEQUENCE: 70
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 71          moltype = DNA  length = 230
FEATURE                Location/Qualifiers
source                 1..230
                       mol_type = other DNA
                       organism = synthetic construct
SEQUENCE: 71
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 72          moltype = DNA  length = 230
FEATURE                Location/Qualifiers
source                 1..230
                       mol_type = other DNA
                       organism = synthetic construct
SEQUENCE: 72
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 73          moltype = DNA  length = 230
FEATURE                Location/Qualifiers
source                 1..230
                       mol_type = other DNA
                       organism = synthetic construct
SEQUENCE: 73
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 74          moltype = DNA  length = 230
FEATURE                Location/Qualifiers
source                 1..230
                       mol_type = other DNA
                       organism = synthetic construct
SEQUENCE: 74
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 75          moltype = DNA  length = 230
FEATURE                Location/Qualifiers
source                 1..230
```

```
                        mol_type = other DNA
                        organism = synthetic construct
SEQUENCE: 75
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 76           moltype = DNA  length = 230
FEATURE                 Location/Qualifiers
source                  1..230
                        mol_type = other DNA
                        organism = synthetic construct
SEQUENCE: 76
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 77           moltype = DNA  length = 230
FEATURE                 Location/Qualifiers
source                  1..230
                        mol_type = other DNA
                        organism = synthetic construct
SEQUENCE: 77
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 78           moltype = DNA  length = 230
FEATURE                 Location/Qualifiers
source                  1..230
                        mol_type = other DNA
                        organism = synthetic construct
SEQUENCE: 78
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 79           moltype = DNA  length = 230
FEATURE                 Location/Qualifiers
source                  1..230
                        mol_type = other DNA
                        organism = synthetic construct
SEQUENCE: 79
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 80           moltype = DNA  length = 230
FEATURE                 Location/Qualifiers
source                  1..230
                        mol_type = other DNA
                        organism = synthetic construct
SEQUENCE: 80
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 81           moltype = DNA  length = 230
FEATURE                 Location/Qualifiers
source                  1..230
                        mol_type = other DNA
                        organism = synthetic construct
SEQUENCE: 81
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 82           moltype = DNA  length = 230
FEATURE                 Location/Qualifiers
source                  1..230
                        mol_type = other DNA
                        organism = synthetic construct
```

```
SEQUENCE: 82
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 83          moltype = DNA  length = 230
FEATURE                Location/Qualifiers
source                 1..230
                       mol_type = other DNA
                       organism = synthetic construct
SEQUENCE: 83
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 84          moltype = DNA  length = 230
FEATURE                Location/Qualifiers
source                 1..230
                       mol_type = other DNA
                       organism = synthetic construct
SEQUENCE: 84
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 85          moltype = DNA  length = 230
FEATURE                Location/Qualifiers
source                 1..230
                       mol_type = other DNA
                       organism = synthetic construct
SEQUENCE: 85
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 86          moltype = DNA  length = 230
FEATURE                Location/Qualifiers
source                 1..230
                       mol_type = other DNA
                       organism = synthetic construct
SEQUENCE: 86
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 87          moltype = DNA  length = 230
FEATURE                Location/Qualifiers
source                 1..230
                       mol_type = other DNA
                       organism = synthetic construct
SEQUENCE: 87
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 88          moltype = DNA  length = 230
FEATURE                Location/Qualifiers
source                 1..230
                       mol_type = other DNA
                       organism = synthetic construct
SEQUENCE: 88
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 89          moltype = DNA  length = 230
FEATURE                Location/Qualifiers
source                 1..230
                       mol_type = other DNA
                       organism = synthetic construct
SEQUENCE: 89
actatgcgat tgctttcctg gacccgtgca gctgcggtgg catgggaggc cggcaagcca  60
```

```
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 90          moltype = DNA  length = 230
FEATURE                Location/Qualifiers
source                 1..230
                       mol_type = other DNA
                       organism = synthetic construct
SEQUENCE: 90
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 91          moltype = DNA  length = 230
FEATURE                Location/Qualifiers
source                 1..230
                       mol_type = other DNA
                       organism = synthetic construct
SEQUENCE: 91
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 92          moltype = DNA  length = 230
FEATURE                Location/Qualifiers
source                 1..230
                       mol_type = other DNA
                       organism = synthetic construct
SEQUENCE: 92
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 93          moltype = DNA  length = 230
FEATURE                Location/Qualifiers
source                 1..230
                       mol_type = other DNA
                       organism = synthetic construct
SEQUENCE: 93
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 94          moltype = DNA  length = 230
FEATURE                Location/Qualifiers
source                 1..230
                       mol_type = other DNA
                       organism = synthetic construct
SEQUENCE: 94
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 95          moltype = DNA  length = 230
FEATURE                Location/Qualifiers
source                 1..230
                       mol_type = other DNA
                       organism = synthetic construct
SEQUENCE: 95
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 96          moltype = DNA  length = 230
FEATURE                Location/Qualifiers
source                 1..230
                       mol_type = other DNA
                       organism = synthetic construct
SEQUENCE: 96
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
```

```
ccatcccatt tgtgatcttt gtcagtagat atgatacaac aactcgcggt            230

SEQ ID NO: 97          moltype = DNA  length = 230
FEATURE                Location/Qualifiers
source                 1..230
                       mol_type = other DNA
                       organism = synthetic construct
SEQUENCE: 97
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 98          moltype = DNA  length = 230
FEATURE                Location/Qualifiers
source                 1..230
                       mol_type = other DNA
                       organism = synthetic construct
SEQUENCE: 98
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 99          moltype = DNA  length = 230
FEATURE                Location/Qualifiers
source                 1..230
                       mol_type = other DNA
                       organism = synthetic construct
SEQUENCE: 99
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 100         moltype = DNA  length = 230
FEATURE                Location/Qualifiers
source                 1..230
                       mol_type = other DNA
                       organism = synthetic construct
SEQUENCE: 100
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 101         moltype = DNA  length = 230
FEATURE                Location/Qualifiers
source                 1..230
                       mol_type = other DNA
                       organism = synthetic construct
SEQUENCE: 101
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 102         moltype = DNA  length = 230
FEATURE                Location/Qualifiers
source                 1..230
                       mol_type = other DNA
                       organism = synthetic construct
SEQUENCE: 102
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 103         moltype = DNA  length = 230
FEATURE                Location/Qualifiers
source                 1..230
                       mol_type = other DNA
                       organism = synthetic construct
SEQUENCE: 103
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230
```

```
SEQ ID NO: 104          moltype = DNA  length = 230
FEATURE                 Location/Qualifiers
source                  1..230
                        mol_type = other DNA
                        organism = synthetic construct
SEQUENCE: 104
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 105          moltype = DNA  length = 230
FEATURE                 Location/Qualifiers
source                  1..230
                        mol_type = other DNA
                        organism = synthetic construct
SEQUENCE: 105
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 106          moltype = DNA  length = 230
FEATURE                 Location/Qualifiers
source                  1..230
                        mol_type = other DNA
                        organism = synthetic construct
SEQUENCE: 106
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 107          moltype = DNA  length = 230
FEATURE                 Location/Qualifiers
source                  1..230
                        mol_type = other DNA
                        organism = synthetic construct
SEQUENCE: 107
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 108          moltype = DNA  length = 230
FEATURE                 Location/Qualifiers
source                  1..230
                        mol_type = other DNA
                        organism = synthetic construct
SEQUENCE: 108
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 109          moltype = DNA  length = 230
FEATURE                 Location/Qualifiers
source                  1..230
                        mol_type = other DNA
                        organism = synthetic construct
SEQUENCE: 109
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 110          moltype = DNA  length = 230
FEATURE                 Location/Qualifiers
source                  1..230
                        mol_type = other DNA
                        organism = synthetic construct
SEQUENCE: 110
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 111          moltype = DNA  length = 230
FEATURE                 Location/Qualifiers
```

```
source                  1..230
                        mol_type = other DNA
                        organism = synthetic construct
SEQUENCE: 111
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 112          moltype = DNA  length = 230
FEATURE                 Location/Qualifiers
source                  1..230
                        mol_type = other DNA
                        organism = synthetic construct
SEQUENCE: 112
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 113          moltype = DNA  length = 230
FEATURE                 Location/Qualifiers
source                  1..230
                        mol_type = other DNA
                        organism = synthetic construct
SEQUENCE: 113
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 114          moltype = DNA  length = 230
FEATURE                 Location/Qualifiers
source                  1..230
                        mol_type = other DNA
                        organism = synthetic construct
SEQUENCE: 114
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 115          moltype = DNA  length = 230
FEATURE                 Location/Qualifiers
source                  1..230
                        mol_type = other DNA
                        organism = synthetic construct
SEQUENCE: 115
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 116          moltype = DNA  length = 230
FEATURE                 Location/Qualifiers
source                  1..230
                        mol_type = other DNA
                        organism = synthetic construct
SEQUENCE: 116
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 117          moltype = DNA  length = 230
FEATURE                 Location/Qualifiers
source                  1..230
                        mol_type = other DNA
                        organism = synthetic construct
SEQUENCE: 117
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 118          moltype = DNA  length = 230
FEATURE                 Location/Qualifiers
source                  1..230
                        mol_type = other DNA
```

```
                         organism = synthetic construct
SEQUENCE: 118
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 119           moltype = DNA  length = 230
FEATURE                  Location/Qualifiers
source                   1..230
                         mol_type = other DNA
                         organism = synthetic construct
SEQUENCE: 119
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 120           moltype = DNA  length = 230
FEATURE                  Location/Qualifiers
source                   1..230
                         mol_type = other DNA
                         organism = synthetic construct
SEQUENCE: 120
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 121           moltype = DNA  length = 230
FEATURE                  Location/Qualifiers
source                   1..230
                         mol_type = other DNA
                         organism = synthetic construct
SEQUENCE: 121
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 122           moltype = DNA  length = 230
FEATURE                  Location/Qualifiers
source                   1..230
                         mol_type = other DNA
                         organism = synthetic construct
SEQUENCE: 122
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 123           moltype = DNA  length = 230
FEATURE                  Location/Qualifiers
source                   1..230
                         mol_type = other DNA
                         organism = synthetic construct
SEQUENCE: 123
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 124           moltype = DNA  length = 230
FEATURE                  Location/Qualifiers
source                   1..230
                         mol_type = other DNA
                         organism = synthetic construct
SEQUENCE: 124
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt            230

SEQ ID NO: 125           moltype = DNA  length = 230
FEATURE                  Location/Qualifiers
source                   1..230
                         mol_type = other DNA
                         organism = synthetic construct
SEQUENCE: 125
```

```
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 126          moltype = DNA  length = 230
FEATURE                 Location/Qualifiers
source                  1..230
                        mol_type = other DNA
                        organism = synthetic construct
SEQUENCE: 126
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 127          moltype = DNA  length = 230
FEATURE                 Location/Qualifiers
source                  1..230
                        mol_type = other DNA
                        organism = synthetic construct
SEQUENCE: 127
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 128          moltype = DNA  length = 230
FEATURE                 Location/Qualifiers
source                  1..230
                        mol_type = other DNA
                        organism = synthetic construct
SEQUENCE: 128
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 129          moltype = DNA  length = 230
FEATURE                 Location/Qualifiers
source                  1..230
                        mol_type = other DNA
                        organism = synthetic construct
SEQUENCE: 129
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 130          moltype = DNA  length = 230
FEATURE                 Location/Qualifiers
source                  1..230
                        mol_type = other DNA
                        organism = synthetic construct
SEQUENCE: 130
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 131          moltype = DNA  length = 230
FEATURE                 Location/Qualifiers
source                  1..230
                        mol_type = other DNA
                        organism = synthetic construct
SEQUENCE: 131
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 132          moltype = DNA  length = 230
FEATURE                 Location/Qualifiers
source                  1..230
                        mol_type = other DNA
                        organism = synthetic construct
SEQUENCE: 132
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
```

```
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 133          moltype = DNA  length = 230
FEATURE                 Location/Qualifiers
source                  1..230
                        mol_type = other DNA
                        organism = synthetic construct
SEQUENCE: 133
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 134          moltype = DNA  length = 230
FEATURE                 Location/Qualifiers
source                  1..230
                        mol_type = other DNA
                        organism = synthetic construct
SEQUENCE: 134
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 135          moltype = DNA  length = 230
FEATURE                 Location/Qualifiers
source                  1..230
                        mol_type = other DNA
                        organism = synthetic construct
SEQUENCE: 135
actatgcgat tgctttcctg gacccgtgca gctgcggtgg catgggaggc cggcaagcca  60
ctgtcgatcg aggaggtgga ggtagcgcct ccgcaggcca tggaggtgcg cgtcaagatc  120
ctcttcacct cgctctgcca caccgacgtc tacttctggg aggccaaggt atctaatcag  180
ccatcccatt tgtgatcttt gtcagtagat atgatacaac aactcgcggt             230

SEQ ID NO: 136          moltype = DNA  length = 3079
FEATURE                 Location/Qualifiers
source                  1..3079
                        mol_type = other DNA
                        organism = synthetic construct
SEQUENCE: 136
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtggaat tctaaagatc taaaataaat  420
ggtaaaatgt caaatcaaaa ctaggctgca gtatgcagag cagagtcatg atgatactac  480
ttactacacc gattcttgtg tgcagaaaaa tatgttaaaa taattgaatc tttctctagc  540
caaatttgac aacaatgtac accgttcata ttgagagacg atgcttcttg tttgctttcg  600
gtggaagctg catatactca acattactcc ttcagcgagt tttccaactg agtcccacat  660
tgcccagacc taacacggta ttcttgttta taatgaaatg tgccaccaca tggattgaag  720
caagagacgt tctagggttt tagagctaga aatagcaagt taaaataagg ctagtccgtt  780
atcaacttga aaaagtggca ccgagtcggt gctttttttg gatccggcgc gccgcatgca  840
agcttggcgt aatcatggtc atagctgttt cctgtgtgaa attgttatcc gctcacaatt  900
ccacacaaca tacgagccgg aagcataaag tgtaaagcct ggggtgccta atgagtgagc  960
taactcacat taattgcgtt gcgctcactg cccgctttcc agtcgggaaa cctgtcgtgc  1020
cagctgcatt aatgaatcgg ccaacgcgcg gggagaggcg gtttgcgtat tgggcgctct  1080
tccgcttcct cgctcactga ctcgctgcgc tcggtcgttc ggctgcggcg agcggtatca  1140
gctcactcaa aggcggtaat acggttatcc acagaatcag gggataacgc aggaaagaac  1200
atgtgagcaa aaggccagca aaaggccagg aaccgtaaaa aggccgcgtt gctggcgttt  1260
ttccataggc tccgcccccc tgacgagcat cacaaaaatc gacgctcaag tcagaggtgg  1320
cgaaacccga caggactata aagataccag gcgtttcccc ctggaagctc cctcgtgcgc  1380
tctcctgttc cgaccctgcc gcttaccgga tacctgtccg cctttctccc ttcgggaagc  1440
gtggcgcttt ctcatagctc acgctgtagg tatctcagtt cggtgtaggt cgttcgctcc  1500
aagctgggct gtgtgcacga accccccgtt cagcccgacc gctgcgcctt atccggtaac  1560
tatcgtcttg agtccaaccc ggtaagacac gacttatcgc cactggcagc agccactggt  1620
aacaggatta gcagagcgag gtatgtaggc ggtgctacag agttcttgaa gtggtggcct  1680
aactacggct acactagaag aacagtattt ggtatctgcg ctctgctgaa gccagttacc  1740
ttcggaaaaa gagttggtag ctcttgatcc ggcaaacaaa ccaccgctgg tagcggtggt  1800
tttttgttt gcaagcagca gattacgcgc agaaaaaaag gatctcaaga agatcctttg  1860
atcttttcta cggggtctga cgctcagtgg aacgaaaact cacgttaagg gattttggtc  1920
atgagattat caaaaaggat cttcacctag atccttttaa attaaaaatg aagttttaaa  1980
tcaatctaaa gtatatatga gtaaacttgg tctgacagtt accaatgctt aatcagtgag  2040
gcacctatct cagcgatctg tctatttcgt tcatccatag ttgcctgact ccccgtcgtg  2100
tagataacta cgatacggga gggcttacca tctggcccca gtgctgcaat gataccgcga  2160
gacccacgct caccggctcc agatttatca gcaataaacc agccagccgg aagggccgag  2220
```

```
cgcagaagtg gtcctgcaac tttatccgcc tccatccagt ctattaattg ttgccgggaa  2280
gctagagtaa gtagttcgcc agttaatagt ttgcgcaacg ttgttgccat tgctacaggc  2340
atcgtggtgt cacgctcgtc gtttggtatg gcttcattca gctccggttc ccaacgatca  2400
aggcgagtta catgatcccc catgttgtgc aaaaaagcgg ttagctcctt cggtcctccg  2460
atcgttgtca gaagtaagtt ggccgcagtg ttatcactca tggttatggc agcactgcat  2520
aattctctta ctgtcatgcc atccgtaaga tgcttttctg tgactggtga gtactcaacc  2580
aagtcattct gagaatagtg tatgcggcga ccgagttgct cttgcccggc gtcaatacgg  2640
gataataccg cgccacatag cagaacttta aaagtgctca tcattggaaa acgttcttcg  2700
gggcgaaaac tctcaaggat cttaccgctg ttgagatcca gttcgatgta acccactcgt  2760
gcacccaact gatcttcagc atcttttact ttcaccagcg tttctgggtg agcaaaaaca  2820
ggaaggcaaa atgccgcaaa aaagggaata agggcgacac ggaaatgttg aatactcata  2880
ctcttccttt ttcaatatta ttgaagcatt tatcagggtt attgtctcat gagcggatac  2940
atatttgaat gtatttagaa aaataaacaa ataggggttc cgcgcacatt tccccgaaaa  3000
gtgccacctg acgtctaaga aaccattatt atcatgacat taacctataa aaataggcgt  3060
atcacgaggc cctttcgtc                                               3079

SEQ ID NO: 137          moltype = DNA  length = 20
FEATURE                 Location/Qualifiers
source                  1..20
                        mol_type = other DNA
                        organism = synthetic construct
SEQUENCE: 137
gaagcaagag acgttctagg                                              20

SEQ ID NO: 138          moltype = DNA  length = 76
FEATURE                 Location/Qualifiers
source                  1..76
                        mol_type = other DNA
                        organism = synthetic construct
SEQUENCE: 138
gttttagagc tagaaatagc aagttaaaat aaggctagtc cgttatcaac ttgaaaaagt  60
ggcaccgagt cggtgc                                                  76

SEQ ID NO: 139          moltype = DNA  length = 96
FEATURE                 Location/Qualifiers
source                  1..96
                        mol_type = other DNA
                        organism = synthetic construct
SEQUENCE: 139
gaagcaagag acgttctagg gttttagagc tagaaatagc aagttaaaat aaggctagtc  60
cgttatcaac ttgaaaaagt ggcaccgagt cggtgc                            96

SEQ ID NO: 140          moltype = DNA  length = 8569
FEATURE                 Location/Qualifiers
source                  1..8569
                        mol_type = other DNA
                        organism = synthetic construct
SEQUENCE: 140
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtgaatt ctaaagatct ggcgcgccgg  420
cccgggctgg ttattgtttt tgtcaatgag ctatctttta gtcttatgtt attggtgaat  480
ctgtccttaa gttgcatcat ttaacacatc tcctcattag agaaaaaaat tcttccctaa  540
acgattggta gtaaaaacat ctaataagaa ataagaaaga aaaattagga aaaaggaaag  600
ttcattaaaa aaaatatttt gaattatttt ttaaaaaata tctaaatatt ttttaaatga  660
ataattttat ataaactgta actaaatgta tacaagtaat gtatgttaaa aaaatacttg  720
aaaaatctac tgaaaatata tcttacaagg tgaaattaaa taagaaagaa tttagtggaa  780
taattatgat tttatttaaa aaataattat taaagatttt tttgctccat aataagaaaa  840
cttttcaatt attcttttct ggtccataat aaaaaaaatc tagcatgaca gcttttccat  900
agatttttaa taatgtaaaa gcagccgact tcaggcaatg gatagtgggg cccgtatcaa  960
cttcggacgc tccacttgca acggggtggg cccaatataa caacgacgtc gtaacagata  1020
aagcgaagat tgaaggtgca tgtgactccg tcaagattac gaaaccgcca actaccacgc  1080
aaattgcaat tctcaatttc ctagaaggac tctccgaaaa tgcatccaat accaaatatt  1140
acccgtgtca taggcaccaa gtgacaccat acatgaacac gcgtcacaat atgactggag  1200
aagggttcca caccttatgc tataaaacgc ccccacaccc tcctccttcc ttcgcagttc  1260
aattccaata tattccattc tctctgtgta tttccctacc tctcccttca aggttagtcg  1320
atttcttctg tttttcttct tcgttctttc catgaattgt gtatgttctt tgatcaatac  1380
gatgttgatt tgattgtgtt ttgtttggtt tcatcgatct tcaattttca taatcagatt  1440
cagcttttat tatctttaca acaacgtcct taatttgatg attctttaat cgtagatttg  1500
ctctaattag agctttttca tgtcagatcc ctttacaaca agccttaatt gttgattcat  1560
taatcgtaga ttagggcttt tttcattgat tacttcagat ccgttaaacg taaccataga  1620
tcagggcttt ttcatgaatt acttcagatc cgttaaacaa cagccttatt ttttatactt  1680
ctgtggtttt tcaagaaatt gttcagatcc gttgacaaaa agccttattc gttgattcta  1740
tatcgttttt cgagagatat tgctcagatg tgttagcaac tgccttgttt gttgattcta  1800
ttgccgtgga ttagggtttt ttttcacgag attgcttcag atccgtactt aagattacgt  1860
```

```
aatggatttt gattctgatt tatctgtgat tgttgactcg acaggatcgg taccccatgg  1920
ataagaagta ctctatcgga ctcgatatcg gaactaactc tgtgggatgg gctgtgatca  1980
ccgatgagta caaggtgcca tctaagaagt tcaaggttct cggaaacacc gataggcact  2040
ctatcaagaa aaaccttatc ggtgctctcc tcttcgattc tggtgaaact gctgaggcta  2100
ccagactcaa gagaaccgct agaagaaggt acaccagaag aaagaacagg atctgctacc  2160
tccaagagat cttctctaac gagatggcta aagtggatga ttcattcttc cacaggctcg  2220
aagagtcatt cctcgtggaa gaagataaga agcacgagag gcaccctatc ttcggaaaca  2280
tcgttgatga ggtggcatac cacgagaagt accctactat ctaccacctc agaaagaagc  2340
tcgttgattc tactgataag gctgatctca ggctcatcta cctcgctctc gctcacatga  2400
tcaagttcag aggacacttc ctcatcgagg gtgatctcaa ccctgataac tctgatgtgg  2460
ataagttgtt catccagctc gtgcagacct acaaccagct tttcgaagag aaccctatca  2520
acgcttcagg tgtggatgct aaggctatcc tctctgctag gctctctaag tcaagaaggc  2580
ttgagaacct cattgctcag ctccctggtg agaagaagaa cggacttttc ggaaacttga  2640
tcgctctctc tctcggactc acccctaact tcaagtctaa cttcgatctc gctgaggatg  2700
caaagctcca gctctcaaag gatacctacg atgatgatct cgataacctc ctcgctcaga  2760
tcggagatca gtacgctgat ttgttcctcg ctgctaagaa cctctctgat gctatcctcc  2820
tcagtgatat cctcagagtg aacaccgaga tcaccaaggc tccactctca gcttctatga  2880
tcaagagata cgatgagcac caccaggatc tcacacttct caaggctctt gttagacagc  2940
agctcccaga gaagtacaaa gagattttct tcgatcagtc taagaacgga tacgctggtt  3000
acatcgatgg tggtgcatct caagaagagt tctacaagtt catcaagcct atcctcgaga  3060
agatggatgg aaccgaggaa ctcctcgtga agctcaatag agaggatctt ctcagaaagc  3120
agaggacctt cgataacgga tctatccctc atcagatcca cctcggagag ttgcacgcta  3180
tccttagaag gcaagaggat ttctacccat tcctcaagga taacagggaa aagattgaga  3240
agattctcac cttcagaatc ccttactacg tgggacctct cgctagagga aactcaagat  3300
tcgcttggat gaccagaaag tctgaggaaa ccatcacccc ttggaacttc gaagaggtgg  3360
tggataaggg tgctagtgct cagtctttca tcgagaggat gaccaacttc gataagaacc  3420
ttccaaacga gaaggtgctc cctaagcact ctttgctcta cgagtacttc accgtgtaca  3480
acgagttgac caaggttaag tacgtgaccg agggaatgag gaagcctgct tttttgtcag  3540
gtgagcaaaa gaaggctatc gttgatctct tgttcaagac caacagaaag gtgaccgtga  3600
agcagctcaa agaggattac ttcaagaaaa tcgagtgctt cgattcagtt gagatttctg  3660
gtgttgagga taggttcaac gcatctctcg gaacctacca cgatctcctc aagatcatta  3720
aggataagga tttcttggat aacgaggaaa acgaggatat cttggaggat atcgttctta  3780
ccctcaccct ctttgaagat agagagatga ttgaagaaag gctcaagacc tacgctcatc  3840
tcttcgatga taaggtgatg aagcagttga agagaagaag atacactggt tggggaaggc  3900
tctcaagaaa gctcattaac ggaatcaggg ataagcagtc tggaaagaca atccttgatt  3960
tcctcaagtc tgatggattc gctaacagaa acttcatgca gctcatccac gatgattctc  4020
tcacctttaa agaggatatc cagaaggctc aggtttcagg acagggtgat agtctccatg  4080
agcatatcgc taacctcgct ggatctcctg caatcaagaa gggaatcctc cagactgtga  4140
aggttgtgga tgagttggtg aaggtgatgg gaaggcataa gcctgagaac atcgtgatcg  4200
aaatggctag agagaaccag accactcaga agggacagaa gaactctagg gaaaggatga  4260
agaggatcga ggaaggtatc aaagagcttg gatctcagat cctcaaagag caccctgttg  4320
agaacactca gctccagaat gagaagctct acctctacta cctccagaac ggaagggata  4380
tgtatgtgga tcaagagttg gatatcaaca ggctctctga ttacgatgtt gatcatatcg  4440
tgccacagtc attcttgaag gatgattcta tcgataacaa ggtgctcacc aggtctgata  4500
agaacagggg taagagtgat aacgtgccaa gtgaagaggt tgtgaagaaa atgaagaact  4560
attggaggca gctcctcaac gctaagctca tcactcagag aaagttcgat aacttgacta  4620
aggctgagag gggaggactc tctgaattgg ataaggcagg attcatcaag aggcagcttg  4680
tggaaaccag gcagatcact aagcacgttg cacagatcct cgattctagg atgaacacca  4740
agtacgatga gaacgataag ttgatcaggg aagtgaaggt tatcaccctc aagtcaaagc  4800
tcgtgtctga tttcagaaag gatttccaat tctacaaggt gagggaaatc aacaactacc  4860
accacgctca cgatgcttac cttaacgctg ttgttggaac cgctctcatc aagaagtatc  4920
ctaagctcga gtcagagttc gtgtacggtg attacaaggt gtacgatgtg aggaagatga  4980
tcgctaagtc tgagcaagag atcggaaagg ctaccgctaa gtatttcttc tactctaaca  5040
tcatgaattt cttcaagacc gagattaccc tcgctaacgg tgagatcaga aagaggccac  5100
tcatcgagac aaacggtgaa acaggtgaga tcgtgtggga taagggaagg gatttcgcta  5160
ccgttagaaa ggtgctctct atgccacagg tgaacatcgt taagaaaacc gaggtgcaga  5220
ccggtggatt ctctaaagag tctatcctcc ctaagaggaa ctctgataag ctcattgcta  5280
ggaagaagga ttgggaccct aagaaatacg gtggtttcga ttctcctacc gtggcttact  5340
ctgttctcgt tgtggctaag gttgagaagg gaaagagtaa gaagctcaag tctgttaagg  5400
aacttctcgg aatcactatc atggaaaggt catctttcga gaagaaccca atcgatttcc  5460
tcgaggctaa gggatacaaa gaggttaaga aggatctcat catcaagctc ccaaagtact  5520
cactcttcga actcgagaac ggtagaaaga ggatgctcgc ttctgctggt gagcttcaaa  5580
agggaaacga gcttgctctc ccatctaagt acgttaactt tctttacctc gcttctcact  5640
acgagaagtt gaagggatct ccagaagata acgagcagaa gcaacttttc gttgagcagc  5700
acaagcacta cttggatgag atcatcgagc agatctctga gttctctaaa agggtgatcc  5760
tcgctgatgc aaacctcgat aaggtgttgt ctgcttacaa caagcacaga gataagccta  5820
tcagggaaca ggcagagaac atcatccatc tcttcaccct taccaacctc ggtgctcctg  5880
ctgctttcaa gtacttcgat acaaccatcg ataggaagag atacacctct accaaagaag  5940
tgctcgatgc taccctcatc catcagtcta tcactggact ctacgagact aggatcgatc  6000
tctcacagct cggtggtgat tcaagggctg atcctaagaa gaagaggaag gtttgagcgg  6060
ccgcgatcgt tcaaacattt ggcaataaag tttcttaaga ttgaatcctg ttgccggtct  6120
tgcgatgatt atcatataat ttctgttgaa ttacgttaag catgtaataa ttaacatgta  6180
atgcatgacg ttatttatga gatgggtttt tatgattaga gtcccgcaat tatacattta  6240
atacgcgata gaaaacaaaa tatagcgcgc aaactaggat aaattatcgc gcgcggtgtc  6300
atctatgtta ctagatcgga tccgcatgca agcttggcgt aatcatggtc atagctgttt  6360
cctgtgtgaa attgttatcc gctcacaatt ccacacaaca tacgagccgg aagcataaag  6420
tgtaaagcct ggggtgccta atgagtgagc taactcacat taattgcgtt gcgctcactg  6480
cccgctttcc agtcgggaaa cctgtcgtgc cagctgcatt aatgaatcgg ccaacgcgcg  6540
gggagaggcg gtttgcgtat tgggcgctct tccgcttcct cgctcactga ctcgctgcgc  6600
```

```
tcggtcgttc ggctgcggcg agcggtatca gctcactcaa aggcggtaat acggttatcc  6660
acagaatcag gggataacgc aggaaagaac atgtgagcaa aaggccagca aaaggccagg  6720
aaccgtaaaa aggccgcgtt gctggcgttt ttccataggc tccgcccccc tgacgagcat  6780
cacaaaaatc gacgctcaag tcagaggtgg cgaaacccga caggactata aagataccag  6840
gcgtttcccc ctggaagctc cctcgtgcgc tctcctgttc cgaccctgcc gcttaccgga  6900
tacctgtccg cctttctccc ttcgggaagc gtggcgcttt ctcatagctc acgctgtagg  6960
tatctcagtt cggtgtaggt cgttcgctcc aagctgggct gtgtgcacga accccccgtt  7020
cagcccgacc gctgcgcctt atccggtaac tatcgtcttg agtccaaccc ggtaagacac  7080
gacttatcgc cactggcagc agccactggt aacaggatta gcagagcgag gtatgtaggc  7140
ggtgctacag agttcttgaa gtggtggcct aactacggct acactagaag aacagtattt  7200
ggtatctgcg ctctgctgaa gccagttacc ttcggaaaaa gagttggtag ctcttgatcc  7260
ggcaaacaaa ccaccgctgg tagcggtggt ttttttgttt gcaagcagca gattacgcgc  7320
agaaaaaaag gatctcaaga agatcctttg atcttttcta cggggtctga cgctcagtgg  7380
aacgaaaact cacgttaagg gattttggtc atgagattat caaaaaggat cttcacctag  7440
atccttttaa attaaaaatg aagttttaaa tcaatctaaa gtatatatga gtaaacttgg  7500
tctgacagtt accaatgctt aatcagtgag gcacctatct cagcgatctg tctatttcgt  7560
tcatccatag ttgcctgact ccccgtcgtg tagataacta cgatacggga gggcttacca  7620
tctggcccca gtgctgcaat gataccgcga gacccacgct caccggctcc agatttatca  7680
gcaataaacc agccagccgg aagggccgag cgcagaagtg gtcctgcaac tttatccgcc  7740
tccatccagt ctattaattg ttgccgggaa gctagagtaa gtagttcgcc agttaatagt  7800
ttgcgcaacg ttgttgccat tgctacaggc atcgtggtgt cacgctcgtc gtttggtatg  7860
gcttcattca gctccggttc ccaacgatca aggcgagtta catgatcccc catgttgtgc  7920
aaaaaagcgg ttagctcctt cggtcctccg atcgttgtca gaagtaagtt ggccgcagtg  7980
ttatcactca tggttatggc agcactgcat aattctctta ctgtcatgcc atccgtaaga  8040
tgcttttctg tgactggtga gtactcaacc aagtcattct gagaatagtg tatgcggcga  8100
ccgagttgct cttgcccggc gtcaatacgg gataataccg cgccacatag cagaacttta  8160
aaagtgctca tcattggaaa acgttcttcg gggcgaaaac tctcaaggat cttaccgctg  8220
ttgagatcca gttcgatgta acccactcgt gcacccaact gatcttcagc atcttttact  8280
ttcaccagcg tttctgggtg agcaaaaaca ggaaggcaaa atgccgcaaa aaagggaata  8340
agggcgacac ggaaatgttg aatactcata ctcttccttt ttcaatatta ttgaagcatt  8400
tatcagggtt attgtctcat gagcggatac atatttgaat gtatttagaa aaataaacaa  8460
ataggggttc cgcgcacatt tccccgaaaa gtgccacctg acgtctaaga aaccattatt  8520
atcatgacat taacctataa aaataggcgt atcacgaggc cctttcgtc             8569

SEQ ID NO: 141         moltype = DNA  length = 4104
FEATURE                Location/Qualifiers
source                 1..4104
                       mol_type = other DNA
                       organism = synthetic construct
SEQUENCE: 141
atggataaga agtactctat cggactcgat atcggaacta actctgtggg atgggctgtg  60
atcaccgatg agtacaaggt gccatctaag aagttcaagg ttctcggaaa caccgatagg  120
cactctatca agaaaaacct tatcggtgct ctcctcttcg attctggtga aactgctgag  180
gctaccagac tcaagagaac cgctagaaga aggtacacca gaagaaagaa caggatctgc  240
tacctccaag agatcttctc taacgagatg gctaaagtgg atgattcatt cttccacagg  300
ctcgaagagt cattcctcgt ggaagaagat aagaagcacg agaggcaccc tatcttcgga  360
aacatcgttg atgaggtggc ataccacgag aagtacccta ctatctacca cctcagaaag  420
aagctcgttg attctactga taaggctgat ctcaggctca tctacctcgc tctcgctcac  480
atgatcaagt tcagaggaca cttcctcatc gagggtgatc tcaaccctga taactctgat  540
gtggataagt tgttcatcca gctcgtgcag acctacaacc agcttttcga agagaaccct  600
atcaacgctt caggtgtgga tgctaaggct atcctctctg ctaggctctc taagtcaaga  660
aggcttgaga acctcattgc tcagctccct ggtgagaaga agaacggact tttcggaaac  720
ttgatcgctc tctctctcgg actcacccct aacttcaagt ctaacttcga tctcgctgag  780
gatgcaaagc tccagctctc aaaggatacc tacgatgatg atctcgataa cctcctcgct  840
cagatcggag atcagtacgc tgatttgttc ctcgctgcta agaacctctc tgatgctatc  900
ctcctcagtg atatcctcag agtgaacacc gagatcacca aggctccact ctcagcttct  960
atgatcaaga gatacgatga gcaccaccag gatctcacac ttctcaaggc tcttgttaga  1020
cagcagctcc cagagaagta caaagagatt ttcttcgatc agtctaagaa cggatacgct  1080
ggttacatcg atggtggtgc atctcaagaa gagttctaca agttcatcaa gcctatcctc  1140
gagaagatgg atggaaccga ggaactcctc gtgaagctca atagagagga tcttctcaga  1200
aagcagagga ccttcgataa cggatctatc cctcatcaga tccacctcgg agagttgcac  1260
gctatcctta gaaggcaaga ggatttctac ccattcctca aggataacag ggaaaagatt  1320
gagaagattc tcaccttcag aatcccttac tacgtgggac ctctcgctag aggaaactca  1380
agattcgctt ggatgaccag aaagtctgag gaaaccatca ccccttggaa cttcgaagag  1440
gtggtggata agggtgctag tgctcagtct ttcatcgaga ggatgaccaa cttcgataag  1500
aaccttccaa acgagaaggt gctccctaag cactctttgc tctacgagta cttcaccgtg  1560
tacaacgagt tgaccaaggt taagtacgtg accgagggaa tgaggaagcc tgcttttttg  1620
tcaggtgagc aaaagaaggc tatcgttgat ctcttgttca agaccaacag aaaggtgacc  1680
gtgaagcagc tcaaagagga ttacttcaag aaaatcgagt gcttcgattc agttgagatt  1740
tctggtgttg aggataggtt caacgcatct ctcggaacct accacgatct cctcaagatc  1800
attaaggata aggatttctt ggataacgag gaaaacgagg atatcttgga ggatatcgtt  1860
cttaccctca ccctctttga agatagagag atgattgaag aaaggctcaa gacctacgct  1920
catctcttcg atgataaggt gatgaagcag ttgaagagaa gaagatacac tggttgggga  1980
aggctctcaa gaaagctcat taacggaatc agggataagc agtctggaaa gacaatcctt  2040
gatttcctca agtctgatgg attcgctaac agaaacttca tgcagctcat ccacgatgat  2100
tctctcacct ttaaagagga tatccagaag gctcaggttt caggacaggg tgatagtctc  2160
catgagcata tcgctaacct cgctggatct cctgcaatca agaagggaat cctccagact  2220
gtgaaggttg tggatgagtt ggtgaaggtg atgggaaggc ataagcctga gaacatcgtg  2280
atcgaaatgg ctagagagaa ccagaccact cagaagggac agaagaactc tagggaaagg  2340
```

```
atgaagagga tcgaggaagg tatcaaagag cttggatctc agatcctcaa agagcaccct  2400
gttgagaaca ctcagctcca gaatgagaag ctctacctct actacctcca gaacggaagg  2460
gatatgtatg tggatcaaga gttggatatc aacaggctct ctgattacga tgttgatcat  2520
atcgtgccac agtcattctt gaaggatgat tctatcgata acaaggtgct caccaggtct  2580
gataagaaca ggggtaagag tgataacgtg ccaagtgaag aggttgtgaa gaaaatgaag  2640
aactattgga ggcagctcct caacgctaag ctcatcactc agagaaagtt cgataacttg  2700
actaaggctg agaggggagg actctctgaa ttggataagg caggattcat caagaggcag  2760
cttgtggaaa ccaggcagat cactaagcac gttgcacaga tcctcgattc taggatgaac  2820
accaagtacg atgagaacga taagttgatc agggaagtga aggttatcac cctcaagtca  2880
aagctcgtgt ctgatttcag aaaggatttc caattctaca aggtgaggga aatcaacaac  2940
taccaccacg ctcacgatgc ttaccttaac gctgttgttg gaaccgctct catcaagaag  3000
tatcctaagc tcgagtcaga gttcgtgtac ggtgattaca aggtgtacga tgtgaggaag  3060
atgatcgcta agtctgagca agagatcgga aaggctaccg ctaagtattt cttctactct  3120
aacatcatga atttcttcaa gaccgagatt accctcgcta acggtgagat cagaaagagg  3180
ccactcatcg agacaaacgg tgaaacaggt gagatcgtgt gggataaggg aagggatttc  3240
gctaccgtta gaaaggtgct ctctatgcca caggtgaaca tcgttaagaa aaccgaggtg  3300
cagaccggtg gattctctaa agagtctatc ctccctaaga ggaactctga taagctcatt  3360
gctaggaaga aggattggga ccctaagaaa tacggtggtt tcgattctcc taccgtggct  3420
tactctgttc tcgttgtggc taaggttgag aagggaaaga gtaagaagct caagtctgtt  3480
aaggaacttc tcggaatcac tatcatggaa aggtcatctt tcgagaagaa cccaatcgat  3540
ttcctcgagg ctaagggata caaagaggtt aagaaggatc tcatcatcaa gctcccaaag  3600
tactcactct tcgaactcga gaacggtaga aagaggatgc tcgcttctgc tggtgagctt  3660
caaaagggaa acgagcttgc tctcccatct aagtacgtta actttcttta cctcgcttct  3720
cactacgaga agttgaaggg atctccagaa gataacgagc agaagcaact tttcgttgag  3780
cagcacaagc actacttgga tgagatcatc gagcagatct ctgagttctc taaaagggtg  3840
atcctcgctg atgcaaacct cgataaggtg ttgtctgctt acaacaagca cagagataag  3900
cctatcaggg aacaggcaga gaacatcatc catctcttca cccttaccaa cctcggtgct  3960
cctgctgctt tcaagtactt cgatacaacc atcgatagga agagatacac ctctaccaaa  4020
gaagtgctcg atgctaccct catccatcag tctatcactg gactctacga gactaggatc  4080
gatctctcac agctcggtgg tgat                                        4104

SEQ ID NO: 142         moltype = AA  length = 1368
FEATURE                Location/Qualifiers
source                 1..1368
                       mol_type = protein
                       organism = Streptococcus pyogenes
SEQUENCE: 142
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD               1368

SEQ ID NO: 143         moltype = DNA  length = 21
FEATURE                Location/Qualifiers
source                 1..21
                       mol_type = other DNA
                       organism = synthetic construct
SEQUENCE: 143
cctaagaaga agaggaaggt t                                            21

SEQ ID NO: 144         moltype = AA  length = 7
FEATURE                Location/Qualifiers
source                 1..7
                       mol_type = protein
                       organism = synthetic construct
SEQUENCE: 144
PKKKRKV                                                            7

SEQ ID NO: 145         moltype = DNA  length = 4137
FEATURE                Location/Qualifiers
```

```
source                  1..4137
                        mol_type = other DNA
                        organism = synthetic construct
SEQUENCE: 145
atggataaga agtactctat cggactcgat atcggaacta actctgtggg atgggctgtg  60
atcaccgatg agtacaaggt gccatctaag aagttcaagg ttctcggaaa caccgatagg  120
cactctatca agaaaaacct tatcggtgct ctcctcttcg attctggtga aactgctgag  180
gctaccagac tcaagagaac cgctagaaga aggtacacca gaagaaagaa caggatctgc  240
tacctccaag agatcttctc taacgagatg gctaaagtgg atgattcatt cttccacagg  300
ctcgaagagt cattcctcgt ggaagaagat aagaagcacg agaggcaccc tatcttcgga  360
aacatcgttg atgaggtggc ataccacgag aagtacccta ctatctacca cctcagaaag  420
aagctcgttg attctactga taaggctgat ctcaggctca tctacctcgc tctcgctcac  480
atgatcaagt tcagaggaca cttcctcatc gagggtgatc tcaaccctga taactctgat  540
gtggataagt tgttcatcca gctcgtgcag acctacaacc agcttttcga agagaaccct  600
atcaacgctt caggtgtgga tgctaaggct atcctctctg ctaggctctc taagtcaaga  660
aggcttgaga acctcattgc tcagctccct ggtgagaaga agaacggact tttcggaaac  720
ttgatcgctc tctctctcgg actcacccct aacttcaagt ctaacttcga tctcgctgag  780
gatgcaaagc tccagctctc aaaggatacc tacgatgatg atctcgataa cctcctcgct  840
cagatcggag atcagtacgc tgatttgttc ctcgctgcta agaacctctc tgatgctatc  900
ctcctcagtg atatcctcag agtgaacacc gagatcacca aggctccact ctcagcttct  960
atgatcaaga gatacgatga gcaccaccag gatctcacac ttctcaaggc tcttgttaga  1020
cagcagctcc cagagaagta caaagagatt ttcttcgatc agtctaagaa cggatacgct  1080
ggttacatcg atggtggtgc atctcaagaa gagttctaca agttcatcaa gcctatcctc  1140
gagaagatgg atggaaccga ggaactcctc gtgaagctca atagagagga tcttctcaga  1200
aagcagagga ccttcgataa cggatctatc cctcatcaga tccacctcgg agagttgcac  1260
gctatcctta gaaggcaaga ggatttctac ccattcctca aggataacag ggaaaagatt  1320
gagaagattc tcaccttcag aatcccttac tacgtgggac ctctcgctag aggaaactca  1380
agattcgctt ggatgaccag aaagtctgag gaaaccatca ccccttggaa cttcgaagag  1440
gtggtggata agggtgctag tgctcagtct ttcatcgaga ggatgaccaa cttcgataag  1500
aaccttccaa acgagaaggt gctccctaag cactctttgc tctacgagta cttcaccgtg  1560
tacaacgagt tgaccaaggt taagtacgtg accgagggaa tgaggaagcc tgcttttttg  1620
tcaggtgagc aaaagaaggc tatcgttgat ctcttgttca agaccaacag aaaggtgacc  1680
gtgaagcagc tcaaagagga ttacttcaag aaaatcgagt gcttcgattc agttgagatt  1740
tctggtgttg aggataggtt caacgcatct ctcggaacct accacgatct cctcaagatc  1800
attaaggata aggatttctt ggataacgag gaaaacgagg atatcttgga ggatatcgtt  1860
cttaccctca ccctctttga agatagagag atgattgaag aaaggctcaa gacctacgct  1920
catctcttcg atgataaggt gatgaagcag ttgaagagaa gaagatacac tggttgggga  1980
aggctctcaa gaaagctcat taacggaatc agggataagc agtctggaaa gacaatcctt  2040
gatttcctca agtctgatgg attcgctaac agaaacttca tgcagctcat ccacgatgat  2100
tctctcacct ttaaagagga tatccagaag gctcaggttt caggacaggg tgatagtctc  2160
catgagcata tcgctaacct cgctggatct cctgcaatca agaagggaat cctccagact  2220
gtgaaggttg tggatgagtt ggtgaaggtg atgggaaggc ataagcctga gaacatcgtg  2280
atcgaaatgg ctagagagaa ccagaccact cagaagggac agaagaactc tagggaaagg  2340
atgaagagga tcgaggaagg tatcaaagag cttggatctc agatcctcaa agagcaccct  2400
gttgagaaca ctcagctcca gaatgagaag ctctacctct actacctcca gaacggaagg  2460
gatatgtatg tggatcaaga gttggatatc aacaggctct ctgattacga tgttgatcat  2520
atcgtgccac agtcattctt gaaggatgat tctatcgata acaaggtgct caccaggtct  2580
gataagaaca ggggtaagag tgataacgtg ccaagtgaag aggttgtgaa gaaaatgaag  2640
aactattgga ggcagctcct caacgctaag ctcatcactc agagaaagtt cgataacttg  2700
actaaggctg agaggggagg actctctgaa ttggataagg caggattcat caagaggcag  2760
cttgtggaaa ccaggcagat cactaagcac gttgcacaga tcctcgattc taggatgaac  2820
accaagtacg atgagaacga taagttgatc agggaagtga aggttatcac cctcaagtca  2880
aagctcgtgt ctgatttcag aaaggatttc caattctaca aggtgaggga aatcaacaac  2940
taccaccacg ctcacgatgc ttaccttaac gctgttgttg gaaccgctct catcaagaag  3000
tatcctaagc tcgagtcaga gttcgtgtac ggtgattaca aggtgtacga tgtgaggaag  3060
atgatcgcta agtctgagca agagatcgga aaggctaccg ctaagtattt cttctactct  3120
aacatcatga atttcttcaa gaccgagatt accctcgcta acggtgagat cagaaagagg  3180
ccactcatcg agacaaacgg tgaaacaggt gagatcgtgt gggataaggg aaggatttc  3240
gctaccgtta gaaaggtgct ctctatgcca caggtgaaca tcgttaagaa aaccgaggtg  3300
cagaccggtg gattctctaa agagtctatc ctccctaaga ggaactctga taagctcatt  3360
gctaggaaga aggattggga ccctaagaaa tacggtggtt tcgattctcc taccgtggct  3420
tactctgttc tcgttgtggc taaggttgag aagggaaaga gtaagaagct caagtctgtt  3480
aaggaacttc tcggaatcac tatcatggaa aggtcatctt tcgagaagaa cccaatcgat  3540
ttcctcgagg ctaagggata caaagaggtt aagaaggatc tcatcatcaa gctcccaaag  3600
tactcactct tcgaactcga gaacggtaga aagaggatgc tcgcttctgc tggtgagctt  3660
caaaagggaa acgagcttgc tctcccatct aagtacgtta actttcttta cctcgcttct  3720
cactacgaga agttgaaggg atctccagaa gataacgagc agaagcaact tttcgttgag  3780
cagcacaagc actacttgga tgagatcatc gagcagatct ctgagttctc taaaagggtg  3840
atcctcgctg atgcaaacct cgataaggtg ttgtctgctt acaacaagca cagagataag  3900
cctatcaggg aacaggcaga gaacatcatc catctcttca cccttaccaa cctcggtgct  3960
cctgctgctt tcaagtactt cgatacaacc atcgatagga agagatacac ctctaccaaa  4020
gaagtgctcg atgctaccct catccatcag tctatcactg gactctacga gactaggatc  4080
gatctctcac agctcggtgg tgattcaagg gctgatccta agaagaagag gaaggtt     4137

SEQ ID NO: 146          moltype = AA  length = 1379
FEATURE                 Location/Qualifiers
source                  1..1379
                        mol_type = protein
                        organism = synthetic construct
```

```
SEQUENCE: 146
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDSR ADPKKKRKV   1379

SEQ ID NO: 147          moltype = AA  length = 13
FEATURE                 Location/Qualifiers
source                  1..13
                        mol_type = protein
                        organism = synthetic construct
SEQUENCE: 147
GRKKRRQRRR PPQ                                                     13

SEQ ID NO: 148          moltype = AA  length = 12
FEATURE                 Location/Qualifiers
source                  1..12
                        mol_type = protein
                        organism = synthetic construct
SEQUENCE: 148
GRKKRRQRRR PQ                                                      12

SEQ ID NO: 149          moltype = AA  length = 11
FEATURE                 Location/Qualifiers
source                  1..11
                        mol_type = protein
                        organism = synthetic construct
SEQUENCE: 149
YGRKKRRQRR R                                                       11

SEQ ID NO: 150          moltype = AA  length = 18
FEATURE                 Location/Qualifiers
source                  1..18
                        mol_type = protein
                        organism = synthetic construct
SEQUENCE: 150
KLALKLALKA LKAALKLA                                                18

SEQ ID NO: 151          moltype = AA  length = 16
FEATURE                 Location/Qualifiers
source                  1..16
                        mol_type = protein
                        organism = synthetic construct
SEQUENCE: 151
RQIRIWFQNR RMRWRR                                                  16

SEQ ID NO: 152          moltype = AA  length = 17
FEATURE                 Location/Qualifiers
source                  1..17
                        mol_type = protein
                        organism = synthetic construct
SEQUENCE: 152
CSIPPEVKFN KPFVYLI                                                 17

SEQ ID NO: 153          moltype = AA  length = 30
FEATURE                 Location/Qualifiers
source                  1..30
                        mol_type = protein
                        organism = synthetic construct
SEQUENCE: 153
```

RRRQRRKKRG GDIMGEWGNE IFGAIAGFLG 30

SEQ ID NO: 154 moltype = AA length = 13
FEATURE Location/Qualifiers
source 1..13
mol_type = protein
organism = synthetic construct
SEQUENCE: 154
FVQWFSKFLG RIL 13

SEQ ID NO: 155 moltype = AA length = 18
FEATURE Location/Qualifiers
source 1..18
mol_type = protein
organism = synthetic construct
SEQUENCE: 155
LLIILRRRIR KQAHAHSK 18

SEQ ID NO: 156 moltype = AA length = 24
FEATURE Location/Qualifiers
source 1..24
mol_type = protein
organism = synthetic construct
SEQUENCE: 156
LGTYTQDFNK FHTFPQTAIG VGAP 24

SEQ ID NO: 157 moltype = AA length = 30
FEATURE Location/Qualifiers
source 1..30
mol_type = protein
organism = synthetic construct
SEQUENCE: 157
GAAEAAARVY DLGLRRLRQR RRLRRERVRA 30

SEQ ID NO: 158 moltype = AA length = 27
FEATURE Location/Qualifiers
source 1..27
mol_type = protein
organism = synthetic construct
SEQUENCE: 158
MGLGLHLLVL AAALQGAWSQ PKKKRKV 27

SEQ ID NO: 159 moltype = AA length = 18
FEATURE Location/Qualifiers
source 1..18
mol_type = protein
organism = synthetic construct
SEQUENCE: 159
RQIKIWFQNR RMKWKKGG 18

SEQ ID NO: 160 moltype = AA length = 8
FEATURE Location/Qualifiers
source 1..8
mol_type = protein
organism = synthetic construct
SEQUENCE: 160
RRRRRRRR 8

SEQ ID NO: 161 moltype = AA length = 9
FEATURE Location/Qualifiers
source 1..9
mol_type = protein
organism = synthetic construct
SEQUENCE: 161
RRRRRRRRR 9

SEQ ID NO: 162 moltype = AA length = 30
FEATURE Location/Qualifiers
source 1..30
mol_type = protein
organism = synthetic construct
SEQUENCE: 162
KKLFKKILKY LKKLFKKILK YLKKKKKKKK 30

SEQ ID NO: 163 moltype = DNA length = 14548
FEATURE Location/Qualifiers
source 1..14548
mol_type = other DNA
organism = synthetic construct

```
SEQUENCE: 163
agtactttga tccaacccct ccgctgctat agtgcagtcg gcttctgacg ttcagtgcag  60
ccgtcttctg aaaacgacat gtcgcacaag tcctaagtta cgcgacaggc tgccgccctg  120
ccctttttcct ggcgttttct tgtcgcgtgt tttagtcgca taaagtagaa tacttgcgac  180
tagaaccgga gacattacgc catgaacaag agcgccgccg ctggcctgct gggctatgcc  240
cgcgtcagca ccgacgacca ggacttgacc aaccaacggg ccgaactgca cgcggccggc  300
tgcaccaagc tgttttccga gaagatcacc ggcaccaggc gcgaccgccc ggagctggcc  360
aggatgcttg accacctacg ccctggcgac gttgtgacag tgaccaggct agaccgcctg  420
gcccgcagca cccgcgacct actggacatt gccgagcgca tccaggaggc cggcgcgggc  480
ctgcgtagcc tggcagagcc gtgggccgac accaccacgc cggccggccg catggtgttg  540
accgtgttcg ccggcattgc cgagttcgag cgttccctaa tcatcgaccg cacccggagc  600
gggcgcgagg ccgccaaggc ccgaggcgtg aagtttggcc cccgccctac cctcaccccg  660
gcacagatcg cgcacgcccg cgagctgatc gaccaggaag gccgcaccgt gaaagaggcg  720
gctgcactgc ttggcgtgca tcgctcgacc ctgtaccgcg cacttgagcg cagcgaggaa  780
gtgacgccca ccgaggccag gcggcgcggt gccttccgtg aggacgcatt gaccgaggcc  840
gacgccctgg cggccgccga gaatgaacgc caagaggaac aagcatgaaa ccgcaccagg  900
acggccagga cgaaccgttt ttcattaccg aagagatcga ggcggagatg atcgcggccg  960
ggtacgtgtt cgagccgccc gcgcacgtct caaccgtgcg gctgcatgaa atcctggccg  1020
gtttgtctga tgccaagctg gcggcctggc cggccagctt ggccgctgaa gaaaccgagc  1080
gccgccgtct aaaaaggtga tgtgtatttg agtaaaacag cttgcgtcat gcggtcgctg  1140
cgtatatgat gcgatgagta aataaacaaa tacgcaaggg gaacgcatga aggttatcgc  1200
tgtacttaac cagaaaggcg ggtcaggcaa gacgaccatc gcaacccatc tagcccgcgc  1260
cctgcaactc gccggggccg atgttctgtt agtcgattcc gatccccagg gcagtgcccg  1320
cgattgggcg gccgtgcggg aagatcaacc gctaaccgtt gtcggcatcg accgcccgac  1380
gattgaccgc gacgtgaagg ccatcggccg gcgcgacttc gtagtgatcg acggagcgcc  1440
ccaggcggcg gacttggctg tgtccgcgat caaggcagcc gacttcgtgc tgattccggt  1500
gcagccaagc ccttacgaca tatgggccac cgccgacctg gtggagctgg ttaagcagcg  1560
cattgaggtc acggatggaa ggctacaagc ggcctttgtc gtgtcgcggg cgatcaaagg  1620
cacgcgcatc ggcggtgagg ttgccgaggc gctggccggg tacgagctgc ccattcttga  1680
gtcccgtatc acgcagcgcg tgagctaccc aggcactgcc gccgccggca caaccgttct  1740
tgaatcagaa cccgagggcg acgctgcccg cgaggtccag gcgctggccg ctgaaattaa  1800
atcaaaactc atttgagtta atgaggtaaa gagaaaatga gcaaaagcac aaacacgcta  1860
agtgccggcc gtccgagcgc acgcagcagc aaggctgcaa cgttggccag cctggcagac  1920
acgccagcca tgaagcgggt caactttcag ttgccggcgg aggatcacac caagctgaag  1980
atgtacgcgg tacgccaagg caagaccatt accgagctgc tatctgaata catcgcgcag  2040
ctaccagagt aaatgagcaa atgaataaat gagtagatga attttagcgg ctaaaggagg  2100
cggcatggaa aatcaagaac aaccaggcac cgacgccgtg gaatgcccca tgtgtggagg  2160
aacgggcggt tggccaggcg taagcggctg ggttgtctgc cggccctgca atggcactgg  2220
aacccccaag cccgaggaat cggcgtgacg gtcgcaaacc atccggcccg gtacaaatcg  2280
gcgcggcgct gggtgatgac ctggtggaga agttgaaggc cgcgcaggcc gcccagcggc  2340
aacgcatcga ggcagaagca cgccccggtg aatcgtggca agcggccgct gatcgaatcc  2400
gcaaagaatc ccggcaaccg ccggcagccg gtgcgccgtc gattaggaag ccgcccaagg  2460
gcgacgagca accagatttt ttcgttccga tgctctatga cgtgggcacc cgcgatagtc  2520
gcagcatcat ggacgtggcc gttttccgtc tgtcgaagcg tgaccgacga gctggcgagg  2580
tgatccgcta cgagcttcca gacgggcacg tagaggtttc cgcagggccg gccggcatgg  2640
ccagtgtgtg ggattacgac ctggtactga tggcggtttc ccatctaacc gaatccatga  2700
accgataccg ggaagggaag ggagacaagc ccggccgcgt gttccgtcca cacgttgcgg  2760
acgtactcaa gttctgccgg cgagccgatg gcggaaagca gaaagacgac ctggtagaaa  2820
cctgcattcg gttaaacacc acgcacgttg ccatgcagcg tacgaagaag gccaagaacg  2880
gccgcctggt gacggtatcc gagggtgaag ccttgattag ccgctacaag atcgtaaaga  2940
gcgaaaccgg gcggccggag tacatcgaga tcgagctagc tgattggatg taccgcgaga  3000
tcacagaagg caagaacccg gacgtgctga cggttcaccc cgattacttt ttgatcgatc  3060
ccggcatcgg ccgttttctc taccgcctgg cacgccgcgc cgcaggcaag gcagaagcca  3120
gatggttgtt caagacgatc tacgaacgca gtggcagcgc cggagagttc aagaagttct  3180
gtttcaccgt gcgcaagctg atcgggtcaa atgacctgcc ggagtacgat ttgaaggagg  3240
aggcggggca ggctggcccg atcctagtca tgcgctaccg caacctgatc gagggcgaag  3300
catccgccgg ttcctaatgt acggagcaga tgctagggca aattgcccta gcaggggaaa  3360
aaggtcgaaa aggtctcttt cctgtggata gcacgtacat tgggaaccca aagccgtaca  3420
ttgggaaccg gaacccgtac attgggaacc caaagccgta cattgggaac cggtcacaca  3480
tgtaagtgac tgatataaaa gagaaaaaag gcgatttttc cgcctaaaac tctttaaaac  3540
ttattaaaac tcttaaaacc cgcctggcct gtgcataact gtctggccag cgcacagccg  3600
aagagctgca aaaagcgcct acccttcggt cgctgcgctc cctacgcccc gccgcttcgc  3660
gtcggcctat cgcggccgct ggccgctcaa aaatggctgg cctacggcca ggcaatctac  3720
cagggcgcgg acaagccgcg ccgtcgccac tcgaccgccg gcgcccacat caaggcaccc  3780
tgcctcgcgc gtttcggtga tgacggtgaa aacctctgac acatgcagct cccggagacg  3840
gtcacagctt gtctgtaagc ggatgccggg agcagacaag cccgtcaggg cgcgtcagcg  3900
ggtgttggcg ggtgtcgggg cgcagccatg acccagtcac gtagcgatag cggagtgtat  3960
actggcttaa ctatgcggca tcagagcaga ttgtactgag agtgcaccat atgcggtgtg  4020
aaataccgca cagatgcgta aggagaaaat accgcatcag gcgctcttcc gcttcctcgc  4080
tcactgactc gctgcgctcg gtcgttcggc tgcggcgagc ggtatcagct cactcaaagg  4140
cggtaatacg gttatccaca gaatcagggg ataacgcagg aaagaacatg tgagcaaaag  4200
gccagcaaaa ggccaggaac cgtaaaaagg ccgcgttgct ggcgtttttc cataggctcc  4260
gcccccctga cgagcatcac aaaaatcgac gctcaagtca gaggtggcga aacccgacag  4320
gactataaag ataccaggcg tttccccctg gaagctccct cgtgcgctct cctgttccga  4380
ccctgccgct taccggatac ctgtccgcct ttctcccttc gggaagcgtg gcgctttctc  4440
atagctcacg ctgtaggtat ctcagttcgg tgtaggtcgt tcgctccaag ctgggctgtg  4500
tgcacgaacc ccccgttcag cccgaccgct gcgccttatc cggtaactat cgtcttgagt  4560
ccaacccggt aagacacgac ttatcgccac tggcagcagc cactggtaac aggattagca  4620
gagcgaggta tgtaggcggt gctacagagt tcttgaagtg gtggcctaac tacggctaca  4680
```

```
ctagaaggac agtatttggt atctgcgctc tgctgaagcc agttaccttc ggaaaaagag  4740
ttggtagctc ttgatccggc aaacaaacca ccgctggtag cggtggtttt tttgtttgca  4800
agcagcagat tacgcgcaga aaaaaaggat ctcaagaaga tcctttgatc ttttctacgg  4860
ggtctgacgc tcagtggaac gaaaactcac gttaagggat tttggtcatg catgatatat  4920
ctcccaattt gtgtagggct tattatgcac gcttaaaaat aataaaagca gacttgacct  4980
gatagtttgg ctgtgagcaa ttatgtgctt agtgcatcta atcgcttgag ttaacgccgg  5040
cgaagcggcg tcggcttgaa cgaatttcta gctagacatt atttgccgac taccttggtg  5100
atctcgcctt tcacgtagtg gacaaattct tccaactgat ctgcgcgcga ggccaagcga  5160
tcttcttctt gtccaagata agcctgtcta gcttcaagta tgacgggctg atactgggcc  5220
ggcaggcgct ccattgccca gtcggcagcg acatccttcg gcgcgatttt gccggttact  5280
gcgctgtacc aaatgcggga caacgtaagc actacatttc gctcatcgcc agcccagtcg  5340
ggcggcgagt tccatagcgt taaggtttca tttagcgcct caaatagatc ctgttcagga  5400
accggatcaa agagttcctc cgccgctgga cctaccaagg caacgctatg ttctcttgct  5460
tttgtcagca agatagccag atcaatgtcg atcgtggctg gctcgaagat acctgcaaga  5520
atgtcattgc gctgccattc tccaaattgc agttcgcgct tagctggata acgccacgga  5580
atgatgtcgt cgtgcacaac aatggtgact tctacagcgc ggagaatctc gctctctcca  5640
ggggaagccg aagtttccaa aaggtcgttg atcaaagctc gccgcgttgt ttcatcaagc  5700
cttacggtca ccgtaaccag caaatcaata tcactgtgtg gcttcaggcc gccatccact  5760
gcggagccgt acaaatgtac ggccagcaac gtcggttcga gatggcgctc gatgacgcca  5820
actacctctg atagttgagt cgatacttcg gcgatcaccg cttcccccat gatgtttaac  5880
tttgttttag ggcgactgcc ctgctgcgta acatcgttgc tgctccataa catcaaacat  5940
cgacccacgg cgtaacgcgc ttgctgcttg gatgcccgag gcatagactg taccccaaaa  6000
aaacatgtca taacaagaag ccatgaaaac cgccactgcg ccgttaccac cgctgcgttc  6060
ggtcaaggtt ctggaccagt tgcgtgacgg cagttacgct acttgcatta cagcttacga  6120
accgaacgag gcttatgtcc actgggttcg tgcccgaatt gatcacaggc agcaacgctc  6180
tgtcatcgtt acaatcaaca tgctaccctc cgcgagatca tccgtgtttc aaacccggca  6240
gcttagttgc cgttcttccg aatagcatcg gtaacatgag caaagtctgc cgccttacaa  6300
cggctctccc gctgacgccg tcccggactg atgggctgcc tgtatcgagt ggtgattttg  6360
tgccgagctg ccggtcgggg agctgttggc tggctggtgg caggatatat tgtggtgtaa  6420
acaaattgac gcttagacaa cttaataaca cattgcggac gtttttaatg tactgaatta  6480
acgccgaatt gctctagcca atacgcaaac cgcctctccc cgcgcgttgg ccgattcatt  6540
aatgcagctg gcacgacagg tttcccgact ggaaagcggg cagtgagcgc aacgcaatta  6600
atgtgagtta gctcactcat taggcacccc aggctttaca ctttatgctt ccggctcgta  6660
tgttgtgtgg aattgtgagc ggataacaat ttcacacagg aaacagctat gacatgatta  6720
cgaattcaaa aattacggat atgaatatag gcatatccgt atccgaatta tccgtttgac  6780
agctagcaac gattgtacaa ttgcttcttt aaaaaaggaa gaaagaaaga aagaaaagaa  6840
tcaacatcag cgttaacaaa cggccccgtt acggcccaaa cggtcatata gagtaacggc  6900
gttaagcgtt gaaagactcc tatcgaaata cgtaaccgca aacgtgtcat agtcagatcc  6960
cctcttcctt caccgcctca aacacaaaaa taatcttcta cagcctatat atacaacccc  7020
cccttctatc tctcctttcc cacaattcat catctttctt tctctacccc caattttaag  7080
aaatcctctc ttctcctctt cattttcaag gtaaatctct ctctctctct ctctctctgt  7140
tattccttgt tttaattagg tatgtattat tgctagtttg ttaatctgct tatcttatgt  7200
atgccttatg tgaatatctt tatcttgttc atctcatccg tttagaagct ataaatttgt  7260
tgatttgact gtgtatctac acgtggttat gtttatatct aatcagatat gaatttcttc  7320
atattgttgc gtttgtgtgt accaatccga aatcgttgat ttttttcatt taatcgtgta  7380
gctaattgta cgtatacata tggatctacg tatcaattgt tcatctgttt gtgtttgtat  7440
gtatacagat ctgaaaacat cacttctctc atctgattgt gttgttacat acatagatat  7500
agatctgtta tatcattttt tttattaatt gtgtatatat atatgtgcat agatctggat  7560
tacatgattg tgattattta catgattttg ttatttacgt atgtatatat gtagatctgg  7620
actttttgga gttgttgact tgattgtatt tgtgtgtgta tatgtgtgtt ctgatcttga  7680
tatgttatgt atgtgcagcg aattcggcgc gccatggata agaagtactc tatcggactc  7740
gatatcggaa ctaactctgt gggatgggct gtgatcaccg atgagtacaa ggtgccatct  7800
aagaagttca aggttctcgg aaacaccgat aggcactcta tcaagaaaaa ccttatcggt  7860
gctctcctct tcgattctgg tgaaactgct gaggctacca gactcaagag aaccgctaga  7920
agaaggtaca ccagaagaaa gaacaggatc tgctacctcc aagagatctt ctctaacgag  7980
atggctaaag tggatgattc attcttccac aggctcgaag agtcattcct cgtggaagaa  8040
gataagaagc acgagaggca ccctatcttc ggaaacatcg ttgatgaggt ggcataccac  8100
gagaagtacc ctactatcta ccacctcaga aagaagctcg ttgattctac tgataaggct  8160
gatctcaggc tcatctacct cgctctcgct cacatgatca agttcagagg acacttcctc  8220
atcgagggtg atctcaaccc tgataactct gatgtggata agttgttcat ccagctcgtg  8280
cagacctaca accagctttt cgaagagaac cctatcaacg cttcaggtgt ggatgctaag  8340
gctatcctct ctgctaggct ctctaagtca agaaggcttg agaacctcat tgctcagctc  8400
cctggtgaga agaagaacgg acttttcgga aacttgatcg ctctctctct cggactcacc  8460
cctaacttca agtctaactt cgatctcgct gaggatgcaa agctccagct ctcaaaggat  8520
acctacgatg atgatctcga taacctcctc gctcagatcg gagatcagta cgctgatttg  8580
ttcctcgctg ctaagaacct ctctgatgct atcctcctca gtgatatcct cagagtgaac  8640
accgagatca ccaaggctcc actctcagct tctatgatca agagatacga tgagcaccac  8700
caggatctca cacttctcaa ggctcttgtt agacagcagc tcccagagaa gtacaaagag  8760
attttcttcg atcagtctaa gaacggatac gctggttaca tcgatggtgg tgcatctcaa  8820
gaagagttct acaagttcat caagcctatc ctcgagaaga tggatggaac cgaggaactc  8880
ctcgtgaagc tcaatagaga ggatcttctc agaaagcaga ggaccttcga taacggatct  8940
atccctcatc agatccacct cggagagttg cacgctatcc ttagaaggca agaggatttc  9000
tacccattcc tcaaggataa cagggaaaag attgagaaga ttctcacctt cagaatccct  9060
tactacgtgg gacctctcgc tagaggaaac tcaagattcg cttggatgac cagaaagtct  9120
gaggaaacca tcacccottg gaacttcgaa gaggtggtgg ataagggtgc tagtgctcag  9180
tctttcatcg agaggatgac caacttcgat aagaaccttc caaacgagaa ggtgctccct  9240
aagcactctt tgctctacga gtacttcacc gtgtacaacg agttgaccaa ggttaagtac  9300
gtgaccgagg gaatgaggaa gcctgctttt ttgtcaggtg agcaaaagaa ggctatcgtt  9360
gatctcttgt tcaagaccaa cagaaaggtg accgtgaagc agctcaaaga ggattacttc  9420
```

```
aagaaaatcg agtgcttcga ttcagttgag atttctggtg ttgaggatag gttcaacgca  9480
tctctcggaa cctaccacga tctcctcaag atcattaagg ataaggattt cttggataac  9540
gaggaaaacg aggatatctt ggaggatatc gttcttaccc tcaccctctt tgaagataga  9600
gagatgattg aagaaaggct caagacctac gctcatctct tcgatgataa ggtgatgaag  9660
cagttgaaga gaagaagata cactggttgg ggaaggctct caagaaagct cattaacgga  9720
atcagggata agcagtctgg aaagacaatc cttgatttcc tcaagtctga tggattcgct  9780
aacagaaact tcatgcagct catccacgat gattctctca cctttaaaga ggatatccag  9840
aaggctcagg tttcaggaca gggtgatagt ctccatgagc atatcgctaa cctcgctgga  9900
tctcctgcaa tcaagaaggg aatcctccag actgtgaagg ttgtggatga gttggtgaag  9960
gtgatgggaa ggcataagcc tgagaacatc gtgatcgaaa tggctagaga gaaccagacc  10020
actcagaagg gacagaagaa ctctagggaa aggatgaaga ggatcgagga aggtatcaaa  10080
gagcttggat ctcagatcct caaagagcac cctgttgaga acactcagct ccagaatgag  10140
aagctctacc tctactacct ccagaacgga agggatatgt atgtggatca agagttggat  10200
atcaacaggc tctctgatta cgatgttgat catatcgtgc cacagtcatt cttgaaggat  10260
gattctatcg ataacaaggt gctcaccagg tctgataaga acaggggtaa gagtgataac  10320
gtgccaagtg aagaggttgt gaagaaaatg aagaactatt ggaggcagct cctcaacgct  10380
aagctcatca ctcagagaaa gttcgataac ttgactaagg ctgagagggg aggactctct  10440
gaattggata aggcaggatt catcaagagg cagcttgtgg aaaccaggca gatcactaag  10500
cacgttgcac agatcctcga ttctaggatg aacaccaagt acgatgagaa cgataagttg  10560
atcagggaag tgaaggttat caccctcaag tcaaagctcg tgtctgattt cagaaaggat  10620
ttccaattct acaaggtgag ggaaatcaac aactaccacc acgctcacga tgcttacctt  10680
aacgctgttg ttggaaccgc tctcatcaag aagtatccta agctcgagtc agagttcgtg  10740
tacggtgatt acaaggtgta cgatgtgagg aagatgatcg ctaagtctga gcaagagatc  10800
ggaaaggcta ccgctaagta tttcttctac tctaacatca tgaatttctt caagaccgag  10860
attaccctcg ctaacggtga gatcagaaag aggccactca tcgagacaaa cggtgaaaca  10920
ggtgagatcg tgtgggataa gggaagggat ttcgctaccg ttagaaaggt gctctctatg  10980
ccacaggtga acatcgttaa gaaaaccgag gtgcagaccg gtggattctc taaagagtct  11040
atcctcccta agaggaactc tgataagctc attgctagga agaaggattg ggaccctaag  11100
aaatacggtg gtttcgattc tcctaccgtg gcttactctg ttctcgttgt ggctaaggtt  11160
gagaagggaa agagtaagaa gctcaagtct gttaaggaac ttctcggaat cactatcatg  11220
gaaaggtcat ctttcgagaa gaacccaatc gatttcctcg aggctaaggg atacaaagag  11280
gttaagaagg atctcatcat caagctccca aagtactcac tcttcgaact cgagaacggt  11340
agaaagagga tgctcgcttc tgctggtgag cttcaaaagg gaaacgagct tgctctccca  11400
tctaagtacg ttaactttct ttacctcgct tctcactacg agaagttgaa gggatctcca  11460
gaagataacg agcagaagca acttttcgtt gagcagcaca agcactactt ggatgagatc  11520
atcgagcaga tctctgagtt ctctaaaagg gtgatcctcg ctgatgcaaa cctcgataag  11580
gtgttgtctg cttacaacaa gcacagagat aagcctatca gggaacaggc agagaacatc  11640
atccatctct tcacccttac caacctcggt gctcctgctg ctttcaagta cttcgataca  11700
accatcgata ggaagagata cacctctacc aaagaagtgc tcgatgctac cctcatccat  11760
cagtctatca ctggactcta cgagactagg atcgatctct cacagctcgg tggtgattca  11820
agggctgatc ctaagaagaa gaggaaggtt tgaggcgcgc cgagctccag gcctcccagc  11880
tttcgtccgt atcatcggtt tcgacaacgt tcgtcaagtt caatgcatca gtttcattgc  11940
ccacacacca gaatcctact aagtttgagt attatggcat tggaaaagct gttttcttct  12000
atcatttgtt ctgcttgtaa tttactgtgt tctttcagtt tttgttttcg gacatcaaaa  12060
tgcaaatgga tggataagag ttaataaatg atatggtcct tttgttcatt ctcaaattat  12120
tattatctgt tgtttttact ttaatgggtt gaatttaagt aagaaaggaa ctaacagtgt  12180
gatattaagg tgcaatgtta gacatataaa acagtctttc acctctcttt ggttatgtct  12240
tgaattggtt tgtttcttca cttatctgtg taatcaagtt tactatgagt ctatgatcaa  12300
gtaattatgc aatcaagtta agtacagtat aggcttgagc tccctaggct tttttttcttc  12360
ttcttcgttc atacagtttt tttttgttta tcagcttaca ttttcttgaa ccgtagcttt  12420
cgttttcttc tttttaactt tccattcgga gtttttgtat cttgtttcat agtttgtccc  12480
aggattagaa tgattaggca tcgaaccttc aagaatttga ttgaataaaa catcttcatt  12540
cttaagatat gaagataatc ttcaaaaggc ccctgggaat ctgaaagaag agaagcaggc  12600
ccatttatat gggaaagaac aatagtattt cttatatagg cccatttaag ttgaaaacaa  12660
tcttcaaaag tcccacatcg cttagataag aaaacgaagc tgagtttata tacagctaga  12720
gtcgaagtag tgattggaag caagagacgt tctagggttt tagagctaga aatagcaagt  12780
taaaataagg ctagtccgtt atcaacttga aaaagtggca ccgagtcggt gcttttttttc  12840
tagacccagc tttcttgtac aaagttggca ttacctaggc ccgggcctga ggacgcgtcc  12900
atggttaatt aagacgtccg gaccgactag tggatcctct agagtcgacc tgcaggcatg  12960
caagcttctt cgtcaacatg gtggagcacg acacgcttgt ctactccaaa aatatcaaag  13020
atacagtctc agaagaccaa agggcaattg agacttttca acaaagggta atatccggaa  13080
acctcctcgg attccattgc ccagctatct gtcactttat tgtgaagata gtggaaaagg  13140
aaggtggctc ctacaaatgc catcattgcg ataaaggaaa ggccatcgtt gaagatgcct  13200
ctgccgacag tggtcccaaa gatggacccc cacccacgag gagcatcgtg gaaaaagaag  13260
acgttccaac cacgtcttca aagcaagtgg attgatgtga tatctccact gacgtaaggg  13320
atgacgcaca atcaatccca ctatccttcg caagaccctt ttaaggggga agttcatttc  13380
atttggagag gacacgctga aatcaccagt ctctctgtac aaatcnatct ctctctataa  13440
tattgtgtaa gtagttccca gataagggaa ttagggttct tatagggttt cgctcagctg  13500
ttgagcatat aagaaaccct tagtcgatag atctgttggg gatctaccat gagcccagaa  13560
cgacgcccgg ccgacatccg ccgtgccacc gaggcggaca tgccggcggt ctgcaccatc  13620
gtcaaccact acatcgagac aagcacggtc aacttccgta ccgagccgca ggaaccgcag  13680
gagtggacgg acgacctcgt ccgtctgcgg gagcgctatc cctggctcgt cgccgaggtg  13740
gacggcgagg tcgccggcat cgcctacgcg ggcccctgga aggcacgcaa cgcctacgac  13800
tggacggccg agtcgaccgt gtacgtctcc ccccgccacc agcggacggg actgggctcc  13860
acgctctaca cccacctgct gaagtccctg gaggcacagg gcttcaagag cgtggtcgct  13920
gtcatcgggc tgcccaacga cccgagcgtg cgcatgcacg aggcgctcgg atatgccccc  13980
cgcggcatgc tgcgggcggc cggcttcaag cacgggaact ggcatgacgt gggtttctgg  14040
cagctggact tcagcctgcc ggtaccgccc cgtccggtcc tgcccgtcac cgagatctga  14100
tgacccaact tagtatgtat ttgtatttgt aaaatacttc tatcaataaa atttctaatt  14160
```

```
cctaaaacca aaatccaggg gtaccgaaca agcttggcac tggccgtcgt tttacaacgt  14220
cgtgactggg aaaaccctgg cgttacccaa cttaatcgcc ttgcagcaca tccccctttc  14280
gccagctggc gtaatagcga agaggcccgc accgatcgcc cttcccaaca gttgcgcagc  14340
ctgaatggcg aatgagcttg agcttggatc agattgtcgt ttcccgcctt cagtttaaac  14400
tatcagtgtt tgacaggata tattggcggg taaacctaag agaaaagagc gtttattaga  14460
ataacggata tttaaaaggg cgtgaaaagg tttatccgtt cgtccatttg tatgtgcatg  14520
ccaaccacag ggttcccctc gggatcaa                                     14548

SEQ ID NO: 164          moltype = DNA  length = 14548
FEATURE                 Location/Qualifiers
source                  1..14548
                        mol_type = other DNA
                        organism = synthetic construct
SEQUENCE: 164
agtactttga tccaacccct ccgctgctat agtgcagtcg gcttctgacg ttcagtgcag  60
ccgtcttctg aaaacgacat gtcgcacaag tcctaagtta cgcgacaggc tgccgccctg  120
cccttttcct ggcgttttct tgtcgcgtgt tttagtcgca taaagtagaa tacttgcgac  180
tagaaccgga gacattacgc catgaacaag agcgccgccg ctggcctgct gggctatgcc  240
cgcgtcagca ccgacgacca ggacttgacc aaccaacggg ccgaactgca cgcggccggc  300
tgcaccaagc tgttttccga gaagatcacc ggcaccaggc gcgaccgccc ggagctggcc  360
aggatgcttg accacctacg ccctggcgac gttgtgacag tgaccaggct agaccgcctg  420
gcccgcagca cccgcgacct actggacatt gccgagcgca tccaggaggc cggcgcgggc  480
ctgcgtagcc tggcagagcc gtgggccgac accaccacgc cggccggccg catggtgttg  540
accgtgttcg ccggcattgc cgagttcgag cgttccctaa tcatcgaccg cacccggagc  600
gggcgcgagg ccgccaaggc ccgaggcgtg aagtttggcc cccgccctac cctcaccccg  660
gcacagatcg cgcacgcccg cgagctgatc gaccaggaag gccgcaccgt gaaagaggcg  720
gctgcactgc ttggcgtgca tcgctcgacc ctgtaccgcg cacttgagcg cagcgaggaa  780
gtgacgccca ccgaggccag gcggcgcggt gccttccgtg aggacgcatt gaccgaggcc  840
gacgccctgg cggccgccga gaatgaacgc caagaggaac aagcatgaaa ccgcaccagg  900
acggccagga cgaaccgttt ttcattaccg aagagatcga ggcggagatg atcgcggccg  960
ggtacgtgtt cgagccgccc gcgcacgtct caaccgtgcg gctgcatgaa atcctggccg  1020
gtttgtctga tgccaagctg gcggcctggc cggccagctt ggccgctgaa gaaaccgagc  1080
gccgccgtct aaaaaggtga tgtgtatttg agtaaaacag cttgcgtcat gcggtcgctg  1140
cgtatatgat gcgatgagta aataaacaaa tacgcaaggg gaacgcatga aggttatcgc  1200
tgtacttaac cagaaaggcg ggtcaggcaa gacgaccatc gcaacccatc tagcccgcgc  1260
cctgcaactc gccggggccg atgttctgtt agtcgattcc gatccccagg gcagtgcccg  1320
cgattgggcg gccgtgcggg aagatcaacc gctaaccgtt gtcggcatcg accgcccgac  1380
gattgaccgc gacgtgaagg ccatcggccg gcgcgacttc gtagtgatcg acggagcgcc  1440
ccaggcggcg gacttggctg tgtccgcgat caaggcagcc gacttcgtgc tgattccggt  1500
gcagccaagc ccttacgaca tatgggccac cgccgacctg gtggagctgg ttaagcagcg  1560
cattgaggtc acggatggaa ggctacaagc ggcctttgtc gtgtcgcggg cgatcaaagg  1620
cacgcgcatc ggcggtgagg ttgccgaggc gctggccggg tacgagctgc ccattcttga  1680
gtcccgtatc acgcagcgcg tgagctaccc aggcactgcc gccgccggca caaccgttct  1740
tgaatcagaa cccgagggcg acgctgcccg cgaggtccag gcgctggccg ctgaaattaa  1800
atcaaaactc atttgagtta atgaggtaaa gagaaaatga gcaaaagcac aaacacgcta  1860
agtgccggcc gtccgagcgc acgcagcagc aaggctgcaa cgttggccag cctggcagac  1920
acgccagcca tgaagcgggt caactttcag ttgccggcgg aggatcacac caagctgaag  1980
atgtacgcgg tacgccaagg caagaccatt accgagctgc tatctgaata catcgcgcag  2040
ctaccagagt aaatgagcaa atgaataaat gagtagatga attttagcgg ctaaaggagg  2100
cggcatggaa aatcaagaac aaccaggcac cgacgccgtg gaatgcccca tgtgtggagg  2160
aacgggcggt tggccaggcg taagcggctg ggttgtctgc cggccctgca atggcactgg  2220
aacccccaag cccgaggaat cggcgtgacg gtcgcaaacc atccggcccg gtacaaatcg  2280
gcgcggcgct gggtgatgac ctggtggaga agttgaaggc cgcgcaggcc gcccagcggc  2340
aacgcatcga ggcagaagca cgccccggtg aatcgtggca agcggccgct gatcgaatcc  2400
gcaaagaatc ccggcaaccg ccggcagccg gtgcgccgtc gattaggaag ccgcccaagg  2460
gcgacgagca accagatttt ttcgttccga tgctctatga cgtgggcacc cgcgatagtc  2520
gcagcatcat ggacgtggcc gttttccgtc tgtcgaagcg tgaccgacga gctggcgagg  2580
tgatccgcta cgagcttcca gacgggcacg tagaggtttc cgcagggccg gccggcatgg  2640
ccagtgtgtg ggattacgac ctggtactga tggcggtttc ccatctaacc gaatccatga  2700
accgataccg ggaagggaag ggagacaagc ccggccgcgt gttccgtcca cacgttgcgg  2760
acgtactcaa gttctgccgg cgagccgatg gcggaaagca gaaagacgac ctggtagaaa  2820
cctgcattcg gttaaacacc acgcacgttg ccatgcagcg tacgaagaag gccaagaacg  2880
gccgcctggt gacggtatcc gagggtgaag ccttgattag ccgctacaag atcgtaaaga  2940
gcgaaaccgg gcggccggag tacatcgaga tcgagctagc tgattggatg taccgcgaga  3000
tcacagaagg caagaacccg gacgtgctga cggttcaccc cgattacttt ttgatcgatc  3060
ccggcatcgg ccgttttctc taccgcctgg cacgccgcgc cgcaggcaag gcagaagcca  3120
gatggttgtt caagacgatc tacgaacgca gtggcagcgc cggagagttc aagaagttct  3180
gtttcaccgt gcgcaagctg atcgggtcaa atgacctgcc ggagtacgat ttgaaggagg  3240
aggcggggca ggctggcccg atcctagtca tgcgctaccg caacctgatc gagggcgaag  3300
catccgccgg ttcctaatgt acggagcaga tgctagggca aattgcccta gcaggggaaa  3360
aaggtcgaaa aggtctcttt cctgtggata gcacgtacat tgggaaccca aagccgtaca  3420
ttgggaaccg gaacccgtac attgggaacc caaagccgta cattgggaac cggtcacaca  3480
tgtaagtgac tgatataaaa gagaaaaaag gcgatttttc cgcctaaaac tctttaaaac  3540
ttattaaaac tcttaaaacc cgcctggcct gtgcataact gtctggccag cgcacagccg  3600
aagagctgca aaaagcgcct acccttcggt cgctgcgctc cctacgcccc gccgcttcgc  3660
gtcggcctat cgcggccgct ggccgctcaa aaatggctgg cctacggcca ggcaatctac  3720
cagggcgcgg acaagccgcg ccgtcgccac tcgaccgccg gcgcccacat caaggcaccc  3780
tgcctcgcgc gtttcggtga tgacggtgaa aacctctgac acatgcagct cccggagacg  3840
gtcacagctt gtctgtaagc ggatgccggg agcagacaag cccgtcaggg cgcgtcagcg  3900
```

```
ggtgttggcg ggtgtcgggg cgcagccatg acccagtcac gtagcgatag cggagtgtat  3960
actggcttaa ctatgcggca tcagagcaga ttgtactgag agtgcaccat atgcggtgtg  4020
aaataccgca cagatgcgta aggagaaaat accgcatcag gcgctcttcc gcttcctcgc  4080
tcactgactc gctgcgctcg gtcgttcggc tgcggcgagc ggtatcagct cactcaaagg  4140
cggtaatacg gttatccaca gaatcagggg ataacgcagg aaagaacatg tgagcaaaag  4200
gccagcaaaa ggccaggaac cgtaaaaagg ccgcgttgct ggcgtttttc cataggctcc  4260
gcccccctga cgagcatcac aaaaatcgac gctcaagtca gaggtggcga aacccgacag  4320
gactataaag ataccaggcg tttccccctg gaagctccct cgtgcgctct cctgttccga  4380
ccctgccgct taccggatac ctgtccgcct ttctcccttc gggaagcgtg gcgctttctc  4440
atagctcacg ctgtaggtat ctcagttcgg tgtaggtcgt tcgctccaag ctgggctgtg  4500
tgcacgaacc ccccgttcag cccgaccgct gcgccttatc cggtaactat cgtcttgagt  4560
ccaacccggt aagacacgac ttatcgccac tggcagcagc cactggtaac aggattagca  4620
gagcgaggta tgtaggcggt gctacagagt tcttgaagtg gtggcctaac tacggctaca  4680
ctagaaggac agtatttggt atctgcgctc tgctgaagcc agttaccttc ggaaaaagag  4740
ttggtagctc ttgatccggc aaacaaacca ccgctggtag cggtggtttt tttgtttgca  4800
agcagcagat tacgcgcaga aaaaaaggat ctcaagaaga tcctttgatc ttttctacgg  4860
ggtctgacgc tcagtggaac gaaaactcac gttaagggat tttggtcatg catgatatat  4920
ctcccaattt gtgtagggct tattatgcac gcttaaaaat aataaaagca gacttgacct  4980
gatagtttgg ctgtgagcaa ttatgtgctt agtgcatcta atcgcttgag ttaacgccgg  5040
cgaagcggcg tcggcttgaa cgaatttcta gctagacatt atttgccgac taccttggtg  5100
atctcgcctt tcacgtagtg gacaaattct tccaactgat ctgcgcgcga ggccaagcga  5160
tcttcttctt gtccaagata agcctgtcta gcttcaagta tgacgggctg atactgggcc  5220
ggcaggcgct ccattgccca gtcggcagcg acatccttcg gcgcgatttt gccggttact  5280
gcgctgtacc aaatgcggga caacgtaagc actacatttc gctcatcgcc agcccagtcg  5340
ggcggcgagt tccatagcgt taaggtttca tttagcgcct caaatagatc ctgttcagga  5400
accggatcaa agagttcctc cgccgctgga cctaccaagg caacgctatg ttctcttgct  5460
tttgtcagca agatagccag atcaatgtcg atcgtggctg gctcgaagat acctgcaaga  5520
atgtcattgc gctgccattc tccaaattgc agttcgcgct tagctggata acgccacgga  5580
atgatgtcgt cgtgcacaac aatggtgact tctacagcgc ggagaatctc gctctctcca  5640
ggggaagccg aagtttccaa aaggtcgttg atcaaagctc gccgcgttgt ttcatcaagc  5700
cttacggtca ccgtaaccag caaatcaata tcactgtgtg gcttcaggcc gccatccact  5760
gcggagccgt acaaatgtac ggccagcaac gtcggttcga gatggcgctc gatgacgcca  5820
actacctctg atagttgagt cgatacttcg gcgatcaccg cttccccccat gatgtttaac  5880
tttgttttag ggcgactgcc ctgctgcgta acatcgttgc tgctccataa catcaaacat  5940
cgacccacgg cgtaacgcgc ttgctgcttg gatgcccgag gcatagactg taccccaaaa  6000
aaacatgtca taacaagaag ccatgaaaac cgccactgcg ccgttaccac cgctgcgttc  6060
ggtcaaggtt ctggaccagt tgcgtgacgg cagttacgct acttgcatta cagcttacga  6120
accgaacgag gcttatgtcc actgggttcg tgcccgaatt gatcacaggc agcaacgctc  6180
tgtcatcgtt acaatcaaca tgctaccctc cgcgagatca tccgtgtttc aaacccggca  6240
gcttagttgc cgttcttccg aatagcatcg gtaacatgag caaagtctgc cgccttacaa  6300
cggctctccc gctgacgccg tcccggactg atgggctgcc tgtatcgagt ggtgattttg  6360
tgccgagctg ccggtcgggg agctgttggc tggctggtgg caggatatat tgtggtgtaa  6420
acaaattgac gcttagacaa cttaataaca cattgcggac gtttttaatg tactgaatta  6480
acgccgaatt gctctagcca atacgcaaac cgcctctccc cgcgcgttgg ccgattcatt  6540
aatgcagctg gcacgacagg tttcccgact ggaaagcggg cagtgagcgc aacgcaatta  6600
atgtgagtta gctcactcat taggcacccc aggctttaca ctttatgctt ccggctcgta  6660
tgttgtgtgg aattgtgagc ggataacaat ttcacacagg aaacagctat gacatgatta  6720
cgaattcaaa aattacggat atgaatatag gcatatccgt atccgaatta tccgtttgac  6780
agctagcaac gattgtacaa ttgcttcttt aaaaaaggaa gaaagaaaga aagaaaagaa  6840
tcaacatcag cgttaacaaa cggccccgtt acggcccaaa cggtcatata gagtaacggc  6900
gttaagcgtt gaaagactcc tatcgaaata cgtaaccgca aacgtgtcat agtcagatcc  6960
cctcttcctt caccgcctca aacacaaaaa taatcttcta cagcctatat atacaacccc  7020
cccttctatc tctcctttct cacaattcat catctttctt tctctacccc caattttaag  7080
aaatcctctc ttctcctctt cattttcaag gtaaatctct ctctctctct ctctctctgt  7140
tattccttgt tttaattagg tatgtattat tgctagtttg ttaatctgct tatcttatgt  7200
atgccttatg tgaatatctt tatcttgttc atctcatccg tttagaagct ataaatttgt  7260
tgatttgact gtgtatctac acgtggttat gtttatatct aatcagatat gaatttcttc  7320
atattgttgc gtttgtgtgt accaatccga aatcgttgat ttttttcatt taatcgtgta  7380
gctaattgta cgtatacata tggatctacg tatcaattgt tcatctgttt gtgtttgtat  7440
gtatacagat ctgaaaacat cacttctctc atctgattgt gttgttacat acatagatat  7500
agatctgtta tatcattttt tttattaatt gtgtatatat atatgtgcat agatctggat  7560
tacatgattg tgattattta catgattttg ttatttacgt atgtatatat gtagatctgg  7620
actttttgga gttgttgact tgattgtatt tgtgtgtgta tatgtgtgtt ctgatcttga  7680
tatgttatgt atgtgcagcg aattcggcgc gccatggata agaagtactc tatcggactc  7740
gatatcggaa ctaactctgt gggatgggct gtgatcaccg atgagtacaa ggtgccatct  7800
aagaagttca aggttctcgg aaacaccgat aggcactcta tcaagaaaaa ccttatcggt  7860
gctctcctct tcgattctgg tgaaactgct gaggctacca gactcaagag aaccgctaga  7920
agaaggtaca ccagaagaaa gaacaggatc tgctacctcc aagagatctt ctctaacgag  7980
atggctaaag tggatgattc attcttccac aggctcgaag agtcattcct cgtggaagaa  8040
gataagaagc acgagaggca ccctatcttc ggaaacatcg ttgatgaggt ggcataccac  8100
gagaagtacc ctactatcta ccacctcaga aagaagctcg ttgattctac tgataaggct  8160
gatctcaggc tcatctacct cgctctcgct cacatgatca agttcagagg acacttcctc  8220
atcgagggtg atctcaaccc tgataactct gatgtggata agttgttcat ccagctcgtg  8280
cagacctaca accagctttt cgaagagaac cctatcaacg cttcaggtgt ggatgctaag  8340
gctatcctct ctgctaggct ctctaagtca agaaggcttg agaacctcat tgctcagctc  8400
cctggtgaga agaagaacgg acttttcgga aacttgatcg ctctctctct cggactcacc  8460
cctaacttca agtctaactt cgatctcgct gaggatgcaa agctccagct ctcaaaggat  8520
acctacgatg atgatctcga taacctcctc gctcagatcg gagatcagta cgctgatttg  8580
ttcctcgctg ctaagaacct ctctgatgct atcctcctca gtgatatcct cagagtgaac  8640
```

```
accgagatca ccaaggctcc actctcagct tctatgatca agagatacga tgagcaccac  8700
caggatctca cacttctcaa ggctcttgtt agacagcagc tcccagagaa gtacaaagag  8760
attttcttcg atcagtctaa gaacggatac gctggttaca tcgatggtgg tgcatctcaa  8820
gaagagttct acaagttcat caagcctatc ctcgagaaga tggatggaac cgaggaactc  8880
ctcgtgaagc tcaatagaga ggatcttctc agaaagcaga ggaccttcga taacggatct  8940
atccctcatc agatccacct cggagagttg cacgctatcc ttagaaggca agaggatttc  9000
tacccattcc tcaaggataa cagggaaaag attgagaaga ttctcacctt cagaatccct  9060
tactacgtgg gacctctcgc tagaggaaac tcaagattcg cttggatgac cagaaagtct  9120
gaggaaacca tcaccccttg gaacttcgaa gaggtggtgg ataagggtgc tagtgctcag  9180
tctttcatcg agaggatgac caacttcgat aagaaccttc caaacgagaa ggtgctccct  9240
aagcactctt tgctctacga gtacttcacc gtgtacaacg agttgaccaa ggttaagtac  9300
gtgaccgagg gaatgaggaa gcctgctttt ttgtcaggtg agcaaaagaa ggctatcgtt  9360
gatctcttgt tcaagaccaa cagaaaggtg accgtgaagc agctcaaaga ggattacttc  9420
aagaaaatcg agtgcttcga ttcagttgag atttctggtg ttgaggatag gttcaacgca  9480
tctctcggaa cctaccacga tctcctcaag atcattaagg ataaggattt cttggataac  9540
gaggaaaacg aggatatctt ggaggatatc gttcttaccc tcaccctctt tgaagataga  9600
gagatgattg aagaaaggct caagacctac gctcatctct tcgatgataa ggtgatgaag  9660
cagttgaaga gaagaagata cactggttgg ggaaggctct caagaaagct cattaacgga  9720
atcagggata agcagtctgg aaagacaatc cttgatttcc tcaagtctga tggattcgct  9780
aacagaaact tcatgcagct catccacgat gattctctca cctttaaaga ggatatccag  9840
aaggctcagg tttcaggaca gggtgatagt ctccatgagc atatcgctaa cctcgctgga  9900
tctcctgcaa tcaagaaggg aatcctccag actgtgaagg ttgtggatga gttggtgaag  9960
gtgatgggaa ggcataagcc tgagaacatc gtgatcgaaa tggctagaga gaaccagacc  10020
actcagaagg gacagaagaa ctctagggaa aggatgaaga ggatcgagga aggtatcaaa  10080
gagcttggat ctcagatcct caaagagcac cctgttgaga acactcagct ccagaatgag  10140
aagctctacc tctactacct ccagaacgga agggatatgt atgtggatca agagttggat  10200
atcaacaggc tctctgatta cgatgttgat catatcgtgc cacagtcatt cttgaaggat  10260
gattctatcg ataacaaggt gctcaccagg tctgataaga acaggggtaa gagtgataac  10320
gtgccaagtg aagaggttgt gaagaaaatg aagaactatt ggaggcagct cctcaacgct  10380
aagctcatca ctcagagaaa gttcgataac ttgactaagg ctgagagggg aggactctct  10440
gaattggata aggcaggatt catcaagagg cagcttgtgg aaaccaggca gatcactaag  10500
cacgttgcac agatcctcga ttctaggatg aacaccaagt acgatgagaa cgataagttg  10560
atcagggaag tgaaggttat caccctcaag tcaaagctcg tgtctgattt cagaaaggat  10620
ttccaattct acaaggtgag ggaaatcaac aactaccacc acgctcacga tgcttacctt  10680
aacgctgttg ttggaaccgc tctcatcaag aagtatccta agctcgagtc agagttcgtg  10740
tacggtgatt acaaggtgta cgatgtgagg aagatgatcg ctaagtctga gcaagagatc  10800
ggaaaggcta ccgctaagta tttcttctac tctaacatca tgaatttctt caagaccgag  10860
attaccctcg ctaacggtga gatcagaaag aggccactca tcgagacaaa cggtgaaaca  10920
ggtgagatcg tgtgggataa gggaagggat ttcgctaccg ttagaaaggt gctctctatg  10980
ccacaggtga acatcgttaa gaaaaccgag gtgcagaccg gtggattctc taaagagtct  11040
atcctcccta agaggaactc tgataagctc attgctagga agaaggattg ggaccctaag  11100
aaatacggtg gtttcgattc tcctaccgtg gcttactctg ttctcgttgt ggctaaggtt  11160
gagaagggaa agagtaagaa gctcaagtct gttaaggaac ttctcggaat cactatcatg  11220
gaaaggtcat ctttcgagaa gaacccaatc gatttcctcg aggctaaggg atacaaagag  11280
gttaagaagg atctcatcat caagctccca aagtactcac tcttcgaact cgagaacggt  11340
agaaagagga tgctcgcttc tgctggtgag cttcaaaagg gaaacgagct tgctctccca  11400
tctaagtacg ttaactttct ttacctcgct tctcactacg agaagttgaa gggatctcca  11460
gaagataacg agcagaagca acttttcgtt gagcagcaca agcactactt ggatgagatc  11520
atcgagcaga tctctgagtt ctctaaaagg gtgatcctcg ctgatgcaaa cctcgataag  11580
gtgttgtctg cttacaacaa gcacagagat aagcctatca gggaacaggc agagaacatc  11640
atccatctct tcacccttac caacctcggt gctcctgctg ctttcaagta cttcgataca  11700
accatcgata ggaagagata cacctctacc aaagaagtgc tcgatgctac cctcatccat  11760
cagtctatca ctggactcta cgagactagg atcgatctct cacagctcgg tggtgattca  11820
agggctgatc ctaagaagaa gaggaaggtt tgaggcgcgc cgagctccag gcctcccagc  11880
tttcgtccgt atcatcggtt tcgacaacgt tcgtcaagtt caatgcatca gtttcattgc  11940
ccacacacca gaatcctact aagtttgagt attatggcat tggaaaagct gttttcttct  12000
atcatttgtt ctgcttgtaa tttactgtgt tctttcagtt tttgttttcg gacatcaaaa  12060
tgcaaatgga tggataagag ttaataaatg atatggtcct tttgttcatt ctcaaattat  12120
tattatctgt tgtttttact ttaatgggtt gaatttaagt aagaaaggaa ctaacagtgt  12180
gatattaagg tgcaatgtta gacatataaa acagtctttc acctctcttt ggttatgtct  12240
tgaattggtt tgtttcttca cttatctgtg taatcaagtt tactatgagt ctatgatcaa  12300
gtaattatgc aatcaagtta agtacagtat aggcttgagc tccctaggct ttttttcttc  12360
ttcttcgttc atacagtttt tttttgttta tcagcttaca ttttcttgaa ccgtagcttt  12420
cgttttcttc tttttaactt tccattcgga gtttttgtat cttgtttcat agtttgtccc  12480
aggattagaa tgattaggca tcgaaccttc aagaatttga ttgaataaaa catcttcatt  12540
cttaagatat gaagataatc ttcaaaaggc ccctgggaat ctgaaagaag agaagcaggc  12600
ccatttatat gggaaagaac aatagtattt cttatatagg cccatttaag ttgaaaacaa  12660
tcttcaaaag tcccacatcg cttagataag aaaacgaagc tgagtttata tacagctaga  12720
gtcgaagtag tgattggccg ttaatttgag agtccagttt tagagctaga aatagcaagt  12780
taaaataagg ctagtccgtt atcaacttga aaaagtggca ccgagtcggt gctttttttc  12840
tagacccagc tttcttgtac aaagttggca ttacctaggc ccgggcctga ggacgcgtcc  12900
atggttaatt aagacgtccg gaccgactag tggatcctct agagtcgacc tgcaggcatg  12960
caagcttctt cgtcaacatg gtggagcacg acacgcttgt ctactccaaa aatatcaaag  13020
atacagtctc agaagaccaa agggcaattg agacttttca acaaagggta atatccggaa  13080
acctcctcgg attccattgc ccagctatct gtcactttat tgtgaagata gtggaaaagg  13140
aaggtggctc ctacaaatgc catcattgcg ataaaggaaa ggccatcgtt gaagatgcct  13200
ctgccgacag tggtcccaaa gatggacccc cacccacgag gagcatcgtg gaaaaagaag  13260
acgttccaac cacgtcttca aagcaagtgg attgatgtga tatctccact gacgtaaggg  13320
atgacgcaca atcaatccca ctatccttcg caagaccctt ttaaggggga agttcatttc  13380
```

```
atttggagag gacacgctga aatcaccagt ctctctgtac aaatcnatct ctctctataa  13440
tattgtgtaa gtagttccca gataagggaa ttagggttct tatagggttt cgctcagctg  13500
ttgagcatat aagaaaccct tagtcgatag atctgttggg gatctaccat gagcccagaa  13560
cgacgcccgg ccgacatccg ccgtgccacc gaggcggaca tgccggcggt ctgcaccatc  13620
gtcaaccact acatcgagac aagcacggtc aacttccgta ccgagccgca ggaaccgcag  13680
gagtggacgg acgacctcgt ccgtctgcgg gagcgctatc cctggctcgt cgccgaggtg  13740
gacggcgagg tcgccggcat cgcctacgcg ggcccctgga aggcacgcaa cgcctacgac  13800
tggacggccg agtcgaccgt gtacgtctcc ccccgccacc agcggacggg actgggctcc  13860
acgctctaca cccacctgct gaagtccctg gaggcacagg gcttcaagag cgtggtcgct  13920
gtcatcgggc tgcccaacga cccgagcgtg cgcatgcacg aggcgctcgg atatgccccc  13980
cgcggcatgc tgcgggcggc cggcttcaag cacgggaact ggcatgacgt gggtttctgg  14040
cagctggact tcagcctgcc ggtaccgccc cgtccggtcc tgcccgtcac cgagatctga  14100
tgacccaact tagtatgtat ttgtatttgt aaaatacttc tatcaataaa atttctaatt  14160
cctaaaacca aaatccaggg gtaccgaaca agcttggcac tggccgtcgt tttacaacgt  14220
cgtgactggg aaaaccctgg cgttacccaa cttaatcgcc ttgcagcaca tccccctttc  14280
gccagctggc gtaatagcga agaggcccgc accgatcgcc cttcccaaca gttgcgcagc  14340
ctgaatggcg aatgagcttg agcttggatc agattgtcgt ttcccgcctt cagtttaaac  14400
tatcagtgtt tgacaggata tattggcggg taaacctaag agaaaagagc gtttattaga  14460
ataacggata tttaaaaggg cgtgaaaagg tttatccgtt cgtccatttg tatgtgcatg  14520
ccaaccacag ggttcccctc gggatcaa                                      14548

SEQ ID NO: 165         moltype = DNA  length = 20
FEATURE                Location/Qualifiers
source                 1..20
                       mol_type = other DNA
                       organism = synthetic construct
SEQUENCE: 165
gccgttaatt tgagagtcca                                               20

SEQ ID NO: 166         moltype = DNA  length = 96
FEATURE                Location/Qualifiers
source                 1..96
                       mol_type = other DNA
                       organism = synthetic construct
SEQUENCE: 166
gccgttaatt tgagagtcca gttttagagc tagaaatagc aagttaaaat aaggctagtc  60
cgttatcaac ttgaaaaagt ggcaccgagt cggtgc                             96

SEQ ID NO: 167         moltype =   length =
SEQUENCE: 167
000

SEQ ID NO: 168         moltype =   length =
SEQUENCE: 168
000

SEQ ID NO: 169         moltype =   length =
SEQUENCE: 169
000

SEQ ID NO: 170         moltype = DNA  length = 10
FEATURE                Location/Qualifiers
source                 1..10
                       mol_type = genomic DNA
                       organism = Arabidopsis thaliana
SEQUENCE: 170
gacacgtaga                                                          10

SEQ ID NO: 171         moltype =   length =
SEQUENCE: 171
000

SEQ ID NO: 172         moltype = DNA  length = 11
FEATURE                Location/Qualifiers
source                 1..11
                       mol_type = genomic DNA
                       organism = Arabidopsis thaliana
SEQUENCE: 172
ccatttttag t                                                        11

SEQ ID NO: 173         moltype = DNA  length = 10
FEATURE                Location/Qualifiers
source                 1..10
                       mol_type = genomic DNA
                       organism = Arabidopsis thaliana
SEQUENCE: 173
ccatttttgg                                                          10

SEQ ID NO: 174         moltype =   length =
```

```
SEQUENCE: 174
000

SEQ ID NO: 175          moltype =   length =
SEQUENCE: 175
000

SEQ ID NO: 176          moltype =   length =
SEQUENCE: 176
000

SEQ ID NO: 177          moltype = DNA  length = 10
FEATURE                 Location/Qualifiers
source                  1..10
                        mol_type = genomic DNA
                        organism = Arabidopsis thaliana
SEQUENCE: 177
ccatttttag                                                  10

SEQ ID NO: 178          moltype = DNA  length = 10
FEATURE                 Location/Qualifiers
source                  1..10
                        mol_type = genomic DNA
                        organism = Arabidopsis thaliana
SEQUENCE: 178
ccatttttgg                                                  10

SEQ ID NO: 179          moltype =   length =
SEQUENCE: 179
000

SEQ ID NO: 180          moltype =   length =
SEQUENCE: 180
000

SEQ ID NO: 181          moltype =   length =
SEQUENCE: 181
000

SEQ ID NO: 182          moltype =   length =
SEQUENCE: 182
000

SEQ ID NO: 183          moltype =   length =
SEQUENCE: 183
000

SEQ ID NO: 184          moltype =   length =
SEQUENCE: 184
000

SEQ ID NO: 185          moltype =   length =
SEQUENCE: 185
000

SEQ ID NO: 186          moltype =   length =
SEQUENCE: 186
000

SEQ ID NO: 187          moltype =   length =
SEQUENCE: 187
000

SEQ ID NO: 188          moltype =   length =
SEQUENCE: 188
000

SEQ ID NO: 189          moltype = DNA  length = 18
FEATURE                 Location/Qualifiers
source                  1..18
                        mol_type = genomic DNA
                        organism = Arabidopsis thaliana
SEQUENCE: 189
gtttacataa atggaaaa                                         18

SEQ ID NO: 190          moltype = DNA  length = 18
FEATURE                 Location/Qualifiers
source                  1..18
                        mol_type = genomic DNA
```

```
                        organism = Arabidopsis thaliana
SEQUENCE: 190
cttacctttc atggatta                                                18

SEQ ID NO: 191          moltype = DNA  length = 18
FEATURE                 Location/Qualifiers
source                  1..18
                        mol_type = genomic DNA
                        organism = Arabidopsis thaliana
SEQUENCE: 191
ctttccattt ttagtaac                                                18

SEQ ID NO: 192          moltype =   length =
SEQUENCE: 192
000

SEQ ID NO: 193          moltype =   length =
SEQUENCE: 193
000

SEQ ID NO: 194          moltype =   length =
SEQUENCE: 194
000

SEQ ID NO: 195          moltype = DNA  length = 10
FEATURE                 Location/Qualifiers
source                  1..10
                        mol_type = genomic DNA
                        organism = Arabidopsis thaliana
SEQUENCE: 195
aaacaatcta                                                         10

SEQ ID NO: 196          moltype = DNA  length = 15
FEATURE                 Location/Qualifiers
source                  1..15
                        mol_type = genomic DNA
                        organism = Arabidopsis thaliana
SEQUENCE: 196
aaaaaaaatc tatga                                                   15

SEQ ID NO: 197          moltype =   length =
SEQUENCE: 197
000

SEQ ID NO: 198          moltype =   length =
SEQUENCE: 198
000

SEQ ID NO: 199          moltype =   length =
SEQUENCE: 199
000

SEQ ID NO: 200          moltype =   length =
SEQUENCE: 200
000

SEQ ID NO: 201          moltype =   length =
SEQUENCE: 201
000

SEQ ID NO: 202          moltype =   length =
SEQUENCE: 202
000

SEQ ID NO: 203          moltype =   length =
SEQUENCE: 203
000

SEQ ID NO: 204          moltype = DNA  length = 23
FEATURE                 Location/Qualifiers
source                  1..23
                        mol_type = genomic DNA
                        organism = Arabidopsis thaliana
SEQUENCE: 204
ttcaaggggg catgtatctt gaa                                          23

SEQ ID NO: 205          moltype = DNA  length = 23
FEATURE                 Location/Qualifiers
source                  1..23
```

```
                        mol_type = genomic DNA
                        organism = Arabidopsis thaliana
SEQUENCE: 205
ttcaaggggg catgtatctt gaa                                         23

SEQ ID NO: 206          moltype = DNA  length = 23
FEATURE                 Location/Qualifiers
source                  1..23
                        mol_type = genomic DNA
                        organism = Arabidopsis thaliana
SEQUENCE: 206
ttcaaggggg catgtatctt gaa                                         23

SEQ ID NO: 207          moltype = DNA  length = 29
FEATURE                 Location/Qualifiers
source                  1..29
                        mol_type = genomic DNA
                        organism = Arabidopsis thaliana
SEQUENCE: 207
ggattcaagg gggcatgtat cttgaatcc                                   29

SEQ ID NO: 208          moltype = DNA  length = 11
FEATURE                 Location/Qualifiers
source                  1..11
                        mol_type = genomic DNA
                        organism = Arabidopsis thaliana
SEQUENCE: 208
taagagccgc c                                                      11

SEQ ID NO: 209          moltype =   length =
SEQUENCE: 209
000

SEQ ID NO: 210          moltype =   length =
SEQUENCE: 210
000

SEQ ID NO: 211          moltype =   length =
SEQUENCE: 211
000

SEQ ID NO: 212          moltype =   length =
SEQUENCE: 212
000

SEQ ID NO: 213          moltype =   length =
SEQUENCE: 213
000

SEQ ID NO: 214          moltype =   length =
SEQUENCE: 214
000

SEQ ID NO: 215          moltype = DNA  length = 15
FEATURE                 Location/Qualifiers
source                  1..15
                        mol_type = genomic DNA
                        organism = Arabidopsis thaliana
SEQUENCE: 215
tgtgtggtta atatg                                                  15

SEQ ID NO: 216          moltype =   length =
SEQUENCE: 216
000

SEQ ID NO: 217          moltype =   length =
SEQUENCE: 217
000

SEQ ID NO: 218          moltype =   length =
SEQUENCE: 218
000

SEQ ID NO: 219          moltype = DNA  length = 10
FEATURE                 Location/Qualifiers
source                  1..10
                        mol_type = genomic DNA
                        organism = Arabidopsis thaliana
SEQUENCE: 219
```

```
cgtcaatgaa                                                          10

SEQ ID NO: 220          moltype = DNA  length = 13
FEATURE                 Location/Qualifiers
source                  1..13
                        mol_type = genomic DNA
                        organism = Arabidopsis thaliana
SEQUENCE: 220
catacgtcgt caa                                                      13

SEQ ID NO: 221          moltype =   length =
SEQUENCE: 221
000

SEQ ID NO: 222          moltype = DNA  length = 10
FEATURE                 Location/Qualifiers
source                  1..10
                        mol_type = genomic DNA
                        organism = Arabidopsis thaliana
SEQUENCE: 222
acgtcataga                                                          10

SEQ ID NO: 223          moltype = DNA  length = 10
FEATURE                 Location/Qualifiers
source                  1..10
                        mol_type = genomic DNA
                        organism = Arabidopsis thaliana
SEQUENCE: 223
tctacgtcac                                                          10

SEQ ID NO: 224          moltype =   length =
SEQUENCE: 224
000

SEQ ID NO: 225          moltype = DNA  length = 12
FEATURE                 Location/Qualifiers
source                  1..12
                        mol_type = genomic DNA
                        organism = Arabidopsis thaliana
SEQUENCE: 225
tctaacctac ca                                                       12

SEQ ID NO: 226          moltype =   length =
SEQUENCE: 226
000

SEQ ID NO: 227          moltype =   length =
SEQUENCE: 227
000

SEQ ID NO: 228          moltype =   length =
SEQUENCE: 228
000

SEQ ID NO: 229          moltype =   length =
SEQUENCE: 229
000

SEQ ID NO: 230          moltype =   length =
SEQUENCE: 230
000

SEQ ID NO: 231          moltype =   length =
SEQUENCE: 231
000

SEQ ID NO: 232          moltype = DNA  length = 26
FEATURE                 Location/Qualifiers
source                  1..26
                        mol_type = genomic DNA
                        organism = Arabidopsis thaliana
SEQUENCE: 232
atcttatgtc attgatgacg acctcc                                        26

SEQ ID NO: 233          moltype = DNA  length = 11
FEATURE                 Location/Qualifiers
source                  1..11
                        mol_type = genomic DNA
                        organism = Arabidopsis thaliana
```

```
SEQUENCE: 233
tacactttg g                                                    11

SEQ ID NO: 234          moltype = DNA  length = 20
FEATURE                 Location/Qualifiers
misc_feature            6
                        note = n is c or t
misc_feature            10
                        note = n is c or g
misc_feature            11
                        note = n is a or g
misc_feature            12
                        note = n is a or c
misc_feature            14
                        note = n is g or t
misc_feature            18
                        note = n is c or t
misc_feature            19..20
                        note = n is a or c
source                  1..20
                        mol_type = genomic DNA
                        organism = Arabidopsis thaliana
SEQUENCE: 234
tgacgnaagn nntnacgnnn                                          20

SEQ ID NO: 235          moltype =   length =
SEQUENCE: 235
000

SEQ ID NO: 236          moltype =   length =
SEQUENCE: 236
000

SEQ ID NO: 237          moltype = DNA  length = 20
FEATURE                 Location/Qualifiers
source                  1..20
                        mol_type = genomic DNA
                        organism = Arabidopsis thaliana
SEQUENCE: 237
ttggttttga tcaaaaccaa                                          20

SEQ ID NO: 238          moltype = DNA  length = 15
FEATURE                 Location/Qualifiers
source                  1..15
                        mol_type = genomic DNA
                        organism = Arabidopsis thaliana
SEQUENCE: 238
taattgactc aatta                                               15

SEQ ID NO: 239          moltype =   length =
SEQUENCE: 239
000

SEQ ID NO: 240          moltype =   length =
SEQUENCE: 240
000

SEQ ID NO: 241          moltype =   length =
SEQUENCE: 241
000

SEQ ID NO: 242          moltype =   length =
SEQUENCE: 242
000

SEQ ID NO: 243          moltype =   length =
SEQUENCE: 243
000

SEQ ID NO: 244          moltype = DNA  length = 16
FEATURE                 Location/Qualifiers
source                  1..16
                        mol_type = genomic DNA
                        organism = Arabidopsis thaliana
SEQUENCE: 244
aggggcataa tggtaa                                              16

SEQ ID NO: 245          moltype =   length =
SEQUENCE: 245
```

```
000

SEQ ID NO: 246          moltype =   length =
SEQUENCE: 246
000

SEQ ID NO: 247          moltype =   length =
SEQUENCE: 247
000

SEQ ID NO: 248          moltype =   length =
SEQUENCE: 248
000

SEQ ID NO: 249          moltype = DNA  length = 16
FEATURE                 Location/Qualifiers
source                  1..16
                        mol_type = genomic DNA
                        organism = Arabidopsis thaliana
SEQUENCE: 249
aaaacagaat aggaaa                                                   16

SEQ ID NO: 250          moltype =   length =
SEQUENCE: 250
000

SEQ ID NO: 251          moltype =   length =
SEQUENCE: 251
000

SEQ ID NO: 252          moltype =   length =
SEQUENCE: 252
000

SEQ ID NO: 253          moltype = DNA  length = 12
FEATURE                 Location/Qualifiers
source                  1..12
                        mol_type = genomic DNA
                        organism = Arabidopsis thaliana
SEQUENCE: 253
ccaatttaat gg                                                       12

SEQ ID NO: 254          moltype =   length =
SEQUENCE: 254
000

SEQ ID NO: 255          moltype = DNA  length = 19
FEATURE                 Location/Qualifiers
source                  1..19
                        mol_type = genomic DNA
                        organism = Arabidopsis thaliana
SEQUENCE: 255
cttaaaccct aggggtaat                                                19

SEQ ID NO: 256          moltype =   length =
SEQUENCE: 256
000

SEQ ID NO: 257          moltype =   length =
SEQUENCE: 257
000

SEQ ID NO: 258          moltype =   length =
SEQUENCE: 258
000

SEQ ID NO: 259          moltype =   length =
SEQUENCE: 259
000

SEQ ID NO: 260          moltype = DNA  length = 10
FEATURE                 Location/Qualifiers
source                  1..10
                        mol_type = genomic DNA
                        organism = Arabidopsis thaliana
SEQUENCE: 260
ttgcatgact                                                          10

SEQ ID NO: 261          moltype =   length =
```

```
SEQUENCE: 261
000

SEQ ID NO: 262          moltype =   length =
SEQUENCE: 262
000

SEQ ID NO: 263          moltype =   length =
SEQUENCE: 263
000

SEQ ID NO: 264          moltype =   length =
SEQUENCE: 264
000

SEQ ID NO: 265          moltype =   length =
SEQUENCE: 265
000

SEQ ID NO: 266          moltype =   length =
SEQUENCE: 266
000

SEQ ID NO: 267          moltype = DNA  length = 34
FEATURE                 Location/Qualifiers
source                  1..34
                        mol_type = other DNA
                        organism = synthetic construct
SEQUENCE: 267
gtttaattga gttgtcatat gttaataacg gtat                             34

SEQ ID NO: 268          moltype = DNA  length = 34
FEATURE                 Location/Qualifiers
source                  1..34
                        mol_type = other DNA
                        organism = synthetic construct
SEQUENCE: 268
ataccgttat taacatatga caactcaatt aaac                             34

SEQ ID NO: 269          moltype = DNA  length = 97
FEATURE                 Location/Qualifiers
source                  1..97
                        mol_type = genomic DNA
                        organism = Zea mays
SEQUENCE: 269
tggaggtgcg cgtcaagatc ctcttcacct cgctctgcca caccgacgtc tacttctggg  60
aggccaaggt atctaatcag ccatcccatt tgtgatc                          97

SEQ ID NO: 270          moltype = DNA  length = 97
FEATURE                 Location/Qualifiers
source                  1..97
                        mol_type = other DNA
                        organism = synthetic construct
SEQUENCE: 270
tggaggtgcg cgtcaagatc ctcttcacct cgctctgcca caccgacgtc tacttctggg  60
aggccaaggt atctaatcag ccatcccatt tgtgatc                          97

SEQ ID NO: 271          moltype = DNA  length = 131
FEATURE                 Location/Qualifiers
source                  1..131
                        mol_type = other DNA
                        organism = synthetic construct
SEQUENCE: 271
tggaggtgcg cgtcaagatc ctcttcacct cgctctgcca caccgacgat accgttatta  60
acatatgaca actcaattaa actctacttc tgggaggcca aggtatctaa tcagccatcc  120
catttgtgat c                                                      131

SEQ ID NO: 272          moltype = DNA  length = 98
FEATURE                 Location/Qualifiers
source                  1..98
                        mol_type = other DNA
                        organism = synthetic construct
SEQUENCE: 272
tggaggtgcg cgtcaagatc ctcttcacct cgctctgcca caccgacgtt ctacttctgg  60
gaggccaagg tatctaatca gccatcccat ttgtgatc                         98

SEQ ID NO: 273          moltype = DNA  length = 159
FEATURE                 Location/Qualifiers
source                  1..159
```

```
                        mol_type = other DNA
                        organism = synthetic construct
SEQUENCE: 273
tggaggtgcg cgtcaagatc ctcttcacct cgctctgcca caccgnnnnn gagttgtcat  60
atgttaataa cggtatgttt aattgagttg tcatatgtta ataacggtat tctacttctg  120
ggaggccaag gtatctaatc agccatccca tttgtgatc                         159

SEQ ID NO: 274          moltype = DNA  length = 129
FEATURE                 Location/Qualifiers
source                  1..129
                        mol_type = other DNA
                        organism = synthetic construct
SEQUENCE: 274
tggaggtgcg cgtcaagatc ctcttcacct cgctctgcca caccgacgtt taattgagtt  60
gtcatatgtt aataacggta tctacttctg ggaggccaag gtatctaatc agccatccca  120
tttgtgatc                                                          129

SEQ ID NO: 275          moltype = DNA  length = 97
FEATURE                 Location/Qualifiers
source                  1..97
                        mol_type = other DNA
                        organism = synthetic construct
SEQUENCE: 275
tggaggtgcg cgtcaagatc ctcttcacct cgctctgcca caccgacgtc tacttctggg  60
aggccaaggt atctaatcag ccatcccatt tgtgatc                           97

SEQ ID NO: 276          moltype = DNA  length = 129
FEATURE                 Location/Qualifiers
source                  1..129
                        mol_type = other DNA
                        organism = synthetic construct
SEQUENCE: 276
tggaggtgcg cgtcaagatc ctcttcacct cgctctgcca caccgacgat accgttatta  60
acatatgaca actcaattaa actacttctg ggaggccaag gtatctaatc agccatccca  120
tttgtgatc                                                          129

SEQ ID NO: 277          moltype = DNA  length = 159
FEATURE                 Location/Qualifiers
source                  1..159
                        mol_type = other DNA
                        organism = synthetic construct
SEQUENCE: 277
tggaggtgcg cgtcaagatc ctcttcacct cgctctgcca caccgnnnnn tgagttgtca  60
tatgttaata acggtatgtt aattgagttg tcatatgtta ataacggtat tctacttctg  120
ggaggccaag gtatctaatc agccatccca tttgtgatc                         159

SEQ ID NO: 278          moltype = DNA  length = 92
FEATURE                 Location/Qualifiers
source                  1..92
                        mol_type = other DNA
                        organism = synthetic construct
SEQUENCE: 278
tggaggtgcg cgtcaagatc ctcttcacct cgctctgcca caccgacgtt ctgggaggcc  60
aaggtatcta atcagccatc ccatttgtga tc                                92

SEQ ID NO: 279          moltype = DNA  length = 159
FEATURE                 Location/Qualifiers
source                  1..159
                        mol_type = other DNA
                        organism = synthetic construct
SEQUENCE: 279
tggaggtgcg cgtcaagatc ctcttcacct cgctctgcca caccgnnnnn tattaacata  60
tgacaactca attaaactac cgttattaac atatgacaac tcaattaaac tctacttctg  120
ggaggccaag gtatctaatc agccatccca tttgtgatc                         159

SEQ ID NO: 280          moltype = DNA  length = 159
FEATURE                 Location/Qualifiers
source                  1..159
                        mol_type = other DNA
                        organism = synthetic construct
SEQUENCE: 280
tggaggtgcg cgtcaagatc ctcttcacct cgctctgcca caccgnnnnn gtttaattga  60
gttgtcatat gttaataacg gtattaccgt tattaacata tgacaactca attaaacctg  120
ggaggccaag gtatctaatc agccatccca tttgtgatc                         159

SEQ ID NO: 281          moltype = DNA  length = 159
FEATURE                 Location/Qualifiers
source                  1..159
                        mol_type = other DNA
```

```
                         organism = synthetic construct
SEQUENCE: 281
tggaggtgcg cgtcaagatc ctcttcacct cgctctgcca caccgnnnnn ggtttaattg  60
agttgtcata tgttaataac ggtagtttaa ttgagttgtc atatgttaat aacggtattg  120
ggaggccaag gtatctaatc agccatccca tttgtgatc                         159

SEQ ID NO: 282           moltype = DNA  length = 91
FEATURE                  Location/Qualifiers
source                   1..91
                         mol_type = other DNA
                         organism = synthetic construct
SEQUENCE: 282
tggaggtgcg cgtcaagatc ctcttcacct cgctctgcca caccgacttc tgggaggcca  60
aggtatctaa tcagccatcc catttgtgat c                                 91

SEQ ID NO: 283           moltype = DNA  length = 94
FEATURE                  Location/Qualifiers
source                   1..94
                         mol_type = other DNA
                         organism = synthetic construct
SEQUENCE: 283
tggaggtgcg cgtcaagatc ctcttcacct cgctctgcca caccgacgac ttctgggagg  60
ccaaggtatc taatcagcca tcccatttgt gatc                              94

SEQ ID NO: 284           moltype = DNA  length = 98
FEATURE                  Location/Qualifiers
source                   1..98
                         mol_type = other DNA
                         organism = synthetic construct
SEQUENCE: 284
tggaggtgcg cgtcaagatc ctcttcacct cgctctgcca caccgacgct ctacttctgg  60
gaggccaagg tatctaatca gccatcccat ttgtgatc                          98

SEQ ID NO: 285           moltype = DNA  length = 159
FEATURE                  Location/Qualifiers
source                   1..159
                         mol_type = other DNA
                         organism = synthetic construct
SEQUENCE: 285
tggaggtgcg cgtcaagatc ctcttcacct cgctctgcca caccgnnnnn gagttgtcat  60
atgttaataa cggtatatac cgttattaac atatgacaac tcaattaaac tctacttctg  120
ggaggccaag gtatctaatc agccatccca tttgtgatc                         159

SEQ ID NO: 286           moltype = DNA  length = 159
FEATURE                  Location/Qualifiers
source                   1..159
                         mol_type = other DNA
                         organism = synthetic construct
SEQUENCE: 286
tggaggtgcg cgtcaagatc ctcttcacct cgctctgcca caccgnnnnn ttgagttgtc  60
atatgttaat aacggtatac cgttattaac atatgacaac tcaattaaac tctacttctg  120
ggaggccaag gtatctaatc agccatccca tttgtgatc                         159

SEQ ID NO: 287           moltype = DNA  length = 159
FEATURE                  Location/Qualifiers
source                   1..159
                         mol_type = other DNA
                         organism = synthetic construct
SEQUENCE: 287
tggaggtgcg cgtcaagatc ctcttcacct cgctctgcca caccgnnnnn ttaattgagt  60
tgtcatatgt taataacggt ataccgttat taacatatga caactcaatt aaaccttctg  120
ggaggccaag gtatctaatc agccatccca tttgtgatc                         159

SEQ ID NO: 288           moltype = DNA  length = 96
FEATURE                  Location/Qualifiers
source                   1..96
                         mol_type = other DNA
                         organism = synthetic construct
SEQUENCE: 288
tggaggtgcg cgtcaagatc ctcttcacct cgctctgcca caccgactct acttctggga  60
ggccaaggta tctaatcagc catcccattt gtgatc                            96

SEQ ID NO: 289           moltype = DNA  length = 127
FEATURE                  Location/Qualifiers
source                   1..127
                         mol_type = other DNA
                         organism = synthetic construct
SEQUENCE: 289
tggaggtgcg cgtcaagatc ctcttcacct cgctctgcca caccgacggt ttaattgagt  60
```

```
tgtcatatgt taataacggt atcttctggg aggccaaggt atctaatcag ccatcccatt  120
tgtgatc                                                            127

SEQ ID NO: 290          moltype = DNA  length = 126
FEATURE                 Location/Qualifiers
source                  1..126
                        mol_type = other DNA
                        organism = synthetic construct
SEQUENCE: 290
tggaggtgcg cgtcaagatc ctcttcacct cgctctgcca caccgacgat accgttatta  60
acatatgaca actcaattaa acttctggga ggccaaggta tctaattagc catcccattt  120
gtgatc                                                             126

SEQ ID NO: 291          moltype = DNA  length = 125
FEATURE                 Location/Qualifiers
source                  1..125
                        mol_type = other DNA
                        organism = synthetic construct
SEQUENCE: 291
tggaggtgcg cgtcaagatc ctcttcacct cgctctgcca caccgacggt ttaattgagt  60
tgtcatatgt taataacggt attctgggag gccaaggtat ctaatcagcc atcccatttg  120
tgatc                                                              125

SEQ ID NO: 292          moltype = DNA  length = 128
FEATURE                 Location/Qualifiers
source                  1..128
                        mol_type = other DNA
                        organism = synthetic construct
SEQUENCE: 292
tggaggtgcg cgtcaagatc ctcttcacct cgctctgcca caccgatacc gttattaaca  60
tatgacaact caattaaact ctacttctgg gaggccaagg tatctaatca gccatcccat  120
ttgtgatc                                                           128

SEQ ID NO: 293          moltype = DNA  length = 110
FEATURE                 Location/Qualifiers
source                  1..110
                        mol_type = other DNA
                        organism = synthetic construct
SEQUENCE: 293
tggaggtgcg cgtcaagatc ctcttcacct accgttatta acatatgaca actcaattaa  60
acctacttct gggaggccaa ggtatctaat cagccatccc atttgtgatc             110

SEQ ID NO: 294          moltype = DNA  length = 88
FEATURE                 Location/Qualifiers
source                  1..88
                        mol_type = other DNA
                        organism = synthetic construct
SEQUENCE: 294
tggaggtgcg cgtcaagatc ctcttcacct cgctctgcca caccgacggg gaggccaagg  60
tatctaatca gccatcccat ttgtgatc                                     88

SEQ ID NO: 295          moltype = DNA  length = 104
FEATURE                 Location/Qualifiers
source                  1..104
                        mol_type = other DNA
                        organism = synthetic construct
SEQUENCE: 295
tggaggtgcg cgtcaagatc ctcttcacct cgctctgcca caccgacggt ttaattctac  60
ttctgggagg ccaaggtatc taatcagcca tcccatttgt gatc                   104

SEQ ID NO: 296          moltype = DNA  length = 159
FEATURE                 Location/Qualifiers
source                  1..159
                        mol_type = other DNA
                        organism = synthetic construct
SEQUENCE: 296
tggaggtgcg cgtcaagatc ctcttcacct cgctctgcca caccgnnnnn ccgttattaa  60
catatgacaa ctcaattata ccgttattaa catatgacaa ctcaattaaa cctacttctg  120
ggaggccaag gtatctaatc agccatccca tttgtgatc                         159

SEQ ID NO: 297          moltype = DNA  length = 130
FEATURE                 Location/Qualifiers
source                  1..130
                        mol_type = other DNA
                        organism = synthetic construct
SEQUENCE: 297
tggaggtgcg cgtcaagatc ctcttcacct cgctctgcca caccgacggt ttaattgagt  60
tgtcatatgt taataacggt atctacttct gggaggccaa ggtatctaat cagccatccc  120
atttgtgatc                                                         130
```

```
SEQ ID NO: 298          moltype = DNA  length = 94
FEATURE                 Location/Qualifiers
source                  1..94
                        mol_type = other DNA
                        organism = synthetic construct
SEQUENCE: 298
tggaggtgcg cgtcaagatc ctcttcacct cgctctgcca caccgactac ttctgggagg  60
ccaaggtatc taatcagcca tcccatttgt gatc                              94

SEQ ID NO: 299          moltype = DNA  length = 131
FEATURE                 Location/Qualifiers
source                  1..131
                        mol_type = other DNA
                        organism = synthetic construct
SEQUENCE: 299
tggaggtgcg cgtcaagatc ctcttcacct cgctctgcca caccgacgat accgttatta  60
acatatgaca actcaattaa actctacttc tgggaggcca aggtatctaa tcagccatcc  120
catttgtgat c                                                       131

SEQ ID NO: 300          moltype = DNA  length = 93
FEATURE                 Location/Qualifiers
source                  1..93
                        mol_type = other DNA
                        organism = synthetic construct
SEQUENCE: 300
tggaggtgcg cgtcaagatc ctcttcacct cgctctgcca caccgacact tctgggaggc  60
caaggtatct aatcagccat cccatttgtg atc                               93

SEQ ID NO: 301          moltype = DNA  length = 131
FEATURE                 Location/Qualifiers
source                  1..131
                        mol_type = other DNA
                        organism = synthetic construct
SEQUENCE: 301
tggaggtgcg cgtcaagatc ctcttcacct cgctctgcca caccgacggt ttaattgagt  60
tgtcatatgt taataacggt attctacttc tgggaggcca aggtatctaa tcagccatcc  120
catttgtgat c                                                       131

SEQ ID NO: 302          moltype = DNA  length = 159
FEATURE                 Location/Qualifiers
source                  1..159
                        mol_type = other DNA
                        organism = synthetic construct
SEQUENCE: 302
tggaggtgcg cgtcaagatc ctcttcacct cgctctgcca caccgnnnnn agttgtcata  60
tgttaataac ggtatatacc gttattaaca tatgacaact caattaaaca tctacttctg  120
ggaggccaag gtatctaatc agccatccca tttgtgatc                         159

SEQ ID NO: 303          moltype = DNA  length = 159
FEATURE                 Location/Qualifiers
source                  1..159
                        mol_type = other DNA
                        organism = synthetic construct
SEQUENCE: 303
tggaggtgcg cgtcaagatc ctcttcacct cgctctgcca caccgnnnnn tataatcctc  60
atgtcagcca tggagtattt ggaaatacag aaattcatgg ttggtggaca tctacttctg  120
ggaggccaag gtatctaatc agccatccca tttgtgatc                         159

SEQ ID NO: 304          moltype = DNA  length = 96
FEATURE                 Location/Qualifiers
source                  1..96
                        mol_type = other DNA
                        organism = synthetic construct
SEQUENCE: 304
tggaggtgcg cgtcaagatc ctcttcacct cgctctgcca caccgacgct acttctggga  60
ggccaaggta tctaatcagc catcccattt gtgatc                            96

SEQ ID NO: 305          moltype = DNA  length = 497
FEATURE                 Location/Qualifiers
source                  1..497
                        mol_type = genomic DNA
                        organism = Zea mays
SEQUENCE: 305
gggttgttgt gggttgaacc cgtcccaacc atcatcaact cgctagccaa acacacgctt  60
aggggccaaa gcagtgctat aatatgagtg gtggcgctat tatatatagc gtcagagaac  120
ttagatctga tattctgatg aagaaaaaat gactttactg actacgaaag aagaagaaag  180
gagctataga gagagagaaa aagaggggtc gtgtagtgct taaactgtac atgaacagca  240
gtagtgttac agaagctaaa ctcaaccaga gctccaccaa agacaaagag ggtctacttc  300
```

```
catcaccgtc ttgctcggtc acttggagct ctgtccataa attaaaccca tcttggatcc  360
caaggttcgt ggcatatctg taggcatcta ccccgtcttc gtcgtccgct cctcactagc  420
taccaagagg tcgccattat tgccaacata gagtgtacgt ggatgtctat atatatgcct  480
acttgcaccc atatggc                                                 497

SEQ ID NO: 306          moltype = DNA  length = 34
FEATURE                 Location/Qualifiers
source                  1..34
                        mol_type = other DNA
                        organism = synthetic construct
SEQUENCE: 306
ccgacaaaag gccgacaaaa ggccgacaaa aggt                              34

SEQ ID NO: 307          moltype = DNA  length = 34
FEATURE                 Location/Qualifiers
source                  1..34
                        mol_type = other DNA
                        organism = synthetic construct
SEQUENCE: 307
accttttgtc ggccttttgt cggccttttg tcgg                              34

SEQ ID NO: 308          moltype = DNA  length = 11
FEATURE                 Location/Qualifiers
source                  1..11
                        mol_type = other DNA
                        organism = synthetic construct
SEQUENCE: 308
ccttttgtcg g                                                       11

SEQ ID NO: 309          moltype = DNA  length = 68
FEATURE                 Location/Qualifiers
source                  1..68
                        mol_type = other DNA
                        organism = synthetic construct
SEQUENCE: 309
gccgacaaaa ggccgacaaa aggccgacaa aaggccgaca aaaggccgac aaaaggccga  60
caaaaggt                                                           68

SEQ ID NO: 310          moltype = DNA  length = 68
FEATURE                 Location/Qualifiers
source                  1..68
                        mol_type = other DNA
                        organism = synthetic construct
SEQUENCE: 310
accttttgtc ggccttttgt cggccttttg tcggcctttt gtcggccttt tgtcggcctt  60
ttgtcggc                                                           68

SEQ ID NO: 311          moltype = DNA  length = 100
FEATURE                 Location/Qualifiers
source                  1..100
                        mol_type = other DNA
                        organism = synthetic construct
SEQUENCE: 311
ccgacaaaag gccgacaaaa ggccgacaaa aggccgacaa aaggccgaca aaaggccgac  60
aaaaggccga caaaaggccg acaaaaggcc gacaaaaggt                        100

SEQ ID NO: 312          moltype = DNA  length = 100
FEATURE                 Location/Qualifiers
source                  1..100
                        mol_type = other DNA
                        organism = synthetic construct
SEQUENCE: 312
accttttgtc ggccttttgt cggccttttg tcggcctttt gtcggccttt tgtcggcctt  60
ttgtcggcct tttgtcggcc ttttgtcggc cttttgtcgg                        100

SEQ ID NO: 313          moltype = DNA  length = 21
FEATURE                 Location/Qualifiers
source                  1..21
                        mol_type = other DNA
                        organism = synthetic construct
SEQUENCE: 313
ctccaccaaa gacaaagagg g                                            21

SEQ ID NO: 314          moltype = DNA  length = 21
FEATURE                 Location/Qualifiers
source                  1..21
                        mol_type = other DNA
                        organism = synthetic construct
SEQUENCE: 314
```

```
gccatatggg tgcaagtagg c                                            21

SEQ ID NO: 315          moltype = DNA  length = 226
FEATURE                 Location/Qualifiers
source                  1..226
                        mol_type = other DNA
                        organism = synthetic construct
SEQUENCE: 315
ctccaccaaa gacaaagagg gtctacttcc atcaccgtct tgctcggtca cttggagctc  60
tgtccataaa ttaaacccat cttggatccc aaggttcgtg gcatatctgt aggcatctac  120
cccgtcttcg tcgtccgctc ctcactagct accaagaggt cgccattatt gccaacatag  180
agtgtacgtg gatgtctata tatatgccta cttgcaccca tatggc                 226

SEQ ID NO: 316          moltype = DNA  length = 34
FEATURE                 Location/Qualifiers
source                  1..34
                        mol_type = other DNA
                        organism = synthetic construct
SEQUENCE: 316
ataacttcgt atagcataca ttatacgaag ttat                              34

SEQ ID NO: 317          moltype = DNA  length = 34
FEATURE                 Location/Qualifiers
source                  1..34
                        mol_type = other DNA
                        organism = synthetic construct
SEQUENCE: 317
ataacttcgt ataatgtatg ctatacgaag ttat                              34

SEQ ID NO: 318          moltype = DNA  length = 34
FEATURE                 Location/Qualifiers
source                  1..34
                        mol_type = other DNA
                        organism = synthetic construct
SEQUENCE: 318
ataacttcgt atannntann ntatacgaag ttat                              34

SEQ ID NO: 319          moltype = DNA  length = 34
FEATURE                 Location/Qualifiers
source                  1..34
                        mol_type = other DNA
                        organism = synthetic construct
SEQUENCE: 319
ataacttcgt ataatgtata ctatacgaag ttat                              34

SEQ ID NO: 320          moltype = DNA  length = 34
FEATURE                 Location/Qualifiers
source                  1..34
                        mol_type = other DNA
                        organism = synthetic construct
SEQUENCE: 320
ataacttcgt ataatgtgta ctatacgaag ttat                              34

SEQ ID NO: 321          moltype = DNA  length = 34
FEATURE                 Location/Qualifiers
source                  1..34
                        mol_type = other DNA
                        organism = synthetic construct
SEQUENCE: 321
ataacttcgt ataaagtatc ctatacgaag ttat                              34

SEQ ID NO: 322          moltype = DNA  length = 34
FEATURE                 Location/Qualifiers
source                  1..34
                        mol_type = other DNA
                        organism = synthetic construct
SEQUENCE: 322
ataacttcgt ataagaaacc atatacgaag ttat                              34

SEQ ID NO: 323          moltype = DNA  length = 34
FEATURE                 Location/Qualifiers
source                  1..34
                        mol_type = other DNA
                        organism = synthetic construct
SEQUENCE: 323
ataacttcgt atataatacc atatacgaag ttat                              34

SEQ ID NO: 324          moltype = DNA  length = 34
FEATURE                 Location/Qualifiers
```

```
source                  1..34
                        mol_type = other DNA
                        organism = synthetic construct
SEQUENCE: 324
ataacttcgt ataagataga atatacgaag ttat                                    34

SEQ ID NO: 325          moltype = DNA  length = 34
FEATURE                 Location/Qualifiers
source                  1..34
                        mol_type = other DNA
                        organism = synthetic construct
SEQUENCE: 325
ataacttcgt ataagataga atatacgaag ttat                                    34

SEQ ID NO: 326          moltype = DNA  length = 34
FEATURE                 Location/Qualifiers
source                  1..34
                        mol_type = other DNA
                        organism = synthetic construct
SEQUENCE: 326
taccgttcgt atannntann ntatacgaag ttat                                    34

SEQ ID NO: 327          moltype = DNA  length = 34
FEATURE                 Location/Qualifiers
source                  1..34
                        mol_type = other DNA
                        organism = synthetic construct
SEQUENCE: 327
ataacttcgt atannntann ntatacgaac ggta                                    34

SEQ ID NO: 328          moltype = DNA  length = 11
FEATURE                 Location/Qualifiers
source                  1..11
                        mol_type = other DNA
                        organism = synthetic construct
SEQUENCE: 328
cctcgtgtct c                                                             11

SEQ ID NO: 329          moltype = DNA  length = 11
FEATURE                 Location/Qualifiers
source                  1..11
                        mol_type = other DNA
                        organism = synthetic construct
SEQUENCE: 329
ccttttgtct c                                                             11

SEQ ID NO: 330          moltype = DNA  length = 11
FEATURE                 Location/Qualifiers
misc_feature            10
                        note = n is a, c, or g
source                  1..11
                        mol_type = other DNA
                        organism = synthetic construct
SEQUENCE: 330
ccttttgtcn c                                                             11

SEQ ID NO: 331          moltype =   length =
SEQUENCE: 331
000

SEQ ID NO: 332          moltype =   length =
SEQUENCE: 332
000

SEQ ID NO: 333          moltype = AA  length = 6
FEATURE                 Location/Qualifiers
REGION                  4..5
                        note = MISC_FEATURE - X is any amino acid
source                  1..6
                        mol_type = protein
                        organism = synthetic construct
SEQUENCE: 333
DLNXXP                                                                   6

SEQ ID NO: 334          moltype = RNA  length = 36
FEATURE                 Location/Qualifiers
source                  1..36
                        mol_type = other RNA
                        organism = synthetic construct
```

```
SEQUENCE: 334
ctccaagtga ccgagcaaga gttttagagc tatgct                          36

SEQ ID NO: 335         moltype = DNA  length = 392
FEATURE                Location/Qualifiers
source                 1..392
                       mol_type = genomic DNA
                       organism = Zea mays
SEQUENCE: 335
acaacaaaaa aaggtaacct cgctactaac ataacaaaat acttgttgct tattaattat  60
atgtttttta atctttgatc aggggacaac agtggttgat aacctgttga acagtgagga  120
tgtccactac atgctcgggg ccttgaggac tcttggtctc tctgtcgaag cggacaaagc  180
tgccaaaaga gctgtagttg ttggctgtgg tggaaagttc ccagttgagg attctaaaga  240
ggaagtgcag ctcttcttgg ggaatgctgg aactgcaatg cggccattga cagcagctgt  300
tactgctgct ggtggaaatg caacgtatgt ttcctctctt tctctctaca atacttgctg  360
gagttagtat gaaacccatg ggtatgtcta gt                              392

SEQ ID NO: 336         moltype = RNA  length = 36
FEATURE                Location/Qualifiers
source                 1..36
                       mol_type = other RNA
                       organism = synthetic construct
SEQUENCE: 336
attttgttat gttagtagcg gttttagagc tatgct                          36

SEQ ID NO: 337         moltype = RNA  length = 36
FEATURE                Location/Qualifiers
source                 1..36
                       mol_type = other RNA
                       organism = synthetic construct
SEQUENCE: 337
ggagttagta tgaaacccat gttttagagc tatgct                          36

SEQ ID NO: 338         moltype = DNA  length = 23
FEATURE                Location/Qualifiers
source                 1..23
                       mol_type = other DNA
                       organism = synthetic construct
SEQUENCE: 338
tactaacata acaaaatact tgt                                        23

SEQ ID NO: 339         moltype = DNA  length = 23
FEATURE                Location/Qualifiers
source                 1..23
                       mol_type = other DNA
                       organism = synthetic construct
SEQUENCE: 339
ggtttcatac taactccagc aag                                        23

SEQ ID NO: 340         moltype = DNA  length = 353
FEATURE                Location/Qualifiers
source                 1..353
                       mol_type = other DNA
                       organism = synthetic construct
SEQUENCE: 340
tactaacata acaaaatact tgttgcttat taattatatg ttttttaatc tttgatcagg  60
ggacaacagt ggttgataac ctgttgaaca gtgaggatgt ccactacatg ctcggggcct  120
tgaggactct tggtctctct gtcgaagcgg acaaagctgc caaaagagct gtagttgttg  180
gctgtggtgg aaagttccca gttgaggatt ctaaagagga agtgcagctc ttcttgggga  240
atgctggaat tgcaatgcgg gcattgacag cagctgttac tgctgctggt ggaaatgcaa  300
cgtatgtttc ctctctttct ctctacaata cttgctggag ttagtatgaa acc        353

SEQ ID NO: 341         moltype = DNA  length = 16
FEATURE                Location/Qualifiers
source                 1..16
                       mol_type = genomic DNA
                       organism = Agrobacterium tumefaciens
SEQUENCE: 341
acgtaagcgc ttacgt                                                16

SEQ ID NO: 342         moltype = DNA  length = 15
FEATURE                Location/Qualifiers
source                 1..15
                       mol_type = genomic DNA
                       organism = Zea mays
SEQUENCE: 342
acgtaagcgc ttacg                                                 15

SEQ ID NO: 343         moltype = DNA  length = 12
```

```
FEATURE                Location/Qualifiers
source                 1..12
                       mol_type = genomic DNA
                       organism = Zea mays
SEQUENCE: 343
gtaagcgctt ac                                                  12

SEQ ID NO: 344         moltype = RNA  length = 36
FEATURE                Location/Qualifiers
source                 1..36
                       mol_type = other RNA
                       organism = synthetic construct
SEQUENCE: 344
atagagagag agaaaaagag gttttagagc tatgct                        36

SEQ ID NO: 345         moltype = DNA  length = 672
FEATURE                Location/Qualifiers
source                 1..672
                       mol_type = genomic DNA
                       organism = Zea mays
SEQUENCE: 345
cgataaacgc cactaaaaat ggttttacga ccgccagtat atatcttctc tgtactagtg  60
tgatactatc aggccgcatg cagattcctt tcgattgttt atagggtttt ttttttttata  120
aagactgctg gttttcaagc cttgaatctt gtagctaggt agccagaccg gtcccggccg  180
ggtcgaggaa gacgcaaaac tcagcaagca cagttgtgct agcctgctag gcacggtgtg  240
tagcaagaga cagaaacgag cgtataacca tggcgattaa ctgatagctg tggaattttg  300
agcacatagt cctccaaaca tttgcatttg tattgtacta ttgtttatgt agcgaagttt  360
aaaatgcagt ttggtaggcc taacccgcat gcgagggcac cgcacagtga ggctgaggaa  420
cggaaccact ccagctaaga ttccgcaccg cagcaaccct gggatcctgc tgtcagcgcg  480
ggccgcggga ggggagattc actggcagca gggccccaca ccccttccca ggcttcccat  540
ctcagaaaac agaagccgat ctgttttgtt ctgccgaatc aaaagtgcga tatgatcgtc  600
atctcttcga cagcacccgc ccaaccatct cctataaatc cgatcgccgc cactggccgt  660
tcgtccccca tc                                                  672

SEQ ID NO: 346         moltype = RNA  length = 36
FEATURE                Location/Qualifiers
source                 1..36
                       mol_type = other RNA
                       organism = synthetic construct
SEQUENCE: 346
ccagtgaatc tcccctcccg gttttagagc tatgct                        36

SEQ ID NO: 347         moltype = RNA  length = 36
FEATURE                Location/Qualifiers
source                 1..36
                       mol_type = other RNA
                       organism = synthetic construct
SEQUENCE: 347
cgttcctcag cctcactgtg gttttagagc tatgct                        36

SEQ ID NO: 348         moltype = RNA  length = 36
FEATURE                Location/Qualifiers
source                 1..36
                       mol_type = other RNA
                       organism = synthetic construct
SEQUENCE: 348
cagaaacgag cgtataacca gttttagagc tatgct                        36

SEQ ID NO: 349         moltype = DNA  length = 43
FEATURE                Location/Qualifiers
source                 1..43
                       mol_type = other DNA
                       organism = synthetic construct
SEQUENCE: 349
aagagatgag ctcttgagca atgtaaaggg tcaagttgtt tct                43

SEQ ID NO: 350         moltype = DNA  length = 43
FEATURE                Location/Qualifiers
source                 1..43
                       mol_type = other DNA
                       organism = synthetic construct
SEQUENCE: 350
agaaacaact tgaccctttta cattgctcaa gagctcatct ctt               43

SEQ ID NO: 351         moltype = RNA  length = 34
FEATURE                Location/Qualifiers
source                 1..34
                       mol_type = other RNA
                       organism = synthetic construct
```

```
SEQUENCE: 351
accttttgtc ggccttttgt cggccttttg tcgg                          34

SEQ ID NO: 352         moltype = RNA  length = 21
FEATURE                Location/Qualifiers
source                 1..21
                       mol_type = other RNA
                       organism = synthetic construct
SEQUENCE: 352
tggacagagc tccaagtgac c                                        21

SEQ ID NO: 353         moltype = DNA  length = 38
FEATURE                Location/Qualifiers
source                 1..38
                       mol_type = other DNA
                       organism = synthetic construct
SEQUENCE: 353
tcggtccgac aaaaggccga caaaaggcgg acaaaagg                      38

SEQ ID NO: 354         moltype = DNA  length = 38
FEATURE                Location/Qualifiers
source                 1..38
                       mol_type = other DNA
                       organism = synthetic construct
SEQUENCE: 354
accgaccttt tgtcggcctt ttgtcggcct tttgtcgg                      38

SEQ ID NO: 355         moltype = DNA  length = 346
FEATURE                Location/Qualifiers
source                 1..346
                       mol_type = genomic DNA
                       organism = Oryza sativa
SEQUENCE: 355
aagcggaggt ccggaggagg aagcggcgag agaagctcag ctaggcaggg cgacgggcag  60
aaacgcgacc acggcaacaa accccgccgc gcgcgcccac cgtgccggtt acatgggagt  120
agaggcgggc ggcggctgcg gtgggagggc ggtagtcacc ggattctacg tctggggctg  180
ggagttcctc accgccctcc tgctcttctc ggccaccacc tcctactagc tatacacacc  240
catctcacca taacacacat acatagatag atagatagat agatacatac acacaaacat  300
aagtagctag gtagagaaag agatcatagc gttaggtgat cgatcg                 346

SEQ ID NO: 356         moltype = DNA  length = 117
FEATURE                Location/Qualifiers
source                 1..117
                       mol_type = genomic DNA
                       organism = Oryza sativa
SEQUENCE: 356
atgggagtag aggcgggcgg cggctgcggt gggagggcgg tagtcaccgg attctacgtc  60
tggggctggg agttcctcac cgccctcctg ctcttctcgg ccaccacctc ctactag     117

SEQ ID NO: 357         moltype = DNA  length = 89
FEATURE                Location/Qualifiers
source                 1..89
                       mol_type = genomic DNA
                       organism = Oryza sativa
SEQUENCE: 357
gaggcctcct cctcgcctcg cctcgccacg ccgcgccgcg acgcgacgcg ccgtggtcag  60
ctggtcgccg gtgcgggtgc gggtgcgca                                    89

SEQ ID NO: 358         moltype = DNA  length = 15
FEATURE                Location/Qualifiers
source                 1..15
                       mol_type = other DNA
                       organism = synthetic construct
SEQUENCE: 358
aaaaaaaaaa aaaaa                                                   15

SEQ ID NO: 359         moltype = DNA  length = 25
FEATURE                Location/Qualifiers
source                 1..25
                       mol_type = genomic DNA
                       organism = Arabidopsis thaliana
SEQUENCE: 359
cacatacaca caaaaataaa aaaga                                        25

SEQ ID NO: 360         moltype = DNA  length = 325
FEATURE                Location/Qualifiers
source                 1..325
                       mol_type = genomic DNA
                       organism = Oryza sativa
```

```
SEQUENCE: 360
caaacgccaa aacgccacgg aaacaaatca acaatttcct ctcctgtcaa tgaacttgtg  60
tgcacgacaa ctcatctgac agtgatccat cgtccttttt ctttgactcg atgactttgt  120
gagagatgtt ttatgccgat tttatctact aaagtactta ctaatcctgc ggttgatcca  180
tcgccgcgcg gttcacgcgc caaatgacga gtcgaaatgt atgcgtagtt tgaccacatg  240
catagctcac tggagaagct attagctata tataccgctg caatgctcgc tagcttagct  300
aagcaactgc aagtgaagcg gcgac                                         325

SEQ ID NO: 361          moltype = RNA  length = 36
FEATURE                 Location/Qualifiers
source                  1..36
                        mol_type = other RNA
                        organism = synthetic construct
SEQUENCE: 361
caaacaaaaa agaatgcatg gttttagagc tatgct                             36

SEQ ID NO: 362          moltype = RNA  length = 36
FEATURE                 Location/Qualifiers
source                  1..36
                        mol_type = other RNA
                        organism = synthetic construct
SEQUENCE: 362
tgtatccgta tttatacgtg gttttagagc tatgct                             36

SEQ ID NO: 363          moltype = RNA  length = 36
FEATURE                 Location/Qualifiers
source                  1..36
                        mol_type = other RNA
                        organism = synthetic construct
SEQUENCE: 363
gacgcgagtg ggggcccacg gttttagagc tatgct                             36

SEQ ID NO: 364          moltype = DNA  length = 16
FEATURE                 Location/Qualifiers
source                  1..16
                        mol_type = other DNA
                        organism = synthetic construct
SEQUENCE: 364
gaatatatat atattc                                                   16

SEQ ID NO: 365          moltype = RNA  length = 36
FEATURE                 Location/Qualifiers
source                  1..36
                        mol_type = other RNA
                        organism = synthetic construct
SEQUENCE: 365
gcgctccttc tcctccatgg gttttagagc tatgct                             36

SEQ ID NO: 366          moltype = RNA  length = 36
FEATURE                 Location/Qualifiers
source                  1..36
                        mol_type = other RNA
                        organism = synthetic construct
SEQUENCE: 366
cctcggcgtg gcgctctcgg gttttagagc tatgct                             36

SEQ ID NO: 367          moltype = DNA  length = 550
FEATURE                 Location/Qualifiers
source                  1..550
                        mol_type = genomic DNA
                        organism = Zea mays
SEQUENCE: 367
gtgaacaacc ttatgaaatt tgggcgcaaa gaactcgccc tcaagggttg atcttatgcc  60
atcgtcatga taaacagtgg agcacggacg atcctttacg ttgtttttaa caaactttgt  120
cagaaaacta gcatcattaa cttcttaatg acgatttcac aacaaaaaaa ggtaacctcg  180
ctactaacat aacaaaatac ttgttgctta ttaattatat gtttttttaat ctttgatcag  240
gggacaacag tggttgataa cctgttgaac agtgaggatg tccactacat gctcggggcc  300
ttgaggactc ttggtctctc tgtcgaagcg gacaaagctg ccaaaagagc tgtagttgtt  360
ggctgtggtg gaaagttccc agttgaggat tctaaagagg aagtgcagct cttcttgggg  420
aatgctggaa ctgcaatgcg gccattgaca gcagctgtta ctgctgctgg tggaaatgca  480
acgtatgttt cctctctttc tctctacaat acttgctgga gttagtatga aacccatggg  540
tatgtctagt                                                          550

SEQ ID NO: 368          moltype = RNA  length = 41
FEATURE                 Location/Qualifiers
source                  1..41
                        mol_type = other RNA
                        organism = synthetic construct
SEQUENCE: 368
```

```
taatttctac tcttgtagat ggcgcaaaga actcgccctc a                    41

SEQ ID NO: 369          moltype = RNA  length = 41
FEATURE                 Location/Qualifiers
source                  1..41
                        mol_type = other RNA
                        organism = synthetic construct
SEQUENCE: 369
taatttctac tcttgtagat atactaactc cagcaagtat t                    41

SEQ ID NO: 370          moltype = DNA  length = 45
FEATURE                 Location/Qualifiers
source                  1..45
                        mol_type = other DNA
                        organism = synthetic construct
SEQUENCE: 370
tcaagggtat aacttcgtat agcatacatt atacgaagtt attca                45

SEQ ID NO: 371          moltype = DNA  length = 45
FEATURE                 Location/Qualifiers
source                  1..45
                        mol_type = other DNA
                        organism = synthetic construct
SEQUENCE: 371
cttgatgaat aacttcgtat aatgtatgct atacgaagtt atacc                45

SEQ ID NO: 372          moltype = DNA  length = 45
FEATURE                 Location/Qualifiers
source                  1..45
                        mol_type = other DNA
                        organism = synthetic construct
SEQUENCE: 372
acaatggtat aacttcgtat aaagtatcct atacgaagtt attca                45

SEQ ID NO: 373          moltype = DNA  length = 45
FEATURE                 Location/Qualifiers
source                  1..45
                        mol_type = other DNA
                        organism = synthetic construct
SEQUENCE: 373
attgttgaat aacttcgtat aggatacttt atacgaagtt atacc                45

SEQ ID NO: 374          moltype = DNA  length = 24
FEATURE                 Location/Qualifiers
source                  1..24
                        mol_type = other DNA
                        organism = synthetic construct
SEQUENCE: 374
gtgaacaacc ttatgaaatt tggg                                       24

SEQ ID NO: 375          moltype = DNA  length = 24
FEATURE                 Location/Qualifiers
source                  1..24
                        mol_type = other DNA
                        organism = synthetic construct
SEQUENCE: 375
actagacata cccatgggtt tcat                                       24

SEQ ID NO: 376          moltype = DNA  length = 618
FEATURE                 Location/Qualifiers
source                  1..618
                        mol_type = other DNA
                        organism = synthetic construct
SEQUENCE: 376
gtgaacaacc ttatgaaatt tgggcgcata acttcgtata gcatacatta tacgaagtta  60
taaagaactc gccctcaagg gttgatctta tgccatcgtc atgataaaca gtggagcacg  120
gacgatcctt tacgttgttt ttaacaaact ttgtcagaaa actagcatca ttaacttctt  180
aatgacgatt tcacaacaaa aaaaggtaac ctcgctacta acataacaaa atacttgttg  240
cttattaatt atatgttttt taatctttga tcaggggaca acagtggttg ataacctgtt  300
gaacagtgag gatgtccact acatgctcgg ggccttgagg actcttggtc tctctgtcga  360
agcggacaaa gctgccaaaa gagctgtagt tgttggctgt ggtggaaagt tcccagttga  420
ggattctaaa gaggaagtgc agctcttctt ggggaatgct ggaattgcaa tgcgggcatt  480
gacagcagct gttactgctg ctggtggaaa tgcaacgtat gtttcctctc tttctctcta  540
caatacttgc ataacttcgt ataaagtatc ctatacgaag ttattggagt tagtatgaaa  600
cccatgggta tgtctagt                                               618

SEQ ID NO: 377          moltype = DNA  length = 92
FEATURE                 Location/Qualifiers
source                  1..92
```

```
                        mol_type = other DNA
                        organism = synthetic construct
SEQUENCE: 377
attaaaaaaa taaataagat attattaaaa aaataaataa gatattatta aaaaaataaa  60
taagatatta ttaaaaaaat aaataagata tt                                92

SEQ ID NO: 378          moltype = DNA  length = 36
FEATURE                 Location/Qualifiers
source                  1..36
                        mol_type = other DNA
                        organism = synthetic construct
SEQUENCE: 378
ttatttattt tatttatttt atttatttta tttatt                            36

SEQ ID NO: 379          moltype = DNA  length = 111
FEATURE                 Location/Qualifiers
source                  1..111
                        mol_type = other DNA
                        organism = synthetic construct
SEQUENCE: 379
atggaagaaa ccaaacgaaa ctccgatctt ctccgttctc gtgttttcct ctctggcttt  60
tattgctggg attgggaatt tctcaccgct ctcttgcttt ttagttgctg a           111

SEQ ID NO: 380          moltype = DNA  length = 92
FEATURE                 Location/Qualifiers
source                  1..92
                        mol_type = other DNA
                        organism = synthetic construct
SEQUENCE: 380
agatctagga gactgacata gattggagga gacattttgt ataataagat ctaggagact  60
gacatagatt ggaggagaca ttttgtataa ta                                92

SEQ ID NO: 381          moltype = DNA  length = 201
FEATURE                 Location/Qualifiers
source                  1..201
                        mol_type = genomic DNA
                        organism = Zea mays
SEQUENCE: 381
tccatcctcg ctctacctgc ctgctgccag tttcaactct ccaaggtcaa cgccagccct  60
cgcgcgcttg gtgtactcta gtttagtaca ccaatccgca tgcattcttt tttgtttgtt  120
tgtttgtttg tttgttttga ttgacaaata tatgcggcag agttaagaac gaatcgactc  180
cgtcgtctcg gctagtcgac c                                            201

SEQ ID NO: 382          moltype = DNA  length = 201
FEATURE                 Location/Qualifiers
source                  1..201
                        mol_type = genomic DNA
                        organism = Zea mays
SEQUENCE: 382
aggggcttga cgccttacca gtacgcggtg ctccctcttc tcgcacctac cgcacggagg  60
atatgaccta atacaattaa tttacgcgga actcgaaatg tatccgtatt tatacgtgtg  120
gaacgtacaa gtatacgtat tttgttggtt ttttttttac tttttacccg gctggacgcc  180
aaccaactgg tttcccgtcc t                                            201

SEQ ID NO: 383          moltype = DNA  length = 201
FEATURE                 Location/Qualifiers
source                  1..201
                        mol_type = genomic DNA
                        organism = Zea mays
SEQUENCE: 383
cgggcccacg ggaggtcgcg tcgattcgca gcagcgcgcc gcccccctcc ccaccaccac  60
gtcaagcggc gtgggcttcc gcccctccct gcccgccgcg tgggccccca ctcgcgtcct  120
gtaaccggga tagcgtgagc acgtcgctat cgtccgtaac ggcgaccgcg accataagag  180
aggaggcaaa gccagccccc g                                            201

SEQ ID NO: 384          moltype = DNA  length = 201
FEATURE                 Location/Qualifiers
source                  1..201
                        mol_type = genomic DNA
                        organism = Zea mays
SEQUENCE: 384
agcacggacg atcctttacg ttgtttttaa caaactttgt cagaaaacta gcatcattaa  60
cttcttaatg acgatttcac aacaaaaaaa ggtaacctcg ctactaacat aacaaaatac  120
ttgttgctta ttaattatat gttttttaat ctttgatcag gggacaacag tggttgataa  180
cctgttgaac agtgaggatg t                                            201

SEQ ID NO: 385          moltype = DNA  length = 201
FEATURE                 Location/Qualifiers
source                  1..201
```

```
                        mol_type = genomic DNA
                        organism = Zea mays
SEQUENCE: 385
attccgttgg acccctaccg ctcctcagtc agtcctcgcc cctcccagca ccggccaaca  60
atccctcacg ttattccctg tagctactat gctgccctct tggatccctt tttcacttgt  120
ctgagattta gccaccgccc ggtaggaaga agaaggggaa gcaccatatt ttctgttcct  180
ggcctgacgc agcgccggtg a                                           201

SEQ ID NO: 386          moltype = DNA  length = 280
FEATURE                 Location/Qualifiers
source                  1..280
                        mol_type = genomic DNA
                        organism = Zea mays
SEQUENCE: 386
caagcaagca ggttcagaag aagaacacgg agaaacttga agtaatgcta ggtaggttag  60
cacgaagtag tttctgcgcg ttctctgtga tcttttggca tttgtttttg gctgctggtg  120
gcttaccatc gtcagatggt gacggaggaa ggagggaaca tggatctgga tggtgtgagc  180
cacagattac attacagtag tagagtaaac tatgagagtt cttgtggact gaaggtgtgt  240
agtggtggat agggtagctt ctccggggtt cttttgtgtg                       280

SEQ ID NO: 387          moltype = DNA  length = 307
FEATURE                 Location/Qualifiers
source                  1..307
                        mol_type = genomic DNA
                        organism = Zea mays
SEQUENCE: 387
gacttctgag cgaggagtgg acgagtggtg tgccgtcgtc cggttcccgt tggtttggcg  60
atgaggcgcg ctcgcggtcg ccgcgggctg ctgcttctcc tcggcgtggc gctctcggcg  120
gctgcgctgc tccgtggctg cgcggggcag caaggggagg acggctcgga cgcccctgcg  180
gcggcggcgg cggagacggc ccccatggag gagaaggagc gcagggcgct gtacgccgcc  240
atcgagagct tcgtcggcaa ggggtggaac ggctccgggc tctacccaga cccctgcggc  300
tggtctc                                                           307

SEQ ID NO: 388          moltype = DNA  length = 546
FEATURE                 Location/Qualifiers
source                  1..546
                        mol_type = genomic DNA
                        organism = Glycine max
SEQUENCE: 388
aatttaatct aatggtagat aatgtgttca aaggaacgct tgataacatt tctcgtgata  60
aatacgtatt tatgagacta tttagttatg atcatccatg tcaattaatt tccaacccaa  120
agtaatgatc atgtgccaag ttgccaccca taatttatct caaaattaat gaaacccaaa  180
taaaggcgtt gaataatacc accatacaaa agtgtgttat ttagcagcat atgtaactag  240
gcatatatct atctgtatat atgagagttg attatgtgtc acatatgaac ctttgagaca  300
taccatgggt tctttttggc atacgcggcg aaatggatta cgtcaaatac agcttttgtt  360
taatgcttaa agctttggca gccgatggaa atttcattgg cattgtcaac gccttcccct  420
actataagta caatcacact ccttgtctct ccctcacaac actaggcctt caatttggtt  480
ttgtttcatc agttttccag atacagcaca ttgattgtta aggcgaaatg gctgatattg  540
agggtt                                                            546

SEQ ID NO: 389          moltype = DNA  length = 474
FEATURE                 Location/Qualifiers
source                  1..474
                        mol_type = genomic DNA
                        organism = Glycine max
SEQUENCE: 389
ttgtttactc ctagttatta tcttaaaaaa attgaatcat ataattatat attaagtttt  60
gaatatgtgt ttccatctta tagtttatga gattaccatg tgtttaacag attgggatct  120
acaaacttta aaagtaagca gtagatacat aatagtttta taggcctggt tggttagctg  180
aaatttacag ctactacgcg gataatgaac cccaatgatg aaaacatgca gacgcatgtt  240
gcagcatgga agtattttat ttaataagaa taataataag gtaagtggta gtaattaaat  300
tccatattca gtatcatggg aaatgagatt ctttgccttt gggatacacc attaggcttt  360
tagccgttcc actgtgtata tgcggcgaaa tgcattactc catggccctt gggaatccac  420
ttgcctccta tcagactctt acgtagtcaa cgccttcgcc tactataaaa acac       474

SEQ ID NO: 390          moltype = DNA  length = 514
FEATURE                 Location/Qualifiers
source                  1..514
                        mol_type = genomic DNA
                        organism = Glycine max
SEQUENCE: 390
aaagaagcta tgaggtgcaa gaaccgatca catggagaag gcaatgaaag acaaggagga  60
gcaatggaag agagaaaatg agaagatgga agggatgtga aaatgtttga aaaaaacgag  120
gtgatcagtt ttaaaatacg aatttagtat tttcttttta agaaaattct ttcggaaagt  180
cgtgttttaa aacatgactt ttatttattt gaagtcgtgt tctaaaacat gactttattt  240
catatccttt aatattttat atccttaata tttttaaaat ttatccattt gtaatatttt  300
ttaaaaattg acccatatat gtaaaatacc cgtcaagatc tctttattat tttgaaagcg  360
aaagcatatc acttcaaaca caatggaatc gaggctattg actaagtata aatagagaag  420
acttcatatc ggggttcata attcataaca aagcaaacga gtatataaga aagcataagc  480
```

```
caaattttga gtaaactagt gtgcacacta tccc                              514

SEQ ID NO: 391         moltype = DNA  length = 476
FEATURE                Location/Qualifiers
source                 1..476
                       mol_type = genomic DNA
                       organism = Glycine max
SEQUENCE: 391
cacgtggccc cacacacatt tttttccct caacagttaa actctcttcc tccatctttc  60
ttggtaggtg gcacttctcg gagcatagta aaactaaccc cacattttc tttttcattt  120
tcattttcat tatattataa acctatatat atacccaatt ggttattggt gtctggtgtc  180
ccttcaacct ttaaaacaaa caaatccatt ttctttttct tttttttttc attttatttt  240
ttccattatt ttatcaacac aattaattcc atgtgtatcc tttggtcctt tctgtcccac  300
agcacatata tatagtctcg ctttacatac tcattccatg gccagtacac acaccacacc  360
tcattatatc tttctttcaa ttcctatcct cttccttgta gtgtacccat tttgaatgtg  420
ttctctctct ctctctcttt ctttaggtcc ctggtgaata tctagaacca ctctct      476

SEQ ID NO: 392         moltype = DNA  length = 367
FEATURE                Location/Qualifiers
source                 1..367
                       mol_type = genomic DNA
                       organism = Solanum lycopersicum
SEQUENCE: 392
ataagtatgt gcgtaaaagt ctaagtggag tcacgtgtgt atgatatgag gtcacattag  60
aattgttact agaaaagata tgaaggaatc ttttcatttt tattttattt tctttttaca  120
tagagtaaac aaaaaaaatt gactggaatt gaagtggtaa gccaaaaaat gtgagaatac  180
atgaaaaagt gtgagagaag tcacgtgtgt atggtatgag gtcacatgaa tattattgcc  240
gaaaatgata tgagagaatc ttttcatttt tattttattt tctttttaa acagagtaaa  300
aaaaattaag tgtgtatata tatatatgag aaatggggaa acaaattatc aaacataatt  360
accattg                                                            367

SEQ ID NO: 393         moltype = DNA  length = 464
FEATURE                Location/Qualifiers
source                 1..464
                       mol_type = genomic DNA
                       organism = Solanum lycopersicum
SEQUENCE: 393
attacataaa gatacaacta taatctgacc tagcttataa aggatgtgaa atctaaaatg  60
atgatatata ccttgataaa aaaattttgc tacatcgcct tttgcaatta tttcattttg  120
aaagtattca tatttgttta taaaaaattt tcaaatattt taataaataa ataaataaaa  180
ttatatttta tttatgattt tcaaatatgt caatgatata aatgattagc tataaatctc  240
ataaatttct atatagactt attaaaataa agtataaaaa gattttattt tatttttgaa  300
atacgaaaaa tatgcgtgct tgagcctcta actacctcct atataaatga tgaaagaaaa  360
tgttaggtgt gagaagtata tatccttatc ccaactttgg aatttcaaat cgtttgatta  420
ttaagttatt tgtttgttgt ggaaattaaa tatgattcaa aggg                   464

SEQ ID NO: 394         moltype = DNA  length = 376
FEATURE                Location/Qualifiers
source                 1..376
                       mol_type = genomic DNA
                       organism = Solanum lycopersicum
SEQUENCE: 394
caacccttta atgtcacatt tcttgtttgg tcttgtgaat ttaagtctgc aactgtcaca  60
aaaatcatac tactatatta atgtgttgca tttatcgcca tttttttaat actgttttct  120
tgcttagcaa atattactat acttgggcgg attctccaaa tcccatgtgc aattaaaatt  180
acaaactttg ttatttactc cattttcttg gatctctcta tgacttgtct ttttctaatt  240
ttctatatat ttaccaacat gttatgttga attaaaagaa gaaaaaaaac aagaagattt  300
agttttttttt atttttgtgt gtgtgtgttt gagaaaatga gtagtattac ttattctaat  360
ttgatattga agagga                                                  376

SEQ ID NO: 395         moltype = DNA  length = 434
FEATURE                Location/Qualifiers
source                 1..434
                       mol_type = genomic DNA
                       organism = Glycine max
SEQUENCE: 395
caaaaattaa ttcttttagt aatgatagaa tctaatatct taattcaatg attaattata  60
acttaagtct tcctttaaaa taaatctcat ctcatctcct tcttcctttt ttgagagaga  120
atctcatctc attcttcggt gatcaaatct agtgccagta ccgtacttgg tacgctacct  180
tcacttgcct atgtgcttat cagctatcac ctacctttca taatttaata taaaaaataa  240
ataaacaatg tcgctgcaaa gcatgttcat gttcattaat tcatttttat tattaaaaaa  300
aaaacacccc tttattaggc ggcggaaaaa ctcacggtat ctttccacca ctttctttat  360
ctttagagat cttcttttat atatatatat atatatagat agatagatag atagatacag  420
agatgaaaaa tact                                                    434

SEQ ID NO: 396         moltype = DNA  length = 269
FEATURE                Location/Qualifiers
source                 1..269
                       mol_type = genomic DNA
```

```
                         organism = Glycine max
SEQUENCE: 396
atcggatttc attgggatcc atataattgc gttttcaatt tctgtgtcct taaacaagct  60
atgccagaga attaatttaa ttttaagtgt tagctttatt attttacttt caaatcattg  120
aggaaaacaa tggcctatat attattccta tatgtaacat acaataatgt tattgcaata  180
gcgtgtactt caacctaatt atttaatacc aagtttctat attaatgttg tatcttatga  240
aatccttcta ttttccattc tataaatta                                     269

SEQ ID NO: 397           moltype = RNA  length = 36
FEATURE                  Location/Qualifiers
source                   1..36
                         mol_type = other RNA
                         organism = synthetic construct
SEQUENCE: 397
caaacaaaaa agaatgcatg gttttagagc tatgct                             36

SEQ ID NO: 398           moltype = RNA  length = 36
FEATURE                  Location/Qualifiers
source                   1..36
                         mol_type = other RNA
                         organism = synthetic construct
SEQUENCE: 398
tgtatccgta tttatacgtg gttttagagc tatgct                             36

SEQ ID NO: 399           moltype = RNA  length = 36
FEATURE                  Location/Qualifiers
source                   1..36
                         mol_type = other RNA
                         organism = synthetic construct
SEQUENCE: 399
gacgcgagtg ggggcccacg gttttagagc tatgct                             36

SEQ ID NO: 400           moltype = RNA  length = 36
FEATURE                  Location/Qualifiers
source                   1..36
                         mol_type = other RNA
                         organism = synthetic construct
SEQUENCE: 400
attttgttat gttagtagcg gttttagagc tatgct                             36

SEQ ID NO: 401           moltype = RNA  length = 36
FEATURE                  Location/Qualifiers
source                   1..36
                         mol_type = other RNA
                         organism = synthetic construct
SEQUENCE: 401
aagtgaaaaa gggatccaag gttttagagc tatgct                             36

SEQ ID NO: 402           moltype = RNA  length = 36
FEATURE                  Location/Qualifiers
source                   1..36
                         mol_type = other RNA
                         organism = synthetic construct
SEQUENCE: 402
gcaggttcag aagaagaaca gttttagagc tatgct                             36

SEQ ID NO: 403           moltype = RNA  length = 35
FEATURE                  Location/Qualifiers
source                   1..35
                         mol_type = other RNA
                         organism = synthetic construct
SEQUENCE: 403
ccatgtcaga tggtgacggg ttttagagct atgct                              35

SEQ ID NO: 404           moltype = RNA  length = 36
FEATURE                  Location/Qualifiers
source                   1..36
                         mol_type = other RNA
                         organism = synthetic construct
SEQUENCE: 404
tggatagggt agcttctccg gttttagagc tatgct                             36

SEQ ID NO: 405           moltype = RNA  length = 34
FEATURE                  Location/Qualifiers
source                   1..34
                         mol_type = other RNA
                         organism = synthetic construct
SEQUENCE: 405
gcgctccttc tcctccatgt tttagagcta tgct                               34
```

```
SEQ ID NO: 406          moltype = RNA  length = 36
FEATURE                 Location/Qualifiers
source                  1..36
                        mol_type = other RNA
                        organism = synthetic construct
SEQUENCE: 406
cctcggcgtg gcgctctcgg gttttagagc tatgct                          36

SEQ ID NO: 407          moltype = RNA  length = 36
FEATURE                 Location/Qualifiers
source                  1..36
                        mol_type = other RNA
                        organism = synthetic construct
SEQUENCE: 407
agtgttgtga gggagagaca gttttagagc tatgct                          36

SEQ ID NO: 408          moltype = RNA  length = 36
FEATURE                 Location/Qualifiers
source                  1..36
                        mol_type = other RNA
                        organism = synthetic construct
SEQUENCE: 408
gaacctttga gacataccat gttttagagc tatgct                          36

SEQ ID NO: 409          moltype = RNA  length = 36
FEATURE                 Location/Qualifiers
source                  1..36
                        mol_type = other RNA
                        organism = synthetic construct
SEQUENCE: 409
gggttggaaa ttaattgaca gttttagagc tatgct                          36

SEQ ID NO: 410          moltype = RNA  length = 36
FEATURE                 Location/Qualifiers
source                  1..36
                        mol_type = other RNA
                        organism = synthetic construct
SEQUENCE: 410
atttcgccgc atatacacag gttttagagc tatgct                          36

SEQ ID NO: 411          moltype = RNA  length = 36
FEATURE                 Location/Qualifiers
source                  1..36
                        mol_type = other RNA
                        organism = synthetic construct
SEQUENCE: 411
tgaaatttac agctactacg gttttagagc tatgct                          36

SEQ ID NO: 412          moltype = RNA  length = 36
FEATURE                 Location/Qualifiers
source                  1..36
                        mol_type = other RNA
                        organism = synthetic construct
SEQUENCE: 412
atcccaatct gttaaacaca gttttagagc tatgct                          36

SEQ ID NO: 413          moltype = RNA  length = 36
FEATURE                 Location/Qualifiers
source                  1..36
                        mol_type = other RNA
                        organism = synthetic construct
SEQUENCE: 413
gtgatagctg ataagcacat gttttagagc tatgct                          36

SEQ ID NO: 414          moltype = RNA  length = 36
FEATURE                 Location/Qualifiers
source                  1..36
                        mol_type = other RNA
                        organism = synthetic construct
SEQUENCE: 414
ttaggcggcg gaaaaactca gttttagagc tatgct                          36

SEQ ID NO: 415          moltype = RNA  length = 36
FEATURE                 Location/Qualifiers
source                  1..36
                        mol_type = other RNA
                        organism = synthetic construct
SEQUENCE: 415
```

```
tctctctcaa aaaaggaaga gttttagagc tatgct                          36

SEQ ID NO: 416          moltype = RNA  length = 36
FEATURE                 Location/Qualifiers
source                  1..36
                        mol_type = other RNA
                        organism = synthetic construct
SEQUENCE: 416
gaaaatgttt gaaaaaaacg gttttagagc tatgct                          36

SEQ ID NO: 417          moltype = RNA  length = 36
FEATURE                 Location/Qualifiers
source                  1..36
                        mol_type = other RNA
                        organism = synthetic construct
SEQUENCE: 417
atagagaaga cttcatatcg gttttagagc tatgct                          36

SEQ ID NO: 418          moltype = RNA  length = 36
FEATURE                 Location/Qualifiers
source                  1..36
                        mol_type = other RNA
                        organism = synthetic construct
SEQUENCE: 418
aataataaag agatcttgac gttttagagc tatgct                          36

SEQ ID NO: 419          moltype = RNA  length = 36
FEATURE                 Location/Qualifiers
source                  1..36
                        mol_type = other RNA
                        organism = synthetic construct
SEQUENCE: 419
attttacttt caaatcattg gttttagagc tatgct                          36

SEQ ID NO: 420          moltype = RNA  length = 36
FEATURE                 Location/Qualifiers
source                  1..36
                        mol_type = other RNA
                        organism = synthetic construct
SEQUENCE: 420
cattattgta tgttacatat gttttagagc tatgct                          36

SEQ ID NO: 421          moltype = RNA  length = 36
FEATURE                 Location/Qualifiers
source                  1..36
                        mol_type = other RNA
                        organism = synthetic construct
SEQUENCE: 421
aaatgaaaaa gaaaaatgtg gttttagagc tatgct                          36

SEQ ID NO: 422          moltype = RNA  length = 36
FEATURE                 Location/Qualifiers
source                  1..36
                        mol_type = other RNA
                        organism = synthetic construct
SEQUENCE: 422
aaaggaccaa aggatacaca gttttagagc tatgct                          36

SEQ ID NO: 423          moltype = RNA  length = 36
FEATURE                 Location/Qualifiers
source                  1..36
                        mol_type = other RNA
                        organism = synthetic construct
SEQUENCE: 423
aagaaagata taatgaggtg gttttagagc tatgct                          36

SEQ ID NO: 424          moltype = RNA  length = 36
FEATURE                 Location/Qualifiers
source                  1..36
                        mol_type = other RNA
                        organism = synthetic construct
SEQUENCE: 424
agtcacgtgt gtatgatatg gttttagagc tatgct                          36

SEQ ID NO: 425          moltype = RNA  length = 36
FEATURE                 Location/Qualifiers
source                  1..36
                        mol_type = other RNA
                        organism = synthetic construct
```

```
SEQUENCE: 425
agtcacgtgt gtatggtatg gttttagagc tatgct                          36

SEQ ID NO: 426          moltype = RNA  length = 36
FEATURE                 Location/Qualifiers
source                  1..36
                        mol_type = other RNA
                        organism = synthetic construct
SEQUENCE: 426
atatatatat atgagaaatg gttttagagc tatgct                          36

SEQ ID NO: 427          moltype = RNA  length = 36
FEATURE                 Location/Qualifiers
source                  1..36
                        mol_type = other RNA
                        organism = synthetic construct
SEQUENCE: 427
tttatatagg aggtagttag gttttagagc tatgct                          36

SEQ ID NO: 428          moltype = RNA  length = 36
FEATURE                 Location/Qualifiers
source                  1..36
                        mol_type = other RNA
                        organism = synthetic construct
SEQUENCE: 428
caaaatgaaa taattgcaaa gttttagagc tatgct                          36

SEQ ID NO: 429          moltype = RNA  length = 36
FEATURE                 Location/Qualifiers
source                  1..36
                        mol_type = other RNA
                        organism = synthetic construct
SEQUENCE: 429
aaatgatgaa agaaaatgtt gttttagagc tatgct                          36

SEQ ID NO: 430          moltype = RNA  length = 36
FEATURE                 Location/Qualifiers
source                  1..36
                        mol_type = other RNA
                        organism = synthetic construct
SEQUENCE: 430
tttgtaattt taattgcaca gttttagagc tatgct                          36

SEQ ID NO: 431          moltype = RNA  length = 36
FEATURE                 Location/Qualifiers
source                  1..36
                        mol_type = other RNA
                        organism = synthetic construct
SEQUENCE: 431
tttaattcaa cataacatgt gttttagagc tatgct                          36

SEQ ID NO: 432          moltype = RNA  length = 36
FEATURE                 Location/Qualifiers
source                  1..36
                        mol_type = other RNA
                        organism = synthetic construct
SEQUENCE: 432
agaaaacagt attaaaaaaa gttttagagc tatgct                          36

SEQ ID NO: 433          moltype = DNA  length = 32
FEATURE                 Location/Qualifiers
source                  1..32
                        mol_type = other DNA
                        organism = synthetic construct
SEQUENCE: 433
tttcccgctt tcccgctttc ccgctttccc gc                              32

SEQ ID NO: 434          moltype = DNA  length = 32
FEATURE                 Location/Qualifiers
source                  1..32
                        mol_type = other DNA
                        organism = synthetic construct
SEQUENCE: 434
gcgggaaagc gggaaagcgg gaaagcggga aa                              32

SEQ ID NO: 435          moltype = DNA  length = 1440
FEATURE                 Location/Qualifiers
source                  1..1440
                        mol_type = genomic DNA
```

```
                         organism = Zea mays
SEQUENCE: 435
atgtcggggg tcggcagcgg caggccgccg gccgcccaga agatcctgca gtcgctgcga  60
ccgccgctgt ccttcgccac gccgtcgcgg tcgcccttcg ccgcgcccga cgactaccac  120
cgctttccga caccggctgc ggccacggca cccgccgcca cctcaggcgg cgtcggtgcg  180
ggggctcctc ctcgtgatac tatcgaggag gggctgttca tacggactcc gctgaaaagg  240
aaagctacat ctgaagaaaa tgatgctgct gctgagccaa gcgattgtat cattaccagt  300
ccaatgccca cttcggtctc tggtaaaact gttaaagctt ctaaggcaaa agctaagaac  360
agtaaaactg ggcctcagac acctacatca aatgttggtt caccactcaa tccaccaact  420
cctgttggca cgtgccgcta tgacagttca ctaggacttc tgacaaaaaa gttcattaac  480
ttgctcaagc aagcgccaga tggcattcta gatttgaaca atgctgcaga aacactagag  540
gttcaaaagc gacgcatata tgacattact aatgtccttg aaggcattgg actaatagag  600
aagacactta agaatagaat ccgttggaag gccctggatg attcaagtgt tcaattagat  660
aatggtattt ccgctttgca ggtcttaaca aaaatattat ctaatcaagt gctttgtatc  720
ccattcagtg acatgcgtga aaaactaagg gggttaactg aagatgaaaa taataaaagg  780
tggctctatg tgactgaaga cgacatcaag ggattaccca gctttcagaa tgaaacacta  840
attgctatta aagcacctca tggtactaca cttgaagtac ctgatccaga tgaggcgggt  900
gattatctcc aaaggagata tagaattgta ttaagaagta cgatgggacc aatagatgtt  960
tacttagtta gtcaatttga tgagaaattt gaggaactgg gtggtgttgc gacacccgtc  1020
aagcattcca gtgtgcccag acatcaaccc gcggaagatt tcaatactta tgctggacaa  1080
agtagcacac caatggacgt ggcacatgat gtacagcatg gccagaagat tccccaggat  1140
cctagtgctt tgcatgactt tggagggatg acaaggatta gtccttccga cgtccatacg  1200
gattctgatt actggctcct aacagagggg gatgttagca tgactgatat gtggaaaaca  1260
ggacgtatcc ttgatgatca tgcattaaga tgcttgaatt tcttaacatg gaaaatagaa  1320
gaagtgcagt gggaccagat ggatttcctg tcagaagatg ttgtcacccc tcgagcccat  1380
aatcagcagc cggtcacagt tgacgggcca catatggagg ttccaagcat ggacccataa  1440

SEQ ID NO: 436           moltype = DNA  length = 6507
FEATURE                  Location/Qualifiers
source                   1..6507
                         mol_type = genomic DNA
                         organism = Saccharum officinarum
SEQUENCE: 436
tctcccgtcc cggtgggtcc cggtggtggg tggttcagtg gttggattgg aggacgccac  60
gagtaccgtg ctagtacttg agattgtttt ccctcgcgtc tgggctgcta tttctctcgg  120
atctggagtc cctcgtccga ttcctcatgc cttgttgggt gttttcttcc ccgatcgatg  180
tgttctcgtg atgtcgcgtg aattgctggc gtcaaatcaa ttgcgccgcc gcccgattgc  240
aagctgatgc catcgatgat cgcatcgcag gtgtgggagc tggtgcggag cttcgaccag  300
ccgcagcggt acaagccgtt cgtccggaac tgcgtcgtgc gcggggacca gctcgaggtc  360
ggcagcctgc gcgacgtcaa cgtcaagacc ggcctgccgg cgacaaccag cactgagcgc  420
ctcgagcagc tcgacgacga cctgcacata ctcggcgtca agttcgtcgg cggggaccac  480
cgcctccagg tgagtgctgc tgctccgttt gttgcttccc tgcacatgct ttgtttcatg  540
agccctcctt ggttgtcagt gtactcccat ttttttagta tgcttgcttt gttaccattt  600
tttcttcttt aaattaaatt gtgctttctt gttaccattt cactacaatc gtgatcgctg  660
ggtgctatga atgaaatgca tttgctatgc ttgcgagatt gggaattttt attttttgtg  720
acagataaca tcttggtcct gtttggaagc tgggattggg aatcaaattc ttatgattta  780
ttaggagtat ccagttgaac ctaatcattg tagccatctg ttgaaataaa agcaattagc  840
ttctcgtgag gcactcatcc gctaaaacga gataagccat tggcctaatt accttccttc  900
tcgtgattgt ttgccaccct gaaaggatat gctcacaacc cgtactgttt tgacttctta  960
tccacatata ctatttagta cgaaaggaca tgtcttagag actgttacta cttccattcg  1020
ctgttcttcg tctagccttc agattgataa tataaggtgt aaaactttga tgtttcgtgt  1080
gctgtcaagt gattgtgtag cgaagttttt gtttgtgtca atgcctacag gctacagtgg  1140
ccatctttac tcctacttga agcatgatcc acactgatga tgagttgtgt ttgccacttt  1200
ttcagaacta ctcatccatc ataactgtcc acccggagag cattgacggg aggccaggta  1260
cccttgtgat cgagtcgttc gtggtcgatg tgcctgatgg caacacaaag gatgagacat  1320
gctacttcgt cgaggctgtg atcaagtgca acctcaagtc tcttgcagag gtatctgagc  1380
agctagcagt tgagccacct acatcgccga ttgatcagtg agtcacctgc atcgccggtc  1440
catcagtaac accggtacaa agacgggaat cggcaccaaa taagaagctt caaaggctgg  1500
ctgaagagtt catccttttt gagactggtg gttccgccat cgtcttctgc gtgtatgtct  1560
cttggaatat cgaaggatta gtgttatgta ggattaaata tctgtagtag cttgtatgtt  1620
agggatgatt tagccgtagg aactgcacct acatacctca tggcatgtat gcatactgct  1680
agtatgtgta gaaatcaggg aaagcatgga gctgtttttg ccactttggt gcatggagat  1740
ctatcctttt ttctccattt tgcggtggtt actatattgg ttggggttct tcgataaata  1800
tactttcccg cagacactag ggtctggatc ttggattcta caatgttatt gggatttggg  1860
atttgaactg gatagtggat agtgtctgat ttaatatgtt gttcgaccga tggtttttgc  1920
ggctaataag ccggctgacg ttgttttgct gtgagagaaa aataccgtac catggctaat  1980
aagctggact gataatttca agcgaacaag gtaagctggt tttgttgaca gcaaaataag  2040
atctgcgaga cagatttgaa ccgaagcaat caaaaattcg catcaaatta tatgcaaatt  2100
tacaaatatg gacaaactag cccagttaca aatatggcct agtccggttt ggactgagtg  2160
tgcacagtta gataaaaccg gctcaagctg gttttgaggc tagttttgac tgttaaagga  2220
ggttttgacc tgatctcttt gaaaactcat ccgatcttgt ggccttgcac acctctatgt  2280
atgagagaat cacagccgaa tccaacatac gatcaatcac aaaaacacaa tatctatatt  2340
ttcccatcta tcctactttt ccaatctacc ttttcttctc attcttcatt gtcgctggtg  2400
tttgtcggtt caacaatgac aaagctctag agcgaccagg ccggccctag caacccatcc  2460
caacccatgc cacccatgcc ggggtccctt ctaggctata gattttgggg ggtttcaaca  2520
gaatttacta gcgtgtcttg cgtattgcgc tcctgatgag gttcctttac tgatgtgtct  2580
tgcatgtcat tgtcactgct agaggcacaa ggaaatgttc gtgtgcaaac acacttttag  2640
gcgatggcca acttgaaagt cgtctaggct gattttggcc taccctactg cttttctatc  2700
caagtgttct agctccttgt tgtgaccgat ctttaccatc aacaggtttg ttagaccatt  2760
```

```
taatttaagc aaatcaaata attcatcaaa taattctaag actcattgtt taatgctagg  2820
agttgtgttc ctgtgcaggt ggagtcatgt tgagtgttca agtattgact agtctttttg  2880
agttatgttg gattctcaaa tgtggactac cgagtgctga gttgaagtat tcgtgagtcg  2940
gatgtgaatt gtcgtggatc agagtatgat tttgcaccat ttggattgat ggttatttta  3000
tgaccattga tgatggagta ttaatagaca aattagttat gtcaattaaa aggatcaaga  3060
tgcgaaagag ggaagtggat tgaattaggc taatctaaac ttctcatgga attaaaacct  3120
atcacttagc tcatttcacc cttatgctta aacaagtgtt cctagcttac cgcataaagt  3180
tttgcaccct agttccaatc ctgttctaac atggcaattc tataggaatg taattgaatg  3240
acagtaaatg ttcaaagtaa agaaagggtt aggaacatgt cggtactttc ctaaggtatt  3300
agagagtcgg cactcccgta ctaatcctca ttggagcacc cacgcaaggg tattgctctc  3360
ccttgatccg cgcaaggacc aagtgctctc tacggattga ttcttcacca ctctggcatg  3420
gtgaatcacc tacaaccatt tataccatga gttgggcctc tcacaatcgc caccaagaga  3480
tcaccaagct cctcatcaca accaagcgat ctaggtgatg ccgcgatcac caagagtaac  3540
aagcaaaaac tctcgcttaa cctgaccaag cctaataaga aaagtggatg cacacttgct  3600
acttcttaag cactaatgga gtccttaatg tttgattata gaattcaaat cactctaata  3660
ggccaaagct ctcttgtaca cccataagtg tatgtgtatg ctctgaatgc tgagagagct  3720
tcgagatgag gggcatatag ggcatgtttg gttccctgcc tatcccctaa gcaggcttct  3780
tggagccaac ttaagcctat ttggttggct gaacaaacct cctagctagg ccctagcaag  3840
ccacctaggg gtcttagcct ggctccagta agacgccaaa ctcctgcgtt tttctagagc  3900
caggctctgg ctagccatcg cacgagttct cctcaccgcc tcggcttcga ttttgtttgg  3960
tagttgtgct cctcctcatc attccctact cctctccatc gttccctact cctccccgtt  4020
gttcccgata gtggcgcgag tccaagttgt ggaggagcgg cagcatgcag cggaggaggt  4080
ccacggcagt agtgggctag ccgatgtggc agtatgtgga ggtgaggatg cagaatgtaa  4140
gtacgttggc gcaaaggagc acaatagggg cggtgccgag gagcgccgaa gaatgatagg  4200
acaatgcgac gagggcaacg gtgcaagcta gccatggagc tccaatgacg tgattgagta  4260
ctggccgagc gtgagctcct tctagtggag ttgcaggccg gacacaaaga cgctaccgta  4320
gagcacctcg gtgcgggagg tggaggtgac gcagaggcca tggcatggcg gaggtgatgg  4380
acgcggaggt ggaggtggag gtgttccagc tgaggtcatg ggcatggagg tggaggtggc  4440
gcggcagagg ccatatagag ctgacgtcga gcacaagcga gagcagtcca ccacctgttc  4500
gatagaatgc ttcaatgggg gtaaccttat caagctagag atgcggtgat tctatacaag  4560
acaaagcaag caaccaaata aacaaactct tatggaaacc aggccagaga tagcaaccca  4620
accaaacaaa ccctatttgg cttgctgggg ataggcctag cctaaccagg ctccaatcct  4680
agctaggctc cagctaaggc aggaaaccaa ataggcccat ataggctaca ccccaaaaac  4740
tagtcattgg aaactcactc agccttttct gtactcacca gaaacttcgg tgtagtcttg  4800
tagtgagcac cggaggattc tagtggtcct tctaagtttg ttagaaaact agccattatt  4860
gcgctagcca caataacctt ttctccggtg attctctagt ggtacccacc gaattatgcc  4920
ggtgagccaa aaacctcttt ggatcctctc tgttcactgc tcttttttct ccagtggtct  4980
acacaccctg tgtttcctat gttcattttc ggtgaacctt tctctagtgc tcatcgaaga  5040
aagcggtcaa gtgcatagtg agcatgcctc tgaaaagcac taccattaac tcatgtcctt  5100
cactaaccag agcatcggat aaatctggtg gtcaagaaac acctcccttt tcatccaatt  5160
caagcgcctt tgaaaatggt tcaacttcca attgatctta tggccttcat ctgagctacc  5220
tagtgctagg tttgacaagt gtgcaccaca tacactcact agattgactt aactaagtcg  5280
agctactcgt tcataccgcc ttaatagtac gactaaagaa aaaacaaagt cttaaactac  5340
tctaagtgtc tctcaactca aaacgacact tagaactagt ctgtctttaa ccttgtcgct  5400
catcttttga aaaactaaac aatcaatcat caataggggc atgaaaacca tgattacccc  5460
atcaatcaat aatcattgtg acctcaggaa gtaatgccac tgcaaaacac acattggtca  5520
tcacaattat tgtatcgtca ttaatcacca aaactaaatt agaggcctag atgctttcat  5580
caattactag taatgaacat cattgattct accatcacta gttgttgacg gtctgtactg  5640
ccaaaataaa ccgtcaattt cacttgttag aatccttaaa atcaaacatc accataggtt  5700
tagaagcttt aaactaacaa attccacaag ttttggtgaa tgtttgcatg caggtgaatt  5760
cagtcattct acaggttaaa atggaccaaa gcaagccaat taggaagatc aaaggattct  5820
ggtttacttc acaggatcag cgggcccatt gtcatacaca tcaagtatat aaactgatgt  5880
caacaaatgt gcaagcatgt atatatgtga ccctaggagg tggatccacc tgtctacaaa  5940
aagatggggt caaatggtgc tggaagcagg ccgcccgacc tgtggggatg ccgagtcccc  6000
ccttcgatgt ggactctcca ccgcctctaa ggatcaatct ccaccatgca tgaaggtcgg  6060
tttgaagtca attcatccaa cggtgatcaa ggagttgacg tggactgatg atgtggcaat  6120
gccttgcccc tactccatct cccctataa aggacccct tgacctcctc caaaaggcca  6180
tccattgagt gcaatctcat ttggatcaag acacactagg aggaataggt ctagagctct  6240
ccaatgtagt agattagtag cttgggagtg agggtcgagt tgggctcatg ctcaggttcc  6300
agattaagtc ttggaggctc ggtaaagcca ttgtatcttc acttaaatat cttgtgagac  6360
ttaattatca ctatatcatt cttatctaca tggctatact tactttgaat atatatcttc  6420
cttagttaag gttctcttta cttttgtgtg tgggtttata gagtgcttag cttgctagtt  6480
tgtctactgg gttgagtagc cgagcct                                      6507
```

```
SEQ ID NO: 437          moltype = AA  length = 197
FEATURE                 Location/Qualifiers
source                  1..197
                        mol_type = protein
                        organism = Saccharum officinarum
SEQUENCE: 437
MVGLVGGSTA RAEHVVANAG GETEYVRRLH RHAPAEHQCT STLVKHIKAP VHLVWELVRS  60
FDQPQRYKPF VRNCVVRGDQ LEVGSLRDVN VKTGLPATTS TERLEQLDDD LHILGVKFVG  120
GDHRLQNYSS IITVHPESID GRPGTLVIES FVVDVPDGNT KDETCYFVEA VIKCNLKSLA  180
EVSEQLAVEP PTSPIDQ                                                197
```

```
SEQ ID NO: 438          moltype = DNA  length = 20
FEATURE                 Location/Qualifiers
source                  1..20
                        mol_type = other DNA
```

```
                         organism = synthetic construct
SEQUENCE: 438
ccttgtgatc gagtcgttcg                                          20

SEQ ID NO: 439           moltype = DNA  length = 20
FEATURE                  Location/Qualifiers
source                   1..20
                         mol_type = other DNA
                         organism = synthetic construct
SEQUENCE: 439
ccacgaacga ctcgatcaca                                          20

SEQ ID NO: 440           moltype = RNA  length = 33
FEATURE                  Location/Qualifiers
source                   1..33
                         mol_type = other RNA
                         organism = synthetic construct
SEQUENCE: 440
gtcgacggta tcgataagct tgatatcgaa ttc                           33

SEQ ID NO: 441           moltype = RNA  length = 135
FEATURE                  Location/Qualifiers
source                   1..135
                         mol_type = other RNA
                         organism = synthetic construct
SEQUENCE: 441
ccttgtgatc gagtcgttcg gttttagagc tagaaatagc aagttaaaat aaggctagtc  60
cgttatcaac ttgaaaaagt ggcaccgagt cggtgctttt ttgtcgacgg tatcgataag  120
cttgatatcg aattc                                               135

SEQ ID NO: 442           moltype = DNA  length = 90
FEATURE                  Location/Qualifiers
source                   1..90
                         mol_type = other DNA
                         organism = synthetic construct
SEQUENCE: 442
cccggagagc attgacggga ggccaggtac ccttgtgatc ctgtcgttcg tcgtcgatgt  60
gcctgatggc aacacaaagg atgagacatg                               90

SEQ ID NO: 443           moltype = DNA  length = 33
FEATURE                  Location/Qualifiers
source                   1..33
                         mol_type = other DNA
                         organism = synthetic construct
SEQUENCE: 443
gaattcgata tcaagcttat cgataccgtc gac                           33

SEQ ID NO: 444           moltype = DNA  length = 123
FEATURE                  Location/Qualifiers
source                   1..123
                         mol_type = other DNA
                         organism = synthetic construct
SEQUENCE: 444
cccggagagc attgacggga ggccaggtac ccttgtgatc ctgtcgttcg tcgtcgatgt  60
gcctgatggc aacacaaagg atgagacatg gaattcgata tcaagcttat cgataccgtc  120
gac                                                            123

SEQ ID NO: 445           moltype = DNA  length = 594
FEATURE                  Location/Qualifiers
source                   1..594
                         mol_type = genomic DNA
                         organism = Saccharum officinarum
SEQUENCE: 445
atggtgggtc tcgtcggcgg cagcacggcg cgggcggagc acgtcgtggc caacgccgga  60
ggggagacgg agtacgtgcg ccgcctgcac cgccacgcgc ccgccgagca ccagtgcacc  120
tccaccctcg tcaagcacat caaggcgccc gtccacctcg tgtgggagct ggtgcggagc  180
ttcgaccagc cgcagcggta caagccgttc gtccggaact gcgtcgtgcg cggggaccag  240
ctcgaggtcg gcagcctgcg cgacgtcaac gtcaagaccg gcctgccggc gacaaccagc  300
actgagcgcc tcgagcagct cgacgacgac ctgcacatac tcggcgtcaa gttcgtcggc  360
ggggaccacc gcctccagaa ctactcatcc atcataactg tccacccgga gagcattgac  420
gggaggccag gtacccttgt gatcctgtcg ttcgtcgtcg atgtgcctga tggcaacaca  480
aaggatgaga catgctactt cgtcgaggct gtgatcaagt gcaacctcaa gtctcttgca  540
gaggtatctg agcagctagc agttgagcca cctacatcgc cgattgatca gtga      594

SEQ ID NO: 446           moltype = DNA  length = 426
FEATURE                  Location/Qualifiers
source                   1..426
                         mol_type = other DNA
                         organism = Saccharum officinarum
```

```
SEQUENCE: 446
atggagtacg gtcagcaggg gcagcacggc tacggcacca cgggccgtgt cgaccagtac  60
ggcaatccag ttggcggcgt cgagcacggc accaccggaa ccggcggcat gggccagcac  120
ggcggcgctg gcatgggtgg cgggcagttc cagccagcga gggaggagca caagaccggc  180
ggcatcctgc atcgctccgg cagctccagc tccagctcgt ctgaggacga cggcatgggc  240
ggaaggagga agaagggaat caaggagaag ctgcccggag gccacaagga caaccagcac  300
gccacggcga ccggcggcgc ctacgggcag cagggacaca ccggcggaac ctacggtacc  360
gagggcaccg gcgagaagaa aggcatcatg gacaagatca aggagaagct gcccggacag  420
cactaa                                                             426

SEQ ID NO: 447          moltype = AA  length = 141
FEATURE                 Location/Qualifiers
source                  1..141
                        mol_type = protein
                        organism = Saccharum officinarum
SEQUENCE: 447
MEYGQQGQHG YGTTGRVDQY GNPVGGVEHG TTGTGGMGQH GGAGMGGGQF QPAREEHKTG  60
GILHRSGSSS SSSSEDDGMG GRRKKGIKEK LPGGHKDNQH ATATGGAYGQ QGHTGGTYGT  120
EGTGEKKGIM DKIKEKLPGQ H                                            141

SEQ ID NO: 448          moltype = DNA  length = 7701
FEATURE                 Location/Qualifiers
source                  1..7701
                        mol_type = genomic DNA
                        organism = Solanum tuberosum
SEQUENCE: 448
cttattgtgc tgattttttt ttgcataggg gaagtccttg aagaccttag gtggtcaagt  60
ctgtcagatc tgtggtgatg gtgttggcac tactgtgaat ggcgagccat ttgttgcttg  120
cgatgtctgt gccttccctg tttgtaggcc atgctatgaa tatgagagga aggacgggaa  180
tcaatcttgc ccacagtgca agaccagata caagagacat aaaggtatgg atgattctga  240
ttgagcaatt gagttgaata gctaatagat cattcaagac ctgttggcca agagaagtaa  300
gagaccttta gtttttgagt ctggtacatg attgtatatg ctgactggca actttttttct  360
ataagatgat aaaatggttt tgctaaaacg attatttacc atcaagagaa tatgcatgaa  420
gtaaacttgc cttcatccca agcaacaaag aacacactaa agagaagaaa aaaaggatct  480
gcatcttgct aatctactga aagatttgaa tggcagtcaa ctcgattaag tcctagacta  540
ttctgatttg agatcttgat gtgctgtatt acttgattgt aacaggaagt cctgctatta  600
gtggtgaaag tgtagaagat ggtgatgctg atgatggtgc cagtgaacta aattactctt  660
ctgaaaatct gaatgagaag caaaaagtgg ctgaccgtgt gttgagctgg cacgcgactt  720
acgggcgggg tgaggagact ggtgctccaa agtatgataa ggaggtctcc cacaatcata  780
ttcctctgct tacaaatgga acagatgtat gattcacagt tgctaatttt ttatgttatt  840
atcttccccc tttccttgac tgtcttgcct ggtataagta attgaatgag tgactgaatg  900
cttgttgtct tcttacctct aggtttctgg ggaattgtct gcagcatcac ctgaacgcta  960
ttcaatggca tctcctggac ctgctggtgg tgcaaaacac atccatccac ttacatattc  1020
aacagatgct aaccaatcac gtatgttcct ggtttgttcg acaagtggtt acagaattat  1080
ctcttcctca tctctgattc tagatatttg aggctctatg tacttttctt attttggcag  1140
ctaacatcag ggttgtggac ccggtaaggg agtttggatc ccctggactt ggcaatgttg  1200
cttggaaaga aagagttgat ggctggaaaa tgaagcagga taagaatgtt gttccgatga  1260
ccactagcca tcctccttcg gaacgaggag ttggagatat tgatgctagt actgatattc  1320
tgggggatga ctctttactg tgagtttttt ttttcttctg ctggctatgt tatgtatttt  1380
ctggtttctg agtggctgtt ttggtagatc atctctgata tctttctatt gtaaagaaaa  1440
taaaaaagga gaagagaaca gagtattctg tattcgtgat atgtgctgat cagcattctg  1500
atggaatgtt gaagcattca aattttgtgt tgtctttgaa tatagaatga gtttcctcta  1560
atggtacatc tttgttggtg cagcaatgat gaggctagac aacctctttc aaggaaggtg  1620
tctattccat cgtctaggat aaatccttac aggatggtta ttgtcctccg gcttgtcatt  1680
ctttgtattt tcttgcacta tcggataatg aatccagtgc ccaatgcaat tccgttatgg  1740
ttgttatctg tgatatgcga gatttggttt gcagtatctt ggattttgga tcagttcccc  1800
aagtggcttc caatcaaccg tgagacatat cttgataggc ttgcacttag gtaagagctt  1860
gatctttttc tcttcgttct tttcttttct attttgtttt gcttgtttcc atttttattt  1920
cttatactta gttttaatca tgatgtgcga taggtatgat cgtgaaggag agccatcaca  1980
attagctgct gttgacatat ttgttagtac tgtggatcct ttgaaggagc ctcctcttgt  2040
tacagcaaat actgtcctgt ccattcttgc agttgactat cctgttgata aggtgtcctg  2100
ttatgtgtct gatgatggtg ctgccatgtt gacatttgaa gccctatctg aaacagcaga  2160
gtttgcaagg aaatgggttc ctttctctaa gaagtacagc atagagccac gagctccaga  2220
gtggtatttt tctcagaagg ttgactactt gaaggataaa gttcaaacat catttgtaaa  2280
agaccgcagg gcaatgaagg tcagttttag tgtttgcact accttctgtt gttttctgtt  2340
tgttgtgtgc tcataatgtt tcttggaatc ataatacaga gggagtatga agagttcaaa  2400
attcgcatca atgccctcgt tgcaaaagct caaaaggtcc ctgaagaagg atggattatg  2460
caagatggta caccatggcc tggaaataac actagggatc atcctgggat gattcaggta  2520
acttttaatt cttctttgtt ggatgtattt ttaattttta agaacaaact atatcagtgt  2580
ttttcaatta ctctaacttg caggtattga ggattggatc ttactttaat ccacgagttt  2640
gacattggtc ttgcgtactt acgattagct tttctctgaa atttaaactt ttgtcggggc  2700
attttctgtt ctgggagtat aactgtgtta tctctgtttg ttgcgtacag gttttcttgg  2760
gacaaagtgg aggacttgac agtgatggaa atgagttgcc acgactagtg tatgtttctc  2820
gtgagaagcg tcctggcttc caacatcaca aaaaggccgg tgccatgaat gcactggtaa  2880
gttgttaata ttggagtagt ttatccccccc acccaccaac aatcttgaca taaatggggc  2940
atctttatca tatacaatga tcgtgcaggt tcgcgtgtca gcggttctta ctaatggacc  3000
gtttatgttg aatcttgatt gtgatcatta cataaacaac agcaaggcat tgagagaagc  3060
aatgtgcttt ttgatggatc ctaaccttgg aaaatatgtc tgctatgtac aattccctca  3120
gagattcgat ggtattgata ggaacgatcg atatgccaac aggaatacag tttttttcga  3180
```

```
tgtaagtttg gtgttttatg cagttcatgc gcttttatga gattatttca tgtggatctt  3240
ggtgtgaaat ctttttttgt tgttgaacca gattaacttg agaggtttgg atggaattca  3300
aggcccagtg tatgtgggta ctggatgtgt cttcaataga acagctttat atggttatga  3360
acctccaatt aagccaaagc ataagaaggc agggttcctc tcttcctgct tcggtggatc  3420
aagaaagaag ggttctaaat caagtaaaaa aggctcagac aagaagaaat ctagtaagaa  3480
tgttgatccc actgtgccaa tattcaatct ggaggatata gaggagggag ttgaaggtat  3540
agttcaaatt actaaatctt ttcacttcat gttatctttg tccaagtact tcaccaatcc  3600
cagaatgatc actctgatgc tttataccac accttactca gcaactccct ttagtaagtt  3660
aattggcaaa gctgttgcat catcagcgaa aaaaaaagga aaaattgcaa gttgctaact  3720
cccatggatt tcaataccaa tacttttcaa catcagtaga cagtcacttc cttcatcatt  3780
tagacttatc taacttgtag ttcattgctt tggattacct caaatattct tcatgaaatt  3840
acttctgaac cggaaaatag aagatgaccc ctacctttag tgagtaggac ttgtagagta  3900
ccgggacaca ccaagtaatg gttgttcgac aattagaatt ttgtcctata ttcttttgct  3960
ttcttaagag tgaaccgtgc gtgttctcct gtcttctgga atcaggtttg ccatcgtcca  4020
ataatggaag taaaaaaatt gacaacaatg tcatttctaa gtctggattg tgttggacca  4080
ccttccctgg caaacagaaa tatagctatg cttttcctga accttttaaa atggacctaa  4140
gttcagattt tagaaatgtt gaaaagagga gatgcacatg gaacttcttt atgctgttga  4200
ctagctttta gaatatcaat taaccaattg tgatccaatc catattgttg ctgtaggaat  4260
tctcccccat tacctcactt tatttattag attgttgaat atggttttgt aaaatttgta  4320
actgctgatt gacacacaaa actgcaagaa gtatactatt tctaggtaag catacactta  4380
tgtgttgctt gccctcacca cttcttctta cctgtttcaa tttgtttgtc tggttttgac  4440
ttggcaagga gtttaataaa gtaaagaaga tttttaaatc ttgtggtctt aaactaaaga  4500
taggtggaat gtaccaaaat accctttaat cttgtggtct taaacatgta tgtggaagtt  4560
agaattaaag agttttcaaa aaaggaaaga gacattcttt tgaaatgact aaaaaagaag  4620
ttaaggcaaa cacattgaaa caggggagta cttactaagg aaacagttaa aaacactaac  4680
tgtaggcatg cattttatat gttgggttaa ttgcttcttg attaccatgc taaagttata  4740
agcaaggaat gcaactcatc ccaggcaaat atacacttct atcaagtttg agaattgaag  4800
tacacttttg tcctctttat gcttcttgtg cactcattct ttataggatt atcctatttc  4860
tttatgcttg aagtcccata cgtttatgtg gtggttcact atattcttga agtttttcca  4920
acttctcaca cccactgttt ctcctctctc tttcaatcat gaaatcaggt gctggatttg  4980
atgatgagaa gtcacttctc atgtcacaaa tgagcctgga gaagagattt gggcaatcgg  5040
ctgtttttgt tgcttcaaca ctcatggaga atggtggtgt tcctcaatcg gctaccccgg  5100
agaccctttt gaaagaggct attcatgtta tcagttgtgg ttatgaagat aaatcagaat  5160
ggggaactga ggtaatgctg tgttctagat tcccgcccca ccagagtcta ggataggtag  5220
ggaagagcct gtaagtgatg tgaattaagc tcaccattta aaaagttcta ggatgagtag  5280
gaaattgtag atggacaatc attgccacgg aactctatta actgaatttt aggtgacatg  5340
ttacttagta tttgaccttc tgacagaaaa aataaaccaa aaagagatcc agtgtctagt  5400
gttataccga aaataatatc tatttcctta gatctggtga aaggaaaatg agagttgcag  5460
catataccct ttaaagaaaa tgtcgagcta cttgtacatc actaaattcc cagatgcatc  5520
ggtttttggt acattgtaga cacgagaatt tctttgtggt actacttatt gtagactcta  5580
attggaccat gattgttgtt actattgtgt gtttgaatac ttaaatttcg ttgtgtatgt  5640
gcagattgga tggatctatg gttccgtcac agaggatatt cttactggat ttaagatgca  5700
tgcccgtggt tggcgatcta tttactgtat gcccaagaga cccgccttca aagggtcagc  5760
tcctattaat ctttcagatc gtctgaacca agtgcttcga tgggctttag ggtcagtgga  5820
aattcttttc agtaggcatt gtcctatatg gtatggatac aatggacggt tgaagtggtt  5880
ggagagattt gcttatgtca acaccaccat ttatccaatc acttccattc cacttcttat  5940
atactgcatg cttccagcta tctgtctact tactgggaaa ttcattatcc ctcaggttag  6000
cattggatct ctaaattctt gtcaacttgt ttgcatgcat gttatatctt ggcttctttt  6060
gcatatccaa ggttatttga tactactgtt tatatgacac ttttttccct ctcttaagaa  6120
aaaaatgaca cttttctaga tctagaaata atttacttt taaattttca ttttaccatt  6180
aatgacgtga ttatagagcc acagaaatgg tatggcatgt ttaagatcac aagttccgaa  6240
agtcaaaagt ctttctttct taagctccgg gcccagtcaa acactctcac agtcttatga  6300
aaaaaagtgc acgccttcat ataaaatgaa acagaatatt gtatttgcta cacctatgat  6360
ccccccattt aatttgagtt cttcaagtaa cccgtcagtt ggtcttaaac tgcacgtagt  6420
tactaaactt gtccttacat tcaacatact ttcttaagtt gctttaaccc aaaggggtgg  6480
cccagtggtt tgggacttcc atgttggagg tctcaagttt gaaacccctt gccaacgaaa  6540
acaagggggt tgccttctgg gtcaagctcg tcgcaccggg attgcctagt gtgggctacc  6600
tctcctatgt ggtttgcgag ctattgcata ggagcgaggg aaccccctgt gcacacaccc  6660
aaagggtagc ggctgcgggt tttccttgtc atccaaaaaa aaaagttgtt ttatcataca  6720
tttaccaaga tatcatgtca taggatttat gatatgttta ttttactttt gcagattagt  6780
aaccttgcaa gcatctggtt tatatccctc tttctttcca ttttcgctac tggtattctg  6840
gagatgagat ggagtggggt tggaattgat gaatggtgga gaaatgaaca gttttgggtc  6900
attggtggtg tgtcagctca cctgtttgcc gtcttccaag ggttgctcaa agtgcttgct  6960
ggtattgata ccaactttac tgtcacatcc aaggcatcag atgaagatgg ggactttgcg  7020
gaactctact tgttcaaatg gacaactctt cttataccoc ccactactct cctcattgta  7080
aacctggtag gagttgtggc aggcatctca tatgccatca acagtggtta ccaatcatgg  7140
ggtcccctct ttggtaaatt attctttgct ttctgggtga tcgttcacct ttaccccttc  7200
ctcaaaggtc ttatgggtcg tcagaaccgg acacccacta tcgtggtcgt gtggtctatt  7260
cttctggcct ccattttctc tttgttatgg gtgcggattg atcccttcac aacaagagtt  7320
actggaccag atgttcaggc gtgtggtatc aattgctagg aaggaactct caagttttgc  7380
atgcaaagca aataatagcg cgaaggtcat ccaagtgatg ttatcaacca tgcaaaatga  7440
gttgaagatg ttctgtagct gtgtaatctg tcatgttttt catccaaact tgggtgtgtc  7500
cttgttgttt gtccatgtga agtgtacttt attttgtgca gaatgtagcc atgtaaaagc  7560
tcctaatcga tccaagatca aacaagagac accaaatcaa aattttatcc ccagatagga  7620
actctgcttg atgtatacga atttcatatt ttgccccatt gagatggatg caatgttgta  7680
acttatagta cccttaatgt t                                           7701
```

SEQ ID NO: 449 moltype = AA length = 1083
FEATURE Location/Qualifiers

```
source                  1..1083
                        mol_type = protein
                        organism = Solanum tuberosum
SEQUENCE: 449
MDPEGDVKGK SLKTLGGQVC QICGDGVGTT VNGEPFVACD VCAFPVCRPC YEYERKDGNQ  60
SCPQCKTRYK RHKGSPAISG ESVEDGDADD GASELNYSSE NLNEKQKVAD RVLSWHATYG  120
RGEETGAPKY DKEVSHNHIP LLTNGTDVSG ELSAASPERY SMASPGPAGG AKHIHPLTYS  180
TDANQSPNIR VVDPVREFGS PGLGNVAWKE RVDGWKMKQD KNVVPMTTSH PPSERGVGDI  240
DASTDILGDD SLLNDEARQP LSRKVSIPSS RINPYRMVIV LRLVILCIFL HYRIMNPVPN  300
AIPLWLLSVI CEIWFAVSWI LDQFPKWLPI NRETYLDRLA LRYDREGEPS QLAAVDIFVS  360
TVDPLKEPPL VTANTVLSIL AVDYPVDKVS CYVSDDGAAM LTFEALSETA EFARKWVPFS  420
KKYSIEPRAP EWYFSQKVDY LKDKVQTSFV KDRRAMKREY EEFKIRINAL VAKAQKVPEE  480
GWIMQDGTPW PGNNTRDHPG MIQVFLGQSG GLDSDGNELP RLVYVSREKR PGFQHHKKAG  540
AMNALVRVSA VLTNGPFMLN LDCDHYINNS KALREAMCFL MDPNLGKYVC YVQFPQRFDG  600
IDRNDRYANR NTVFFDINLR GLDGIQGPVY VGTGCVFNRT ALYGYEPPIK PKHKKAGFLS  660
SCFGGSRKKG SKSSKKGSDK KKSSKNVDPT VPIFNLEDIE EGVEGAGFDD EKSLLMSQMS  720
LEKRFGQSAV FVASTLMENG GVPQSATPET LLKEAIHVIS CGYEDKSEWG TEIGWIYGSV  780
TEDILTGFKM HARGWRSIYC MPKRPAFKGS APINLSDRLN QVLRWALGSV EILFSRHCPI  840
WYGYNGRLKW LERFAYVNTT IYPITSIPLL IYCMLPAICL LTGKFIIPQI SNLASIWFIS  900
LFLSIFATGI LEMRWSGVGI DEWWRNEQFW VIGGVSAHLF AVFQGLLKVL AGIDTNFTVT  960
SKASDEDGDF AELYLFKWTT LLIPPTTLLI VNLVGVVAGI SYAINSGYQS WGPLFGKLFF  1020
AFWVIVHLYP FLKGLMGRQN RTPTIVVVWS ILLASIFSLL WVRIDPFTTR VTGPDVQACG  1080
INC                                                               1083

SEQ ID NO: 450          moltype = DNA  length = 3252
FEATURE                 Location/Qualifiers
source                  1..3252
                        mol_type = other DNA
                        organism = Solanum tuberosum
SEQUENCE: 450
atggatccag aaggtgatgt gaaggggaag tccttgaaga ccttaggtgg tcaagtctgt  60
cagatctgtg gtgatggtgt tggcactact gtgaatggcg agccatttgt tgcttgcgat  120
gtctgtgcct tccctgtttg taggccatgc tatgaatatg agaggaagga cgggaatcaa  180
tcttgcccac agtgcaagac cagatacaag agacataaag gaagtcctgc tattagtggt  240
gaaagtgtag aagatggtga tgctgatgat ggtgccagtg aactaaatta ctcttctgaa  300
aatctgaatg agaagcaaaa agtggctgac cgtgtgttga gctggcacgc gacttacggg  360
cggggtgagg agactggtgc tccaaagtat gataaggagg tctcccacaa tcatattcct  420
ctgcttacaa atggaacaga tgtttctggg gaattgtctg cagcatcacc tgaacgctat  480
tcaatggcat ctcctggacc tgctggtggt gcaaaacaca tccatccact tacatattca  540
acagatgcta accaatcacc taacatcagg gttgtggacc cggtaaggga gtttggatcc  600
cctggacttg gcaatgttgc ttggaaagaa agagttgatg gctggaaaat gaagcaggat  660
aagaatgttg ttccgatgac cactagccat cctccttcgg aacgaggagt tggagatatt  720
gatgctagta ctgatattct gggggatgac tctttactca atgatgaggc tagacaacct  780
ctttcaagga aggtgtctat tccatcgtct aggataaatc cttacaggat ggttattgtc  840
ctccggcttg tcattctttg tattttcttg cactatcgga taatgaatcc agtgcccaat  900
gcaattccgt tatggttgtt atctgtgata tgcgagattt ggtttgcagt atcttggatt  960
ttggatcagt tccccaagtg gcttccaatc aaccgtgaga catatcttga taggcttgca  1020
cttaggtatg atcgtgaagg agagccatca caattagctg ctgttgacat atttgttagt  1080
actgtggatc ctttgaagga gcctcctctt gttacagcaa atactgtcct gtccattctt  1140
gcagttgact atcctgttga taaggtgtcc tgttatgtgt ctgatgatgg tgctgccatg  1200
ttgacatttg aagccctatc tgaaacagca gagtttgcaa ggaaatgggt tcctttctct  1260
aagaagtaca gcatagagcc acgagctcca gagtggtatt tttctcagaa ggttgactac  1320
ttgaaggata aagttcaaac atcatttgta aaagaccgca gggcaatgaa gagggagtat  1380
gaagagttca aaattcgcat caatgccctc gttgcaaaag ctcaaaaggt ccctgaagaa  1440
ggatggatta tgcaagatgg tacaccatgg cctggaaata acactaggga tcatcctggg  1500
atgattcagg ttttcttggg acaaagtgga ggacttgaca gtgatggaaa tgagttgcca  1560
cgactagtgt atgtttctcg tgagaagcgt cctggcttcc aacatcacaa aaaggccggt  1620
gccatgaatg cactggttcg cgtgtcagcg gttcttacta atggaccgtt tatgttgaat  1680
cttgattgtg atcattacat aaacaacagc aaggcattga gagaagcaat gtgctttttg  1740
atggatccta accttggaaa atatgtctgc tatgtacaat tccctcagag attcgatggt  1800
attgatagga acgatcgata tgccaacagg aatacagttt ttttcgatat taacttgaga  1860
ggtttggatg gaattcaagg cccagtgtat gtgggtactg gatgtgtctt caatagaaca  1920
gctttatatg gttatgaacc tccaattaag ccaaagcata agaaggcagg gttcctctct  1980
tcctgcttcg gtggatcaag aaagaagggt tctaaatcaa gtaaaaaagg ctcagacaag  2040
aagaaatcta gtaagaatgt tgatcccact gtgccaatat tcaatctgga ggatatagag  2100
gagggagttg aaggtgctgg atttgatgat gagaagtcac ttctcatgtc acaaatgagc  2160
ctggagaaga gatttgggca atcggctgtt tttgttgctt caacactcat ggagaatggt  2220
ggtgttcctc aatcggctac cccggagacc cttttgaaag aggctattca tgttatcagt  2280
tgtggttatg aagataaatc agaatgggga actgagattg gatggatcta tggttccgtc  2340
acagaggata ttcttactgg atttaagatg catgcccgtg gttggcgatc tatttactgt  2400
atgcccaaga gacccgcctt caaagggtca gctcctatta atctttcaga tcgtctgaac  2460
caagtgcttc gatgggcttt agggtcagtg gaaattcttt tcagtaggca ttgtcctata  2520
tggtatggat acaatggacg gttgaagtgg ttggagagat ttgcttatgt caacaccacc  2580
atttatccaa tcacttccat tccacttctt atatactgca tgcttccagc tatctgtcta  2640
cttactggga aattcattat ccctcagatt agtaaccttg caagcatctg gtttatatcc  2700
ctctttcttt ccattttcgc tactggtatt ctggagatga gatggagtgg ggttggaatt  2760
gatgaatggt ggagaaatga acagttttgg gtcattggtg gtgtgtcagc tcacctgttt  2820
gccgtcttcc aagggttgct caaagtgctt gctggtattg ataccaactt tactgtcaca  2880
tccaaggcat cagatgaaga tggggacttt gcggaactct acttgttcaa atggacaact  2940
```

```
cttcttatac cccccactac tctcctcatt gtaaacctgg taggagttgt ggcaggcatc  3000
tcatatgcca tcaacagtgg ttaccaatca tggggtcccc tctttggtaa attattcttt  3060
gctttctggg tgatcgttca cctttacccc ttcctcaaag gtcttatggg tcgtcagaac  3120
cggacaccca ctatcgtggt cgtgtggtct attcttctgg cctccatttt ctctttgtta  3180
tgggtgcgga ttgatccctt cacaacaaga gttactggac cagatgttca ggcgtgtggt  3240
atcaattgct ag                                                      3252

SEQ ID NO: 451          moltype = DNA  length = 20
FEATURE                 Location/Qualifiers
source                  1..20
                        mol_type = other DNA
                        organism = synthetic construct
SEQUENCE: 451
tctgtgcctt ccctgtttgt                                              20

SEQ ID NO: 452          moltype = DNA  length = 20
FEATURE                 Location/Qualifiers
source                  1..20
                        mol_type = other DNA
                        organism = synthetic construct
SEQUENCE: 452
ttgagctggc acgcgactta                                              20

SEQ ID NO: 453          moltype = DNA  length = 20
FEATURE                 Location/Qualifiers
source                  1..20
                        mol_type = other DNA
                        organism = synthetic construct
SEQUENCE: 453
atggcatctc ctggacctgc                                              20

SEQ ID NO: 454          moltype = DNA  length = 6001
FEATURE                 Location/Qualifiers
source                  1..6001
                        mol_type = genomic DNA
                        organism = Solanum tuberosum
SEQUENCE: 454
gctaaaggtg tttattttag tttgatatat ttcactagat tatagtgttc cttaatgtat  60
aacaaaaaat gttcattttg tcttttatcc taagcctaat tgatttaaca aaaaagaaag  120
tgttaaattc aactatggac catacgtggc tgacaaaatt caccatttgt tatctttttt  180
gttagctcca aaaaaagaat tccataaaat ctaacactat tttctttact ttctccaaca  240
aaatttatta ttttatcttt caaaatatca ttccactgac tcaatactca tttatgtttt  300
aagcaagaga aaataataaa ttttgttaga gaaagtagaa acaatgacat tagatttcat  360
ggagctttca ttagagctaa caaagcgaag acaacaatgg tgattttgtt ggcctcgtac  420
ggtccacggt taatttaata tatatttttg ataaatctat taggtttatg acaaagaacc  480
aaaatgaacc tattttgtta tacattaata atcatttcaa tcaagtgaaa tatattaagg  540
accaaaataa acacatttta tataccttag accatttcaa taaagtgaaa tatattaacg  600
ggtcgtttgg tgtgaaggat aataccaaat aatcctgaga ttaaattata gtaccactta  660
atttgttgtt tggttggcaa gttcgggata agttatcccg ggattaataa ttagtaccgg  720
gataagttat ccctccccctt ggggatatag taatcccggg ataaaatagg taaatgacaa  780
aaatgtcttt ttcaaccctt ttgttacatt actttttaca ttcatgaaag acatttttat  840
aaacaaataa attgttctta aaatttatta ttttgaatac aacaaaccaa acactcaata  900
aaaaataatc tcatcataaa cttatctcat cataacttga attcaaacca aactagccta  960
aggaccaaaa taaagaattt gccaaacagt aaggatcatt ttggtcattt ctctaatccc  1020
aagtgtacct caaactatac aagccttttc tcactcaatt cagttgcccc ctgtcatttt  1080
ctgtgttcat cacctatata taaagcagta gactggtagc ttccccaatc ctctaccttc  1140
cattatggcc acccagtacc attccagtta tgacctggaa aactccgcct cccattacac  1200
attcctcccg gatcaacccg attccggcca ccggaagtcc cttaaaatca tctccggcat  1260
tttcctctcc tctttccttt tgctttctgt agccttcttt ccgatcctca acaaccaatc  1320
accggacttg cagagtaact cccgttcgcc ggcgccgccg tcaagaggtg tttctcaggg  1380
agtctccgat aagacttttc gagatgtcgt caatgctagt cacgtttctt atgcgtggtc  1440
caatgctatg cttagctggc aaagaactgc ttaccatttt caacctcaaa aaaattggat  1500
gaacggtaat taactttctt attttgactt ttctgtaatt tcctatttat ttgatcttag  1560
aattgaaaaa aattataaat acttataccg tttttttttt tcttaatgat atttatggct  1620
attgatctgt tggggtatct tttggattct gattggatgc tattctgcag atcctaatgg  1680
tgagttcaaa gttaattatc atcactattt tctgttagta tttaattaat tatattctta  1740
aaccatgaat taaaacttta aaggcagtaa aattctctca tgaggtaatt atggttttat  1800
ttgatttaag cctataagtg ccaaccaatc catgtatgag caaatcatta attcgggtat  1860
gtcatctcgg ttaatccttt taccttttac tcaaaaggaa ctattactcc gtccaaaata  1920
attgatgttt cacataatca atgtgatgtt taattttttt tttcaaattt acccttggta  1980
tatacctaat ccctataatg attatgccaa atctaatatg aaaagaaaat cataattaca  2040
gatattttag tcacaattaa ttcatgttaa aatatcaata attttggatt ggaggtagta  2100
ctaattagga aaataattaa gttaaatcat tttcactaaa cattgtttag actaaggatg  2160
aaatagggga ggaatcaatt atcttatttt tgtaaatgga taagtatttt gaaataacaa  2220
attttaagaa aacacgacaa gtcaaataga gtaggattga tggagtgtat tctaaccttt  2280
ctagatattc ataaaaattg gttgaatttt ttttaataaa cacgacaagt tgatggatta  2340
ggcttgttgt tccaatataa ttgggattaa catgagatcg tgtggcagca aagtttttttg  2400
gttttgggta attttccaat aaaaattaaa cacatgattg gccagtttta tacaagtttg  2460
gaaatcaatc acgttatgtg ggtcatactt ttttgtagta atgtaataat tccattagtt  2520
```

```
ggcccccat ccaaattatt tgtccatctt tccacttggt cattttctct tcttttattt  2580
ttttgaaatg gagtaggtta tcttgtgccg cttagaagca attactatta ccatttcgaa  2640
gtcataaaaa aatcaatata tattataagg ataaaaatat ataacataaa tttcatgagt  2700
ttatttattt aaattttagg ggaggaggac ataacatagt aacatatcac tagtaaaatt  2760
tgtttaagta gcttgttgaa gataatctta attattcaaa ggtcaaaaat aataactcat  2820
ggcgaaattt tcaataaaag aacgttatct ttttgccgca aaaagcatag caattttggt  2880
acggaacata ttgagatttc gtagagtatt ttacaattca aattgcatag aaaagtctta  2940
cctaatgcaa gtaaaataca taattacttt gaaatttcta ctaacgtgaa taaattggtc  3000
aacaggtcca ttgtaccaca agggatggta tcatcttttt tatcaataca atccagattc  3060
agctatttgg ggaaatatca catggggcca tgccgtatcc aaggacttga tccactggct  3120
ctacttgcct tttgccatgg ttcctgatca atggtacgat ataaacggtg tctggactgg  3180
gtccgctacc atcctacccg atggtcagat catgatgctt tataccggtg acactgatga  3240
ttatgtacaa gtgcaaaatc ttgcgtaccc caccaactta tctgatcctc tccttctaga  3300
ctgggtcaag tacaaaggca acccggttct ggttcctcca cccggcattg gtgtcaagga  3360
ctttagagac ccgaccactg cttggaccgg accccaaaat gggcaatggc ttttaacaat  3420
cgggtctaag attggtaaaa cgggtattgc acttgtttat gaaacttcca acttcacaag  3480
ctttaagcta ttggatgaag tgctgcatgc ggttccgggt acgggtatgt gggagtgtgt  3540
ggacttttac ccggtatcga ctgaaaaaac aaacgggttg gacacatcat ataacggccc  3600
gggtgtaaag catgtgttaa aagcaagttt agatgacaat aagcaagatc actatgctat  3660
tgggacgtat gacttgacaa agaataaatg gacacccgat aacccggaat tggattgtgg  3720
aattgggttg aagctggatt atgggaaata ttatgcatca aagacatttt atgacccgaa  3780
gaaacaacga agagtactgt ggggatggat tggggaaact gatagtgaat ctgctgacct  3840
gcagaaggga tgggcatctg tacaggtatg gacttcgatt aacacattgt tttgttgttt  3900
tagtttgcac catacacaat aatcgtgcga aattatatct atcagtaggg aaatttctta  3960
tttagaaaaa agttgtataa tcaatgcatt tgttggtgaa gtgaattgga atttttgttg  4020
aagtatattc tcaattatat atgaaacatc tctaataatt ttgtaatacg aataataaca  4080
gagtattcca aggacagtgc tttacgacaa gaagacaggg acacatctac ttcagtggcc  4140
agttgaagaa attgaaagct taagagcggg tgatcctatt gttaagcaag tcaatcttca  4200
accaggttca attgagctac tccatgttga ctcagctgca gaggtttgtt gcgcgacttt  4260
gtttaaaatt acaaacttta tacttatacg cgcttaatct gcagtcttaa aacttgttgg  4320
ctattgtgca gttggatata gaagcctcat ttgaagtgga caaagtcgcg ctccagggaa  4380
taattgaagc agatcatgta ggtttcagct gctctactag tggaggtgct gctagcagag  4440
gcatttttggg accatttggt gtcgttgtaa ttgctgatca aacgctatct gagctaacgc  4500
cagtttactt ctacatttct aaaggagctg atggccgagc tgagactcac ttctgtgctg  4560
atcaaaccag gtttgcttct attttctcta tctggcacaa ttaatttgtc ataatagtcc  4620
ttgtaaaatg gagatggata aaagtagcgc gttatgatct gatatatgca gatcctcaga  4680
ggctccggga gttgctaaac aagtttatgg tagttcagta cccgtgttgg acggtgaaaa  4740
acattcgatg agattattgg taagtgatga tgattccctt atttaccttt gtttatatca  4800
agcttatatt cagttcttgt agtctagttg gttcactata aaaaaagtac ttggcagttg  4860
catttgagta aaagttttat aaactgaatt ttaggtggac cactcaattg tggagagctt  4920
tgctcaagga ggaagaacag tcataacatc gcgaatttac ccaacaaagg cagtgaatgg  4980
agcagcacga ctcttcgttt tcaacaatgc cacagggtct agcgtgactg cctccgtcaa  5040
gatttggtca cttgagtcgg ctaatattca atccttcccc ttgcaagact tgtaattcat  5100
caagccatat cttcttcatt cttttttttca tttgaaggtt atttcaccga tgtcccatca  5160
agaaagggaa gagagggaga atatgtagtg ttatactact tattcgccat tttagtgatt  5220
tttctactgg actttttgcta ttcgccataa ggtttagttg ttgtctagca atgtcagcag  5280
cggggcggat ctatagtgta atgtatgggt tcctggaaac cgaataggtc ttacttggat  5340
tttatgtaaa ctaagaaaat tcagcaaata catacaaata atttatcgat ttcttattgt  5400
tggtgaggat acggttccct ggcagttaca aaactgacat gggcacctaa atatttgggg  5460
caacgagatt gacatttgag cttaagcagt tgcttagagc acgtgatttc gccggagttt  5520
atataaaaac cgtaaaatca tcaaatctat gatcgtttgg tatagaacta actggtttga  5580
taaacttatt tgacgctctt cattttttcct ccgataattc ttgcatgcat gtgtataaat  5640
agtgtataag aactgtataa gattatatta ttagtgtgta tacattatac attgattcta  5700
tatatttttt atttagttat ttttactaat ccctagttac ttcccttttg tgacccgagc  5760
cgacaacctt aaggttggag gtgaatggtg tttatcatcc gaccaacact gattatacat  5820
ttattacata tttattttac acaaaacata caacaatgat tcatcttcta tatacatact  5880
ctagggatac atattttata caacaatgat acaattctat atgcaaggtc gaatttagga  5940
gggagtgagg gtgctcactt gaaccaactt ggtaaaaaat acattgtata aatatggcat  6000
t                                                                  6001
```

```
SEQ ID NO: 455         moltype = AA  length = 639
FEATURE                Location/Qualifiers
source                 1..639
                       mol_type = protein
                       organism = Solanum tuberosum
SEQUENCE: 455
MATQYHSSYD LENSASHYTF LPDQPDSGHR KSLKIISGIF LSSFLLLSVA FFPILNNQSP  60
DLQSNSRSPA PPSRGVSQGV SDKTFRDVVN ASHVSYAWSN AMLSWQRTAY HFQPQKNWMN  120
DPNGPLYHKG WYHLFYQYNP DSAIWGNITW GHAVSKDLIH WLYLPFAMVP DQWYDINGVW  180
TGSATILPDG QIMMLYTGDT DDYVQVQNLA YPTNLSDPLL LDWVKYKGNP VLVPPPGIGV  240
KDFRDPTTAW TGPQNGQWLL TIGSKIGKTG IALVYETSNF TSFKLLDEVL HAVPGTGMWE  300
CVDFYPVSTE KTNGLDTSYN GPGVKHVLKA SLDDNKQDHY AIGTYDLTKN KWTPDNPELD  360
CGIGLKLDYG KYYASKTFYD PKKQRRVLWG WIGETDSESA DLQKGWASVQ SIPRTVLYDK  420
KTGTHLLQWP VEEIESLRAG DPIVKQVNLQ PGSIELLHVD SAAELDIEAS FEVDKVALQG  480
IIEADHVGFS CSTSGGAASR GILGPFGVVV IADQTLSELT PVYFYISKGA DGRAETHFCA  540
DQTRSSEAPG VAKQVYGSSV PVLDGEKHSM RLLVDHSIVE SFAQGGRTVI TSRIYPTKAV  600
NGAARLFVFN NATGSSVTAS VKIWSLESAN IQSFPLQDL                        639

SEQ ID NO: 456         moltype = DNA  length = 1920
```

```
FEATURE                Location/Qualifiers
source                 1..1920
                       mol_type = other DNA
                       organism = Solanum tuberosum
SEQUENCE: 456
atggccaccc agtaccattc cagttatgac ctggaaaact ccgcctccca ttacacattc  60
ctcccggatc aacccgattc cggccaccgg aagtccctta aaatcatctc cggcattttc  120
ctctcctctt tccttttgct ttctgtagcc ttctttccga tcctcaacaa ccaatcaccg  180
gacttgcaga gtaactcccg ttcgccggcg ccgccgtcaa gaggtgtttc tcagggagtc  240
tccgataaga cttttcgaga tgtcgtcaat gctagtcacg tttcttatgc gtggtccaat  300
gctatgctta gctggcaaag aactgcttac cattttcaac ctcaaaaaaa ttggatgaac  360
gatcctaatg gtccattgta ccacaaggga tggtatcatc ttttttatca atacaatcca  420
gattcagcta tttggggaaa tatcacatgg ggccatgccg tatccaagga cttgatccac  480
tggctctact tgccttttgc catggttcct gatcaatggt acgatataaa cggtgtctgg  540
actgggtccg ctaccatcct acccgatggt cagatcatga tgctttatac cggtgacact  600
gatgattatg tacaagtgca aaatcttgcg taccccacca acttatctga tcctctcctt  660
ctagactggg tcaagtacaa aggcaacccg gttctggttc ctccacccgg cattggtgtc  720
aaggacttta gagacccgac cactgcttgg accggacccc aaaatgggca atggctttta  780
acaatcgggt ctaagattgg taaaacgggt attgcacttg tttatgaaac ttccaacttc  840
acaagcttta agctattgga tgaagtgctg catgcggttc cgggtacggg tatgtgggag  900
tgtgtggact tttacccggt atcgactgaa aaaacaaacg ggttggacac atcatataac  960
ggcccgggtg taaagcatgt gttaaaagca agtttagatg acaataagca agatcactat  1020
gctattggga cgtatgactt gacaaagaat aaatggacac ccgataaccc ggaattggat  1080
tgtggaattg ggttgaagct ggattatggg aaatattatg catcaaagac attttatgac  1140
ccgaagaaac aacgaagagt actgtgggga tggattgggg aaactgatag tgaatctgct  1200
gacctgcaga agggatgggc atctgtacag agtattccaa ggacagtgct ttacgacaag  1260
aagacaggga cacatctact tcagtggcca gttgaagaaa ttgaaagctt aagagcgggt  1320
gatcctattg ttaagcaagt caatcttcaa ccaggttcaa ttgagctact ccatgttgac  1380
tcagctgcag agttggatat agaagcctca tttgaagtgg acaaagtcgc gctccaggga  1440
ataattgaag cagatcatgt aggtttcagc tgctctacta gtggaggtgc tgctagcaga  1500
ggcattttgg gaccatttgg tgtcgttgta attgctgatc aaacgctatc tgagctaacg  1560
ccagtttact tctacatttc taaaggagct gatggccgag ctgagactca cttctgtgct  1620
gatcaaacca gatcctcaga ggctccggga gttgctaaac aagtttatgg tagttcagta  1680
cccgtgttgg acggtgaaaa acattcgatg agattattgg tggaccactc aattgtggag  1740
agctttgctc aaggaggaag aacagtcata acatcgcgaa tttacccaac aaaggcagtg  1800
aatggagcag cacgactctt cgttttcaac aatgccacag ggtctagcgt gactgcctcc  1860
gtcaagattt ggtcacttga gtcggctaat attcaatcct tcccccttgca agacttgtaa  1920

SEQ ID NO: 457         moltype = DNA  length = 20
FEATURE                Location/Qualifiers
source                 1..20
                       mol_type = other DNA
                       organism = synthetic construct
SEQUENCE: 457
tttaagggac ttccggtggc                                              20

SEQ ID NO: 458         moltype = DNA  length = 20
FEATURE                Location/Qualifiers
source                 1..20
                       mol_type = other DNA
                       organism = synthetic construct
SEQUENCE: 458
cggaatcggg ttgatccggg                                              20

SEQ ID NO: 459         moltype = DNA  length = 20
FEATURE                Location/Qualifiers
source                 1..20
                       mol_type = other DNA
                       organism = synthetic construct
SEQUENCE: 459
gttgttgagg atcggaaaga                                              20

SEQ ID NO: 460         moltype = DNA  length = 84
FEATURE                Location/Qualifiers
source                 1..84
                       mol_type = other DNA
                       organism = synthetic construct
SEQUENCE: 460
tactccctcc gtttcttttt attagtcgct ggatagtgca attttgcact atccagcgac  60
taataaaaag aaacggaggg agta                                         84

SEQ ID NO: 461         moltype = DNA  length = 84
FEATURE                Location/Qualifiers
source                 1..84
                       mol_type = other DNA
                       organism = synthetic construct
SEQUENCE: 461
tactccctcc gtttcttttt attagtcgct ggatagtgca aaattgcact atccagcgac  60
taataaaaag aaacggaggg agta                                         84
```

```
SEQ ID NO: 462          moltype = DNA  length = 22
FEATURE                 Location/Qualifiers
source                  1..22
                        mol_type = other DNA
                        organism = synthetic construct
SEQUENCE: 462
tcgccacttt ggagtcgcaa tc                                              22

SEQ ID NO: 463          moltype = DNA  length = 22
FEATURE                 Location/Qualifiers
source                  1..22
                        mol_type = other DNA
                        organism = synthetic construct
SEQUENCE: 463
acacacatac gttcgtgctt cg                                              22

SEQ ID NO: 464          moltype = DNA  length = 24
FEATURE                 Location/Qualifiers
source                  1..24
                        mol_type = other DNA
                        organism = synthetic construct
SEQUENCE: 464
aagggatgag atgacctggg acac                                            24

SEQ ID NO: 465          moltype = DNA  length = 23
FEATURE                 Location/Qualifiers
source                  1..23
                        mol_type = other DNA
                        organism = synthetic construct
SEQUENCE: 465
tgctggacaa tgaggccatc tac                                             23

SEQ ID NO: 466          moltype = DNA  length = 28
FEATURE                 Location/Qualifiers
source                  1..28
                        mol_type = other DNA
                        organism = synthetic construct
SEQUENCE: 466
acacgtgaca cgtgacacgt gacacgtg                                        28

SEQ ID NO: 467          moltype = RNA  length = 20
FEATURE                 Location/Qualifiers
source                  1..20
                        mol_type = other RNA
                        organism = Zea mays
SEQUENCE: 467
gtgctctctc tcttctgtca                                                 20

SEQ ID NO: 468          moltype = RNA  length = 20
FEATURE                 Location/Qualifiers
source                  1..20
                        mol_type = other RNA
                        organism = Zea mays
SEQUENCE: 468
ctgctctctc tcttctgtca                                                 20

SEQ ID NO: 469          moltype = RNA  length = 20
FEATURE                 Location/Qualifiers
source                  1..20
                        mol_type = other RNA
                        organism = Zea mays
SEQUENCE: 469
ttgcttactc tcttctgtca                                                 20

SEQ ID NO: 470          moltype = RNA  length = 20
FEATURE                 Location/Qualifiers
source                  1..20
                        mol_type = other RNA
                        organism = Zea mays
SEQUENCE: 470
ccgctctctc tcttctgtca                                                 20

SEQ ID NO: 471          moltype = RNA  length = 21
FEATURE                 Location/Qualifiers
source                  1..21
                        mol_type = other RNA
                        organism = Zea mays
SEQUENCE: 471
```

```
tggagctccc ttcattccaa t                                          21

SEQ ID NO: 472          moltype = RNA  length = 21
FEATURE                 Location/Qualifiers
source                  1..21
                        mol_type = other RNA
                        organism = Zea mays
SEQUENCE: 472
tcgagttccc ttcattccaa t                                          21

SEQ ID NO: 473          moltype = RNA  length = 21
FEATURE                 Location/Qualifiers
source                  1..21
                        mol_type = other RNA
                        organism = Zea mays
SEQUENCE: 473
atgagctctc ttcaaaccaa a                                          21

SEQ ID NO: 474          moltype = RNA  length = 21
FEATURE                 Location/Qualifiers
source                  1..21
                        mol_type = other RNA
                        organism = Zea mays
SEQUENCE: 474
tggagctccc ttcattccaa g                                          21

SEQ ID NO: 475          moltype = RNA  length = 21
FEATURE                 Location/Qualifiers
source                  1..21
                        mol_type = other RNA
                        organism = Zea mays
SEQUENCE: 475
tagagcttcc ttcaaaccaa a                                          21

SEQ ID NO: 476          moltype = RNA  length = 21
FEATURE                 Location/Qualifiers
source                  1..21
                        mol_type = other RNA
                        organism = Zea mays
SEQUENCE: 476
tggagctcca ttcgatccaa a                                          21

SEQ ID NO: 477          moltype = RNA  length = 21
FEATURE                 Location/Qualifiers
source                  1..21
                        mol_type = other RNA
                        organism = Zea mays
SEQUENCE: 477
agcagctccc ttcaaaccaa a                                          21

SEQ ID NO: 478          moltype = RNA  length = 21
FEATURE                 Location/Qualifiers
source                  1..21
                        mol_type = other RNA
                        organism = Zea mays
SEQUENCE: 478
cagagctccc ttcactccaa t                                          21

SEQ ID NO: 479          moltype = RNA  length = 21
FEATURE                 Location/Qualifiers
source                  1..21
                        mol_type = other RNA
                        organism = Zea mays
SEQUENCE: 479
tggagctccc ttcactccaa t                                          21

SEQ ID NO: 480          moltype = RNA  length = 21
FEATURE                 Location/Qualifiers
source                  1..21
                        mol_type = other RNA
                        organism = Zea mays
SEQUENCE: 480
tggagctccc ttcactccaa g                                          21

SEQ ID NO: 481          moltype = RNA  length = 21
FEATURE                 Location/Qualifiers
source                  1..21
                        mol_type = other RNA
                        organism = Zea mays
```

```
SEQUENCE: 481
tggagctccc tttaatccaa t                                              21

SEQ ID NO: 482          moltype = RNA  length = 21
FEATURE                 Location/Qualifiers
source                  1..21
                        mol_type = other RNA
                        organism = Zea mays
SEQUENCE: 482
ttgggatgaa gcctggtccg g                                              21

SEQ ID NO: 483          moltype = RNA  length = 21
FEATURE                 Location/Qualifiers
source                  1..21
                        mol_type = other RNA
                        organism = Zea mays
SEQUENCE: 483
ctgggatgaa gcctggtccg g                                              21

SEQ ID NO: 484          moltype = RNA  length = 21
FEATURE                 Location/Qualifiers
source                  1..21
                        mol_type = other RNA
                        organism = Zea mays
SEQUENCE: 484
ctggaatgaa gcctggtccg g                                              21

SEQ ID NO: 485          moltype = RNA  length = 20
FEATURE                 Location/Qualifiers
source                  1..20
                        mol_type = other RNA
                        organism = Zea mays
SEQUENCE: 485
cgggatgaag cctggtccgg                                                20

SEQ ID NO: 486          moltype = RNA  length = 21
FEATURE                 Location/Qualifiers
source                  1..21
                        mol_type = other RNA
                        organism = Zea mays
SEQUENCE: 486
gagatcaggc tggcagcttg t                                              21

SEQ ID NO: 487          moltype = RNA  length = 21
FEATURE                 Location/Qualifiers
source                  1..21
                        mol_type = other RNA
                        organism = Zea mays
SEQUENCE: 487
tagatcaggc tggcagcttg t                                              21

SEQ ID NO: 488          moltype = RNA  length = 21
FEATURE                 Location/Qualifiers
source                  1..21
                        mol_type = other RNA
                        organism = Zea mays
SEQUENCE: 488
aagatcaggc tggcagcttg t                                              21

SEQ ID NO: 489          moltype = RNA  length = 20
FEATURE                 Location/Qualifiers
source                  1..20
                        mol_type = other RNA
                        organism = Zea mays
SEQUENCE: 489
gtgctctctc tcttctgtca                                                20

SEQ ID NO: 490          moltype = RNA  length = 20
FEATURE                 Location/Qualifiers
source                  1..20
                        mol_type = other RNA
                        organism = Zea mays
SEQUENCE: 490
ctgctctctc tcttctgtca                                                20

SEQ ID NO: 491          moltype = RNA  length = 20
FEATURE                 Location/Qualifiers
source                  1..20
                        mol_type = other RNA
```

```
                       organism = Zea mays
SEQUENCE: 491
ttgcttactc tcttctgtca                                             20

SEQ ID NO: 492         moltype = RNA  length = 20
FEATURE                Location/Qualifiers
source                 1..20
                       mol_type = other RNA
                       organism = Zea mays
SEQUENCE: 492
ccgctctctc tcttctgtca                                             20

SEQ ID NO: 493         moltype = RNA  length = 21
FEATURE                Location/Qualifiers
source                 1..21
                       mol_type = other RNA
                       organism = Zea mays
SEQUENCE: 493
tggcatgcag ggagccaggc a                                           21

SEQ ID NO: 494         moltype = RNA  length = 21
FEATURE                Location/Qualifiers
source                 1..21
                       mol_type = other RNA
                       organism = Zea mays
SEQUENCE: 494
aggaatacag ggagccaggc a                                           21

SEQ ID NO: 495         moltype = RNA  length = 21
FEATURE                Location/Qualifiers
source                 1..21
                       mol_type = other RNA
                       organism = Zea mays
SEQUENCE: 495
gggtttacag ggagccaggc a                                           21

SEQ ID NO: 496         moltype = RNA  length = 21
FEATURE                Location/Qualifiers
source                 1..21
                       mol_type = other RNA
                       organism = Zea mays
SEQUENCE: 496
aggcatacag ggagccaggc a                                           21

SEQ ID NO: 497         moltype = RNA  length = 21
FEATURE                Location/Qualifiers
source                 1..21
                       mol_type = other RNA
                       organism = Zea mays
SEQUENCE: 497
aaacaatgcg atccctttgg a                                           21

SEQ ID NO: 498         moltype = RNA  length = 21
FEATURE                Location/Qualifiers
source                 1..21
                       mol_type = other RNA
                       organism = Zea mays
SEQUENCE: 498
agaccatgcg atccctttgg a                                           21

SEQ ID NO: 499         moltype = RNA  length = 21
FEATURE                Location/Qualifiers
source                 1..21
                       mol_type = other RNA
                       organism = Zea mays
SEQUENCE: 499
ggtcagagcg atccctttgg c                                           21

SEQ ID NO: 500         moltype = RNA  length = 21
FEATURE                Location/Qualifiers
source                 1..21
                       mol_type = other RNA
                       organism = Zea mays
SEQUENCE: 500
agacaatgcg atccctttgg a                                           21

SEQ ID NO: 501         moltype = RNA  length = 22
FEATURE                Location/Qualifiers
source                 1..22
```

```
                        mol_type = other RNA
                        organism = Zea mays
SEQUENCE: 501
tcgttcaaga aagcctgtgg aa                                           22

SEQ ID NO: 502          moltype = RNA  length = 21
FEATURE                 Location/Qualifiers
source                  1..21
                        mol_type = other RNA
                        organism = Zea mays
SEQUENCE: 502
cgttcaagaa agcctgtgga a                                            21

SEQ ID NO: 503          moltype = RNA  length = 22
FEATURE                 Location/Qualifiers
source                  1..22
                        mol_type = other RNA
                        organism = Zea mays
SEQUENCE: 503
tcgttcaaga aagcatgtgg aa                                           22

SEQ ID NO: 504          moltype = RNA  length = 22
FEATURE                 Location/Qualifiers
source                  1..22
                        mol_type = other RNA
                        organism = Zea mays
SEQUENCE: 504
acgttcaaga aagcttgtgg aa                                           22

SEQ ID NO: 505          moltype = RNA  length = 21
FEATURE                 Location/Qualifiers
source                  1..21
                        mol_type = other RNA
                        organism = Zea mays
SEQUENCE: 505
cgttcaagaa agcctgtgga a                                            21

SEQ ID NO: 506          moltype = DNA  length = 300
FEATURE                 Location/Qualifiers
source                  1..300
                        mol_type = other DNA
                        organism = Zea mays
SEQUENCE: 506
ggacaacaag caccttcttg ccttgcaagg cctcccttcc ctatggtagc cacttgagtg  60
gatgacttca ccttaaagct attgattccc taagtgccag acataatagg ctatacattc  120
tctctggtgg caacaatgag ccattttggt tggtgtggta gtctattatt gagtttttt  180
tggcaccgta ctcccatgga gagtagaaga caaactcttc accgttgtag tcgttgatgg  240
tattggtggt gacgacatcc ttggtgtgca tgcactggtg agtcactgtt gtactcggcg  300

SEQ ID NO: 507          moltype = DNA  length = 104
FEATURE                 Location/Qualifiers
source                  1..104
                        mol_type = other DNA
                        organism = Zea mays
SEQUENCE: 507
ggacaacaag caccttcttg ccttgcaagg cctcccttcc ctatggtagc cacttgagtg  60
gatgacttca ccttaaagct atcgattccc taagtgccag acat                   104

SEQ ID NO: 508          moltype = DNA  length = 80
FEATURE                 Location/Qualifiers
source                  1..80
                        mol_type = other DNA
                        organism = Zea mays
SEQUENCE: 508
ctcttcaccg ttgtagtcgt tgatggtatt ggtggtgacg acatccttgg tgtgcatgca  60
ctggtgagtc actgttgtac                                              80

SEQ ID NO: 509          moltype = DNA  length = 184
FEATURE                 Location/Qualifiers
source                  1..184
                        mol_type = other DNA
                        organism = Zea mays
SEQUENCE: 509
ggacaacaag caccttcttg ccttgcaagg cctcccttcc ctatggtagc cacttgagtg  60
gatgacttca ccttaaagct atcgattccc taagtgccag acatctcttc accgttgtag  120
tcgttgatgg tattggtggt gacgacatcc ttggtgtgca tgcactggtg agtcactgtt  180
gtac                                                               184

SEQ ID NO: 510          moltype = DNA  length = 36
```

-continued

```
FEATURE                   Location/Qualifiers
source                    1..36
                          mol_type = other DNA
                          organism = synthetic construct
SEQUENCE: 510
aattttaatt ttaattttaa ttttaatttt aatttt                          36

SEQ ID NO: 511            moltype = DNA  length = 36
FEATURE                   Location/Qualifiers
source                    1..36
                          mol_type = other DNA
                          organism = synthetic construct
SEQUENCE: 511
ttatttattt tatttatttt atttatttta tttatt                          36

SEQ ID NO: 512            moltype = DNA  length = 36
FEATURE                   Location/Qualifiers
source                    1..36
                          mol_type = other DNA
                          organism = synthetic construct
SEQUENCE: 512
tctctttctc tttctctttc tctttctctt tctctt                          36

SEQ ID NO: 513            moltype = RNA  length = 36
FEATURE                   Location/Qualifiers
source                    1..36
                          mol_type = other RNA
                          organism = synthetic construct
SEQUENCE: 513
tggatagggt agcttctccg gttttagagc tatgct                          36

SEQ ID NO: 514            moltype = RNA  length = 36
FEATURE                   Location/Qualifiers
source                    1..36
                          mol_type = other RNA
                          organism = synthetic construct
SEQUENCE: 514
ccatcgtcag atggtgacgg gttttagagc tatgct                          36

SEQ ID NO: 515            moltype = RNA  length = 36
FEATURE                   Location/Qualifiers
source                    1..36
                          mol_type = other RNA
                          organism = synthetic construct
SEQUENCE: 515
gcaggttcag aagaagaaca gttttagagc tatgct                          36
```

PLANT CELLS, PLANTS, AND SEEDS HAVING TARGETED ENHANCER ELEMENT INSERTIONS

CROSS-REFERENCE TO RELATED APPLICATIONS

This application is a divisional of U.S. patent application Ser. No. 16/480,992, filed Jul. 25, 2019, which is a 35 U.S.C. § 371 U.S. National Stage Application of International Patent Application No. PCT/US2018/015793, filed Jan. 29, 2018, which claims the benefit of U.S. Provisional Patent Application Ser. Nos. 62/451,708, filed Jan. 28, 2017; 62/451,710, filed Jan. 28, 2017; 62/452,610, filed Jan. 31, 2017; 62/477,244, filed Mar. 27, 2017; 62/480,989, filed Apr. 3, 2017; 62/510,645, filed May 24, 2017; 62/523,675, filed Jun. 22, 2017; 62/530,495, filed Jul. 10, 2017; 62/530,839, filed Jul. 10, 2017; and 62/531,305, filed Jul. 11, 2017, which are incorporated herein by reference in their entireties.

INCORPORATION OF SEQUENCE LISTING

The instant application contains a sequence listing, which has been submitted in XML file format by electronic submission and is hereby incorporated by reference in its entirety. The XML file, created on Feb. 9, 2023, is named P13440US12.xml and is 527,878 bytes in size.

FIELD OF THE INVENTION

Aspects of this invention relate to plant breeding methods and compositions. Disclosed herein are novel plant cells, plants and seeds derived from such plant cells and having enhanced traits, and methods of making and using such plant cells and derived plants and seeds.

BACKGROUND

Plant breeding and engineering has relied primarily on Mendelian genetics or recombinant techniques. More recent examples of methods for editing the genomes of plants include, e.g., Wang et al., *Nature Biotechnology,* 32(9), (2014), which describes TALEN-mediated editing (indels) of wheat MLO genes. The method requires transforming wheat protoplasts with a TALEN plasmid and a plasmid carrying a selectable marker (bar), followed by the selection of herbicide resistant calli and the regeneration of transgenic seedlings. Wang also describes the non-homologous end joining (NHEJ)-mediated knock-in of a GFP coding sequence at a TaMLO site in wheat protoplasts. The method requires transformation of protoplasts with T-MLO plus GFP donor plasmids (promoter-less GFP coding sequence and CaMV 35S terminator, flanked by T-MLO recognition sites).

Zhang et al., *Nat. Commun.,* 7:12617 (2016), describes a method of introducing a targeted indel into a locus within the wheat genome. The method requires the use of plasmids encoding or expressing CRISPR/Cas9 RNA and guide RNA sequences and the insertion of those sequences into wheat callus cells.

Liang, Z. et al., *Nat. Commun.,* 8:14261 (2017) describes a method for introducing targeted indels into homologs of a wheat gene (TaGW2). The method requires the delivery of Cas9/sgRNA RNPs into embryonic wheat calli using particle bombardment or PEG-mediated transformation.

PCT application WO2016007948, published Jan. 14, 2016, and titled "Agronomic trait modification using guide RNA/cas endonuclease systems and methods of use," describes methods for introducing targeted modifications to the maize genome. The methods require homologous recombination and/or the transformation of maize embryos with plasmids, and/or the use of selectable markers.

SUMMARY

Disclosed herein are methods for providing novel plant cells or plant protoplasts, plant callus, tissues or parts, whole plants, and seeds having one or more altered genetic sequences. Among other features, the methods and compositions described herein enable the stacking of preferred alleles without introducing unwanted genetic or epigenetic variation in the modified plants or plant cells. The efficiency and reliability of these targeted modification methods are significantly improved relative to traditional plant breeding, and can be used not only to augment traditional breeding techniques but also as a substitute for them.

Disclosed herein are methods for providing novel plant cells or plant protoplasts, plant callus, tissues or parts, whole plants, and seeds having one or more altered genetic sequences.

In one aspect, the invention provides a method of changing expression of a sequence of interest in a genome, including integrating a sequence encoded by a polynucleotide, such as double-stranded or single-stranded polynucleotides including DNA, RNA, or a combination of DNA and RNA, at the site of at least one double-strand break (DSB) in a genome, which can be the genome of a eukaryotic nucleus (e. g., the nuclear genome of a plant cell) or a genome of an organelle (e. g., a mitochondrion or a plastid in a plant cell). Effector molecules (or targeting agents) for site-specific introduction of a DSB into a genome include various endonucleases (e. g., RNA-guided nucleases such as a type II Cas nuclease, a Cas9, a type V Cas nuclease, a Cpf1, a CasY, a CasX, a C2c1, or a C2c3) and guide RNAs that direct cleavage by an RNA-guided nuclease. Embodiments include those where the DSB is introduced into a genome by a ribonucleoprotein complex containing both a site-specific nuclease (e. g., Cas9, Cpf1, CasX, CasY, C2c1, C2c3) and at least one guide RNA, or by a site-specific nuclease in combination with at least one guide RNA; in some of these embodiments no plasmid or other expression vector is utilized to provide the nuclease, the guide RNA, or the polynucleotide. These effector molecules are delivered to the cell or organelle wherein the DSB is to be introduced by the use of one or more suitable composition or treatment, such as at least one chemical, enzymatic, or physical agent, or application of heat or cold, ultrasonication, centrifugation, electroporation, particle bombardment, and bacterially mediated transformation. It is generally desirable that the DSB is induced at high efficiency. One measure of efficiency is the percentage or fraction of the population of cells that have been treated with a DSB-inducing agent and in which the DSB is successfully introduced at the correct site in the genome. The efficiency of genome editing is assessed by any suitable method such as a heteroduplex cleavage assay or by sequencing, as described elsewhere in this disclosure. In various embodiments, the DSB is introduced at a comparatively high efficiency, e. g., at about 20, about 30, about 40, about 50, about 60, about 70, or about 80 percent efficiency, or at greater than 80, 85, 90, or 95 percent efficiency. In embodiments, the DSB is introduced upstream of, downstream of, or within the sequence of interest, which is coding, non-coding, or a combination of coding and non-coding sequence. In embodiments, a sequence encoded by the polynucleotide (such as a double-stranded DNA, a single-stranded DNA, a single-stranded DNA/RNA hybrid, or a double-stranded DNA/RNA hybrid), when integrated into the site of the DSB in the genome, is then functionally or operably linked to the sequence of interest, e. g., linked in a manner that modifies the transcription or the translation of the sequence of interest or that modifies the stability of a transcript including that of the sequence of interest. Embodiments include those where two or more DSBs are introduced into a genome, and wherein a sequence encoded by a polynucleotide (such as a double-stranded DNA, a single-stranded DNA, a single-stranded DNA/RNA hybrid, or a double-stranded DNA/RNA hybrid) that is integrated into each DSB is the same or different for each of the DSBs. In embodiments, at least two DSBs are introduced into a genome by one or more nucleases in such a way that genomic sequence (coding, non-coding, or a combination of coding and non-coding sequence) is deleted between the DSBs (leaving a deletion with blunt ends, overhangs or a combination of a blunt end and an overhang), and a sequence encoded by a polynucleotide (such as a double-stranded DNA, a single-stranded DNA, a single-stranded DNA/RNA hybrid, or a double-stranded DNA/RNA hybrid) molecule is integrated between the DSBs (i. e., at the location of the deleted genomic sequence). The method is particularly useful for integrating into the site of a DSB a heterologous nucleotide sequence that provides a useful function or use. For example, the method is useful for integrating or introducing into the genome a heterologous sequence that stops or knocks out expression of a sequence of interest (such as a gene encoding a protein), or a heterologous sequence that is a unique identifier nucleotide sequence, or a heterologous sequence that is (or that encodes) a sequence recognizable by a specific binding agent or that binds to a specific molecule, or a heterologous sequence that stabilizes or destabilizes a transcript containing it. Embodiments include use of the method to integrate or introduce into a genome sequence of a promoter or promoter-like element (e. g., sequence of an auxin-binding or hormone-binding or transcription-factor-binding element, or sequence of or encoding an aptamer or riboswitch), or a sequence-specific binding or cleavage site sequence (e. g., sequence of or encoding an endonuclease cleavage site, a small RNA recognition site, a recombinase site, a splice site, or a transposon recognition site). In embodiments, the method is used to delete or otherwise modify to make non-functional an endogenous functional sequence, such as a hormone- or transcription-factor-binding element, or a small RNA or recombinase or transposon recognition site. In embodiments, additional molecules are used to effect a desired expression result or a desired genomic change. For example, the method is used to integrate heterologous recombinase recognition site sequences at two DSBs in a genome, and the appropriate recombinase molecule is employed to excise genomic sequence located between the recombinase recognition sites. In another example, the method is used to integrate a polynucleotide-encoded heterologous small RNA recognition site sequence at a DSB in a sequence of interest in a genome, wherein when the small RNA is present (e. g., expressed endogenously or transiently or transgenically), the small RNA binds to and cleaves the transcript of the sequence of interest that contains the integrated small RNA recognition site. In another example, the method is used to integrate in the genome of a plant or plant cell a polynucleotide-encoded promoter or promoter-like element that is responsive to a specific molecule (e. g., an auxin, a hormone, a drug, an herbicide, or a polypeptide), wherein a specific level of expression of the sequence of interest is obtained by providing the corresponding specific molecule to the plant or plant cell; in a non-limiting example, an auxin-binding element is integrated into the promoter region of a protein-coding sequence in the genome of a plant or plant cell, whereby the expression of the protein is upregulated when the corresponding auxin is exogenously provided to the plant or plant cell (e. g., by adding the auxin to the medium of the plant cell or by spraying the auxin onto the plant). Another aspect of the invention is a cell including in its genome a heterologous DNA sequence, wherein the heterologous sequence includes (a) nucleotide sequence of a polynucleotide integrated by the method at the site of a DSB in the genome, and (b) genomic nucleotide sequence adjacent to the site of the DSB; related aspects include a plant containing such a cell including in its genome a heterologous DNA sequence, progeny seed or plants (including hybrid progeny seed or plants) of the plant, and processed or commodity products derived from the plant or from progeny seed or plants. In another aspect, the invention provides a heterologous nucleotide sequence including (a) nucleotide sequence of a polynucleotide (such as a double-stranded DNA, a single-stranded DNA, a single-stranded DNA/RNA hybrid, or a double-stranded DNA/RNA hybrid) molecule integrated by the method at the site of a DSB in a genome, and (b) genomic nucleotide sequence adjacent to the site of the DSB; related aspects include larger polynucleotides such as a plasmid, vector, or chromosome including the heterologous nucleotide sequence, as well as a polymerase primer for amplification of the heterologous nucleotide sequence.

In another aspect, the invention provides a composition including a plant cell and a polynucleotide (such as a double-stranded DNA, a single-stranded DNA, a single-stranded DNA/RNA hybrid, or a double-stranded DNA/RNA hybrid) donor molecule that is capable of being integrated at (or having its sequence integrated at) a double-strand break in genomic sequence in the plant cell. In various embodiments, the plant cell is an isolated plant cell or plant protoplast, or is in a monocot plant or dicot plant, a zygotic or somatic embryo, seed, plant part, or plant tissue. In embodiments the plant cell is capable of division or differentiation. In embodiments the plant cell is haploid, diploid, or polyploid. In embodiments, the plant cell includes a double-strand break (DSB) in its genome, at which DSB site the polynucleotide donor molecule is integrated using methods disclosed herein. In embodiments, at least one DSB is induced in the plant cell's genome by including in the composition a DSB-inducing agent, for example, various endonucleases (e. g., RNA-guided nucleases such as a type II Cas nuclease, a Cas9, a type V Cas nuclease, a Cpf1, a CasY, a CasX, a C2c1, or a C2c3) and guide RNAs that direct cleavage by an RNA-guided nuclease; the dsDNA molecule is integrated into the DSB thus induced using methods disclose herein. Specific embodiments include compositions including a plant cell, at least one dsDNA molecule, and at least one ribonucleoprotein complex containing both a site-specific nuclease (e. g., Cas9, Cpf1, CasX, CasY, C2c1, C2c3) and at least one guide RNA; in some of these embodiments, the composition contains no plasmid or other expression vector for providing the nuclease, the guide RNA, or the dsDNA. In embodiments of the composition, the polynucleotide donor molecule is double-stranded DNA or RNA or a combination of DNA and RNA, and is blunt-ended, or contains one or more terminal overhangs, or contains chemical modifications such as phosphorothioate bonds or a detectable label. In other embodiments, the polynucleotide donor molecule is a single-stranded polynucleotide composed of DNA or RNA or a combination of DNA or RNA, and can further be chemically modified or labelled. In various embodiments of the composition, the polynucleotide donor molecule includes a nucleotide sequence that provides a useful function when integrated into the site of the DSB. For example, in various non-limiting embodiments the polynucleotide donor molecule includes: sequence that is recognizable by a specific binding agent or that binds to a specific molecule or encodes an RNA molecule or an amino acid sequence that binds to a specific molecule, or sequence that is responsive to a specific change in the physical environment or encodes an RNA molecule or an amino acid sequence that is responsive to a specific change in the physical environment, or heterologous sequence, or sequence that serves to stop transcription or translation at the site of the DSB, or sequence having secondary structure (e. g., double-stranded stems or stem-loops) or than encodes a transcript having secondary structure (e. g., double-stranded RNA that is cleavable by a Dicer-type ribonuclease).

In another aspect, the invention provides a reaction mixture including: (a) a plant cell having at least one double-strand break (DSB) at a locus in its genome; and (b) a polynucleotide (such as a double-stranded DNA, a single-stranded DNA, a single-stranded DNA/RNA hybrid, or a double-stranded DNA/RNA hybrid) donor molecule capable of being integrated at (or having its sequence integrated at) the DSB (preferably by non-homologous end-joining (NHEJ)), wherein the polynucleotide donor molecule has a length of between about 18 to about 300 base-pairs (or nucleotides, if single-stranded), or between about 30 to about 100 base-pairs (or nucleotides, if single-stranded); wherein the polynucleotide donor molecule includes a sequence which, if integrated at the DSB, forms a heterologous insertion (wherein the sequence of the polynucleotide molecule is heterologous with respect to the genomic sequence flanking the insertion site or DSB). In embodiments of the reaction mixture, the plant cell is an isolated plant cell or plant protoplast. In various embodiments, the plant cell is an isolated plant cell or plant protoplast, or is in a monocot plant or dicot plant, a zygotic or somatic embryo, seed, plant part, or plant tissue. In embodiments the plant cell is capable of division or differentiation. In embodiments the plant cell is haploid, diploid, or polyploid. In embodiments of the reaction mixture, the polynucleotide donor molecule includes a nucleotide sequence that provides a useful function or use when integrated into the site of the DSB. For example, in various non-limiting embodiments the polynucleotide donor molecule includes: sequence that is recognizable by a specific binding agent or that binds to a specific molecule or encodes an RNA molecule or an amino acid sequence that binds to a specific molecule, or sequence that is responsive to a specific change in the physical environment or encodes an RNA molecule or an amino acid sequence that is responsive to a specific change in the physical environment, or heterologous sequence, or sequence that serves to stop transcription or translation at the site of the DSB, or sequence having secondary structure (e. g., double-stranded stems or stem-loops) or than encodes a transcript having secondary structure (e. g., double-stranded RNA that is cleavable by a Dicer-type ribonuclease). Note that in embodiments where the donor sequence is inserted by NHEJ, the donor polynucleotide contains no nucleotide sequence that is homologous to or complementary to a nucleotide sequence immediately flanking the DSB that is effected in the genome; in other words, the nucleotide sequence at either terminus of the donor polynucleotide does not have sufficient complementarity to genomic sequence flanking the DSB to allow the donor polynucleotide to anneal to one or both sides of the DSB in a manner similar to what occurs during homology-directed repair (HDR). In embodiments described herein, the donor polynucleotide contains no nucleotide sequence that is identical to an *Agrobacterium* T-DNA border sequence. Embodiments of the methods enable the precise insertion of at least one pre-determined, heterologous, non-homologous donor polynucleotide sequence (e. g., non-coding sequence, such as a regulatory or expression-modifying element) at two or more loci in a genome. In embodiments, at least one of these insertions or targeted modifications modifies expression of an endogenous gene or sequence of interest. In embodiments, the two or more loci in a genome are in different genes or sequences of interest. In embodiments, the two or more loci are alleles of a given sequence of interest; when all alleles of a given gene or sequence of interest are modified in the same way, the result is homozygous modification of the gene. For example, embodiments of the method enable targeted modification of both alleles of a gene in a diploid (2n ploidy, where n=1) plant, or targeted modification of all three alleles in a triploid (2n ploidy, where n=1.5) plant, or targeted modification of all six alleles of a gene in a hexaploid (2n ploidy, where n=3) plant.

In another aspect, the invention provides a polynucleotide for disrupting gene expression, wherein the polynucleotide is double-stranded and includes at least 18 contiguous base-pairs and encoding at least one stop codon in each possible reading frame on each strand, or is single-stranded and includes at least 11 contiguous nucleotides; and wherein the polynucleotide encodes at least one stop codon in each possible reading frame on each strand. In embodiments, the polynucleotide is a double-stranded DNA (dsDNA) or a double-stranded DNA/RNA hybrid molecule including at least 18 contiguous base-pairs and encoding at least one stop codon in each possible reading frame on either strand. In embodiments, the polynucleotide is a single-stranded DNA or a single-stranded DNA/RNA hybrid molecule including at least 11 contiguous nucleotides and encoding at least one stop codon in each possible reading frame on the strand. Such a polynucleotide is especially useful in methods disclosed herein, wherein, when a sequence encoded by the polynucleotide is integrated or inserted into a genome at the site of a DSB in a sequence of interest (such as a protein-coding gene), the sequence of the heterologously inserted polynucleotide serves to stop translation of the transcript containing the sequence of interest and the heterologously inserted polynucleotide sequence. Embodiments of the polynucleotide include those wherein the polynucleotide includes one or more chemical modifications or labels, e. g., at least one phosphorothioate modification.

In another aspect, the invention provides a method of identifying the locus of at least one double-stranded break (DSB) in genomic DNA in a cell (such as a plant cell) including the genomic DNA, wherein the method includes the steps of: (a) contacting the genomic DNA having a DSB with a polynucleotide (such as a double-stranded DNA, a single-stranded DNA, a single-stranded DNA/RNA hybrid, or a double-stranded DNA/RNA hybrid) donor molecule, wherein the polynucleotide donor molecule is capable of being integrated (or having its sequence integrated) at the DSB (preferably by non-homologous end-joining (NHEJ)) and has a length of between about 18 to about 300 base-pairs (or nucleotides, if single-stranded), or between about 30 to about 100 base-pairs (or nucleotides, if single-stranded); wherein a sequence encoded by the polynucleotide donor molecule, if integrated at the DSB, forms a heterologous insertion; and (b) using at least part of the sequence of the polynucleotide molecule as a target for PCR primers to allow amplification of DNA in the locus of the DSB. In a related aspect, the invention provides a method of identifying the locus of double-stranded breaks (DSBs) in genomic DNA in a pool of cells (such as plant cells or plant protoplasts), wherein the pool of cells includes cells having genomic DNA with a sequence encoded by a polynucleotide donor molecule inserted at the locus of the double-stranded breaks; wherein the polynucleotide donor molecule is capable of being integrated (or having its sequence integrated) at the DSB and has a length of between about 18 to about 300 base-pairs (or nucleotides, if single-stranded), or between about 30 to about 100 base-pairs (or nucleotides, if single-stranded); wherein a sequence encoded by the polynucleotide donor molecule, if integrated at the DSB, forms a heterologous insertion; and wherein the sequence of the polynucleotide donor molecule is used as a target for PCR primers to allow amplification of DNA in the region of the double-stranded breaks. In embodiments, the pool of cells is a population of plant cells or plant protoplasts, wherein at least some of the cells contain multiple or different DSBs in the genome, each of which can be introduced into the genome by a different guide RNA.

In another aspect, the invention provides a method of identifying the nucleotide sequence of a locus in the genome that is associated with a phenotype, the method including the steps of: (a) providing to a population of cells having the genome: (i) multiple different guide RNAs (gRNAs) to induce multiple different double strand breaks (DSBs) in the genome, wherein each DSB is produced by an RNA-guided nuclease guided to a locus on the genome by one of the gRNAs, and (ii) polynucleotide (such as double-stranded DNA, single-stranded DNA, single-stranded DNA/RNA hybrid, and double-stranded DNA/RNA hybrid) donor molecules having a defined nucleotide sequence, wherein the polynucleotide donor molecules are capable of being integrated (or having their sequence integrated) into the DSBs by non-homologous end-joining (NHEJ); whereby when at least a sequence encoded by some of the polynucleotide donor molecules are inserted into at least some of the DSBs, a genetically heterogeneous population of cells is produced; (b) selecting from the genetically heterogeneous population of cells a subset of cells that exhibit a phenotype of interest; (c) using a pool of PCR primers that bind to at least part of the nucleotide sequence of the polynucleotide donor molecules to amplify from the subset of cells DNA from the locus of a DSB into which one of the polynucleotide donor molecules has been inserted; and (d) sequencing the amplified DNA to identify the locus associated with the phenotype of interest. In embodiments of the method, the gRNA is provided as a polynucleotide, or as a ribonucleoprotein including the gRNA and the RNA-guided nuclease. Related aspects include the cells produced by the method and pluralities, arrays, and genetically heterogeneous populations of such cells, as well as the subset of cells in which the locus associated with the phenotype has been identified, and callus, seedlings, plantlets, and plants and their seeds, grown or regenerated from such cells.

In another aspect, the invention provides a method of modifying a plant cell by creating a plurality of targeted modifications in the genome of the plant cell, wherein the method comprises contacting the genome with one or more targeting agents (or effector molecules), wherein the one or more agents comprise or encode predetermined peptide or nucleic acid sequences (for example, a sequence-specific nuclease or a polynucleotide encoding a sequence-specific nuclease, or a guide RNA), wherein the predetermined peptide or nucleic acid sequences bind preferentially at or near predetermined target sites within the plant genome, and wherein the binding directs or facilitates the generation of the plurality of targeted modifications within the genome; wherein the plurality of targeted modifications occurs without an intervening step of separately identifying an individual modification and without a step of separately selecting for the occurrence of an individual modification among the plurality of targeted modifications mediated by the targeting agents; and wherein the targeted modifications alter at least one trait of the plant cell, or at least one trait of a plant comprising the plant cell, or at least one trait of a plant grown from the plant cell, or result in a detectable phenotype in the modified plant cell; and wherein at least two of the targeted modifications are insertions of predetermined sequences encoded by one or more polynucleotide donor molecules, and wherein at least one of the polynucleotide donor molecules lacks homology to the genome sequences adjacent to the site of insertion. “Lacks homology” in the context of the targeted modification methods describes herein means that the donor sequence lacks homology or complementarity sufficient to allow the donor polynucleotide to bind to the genomic sequences immediately flanking the site of genomic insertion. The methods result in precise insertions, at at least two predetermined target sites in the genome, of at least one defined, heterologous, non-homologous sequence encoded by a polynucleotide donor. The inserted donor sequence can be coding (e.g., protein or RNA coding) sequence or non-coding sequence (e.g., a regulatory element) or a combination of coding and non-coding sequence. The sequence encoded by the polynucleotide donor is heterologous with respect to the genomic locus into which the sequence is inserted. In embodiments, insertion of a non-coding donor sequence modifies expression of an endogenous gene located cis to (e.g., 5' to or 3' to) the inserted sequence. In a related embodiment, at least one of the polynucleotide donor molecules used in the method is a single stranded DNA molecule, a single stranded RNA molecule, a single stranded DNA-RNA hybrid molecule, or a duplex RNA-DNA molecule. In another related embodiment, wherein the modified plant cell of the method is a meristematic cell, embryonic cell, or germline cell. In yet another related embodiment, the methods described in this paragraph, when practiced repeatedly or on a pool of cells, result in an efficiency of at least 1%, e.g., at least 2%, 5%, 7%, 10%, 15%, 20%, 25%, 30%, 35% or more, wherein said efficiency is determined, e.g., by dividing the number of successfully targeted cells by the total number of cells targeted. In a related embodiment, the targeted plant cell has a ploidy of 2n, with n being a value selected from the group consisting of 0.5, 1, 1.5, 2, 2.5, 3, 3.5, 4, 5, and 6, wherein the method generates 2n targeted modifications at 2n loci of the predetermined target sites within the plant cell genome; and wherein 2n of the targeted modifications are insertions or creations of predetermined sequences encoded by one or more polynucleotide donor molecules.

In another related embodiment, the invention provides a method of modifying a plant cell by creating a plurality of targeted modifications in the genome of the plant cell, comprising: contacting the genome with one or more targeting agents, wherein the one or more agents comprise or encode predetermined peptide or nucleic acid sequences, wherein the predetermined peptide or nucleic acid sequences bind preferentially at or near predetermined target sites within the plant genome, and wherein the binding directs the generation of the plurality of targeted modifications within the genome; wherein the plurality of targeted modifications occurs without an intervening step of separately identifying an individual modification and without a step of separately selecting for the occurrence of an individual modification among the plurality of targeted modifications mediated by the targeting agents; and wherein the targeted modifications improve at least one trait of the plant cell, or at least one trait of a plant comprising the plant cell, or at least one trait of a plant grown from the plant cell, or result in a detectable phenotype in the modified plant cell; and wherein at least one of the targeted modifications is an insertion of a predetermined sequence encoded by one or more polynucleotide donor molecules, and wherein at least one of the polynucleotide donor molecules is a single stranded DNA molecule, a single stranded RNA molecule, a single stranded DNA-RNA hybrid molecule, or a duplex RNA-DNA molecule. In a related embodiment, at least one of the polynucleotide donor molecules used in the method lacks homology to the genome sequences adjacent to the site of insertion. In another related embodiment, the modified plant cell is a meristematic cell, embryonic cell, or germline cell. In yet another related embodiment, repetition of the methods described in this paragraph result in an efficiency of at least 1%, e.g., at least 2%, 5%, 7%, 10%, 15%, 20%, 25%, 30%, 35% or more, wherein said efficiency is determined by dividing the number of successfully targeted cells by the total number of cells targeted. In a related embodiment, the targeted plant cell has a ploidy of 2n, with n being a value selected from the group consisting of 0.5, 1, 1.5, 2, 2.5, 3, 3.5, 4, 5, and 6, wherein the method generates 2n targeted modifications at 2n loci of the predetermined target sites within the plant cell genome; and wherein 2n of the targeted modifications are insertions or creations of predetermined sequences encoded by one or more polynucleotide donor molecules.

In another embodiment, the invention provides a method of modifying a plant cell by creating a plurality of targeted modifications in the genome of the plant cell, comprising: contacting the genome with one or more targeting agents, wherein the one or more agents comprise or encode predetermined peptide or nucleic acid sequences, wherein the predetermined peptide or nucleic acid sequences bind preferentially at or near predetermined target sites within the plant genome, and wherein the binding directs the generation of the plurality of targeted modifications within the genome; wherein the plurality of modifications occurs without an intervening step of separately identifying an individual modification and without a step of separately selecting for the occurrence of an individual modification among the plurality of targeted modifications mediated by the targeting agents; wherein the targeted modifications improve at least one trait of the plant cell, or at least one trait of a plant comprising the plant cell, or at least one trait of a plant or seed obtained from the plant cell, or result in a detectable phenotype in the modified plant cell; and wherein the modified plant cell is a meristematic cell, embryonic cell, or germline cell. In a related embodiment, at least one of the targeted modifications is an insertion of a predetermined sequence encoded by one or more polynucleotide donor molecules, and wherein at least one of the polynucleotide donor molecules is a single stranded DNA molecule, a single stranded RNA molecule, a single stranded DNA-RNA hybrid molecule, or a duplex RNA-DNA molecule. In yet another related embodiment, at least one of the polynucleotide donor molecules lacks homology to the genome sequences adjacent to the site of insertion. In yet another embodiment related to the methods of this paragraph, repetition of the method results in an efficiency of at least 1%, e.g., at least 2%, 5%, 7%, 10%, 15%, 20%, 25%, 30%, 35% or more, wherein said efficiency is determined by dividing the number of successfully targeted cells by the total number of cells targeted. In a related embodiment, the targeted plant cell has a ploidy of 2n, with n being a value selected from the group consisting of 0.5, 1, 1.5, 2, 2.5, 3, 3.5, 4, 5, and 6, wherein the method generates 2n targeted modifications at 2n loci of the predetermined target sites within the plant cell genome; and wherein 2n of the targeted modifications are insertions or creations of predetermined sequences encoded by one or more polynucleotide donor molecules.

In another embodiment, the invention provides a method of modifying a plant cell by creating a plurality of targeted modifications in the genome of the plant cell, comprising: contacting the genome with one or more targeting agents, wherein the one or more agents comprise or encode predetermined peptide or nucleic acid sequences, wherein the predetermined peptide or nucleic acid sequences bind preferentially at or near predetermined target sites within the plant genome, and wherein the binding directs the generation of the plurality of targeted modifications within the genome; wherein the plurality of modifications occurs without an intervening step of separately identifying an individual modification and without a step of separately selecting for the occurrence of an individual modification among the plurality of targeted modifications mediated by the targeting agents; and wherein the targeted modifications improve at least one trait of the plant cell, or at least one trait of a plant comprising the plant cell, or at least one trait of a plant or seed obtained from the plant cell, or result in a detectable phenotype in the modified plant cell; and wherein repetition of the aforementioned steps results in an efficiency of at least 1%, e.g., at least 2%, 5%, 7%, 10%, 15%, 20%, 25%, 30%, 35% or more, wherein said efficiency is determined by dividing the number of successfully targeted cells by the total number of cells targeted. In a related embodiment, the modified plant cell is a meristematic cell, embryonic cell, or germline cell. In another related embodiment, at least one of the targeted modifications is an insertion of a predetermined sequence encoded by one or more polynucleotide donor molecules, and wherein at least one of the polynucleotide donor molecules is a single stranded DNA molecule, a single stranded RNA molecule, a single stranded DNA-RNA hybrid molecule, or a duplex RNA-DNA molecule. In yet another related embodiment of the methods of this paragraph, at least one of the polynucleotide donor molecules used in the method lacks homology to the genome sequences adjacent to the site of insertion. In a related embodiment, the targeted plant cell has a ploidy of 2n, with n being a value selected from the group consisting of 0.5, 1, 1.5, 2, 2.5, 3, 3.5, 4, 5, and 6, wherein the method generates 2n targeted modifications at 2n loci of the predetermined target sites within the plant cell genome; and wherein 2n of the targeted modifications are insertions or creations of predetermined sequences encoded by one or more polynucleotide donor molecules.

In various embodiments of the methods described above, at least one of the targeted modifications is an insertion between 3 and 400 nucleotides in length, between 10 and 350 nucleotides in length, between 18 and 350 nucleotides in length, between 18 and 200 nucleotides in length, between 10 and 150 nucleotides in length, or between 11 and 100 nucleotides in length. In certain, embodiments, two of the targeted modifications are insertions between 10 and 350 nucleotides in length, between 18 and 350 nucleotides in length, between 18 and 200 nucleotides in length, between 10 and 150 nucleotides in length, or between 11 and 100 nucleotides in length.

In another variation of the methods described above, at least two insertions are made, and at least one of the insertions is an upregulatory sequence. In yet another variation, the targeted modification methods described above insert or create at least one transcription factor binding site. In yet another variation of the methods described above, the insertion or insertions of predetermined sequences into the plant genome are accompanied by the deletion of sequences from the plant genome.

In yet another embodiment of the targeted modification methods described above, the methods further comprise obtaining a plant from the modified plant cell and breeding the plant. In yet another embodiment, the methods described above comprise a step of introducing additional genetic or epigenetic changes into the modified plant cell or into a plant grown from the modified plant cell.

In an embodiment of the targeted modification methods described above, at least two targeted insertions are made and the targeted insertions independently up- or down-regulate the expression of two or more distinct genes. For example, a targeted insertion may increase expression at least 10%, 15%, 20%, 25%, 30%, 35%, 40%, 50%, 60%, 70%, 80%, 90%, 95%, 100% or greater, e.g., at least a 2-fold, 5-fold, 10-fold, 20-fold, 30-fold, 40-fold, 50-fold change, 100-fold or even 1000-fold change or more. In some embodiments, expression is increased between 10-100%; between 2-fold and 5-fold; between 2 and 10-fold; between 10-fold and 50-fold; between 10-fold and a 100-fold; between 100-fold and 1000-fold; between 1000-fold and 5,000-fold; between 5,000-fold and 10,000 fold. In some embodiments, a targeted insertion may decrease expression by at least 1%, 5%, 10%, 15%, 20%, 25%, 30%, 35%, 40%, 50%, 60%, 70%, 80%, 90%, 95%, 99% or more.

In yet another embodiment of the targeted insertion methods described above, the donor polynucleotide is tethered to a crRNA by a covalent bond, a non-covalent bond, or a combination of covalent and non-covalent bonds. In a related embodiment, the invention provides a composition for targeting a genome comprising a donor polynucleotide tethered to a cRNA by a covalent bond, a non-covalent bond, or a combination of covalent and non-covalent bonds.

In another embodiment of the targeted modification methods described above, the loss of epigenetic marks after modifying occurs in less than 0.1%, 0.08%, 0.05%, 0.02%, or 0.01% of the genome. In yet another embodiment of the targeted modification methods described above, the genome of the modified plant cell is more than 99%, e.g., more than 99.5% or more than 99.9% identical to the genome of the parent cell.

In yet another embodiment of the targeted modification methods described above, at least one of the targeted modifications is an insertion and at least one insertion is in a region of the genome that is recalcitrant to meiotic or mitotic recombination. In general, the compositions and methods disclosed herein are useful in editing multiple loci, alleles, or genes to provide a phenotype directly in germline cells of a plant, such as a crop plant having elite germplasm, without the undesirable effects (e.g., gene drag, random meiotic recombination, epigenetic changes caused by regeneration/tissue culture) obtained by using traditional breeding and/or transgenic techniques. The compositions and methods disclosed herein provide additional advantages over other known techniques, for example: the ability to make simultaneous or consecutive multiple edits (genomic modifications) in closely linked genomic regions; the ability to introduce edits in genomic regions that are recalcitrant to ordinary breeding or recombination; the ability to edit a genome to incorporate genetic sequences found in related species (even distantly related) or unrelated species without needing to resort to traditional breeding and multiple generations of crossing, selfing, or backcrossing; and the ability to introduce precise genomic changes directly into elite germplasm of plant species of interest (e.g., elite inbred maize lines that are relevant to hybrid production or are suited to different geographic locations).

In certain embodiments of the plant cell genome targeting methods described above, the plant cell is a member of a pool of cells being targeted. In related embodiments, the modified cells within the pool are characterized by sequencing after targeting.

The invention also provides modified plant cells comprising at least two separately targeted insertions in its genome, wherein the insertions are determined relative to a parent plant cell, and wherein the modified plant cell is devoid of mitotically or meiotically generated genetic or epigenetic changes relative to the parent plant cell. In certain embodiments, these plant cells are obtained using the multiplex targeted insertion methods described above. In certain embodiments, the modified plant cells comprise at least two separately targeted insertions, wherein the genome of the modified plant cell is at least 95%, at least 96%, at least 97%, at least 98%, at least 99%, at least 99.5%, at least 99.9%, or at least 99.99% identical to the parent cell, taking all genetic or epigenetic changes into account.

While the introgression of certain traits and transgenes into plants has been successful, achieving a homozygous modified plant in one step (i.e., modifying all targeted loci simultaneously) has not been previously described. Plants homozygous for, e.g., targeted insertions could only be obtained by further crossing and/or techniques involving double-haploids. These techniques are not only time consuming and laborious, they also lead to plants which deviate from the original plant not only for the targeted insertion but also for other changes as a consequence of the techniques employed to enable homozygosity. As such changes could have unintended and unpredictable consequences and may require further testing or screening, they are clearly undesired in a breeding process. In certain embodiments, the invention provides methods of making a targeted mutation and/or targeted insertion in all of the 2n targeted loci in a plant genome in one step, resulting a plant that is homozygous with respect to the targeted modification, i.e., all of the targeted alleles in the genome are modified.

The invention also provides modified plant cells resulting from any of the claimed methods described, as well as recombinant plants grown from those modified plant cells. Such plants can consist entirely of the modified plant cells, or can include both the modified plant cells and non-modified plant cells (e.g., genetic mosaics, genetic chimeras, and grafted plants that contain scion and rootstock of different genetics). In yet another embodiment, the invention provides a modified plant cell, having a ploidy of 2n, with n being a value selected from the group consisting of 0.5, 1, 1.5, 2, 2.5, 3, 3.5, 4, 5, and 6, wherein said plant cell comprises at least two precise and separately targeted insertions in its genome at the 2n loci of at least one predetermined target site, wherein the targeted modifications are determined relative to an original plant cell, and wherein the modified plant cell is genetically identical to the original plant with the exception of the targeted modification and any changes as a consequence of multiplying said engineered plant cell. In yet another embodiment, the invention provides a plant, consisting of modified plant cells having a ploidy of 2n, with n being a value selected from the group consisting of 0.5, 1, 1.5, 2, 2.5, 3, 3.5, 4, 5, and 6, wherein each of said plant cells comprises at least two precise and separately targeted modification in its genome at the 2n loci of at least one predetermined target site, wherein the modifications are determined relative to an original plant, and wherein the modified plant is genetically identical to the original plant with the exception of the targeted modification and any changes as a consequence of regenerating or growing said plant from a plant cell of claim 1, and—optionally—further propagating said plant.

In some embodiments, the invention provides a method of manufacturing a processed plant product, comprising: (a) modifying a plant cell according to any of the targeted methods described above; (b) growing an modified plant from said plant cell, and (c) processing the modified plant into a processed product, thereby manufacturing a processed plant product. In related embodiments, the processed product may be meal, oil, juice, sugar, starch, fiber, an extract, wood or wood pulp, flour, cloth or some other commodity plant product. The invention also provides a method of manufacturing a plant product, comprising (a) modifying a plant cell according to any of the targeted methods described above, (b) growing a modified plant from said plant cell, and (c) harvesting a product of the modified plant, thereby manufacturing a plant product. In related embodiments, the plant product is a product may be leaves, fruit, vegetables, nuts, seeds, oil, wood, flowers, cones, branches, hay, fodder, silage, stover, straw, pollen, or some other harvested commodity product. In further related embodiments, the processed products and harvested products are packaged.

BRIEF DESCRIPTION OF THE DRAWINGS

FIGS. 1A-1C depict the Clustal-W (1.83) multiple-sequence alignment of the next-generation sequencing reads of the maize (*Zea mays*) alcohol dehydrogenase ADH1 that were amplified and sequenced as described in detail in Example 4. Sequencing reads are identified by a number beginning with the letter P and are listed from highest to lowest percentage of total NGS reads. P1 identifies the non-edited sequence, i. e., identical to the reference sequence identified at the beginning of the list by an "NCBI_gi" number (NCBI accession number). Asterisks in the last line of the alignment indicate conserved nucleotides.

FIGS. 2A-2F depict the Clustal-W (1.83) multiple-sequence alignment of the next-generation sequencing reads of the kale (*Brassica oleracea*) Myb-like transcription factor 2, BoMYBL2 that were amplified and sequenced as described in detail in Example 5. Sequencing reads are identified by a number beginning with the letter P and are listed from highest to lowest percentage of total NGS reads. P1 identifies the non-edited sequence, i. e., identical to the reference sequence identified at the beginning of the list by an "NCBI_gi" number (NCBI accession number). Asterisks in the last line of the alignment indicate conserved nucleotides.

FIGS. 3A-3C depict the Clustal-W (1.83) multiple-sequence alignment of the next-generation sequencing reads of the kale (*Brassica oleracea*) "*Gigantea*" gene BoGI that were amplified and sequenced as described in detail in Example 5. Sequencing reads are identified by a number beginning with the letter P and are listed from highest to lowest percentage of total NGS reads. P1 identifies the non-edited sequence, i. e., identical to the reference sequence identified at the beginning of the list by an "NCBI_gi" number (NCBI accession number). Asterisks in the last line of the alignment indicate conserved nucleotides.

FIGS. 4A-4D depict the Clustal-W (1.83) multiple-sequence alignment of the next-generation sequencing reads of the maize (*Zea mays*) alcohol dehydrogenase ADH1 that were amplified and sequenced as described in detail in Example 8. Sequencing reads are identified by a number beginning with the letter P and are listed from highest to lowest percentage of total NGS reads. P1 identifies the non-edited sequence, i.e., identical to the reference sequence identified at the beginning of the list by an "NCBI_gi" number (NCBI accession number). Asterisks in the last line of the alignment indicate conserved nucleotides.

FIG. 5 depicts results of experiments described in detail in Example 20. Panel A illustrates mean relative gene expression of Dof1 (solid black bars), NRT2.2 (solid white bars), and Gln1.4 (diagonally hatched bars) genes, normalized to tubulin expression. Null controls are indicated by the "-" symbol. Panel B illustrates mean relative gene expression of the unmodified, endogenous AMT3, normalized to tubulin expression, in the presence of KCl (solid black bars) or $KNO_3$ (solid white bars), in cells where the Dof1, NRT2.2, and Gln1.4 genes were individually modified, or where all three genes were modified ("Multiplex"). Null controls are indicated by the "-" symbol.

DETAILED DESCRIPTION OF THE INVENTION

Definitions

Figure 6:
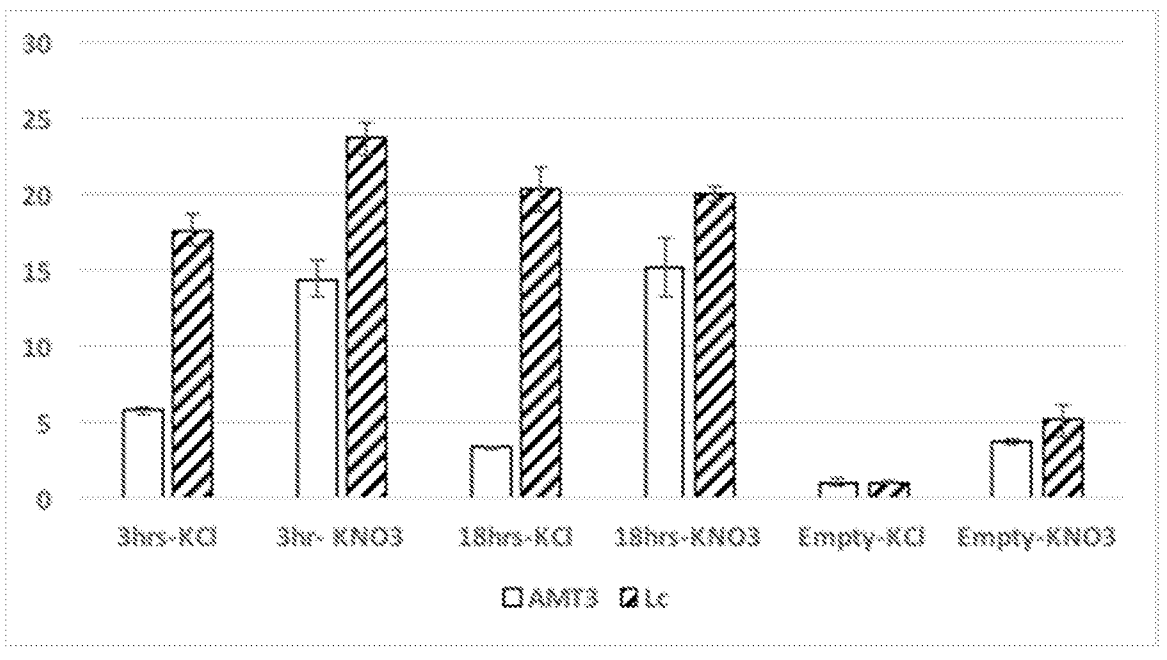
FIG. 6 depicts results of experiments described in detail in Example 23, and illustrates mean relative gene expression of AMT3 (solid white bars) and Lc (diagonally hatched bars) genes, normalized to tubulin expression, in the presence of KCl or $KNO_3$. "3 hrs" and "18 hrs" refer to cells that were subjected to a second (ZmLc-Pro3/OCS homologue) transfection or editing reaction 3 or 18 hours, respectively, after a first (AMT3-Pro1/AtNRE) transfection. Null controls are indicated by "Empty".

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art. Where a term is provided in the singular, the inventors also contemplate aspects of the invention described by the plural of that term.

By "polynucleotide" is meant a nucleic acid molecule containing multiple nucleotides and refers to "oligonucleotides" (defined here as a polynucleotide molecule of between 2-25 nucleotides in length) and polynucleotides of 26 or more nucleotides. Polynucleotides are generally described as single- or double-stranded. Where a polynucleotide contains double-stranded regions formed by intra- or intermolecular hybridization, the length of each double-stranded region is conveniently described in terms of the number of base pairs. Aspects of this invention include the use of polynucleotides or compositions containing polynucleotides; embodiments include one or more oligonucleotides or polynucleotides or a mixture of both, including single- or double-stranded RNA or single- or double-stranded DNA or single- or double-stranded DNA/RNA hybrids or chemically modified analogues or a mixture thereof. In various embodiments, a polynucleotide (such as a single-stranded DNA/RNA hybrid or a double-stranded DNA/RNA hybrid) includes a combination of ribonucleotides and deoxyribonucleotides (e. g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides), or includes non-canonical nucleotides such as inosine, thiouridine, or pseudouridine. In embodiments, the polynucleotide includes chemically modified nucleotides (see, e. g., Verma and Eckstein (1998) *Annu. Rev. Biochem.*, 67:99-134); for example, the naturally occurring phosphodiester backbone of an oligonucleotide or polynucleotide can be partially or completely modified with phosphorothioate, phosphorodithioate, or methylphosphonate internucleotide linkage modifications; modified nucleoside bases or modified sugars can be used in oligonucleotide or polynucleotide synthesis; and oligonucleotides or polynucleotides can be labelled with a fluorescent moiety (e. g., fluorescein or rhodamine or a fluorescence resonance energy transfer or FRET pair of chromophore labels) or other label (e. g., biotin or an isotope). Modified nucleic acids, particularly modified RNAs, are disclosed in U.S. Pat. No. 9,464,124, incorporated by reference in its entirety herein. For some polynucleotides (especially relatively short polynucleotides, e. g., oligonucleotides of 2-25 nucleotides or base-pairs, or polynucleotides of about 25 to about 300 nucleotides or base-pairs), use of modified nucleic acids, such as locked nucleic acids ("LNAs"), is useful to modify physical characteristics such as increased melting temperature ($T_m$) of a polynucleotide duplex incorporating DNA or RNA molecules that contain one or more LNAs; see, e. g., You et al. (2006) *Nucleic Acids Res.*, 34:1-11 (e60), doi:10.1093/nar/gkl175.

In the context of the genome targeting methods described herein, the phrase "contacting a genome" with an agent means that an agent responsible for effecting the targeted genome modification (e.g., a break, a deletion, a rearrangement, or an insertion) is delivered to the interior of the cell so the directed mutagenic action can take place.

In the context of discussing or describing the ploidy of a plant cell, the "n" (as in "a ploidy of 2n") refers to the number of homologous pairs of chromosomes, and is typically equal to the number of homologous pairs of gene loci on all chromosomes present in the cell. For example, the 2n ploidy of a plant cell can be described as haploid (n=0.5), diploid (n=1), triploid (n=1.5), tetraploid (n=2), pentaploid (n=2.5), hexaploid (n=3), heptaploid (n=3.5), octaploid (n=4), decaploid (n=5), or dodecaploid (n=6).

The term "inbred variety" refers to a genetically homozygous or substantially homozygous population of plants that preferably comprises homozygous alleles at about 95%, preferably 98.5% or more of its loci. An inbred line can be developed through inbreeding (i.e., several cycles of selfing, more preferably at least 5, 6, 7 or more cycles of selfing) or doubled haploidy resulting in a plant line with a high uniformity. Inbred lines breed true, e.g., for one or more or all phenotypic traits of interest. An "inbred", "inbred individual, or "inbred progeny" is an individual sampled from an inbred line.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc. "F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis.

Hybrid seed: Hybrid seed is seed produced by crossing two different inbred lines (i.e. a female inbred line with a male inbred). Hybrid seed is heterozygous over a majority of its alleles.

As used herein, the term "variety" refers to a group of similar plants that by structural or genetic features and/or performance can be distinguished from other varieties within the same species.

The term "cultivar" (for cultivated variety) is used herein to denote a variety that is not normally found in nature but that has been created by humans, i.e., having a biological status other than a "wild" status, which "wild" status indicates the original non-cultivated, or natural state of a plant or accession. The term "cultivar" includes, but is not limited to, semi-natural, semi-wild, weedy, traditional cultivar, landrace, breeding material, research material, breeder's line, synthetic population, hybrid, founder stock/base population, inbred line (parent of hybrid cultivar), segregating population, mutant/genetic stock, and advanced/improved cultivar. The term "elite background" is used herein to indicate the genetic context or environment of a targeted mutation of insertion.

The term "dihaploid line" refers to stable inbred lines issued from another culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially not segregating any more (i.e., they are stable).

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome. A "plant line" or "breeding line" refers to a plant and its progeny. "F1", "F2", "F3", etc." refers to the consecutive related generations following a cross between two parent plants or parent lines. The plants grown from the seeds produced by crossing two plants or lines is called the F1 generation. Selfing the F1 plants results in the F2 generation, etc.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural), on a chromosome. One allele is present on each chromosome of the pair of homologous chromosomes. A diploid (or triploid etc.) plant may comprise a large number of different alleles at a particular locus. The alleles at a particular locus may be identical (homozygous) or different (heterozygous).

The term "locus" (loci plural) means a specific place or places or a site on a chromosome where for example a QTL, a gene or genetic marker is found.

"Selectable marker" or "selection marker" refers to a sequence which enables enrichment of a stably transformed plant by adding a substance (i) which is otherwise toxic to cell (negative selection marker) or (ii) which creates a growth advantage in the presence of the marker (positive selection marker).

In *Arabidopsis thaliana*, the spontaneous (non-targeted) mutation rate for a single base pair has been reported to be $7\times10^{-9}$ per bp per generation, which, assuming an estimated 30 replications per generation, leads to an estimated spontaneous (non-targeted) mutation rate of $2\times10^{-10}$ mutations per base pair per replication event; see book[dot]bionumbers [dot]org/what-is-the-mutation-rate-during-genome-replication. Another report provides estimates in germline tissue of *Arabidopsis thaliana* of 40 cell divisions per generation, $6.5\times10^{-9}$ mutations per nucleotide site per generation, and $0.16\times10^{-9}$ mutations per nucleotide site per cell division; see Lynch (2010) *Trends Genet.* 26:345-352, doi:10.1016/j.tig.2010.05.003. Other estimates of spontaneous mutation rates in plants include $2.9\times10^{-8}$ substitutions per site per year (maize) and $3.3\times10^{-8}$ substitutions per site per year (maize); see Clark et al. (2005) *Mol. Biol. Evol.,* 22:2304-2312, doi:10.1093/molbev/msi228.

The term “and/or” where used herein is to be taken as specific disclosure of each of the multiple specified features or components with or without another. Thus, the term and/or” as used in a phrase such as “A and/or B” herein is intended to include “A and B,” “A or B,” “A” (alone), and “B” (alone). Likewise, the term “and/or” as used in a phrase such as “A, B, and/or C” is intended to encompass each of the following embodiments: A, B, and C; A, B, or C; A or C; A or B; B or C; A and C; A and B; B and C; A (alone); B (alone); and C (alone).

Tools and Methods for Multiplex Editing

CRISPR technology for editing the genes of eukaryotes is disclosed in U.S. Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in U.S. Patent Application Publication 2016/0208243 A1. Other CRISPR nucleases useful for editing genomes include C2c1 and C2c3 (see Shmakov et al. (2015) *Mol. Cell,* 60:385-397) and CasX and CasY (see Burstein et al. (2016) *Nature*, doi:10.1038/nature21059). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in in U.S. Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246).

CRISPR (Clustered Regularly Interspaced Short Palindromic Repeats)/Cas (CRISPR-associated) systems, or CRISPR systems, are adaptive defense systems originally discovered in bacteria and archaea. CRISPR systems use RNA-guided nucleases termed CRISPR-associated or “Cas” endonucleases (e. g., Cas9 or Cpf1) to cleave foreign DNA. In a typical CRISPR/Cas system, a Cas endonuclease is directed to a target nucleotide sequence (e. g., a site in the genome that is to be sequence-edited) by sequence-specific, non-coding “guide RNAs” that target single- or double-stranded DNA sequences. In microbial hosts, CRISPR loci encode both Cas endonucleases and “CRISPR arrays” of the non-coding RNA elements that determine the specificity of the CRISPR-mediated nucleic acid cleavage.

Three classes (I-III) of CRISPR systems have been identified across a wide range of bacterial hosts. The well characterized class II CRISPR systems use a single Cas endonuclease (rather than multiple Cas proteins). One class II CRISPR system includes a type II Cas endonuclease such as Cas9, a CRISPR RNA (“crRNA”), and a trans-activating crRNA (“tracrRNA”). The crRNA contains a “guide RNA”, typically a 20-nucleotide RNA sequence that corresponds to (i. e., is identical or nearly identical to, or alternatively is complementary or nearly complementary to) a 20-nucleotide target DNA sequence. The crRNA also contains a region that binds to the tracrRNA to form a partially double-stranded structure which is cleaved by RNase III, resulting in a crRNA/tracrRNA hybrid. The crRNA/tracrRNA hybrid then directs the Cas9 endonuclease to recognize and cleave the target DNA sequence.

The target DNA sequence must generally be adjacent to a “protospacer adjacent motif” (“PAM”) that is specific for a given Cas endonuclease; however, PAM sequences are short and relatively non-specific, appearing throughout a given genome. CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). Some endonucleases, e. g., Cas9 endonucleases, are associated with G-rich PAM sites, e. g., 5'-NGG, and perform blunt-end cleaving of the target DNA at a location 3 nucleotides upstream from (5' from) the PAM site.

Another class II CRISPR system includes the type V endonuclease Cpf1, which is a smaller endonuclease than is Cas9; examples include AsCpf1 (from *Acidaminococcus* sp.) and LbCpf1 (from *Lachnospiraceae* sp.). Cpf1-associated CRISPR arrays are processed into mature crRNAs without the requirement of a tracrRNA; in other words, a Cpf1 system requires only the Cpf1 nuclease and a crRNA to cleave the target DNA sequence. Cpf1 endonucleases, are associated with T-rich PAM sites, e. g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e. g., Zetsche et al. (2015) *Cell,* 163:759-771. Other CRISPR nucleases useful in methods and compositions of the invention include C2c1 and C2c3 (see Shmakov et al. (2015) *Mol. Cell,* 60:385-397). Like other CRISPR nucleases, C2c1 from *Alicyclobacillus acidoterrestris* (AacC2c1; amino acid sequence with accession ID TOD7A2, deposited on-line at www[dot]ncbi[dot]nlm[dot]nih[dot]gov/protein/1076761101) requires a guide RNA and PAM recognition site; C2c1 cleavage results in a staggered seven-nucleotide DSB in the target DNA (see Yang et al. (2016) *Cell,* 167:1814-1828.e12) and is reported to have high mismatch sensitivity, thus reducing off-target effects (see Liu et al. (2016) *Mol. Cell*, available on line at dx[dot]doi[dot]org/10[dot]1016/j[dot]molcel[dot]2016[dot]11.040). Yet other CRISPR nucleases include nucleases identified from the genomes of uncultivated microbes, such as CasX and CasY (e. g., a CRISPR-associated protein CasY from an uncultured Parcubacteria group bacterium, amino acid sequence with accession ID APG80656, deposited on-line at www[dot]ncbi[dot]nlm[dot]nih[dot]gov/protein/APG80656.1]); see Burstein et al. (2016) *Nature*, doi:10.1038/nature21059.

For the purposes of gene editing, CRISPR arrays can be designed to contain one or multiple guide RNA sequences corresponding to a desired target DNA sequence; see, for example, Cong et al. (2013) *Science,* 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) *Cell,* 163:759-771. In practice, guide RNA sequences are generally designed to have a length of between 17-24 nucleotides (frequently 19, 20, or 21 nucleotides) and exact complementarity (i. e., perfect base-pairing) to the targeted gene or nucleic acid sequence; guide RNAs having less than 100% complementarity to the target sequence can be used (e. g., a gRNA with a length of 20 nucleotides and between 1-4 mismatches to the target sequence) but can increase the potential for off-target effects. The design of effective guide RNAs for use in plant genome editing is disclosed in U.S. Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science,* 339:819-823; Xing et al. (2014) *BMC Plant Biol.,* 14:327-340. Chemically modified sgRNAs have been demonstrated to be effective in genome editing; see, for example, Hendel et al. (2015) *Nature Biotech.,* 985-991.

CRISPR-type genome editing has value in various aspects of agriculture research and development. CRISPR elements, i.e., CRISPR endonucleases and CRISPR single-guide RNAs, are useful in effecting genome editing without remnants of the CRISPR elements or selective genetic markers occurring in progeny. Alternatively, genome-inserted CRISPR elements are useful in plant lines adapted for multiplex genetic screening and breeding. For instance, a plant species can be created to express one or more of a CRISPR endonuclease such as a Cas9- or a Cpf1-type endonuclease or combinations with unique PAM recognition sites. Cpf1 endonuclease and corresponding guide RNAs and PAM sites are disclosed in U.S. Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for trait introgression. Multiple endonucleases can be provided in expression cassettes with the appropriate promoters to allow multiple genome editing in a spatially or temporally separated fashion in either in chromosome DNA or episome DNA.

Whereas wild-type Cas9 generates double-strand breaks (DSBs) at specific DNA sequences targeted by a gRNA, a number of CRISPR endonucleases having modified functionalities are available, for example: (1) a "nickase" version of Cas9 generates only a single-strand break; (2) a catalytically inactive Cas9 ("dCas9") does not cut the target DNA but interferes with transcription; (3) dCas9 on its own or fused to a repressor peptide can repress gene expression; (4) dCas9 fused to an activator peptide can activate or increase gene expression; (5) dCas9 fused to Fok1 nuclease ("dCas9-Fok1") can be used to generate DSBs at target sequences homologous to two gRNAs; and (6) dCas9 fused to histone-modifying enzymes (e. g., histone acetyltransferases, histone methyltransferases, histone deacetylases, and histone demethylases) can be used to alter the epigenome in a site-specific manner, for example, by changing the methylation or acetylation status at a particular locus. See, e. g., the numerous CRISPR/Cas9 plasmids disclosed in and publicly available from the Addgene repository (Addgene, 75 Sidney St., Suite 550A, Cambridge, MA 02139; addgene[dot]org/crispr/). A "double nickase" Cas9 that introduces two separate double-strand breaks, each directed by a separate guide RNA, is described as achieving more accurate genome editing by Ran et al. (2013) *Cell,* 154:1380-1389.

In some embodiments, the methods of targeted modification described herein provide a means for avoiding unwanted epigenetic losses that can arise from tissue culturing modified plant cells (see, e.g., Stroud et al. *eLife* 2013; 2:e00354). Using the methods described herein in the absence of tissue culture, a loss of epigenetic marking may occur in less than 0.01% of the genome. This contrasts with results obtained with rice plants where tissue culture methods may result in losses of DNA methylation that occur, on average, as determined by bisulfite sequencing, at 1344 places that are on average 334 base pairs long, which means a loss of DNA methylation at an average of 0.1% of the genome (Stroud, 2013). In other words, the loss in marks using the targeted modification techniques described herein without tissue culture is 10 times lower than the loss observed when tissue culture techniques are relied on. In certain embodiments of the novel modified plant cells described herein, the modified plant cell or plant does not have significant losses of methylation compared to a non-modified parent plant cell or plant; in other words, the methylation pattern of the genome of the modified plant cell or plant is not greatly different from the methylation pattern of the genome of the parent plant cell or plant; in embodiments, the difference between the methylation pattern of the genome of the modified plant cell or plant and that of the parent plant cell or plant is less than 0.1%, 0.05%, 0.02%, or 0.01% of the genome, or less than 0.005% of the genome, or less than 0.001% of the genome (see, e. g., Stroud et al. (2013) eLife 2:e00354; DOI: 10.7554/eLife.00354).

CRISPR technology for editing the genes of eukaryotes is disclosed in U.S. Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in U.S. Patent Application Publication 2016/0208243 A1. Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in in U.S. Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety.

In some embodiments, one or more vectors driving expression of one or more polynucleotides encoding elements of a genome-editing system (e. g., encoding a guide RNA or a nuclease) are introduced into a plant cell or a plant protoplast, whereby these elements, when expressed, result in alteration of a target nucleotide sequence. In embodiments, a vector comprises a regulatory element such as a promoter operably linked to one or more polynucleotides encoding elements of a genome-editing system. In such embodiments, expression of these polynucleotides can be controlled by selection of the appropriate promoter, particularly promoters functional in a plant cell; useful promoters include constitutive, conditional, inducible, and temporally or spatially specific promoters (e. g., a tissue specific promoter, a developmentally regulated promoter, or a cell cycle regulated promoter). In embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e. g., Ferré-D'Amaré and Scott (2014) *Cold Spring Harbor Perspectives Biol.,* 2:a003574). In embodiments, the promoter is a pol II promoter operably linked to a nucleotide sequence encoding one or more guide RNAs. In embodiments, the promoter operably linked to one or more polynucleotides encoding elements of a genome-editing system is a constitutive promoter that drives DNA expression in plant cells; in embodiments, the promoter drives DNA expression in the nucleus or in an organelle such as a chloroplast or mitochondrion. Examples of constitutive promoters include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and an opaline synthase (NOS) and octapine synthase (OCS) promoter from *Agrobacterium tumefaciens*. In embodiments, the promoter operably linked to one or more polynucleotides encoding elements of a genome-editing system is a promoter from figwort mosaic virus (FMV), a RUBISCO promoter, or a pyruvate phosphate dikinase (PDK) promoter, which is active in the chloroplasts of mesophyll cells. Other contemplated promoters include cell-specific or tissue-specific or developmentally regulated promoters, for example, a promoter that limits the expression of the nucleic acid targeting system to germline or reproductive cells (e. g., promoters of genes encoding DNA ligases, recombinases, replicases, or other genes specifically expressed in germline or reproductive cells); in such embodiments, the nuclease-mediated genetic modification (e. g., chromosomal or episomal double-stranded DNA cleavage) is limited only those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

In some embodiments, elements of a genome-editing system (e.g., an RNA-guided nuclease and a guide RNA) are operably linked to separate regulatory elements on separate vectors. In other embodiments, two or more elements of a genome-editing system expressed from the same or different regulatory elements or promoters are combined in a single vector, optionally with one or more additional vectors providing any additional necessary elements of a genome-editing system not included in the first vector. For example, multiple guide RNAs can be expressed from one vector, with the appropriate RNA-guided nuclease expressed from a second vector. In another example, one or more vectors for the expression of one or more guide RNAs (e. g., crRNAs or sgRNAs) are delivered to a cell (e. g., a plant cell or a plant protoplast) that expresses the appropriate RNA-guided nuclease, or to a cell that otherwise contains the nuclease, such as by way of prior administration thereto of a vector for in vivo expression of the nuclease.

Genome-editing system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In embodiments, the endonuclease and the nucleic acid-targeting guide RNA may be operably linked to and expressed from the same promoter. In embodiments, a single promoter drives expression of a transcript encoding an endonuclease and the guide RNA, embedded within one or more intron sequences (e. g., each in a different intron, two or more in at least one intron, or all in a single intron), which can be plant-derived; such use of introns is especially contemplated when the expression vector is being transformed or transfected into a monocot plant cell or a monocot plant protoplast.

Expression vectors provided herein may contain a DNA segment near the 3' end of an expression cassette that acts as a signal to terminate transcription and directs polyadenylation of the resultant mRNA. Such a 3' element is commonly referred to as a "3'-untranslated region" or "3'-UTR" or a "polyadenylation signal". Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in U.S. Patent Application Publication 2002/0192813 A1, incorporated herein by reference.

In certain embodiments, a vector or an expression cassette includes additional components, e. g., a polynucleotide encoding a drug resistance or herbicide gene or a polynucleotide encoding a detectable marker such as green fluorescent protein (GFP) or beta-glucuronidase (gus) to allow convenient screening or selection of cells expressing the vector. In embodiments, the vector or expression cassette includes additional elements for improving delivery to a plant cell or plant protoplast or for directing or modifying expression of one or more genome-editing system elements, for example, fusing a sequence encoding a cell-penetrating peptide, localization signal, transit, or targeting peptide to the RNA-guided nuclease, or adding a nucleotide sequence to stabilize a guide RNA; such fusion proteins (and the polypeptides encoding such fusion proteins) or combination polypeptides, as well as expression cassettes and vectors for their expression in a cell, are specifically claimed. In embodiments, an RNA-guided nuclease (e. g., Cas9, Cpf1, CasY, CasX, C2c1, or C2c3) is fused to a localization signal, transit, or targeting peptide, e. g., a nuclear localization signal (NLS), a chloroplast transit peptide (CTP), or a mitochondrial targeting peptide (MTP); in a vector or an expression cassette, the nucleotide sequence encoding any of these can be located either 5' and/or 3' to the DNA encoding the nuclease. For example, a plant-codon-optimized Cas9 (pco-Cas9) from *Streptococcus pyogenes* and *S. thermophilus* containing nuclear localization signals and codon-optimized for expression in maize is disclosed in PCT/US2015/018104 (published as WO/2015/131101 and claiming priority to U.S.

Provisional Patent Application 61/945,700), incorporated herein by reference. In another example, a chloroplast-targeting RNA is appended to the 5' end of an mRNA encoding an endonuclease to drive the accumulation of the mRNA in chloroplasts; see Gomez, et al. (2010) *Plant Signal Behav.,* 5: 1517-1519. In an embodiment, a Cas9 from *Streptococcus pyogenes* is fused to a nuclear localization signal (NLS), such as the NLS from SV40. In an embodiment, a Cas9 from *Streptococcus pyogenes* is fused to a cell-penetrating peptide (CPP), such as octa-arginine or nona-arginine or a homoarginine 12-mer oligopeptide, or a CPP disclosed in the database of cell-penetrating peptides CPPsite 2.0, publicly available at crdd[dot]osdd[dot]net/raghava/cppsite/. In an example, a Cas9 from *Streptococcus pyogenes* (which normally carries a net positive charge) is modified at the N-terminus with a negatively charged glutamate peptide "tag" and at the C-terminus with a nuclear localization signal (NLS); when mixed with cationic arginine gold nanoparticles (ArgNPs), self-assembled nanoassemblies were formed which were shown to provide good editing efficiency in human cells; see Mout et al. (2017) *ACS Nano*, doi:10.1021/acsnano.6b07600. In an embodiment, a Cas9 from *Streptococcus pyogenes* is fused to a chloroplast transit peptide (CTP) sequence. In embodiments, a CTP sequence is obtained from any nuclear gene that encodes a protein that targets a chloroplast, and the isolated or synthesized CTP DNA is appended to the 5' end of the DNA that encodes a nuclease targeted for use in a chloroplast. Chloroplast transit peptides and their use are described in U.S. Pat. Nos. 5,188,642, 5,728,925, and 8,420,888, all of which are incorporated herein by reference in their entirety. Specifically, the CTP nucleotide sequences provided with the sequence identifier (SEQ ID) numbers 12-15 and 17-22 of U.S. Pat. No. 8,420,888 are incorporated herein by reference. In an embodiment, a Cas9 from *Streptococcus pyogenes* is fused to a mitochondrial targeting peptide (MTP), such as a plant MTP sequence; see, e. g., Jores et al. (2016) *Nature Communications,* 7:12036-12051.

Plasmids designed for use in plants and encoding CRISPR genome editing elements (CRISPR nucleases and guide RNAs) are publicly available from plasmid repositories such as Addgene (Cambridge, MA; also see "addgene[dot]com") or can be designed using publicly disclosed sequences, e. g., sequences of CRISPR nucleases. In embodiments, such plasmids are used to co-express both CRISPR nuclease mRNA and guide RNA(s); in other embodiments, CRISPR endonuclease mRNA and guide RNA are encoded on separate plasmids. In embodiments, the plasmids are *Agrobacterium* TI plasmids. Materials and methods for preparing expression cassettes and vectors for CRISPR endonuclease and guide RNA for stably integrated and/or transient plant transformation are disclosed in PCT/US2015/018104 (published as WO/2015/131101 and claiming priority to U.S. Provisional Patent Application 61/945,700), U.S. Patent Application Publication 2015/0082478 A1, and PCT/US2015/038767 (published as WO/2016/007347 and claiming priority to U.S. Provisional Patent Application 62/023,246), all of which are incorporated herein by reference in their entirety. In embodiments, such expression cassettes are isolated linear fragments, or are part of a larger construct that includes bacterial replication elements and selectable markers; such embodiments are useful, e. g., for particle bombardment or nanoparticle delivery or protoplast transformation. In embodiments, the expression cassette is adjacent to or located between T-DNA borders or contained within a binary vector, e. g., for *Agrobacterium*-mediated transformation. In embodiments, a plasmid encoding a CRISPR nuclease is delivered to cell (such as a plant cell or a plant protoplast) for stable integration of the CRISPR nuclease into the genome of cell, or alternatively for transient expression of the CRISPR nuclease. In embodiments, plasmids encoding a CRISPR nuclease are delivered to a plant cell or a plant protoplast to achieve stable or transient expression of the CRISPR nuclease, and one or multiple guide RNAs (such as a library of individual guide RNAs or multiple pooled guide RNAs) or plasmids encoding the guide RNAs are delivered to the plant cell or plant protoplast individually or in combinations, thus providing libraries or arrays of plant cells or plant protoplasts (or of plant callus or whole plants derived therefrom), in which a variety of genome edits are provided by the different guide RNAs. A pool or arrayed collection of diverse modified plant cells comprising subsets of targeted modifications (e.g., a collection of plant cells or plants where some plants are homozygous and some are heterozygous for one, two, three or more targeted modifications) can be compared to determine the function of modified sequences (e.g., mutated or deleted sequences or genes) or the function of sequences being inserted. In other words, the methods and tools described herein can be used to perform "reverse genetics."

In certain embodiments where the genome-editing system is a CRISPR system, expression of the guide RNA is driven by a plant U6 spliceosomal RNA promoter, which can be native to the genome of the plant cell or from a different species, e. g., a U6 promoter from maize, tomato, or soybean such as those disclosed in PCT/US2015/018104 (published as WO 2015/131101 and claiming priority to U.S. Provisional Patent Application 61/945,700), incorporated herein by reference, or a homologue thereof; such a promoter is operably linked to DNA encoding the guide RNA for directing an endonuclease, followed by a suitable 3' element such as a U6 poly-T terminator. In another embodiment, an expression cassette for expressing guide RNAs in plants is used, wherein the promoter is a plant U3, 7SL (signal recognition particle RNA), U2, or U5 promoter, or chimerics thereof, e. g., as described in PCT/US2015/018104 (published as WO 2015/131101 and claiming priority to U.S. Provisional Patent Application 61/945,700), incorporated herein by reference. When multiple or different guide RNA sequences are used, a single expression construct may be used to correspondingly direct the genome editing activity to the multiple or different target sequences in a cell, such a plant cell or a plant protoplast. In various embodiments, a single vector includes 1, 2, 3, 4, 5, 6, 7, 8, 9, 10, about 15, about 20, or more guide RNA sequences; in other embodiments, 1, 2, 3, 4, 5, 6, 7, 8, 9, 10, about 15, about 20, or more guide RNA sequences are provided on multiple vectors, which can be delivered to one or multiple plant cells or plant protoplasts (e. g., delivered to an array of plant cells or plant protoplasts, or to a pooled population of plant cells or plant protoplasts).

In embodiments, one or more guide RNAs and the corresponding RNA-guided nuclease are delivered together or simultaneously. In other embodiments, one or more guide RNAs and the corresponding RNA-guided nuclease are delivered separately; these can be delivered in separate, discrete steps and using the same or different delivery techniques. In an example, an RNA-guided nuclease is delivered to a cell (such as a plant cell or plant protoplast) by particle bombardment, on carbon nanotubes, or by *Agrobacterium*-mediated transformation, and one or more guide RNAs is delivered to the cell in a separate step using the same or different delivery technique. In embodiments, an RNA-guided nuclease encoded by a DNA molecule or an mRNA is delivered to a cell with enough time prior to delivery of the guide RNA to permit expression of the nuclease in the cell; for example, an RNA-guided nuclease encoded by a DNA molecule or an mRNA is delivered to a plant cell or plant protoplast between 1-12 hours (e. g., about 1, 2, 3, 4, 5, 6, 7, 8, 9, 10, 11, or 12 hours, or between about 1-6 hours or between about 2-6 hours) prior to the delivery of the guide RNA to the plant cell or plant protoplast. In embodiments, whether the RNA-guided nuclease is delivered simultaneously with or separately from an initial dose of guide RNA, succeeding "booster" doses of guide RNA are delivered subsequent to the delivery of the initial dose; for example, a second "booster" dose of guide RNA is delivered to a plant cell or plant protoplast between 1-12 hours (e. g., about 1, 2, 3, 4, 5, 6, 7, 8, 9, 10, 11, or 12 hours, or between about 1-6 hours or between about 2-6 hours) subsequent to the delivery of the initial dose of guide RNA to the plant cell or plant protoplast. Similarly, in some embodiments, multiple deliveries of an RNA-guided nuclease or of a DNA molecule or an mRNA encoding an RNA-guided nuclease are used to increase efficiency of the genome modification.

In embodiments, the desired genome modification involves non-homologous recombination, in this case non-homologous end-joining of genomic sequence across one or more introduced double-strand breaks; generally, such embodiments do not require a donor template having homology "arms" (regions of homologous or complimentary sequence to genomic sequence flanking the site of the DSB). In various embodiments described herein, donor polynucleotides encoding sequences for targeted insertion at double-stranded breaks are single-stranded polynucleotides comprising RNA or DNA or both types of nucleotides; or the donor polynucleotides are at least partially double-stranded and comprise RNA, DNA or both types of nucleotides. Other modified nucleotides may also be used.

In other embodiments, the desired genome modification involves homologous recombination, wherein one or more double-stranded DNA break in the target nucleotide sequence is generated by the RNA-guided nuclease and guide RNA(s), followed by repair of the break(s) using a homologous recombination mechanism ("homology-directed repair"). In such embodiments, a donor template that encodes the desired nucleotide sequence to be inserted or knocked-in at the double-stranded break and generally having homology "arms" (regions of homologous or complimentary sequence to genomic sequence flanking the site of the DSB) is provided to the cell (such as a plant cell or plant protoplast); examples of suitable templates include single-stranded DNA templates and double-stranded DNA templates (e. g., in the form of a plasmid). In general, a donor template encoding a nucleotide change over a region of less than about 50 nucleotides is conveniently provided in the form of single-stranded DNA; larger donor templates (e. g., more than 100 nucleotides) are often conveniently provided as double-stranded DNA plasmids.

In certain embodiments directed to the targeted incorporation of sequences by homologous recombination, a donor template has a core nucleotide sequence that differs from the target nucleotide sequence (e. g., a homologous endogenous genomic region) by at least 1, at least 5, at least 10, at least 20, at least 30, at least 40, at least 50, or more nucleotides. This core sequence is flanked by "homology arms" or regions of high sequence identity with the targeted nucleotide sequence; in embodiments, the regions of high identity include at least 10, at least 50, at least 100, at least 150, at least 200, at least 300, at least 400, at least 500, at least 600, at least 750, or at least 1000 nucleotides on each side of the core sequence. In embodiments where the donor template is in the form of a single-stranded DNA, the core sequence is flanked by homology arms including at least 10, at least 20, at least 30, at least 40, at least 50, at least 60, at least 70, at least 80, or at least 100 nucleotides on each side of the core sequence. In embodiments where the donor template is in the form of a double-stranded DNA plasmid, the core sequence is flanked by homology arms including at least 500, at least 600, at least 700, at least 800, at least 900, or at least 1000 nucleotides on each side of the core sequence. In an embodiment, two separate double-strand breaks are introduced into the cell's target nucleotide sequence with a "double nickase" Cas9 (see Ran et al. (2013) *Cell,* 154: 1380-1389), followed by delivery of the donor template.

Delivery Methods and Agents

Aspects of the invention involve various treatments employed to deliver to a plant cell or protoplast a guide RNA (gRNA), such as a crRNA or sgRNA (or a polynucleotide encoding such), and/or a polynucleotide encoding a sequence for targeted insertion at a double-strand break in a genome. In embodiments, one or more treatments are employed to deliver the gRNA into a plant cell or plant protoplast, e. g., through barriers such as a cell wall or a plasma membrane or nuclear envelope or other lipid bilayer.

Unless otherwise stated, the various compositions and methods described herein for delivering guide RNAs and nucleases to a plant cell or protoplast are also generally useful for delivering donor polynucleotides to the cell. The delivery of donor polynucleotides can be simultaneous with, or separate from (generally after) delivery of the nuclease and guide RNA to the cell. For example, a donor polynucleotide can be transiently introduced into a plant cell or plant protoplast, optionally with the nuclease and/or gRNA; in certain embodiments, the donor template is provided to the plant cell or plant protoplast in a quantity that is sufficient to achieve the desired insertion of the donor polynucleotide sequence but donor polynucleotides do not persist in the plant cell or plant protoplast after a given period of time (e. g., after one or more cell division cycles).

In certain embodiments, a gRNA- or donor polynucleotide, in addition to other agents involved in targeted modifications, can be delivered to a plant cell or protoplast by directly contacting the plant cell or protoplast with a composition comprising the gRNA(s) or donor polynucleotide(s). For example, a gRNA-containing composition in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant cell (or plant part or tissue containing the plant cell) or plant protoplast (e. g., through abrasion or puncture or otherwise disruption of the cell wall or cell membrane, by spraying or dipping or soaking or otherwise directly contacting, or by microinjection). In certain embodiments, a plant cell (or plant part or tissue containing the plant cell) or plant protoplast is soaked in a liquid gRNA-containing composition, whereby the gRNA is delivered to the plant cell or plant protoplast. In embodiments, the gRNA-containing composition is delivered using negative or positive pressure, for example, using vacuum infiltration or application of hydrodynamic or fluid pressure. In embodiments, the gRNA-containing composition is introduced into a plant cell or plant protoplast, e. g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e. g., delivery of materials to cells employing microfluidic flow through a cell-deforming constriction as described in US Published Patent Application 2014/0287509, incorporated by reference in its entirety herein. Other techniques useful for delivering the gRNA-containing composition to a plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e. g., abrasion with carborundum or other particulate abrasive or scarification with a file or sandpaper) or chemical scarification (e. g., treatment with an acid or caustic agent); and electroporation. In embodiments, the gRNA-containing composition is provided by bacterially mediated (e. g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the gRNA; see, e. g., Broothaerts et al. (2005) *Nature,* 433:629-633. Any of these techniques or a combination thereof are alternatively employed on the plant part or tissue or intact plant (or seed) from which a plant cell or plant protoplast is optionally subsequently obtained or isolated; in embodiments, the gRNA-containing composition is delivered in a separate step after the plant cell or plant protoplast has been obtained or isolated.

In embodiments, a treatment employed in delivery of a gRNA to a plant cell or plant protoplast is carried out under a specific thermal regime, which can involve one or more appropriate temperatures, e. g., chilling or cold stress (exposure to temperatures below that at which normal plant growth occurs), or heating or heat stress (exposure to temperatures above that at which normal plant growth occurs), or treating at a combination of different temperatures. In embodiments, a specific thermal regime is carried out on the plant cell or plant protoplast, or on a plant or plant part from which a plant cell or plant protoplast is subsequently obtained or isolated, in one or more steps separate from the gRNA delivery.

In embodiments, a whole plant or plant part or seed, or an isolated plant cell or plant protoplast, or the plant or plant part from which a plant cell or plant protoplast is obtained or isolated, is treated with one or more delivery agents which can include at least one chemical, enzymatic, or physical agent, or a combination thereof. In embodiments, a gRNA-containing composition further includes one or more one chemical, enzymatic, or physical agent for delivery. In embodiments that further include the step of providing an RNA-guided nuclease or a polynucleotide that encodes the RNA-guided nuclease, a gRNA-containing composition including the RNA-guided nuclease or polynucleotide that encodes the RNA-guided nuclease further includes one or more one chemical, enzymatic, or physical agent for delivery. Treatment with the chemical, enzymatic or physical agent can be carried out simultaneously with the gRNA delivery, with the RNA-guided nuclease delivery, or in one or more separate steps that precede or follow the gRNA delivery or the RNA-guided nuclease delivery. In embodiments, a chemical, enzymatic, or physical agent, or a combination of these, is associated or complexed with the polynucleotide composition, with the gRNA or polynucleotide that encodes or is processed to the gRNA, or with the RNA-guided nuclease or polynucleotide that encodes the RNA-guided nuclease; examples of such associations or complexes include those involving non-covalent interactions (e. g., ionic or electrostatic interactions, hydrophobic or hydrophilic interactions, formation of liposomes, micelles, or other heterogeneous composition) and covalent interactions (e. g., peptide bonds, bonds formed using cross-linking agents). In non-limiting examples, a gRNA or polynucleotide that encodes or is processed to the gRNA is provided as a liposomal complex with a cationic lipid; a gRNA or polynucleotide that encodes or is processed to the gRNA is provided as a complex with a carbon nanotube; and an RNA-guided nuclease is provided as a fusion protein between the nuclease and a cell-penetrating peptide. Examples of agents useful for delivering a gRNA or polynucleotide that encodes or is processed to the gRNA or a nuclease or polynucleotide that encodes the nuclease include the various cationic liposomes and polymer nanoparticles reviewed by Zhang et al. (2007) *J. Controlled Release,* 123:1-10, and the cross-linked multilamellar liposomes described in U.S. Patent Application Publication 2014/0356414 A1, incorporated by reference in its entirety herein.

In embodiments, the chemical agent is at least one selected from the group consisting of:

(a) solvents (e. g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);

(b) fluorocarbons (e. g., perfluorodecalin, perfluoromethyldecalin);

(c) glycols or polyols (e. g., propylene glycol, polyethylene glycol);

(d) surfactants, including cationic surfactants, anionic surfactants, non-ionic surfactants, and amphiphilic surfactants, e. g., alkyl or aryl sulfates, phosphates, sulfonates, or carboxylates; primary, secondary, or tertiary amines; quaternary ammonium salts; sultaines, betaines; cationic lipids; phospholipids; tallowamine; bile acids such as cholic acid; long chain alcohols; organosilicone surfactants including nonionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents;

(g) peptides, proteins, or enzymes (e. g., cellulase, pectolyase, maceroenzyme, pectinase), including cell-penetrating or pore-forming peptides (e. g., (BO100)2K8, Genscript; poly-lysine, poly-arginine, or poly-homoarginine peptides; gamma zein, see U.S. Patent Application publication 2011/0247100, incorporated herein by reference in its entirety; transcription activator of human immunodeficiency virus type 1 ("HIV-1 Tat") and other Tat proteins, see, e. g., www[dot]lifetein[dot]com/Cell_Penetrating_Peptides[dot]html and Jarver (2012) *Mol. Therapy—Nucleic Acids,* 1:e27, 1-17); octa-arginine or nona-arginine; poly-homoarginine (see Unnamalai et al. (2004) *FEBS Letters,* 566: 307-310); see also the database of cell-penetrating peptides CPPsite 2.0 publicly available at crdd[dot] osdd[dot]net/raghava/cppsite/

(h) RNase inhibitors;

(i) cationic branched or linear polymers such as chitosan, poly-lysine, DEAE-dextran, polyvinylpyrrolidone ("PVP"), or polyethylenimine ("PEI", e. g., PEI, branched, MW 25,000, CAS #9002-98-6; PEI, linear, MW 5000, CAS #9002-98-6; PEI linear, MW 2500, CAS #9002-98-6);

(j) dendrimers (see, e. g., U.S. Patent Application Publication 2011/0093982, incorporated herein by reference in its entirety);

(k) counter-ions, amines or polyamines (e. g., spermine, spermidine, putrescine), osmolytes, buffers, and salts (e. g., calcium phosphate, ammonium phosphate);

(l) polynucleotides (e. g., non-specific double-stranded DNA, salmon sperm DNA);

(m) transfection agents (e. g., Lipofectin®, Lipofectamine®, and Oligofectamine®, and Invivofectamine® (all from Thermo Fisher Scientific, Waltham, MA), PepFect (see Ezzat et al. (2011) *Nucleic Acids Res.,* 39:5284-5298), TransIt® transfection reagents (Mirus Bio, LLC, Madison, WI), and poly-lysine, poly-homoarginine, and poly-arginine molecules including octo-arginine and nono-arginine as described in Lu et al. (2010) *J. Agric. Food Chem.,* 58:2288-2294);

(n) antibiotics, including non-specific DNA double-strand-break-inducing agents (e. g., phleomycin, bleomycin, talisomycin); and (o) antioxidants (e. g., glutathione, dithiothreitol, ascorbate).

In embodiments, the chemical agent is provided simultaneously with the gRNA (or polynucleotide encoding the gRNA or that is processed to the gRNA), for example, the polynucleotide composition including the gRNA further includes one or more chemical agent. In embodiments, the gRNA or polynucleotide encoding the gRNA or that is processed to the gRNA is covalently or non-covalently linked or complexed with one or more chemical agent; for example, the gRNA or polynucleotide encoding the gRNA or that is processed to the gRNA can be covalently linked to a peptide or protein (e. g., a cell-penetrating peptide or a pore-forming peptide) or non-covalently complexed with cationic lipids, polycations (e. g., polyamines), or cationic polymers (e. g., PEI). In embodiments, the gRNA or polynucleotide encoding the gRNA or that is processed to the gRNA is complexed with one or more chemical agents to form, e. g., a solution, liposome, micelle, emulsion, reverse emulsion, suspension, colloid, or gel.

In embodiments, the physical agent is at least one selected from the group consisting of particles or nanoparticles (e. g., particles or nanoparticles made of materials such as carbon, silicon, silicon carbide, gold, tungsten, polymers, or ceramics) in various size ranges and shapes, magnetic particles or nanoparticles (e. g., silenceMag Magnetotransfection™ agent, OZ Biosciences, San Diego, CA), abrasive or scarifying agents, needles or microneedles, matrices, and grids. In embodiments, particulates and nanoparticulates are useful in delivery of the polynucleotide composition or the nuclease or both. Useful particulates and nanoparticles include those made of metals (e. g., gold, silver, tungsten, iron, cerium), ceramics (e. g., aluminum oxide, silicon carbide, silicon nitride, tungsten carbide), polymers (e. g., polystyrene, polydiacetylene, and poly(3,4-ethylenedioxythiophene) hydrate), semiconductors (e. g., quantum dots), silicon (e. g., silicon carbide), carbon (e. g., graphite, graphene, graphene oxide, or carbon nanosheets, nanocomplexes, or nanotubes), and composites (e. g., polyvinylcarbazole/graphene, polystyrene/graphene, platinum/graphene, palladium/graphene nanocomposites). In embodiments, such particulates and nanoparticulates are further covalently or non-covalently functionalized, or further include modifiers or cross-linked materials such as polymers (e. g., linear or branched polyethylenimine, poly-lysine), polynucleotides (e. g., DNA or RNA), polysaccharides, lipids, polyglycols (e. g., polyethylene glycol, thiolated polyethylene glycol), polypeptides or proteins, and detectable labels (e. g., a fluorophore, an antigen, an antibody, or a quantum dot). In various embodiments, such particulates and nanoparticles are neutral, or carry a positive charge, or carry a negative charge. Embodiments of compositions including particulates include those formulated, e. g., as liquids, colloids, dispersions, suspensions, aerosols, gels, and solids. Embodiments include nanoparticles affixed to a surface or support, e. g., an array of carbon nanotubes vertically aligned on a silicon or copper wafer substrate. Embodiments include polynucleotide compositions including particulates (e. g., gold or tungsten or magnetic particles) delivered by a Biolistic-type technique or with magnetic force. The size of the particles used in Biolistics is generally in the "microparticle" range, for example, gold microcarriers in the 0.6, 1.0, and 1.6 micrometer size ranges (see, e. g., instruction manual for the Helios® Gene Gun System, Bio-Rad, Hercules, CA; Randolph-Anderson et al. (2015) "Sub-micron gold particles are superior to larger particles for efficient Biolistic® transformation of organelles and some cell types", Bio-Rad US/EG Bulletin 2015), but successful Biolistics delivery using larger (40 nanometer) nanoparticles has been reported in cultured animal cells; see O'Brian and Lummis (2011) *BMC Biotechnol.,* 11:66-71. Other embodiments of useful particulates are nanoparticles, which are generally in the nanometer (nm) size range or less than 1 micrometer, e. g., with a diameter of less than about 1 nm, less than about 3 nm, less than about 5 nm, less than about 10 nm, less than about 20 nm, less than about 40 n, less than about 60 nm, less than about 80 n, and less than about 100 n. Specific, non-limiting embodiments of nanoparticles commercially available (all from Sigma-Aldrich Corp., St. Louis, MO) include gold nanoparticles with diameters of 5, 10, or 15 nm; silver nanoparticles with particle sizes of 10, 20, 40, 60, or 100 nm; palladium "nanopowder" of less than 25 nm particle size; single-, double-, and multi-walled carbon nanotubes, e. g., with diameters of 0.7-1.1, 1.3-2.3, 0.7-0.9, or 0.7-1.3 nm, or with nanotube bundle dimensions of 2-10 nm by 1-5 micrometers, 6-9 nm by 5 micrometers, 7-15 nm by 0.5-10 micrometers, 7-12 nm by 0.5-10 micrometers, 110-170 nm by 5-9 micrometers, 6-13 nm by 2.5-20 micrometers. Embodiments include polynucleotide compositions including materials such as gold, silicon, cerium, or carbon, e. g., gold or gold-coated nanoparticles, silicon carbide whiskers, carborundum, porous silica nanoparticles, gelatin/silica nanoparticles, nanoceria or cerium oxide nanoparticles (CNPs), carbon nanotubes (CNTs) such as single-, double-, or multi-walled carbon nanotubes and their chemically functionalized versions (e. g., carbon nanotubes functionalized with amide, amino, carboxylic acid, sulfonic acid, or polyethylene glycol moeities), and graphene or graphene oxide or graphene complexes; see, for example, Wong et al. (2016) *Nano Lett.,* 16:1161-1172; Giraldo et al. (2014) *Nature Materials,* 13:400-409; Shen et al. (2012) *Theranostics,* 2:283-294; Kim et al. (2011) *Bioconjugate Chem.,* 22:2558-

2567; Wang et al. (2010) *J. Am. Chem. Soc. Comm.,* 132: 9274-9276; Zhao et al. (2016) *Nanoscale Res. Lett.,* 11:195-203; and Choi et al. (2016) *J. Controlled Release,* 235:222-235. See also, for example, the various types of particles and nanoparticles, their preparation, and methods for their use, e. g., in delivering polynucleotides and polypeptides to cells, disclosed in U.S. Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety.

In embodiments wherein the gRNA (or polynucleotide encoding the gRNA) is provided in a composition that further includes an RNA-guided nuclease (or a polynucleotide that encodes the RNA-guided nuclease), or wherein the method further includes the step of providing an RNA-guided nuclease or a polynucleotide that encodes the RNA-guided nuclease, one or more one chemical, enzymatic, or physical agent can similarly be employed. In embodiments, the RNA-guided nuclease (or polynucleotide encoding the RNA-guided nuclease) is provided separately, e. g., in a separate composition including the RNA-guided nuclease or polynucleotide encoding the RNA-guided nuclease. Such compositions can include other chemical or physical agents (e. g., solvents, surfactants, proteins or enzymes, transfection agents, particulates or nanoparticulates), such as those described above as useful in the polynucleotide composition used to provide the gRNA. For example, porous silica nanoparticles are useful for delivering a DNA recombinase into maize cells; see, e. g., Martin-Ortigosa et al. (2015) *Plant Physiol.,* 164:537-547. In an embodiment, the polynucleotide composition includes a gRNA and Cas9 nuclease, and further includes a surfactant and a cell-penetrating peptide. In an embodiment, the polynucleotide composition includes a plasmid that encodes both an RNA-guided nuclease and at least on gRNA, and further includes a surfactant and carbon nanotubes. In an embodiment, the polynucleotide composition includes multiple gRNAs and an mRNA encoding the RNA-guided nuclease, and further includes gold particles, and the polynucleotide composition is delivered to a plant cell or plant protoplast by Biolistics.

In related embodiments, one or more one chemical, enzymatic, or physical agent can be used in one or more steps separate from (preceding or following) that in which the gRNA is provided. In an embodiment, the plant or plant part from which a plant cell or plant protoplast is obtained or isolated is treated with one or more one chemical, enzymatic, or physical agent in the process of obtaining or isolating the plant cell or plant protoplast. In embodiments, the plant or plant part is treated with an abrasive, a caustic agent, a surfactant such as Silwet L-77 or a cationic lipid, or an enzyme such as cellulase.

In embodiments, a gRNA is delivered to plant cells or plant protoplasts prepared or obtained from a plant, plant part, or plant tissue that has been treated with the polynucleotide compositions (and optionally the nuclease). In embodiments, one or more one chemical, enzymatic, or physical agent, separately or in combination with the polynucleotide composition, is provided/applied at a location in the plant or plant part other than the plant location, part, or tissue from which the plant cell or plant protoplast is obtained or isolated. In embodiments, the polynucleotide composition is applied to adjacent or distal cells or tissues and is transported (e. g., through the vascular system or by cell-to-cell movement) to the meristem from which plant cells or plant protoplasts are subsequently isolated. In embodiments, a gRNA-containing composition is applied by soaking a seed or seed fragment or zygotic or somatic embryo in the gRNA-containing composition, whereby the gRNA is delivered to the seed or seed fragment or zygotic or somatic embryo from which plant cells or plant protoplasts are subsequently isolated. In embodiments, a flower bud or shoot tip is contacted with a gRNA-containing composition, whereby the gRNA is delivered to cells in the flower bud or shoot tip from which plant cells or plant protoplasts are subsequently isolated. In embodiments, a gRNA-containing composition is applied to the surface of a plant or of a part of a plant (e. g., a leaf surface), whereby the gRNA is delivered to tissues of the plant from which plant cells or plant protoplasts are subsequently isolated. In embodiments a whole plant or plant tissue is subjected to particle- or nanoparticle-mediated delivery (e. g., Biolistics or carbon nanotube or nanoparticle delivery) of a gRNA-containing composition, whereby the gRNA is delivered to cells or tissues from which plant cells or plant protoplasts are subsequently isolated.

Methods of Modulating Expression of a Sequence of Interest in a Genome

In one aspect, the invention provides a method of changing expression of a sequence of interest in a genome, including integrating a sequence encoded by a polynucleotide (such as a double-stranded DNA, a single-stranded DNA, a single-stranded DNA/RNA hybrid, or a double-stranded DNA/RNA hybrid) donor molecule at the site of at least one double-strand break (DSB) in a genome. The method permits site-specific integration of heterologous sequence at the site of at least one DSB, and thus at one or more locations in a genome, such as a genome of a plant cell. In embodiments, the genome is that of a nucleus, mitochondrion, or plastid in a plant cell.

By "integration of heterologous sequence" is meant integration or insertion of one or more nucleotides, resulting in a sequence (including the inserted nucleotide(s) as well as at least some adjacent nucleotides of the genomic sequence flanking the site of insertion at the DSB) that is heterologous, i. e., would not otherwise or does not normally occur at the site of insertion. The term "heterologous" is also used to refer to a given sequence in relationship to another—e.g., the sequence of the polynucleotide donor molecule, in addition to lacking sufficient homology or complementarity for the polynucleotide donor to bind to the genomic sequences immediately flanking the DSB, is heterologous to the sequence at the site of the DSB wherein the polynucleotide is integrated. Thus, in embodiments, the sequence of a polynucleotide donor molecule is both heterologous to, and non-homologous to, the DSB locus in the genome.

The at least one DSB is introduced into the genome by any suitable technique; in embodiments one or more DSBs is introduced into the genome in a site- or sequence-specific manner, for example, by use of at least one of the group of DSB-inducing agents consisting of: (a) a nuclease capable of effecting site-specific alteration of a target nucleotide sequence, selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, and a meganuclease or engineered meganuclease; (b) a polynucleotide encoding one or more nucleases capable of effecting site-specific alteration (such as introduction of a DSB) of a target nucleotide sequence; and (c) a guide RNA (gRNA) for an RNA-guided nuclease, or a DNA encoding a gRNA for an RNA-guided nuclease.

In embodiments, one or more DSBs is introduced into the genome by use of both a guide RNA (gRNA) and the corresponding RNA-guided nuclease. In an example, one or more DSBs is introduced into the genome by use of a ribonucleoprotein (RNP) that includes both a gRNA (e. g., a single-guide RNA or sgRNA that includes both a crRNA and a tracrRNA) and a Cas9. It is generally desirable that the sequence encoded by the polynucleotide donor molecule is integrated at the site of the DSB at high efficiency. One measure of efficiency is the percentage or fraction of the population of cells that have been treated with a DSB-inducing agent and polynucleotide donor molecule, and in which a sequence encoded by the polynucleotide donor molecule is successfully introduced at the DSB correctly located in the genome. The efficiency of genome editing including integration of a sequence encoded by a polynucleotide donor molecule at a DSB in the genome is assessed by any suitable method such as a heteroduplex cleavage assay or by sequencing, as described elsewhere in this disclosure. In various embodiments, the DSB is induced in the correct location in the genome at a comparatively high efficiency, e. g., at about 10, about 15, about 20, about 30, about 40, about 50, about 60, about 70, or about 80 percent efficiency, or at greater than 80, 85, 90, or 95 percent efficiency (measured as the percentage of the total population of cells in which the DSB is induced at the correct location in the genome). In various embodiments, a sequence encoded by the polynucleotide donor molecule is integrated at the site of the DSB at a comparatively high efficiency, e. g., at about 10, about 15, about 20, about 30, about 40, about 50, about 60, about 70, or about 80 percent efficiency, or at greater than 80, 85, 90, or 95 percent efficiency (measured as the percentage of the total population of cells in which the polynucleotide molecule is integrated at the site of the DSB in the correct location in the genome).

Apart from the CRISPR-type nucleases, other nucleases capable of effecting site-specific alteration of a target nucleotide sequence include zinc-finger nucleases (ZFNs), transcription activator-like effector nucleases (TAL-effector nucleases or TALENs), Argonaute proteins, and a meganuclease or engineered meganuclease. Zinc finger nucleases (ZFNs) are engineered proteins comprising a zinc finger DNA-binding domain fused to a nucleic acid cleavage domain, e. g., a nuclease. The zinc finger binding domains provide specificity and can be engineered to specifically recognize any desired target DNA sequence. For a review of the construction and use of ZFNs in plants and other organisms, see, e. g., Urnov et al. (2010) *Nature Rev. Genet.,* 11:636-646. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotides bases outside their target triplet. Typically, the engineered zinc finger DNA binding domain has a novel binding specificity, compared to a naturally-occurring zinc finger protein. Modification methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e. g., U.S. Pat. Nos. 6,453,242 and 6,534,261, both incorporated herein by reference in their entirety. Exemplary selection methods (e. g., phage display and yeast two-hybrid systems) are well known and described in the literature. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e. g., see U.S. Pat. Nos. 6,479,626; 6,903,185; and 7,153,949, incorporated herein by reference in their entirety. The nucleic acid cleavage domain is non-specific and is typically a restriction endonuclease, such as Fok1. This endonuclease must dimerize to cleave DNA. Thus, cleavage by Fok1 as part of a ZFN requires two adjacent and independent binding events, which must occur in both the correct orientation and with appropriate spacing to permit dimer formation. The requirement for two DNA binding events enables more specific targeting of long and potentially unique recognition sites. Fok1 variants with enhanced activities have been described; see, e. g., Guo et al. (2010) *J. Mol. Biol.,* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as Fok1, can be conveniently used. For a description of the use of TALENs in plants, see Mahfouz et al. (2011) *Proc. Natl. Acad. Sci. USA,* 108:2623-2628 and Mahfouz (2011) *GM Crops,* 2:99-103.

Argonauts are proteins that can function as sequence-specific endonucleases by binding a polynucleotide (e. g., a single-stranded DNA or single-stranded RNA) that includes sequence complementary to a target nucleotide sequence) that guides the Argonaut to the target nucleotide sequence and effects site-specific alteration of the target nucleotide sequence; see, e. g., U.S. Patent Application Publication 2015/0089681, incorporated herein by reference in its entirety.

Another method of effecting targeted changes to a genome is the use of triplex-forming peptide nucleic acids (PNAs) designed to bind site-specifically to genomic DNA via strand invasion and the formation of PNA/DNA/PNA triplexes (via both Watson-Crick and Hoogsteen binding) with a displaced DNA strand. PNAs consist of a charge neutral peptide-like backbone and nucleobases. The nucleobases hybridize to DNA with high affinity. The triplexes then recruit the cell's endogenous DNA repair systems to initiate site-specific modification of the genome. The desired sequence modification is provided by single-stranded 'donor DNAs' which are co-delivered as templates for repair. See, e. g., Bahal R et al (2016) *Nature Communications*, Oct. 26, 2016.

In related embodiments, zinc finger nucleases, TALENs, and Argonautes are used in conjunction with other functional domains. For example, the nuclease activity of these nucleic acid targeting systems can be altered so that the enzyme binds to but does not cleave the DNA. Examples of functional domains include transposase domains, integrase domains, recombinase domains, resolvase domains, invertase domains, protease domains, DNA methyltransferase domains, DNA hydroxylmethylase domains, DNA demethylase domains, histone acetylase domains, histone deacetylase domains, nuclease domains, repressor domains, activator domains, nuclear-localization signal domains, transcription-regulatory protein (or transcription complex recruiting) domains, cellular uptake activity associated domains, nucleic acid binding domains, antibody presentation domains, histone modifying enzymes, recruiter of histone modifying enzymes; inhibitor of histone modifying enzymes, histone methyltransferases, histone demethylases, histone kinases, histone phosphatases, histone ribosylases, histone deribosylases, histone ubiquitinases, histone deubiquitinases, histone biotinases and histone tail proteases. Non-limiting examples of functional domains include a transcriptional activation domain, a transcription repression domain, and an SHH1, SUVH2, or SUVH9 polypeptide capable of reducing expression of a target nucleotide sequence via epigenetic modification; see, e. g., U.S. Patent Application Publication 2016/0017348, incorporated herein by reference in its entirety. Genomic DNA may also be modified via base editing using a fusion between a catalytically inactive Cas9 (dCas9) is fused to a cytidine deaminase which convert cytosine (C) to uridine (U), thereby effecting a C to T substitution; see Komor et al. (2016) *Nature,* 533:420-424.

In embodiments, the guide RNA (gRNA) has a sequence of between 16-24 nucleotides in length (e. g., 16, 17, 18, 19, 20, 21, 22, 23, or 24 nucleotides in length). Specific embodiments include gRNAs of 19, 20, or 21 nucleotides in length and having 100% complementarity to the target nucleotide sequence. In many embodiments the gRNA has exact complementarity (i. e., perfect base-pairing) to the target nucleotide sequence; in certain other embodiments the gRNA has less than 100% complementarity to the target nucleotide sequence. The design of effective gRNAs for use in plant genome editing is disclosed in U.S. Patent Application Publication 2015/0082478 A1, the entire specification of which is incorporated herein by reference. In embodiments where multiple gRNAs are employed, the multiple gRNAs can be delivered separately (as separate RNA molecules or encoded by separate DNA molecules) or in combination, e. g., as an RNA molecule containing multiple gRNA sequences, or as a DNA molecule encoding an RNA molecule containing multiple gRNA sequences; see, for example, U.S. Patent Application Publication 2016/0264981 A1, the entire specification of which is incorporated herein by reference, which discloses RNA molecules including multiple RNA sequences (such as gRNA sequences) separated by tRNA cleavage sequences. In other embodiments, a DNA molecule encodes multiple gRNAs which are separated by other types of cleavable transcript, for example, small RNA (e. g., miRNA, siRNA, or ta-siRNA) recognition sites which can be cleaved by the corresponding small RNA, or dsRNA-forming regions which can be cleaved by a Dicer-type ribonuclease, or sequences which are recognized by RNA nucleases such as Cys4 ribonuclease from *Pseudomonas aeruginosa*; see, e. g., U.S. Pat. No. 7,816,581, the entire specification of which is incorporated herein by reference, which discloses in FIG. 27 and elsewhere in the specification pol II promoter-driven DNA constructs encoding RNA transcripts that are released by cleavage. Efficient Cas9-mediated gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). In other embodiments, self-cleaving ribozyme sequences can be used to separate multiple gRNA sequences within a transcript.

Thus, in certain embodiments wherein the nuclease is a Cas9-type nuclease, the gRNA can be provided as a polynucleotide composition including: (a) a CRISPR RNA (crRNA) that includes the gRNA together with a separate tracrRNA, or (b) at least one polynucleotide that encodes a crRNA and a tracrRNA (on a single polynucleotide or on separate polynucleotides), or (c) at least one polynucleotide that is processed into one or more crRNAs and a tracrRNA. In other embodiments wherein the nuclease is a Cas9-type nuclease, the gRNA can be provided as a polynucleotide composition including a CRISPR RNA (crRNA) that includes the gRNA, and the required tracrRNA is provided in a separate composition or in a separate step, or is otherwise provided to the cell (for example, to a plant cell or plant protoplast that stably or transiently expresses the tracrRNA from a polynucleotide encoding the tracrRNA). In other embodiments wherein the nuclease is a Cas9-type nuclease, the gRNA can be provided as a polynucleotide composition comprising: (a) a single guide RNA (sgRNA) that includes the gRNA, or (b) a polynucleotide that encodes a sgRNA, or (c) a polynucleotide that is processed into a sgRNA. Cpf1-mediated gene editing does not require a tracrRNA; thus, in embodiments wherein the nuclease is a Cpf1-type nuclease, the gRNA is provided as a polynucleotide composition comprising (a) a CRISPR RNA (crRNA) that includes the gRNA, or (b) a polynucleotide that encodes a crRNA, or (c) a polynucleotide that is processed into a crRNA. In embodiments, the gRNA-containing composition optionally includes an RNA-guided nuclease, or a polynucleotide that encodes the RNA-guided nuclease. In other embodiments, an RNA-guided nuclease or a polynucleotide that encodes the RNA-guided nuclease is provided in a separate step. In some embodiments of the method, a gRNA is provided to a cell (e. g., a plant cell or plant protoplast) that includes an RNA-guided nuclease or a polynucleotide that encodes an RNA-guided nuclease, e. g., an RNA-guided nuclease selected from the group consisting of an RNA-guided DNA endonuclease, a type II Cas nuclease, a Cas9, a type V Cas nuclease, a Cpf1, a CasY, a CasX, a C2c1, a C2c3, an engineered RNA-guided nuclease, and a codon-optimized RNA-guided nuclease; in an example, the cell (e. g., a plant cell or plant protoplast) stably or transiently expresses the RNA-guided nuclease. In embodiments, the polynucleotide that encodes the RNA-guided nuclease is, for example, DNA that encodes the RNA-guided nuclease and is stably integrated in the genome of a plant cell or plant protoplast, DNA or RNA that encodes the RNA-guided nuclease and is transiently present in or introduced into a plant cell or plant protoplast; such DNA or RNA can be introduced, e. g., by using a vector such as a plasmid or viral vector or as an mRNA, or as vector-less DNA or RNA introduced directly into a plant cell or plant protoplast.

In embodiments that further include the step of providing to a cell (e. g., a plant cell or plant protoplast) an RNA-guided nuclease or a polynucleotide that encodes the RNA-guided nuclease, the RNA-guided nuclease is provided simultaneously with the gRNA-containing composition, or in a separate step that precedes or follows the step of providing the gRNA-containing composition. In embodiments, the gRNA-containing composition further includes an RNA-guided nuclease or a polynucleotide that encodes the RNA-guided nuclease. In other embodiments, there is provided a separate composition that includes an RNA-guided nuclease or a polynucleotide that encodes the RNA-guided nuclease. In embodiments, the RNA-guided nuclease is provided as a ribonucleoprotein (RNP) complex, e. g., a preassembled RNP that includes the RNA-guided nuclease complexed with a polynucleotide including the gRNA or encoding a gRNA, or a preassembled RNP that includes a polynucleotide that encodes the RNA-guided nuclease (and optionally encodes the gRNA, or is provided with a separate polynucleotide including the gRNA or encoding a gRNA), complexed with a protein. In embodiments, the RNA-guided nuclease is a fusion protein, i. e., wherein the RNA-guided nuclease (e. g., Cas9, Cpf1, CasY, CasX, C2c1, or C2c3) is covalently bound through a peptide bond to a cell-penetrating peptide, a nuclear localization signal peptide, a chloroplast transit peptide, or a mitochondrial targeting peptide; such fusion proteins are conveniently encoded in a single nucleotide sequence, optionally including codons for linking amino acids. In embodiments, the RNA-guided nuclease or a polynucleotide that encodes the RNA-guided nuclease is provided as a complex with a cell-penetrating peptide or other transfecting agent. In embodiments, the RNA-guided nuclease or a polynucleotide that encodes the RNA-guided nuclease is complexed with, or covalently or non-covalently bound to, a further element, e. g., a carrier molecule, an antibody, an antigen, a viral movement protein, a polymer, a detectable label (e. g., a moiety detectable by fluorescence, radioactivity, or enzymatic or immunochemical reaction), a quantum dot, or a particulate or nanoparticulate. In embodiments, the RNA-guided nuclease or a polynucleotide that encodes the RNA-guided nuclease is provided in a solution, or is provided in a liposome, micelle, emulsion, reverse emulsion, suspension, or other mixed-phase composition.

An RNA-guided nuclease can be provided to a cell (e. g., a plant cell or plant protoplast) by any suitable technique. In embodiments, the RNA-guided nuclease is provided by directly contacting a plant cell or plant protoplast with the RNA-guided nuclease or the polynucleotide that encodes the RNA-guided nuclease. In embodiments, the RNA-guided nuclease is provided by transporting the RNA-guided nuclease or a polynucleotide that encodes the RNA-guided nuclease into a plant cell or plant protoplast using a chemical, enzymatic, or physical agent as provided in detail in the paragraphs following the heading "Delivery Methods and Delivery Agents". In embodiments, the RNA-guided nuclease is provided by bacterially mediated (e. g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of a plant cell or plant protoplast with a polynucleotide encoding the RNA-guided nuclease; see, e. g., Broothaerts et al. (2005) *Nature,* 433:629-633. In an embodiment, the RNA-guided nuclease is provided by transcription in a plant cell or plant protoplast of a DNA that encodes the RNA-guided nuclease and is stably integrated in the genome of the plant cell or plant protoplast or that is provided to the plant cell or plant protoplast in the form of a plasmid or expression vector (e. g., a viral vector) that encodes the RNA-guided nuclease (and optionally encodes one or more gRNAs, crRNAs, or sgRNAs, or is optionally provided with a separate plasmid or vector that encodes one or more gRNAs, crRNAs, or sgRNAs). In embodiments, the RNA-guided nuclease is provided to the plant cell or plant protoplast as a polynucleotide that encodes the RNA-guided nuclease, e. g., in the form of an mRNA encoding the nuclease.

Where a polynucleotide is concerned (e. g., a crRNA that includes the gRNA together with a separate tracrRNA, or a crRNA and a tracrRNA encoded on a single polynucleotide or on separate polynucleotides, or at least one polynucleotide that is processed into one or more crRNAs and a tracrRNA, or a sgRNA that includes the gRNA, or a polynucleotide that encodes a sgRNA, or a polynucleotide that is processed into a sgRNA, or a polynucleotide that encodes the RNA-guided nuclease), embodiments of the polynucleotide include: (a) double-stranded RNA; (b) single-stranded RNA; (c) chemically modified RNA; (d) double-stranded DNA; (e) single-stranded DNA; (f) chemically modified DNA; or (g) a combination of (a)-(f). Where expression of a polynucleotide is involved (e. g., expression of a crRNA from a DNA encoding the crRNA, or expression and translation of a RNA-guided nuclease from a DNA encoding the nuclease), in some embodiments it is sufficient that expression be transient, i. e., not necessarily permanent or stable in the cell. Certain embodiments of the polynucleotide further include additional nucleotide sequences that provide useful functionality; non-limiting examples of such additional nucleotide sequences include an aptamer or riboswitch sequence, nucleotide sequence that provides secondary structure such as stem-loops or that provides a sequence-specific site for an enzyme (e. g., a sequence-specific recombinase or endonuclease site), T-DNA (e. g., DNA sequence encoding a gRNA, crRNA, tracrRNA, or sgRNA is enclosed between left and right T-DNA borders from *Agrobacterium* spp. or from other bacteria that infect or induce tumours in plants), a DNA nuclear-targeting sequence, a regulatory sequence such as a promoter sequence, and a transcript-stabilizing sequence. Certain embodiments of the polynucleotide include those wherein the polynucleotide is complexed with, or covalently or non-covalently bound to, a non-nucleic acid element, e. g., a carrier molecule, an antibody, an antigen, a viral movement protein, a cell-penetrating or pore-forming peptide, a polymer, a detectable label, a quantum dot, or a particulate or nanoparticulate.

In embodiments, the at least one DSB is introduced into the genome by at least one treatment selected from the group consisting of: (a) bacterially mediated (e. g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection with a DSB-inducing agent; (b) Biolistics or particle bombardment with a DSB-inducing agent; (c) treatment with at least one chemical, enzymatic, or physical agent as provided in detail in the paragraphs following the heading "Delivery Methods and Delivery Agents"; and (d) application of heat or cold, ultrasonication, centrifugation, positive or negative pressure, cell wall or membrane disruption or deformation, or electroporation. It is generally desirable that introduction of the at least one DSB into the genome (i. e., the "editing" of the genome) is achieved with sufficient efficiency and accuracy to ensure practical utility.

One measure of efficiency is the percentage or fraction of the population of cells that have been treated with a DSB-inducing agent and in which the DSB is successfully introduced at the correct site in the genome. The efficiency of genome editing is assessed by any suitable method such as a heteroduplex cleavage assay or by sequencing, as described elsewhere in this disclosure. Accuracy is indicated by the absence of, or minimal occurrence of, off-target introduction of a DSB (i. e., at other than the intended site in the genome).

The location where the at least one DSB is inserted varies according to the desired result, for example whether the intention is to simply disrupt expression of the sequence of interest, or to add functionality (such as placing expression of the sequence of interest under inducible control). Thus, the location of the DSB is not necessarily within or directly adjacent to the sequence of interest. In embodiments, the at least one DSB in a genome is located: (a) within the sequence of interest, (b) upstream of (i. e., 5' to) the sequence of interest, or (c) downstream of (i. e., 3' to) the sequence of interest. In embodiments, a sequence encoded by the polynucleotide (such as a double-stranded DNA, a single-stranded DNA, a single-stranded DNA/RNA hybrid, or a double-stranded DNA/RNA hybrid) donor molecule, when integrated into the genome, is functionally or operably linked (e. g., linked in a manner that modifies the transcription or the translation of the sequence of interest or that modifies the stability of a transcript including that of the sequence of interest) to the sequence of interest. In embodiments, a sequence encoded by the polynucleotide donor molecule is integrated at a location 5' to and operably linked to the sequence of interest, wherein the integration location is selected to provide a specifically modulated (upregulated or downregulated) level of expression of the sequence of interest. For example, a sequence encoded by the polynucleotide donor molecule is integrated at a specific location in the promoter region of a protein-encoding gene that results in a desired expression level of the protein; in an embodiment, the appropriate location is determined empirically by integrating a sequence encoded by the polynucleotide donor molecule at about 50, about 100, about 150, about 200, about 250, about 300, about 350, about 400, about 450, and about 500 nucleotides 5' to (upstream of) the start codon of the coding sequence, and observing the relative expression levels of the protein for each integration location.

In embodiments, the donor polynucleotide sequence of interest includes coding (protein-coding) sequence, non-coding (non-protein-coding) sequence, or a combination of coding and non-coding sequence. Embodiments include a plant nuclear sequence, a plant plastid sequence, a plant mitochondrial sequence, a sequence of a symbiont, pest, or pathogen of a plant, and combinations thereof. Embodiments include exons, introns, regulatory sequences including promoters, other 5' elements and 3' elements, and genomic loci encoding non-coding RNAs including long non-coding RNAs (lncRNAs), microRNAs (miRNAs), and trans-acting siRNAs (ta-siRNAs). In embodiments, multiple sequences are altered, for example, by delivery of multiple gRNAs to the plant cell or plant protoplast; the multiple sequences can be part of the same gene (e. g., different locations in a single coding region or in different exons or introns of a protein-coding gene) or different genes. In embodiments, the sequence of an endogenous genomic locus is altered to delete, add, or modify a functional non-coding sequence; in non-limiting examples, such functional non-coding sequences include, e. g., a miRNA, siRNA, or ta-siRNA recognition or cleavage site, a splice site, a recombinase recognition site, a transcription factor binding site, or a transcriptional or translational enhancer or repressor sequence.

In embodiments, the invention provides a method of changing expression of a sequence of interest in a genome, including integrating a sequence encoded by a polynucleotide (such as a double-stranded DNA, a single-stranded DNA, a single-stranded DNA/RNA hybrid, or a double-stranded DNA/RNA hybrid) donor molecule at the site of two or more DSBs in a genome. In embodiments, the sequence of the polynucleotide donor molecule that is integrated into each of the two or more DSBs is (a) identical, or (b) different, for each of the DSBs. In embodiments, the change in expression of a sequence of interest in genome is manifested as the expression of an altered or edited sequence of interest; in non-limiting examples, the method is used to integrate sequence-specific recombinase recognition site sequences at two DSBs in a genome, whereby, in the presence of the corresponding site-specific DNA recombinase, the genomic sequence flanked on either side by the integrated recombinase recognition sites is excised from the genome (or in some instances is inverted); such an approach is useful, e. g., for deletion of larger lengths of genomic sequence, for example, deletion of all or part of an exon or of one or more protein domains. In other embodiments, at least two DSBs are introduced into a genome by one or more nucleases in such a way that genomic sequence is deleted between the DSBs (leaving a deletion with blunt ends, overhangs or a combination of a blunt end and an overhang), and a sequence encoded by at least one polynucleotide donor molecule is integrated between the DSBs (i. e., a sequence encoded by at least one individual polynucleotide donor molecule is integrated at the location of the deleted genomic sequence), wherein the genomic sequence that is deleted is coding sequence, non-coding sequence, or a combination of coding and non-coding sequence; such embodiments provide the advantage of not requiring a specific PAM site at or very near the location of a region wherein a nucleotide sequence change is desired. In an embodiment, at least two DSBs are introduced into a genome by one or more nucleases in such a way that genomic sequence is deleted between the DSBs (leaving a deletion with blunt ends, overhangs or a combination of a blunt end and an overhang), and at least one sequence encoded by a polynucleotide donor molecule is integrated between the DSBs (i. e., at least one individual sequence encoded by a polynucleotide donor molecule is integrated at the location of the deleted genomic sequence). In an embodiment, two DSBs are introduced into a genome, resulting in excision or deletion of genomic sequence between the sites of the two DSBs, and a sequence encoded by a polynucleotide donor molecule integrated into the genome at the location of the deleted genomic sequence (that is, a sequence encoded by an individual polynucleotide donor molecule is integrated between the two DSBs). Generally, the polynucleotide donor molecule with the sequence to be integrated into the genome is selected in terms of the presence or absence of terminal overhangs to match the type of DSBs introduced. In an embodiment, two blunt-ended DSBs are introduced into a genome, resulting in excision or deletion of genomic sequence between the sites of the two blunt-ended DSBs, and a sequence encoded by a blunt-ended double-stranded DNA or blunt-ended double-stranded DNA/RNA hybrid or a single-stranded DNA or a single-stranded DNA/RNA hybrid donor molecule is integrated into the genome between the two blunt-ended DSBs. In another embodiment, two DSBs are introduced into a genome, wherein the first DSB is blunt-ended and the second DSB has an overhang, resulting in deletion of genomic sequence between the two DSBs, and a sequence encoded by a double-stranded DNA or double-stranded DNA/RNA hybrid donor molecule that is blunt-ended at one terminus and that has an overhang on the other terminus (or, alternatively, a single-stranded DNA or a single-stranded DNA/RNA hybrid molecule) is integrated into the genome between the two DSBs; in an alternative embodiment, two DSBs are introduced into a genome, wherein both DSBs have overhangs but of different overhang lengths (different number of unpaired nucleotides), resulting in deletion of genomic sequence between the two DSBs, and a sequence encoded by a double-stranded DNA or double-stranded DNA/RNA hybrid donor molecule that has overhangs at each terminus, wherein the overhangs are of unequal lengths (or, alternatively, a single-stranded DNA or a single-stranded DNA/RNA hybrid donor molecule), is integrated into the genome between the two DSBs; embodiments with such DSB asymmetry (i. e., a combination of DSBs having a blunt end and an overhang, or a combination of DSBs having overhangs of unequal lengths) provide the opportunity for controlling directionality or orientation of the inserted polynucleotide, e. g., by selecting a double-stranded DNA or double-stranded DNA/RNA hybrid donor molecule having one blunt end and one terminus with unpaired nucleotides, such that the polynucleotide is integrated preferably in one orientations. In another embodiment, two DSBs, each having an overhang, are introduced into a genome, resulting in excision or deletion of genomic sequence between the sites of the two DSBs, and a sequence encoded by a double-stranded DNA or double-stranded DNA/RNA hybrid donor molecule that has an overhang at each terminus (or, alternatively, a single-stranded DNA or a single-stranded DNA/RNA hybrid donor molecule) is integrated into the genome between the two DSBs. The length of genomic sequence that is deleted between two DSBs and the length of a sequence encoded by the polynucleotide donor molecule that is integrated in place of the deleted genomic sequence can be, but need not be equal. In embodiments, the distance between any two DSBs (or the length of the genomic sequence that is to be deleted) is at least 10, at least 15, at least 20, at least 25, at least 30, at least 40, at least 50, at least 60, at least 70, at least 80, or at least 100 nucleotides; in other embodiments the distance between any two DSBs (or the length of the genomic sequence that is to be deleted) is at least 100, at least 150, at least 200, at least 300, at least 400, at least 500, at least 600, at least 750, or at least 1000 nucleotides. In embodiments where more than two DSBs are introduced into genomic sequence, it is possible to effect different deletions of genomic sequence (for example, where three DSBs are introduced, genomic sequence can be deleted between the first and second DSBs, between the first and third DSBs, and between the second and third DSBs). In some embodiments, a sequence encoded by more than one polynucleotide donor molecule (e. g., multiple copies of a sequence encoded by a polynucleotide donor molecule having a given sequence, or multiple sequences encoded by polynucleotide donor molecules with two or more different sequences) is integrated into the genome. For example, different sequences encoded by individual polynucleotide donor molecules can be individually integrated at a single locus where genomic sequence has been deleted between two DSBs, or at multiple locations where genomic sequence has been deleted (e. g., where more than two DSBs have been introduced into the genome). In embodiments, at least one exon is replaced by integrating a sequence encoded by at least one polynucleotide molecule where genomic sequence is deleted between DSBs that were introduced by at least one sequence-specific nuclease into intronic sequence flanking the at least one exon; an advantage of this approach over an otherwise similar method (i. e., differing by having the DSBs introduced into coding sequence instead of intronic sequence) is the avoidance of inaccuracies (nucleotide changes, deletions, or additions at the nuclease cleavage sites) in the resulting exon sequence or messenger RNA.

In embodiments, the methods described herein are used to delete or replace genomic sequence, which can be a relatively large sequence (e. g., all or part of at least one exon or of a protein domain) resulting in the equivalent of an alternatively spliced transcript. Additional related aspects include compositions and reaction mixtures including a plant cell or a plant protoplast and at least two guide RNAs, wherein each guide RNA is designed to effect a DSB in intronic sequence flanking at least one exon; such compositions and reaction mixtures optionally include at least one sequence-specific nuclease capable of being guided by at least one of the guide RNAs to effect a DSB in genomic sequence, and optionally include a polynucleotide donor molecule that is capable of being integrated (or having its sequence integrated) into the genome at the location of at least one DSB or at the location of genomic sequence that is deleted between the DSBs.

Donor Polynucleotide Molecules: Embodiments of the polynucleotide donor molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a polynucleotide donor molecule that is a double-stranded (e. g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the polynucleotide donor molecule that is integrated (or that has a sequence that is integrated) at the site of at least one double-strand break (DSB) in a genome is double-stranded and blunt-ended; in other embodiments the polynucleotide donor molecule is double-stranded and has an overhang or "sticky end" consisting of unpaired nucleotides (e. g., 1, 2, 3, 4, 5, or 6 unpaired nucleotides) at one terminus or both termini. In an embodiment, the DSB in the genome has no unpaired nucleotides at the cleavage site, and the polynucleotide donor molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the polynucleotide donor molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the polynucleotide donor molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e. g., where a Cpf1 nuclease effects an off-set DSB with 5-nucleotide overhangs in the genomic sequence, the polynucleotide donor molecule that is to be integrated (or that has a sequence that is to be integrated) at the site of the DSB is double-stranded and has 5 unpaired nucleotides at one or both termini). Generally, one or both termini of the polynucleotide donor molecule contain no regions of sequence homology (identity or complementarity) to genomic regions flanking the DSB; that is to say, one or both termini of the polynucleotide donor molecule contain no regions of sequence that is sufficiently complementary to permit hybridization to genomic regions immediately adjacent to the location of the DSB. In embodiments, the polynucleotide donor molecule contains no homology to the locus of the DSB, that is to say, the polynucleotide donor molecule contains no nucleotide sequence that is sufficiently complementary to permit hybridization to genomic regions immediately adjacent to the location of the DSB. In an embodiment, the polynucleotide donor molecule that is integrated at the site of at least one double-strand break (DSB) includes between 2-20 nucleotides in one (if single-stranded) or in both strands (if double-stranded), e. g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). In embodiments, the polynucleotide donor molecule is at least partially double-stranded and includes 2-20 base-pairs, e. g., 2, 3, 4, 5, 6, 7, 8, 9, 10, 11, 12, 13, 14, 15, 16, 17, 18, 19, or 20 base-pairs; in embodiments, the polynucleotide donor molecule is double-stranded and blunt-ended and consists of 2-20 base-pairs, e. g., 2, 3, 4, 5, 6, 7, 8, 9, 10, 11, 12, 13, 14, 15, 16, 17, 18, 19, or 20 base-pairs; in other embodiments, the polynucleotide donor molecule is double-stranded and includes 2-20 base-pairs, e. g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. Non-limiting examples of such relatively small polynucleotide donor molecules of 20 or fewer base-pairs (if double-stranded) or 20 or fewer nucleotides (if single-stranded) include polynucleotide donor molecules that have at least one strand including a transcription factor recognition site sequence (e. g., such as the sequences of transcription factor recognition sites provided in the working Examples), or that have at least one strand including a small RNA recognition site, or that have at least one strand including a recombinase recognition site. In an embodiment, the polynucleotide donor molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the polynucleotide donor molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the polynucleotide donor molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the polynucleotide donor molecule includes chemically modified nucleotides (see, e. g., the various modifications of internucleotide linkages, bases, and sugars described in Verma and Eckstein (1998) *Annu. Rev. Biochem.,* 67:99-134); in embodiments, the naturally occurring phosphodiester backbone of the polynucleotide donor molecule is partially or completely modified with phosphorothioate, phosphorodithioate, or methylphosphonate internucleotide linkage modifications, or the polynucleotide donor molecule includes modified nucleoside bases or modified sugars, or the polynucleotide donor molecule is labelled with a fluorescent moiety (e. g., fluorescein or rhodamine or a fluorescent nucleoside analogue) or other detectable label (e. g., biotin or an isotope). In an embodiment, the polynucleotide donor molecule is double-stranded and perfectly base-paired through all or most of its length, with the possible exception of any unpaired nucleotides at either terminus or both termini. In another embodiment, the polynucleotide donor molecule is double-stranded and includes one or more non-terminal mismatches or non-terminal unpaired nucleotides within the otherwise double-stranded duplex. In another embodiment, the polynucleotide donor molecule contains secondary structure that provides stability or acts as an aptamer. Other related embodiments include double-stranded DNA/RNA hybrid molecules, single-stranded DNA/RNA hybrid donor molecules, and single-stranded DNA donor molecules (including single-stranded, chemically modified DNA donor molecules), which in analogous procedures are integrated (or have a sequence that is integrated) at the site of a double-strand break.

In embodiments of the method, the polynucleotide (such as a double-stranded DNA, a single-stranded DNA, a single-stranded DNA/RNA hybrid, or a double-stranded DNA/RNA hybrid) donor molecule that is integrated at the site of at least one double-strand break (DSB) in a genome includes nucleotide sequence(s) on one or on both strands that provide a desired functionality when the polynucleotide is integrated into the genome. In various non-limiting embodiments of the method, the sequence encoded by a donor polynucleotide that is inserted at the site of at least one double-strand break (DSB) in a genome includes at least one sequence selected from the group consisting of:

(a) DNA encoding at least one stop codon, or at least one stop codon on each strand, or at least one stop codon within each reading frame on each strand;

(b) DNA encoding heterologous primer sequence (e. g., a sequence of about 18 to about 22 contiguous nucleotides, or of at least 18 contiguous nucleotides, that can be used to initiate DNA polymerase activity at the site of the DSB);

(c) DNA encoding a unique identifier sequence (e. g., a sequence that when inserted at the DSB creates a heterologous sequence that can be used to identify the presence of the insertion);

(d) DNA encoding a transcript-stabilizing sequence;

(e) DNA encoding a transcript-destabilizing sequence;

(f) a DNA aptamer or DNA encoding an RNA aptamer or amino acid aptamer; and (g) DNA that includes or encodes a sequence recognizable by a specific binding agent.

In an embodiment, the sequence encoded by the polynucleotide (such as a double-stranded DNA, a single-stranded DNA, a single-stranded DNA/RNA hybrid, or a double-stranded DNA/RNA hybrid) donor molecule that is integrated at the site of at least one double-strand break (DSB) in a genome includes DNA encoding at least one stop codon, or at least one stop codon on each strand, or at least one stop codon within each reading frame on each strand. Such sequence encoded by a polynucleotide donor molecule, when integrated at a DSB in a genome can be useful for disrupting the expression of a sequence of interest, such as a protein-coding gene. An example of such a polynucleotide donor molecule is a double-stranded DNA, a single-stranded DNA, a single-stranded DNA/RNA hybrid, or a double-stranded DNA/RNA hybrid donor molecule, of at least 18 contiguous base-pairs if double-stranded or at least 11 contiguous nucleotides if single-stranded, and encoding at least one stop codon in each possible reading frame on either strand. Another example of such a polynucleotide donor molecule is a double-stranded DNA or double-stranded DNA/RNA hybrid donor molecule wherein each strand includes at least 18 and fewer than 200 contiguous base-pairs, wherein the number of base-pairs is not divisible by 3, and wherein each strand encodes at least one stop codon in each possible reading frame in the 5' to 3' direction. Another example of such a polynucleotide donor molecule is a single-stranded DNA or single-stranded DNA/RNA hybrid donor molecule wherein each strand includes at least 11 and fewer than about 300 contiguous nucleotides, wherein the number of base-pairs is not divisible by 3, and wherein the polynucleotide donor molecule encodes at least one stop codon in each possible reading frame in the 5' to 3' direction.

In an embodiment, the polynucleotide (such as a double-stranded DNA, a single-stranded DNA, a single-stranded DNA/RNA hybrid, or a double-stranded DNA/RNA hybrid) donor molecule that is integrated (or that has a sequence that is integrated) at the site of at least one double-strand break (DSB) in a genome includes DNA encoding heterologous primer sequence (e. g., a sequence of about 18 to about 22 contiguous nucleotides, or of at least 18, at least 20, or at least 22 contiguous nucleotides that can be used to initiate DNA polymerase activity at the site of the DSB). Heterologous primer sequence can further include nucleotides of the genomic sequence directly flanking the site of the DSB.

In an embodiment, the polynucleotide (such as a double-stranded DNA, a single-stranded DNA, a single-stranded DNA/RNA hybrid, or a double-stranded DNA/RNA hybrid) donor molecule that is integrated (or that has a sequence that is integrated) at the site of at least one double-strand break (DSB) in a genome includes nucleotides encoding a unique identifier sequence (e. g., a sequence that when inserted at the DSB creates a heterologous sequence that can be used to identify the presence of the insertion)

In an embodiment, the polynucleotide (such as a double-stranded DNA, a single-stranded DNA, a single-stranded DNA/RNA hybrid, or a double-stranded DNA/RNA hybrid) donor molecule that is integrated (or that has a sequence that is integrated) at the site of at least one double-strand break (DSB) in a genome includes nucleotides encoding a transcript-stabilizing sequence. In an example, sequence of a double-stranded or single-stranded DNA or a DNA/RNA hybrid donor molecule encoding a 5' terminal RNA-stabilizing stem-loop (see, e. g., Suay (2005) *Nucleic Acids Rev.,* 33:4754-4761) is integrated at a DSB located 5' to the sequence for which improved transcript stability is desired. In another embodiment, the polynucleotide donor molecule that is integrated (or that has a sequence that is integrated) at the site of at least one double-strand break (DSB) in a genome includes nucleotides encoding a transcript-destabilizing sequence such as the SAUR destabilizing sequences described in detail in U.S. Patent Application Publication 2007/0011761, incorporated herein by reference.

In an embodiment, the polynucleotide (such as a double-stranded DNA, a single-stranded DNA, a single-stranded DNA/RNA hybrid, or a double-stranded DNA/RNA hybrid) donor molecule that is integrated (or that has a sequence that is integrated) at the site of at least one double-strand break (DSB) in a genome includes a DNA aptamer or DNA encoding an RNA aptamer or amino acid aptamer. Nucleic acid (DNA or RNA) aptamers are single- or double-stranded nucleotides that bind specifically to molecules or ligands which include small molecules (e. g., secondary metabolites such as alkaloids, terpenes, flavonoids, and other small molecules, as well as larger molecules such as polyketides and non-ribosomal proteins), proteins, other nucleic acid molecules, and inorganic compounds. Introducing an aptamer at a specific location in the genome is useful, e. g., for adding binding specificity to an enzyme or for placing expression of a transcript or activity of an encoded protein under ligand-specific control. In an example, the polynucleotide donor molecule encodes a poly-histidine "tag" which is integrated at a DSB downstream of a protein or protein subunit, enabling the protein expressed from the resulting transcript to be purified by affinity to nickel, e. g., on nickel resins; in an embodiments, the polynucleotide donor molecule encodes a 6×-His tag, a 10×-His tag, or a 10×-His tag including one or more stop codons following the histidine-encoding codons, where the last is particularly useful when integrated downstream of a protein or protein subunit lacking a stop codon (see, e. g., parts[dot]igem[dot]org/Part:BBa_K844000). In embodiments, the polynucleotide donor molecule encodes a riboswitch, wherein the riboswitch includes both an aptamer which changes its conformation in the presence or absence of a specific ligand, and an expression-controlling region that turns expression on or off, depending on the conformation of the aptamer. See, for example, the regulatory RNA molecules containing ligand-specific aptamers described in U.S. Patent Application Publication 2013/0102651 and the various riboswitches described in U.S. Patent Application Publication 2005/0053951, both of which publications are incorporated herein by reference.

In an embodiment, the polynucleotide (such as a double-stranded DNA, a single-stranded DNA, a single-stranded DNA/RNA hybrid, or a double-stranded DNA/RNA hybrid) donor molecule that is integrated (or that has a sequence that is integrated) at the site of at least one double-strand break (DSB) in a genome includes nucleotides that include or encode a sequence recognizable by (i. e., binds to) a specific binding agent. Non-limiting embodiments of specific binding agents include nucleic acids, peptides or proteins, non-peptide/non-nucleic acid ligands, inorganic molecules, and combinations thereof; specific binding agents also include macromolecular assemblages such as lipid bilayers, cell components or organelles, and even intact cells or organisms. In embodiments, the specific binding agent is an aptamer or riboswitch, or alternatively is recognized by an aptamer or a riboswitch. In an embodiment, the invention provides a method of changing expression of a sequence of interest in a genome, comprising integrating a polynucleotide molecule at the site of a DSB in a genome, wherein the polynucleotide donor molecule includes a sequence recognizable by a specific binding agent, wherein the integrated sequence encoded by the polynucleotide donor molecule is functionally or operably linked to a sequence of interest, and wherein contacting the integrated sequence encoded by the polynucleotide donor molecule with the specific binding agent results in a change of expression of the sequence of interest; in embodiments, sequences encoded by different polynucleotide donor molecules are integrated at multiple DSBs in a genome.

In an embodiment, the polynucleotide (such as a double-stranded DNA, a single-stranded DNA, a single-stranded DNA/RNA hybrid, or a double-stranded DNA/RNA hybrid) donor molecule that is integrated (or that has a sequence that is integrated) at the site of at least one double-strand break (DSB) in a genome includes nucleotides that include or encode a sequence recognizable by (i. e., binds to) a specific binding agent, wherein:

(a) the sequence recognizable by a specific binding agent includes an auxin response element (AuxRE) sequence, the specific binding agent is an auxin, and the change of expression is upregulation; see, e. g., Walker and Estelle (1998) *Curr. Opinion Plant Biol.,* 1:434-439;

(b) the sequence recognizable by a specific binding agent includes at least one D1-4 sequence (CCTCGTGTCTC, SEQ ID NO:328; see Ulmasov et al. (1997) *Plant Cell,* 9:1963-1971), the specific binding agent is an auxin, and the change of expression is upregulation;

(c) the sequence recognizable by a specific binding agent includes at least one DR5 sequence (CCTTTTGTCTC, SEQ ID NO:329; see Ulmasov et al. (1997) *Plant Cell,* 9:1963-1971), the specific binding agent is an auxin, and the change of expression is upregulation;

(d) the sequence recognizable by a specific binding agent includes at least one m5-DR5 sequence (CCTTTTGTCNC, wherein N is A, C, or G, SEQ ID NO:330; see Ulmasov et al. (1997) *Plant Cell,* 9:1963-1971), the specific binding agent is an auxin, and the change of expression is upregulation;

(e) the sequence recognizable by a specific binding agent includes at least one P3 sequence (TGTCTC, SEQ ID NO:331), the specific binding agent is an auxin, and the change of expression is upregulation;

(f) the sequence recognizable by a specific binding agent includes a small RNA recognition site sequence, the specific binding agent is the corresponding small RNA (e. g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein), and the change of expression is downregulation (non-limiting examples are given below, under the heading "Small RNAs");

(g) the sequence recognizable by a specific binding agent includes a microRNA (miRNA) recognition site sequence, the specific binding agent is the corresponding mature miRNA, and the change of expression is downregulation (non-limiting examples are given below, under the heading "Small RNAs");

(h) the sequence recognizable by a specific binding agent includes a microRNA (miRNA) recognition sequence for an engineered miRNA, the specific binding agent is the corresponding engineered mature miRNA, and the change of expression is downregulation;

(i) the sequence recognizable by a specific binding agent includes a transposon recognition sequence, the specific binding agent is the corresponding transposon, and the change of expression is upregulation or downregulation;

(j) the sequence recognizable by a specific binding agent includes an ethylene-responsive element binding-factor-associated amphiphilic repression (EAR) motif (LxLxL, SEQ ID NO:332 or DLNxxP, SEQ ID NO:333) sequence (see, e. g., Ragale and Rozwadowski (2011) *Epigenetics,* 6:141-146), the specific binding agent is ERF (ethylene-responsive element binding factor) or co-repressor (e. g., TOPLESS (TPL)), and the change of expression is downregulation;

(k) the sequence recognizable by a specific binding agent includes a splice site sequence (e. g., a donor site, a branching site, or an acceptor site; see, for example, the splice sites and splicing signals publicly available at the ERIS database, lemur[dot]amu[dot]edu[dot]pl/share/ERISdb/home.html), the specific binding agent is a spliceosome, and the change of expression is expression of an alternatively spliced transcript (in some cases, this can include deletion of a relatively large genomic sequence, such as deletion of all or part of an exon or of a protein domain);

(l) the sequence recognizable by a specific binding agent includes a recombinase recognition site sequence that is recognized by a site-specific recombinase, the specific binding agent is the corresponding site-specific recombinase, and the change of expression is upregulation or downregulation or expression of a transcript having an altered sequence (for example, expression of a transcript that has had a region of DNA excised by the recombinase) (non-limiting examples are given below, under the heading "Recombinases and Recombinase Recognition Sites");

(m) the sequence recognizable by a specific binding agent includes sequence encoding an RNA or amino acid aptamer or an RNA riboswitch, the specific binding agent is the corresponding ligand, and the change in expression is upregulation or downregulation;

(n) the sequence recognizable by a specific binding agent is a hormone responsive element (e. g., a nuclear receptor, or a hormone-binding domain thereof), the specific binding agent is a hormone, and the change in expression is upregulation or downregulation;

(o) the sequence recognizable by a specific binding agent is a transcription factor binding sequence, the specific binding agent is the corresponding transcription factor, and the change in expression is upregulation or downregulation (non-limiting examples are given below, under the heading "Transcription Factors"); or (p) the sequence recognizable by a specific binding agent is a polycomb response element, and the change in expression is polycomb repressive complex 2- (PRC2-)

mediated silencing of a target gene (see Xiao et al. (2017) *Nature Genetics,* 49:1546-1552, doi: 10.1038/ng.3937).

In embodiments, the polynucleotide (such as a double-stranded DNA, a single-stranded DNA, a single-stranded DNA/RNA hybrid, or a double-stranded DNA/RNA hybrid) donor molecule that is integrated (or that has a sequence that is integrated) at the site of at least one double-strand break (DSB) in a genome includes a nucleotide sequence that encodes an RNA molecule or an amino acid sequence that is recognizable by a specific binding agent. In embodiments, the polynucleotide donor molecule includes a nucleotide sequence that binds specifically to a ligand or that encodes an RNA molecule or an amino acid sequence that binds specifically to a ligand. In embodiments, the polynucleotide donor molecule encodes at least one stop codon on each strand, or encodes at least one stop codon within each reading frame on each strand.

In embodiments, the polynucleotide (such as a double-stranded DNA, a single-stranded DNA, a single-stranded DNA/RNA hybrid, or a double-stranded DNA/RNA hybrid) donor molecule includes at least partially self-complementary sequence, such that the polynucleotide donor molecule encodes a transcript that is capable of forming at least partially double-stranded RNA. In embodiments, the at least partially double-stranded RNA is capable of forming secondary structure containing at least one stem-loop (i. e., a substantially or perfectly double-stranded RNA "stem" region and a single-stranded RNA "loop" connecting opposite strands of the dsRNA stem. In embodiments, the at least partially double-stranded RNA is cleavable by a Dicer or other ribonuclease. In embodiments, the at least partially double-stranded RNA includes an aptamer or a riboswitch; see, e. g., the RNA aptamers described in U.S. Patent Application Publication 2013/0102651, which is incorporated herein by reference.

In embodiments, the polynucleotide (such as a double-stranded DNA, a single-stranded DNA, a single-stranded DNA/RNA hybrid, or a double-stranded DNA/RNA hybrid) donor molecule that is integrated (or that has a sequence that is integrated) at the site of at least one double-strand break (DSB) in a genome includes or encodes a nucleotide sequence that is responsive to a specific change in the physical environment (e. g., a change in light intensity or quality, a change in temperature, a change in pressure, a change in osmotic concentration, a change in day length, or addition or removal of a ligand or specific binding agent), wherein exposing the integrated polynucleotide sequence to the specific change in the physical environment results in a change of expression of the sequence of interest. In embodiments, the polynucleotide donor molecule includes a nucleotide sequence encoding an RNA molecule or an amino acid sequence that is responsive to a specific change in the physical environment. In a non-limiting example, the polynucleotide donor molecule encodes an amino acid sequence that is responsive to light, oxygen, redox status, or voltage, such as a Light-Oxygen-Voltage (LOV) domain (see, e. g., Peter et al. (2010) *Nature Communications*, doi:10.1038/ncommsl 121) or a PAS domain (see, e. g., Taylor and Zhulin (1999) *Microbiol. Mol. Biol. Reviews,* 63:479-506), proteins containing such domains, or sub-domains or motifs thereof (see, e. g., the photochemically active 36-residue N-terminal truncation of the VVD protein described by Zoltowski et al. (2007) *Science,* 316:1054-1057). In a non-limiting embodiment, integration of a LOV domain at the site of a DSB within or adjacent to a protein-coding region is used to create a heterologous fusion protein that can be photo-activated.

Small RNAs: In an embodiment, the polynucleotide (such as a double-stranded DNA, a single-stranded DNA, a single-stranded DNA/RNA hybrid, or a double-stranded DNA/RNA hybrid) donor molecule that is integrated (or that has a sequence that is integrated) at the site of at least one double-strand break (DSB) in a genome includes DNA that includes or encodes a small RNA recognition site sequence that is recognized by a corresponding mature small RNA. Small RNAs include siRNAs, microRNAs (miRNAs), trans-acting siRNAs (ta-siRNAs) as described in U.S. Pat. No. 8,030,473, and phased small RNAs (phased sRNAs) as described in U.S. Pat. No. 8,404,928. All mature small RNAs are single-stranded RNA molecules, generally between about 18 to about 26 nucleotides in length, which are produced from longer, completely or substantially double-stranded RNA (dsRNA) precursors. For example, siRNAs are generally processed from perfectly or near-perfectly double-stranded RNA precursors, whereas both miRNAs and phased sRNAs are processed from larger precursors that contain at least some mismatched (non-base-paired) nucleotides and often substantial secondary structure such as loops and bulges in the otherwise largely double-stranded RNA precursor. Precursor molecules include naturally occurring precursors, which are often expressed in a specific (e. g., cell- or tissue-specific, temporally specific, developmentally specific, or inducible) expression pattern. Precursor molecules also include engineered precursor molecules, designed to produce small RNAs (e. g., artificial or engineered siRNAs or miRNAs) that target specific sequences; see, e. g., U.S. Pat. Nos. 7,691,995 and 7,786,350, which are incorporated herein by reference in their entirety. Thus, in embodiments, the polynucleotide (such as a double-stranded DNA, a single-stranded DNA, a single-stranded DNA/RNA hybrid, or a double-stranded DNA/RNA hybrid) donor molecule that is integrated (or that has a sequence that is integrated) at the site of at least one double-strand break (DSB) in a genome includes DNA that includes or encodes a small RNA precursor sequence designed to be processed in vivo to at least one corresponding mature small RNA. In embodiments, the polynucleotide donor molecule that is integrated (or that has a sequence that is integrated) at the site of at least one double-strand break (DSB) in a genome includes DNA that includes or encodes an engineered small RNA precursor sequence that is based on a naturally occurring "scaffold" precursor sequence but wherein the nucleotides of the encoded mature small RNA are designed to target a specific gene of interest that is different from the gene targetted by the natively encoded small RNA; in embodiments, the "scaffold" precursor sequence is one identified from the genome of a plant or a pest or pathogen of a plant; see, e. g., U.S. Pat. No. 8,410,334, which discloses transgenic expression of engineered invertebrate miRNA precursors in a plant, and which is incorporated herein by reference in its entirety.

Regardless of the pathway that generates the mature small RNA, the mechanism of action is generally similar; the mature small RNA binds in a sequence-specific manner to a small RNA recognition site located on an RNA molecule (such as a transcript or messenger RNA), and the resulting duplex is cleaved by a ribonuclease. The integration of a recognition site for a small RNA at the site of a DSB results in cleavage of the transcript including the integrated recognition site when and where the mature small RNA is expressed and available to bind to the recognition site. For example, a recognition site sequence for a mature siRNA or miRNA that is endogenously expressed only in male reproductive tissue of a plant can be integrated into a DSB, whereby a transcript containing the recognition site sequence is cleaved only where the mature siRNA or miRNA is expressed (i. e., in male reproductive tissue); this is useful, e. g., to prevent expression of a protein in male reproductive tissue such as pollen, and can be used in applications such as to induce male sterility in a plant or to prevent pollen development or shedding. Similarly, a recognition site sequence for a mature siRNA or miRNA that is endogenously expressed only in the roots of a plant can be integrated into a DSB, whereby a transcript containing the recognition site sequence is cleaved only in roots; this is useful, e. g., to prevent expression of a protein in roots. Non-limiting examples of useful small RNAs include: miRNAs having tissue-specific expression patterns disclosed in U.S. Pat. No. 8,334,430, miRNAs having temporally specific expression patterns disclosed in U.S. Pat. No. 8,314,290, miRNAs with stress-responsive expression patterns disclosed in U.S. Pat. No. 8,237,017, siRNAs having tissue-specific expression patterns disclosed in U.S. Pat. No. 9,139,838, and various miRNA recognition site sequences and the corresponding miRNAs disclosed in U.S. Patent Application Publication 2009/0293148. All of the patent publications referenced in this paragraph are incorporated herein by reference in their entirety. In embodiments, multiple edits in a genome are employed to obtain a desired phenotype or trait in plant. In an embodiment, one or more edits (addition, deletion, or substitution of one or more nucleotides) of an endogenous nucleotide sequence is made to provide a general phenotype; addition of at least one small RNA recognition site by insertion of the recognition site sequence at a DSB that is functionally linked to the edited endogenous nucleotide sequence achieves more specific control of expression of the edited endogenous nucleotide sequence. In an example, an endogenous plant 5-enolpyruvylshikimate-3-phosphate synthase (EPSPS) is edited to provide a glyphosate-resistant EPSPS; for example, suitable changes include the amino acid substitutions Threonine-102-Isoleucine (T102I) and Proline-106-Serine (P106S) in the maize EPSPS sequence identified by Genbank accession number X63374 (see, for example U.S. Pat. No. 6,762,344, incorporated herein by reference). In another example, an endogenous plant acetolactate synthase (ALS) is edited to increase resistance of the enzyme to various herbicides (e. g., sulfonylurea, imidazolinone, tirazolopyrimidine, pyrimidinylthiobenzoate, sulfonylamino-carbonyltriazolinone); for example, suitable changes include the amino acid substitutions G115, A116, P191, A199, K250, M345, D370, V565, W568, and F572 to the *Nicotiana tabacum* ALS enzyme as described in U.S. Pat. No. 5,605,011, which is incorporated herein by reference. The edited herbicide-tolerant enzyme, combined with integration of at least one small RNA recognition site for a small RNA (e. g., an siRNA or a miRNA) expressed only in a specific tissue (for example, miRNAs specifically expressed in male reproductive tissue or female reproductive tissue, e. g., the miRNAs disclosed in Table 6 of U.S. Pat. No. 8,334,430 or the siRNAs disclosed in U.S. Pat. No. 9,139,838, both incorporated herein by reference) at a DSB functionally linked to (e. g., in the 3' untranslated region of) the edited herbicide-tolerant enzyme results in expression of the edited herbicide-tolerant enzyme being restricted to tissues other than those in which the small RNA is endogenously expressed, and those tissues in which the small RNA is expressed will not be resistant to herbicide application; this approach is useful, e. g., to provide male-sterile or female-sterile plants.

In other embodiments, the sequence of an endogenous genomic locus encoding one or more small RNAs (e. g., miRNAs, siRNAs, ta-siRNAs) is altered in order to express a small RNA having a sequence that is different from that of the endogenous small RNA and is designed to target a new sequence of interest (e. g., a sequence of a plant pest, plant pathogen, symbiont of a plant, or symbiont of a plant pest or pathogen). For example, the sequence of an endogenous or native genomic locus encoding a miRNA precursor can be altered in the mature miRNA and the miR* sequences, while maintaining the secondary structure in the resulting altered miRNA precursor sequence to permit normal processing of the transcript to a mature miRNA with a different sequence from the original, native mature miRNA sequence; see, for example, U.S. Pat. Nos. 7,786,350 and 8,395,023, both of which are incorporated by reference in their entirety herein, and which teach methods of designing engineered miRNAs. In embodiments, the sequence of an endogenous genomic locus encoding one or more small RNAs (e. g., miRNAs, siRNAs, ta-siRNAs) is altered in order to express one or more small RNA cleavage blockers (see, e. g., U.S. Pat. No. 9,040,774, which is incorporated by reference in its entirety herein). In embodiments, the sequence of an endogenous genomic locus is altered to encode a small RNA decoy (e. g., U.S. Pat. No. 8,946,511, which is incorporated by reference in its entirety herein). In embodiments, the sequence of an endogenous genomic locus that natively contains a small RNA (e. g., miRNA, siRNA, or ta-siRNA) recognition or cleavage site is altered to delete or otherwise mutate the recognition or cleavage site and thus decouple the genomic locus from small RNA regulation.

Recombinases and Recombinase Recognition Sites: In an embodiment, the polynucleotide (such as a double-stranded DNA, a single-stranded DNA, a single-stranded DNA/RNA hybrid, or a double-stranded DNA/RNA hybrid) donor molecule that is integrated (or that has a sequence that is integrated) at the site of at least one double-strand break (DSB) in a genome includes DNA that includes or encodes a recombinase recognition site sequence that is recognized by a site-specific recombinase, the specific binding agent is the corresponding site-specific recombinase, and the change of expression is upregulation or downregulation or expression of a transcript having an altered sequence (for example, expression of a transcript that has had a region of DNA excised by the recombinase). The term "recombinase recognition site sequence" refers to the DNA sequences (usually a pair of sequences) that are recognized by a site-specific (i. e., sequence-specific) recombinase in a process that allows the excision (or, in some cases, inversion or translocation) of the DNA located between the sequence-specific recombination sites. For instance, Cre recombinase recognizes either loxP recombination sites or lox511 recombination sites which are heterospecific, which means that loxP and lox511 do not recombine together (see, e. g., Odell et al. (1994) *Plant Physiol.,* 106:447-458); FLP recombinase recognizes frt recombination sites (see, e. g., Lyznik et al. (1996) *Nucleic Acids Res.,* 24:3784-3789); R recombinase recognizes Rs recombination sites (see, e. g., Onounchi et al. (1991) *Nucleic Acids Res.,* 19:6373-6378); Dre recombinase recognizes rox sites (see, e. g., U.S. Pat. No. 7,422,889, incorporated herein by reference); and Gin recombinase recognizes gix sites (see, e. g., Maeser et al. (1991) *Mol. Gen. Genet.,* 230:170-176). In a non-limiting example, a pair of polynucleotides encoding loxP recombinase recognition site sequences encoded by a pair of polynucleotide donor molecules are integrated at two separate DSBs; in the presence of the corresponding site-specific DNA recombinase Cre, the genomic sequence flanked on either side by the integrated loxP recognition sites is excised from the genome (for loxP sequences that are integrated in the same orientation relative to each other within the genome) or is inverted (for loxP sites that are integrated in an inverted orientation relative to each other within the genome) or is translocated (for loxP sites that are integrated on separate DNA molecules); such an approach is useful, e. g., for deletion or replacement of larger lengths of genomic sequence, for example, deletion or replacement of one or more protein domains. In embodiments, the recombinase recognition site sequences that are integrated at two separate DSBs are heterospecific, i. e., will not recombine together; for example, Cre recombinase recognizes either loxP recombination sites or lox511 recombination sites which are heterospecific relative to each other, which means that a loxP site and a lox511 site will not recombine together but only with another recombination site of its own type. In embodiments, one or more of the polynucleotide donor molecules encoding a recombinase recognition site sequences further encode intron splicing signal sequences (both donor and acceptor signal sequences) arranged to provide a heterologous, functionally spliceable intron containing a recombinase recognition site sequence, wherein the recombinase recognition site sequence is located in between the intron splicing signal sequences; one or more such donor molecules can be used to integrate at least one functionally spliceable intron containing a recombinase recognition site sequence into an existing exon, allowing replacement of part of an exon.

Integration of recombinase recognition sites is useful in plant breeding; in an embodiment, the method is used to provide a first parent plant having recombinase recognition site sequences heterologously integrated at two separate DSBs; crossing this first parent plant to a second parent plant that expresses the corresponding recombinase results in progeny plants in which the genomic sequence flanked on either side by the heterologously integrated recognition sites is excised from (or in some cases, inverted in) the genome. This approach is useful, e. g., for deletion of relatively large regions of DNA from a genome, for example, for excising DNA encoding a selectable or screenable marker that was introduced using transgenic techniques. Examples of heterologous arrangements or integration patterns of recombinase recognition sites and methods for their use, particularly in plant breeding, are disclosed in U.S. Pat. No. 8,816,153 (see, for example, the Figures and working examples), the entire specification of which is incorporated herein by reference.

Transcription Factors: In an embodiment, the sequence encoded by the donor polynucleotide (such as a double-stranded DNA, a single-stranded DNA, a single-stranded DNA/RNA hybrid, or a double-stranded DNA/RNA hybrid) donor molecule that is integrated (or that has a sequence that is integrated) at the site of at least one double-strand break (DSB) in a genome includes a transcription factor binding sequence, the specific binding agent is the corresponding transcription factor (or more specifically, the DNA-binding domain of the corresponding transcription factor), and the change in expression is upregulation or downregulation (depending on the type of transcription factor involved). In an embodiment, the transcription factor is an activating transcription factor or activator, and the change in expression is upregulation or increased expression (e.g., increased expression of at least 10%, 15%, 20%, 25%, 30%, 35%, 40%, 50%, 60%, 70%, 80%, 90%, 95%, 100% or greater, e.g., at least a 2-fold, 5-fold, 10-fold, 20-fold, 30-fold, 40-fold, 50-fold change, 100-fold or even 1000-fold change or greater) of a sequence of interest to which the transcription factor binding sequence, when integrated at a DSB in the genome, is operably linked. In some embodiments, expression is increased between 10-100%; between 2-fold and 5-fold; between 2 and 10-fold; between 10-fold and 50-fold; between 10-fold and a 100-fold; between 100-fold and 1000-fold; between 1000-fold and 5,000-fold; between 5,000-fold and 10,000 fold. In some embodiments, a targeted insertion may decrease expression by at least 1%, 5%, 10%, 15%, 20%, 25%, 30%, 35%, 40%, 50%, 60%, 70%, 80%, 90%, 95%, 99% or more. In another embodiment, the transcription factor is a repressing transcription factor or repressor, and the change in expression is downregulation or decreased expression (e.g., decreased expression by at least 1%, 5%, 10%, 15%, 20%, 25%, 30%, 35%, 40%, 50%, 60%, 70%, 80%, 90%, 95%, 99% or more) of a sequence of interest to which the transcription factor binding sequence when integrated at a DSB in the genome, is operably linked. Embodiments of transcription factors include hormone receptors, e. g., nuclear receptors, which include both a hormone-binding domain and a DNA-binding domain; in embodiments, the polynucleotide donor molecule that is integrated (or that has a sequence that is integrated) at the site of at least one double-strand break (DSB) in a genome includes or encodes a hormone-binding domain of a nuclear receptor or a DNA-binding domain of a nuclear receptor. Various non-limiting examples of transcription factor binding sequences and transcription factors are provided in the working Examples. In embodiments, the sequence recognizable by a specific binding agent is a transcription factor binding sequence selected from those publicly disclosed at *arabidopsis*[dot]med[dot]ohio-state[dot]edu/AtcisDB/bindingsites[dot]html and neomorph[dot]salk[dot]edu/dap_web/pages/index[dot]php.

To summarize, the methods described herein permit sequences encoded by donor polynucleotides to be inserted, in a non-multiplexed or multiplexed manner, into a plant cell genome for the purpose of modulating gene expression in a number of distinct ways. Gene expression can be modulated up or down, for example, by tuning expression through the insertion of enhancer elements and transcription start sequences (e.g., nitrate response elements and auxin binding elements). Conditional transcription factor binding sites can be added or modified to allow additional control. Similarly, transcript stabilizing and/or destabilizing sequences can be inserted using the methods herein. Via the targeted insertion of stop codons, RNAi cleavage sites, or sites for recombinases, the methods described herein allow the transcription of particular sequences to be selectively turned off (likewise, the targeted removal of such sequences can be used to turn gene transcription on).

The plant genome targeting methods disclosed herein also enable transcription rates to be adjusted by the modification (optimization or de-optimization) of core promoter sequences (e.g., TATAA boxes). Proximal control elements (e.g., GC boxes; CAAT boxes) can likewise be modified. Enhancer or repressor motifs can be inserted or modified. Three-dimensional structural barriers in DNA that inhibit RNA polymerase can be created or removed via the targeted insertion of sequences, or by the modification of existing sequences. Where intron mediated enhancement is known to affect transcript rate, the relevant rate-affecting sequences can be optimized or de-optimized (by insertion of additional sequences or modification of existing sequences) to further enhance or diminish transcription. Through the insertion or modification of sequences using the targeting methods described herein (including multiplexed targeting methods), mRNA stability and processing can be modulated (thereby modulating gene expression). For example, mRNA stabilizing or destabilizing motifs can be inserted, removed or modified; mRNA splicing donor/acceptor sites can be inserted, removed or modified and, in some instance, create the possibility of increased control over alternate splicing. Similarly, miRNA binding sites can be added, removed or modified using the methods described herein. Epigenetic regulation of transcription can also be adjusted according to the methods described herein (e.g., by increasing or decreasing the degree of methylation of DNA, or the degree of methylation or acetylation of histones). Epigenetic regulation using the tools and methods described herein can be combined with other methods for modifying genetic sequences described herein, for the purpose of modifying a trait of a plant cell or plant, or for creating populations of modified cells and cells from which desired phenotypes can be selected. For example, the methods described herein can be used in combination with, e.g., donor polynucleotide sequences comprising Polycomb response elements to generate cells wherein target genes are regulated by Polycomb repressive complex 2 (PRC-2). See, e.g., Xiao, J. et al, *Nature Genetics,* 49, 1546-1552 (2017).

The plant genome targeting methods described herein can also be used to modulate translation efficiency by, e.g., modifying codon usage towards or away from a particular plant cell's bias. Similarly, through the use of the targeting methods described herein, KOZAK sequences can be optimized or deoptimized, mRNA folding and structures affecting initation of translation can be altered, and upstream reading frames can be created or destroyed. Through alteration of coding sequences using the targeted genome modification methods described herein, the abundance and/or activity of translated proteins can be adjusted. For example, the amino acid sequences in active sites or functional sites of proteins can be modified to increase or decrease the activity of the protein as desired; in addition, or alternatively, protein stabilizing or destabilizing motifs can be added or modified. All of the gene expression and activity modification schemes described herein can be utilized in various combinations to fine-tune gene expression and activity. Using the multiplexed targeting methods described herein, a plurality of specific targeted modifications can be achieved in a plant cell without intervening selection or sequencing steps.

Modified Plant Cells Comprising Specifically Targeted and Modified Genomes

Another aspect of the invention includes the cell, such as a plant cell, provided by the methods disclosed herein. In an embodiment, a plant cell thus provided includes in its genome a heterologous DNA sequence that includes: (a) nucleotide sequence of a polynucleotide (such as a double-stranded DNA, a single-stranded DNA, a single-stranded DNA/RNA hybrid, or a double-stranded DNA/RNA hybrid) molecule integrated at the site of a DSB in a genome; and (b) genomic nucleotide sequence adjacent to the site of the DSB. In embodiments, the methods disclosed herein for integrating a sequence encoded by a polynucleotide donor molecule into the site of a DSB are applied to a plant cell (e. g., a plant cell or plant protoplast isolated from a whole plant or plant part or plant tissue, or an isolated plant cell or plant protoplast in suspension or plate culture); in other embodiments, the methods are applied to non-isolated plant cells in situ or in planta, such as a plant cell located in an intact or growing plant or in a plant part or tissue. The methods disclosed herein for integrating a sequence encoded by a polynucleotide donor molecule into the site of a DSB are also useful in introducing heterologous sequence at the site of a DSB induced in the genome of other photosynthetic eukaryotes (e. g., green algae, red algae, diatoms, brown algae, and dinoflagellates). In embodiments, the plant cell or plant protoplast is capable of division and further differentiation. In embodiments, the plant cell or plant protoplast is obtained or isolated from a plant or part of a plant selected from the group consisting of a plant tissue, a whole plant, an intact nodal bud, a shoot apex or shoot apical meristem, a root apex or root apical meristem, lateral meristem, intercalary meristem, a seedling (e. g., a germinating seed or small seedling or a larger seedling with one or more true leaves), a whole seed (e. g., an intact seed, or a seed with part or all of its seed coat removed or treated to make permeable), a halved seed or other seed fragment, a zygotic or somatic embryo (e. g., a mature dissected zygotic embryo, a developing zygotic or somatic embryo, a dry or rehydrated or freshly excised zygotic embryo), pollen, microspores, epidermis, flower, and callus.

In some embodiments, the method includes the additional step of growing or regenerating a plant from a plant cell containing the heterologous DNA sequence of the polynucleotide donor molecule integrated at the site of a DSB and genomic nucleotide sequence adjacent to the site of the DSB, wherein the plant includes at least some cells that contain the heterologous DNA sequence of the polynucleotide donor molecule integrated at the site of a DSB and genomic nucleotide sequence adjacent to the site of the DSB. In embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast containing sequence encoded by a polynucleotide (such as a double-stranded DNA, a single-stranded DNA, a single-stranded DNA/RNA hybrid, or a double-stranded DNA/RNA hybrid) donor molecule heterologously integrated at the site of a DSB, as well as the seeds of such plants; embodiments include whole seedlings and plants grown or regenerated from the plant cell or plant protoplast containing sequence encoded by a polynucleotide donor molecule heterologously integrated at the site of two or more DSBs, as well as the seeds of such plants. In embodiments, the grown or regenerated plant exhibits a phenotype associated with the sequence encoded by a polynucleotide donor molecule heterologously integrated at the site of a DSB. In embodiments, the grown or regenerated plant includes in its genome two or more genetic modifications that in combination provide at least one phenotype of interest, wherein at least one of the two or more genetic modifications includes the sequence encoded by a polynucleotide donor molecule heterologously integrated at the site of a DSB in the genome, or wherein the two or more genetic modifications include sequence encoded by at least one polynucleotide donor heterologously integrated at two or more DSBs in the genome, or wherein the two or more genetic modifications include sequences encoded by multiple polynucleotides donor molecules heterologously integrated at different DSBs in the genome. In embodiments, a heterogeneous population of plant cells or plant protoplasts, at least some of which include sequence encoded by at least one polynucleotide donor molecule heterologously integrated at the site of a DSB, is provided by the method; related aspects include a plant having a phenotype of interest associated with sequence encoded by the polynucleotide donor molecule heterologously integrated at the site of a DSB, provided by either regeneration of a plant having the phenotype of interest from a plant cell or plant protoplast selected from the heterogeneous population of plant cells or plant protoplasts, or by selection of a plant having the phenotype of interest from a heterogeneous population of plants grown or regenerated from the population of plant cells or plant protoplasts. Examples of phenotypes of interest include (but are not limited to) herbicide resistance; improved tolerance of abiotic stress (e. g., tolerance of temperature extremes, drought, or salt) or biotic stress (e. g., resistance to bacterial or fungal pathogens); improved utilization of nutrients or water; synthesis of new or modified amounts of lipids, carbohydrates, proteins or other chemicals, including medicinal compounds; improved flavour or appearance; improved photosynthesis; improved storage characteristics (e. g., resistance to bruising, browning, or softening); increased yield; altered morphology (e. g., floral architecture or colour, plant height, branching, root structure); and changes in flowering time. In an embodiment, a heterogeneous population of plant cells or plant protoplasts (or seedlings or plants grown or regenerated therefrom) is exposed to conditions permitting expression of the phenotype of interest; e. g., selection for herbicide resistance can include exposing the population of plant cells or plant protoplasts (or seedlings or plants) to an amount of herbicide or other substance that inhibits growth or is toxic, allowing identification and selection of those resistant plant cells or plant protoplasts (or seedlings or plants) that survive treatment. In certain embodiments, a proxy measurement can be taken of an aspect of a modified plant or plant cell, where the measurement is indicative of a desired phenotype or trait. For example, the modification of one or more targeted sequences in a genome may provide a measurable change in a molecule (e.g., a detectable change in the structure of a molecule, or a change in the amount of the molecule that is detected, or the presence or absence of a molecule) that can be used as a biomarker for a presence of a desired phenotype or trait. The proper insertion of an enhancer for increasing expression of an enzyme, for example, may be determined by detecting lower levels of the enyzme's substrate.

In some embodiments, modified plants are produced from cells modified according to the methods described herein without a tissue culturing step. In certain embodiments, the modified plant cell or plant does not have significant losses of methylation compared to a non-modified parent plant cell or plant. For example, the modified plant lacks significant losses of methylation in one or more promoter regions relative to the parent plant cell or plant. Similarly, in certain embodiments, a modified plant or plant cell obtained using the methods described herein lacks significant losses of methylation in protein coding regions relative to the parent cell or parent plant before modification using the modification methods described herein.

Also contemplated are new heterogeneous populations, arrays, or libraries of plant cells and plants created by the introduction of targeted modifications at one more locations in the genome. Plant compositions of the invention include succeeding generations or seeds of modified plants that are grown or regenerated from plant cells or plant protoplasts modified according to the methods herein, as well as parts of those plants (including plant parts used in grafting as scions or rootstocks), or products (e. g., fruits or other edible plant parts, cleaned grains or seeds, edible oils, flours or starches, proteins, and other processed products) made from these plants or their seeds. Embodiments include plants grown or regenerated from the plant cells or plant protoplasts, wherein the plants contain cells or tissues that do not have sequence encoded by the polynucleotide donor molecule heterologously integrated at the site of a DSB, e. g., grafted plants in which the scion or rootstock contains sequence encoded by the polynucleotide donor molecule heterologously integrated at the site of a DSB, or chimeric plants in which some but not all cells or tissues contain sequence encoded by the polynucleotide donor molecule heterologously integrated at the site of a DSB. Plants in which grafting is commonly useful include many fruit trees and plants such as many citrus trees, apples, stone fruit (e. g., peaches, apricots, cherries, and plums), avocados, tomatoes, eggplant, cucumber, melons, watermelons, and grapes as well as various ornamental plants such as roses. Grafted plants can be grafts between the same or different (generally related) species. Additional related aspects include (a) a hybrid plant provided by crossing a first plant grown or regenerated from a plant cell or plant protoplast with sequence encoded by at least one polynucleotide donor molecule heterologously integrated at the site of a DSB, with a second plant, wherein the hybrid plant contains sequence encoded by the polynucleotide donor molecule heterologously integrated at the site of a DSB, and (b) a hybrid plant provided by crossing a first plant grown or regenerated from a plant cell or plant protoplast with sequence encoded by at least one polynucleotide donor molecule heterologously integrated at multiple DSB sites, with a second plant, wherein the hybrid plant contains sequence encoded by at least one polynucleotide donor molecule heterologously integrated at the site of at least one DSB; also contemplated is seed produced by the hybrid plant. Also envisioned as related aspects are progeny seed and progeny plants, including hybrid seed and hybrid plants, having the regenerated plant as a parent or ancestor. In embodiments, the plant cell (or the regenerated plant, progeny seed, and progeny plant) is diploid or polyploid. In embodiments, the plant cell (or the regenerated plant, progeny seed, and progeny plant) is haploid or can be induced to become haploid; techniques for making and using haploid plants and plant cells are known in the art, see, e. g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", a protocol publicly available at www[dot]openwetware[dot]org/images/d/d3/Haploid_*Arabidopsis*_protocol[dot]pdf; Ravi et al. (2014) *Nature Communications,* 5:5334, doi: 10.1038/ncomms6334). Examples of haploid cells include but are not limited to plant cells obtained from haploid plants and plant cells obtained from reproductive tissues, e. g., from flowers, developing flowers or flower buds, ovaries, ovules, megaspores, anthers, pollen, and microspores. In embodiments where the plant cell is haploid, the method can further include the step of chromosome doubling (e. g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell containing heterologous DNA sequence (i. e. sequence of the polynucleotide donor molecule integrated at the site of a DSB in the genome and genomic nucleotide sequence adjacent to the site of the DSB) to produce a doubled haploid plant cell or plant protoplast that is homozygous for the heterologous DNA sequence; yet other embodiments include regeneration of a doubled haploid plant from the doubled haploid plant cell or plant protoplast, wherein the regenerated doubled haploid plant is homozygous for the heterologous DNA sequence. Thus, aspects of the invention are related to the haploid plant cell or plant protoplast having the heterologous DNA sequence of the polynucleotide donor molecule integrated at the site of a DSB and genomic nucleotide sequence adjacent to the site of the DSB, as well as a doubled haploid plant cell or plant protoplast or a doubled haploid plant that is homozygous for the heterologous DNA sequence. Another aspect of the invention is related to a hybrid plant having at least one parent plant that is a doubled haploid plant provided by the method. Production of doubled haploid plants by these methods provides homozygosity in one generation, instead of requiring several generations of self-crossing to obtain homozygous plants; this may be particularly advantageous in slow-growing plants, such as fruit and other trees, or for producing hybrid plants that are offspring of at least one doubled-haploid plant.

Plants and plant cells are of any species of interest, including dicots and monocots. Plants of interest include row crop plants, fruit-producing plants and trees, vegetables, trees, and ornamental plants including ornamental flowers, shrubs, trees, groundcovers, and turf grasses. Examples of commercially important cultivated crops, trees, and plants include: alfalfa (*Medicago sativa*), almonds (*Prunus dulcis*), apples (*Malus* x *domestica*), apricots (*Prunus armeniaca, P. brigantine, P. mandshurica, P. mume, P. sibirica*), *asparagus* (*Asparagus officinalis*), bananas (Musa spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus* caryophyllus), carrots (*Daucus carota sativus*), cassava (*Manihot esculentum*), cherry (*Prunus avium*), chickpea (*Cider arietinum*), chicory (*Cichorium intybus*), chili peppers and other *capsicum* peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), *eucalyptus* (*Eucalyptus* spp.), flax (*Linum usitatissumum* L.), geraniums (*Pelargonium* spp.), grapefruit (*Citrus* x *paradisi*), grapes (*Vitus* spp.) including wine grapes (*Vitus vinfera*), guava (*Psidium guajava*), hops (*Humulus lupulus*), hemp and *cannabis* (*Cannabis sativa* and *Cannabis* spp.), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), *papaya* (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria* x *ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), and yams (*Discorea* spp.).

In another embodiment, targeted multiplex editing methods described herein are useful for modifying the genomes of asexually propagated and cloned plants. In certain embodiments, the multiplex editing is used to alter traits of recessive nature. Examples of plants which are, or often are, asexually propagated include, without limitation, apples (*Malus* x *domestica*), apricots (*Prunus armeniaca, P. brigantine, P. mandshurica, P. mume, P. sibirica*), avocado (*Persea americana*), bananas (*Musa* spp.), cherry (*Prunus avium*), grapefruit (*Citrus* x *paradisi*), grapes (*Vitus* spp.) including wine grapes (*Vitus vinfera*), irises (*Iris* spp.), lemon (*Citrus limon*), limes (*Citrus* spp.), orange (*Citrus sinensis*), peaches and nectarines (*Prunus persica*), pear (*Pyrus* spp.), pineapple (*Ananas comosus*), plantains (*Musa* spp.), plum (*Prunus domestica*), poinsettia (*Euphorbia pulcherrima*), potato (*Solanum tuberosum*), roses (*Rosa* spp.), strawberries (*Fragaria* spp., *Fragaria* x *ananassa*), sugarcanes (*Saccharum* spp.), sweet potato (*Ipomoea batatas*), tangerine (*Citrus tangerina*), tea (*Camellia sinensis*), yams (*Discorea* spp.), hops (*Humulus lupulus*), and hemp and *cannabis* (*Cannabis sativa* and *Cannabis* spp.) and many other plants and crops that form bulbs, bulbils, tubers, or corms, or which may be propagated by cuttings, root divisions, stolons, runners, or pups.

The plant cells and derivative plants and seeds disclosed herein can be used for various purposes useful to the consumer or grower. The intact plant itself may be desirable, e. g., plants grown as cover crops or as ornamentals. In other embodiments, processed products are made from the plant or its seeds, such as extracted proteins, oils, sugars, and starches, fermentation products, animal feed or human food, wood and wood products, pharmaceuticals, and various industrial products. Thus, further related aspects of the invention include a processed or commodity product made from a plant or seed or plant part that includes at least some cells that contain the heterologous DNA sequence including the sequence encoded by the polynucleotide donor molecule integrated at the site of a DSB and genomic nucleotide sequence adjacent to the site of the DSB. Commodity products include, but are not limited to, harvested leaves, roots, shoots, tubers, stems, fruits, seeds, or other parts of a plant, meals, oils (edible or inedible), fiber, extracts, fermentation or digestion products, crushed or whole grains or seeds of a plant, wood and wood pulp, or any food or non-food product. Detection of a heterologous DNA sequence that includes: (a) nucleotide sequence encoded by a polynucleotide donor molecule integrated at the site of a DSB in a genome; and (b) genomic nucleotide sequence adjacent to the site of the DSB in such a commodity product is de facto evidence that the commodity product contains or is derived from a plant cell, plant, or seed of this invention.

In another aspect, the invention provides a heterologous nucleotide sequence including: (a) nucleotide sequence encoded by a polynucleotide donor molecule integrated by the methods disclosed herein at the site of a DSB in a genome, and (b) genomic nucleotide sequence adjacent to the site of the DSB. Related aspects include a plasmid, vector, or chromosome including such a heterologous nucleotide sequence, as well as polymerase primers for amplification (e. g., PCR amplification) of such a heterologous nucleotide sequence.

Compositions and Reaction Mixtures

In one aspect, the invention provides a composition including: (a) a cell; and (b) a polynucleotide (such as a double-stranded DNA, a single-stranded DNA, a single-stranded DNA/RNA hybrid, or a double-stranded DNA/RNA hybrid) donor molecule that is capable of being integrated (or having its sequence integrated) (preferably by non-homologous end-joining (NHEJ)) at one or more double-strand breaks in a genome in the cell. In many embodiments of the composition, the cell is a plant cell, e. g., an isolated plant cell or a plant protoplast, or a plant cell in a plant, plant part, plant tissue, or callus. In certain embodiments, the cell is that of a photosynthetic eukaryote (e. g., green algae, red algae, diatoms, brown algae, and dinoflagellates).

In various embodiments of the composition, the plant cell is a plant cell or plant protoplast isolated from a whole plant or plant part or plant tissue (e. g., a plant cell or plant protoplast cultured in liquid medium or on solid medium), or a plant cell located in callus, an intact plant, seed, or seedling, or in a plant part or tissue. In embodiments, the plant cell is a cell of a monocot plant or of a dicot plant. In many embodiments, the plant cell is a plant cell capable of division and/or differentiation, including a plant cell capable of being regenerated into callus or a plant. In embodiments, the plant cell is capable of division and further differentiation, even capable of being regenerated into callus or into a plant. In embodiments, the plant cell is diploid, polyploid, or haploid (or can be induced to become haploid).

In embodiments, the composition includes a plant cell that includes at least one double-strand break (DSB) in its genome. Alternatively, the composition includes a plant cell in which at least one DSB will be induced in its genome, for example, by providing at least one DSB-inducing agent to the plant cell, e. g., either together with the polynucleotide (such as a double-stranded DNA, a single-stranded DNA, a single-stranded DNA/RNA hybrid, or a double-stranded DNA/RNA hybrid) donor molecule or separately. Thus, the composition optionally further includes at least one DSB-inducing agent. In embodiments, the composition optionally further includes at least one chemical, enzymatic, or physical delivery agent, or a combination thereof; such delivery agents and methods for their use are described in detail in the paragraphs following the heading "Delivery Methods and Delivery Agents". In embodiments, the DSB-inducing agent is at least one of the group consisting of:

(a) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, and a meganuclease or engineered meganuclease;

(b) a polynucleotide encoding one or more nucleases capable of effecting site-specific alteration (such as introduction of a DSB) of a target nucleotide sequence; and (c) a guide RNA (gRNA) for an RNA-guided nuclease, or a DNA encoding a gRNA for an RNA-guided nuclease.

In embodiments, the composition includes (a) a cell; (b) a polynucleotide (such as a double-stranded DNA, a single-stranded DNA, a single-stranded DNA/RNA hybrid, or a double-stranded DNA/RNA hybrid) donor molecule, capable of being integrated (or having its sequence integrated) at a DSB; (c) a Cas9, a Cpf1, a CasY, a CasX, a C2c1, or a C2c3 nuclease; and (d) at least one guide RNA. In an embodiment, the composition includes (a) a cell; (b) a polynucleotide (such as a double-stranded DNA, a single-stranded DNA, a single-stranded DNA/RNA hybrid, or a double-stranded DNA/RNA hybrid) donor molecule, capable of being integrated (or having its sequence integrated) at a DSB; (c) at least one ribonucleoprotein including a CRISPR nuclease and a guide RNA.

In embodiments of the composition, the polynucleotide donor molecule is double-stranded and blunt-ended, or is double-stranded and has an overhang or "sticky end" consisting of unpaired nucleotides (e. g., 1, 2, 3, 4, 5, or 6 unpaired nucleotides) at one terminus or both termini; in other embodiments, the polynucleotide donor molecule is a single-stranded DNA or a single-stranded DNA/RNA hybrid. In an embodiment, the polynucleotide donor molecule is a double-stranded DNA or DNA/RNA hybrid molecule that is blunt-ended or that has an overhang at one terminus or both termini, and that has about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the polynucleotide donor molecule is a double-stranded DNA, a single-stranded DNA, a single-stranded DNA/RNA hybrid, or a double-stranded DNA/RNA hybrid, and includes single strands of at least 11, at least 18, at least 20, at least 30, at least 40, at least 60, at least 80, at least 100, at least 120, at least 140, at least 160, at least 180, at least 200, at least 240, at least 280, or at least 320 nucleotides. In embodiments, the polynucleotide donor molecule includes chemically modified nucleotides; in embodiments, the naturally occurring phosphodiester backbone of the polynucleotide molecule is partially or completely modified with phosphorothioate, phosphorodithioate, or methylphosphonate internucleotide linkage modifications, or the polynucleotide donor molecule includes modified nucleoside bases or modified sugars, or the polynucleotide donor molecule is labelled with a fluorescent moiety or other detectable label. In an embodiment, the polynucleotide donor molecule is double-stranded and perfectly base-paired through all or most of its length, with the possible exception of any unpaired nucleotides at either terminus or both termini. In another embodiment, the polynucleotide donor molecule is double-stranded and includes one or more non-terminal mismatches or non-terminal unpaired nucleotides within the otherwise double-stranded duplex. Other related embodiments include single- or double-stranded DNA/RNA hybrid donor molecules. Additional description of the polynucleotide donor molecule is found above in the paragraphs following the heading "Polynucleotide Molecules".

In embodiments of the composition, the polynucleotide donor molecule includes:

(a) a nucleotide sequence that is recognizable by a specific binding agent;

(b) a nucleotide sequence encoding an RNA molecule or an amino acid sequence that is recognizable by a specific binding agent;

(c) a nucleotide sequence that encodes an RNA molecule or an amino acid sequence that binds specifically to a ligand;

(d) a nucleotide sequence that is responsive to a specific change in the physical environment; or (e) a nucleotide sequence encoding an RNA molecule or an amino acid sequence that is responsive to a specific change in the physical environment;

(f) a nucleotide sequence encoding at least one stop codon on each strand;

(g) a nucleotide sequence encoding at least one stop codon within each reading frame on each strand; or (h) at least partially self-complementary sequence, such that the polynucleotide molecule encodes a transcript that is capable of forming at least partially double-stranded RNA; or (i) a combination of any of (a)-(h).

Additional description relating to these various embodiments of nucleotide sequences included in the polynucleotide donor molecule is found in the section headed "Methods of changing expression of a sequence of interest in a genome".

In another aspect, the invention provides a reaction mixture including: (a) a plant cell having a double-strand break (DSB) at at least one locus in its genome; and (b) a polynucleotide (such as a double-stranded DNA, a single-stranded DNA, a single-stranded DNA/RNA hybrid, or a double-stranded DNA/RNA hybrid) donor molecule capable of being integrated or inserted (or having its sequence integrated or inserted) at the DSB (preferably by non-homologous end-joining (NHEJ)), with a length of between about 18 to about 300 base-pairs (or nucleotides, if single-stranded), or between about 30 to about 100 base-pairs (or nucleotides, if single-stranded); wherein sequence encoded by the polynucleotide donor molecule, if integrated at the DSB, forms a heterologous insertion (that is to say, resulting in a concatenated nucleotide sequence that is a combination of the sequence of the polynucleotide molecule and at least some of the genomic sequence adjacent to the site of DSB, wherein the concatenated sequence is heterologous, i. e., would not otherwise or does not normally occur at the site of insertion). In embodiments, the product of the reaction mixture includes a plant cell in which sequence encoded by the polynucleotide donor molecule has been integrated at the site of the DSB.

In many embodiments of the reaction mixture, the cell is a plant cell, e. g., an isolated plant cell or a plant protoplast, or a plant cell in a plant, plant part, plant tissue, or callus. In various embodiments of the reaction mixture, the plant cell is a plant cell or plant protoplast isolated from a whole plant or plant part or plant tissue (e. g., a plant cell or plant protoplast cultured in liquid medium or on solid medium), or a plant cell located in callus, an intact plant, seed, or seedling, or in a plant part or tissue. In embodiments, the plant cell is a cell of a monocot plant or of a dicot plant. In many embodiments, the plant cell is a plant cell capable of division and/or differentiation, including a plant cell capable of being regenerated into callus or a plant. In embodiments, the plant cell is capable of division and further differentiation, even capable of being regenerated into callus or into a plant. In embodiments, the plant cell is diploid, polyploid, or haploid (or can be induced to become haploid).

In embodiments, the reaction mixture includes a plant cell that includes at least one double-strand break (DSB) in its genome. Alternatively, the reaction mixture includes a plant cell in which at least one DSB will be induced in its genome, for example, by providing at least one DSB-inducing agent to the plant cell, e. g., either together with a polynucleotide (such as a double-stranded DNA, a single-stranded DNA, a single-stranded DNA/RNA hybrid, or a double-stranded DNA/RNA hybrid) donor molecule capable of being integrated or inserted (or having its sequence integrated or inserted) at the DSB, or separately. Thus, the reaction mixture optionally further includes at least one DSB-inducing agent. In embodiments, the reaction mixture optionally further includes at least one chemical, enzymatic, or physical delivery agent, or a combination thereof; such delivery agents and methods for their use are described in detail in the paragraphs following the heading "Delivery Methods and Delivery Agents". In embodiments, the DSB-inducing agent is at least one of the group consisting of:

(a) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, and a meganuclease or engineered meganuclease;

(b) a polynucleotide encoding one or more nucleases capable of effecting site-specific alteration (such as introduction of a DSB) of a target nucleotide sequence; and (c) a guide RNA (gRNA) for an RNA-guided nuclease, or a DNA encoding a gRNA for an RNA-guided nuclease.

In embodiments, the reaction mixture includes (a) a plant cell; (b) a polynucleotide (such as a double-stranded DNA, a single-stranded DNA, a single-stranded DNA/RNA hybrid, or a double-stranded DNA/RNA hybrid) donor molecule capable of being integrated or inserted (or having its sequence integrated or inserted) at the DSB; (c) a Cas9, a Cpf1, a CasY, a CasX, a C2c1, or a C2c3 nuclease; and (d) at least one guide RNA. In an embodiment, the reaction mixture includes (a) a plant cell or a plant protoplast; (b) a polynucleotide (such as a double-stranded DNA, a single-stranded DNA, a single-stranded DNA/RNA hybrid, or a double-stranded DNA/RNA hybrid) donor molecule capable of being integrated or inserted (or having its sequence integrated or inserted) at the DSB; (c) at least one ribonucleoprotein including a CRISPR nuclease and a guide RNA. In an embodiment, the reaction mixture includes (a) plant cell or a plant protoplast; (b) a polynucleotide (such as a double-stranded DNA, a single-stranded DNA, a single-stranded DNA/RNA hybrid, or a double-stranded DNA/RNA hybrid) donor molecule capable of being integrated or inserted (or having its sequence integrated or inserted) at the DSB; (c) at least one ribonucleoprotein including Cas9 and an sgRNA.

In embodiments of the reaction mixture, the polynucleotide (such as a double-stranded DNA, a single-stranded DNA, a single-stranded DNA/RNA hybrid, or a double-stranded DNA/RNA hybrid) donor molecule includes:

(a) a nucleotide sequence that is recognizable by a specific binding agent;

(b) a nucleotide sequence encoding an RNA molecule or an amino acid sequence that is recognizable by a specific binding agent;

(c) a nucleotide sequence that encodes an RNA molecule or an amino acid sequence that binds specifically to a ligand;

(d) a nucleotide sequence that is responsive to a specific change in the physical environment; or (e) a nucleotide sequence encoding an RNA molecule or an amino acid sequence that is responsive to a specific change in the physical environment;

(f) a nucleotide sequence encoding at least one stop codon on each strand;

(g) a nucleotide sequence encoding at least one stop codon within each reading frame on each strand; or (h) at least partially self-complementary sequence, such that the polynucleotide molecule encodes a transcript that is capable of forming at least partially double-stranded RNA; or (i) a combination of any of (a)-(h).

Additional description relating to these various embodiments of nucleotide sequences included in the polynucleotide donor molecule is found in the section headed "Methods of changing expression of a sequence of interest in a genome".

Polynucleotides for Disrupting Gene Expression

In another aspect, the invention provides a polynucleotide (such as a double-stranded DNA, a single-stranded DNA, a single-stranded DNA/RNA hybrid, or a double-stranded DNA/RNA hybrid) molecule for disrupting gene expression, including double-stranded polynucleotides containing at least 18 base-pairs and encoding at least one stop codon in each possible reading frame on each strand and single-stranded polynucleotides containing at least 11 contiguous nucleotides and encoding at least one stop codon in each possible reading frame on the strand. Such a stop-codon-containing polynucleotide, when integrated or inserted at the site of a DSB in a genome, disrupts or hinders translation of an encoded amino acid sequence. In embodiments, the polynucleotide is a double-stranded DNA or double-stranded DNA/RNA hybrid molecule including at least 18 contiguous base-pairs and encoding at least one stop codon in each possible reading frame on either strand; in embodiments, the polynucleotide is a double-stranded DNA or double-stranded DNA/RNA hybrid molecule that is blunt-ended; in other embodiments, the polynucleotide is a double-stranded DNA or double-stranded DNA/RNA hybrid molecule that has one or more overhangs or unpaired nucleotides at one or both termini. In embodiments, the polynucleotide is double-stranded and includes between about 18 to about 300 nucleotides on each strand. In embodiments, the polynucleotide is a single-stranded DNA or a single-stranded DNA/RNA hybrid molecule including at least 11 contiguous nucleotides and encoding at least one stop codon in each possible reading frame on the strand. In embodiments, the polynucleotide is single-stranded and includes between 11 and about 300 contiguous nucleotides in the strand.

In embodiments, the polynucleotide for disrupting gene expression further includes a nucleotide sequence that provides a useful function when integrated into the site of a DSB in a genome. For example, in various non-limiting embodiments the polynucleotide further includes: sequence that is recognizable by a specific binding agent or that binds to a specific molecule or encodes an RNA molecule or an amino acid sequence that binds to a specific molecule, or sequence that is responsive to a specific change in the physical environment or encodes an RNA molecule or an amino acid sequence that is responsive to a specific change in the physical environment, or heterologous sequence, or sequence that serves to stop transcription at the site of the DSB, or sequence having secondary structure (e. g., double-stranded stems or stem-loops) or than encodes a transcript having secondary structure (e. g., double-stranded RNA that is cleavable by a Dicer-type ribonuclease).

In an embodiment, the polynucleotide for disrupting gene expression is a double-stranded DNA or a double-stranded DNA/RNA hybrid molecule, wherein each strand of the polynucleotide includes at least 18 and fewer than 200 contiguous base-pairs, wherein the number of base-pairs is not divisible by 3, and wherein each strand encodes at least one stop codon in each possible reading frame in the 5' to 3' direction. In an embodiment, the polynucleotide is a double-stranded DNA or a double-stranded DNA/RNA hybrid molecule, wherein the polynucleotide includes at least one phosphorothioate modification.

Related aspects include larger polynucleotides such as a plasmid, vector, or chromosome including the polynucleotide for disrupting gene expression, as well as polymerase primers for amplification of the polynucleotide for disrupting gene expression.

Methods of Identifying the Locus of a Double-Stranded Break

In another aspect, the invention provides a method of identifying the locus of at least one double-stranded break (DSB) in genomic DNA in a cell (such as a plant cell or plant protoplast) including the genomic DNA, the method including: (a) contacting the genomic DNA having a DSB with a polynucleotide (such as a double-stranded DNA, a single-stranded DNA, a single-stranded DNA/RNA hybrid, or a double-stranded DNA/RNA hybrid) molecule, wherein the polynucleotide donor molecule is capable of being integrated (or having its sequence integrated) at the DSB and has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded); wherein sequence encoded by the polynucleotide donor molecule, if integrated at the DSB, forms a heterologous insertion; and (b) using at least part of the sequence encoded by the polynucleotide molecule as a target for PCR primers to allow amplification of DNA in the locus of the double-stranded break. In embodiments, the genomic DNA is that of a nucleus, mitochondrion, or plastid. In embodiments, the DSB locus is identified by amplification using primers specific for DNA sequence encoded by the polynucleotide molecule alone; in other embodiments, the DSB locus is identified by amplification using primers specific for a combination of DNA sequence encoded by the polynucleotide donor molecule and genomic DNA sequence flanking the DSB. Such identification using a heterologously integrated DNA sequence (i. e., that encoded by the polynucleotide molecule) is useful, e. g., to distinguish a cell (such as a plant cell or plant protoplast) containing sequence encoded by the polynucleotide molecule integrated at the DSB from a cell that does not. Identification of an edited genome from a non-edited genome is important for various purposes, e. g., for commercial or regulatory tracking of cells or biological material such as plants or seeds containing an edited genome.

In a related aspect, the invention provides a method of identifying the locus of double-stranded breaks (DSBs) in genomic DNA in a pool of cells (such as a pool of plant cells or plant protoplasts), wherein the pool of cells includes cells having genomic DNA with sequence encoded by a polynucleotide (such as a double-stranded DNA, a single-stranded DNA, a single-stranded DNA/RNA hybrid, or a double-stranded DNA/RNA hybrid) donor molecule inserted at the locus of the double-stranded breaks; wherein the polynucleotide donor molecule is capable of being integrated (or having its sequence integrated) at the DSB and has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded); wherein sequence encoded by the polynucleotide donor molecule, if integrated at the DSB, forms a heterologous insertion; wherein the sequence encoded by the polynucleotide molecule is used as a target for PCR primers to allow amplification of DNA in the region of the double-stranded breaks. In embodiments, the genomic DNA is that of a nucleus, mitochondrion, or plastid. In embodiments, the pool of cells is a population of plant cells or plant protoplasts, wherein the population of plant cells or plant protoplasts include multiple different DSBs (e. g., induced by different guide RNAs) in the genome. In embodiments, each DSB locus is identified by amplification using primers specific for DNA sequence encoded by the polynucleotide molecule alone; in other embodiments, each DSB locus is identified by amplification using primers specific for a combination of DNA sequence encoded by the polynucleotide molecule and genomic DNA sequence flanking the DSB. Such identification using a heterologously integrated DNA sequence (i. e., sequence encoded by the polynucleotide molecule) is useful, e. g., to identify a cell (such as a plant cell or plant protoplast) containing sequence encoded by the polynucleotide molecule integrated at a DSB from a cell that does not.

In embodiments, the pool of cells is a pool of isolated plant cells or plant protoplasts in liquid or suspension culture, or cultured in or on semi-solid or solid media. In embodiments, the pool of cells is a pool of plant cells or plant protoplasts encapsulated in a polymer or other encapsulating material, enclosed in a vesicle or liposome, or embedded in or attached to a matrix or other solid support (e. g., beads or microbeads, membranes, or solid surfaces). In embodiments, the pool of cells is a pool of plant cells or plant protoplasts encapsulated in a polysaccharide (e. g., pectin, agarose). In embodiments, the pool of cells is a pool of plant cells located in a plant, plant part, or plant tissue, and the cells are optionally isolated from the plant, plant part, or plant tissue in a step following the integration of a polynucleotide at a DSB.

In embodiments, the polynucleotide donor molecule that is integrated (or has sequence that is integrated) at the DSB is double-stranded and blunt-ended; in other embodiments the polynucleotide donor molecule is double-stranded and has an overhang or "sticky end" consisting of unpaired nucleotides (e. g., 1, 2, 3, 4, 5, or 6 unpaired nucleotides) at one terminus or both termini. In an embodiment, the polynucleotide donor molecule that is integrated (or has sequence that is integrated) at the DSB is a double-stranded DNA or double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the polynucleotide donor molecule includes single strands of at least 11, at least 18, at least 20, at least 30, at least 40, at least 60, at least 80, at least 100, at least 120, at least 140, at least 160, at least 180, at least 200, at least 240, at least 280, or at least 320 nucleotides. In embodiments, the polynucleotide donor molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the polynucleotide donor molecule includes chemically modified nucleotides; in embodiments, the naturally occurring phosphodiester backbone of the polynucleotide donor molecule is partially or completely modified with phosphorothioate, phosphorodithioate, or methylphosphonate internucleotide linkage modifications, or the polynucleotide donor molecule includes modified nucleoside bases or modified sugars, or the polynucleotide donor molecule is labelled with a fluorescent moiety or other detectable label. In an embodiment, the polynucleotide donor molecule is double-stranded and is perfectly base-paired through all or most of its length, with the possible exception of any unpaired nucleotides at either terminus or both termini. In another embodiment, the polynucleotide donor molecule is double-stranded and includes one or more non-terminal mismatches or non-terminal unpaired nucleotides within the otherwise double-stranded duplex. In related embodiments, the polynucleotide donor molecule that is integrated at the DSB is a single-stranded DNA or a single-stranded DNA/RNA hybrid. Additional description of the polynucleotide donor molecule is found above in the paragraphs following the heading "Polynucleotide Molecules".

In embodiments, the polynucleotide (such as a double-stranded DNA, a single-stranded DNA, a single-stranded DNA/RNA hybrid, or a double-stranded DNA/RNA hybrid) donor molecule that is integrated at the DSB includes a nucleotide sequence that, if integrated (or has sequence that is integrated) at the DSB, forms a heterologous insertion that is not normally found in the genome. In embodiments, sequence encoded by the polynucleotide molecule that is integrated at the DSB includes a nucleotide sequence that does not normally occur in the genome containing the DSB; this can be established by sequencing of the genome, or by hybridization experiments. In certain embodiments, sequence encoded by the polynucleotide molecule, when integrated at the DSB, not only permits identification of the locus of the DSB, but also imparts a functional trait to the cell including the genomic DNA, or to an organism including the cell; in non-limiting examples, sequence encoded by the polynucleotide molecule that is integrated at the DSB includes at least one of the nucleotide sequences selected from the group consisting of:

(a) DNA encoding at least one stop codon, or at least one stop codon on each strand, or at least one stop codon within each reading frame on each strand;
(b) DNA encoding heterologous primer sequence (e. g., a sequence of about 18 to about 22 contiguous nucleotides, or of at least 18, at least 20, or at least 22 contiguous nucleotides that can be used to initiate DNA polymerase activity at the site of the DSB);
(c) DNA encoding a unique identifier sequence (e. g., a sequence that when inserted at the DSB creates a heterologous sequence that can be used to identify the presence of the insertion);
(d) DNA encoding a transcript-stabilizing sequence;
(e) DNA encoding a transcript-destabilizing sequence;
(f) a DNA aptamer or DNA encoding an RNA aptamer or amino acid aptamer; and
(g) DNA that includes or encodes a sequence recognizable by a specific binding agent.

Methods of Identifying the Nucleotide Sequence of a Locus in the Genome that is Associated with a Phenotype In another aspect, the invention provides a method of identifying the nucleotide sequence of a locus in the genome that is associated with a phenotype, the method including the steps of:

(a) providing to a population of cells (such as plant cells or plant protoplasts) having the genome:
  (i) multiple different guide RNAs (gRNAs) to induce multiple different double strand breaks (DSBs) in the genome, wherein each DSB is produced by an RNA-guided nuclease guided to a locus on the genome by one of the gRNAs, and
  (ii) polynucleotide (such as a double-stranded DNA, a single-stranded DNA, a single-stranded DNA/RNA hybrid, or a double-stranded DNA/RNA hybrid) donor molecules having a defined nucleotide sequence, wherein the polynucleotide molecules are capable of being integrated (or have sequence that is integrated) into the DSBs by non-homologous end-joining (NHEJ);

whereby when sequence encoded by at least some of the polynucleotide molecules are inserted into at least some of the DSBs, a genetically heterogeneous population of cells is produced;
(b) selecting from the genetically heterogeneous population of cells a subset of cells that exhibit a phenotype of interest;
(c) using a pool of PCR primers that bind to sequence encoded by the polynucleotide molecules to amplify from the subset of cells DNA from the locus of a DSB into which sequence encoded by one of the polynucleotide molecules has been inserted; and
(d) sequencing the amplified DNA to identify the locus associated with the phenotype of interest.

In embodiments, the cells are plant cells or plant protoplasts or algal cells. In embodiments, the genetically heterogeneous population of cells undergoes one or more doubling cycles; for example, the population of cells is provided with growth conditions that should normally result in cell division, and at least some of the cells undergo one or more doublings. In embodiments, the genetically heterogeneous population of cells is subjected to conditions permitting expression of the phenotype of interest. In embodiments, the cells are provided in a single pool or population (e. g., in a single container); in other embodiments, the cells are provided in an arrayed format (e. g., in microwell plates or in droplets in a microfluidics device or attached individually to particles or beads).

In embodiments, the RNA-guided nuclease or a polynucleotide that encodes the RNA-guided nuclease is exogenously provided to the population of cells. In embodiments, each gRNA is provided as a polynucleotide composition including: (a) a CRISPR RNA (crRNA) that includes the gRNA, or a polynucleotide that encodes a crRNA, or a polynucleotide that is processed into a crRNA; or (b) a single guide RNA (sgRNA) that includes the gRNA, or a polynucleotide that encodes a sgRNA, or a polynucleotide that is processed into a sgRNA In embodiments, the multiple guide RNAs are provided as ribonucleoproteins (e. g., Cas9 nuclease molecules complexed with different gRNAs to form different RNPs). In embodiments, each gRNA is provided as a ribonucleoprotein (RNP) including the RNA-guided nuclease and an sgRNA. In embodiments, multiple guide RNAs are provided, as well as a single polynucleotide donor molecule having a sequence to be integrated at the resulting DSBs; in other embodiments, multiple guide RNAs are provided, as well as different polynucleotide donor molecules having a sequence to be integrated at the resulting multiple DSBs.

In another embodiment, a detection method is provided for identifying a plant as having been subjected to genomic modification according to a targeted modification method described herein, where that modification method yields a low frequency of off-target mutations. The detection method comprises a step of identifying the off-target mutations (e.g., an insertion of a non-specific sequence, a deletion, or an indel resulting from the use of the targetting agents, or insertions of part or all of a sequence encoded by one or more polynucleotide donor molecules at one or more coding or non-coding loci in a genome). In a related embodiment, the detection method is used to track of movement of a plant cell or plant or product thereof through a supply chain. The presence of such an identified mutation in a processed product or commodity product is de facto evidence that the product contains or is derived from a plant cell, plant, or seed of this invention. In related embodiments, the presence of the off-target mutations are identified using PCR, a chip-based assay, probes specific for the donor sequences, or any other technique known in the art to be useful for detecting the presence of particular nucleic acid sequences.

The foregoing description and the examples presented in this disclosure describe the subject matter of this invention, including the embodiments set forth in this paragraph as follows: (Embodiment 1) a method of modifying a plant cell by creating a plurality of targeted modifications in the genome of the plant cell, comprising: contacting the genome with one or more targeting agents, wherein the one or more agents comprise or encode predetermined peptide or nucleic acid sequences, wherein the predetermined peptide or nucleic acid sequences bind preferentially at or near predetermined target sites within the plant genome, and wherein the binding facilitates the generation of the plurality of targeted modifications within the genome; wherein the plurality of targeted modifications occurs without an intervening step of separately identifying an individual modification and without a step of separately selecting for the occurrence of an individual modification among the plurality of targeted modifications mediated by the targeting agents; and wherein the targeted modifications alter at least one trait of the plant cell, or at least one trait of a plant comprising the plant cell, or at least one trait of a plant grown from the plant cell, or result in a detectable phenotype in the modified plant cell; and wherein at least two of the targeted modifications are insertions of predetermined sequences encoded by one or more polynucleotide donor molecules, and wherein at least one of the polynucleotide donor molecules lacks homology to the genome sequences adjacent to the site of insertion; (Embodiment 2) the method of embodiment (1), wherein at least one of the polynucleotide donor molecules is a single stranded DNA molecule, a single stranded RNA molecule, a single stranded DNA-RNA hybrid molecule, or a duplex RNA-DNA molecule; (Embodiment 3) the method of embodiment (1) or (2), wherein the modified plant cell is a meristematic cell, embryonic cell, or germline cell; (Embodiment 4) the method of any of embodiments (1), (2) or (3), wherein repetition of the method results in an efficiency of at least 1%, wherein said efficiency is determined by dividing the number of successfully targeted cells by the total number of cells targeted; (Embodiment 5) a method of modifying a plant cell by creating a plurality of targeted modifications in the genome of the plant cell, comprising: contacting the genome with one or more targeting agents, wherein the one or more agents comprise or encode predetermined peptide or nucleic acid sequences, wherein the predetermined peptide or nucleic acid sequences bind preferentially at or near predetermined target sites within the plant genome, and wherein the binding facilitates the generation of the plurality of targeted modifications within the genome; wherein the plurality of targeted modifications occurs without an intervening step of separately identifying an individual modification and without a step of separately selecting for the occurrence of an individual modification among the plurality of targeted modifications mediated by the targeting agents; wherein the targeted modifications improve at least one trait of the plant cell, or at least one trait of a plant comprising the plant cell, or at least one trait of a plant grown from the plant cell, or result in a detectable phenotype in the modified plant cell; and wherein at least one of the targeted modifications is an insertion of a predetermined sequence encoded by one or more polynucleotide donor molecules, and wherein at least one of the polynucleotide donor molecules is a single stranded DNA molecule, a single stranded RNA molecule, a single stranded DNA-RNA hybrid molecule, or a duplex RNA-DNA molecule; (Embodiment 6) the method of embodiment (5), wherein at least one of the polynucleotide donor molecules lacks homology to the genome sequences adjacent to the site of insertion; (Embodiment 7) the method of embodiments (5) or (6), wherein the modified plant cell is a meristematic cell, embryonic cell, or germline cell; (Embodiment 8) the method of any of embodiments (5), (6) or (7), wherein repetition of the method results in an efficiency of at least 1%, wherein said efficiency is determined by dividing the number of successfully targeted cells by the total number of cells targeted; (Embodiment 9) a method of modifying a plant cell by creating a plurality of targeted modifications in the genome of the plant cell, comprising: contacting the genome with one or more targeting agents, wherein the one or more agents comprise or encode predetermined peptide or nucleic acid sequences, wherein the predetermined peptide or nucleic acid sequences bind preferentially at or near predetermined target sites within the plant genome, and wherein the binding facilitates the generation of the plurality of targeted modifications within the genome; wherein the plurality of modifications occurs without an intervening step of separately identifying an individual modification and without a step of separately selecting for the occurrence of an individual modification among the plurality of targeted modifications mediated by the targeting agents; and wherein the targeted modifications improve at least one trait of the plant cell, or at least one trait of a plant comprising the plant cell, or at least one trait of a plant or seed obtained from the plant cell, or result in a detectable phenotype in the modified plant cell; and wherein the modified plant cell is a meristematic cell, embryonic cell, or germline cell; (Embodiment 10) the method of embodiment (9), wherein at least one of the targeted modifications is an insertion of a predetermined sequence encoded by one or more polynucleotide donor molecules, and wherein at least one of the polynucleotide donor molecules is a single stranded DNA molecule, a single stranded RNA molecule, a single stranded DNA-RNA hybrid molecule, or a duplex RNA-DNA molecule; (Embodiment 11) the method of embodiment (9) or (10), wherein at least one of the polynucleotide donor molecules lacks homology to the genome sequences adjacent to the site of insertion; (Embodiment 12) the method of any of embodiments (9), (10) or (11), wherein repetition of the method results in an efficiency of at least 1%, wherein said efficiency is determined by dividing the number of successfully targeted cells by the total number of cells targeted; (Embodiment 13) a method of modifying a plant cell by creating a plurality of targeted modifications in the genome of the plant cell, comprising: contacting the genome with one or more targeting agents, wherein the one or more agents comprise or encode predetermined peptide or nucleic acid sequences, wherein the predetermined peptide or nucleic acid sequences bind preferentially at or near predetermined target sites within the plant genome, and wherein the binding facilitates the generation of the plurality of targeted modifications within the genome; wherein the plurality of modifications occurs without an intervening step of separately identifying an individual modification and without a step of separately selecting for the occurrence of an individual modification among the plurality of targeted modifications mediated by the targeting agents; and wherein the targeted modifications improve at least one trait of the plant cell, or at least one trait of a plant comprising the plant cell, or at least one trait of a plant or seed obtained from the plant cell, or result in a detectable phenotype in the modified plant cell; and wherein repetition of the aforementioned steps results in an efficiency of at least 1%, wherein said efficiency is determined by dividing the number of successfully targeted cells by the total number of cells targeted; (Embodiment 14) the method of embodiment (13), wherein the modified plant cell is a meristematic cell, embryonic cell, or germline cell; (Embodiment 15) the method of embodiment (13) or (14), wherein at least one of the targeted modifications is an insertion of a predetermined sequence encoded by one or more polynucleotide donor molecules, and wherein at least one of the polynucleotide donor molecules is a single stranded DNA molecule, a single stranded RNA molecule, a single stranded DNA-RNA hybrid molecule, or a duplex RNA-DNA molecule; (Embodiment 16) the method of any of embodiments (13), (14), or (15), wherein at least one of the polynucleotide donor molecules lacks homology to the genome sequences adjacent to the site of insertion; (Embodiment 17) the method of any of embodiments (1)-(16), wherein at least one of the targeted modifications is an insertion between 3 and 400 nucleotides in length, between 10 and 350 nucleotides in length, between 18 and 350 nucleotides in length, between 18 and 200 nucleotides in length, between 10 and 150 nucleotides in length, or between 11 and 100 nucleotides in length; (Embodiment 18) the method of embodiment (17), wherein two of the targeted modifications are insertions between 10 and 350 nucleotides in length, between 18 and 350 nucleotides in length, between 18 and 200 nucleotides in length, between 10 and 150 nucleotides in length, or between 11 and 100 nucleotides in length; (Embodiment 19) the method of any of embodiments (1)-(18), comprising at least two insertions, wherein at least one of the insertions is an upregulatory sequence; (Embodiment 20) the method of any of embodiments (1)-(18), comprising the insertion or creation of at least one transcription factor binding site; (Embodiment 21) the method of any of embodiments (1)-(20), comprising the insertion or insertions of predetermined sequences, wherein the insertion or insertions of predetermined sequences are accompanied by the deletion of sequences from the plant genome; (Embodiment 22) the method of any of embodiments (1)-(21) further comprising obtaining a plant from the modified plant cell and breeding the plant; (Embodiment 23) the method of any of embodiments (1)-(21), further comprising a step of introducing additional genetic or epigenetic changes into the modified plant cell or into a plant grown from the modified plant cell; (Embodiment 24) the method of any of embodiments (1)-(23), comprising introducing at least two targeted insertions, wherein at least two of the targeted insertions independently up- or down-regulate the expression of two or more distinct genes; (Embodiment 25) the method of any of embodiments (1)-(24), wherein the donor polynucleotide is tethered to a crRNA by a covalent bond, a non-covalent bond, or a combination of covalent and non-covalent bonds; (Embodiment 26) the method of any of embodiments (1)-(25), wherein a loss of epigenetic marks after modifying occurs in less than 0.01% of the genome; (Embodiment 27) the method of any of embodiments (1)-(25), wherein the genome of the modified plant cell is more than 99.9% identical to the genome of the parent cell; (Embodiment 28) the method of any of embodiments (1)-(27), wherein at least one of the targeted modifications is an insertion, and wherein at least one insertion is in a region of the genome that is recalcitrant to meiotic or mitotic recombination; (Embodiment 29) the method of any of embodiments (1)-(28), wherein the cell is a member of a pool of cells being targeted, and wherein the modified cells within the pool are characterized by sequencing after targeting; (Embodiment 30) the method of any of embodiments (1)-(29), wherein at least one DSB is introduced into the genome by at least one of the group consisting of: (a) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, a meganuclease, an engineered meganuclease, a recombinase, integrase, and a transposase; (b) a polynucleotide encoding one or more nucleases capable of effecting site-specific alteration of a target nucleotide sequence; and (c) a guide RNA (gRNA) for an RNA-guided nuclease, and a DNA encoding a gRNA for an RNA-guided nuclease; (Embodiment 31) The method of any of embodiments (1)-(29), wherein at least one DSB is introduced into the genome by at least one at least one treatment selected from the group consisting of: (a) bacterially mediated (e. g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection; (b) Biolistics or particle bombardment; (c) treatment with at least one chemical, enzymatic, or physical agent; and (d) application of heat or cold, ultrasonication, centrifugation, positive or negative pressure, cell wall or membrane disruption or deformation, or electroporation; (Embodiment 32) the method of any of embodiments (1)-(31), wherein at least one DSB is introduced in the genome: (a) within a sequence of interest, (b) upstream of a sequence of interest, or (c) downstream of a sequence of interest; (Embodiment 33) the method of embodiment (32), wherein a polynucleotide molecule, when integrated into the genome, is functionally or operably linked to the sequence of interest; (Embodiment 34) the method of embodiment (33), wherein the sequence of interest comprises coding sequence, non-coding sequence, or a combination of coding and non-coding sequence; (Embodiment 35) the method of embodiment (32), wherein the at least one DSB is two or more DSBs; (Embodiment 36) the method of embodiment (35), wherein the polynucleotide molecule that is integrated into each of the two or more DSBs is (a) identical, or (b) different, for each of the DSBs; (Embodiment 37) the method of embodiment (33), wherein the polynucleotide molecule comprises at least one of the nucleotide sequences selected from the group consisting of: (a) DNA or RNA encoding at least one stop codon, or at least one stop codon on each strand, or at least one stop codon within each reading frame on each strand; (b) DNA or RNA encoding heterologous primer sequence; (c) DNA or RNA encoding a unique identifier sequence; (d) DNA or RNA encoding a transcript-stabilizing sequence; (e) DNA or RNA encoding a transcript-destabilizing sequence; (f) a DNA or RNA aptamer, or DNA encoding an RNA aptamer, or DNA or RNA encoding an amino acid aptamer; and (g) DNA or RNA encoding a sequence recognizable by a specific binding agent; (Embodiment 38) the method of embodiment (33) wherein the polynucleotide molecule comprises DNA or RNA encoding a sequence recognizable by a specific binding agent, and wherein contacting the integrated polynucleotide molecule with the specific binding agent results in a change of expression of the sequence of interest; (Embodiment 39) the method of embodiment (38) wherein: (a) the sequence recognizable by a specific binding agent comprises an auxin response element sequence, the specific binding agent is an auxin, and the change of expression is upregulation; (b) the sequence recognizable by a specific binding agent comprises at least one D1-4 sequence, the specific binding agent is an auxin, and the change of expression is upregulation; (c) the sequence recognizable by a specific binding agent comprises at least one DR5 sequence, the specific binding agent is an auxin, and the change of expression is upregulation; (d) the sequence recognizable by a specific binding agent comprises at least one m5-DR5 sequence, the specific binding agent is an auxin, and the change of expression is upregulation; (e) the sequence recognizable by a specific binding agent comprises at least one P3 sequence, the specific binding agent is an auxin, and the change of expression is upregulation; (f) the sequence recognizable by a specific binding agent comprises a small RNA recognition site sequence, the specific binding agent is the corresponding small RNA, and the change of expression is downregulation; (g) the sequence recognizable by a specific binding agent comprises a microRNA (miRNA) recognition site sequence, the specific binding agent is the corresponding mature miRNA, and the change of expression is downregulation; (h) the sequence recognizable by a specific binding agent comprises a microRNA (miRNA) recognition site sequence for an engineered miRNA, the specific binding agent is the corresponding engineered mature miRNA, and the change of expression is downregulation; (i) the sequence recognizable by a specific binding agent comprises a transposon recognition sequence, the specific binding agent is the corresponding transposon, and the change of expression is upregulation or downregulation; (j) the sequence recognizable by a specific binding agent comprises an ethylene-responsive element binding-factor-associated amphiphilic repression (EAR)

motif sequence, the specific binding agent is ERF (ethylene-responsive element binding factor) or co-repressor, and the change of expression is downregulation; (k) the sequence recognizable by a specific binding agent comprises a splice site sequence, the specific binding agent is a spliceosome, and the change of expression is expression of a spliced transcript; (l) the sequence recognizable by a specific binding agent comprises a site-specific recombinase recognition site sequence, the specific binding agent is the corresponding site-specific recombinase, and the change of expression is upregulation or downregulation or expression of a transcript having an altered sequence; (m) the sequence recognizable by a specific binding agent comprises sequence encoding an RNA aptamer or an RNA riboswitch, the specific binding agent is the corresponding ligand, and the change in expression is upregulation or downregulation; (n) the sequence recognizable by a specific binding agent is a hormone responsive element, the specific binding agent is a hormone, and the change in expression is upregulation or downregulation; or (o) the sequence recognizable by a specific binding agent is a transcription factor binding sequence, the specific binding agent is the corresponding transcription factor, and the change in expression is upregulation or downregulation; (Embodiment 40) the method of embodiment (38) wherein the polynucleotide molecule comprises a nucleotide sequence that encodes an RNA molecule or an amino acid sequence that is recognizable by a specific binding agent; (Embodiment 41) the method of embodiment (38), wherein the polynucleotide molecule comprises a nucleotide sequence that encodes an RNA molecule or an amino acid sequence that binds specifically to a ligand; (Embodiment 42) the method of embodiment (37), wherein the polynucleotide molecule encodes at least one stop codon on each strand; (Embodiment 43) the method of embodiment (37), wherein the polynucleotide molecule encodes at least one stop codon within each reading frame on each strand; (Embodiment 44) the method of embodiment (37), wherein the polynucleotide molecule comprises at least partially self-complementary sequence, such that the polynucleotide molecule encodes a transcript that is capable of forming at least partially double-stranded RNA; (Embodiment 45) the method of embodiment (37) wherein the polynucleotide molecule comprises a nucleotide sequence that is responsive to a specific change in the physical environment, and wherein exposing the integrated polynucleotide molecule to the specific change in the physical environment results in a change of expression of the sequence of interest; (Embodiment 46) the method of embodiment (45), wherein the specific change in the physical environment is at least one of: a change in light intensity or quality, a change in temperature, a change in pressure, a change in osmotic concentration, or a change in day length; (Embodiment 47) the method of embodiment (37), wherein the polynucleotide molecule comprises a nucleotide sequence encoding an RNA molecule or an amino acid sequence that is responsive to a specific change in the physical environment; (Embodiment 48) the method of embodiment (47), wherein the polynucleotide molecule encodes a Light-Oxygen-Voltage domain; (Embodiment 49) the method of embodiment (30), wherein each gRNA is provided as a polynucleotide composition comprising: (a) a CRISPR RNA (crRNA) that comprises the gRNA, or a polynucleotide that encodes a crRNA, or a polynucleotide that is processed into a crRNA; or (b) a single guide RNA (sgRNA) that comprises the gRNA, or a polynucleotide that encodes a sgRNA, or a polynucleotide that is processed into a sgRNA; (Embodiment 50) the method of embodiment (49), wherein each gRNA is provided as a ribonucleoprotein (RNP) comprising the RNA-guided nuclease and an sgRNA; (Embodiment 51) the method of embodiment (32), wherein: (a) the at least one DSB is two blunt-ended DSBs, resulting in deletion of genomic sequence between the two blunt-ended DSBs, and wherein the polynucleotide molecule is selected from the group consisting of a blunt-ended double-stranded DNA, a single-stranded DNA, a single-stranded DNA/RNA hybrid, and a blunt-ended double-stranded DNA/RNA hybrid and is integrated into the genome between the two blunt-ended DSBs; (b) the at least one DSB is two DSBs, wherein the first DSB is blunt-ended and the second DSB has an overhang, resulting in deletion of genomic sequence between the two DSBs, and wherein the polynucleotide molecule is a double-stranded DNA or double-stranded DNA/RNA hybrid that is blunt-ended at one terminus and has an overhang on the other terminus, or is a single-stranded DNA or a single-stranded DNA/RNA hybrid, and is integrated into the genome between the two DSBs; (c) the at least one DSB is two DSBs, each having an overhang, resulting in deletion of genomic sequence between the two DSBs, and wherein the polynucleotide molecule is a double-stranded DNA or double-stranded DNA/RNA hybrid that has an overhang at each terminus or is a single-stranded DNA or a single-stranded DNA/RNA hybrid, and is integrated into the genome between the two DSBs; (Embodiment 52) an modified plant cell resulting from the method of any embodiments (1)-(51); (Embodiment 53) an modified plant grown from an modified plant cell of embodiment (52); (Embodiment 54) the modified plant cell of embodiment (52), wherein the modified plant cell comprises at least two precise and separately targeted insertions in its genome, wherein the insertions are determined relative to a parent plant cell, and wherein the modified plant cell is devoid of mitotically or meiotically generated genetic or epigenetic changes relative to the parent plant cell; (Embodiment 55) an modified plant cell, wherein the modified plant cell comprises at least two precise and separately targeted insertions in its genome, wherein the insertions are determined relative to a parent plant cell, and wherein the modified plant cell is devoid of mitotically or meiotically generated genetic or epigenetic changes relative to the parent plant cell; (Embodiment 56) a method of manufacturing a processed plant product, comprising: (a) modifying a plant cell according to the method of any one of the preceding embodiments, (b) growing an modified plant from said plant cell, and (c) processing the modified plant into a processed product, thereby manufacturing a processed plant product; (Embodiment 57) the method of embodiment (56), wherein the processed product is meal, oil, juice, sugar, starch, fiber, an extract, wood or wood pulp, flour, or cloth; (Embodiment 58) the method of embodiment (56) or (57), further comprising packaging said product; (Embodiment 59) a method of manufacturing a plant product, comprising: (a) modifying a plant cell according to the method of any one of embodiments 1-51, (b) growing an modified plant from said plant cell, (c) harvesting a product of the modified plant, thereby manufacturing a plant product; (Embodiment 60) the method of embodiment (59), wherein the plant product is a product selected from the group consisting of leaves, fruit, vegetables, nuts, seeds, oil, wood, flowers, cones, branches, hay, fodder, silage, stover, straw and pollen; (Embodiment 61) the method of embodiment (59) or (60), further comprising packaging said plant product; (Embodiment 62) an isolated donor polynucleotide, gRNA or crRNA selected from the polynucleotides described in the Examples herein; (Embodiment 63) the method of any of embodiments (1)-(51) comprising the use of a donor polynucleotide, gRNA or crRNA described in the Examples herein; (Embodiment 64) a method of changing expression of a sequence of interest in a genome, comprising integrating a sequence encoded by a polynucleotide donor molecule at the site of at least one double-strand break (DSB) in a genome, wherein the polynucleotide donor molecule is selected from the group consisting of a double-stranded DNA, a single-stranded DNA, a single-stranded DNA/RNA hybrid, and a double-stranded DNA/RNA hybrid; (Embodiment 65) the method of embodiment (64), wherein the genome is that of a plant; (Embodiment 66) the method of embodiment (65), wherein the genome is that of a nucleus, mitochondrion, or plastid in a plant cell; (Embodiment 67) the method of embodiment (64), wherein the at least one DSB is introduced into the genome by at least one of the group consisting of: (a) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, and a meganuclease or engineered meganuclease; (b) a polynucleotide encoding one or more nucleases capable of effecting site-specific alteration of a target nucleotide sequence; and (c) a guide RNA (gRNA) for an RNA-guided nuclease, or a DNA encoding a gRNA for an RNA-guided nuclease; (Embodiment 68) the method of embodiment (64), wherein the at least one DSB is introduced into the genome by at least one treatment selected from the group consisting of: (a) bacterially mediated (e. g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection; (b) Biolistics or particle bombardment; (c) treatment with at least one chemical, enzymatic, or physical agent; and (d) application of heat or cold, ultrasonication, centrifugation, positive or negative pressure, cell wall or membrane disruption or deformation, or electroporation; (Embodiment 69) the method of embodiment (64), wherein the at least one DSB in a genome is located: (a) within the sequence of interest, (b) upstream of the sequence of interest, or (c) downstream of the sequence of interest; (Embodiment 70) the method of embodiment (64), wherein the sequence encoded by the polynucleotide donor molecule, when integrated into the genome, is functionally or operably linked to the sequence of interest; (Embodiment 71) the method of embodiment (64), wherein the sequence of interest comprises coding sequence, non-coding sequence, or a combination of coding and non-coding sequence; (Embodiment 72) the method of embodiment (64), wherein the at least one DSB is two or more DSBs; (Embodiment 73) the method of embodiment (72), wherein the sequence encoded by the polynucleotide donor molecule that is integrated into each of the two or more DSBs is (a) identical, or (b) different, for each of the DSBs; (Embodiment 74) the method of embodiment (64), wherein the sequence encoded by the polynucleotide donor molecule comprises at least one of the nucleotide sequences selected from the group consisting of: (a) DNA or RNA encoding at least one stop codon, or at least one stop codon on each strand, or at least one stop codon within each reading frame on each strand; (b) DNA or RNA encoding heterologous primer sequence; (c) DNA or RNA encoding a unique identifier sequence; (d) DNA or RNA encoding a transcript-stabilizing sequence; (e) DNA or RNA encoding a transcript-destabilizing sequence; (f) a DNA or RNA aptamer, or DNA encoding an RNA aptamer, or DNA or RNA encoding an amino acid aptamer; and (g) DNA or RNA encoding a sequence recognizable by a specific binding agent; (Embodiment 75) the method of embodiment (64), wherein the sequence encoded by the polynucleotide donor molecule comprises DNA or RNA encoding a sequence recognizable by a specific binding agent, and wherein contacting the integrated sequence encoded by the polynucleotide donor molecule with the specific binding agent results in a change of expression of the sequence of interest; (Embodiment 76) the method of embodiment (75), wherein: (a) the sequence recognizable by a specific binding agent comprises an auxin response element sequence, the specific binding agent is an auxin, and the change of expression is upregulation; (b) the sequence recognizable by a specific binding agent comprises at least one D1-4 sequence, the specific binding agent is an auxin, and the change of expression is upregulation; (c) the sequence recognizable by a specific binding agent comprises at least one DR5 sequence, the specific binding agent is an auxin, and the change of expression is upregulation; (d) the sequence recognizable by a specific binding agent comprises at least one m5-DR5 sequence, the specific binding agent is an auxin, and the change of expression is upregulation; (e) the sequence recognizable by a specific binding agent comprises at least one P3 sequence, the specific binding agent is an auxin, and the change of expression is upregulation; (f) the sequence recognizable by a specific binding agent comprises a small RNA recognition site sequence, the specific binding agent is the corresponding small RNA, and the change of expression is downregulation; (g) the sequence recognizable by a specific binding agent comprises a microRNA (miRNA) recognition site sequence, the specific binding agent is the corresponding mature miRNA, and the change of expression is downregulation; (h) the sequence recognizable by a specific binding agent comprises a microRNA (miRNA) recognition site sequence for an engineered miRNA, the specific binding agent is the corresponding engineered mature miRNA, and the change of expression is downregulation; (i) the sequence recognizable by a specific binding agent comprises a transposon recognition sequence, the specific binding agent is the corresponding transposon, and the change of expression is upregulation or downregulation; (j) the sequence recognizable by a specific binding agent comprises an ethylene-responsive element binding-factor-associated amphiphilic repression (EAR) motif sequence, the specific binding agent is ERF (ethylene-responsive element binding factor) or co-repressor, and the change of expression is downregulation; (k) the sequence recognizable by a specific binding agent comprises a splice site sequence, the specific binding agent is a spliceosome, and the change of expression is expression of a spliced transcript; (l) the sequence recognizable by a specific binding agent comprises a site-specific recombinase recognition site sequence, the specific binding agent is the corresponding site-specific recombinase, and the change of expression is upregulation or downregulation or expression of a transcript having an altered sequence; (m) the sequence recognizable by a specific binding agent comprises sequence encoding an RNA aptamer or an RNA riboswitch, the specific binding agent is the corresponding ligand, and the change in expression is upregulation or downregulation; (n) the sequence recognizable by a specific binding agent is a hormone responsive element, the specific binding agent is a hormone, and the change in expression is upregulation or downregulation; or (o) the sequence recognizable by a specific binding agent is a transcription factor binding sequence, the specific binding agent is the corresponding transcription factor, and the change in expression is upregulation or downregulation; (Embodiment 77) the method of embodiment (75), wherein the sequence encoded by the polynucleotide donor molecule comprises a nucleotide sequence that encodes an RNA molecule or an amino acid sequence that is recognizable by a specific binding agent; (Embodiment 78) the method of embodiment (75), wherein the sequence encoded by the polynucleotide donor molecule comprises a nucleotide sequence that encodes an RNA molecule or an amino acid sequence that binds specifically to a ligand; (Embodiment 79) the method of embodiment (64), wherein the polynucleotide donor molecule encodes at least one stop codon on each strand; (Embodiment 80) the method of embodiment (64), wherein the polynucleotide donor molecule encodes at least one stop codon within each reading frame on each strand; (Embodiment 81) the method of embodiment (64), wherein the polynucleotide donor molecule comprises at least partially self-complementary sequence, such that the polynucleotide donor molecule encodes a transcript that is capable of forming at least partially double-stranded RNA; (Embodiment 82) the method of embodiment (64), wherein the polynucleotide donor molecule comprises a nucleotide sequence that is responsive to a specific change in the physical environment, and wherein exposing the integrated sequence encoded by the polynucleotide donor molecule to the specific change in the physical environment results in a change of expression of the sequence of interest; (Embodiment 83) the method of embodiment (82), wherein the specific change in the physical environment is at least one of: a change in light intensity or quality, a change in temperature, a change in pressure, a change in osmotic concentration, or a change in day length; (Embodiment 84) the method of embodiment (64), wherein the sequence encoded by the polynucleotide donor molecule comprises a nucleotide sequence encoding an RNA molecule or an amino acid sequence that is responsive to a specific change in the physical environment; (Embodiment 85) the method of embodiment (84), wherein the sequence encoded by the polynucleotide donor molecule encodes a Light-Oxygen-Voltage domain; (Embodiment 86) a plant cell comprising in its genome a heterologous DNA sequence that comprises: (a) nucleotide sequence of a polynucleotide donor molecule integrated by the method of embodiment (64) at the site of a DSB in a genome; and (b) genomic nucleotide sequence adjacent to the site of the DSB; (Embodiment 87) a plant comprising the plant cell of embodiment (86); (Embodiment 88) a processed or commodity product of the plant of embodiment (87); (Embodiment 89) a heterologous nucleotide sequence comprising: (a) nucleotide sequence of a polynucleotide donor molecule integrated by the method of embodiment (64) at the site of a DSB in a genome, and (b) genomic nucleotide sequence adjacent to the site of the DSB; (Embodiment 90) a plasmid, vector, or chromosome comprising the heterologous nucleotide sequence of embodiment (89); (Embodiment 91) a polymerase primer for amplification of the heterologous nucleotide sequence of embodiment (89); (Embodiment 92) a composition comprising: (a) a plant cell; and (b) a polynucleotide donor molecule, wherein the polynucleotide donor molecule is selected from the group consisting of a double-stranded DNA, a single-stranded DNA, a single-stranded DNA/RNA hybrid, and a double-stranded DNA/RNA hybrid, and wherein sequence encoded by the polynucleotide donor molecule is capable of being integrated at the DSB; (Embodiment 93) the composition of embodiment (92), wherein the plant cell is an isolated plant cell or plant protoplast; (Embodiment 94) the composition of embodiment (92), wherein the plant cell is a plant cell capable of division or differentiation; (Embodiment 95) the composition of embodiment (92), wherein the plant cell comprises a double-strand break (DSB) in its genome; (Embodiment 96) the composition of embodiment (95), wherein the DSB is induced by providing a DSB-inducing agent to the plant cell; (Embodiment 97) the composition of embodiment (96), wherein the DSB-inducing agent is at least one of the group consisting of: (a) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, and a meganuclease or engineered meganuclease; (b) a polynucleotide encoding one or more nucleases capable of effecting site-specific alteration of a target nucleotide sequence; and (c) a guide RNA (gRNA) for an RNA-guided nuclease, or a DNA encoding a gRNA for an RNA-guided nuclease; (Embodiment 98) the composition of embodiment (92), wherein the polynucleotide donor molecule is: (a) a double-stranded DNA or double-stranded DNA/RNA hybrid molecule that is blunt-ended or that contains one or more terminal overhangs; (b) a single-stranded DNA or single-stranded DNA/RNA hybrid molecule; or (c) modified at one or both termini with at least one phosphorothioate bond between adjacent nucleotides; (Embodiment 99) the composition of embodiment (92), wherein sequence encoded by the polynucleotide donor molecule comprises: (a) a nucleotide sequence that is recognizable by a specific binding agent; (b) a nucleotide sequence encoding an RNA molecule or an amino acid sequence that is recognizable by a specific binding agent; (c) a nucleotide sequence that encodes an RNA molecule or an amino acid sequence that binds specifically to a ligand; (d) a nucleotide sequence that is responsive to a specific change in the physical environment; or (e) a nucleotide sequence encoding an RNA molecule or an amino acid sequence that is responsive to a specific change in the physical environment; (f) a nucleotide sequence encoding at least one stop codon on each strand; (g) a nucleotide sequence encoding at least one stop codon within each reading frame on each strand; or (h) at least partially self-complementary sequence, such that the polynucleotide molecule encodes a transcript that is capable of forming at least partially double-stranded RNA; or (i) a combination of any of (a)-(h); (Embodiment 100) a reaction mixture comprising: (a) a plant cell having a double-strand break (DSB) at a locus in its genome; and (b) a polynucleotide donor molecule encoding sequence capable of being integrated at the DSB, with a length of between about 18 to about 300 nucleotides or base-pairs, or between about 30 to about 100 nucleotides or base-pairs; wherein sequence encoded by the polynucleotide donor molecule, if integrated at the DSB, forms a heterologous insertion; (Embodiment 101) the reaction mixture of embodiment (100), wherein the plant cell is an isolated plant cell or plant protoplast; (Embodiment 102) the reaction mixture of embodiment (100), wherein sequence encoded by the polynucleotide donor molecule comprises: (a) a nucleotide sequence that is recognizable by a specific binding agent; (b) a nucleotide sequence encoding an RNA molecule or an amino acid sequence that is recognizable by a specific binding agent; (c) a nucleotide sequence that encodes an RNA molecule or an amino acid sequence that binds specifically to a ligand; (d) a nucleotide sequence that is responsive to a specific change in the physical environment; or (e) a nucleotide sequence encoding an RNA molecule or an amino acid sequence that is responsive to a specific change in the physical environment; (f) a nucleotide sequence encoding at least one stop codon on each strand; (g) a nucleotide sequence encoding at least one stop codon within each reading frame on each strand; or (h) at least partially self-complementary sequence, such that the polynucleotide molecule encodes a transcript that is capable of forming at least partially double-stranded RNA; or (i) a combination of any of (a)-(h); (Embodiment 103) a polynucleotide for disrupting gene expression, wherein the polynucleotide is double-stranded and comprises at least 18 contiguous base-pairs, or is single-stranded and comprises at least 11 contiguous nucleotides; and wherein the polynucleotide encodes at least one stop codon in each possible reading frame on each strand; (Embodiment 104) the polynucleotide of embodiment (102), wherein the polynucleotide is a double-stranded DNA (dsDNA) or a double-stranded DNA/RNA hybrid molecule comprising at least 18 contiguous base-pairs, or is a single-stranded DNA (ssDNA) or a single-stranded DNA/RNA hybrid molecule, and encodes at least one stop codon in each possible reading frame on either strand; (Embodiment 105) the polynucleotide of embodiment (102), wherein the polynucleotide is double-stranded and blunt-ended, or is double-stranded and contains one or more terminal overhangs, or is modified at one or both termini with at least one phosphorothioate bond between adjacent nucleotides; (Embodiment 106) the polynucleotide of embodiment (102), wherein the polynucleotide is double-stranded and each strand comprises at least 18 and fewer than 200 contiguous base-pairs, or wherein the polynucleotide is single-stranded and comprises at least 11 and fewer than 200 contiguous nucleotides, and wherein the number of nucleotides or base-pairs is not divisible by 3, and wherein each strand encodes at least one stop codon in each possible reading frame in the 5' to 3' direction; (Embodiment 107) the polynucleotide of embodiment (103), wherein the polynucleotide comprises at least one chemical modification; (Embodiment 108) a method of identifying the locus of at least one double-stranded break (DSB) in genomic DNA in a cell comprising the genomic DNA, the method comprising (a) contacting the genomic DNA having a DSB with a polynucleotide donor molecule, wherein sequence encoded by the polynucleotide donor molecule is capable of being integrated at the DSB, and wherein the polynucleotide donor molecule has a length of between 2 to about 500 base-pairs (if double-stranded) or nucleotides (if single-stranded), or between about 18 to about 300 base-pairs (if double-stranded) or nucleotides (if single-stranded), or between about 30 to about 100 base-pairs (if double-stranded) or nucleotides (if single-stranded); and wherein the sequence encoded by the polynucleotide donor molecule, if integrated at the DSB, forms a heterologous insertion; (b) using at least part of the sequence encoded by the polynucleotide donor molecule as a target for PCR primers to allow amplification of DNA in the locus of the double-stranded break; (Embodiment 109) the method of embodiment (108), wherein sequence encoded by the polynucleotide donor molecule, when integrated at the DSB, imparts a functional trait or detectable phenotype to the cell comprising the genomic DNA, or to an organism comprising the cell; (Embodiment 110) a method of identifying the locus of double-stranded breaks (DSBs) in genomic DNA in a pool of cells, wherein the pool of cells comprises cells having genomic DNA with sequence encoded by a polynucleotide donor molecule inserted at the locus of the double-stranded breaks; wherein the sequence encoded by the polynucleotide donor molecule is capable of being integrated at the DSB, and wherein the polynucleotide donor molecule has a length of between 2 to about 500 base-pairs (if double-stranded) or nucleotides (if single-stranded), or between about 18 to about 300 base-pairs (if double-stranded) or nucleotides (if single-stranded), or between about 30 to about 100 base-pairs (if double-stranded) or nucleotides (if single-stranded); wherein the sequence encoded by the polynucleotide donor molecule, if integrated at the DSB, forms a heterologous insertion; and wherein the sequence encoded by the polynucleotide molecule is used as a target for PCR primers to allow amplification of DNA in the region of said double-stranded breaks; (Embodiment 111) the method of embodiment (110), wherein the pool of cells is a population of plant cells or plant protoplasts; (Embodiment 112) the method of embodiment (110), wherein the genomic DNA is that of a nucleus, mitochondrion, or plastid; (Embodiment 113) the method of embodiment (110), wherein the pool of cells is a population of plant cells or plant protoplasts, wherein the population of plant cells or plant protoplasts comprise multiple different DSBs in the genome; (Embodiment 114) the method of embodiment (113), wherein each of the different DSBs is introduced by a different guide RNA; (Embodiment 115) a method of identifying the nucleotide sequence of a locus in the genome that is associated with a phenotype, the method comprising: (a) providing to a population of cells having the genome: (i) multiple different guide RNAs (gRNAs) to induce multiple different double strand breaks (DSBs) in the genome, wherein each DSB is produced by an RNA-guided nuclease guided to a locus on the genome by one of the gRNAs, and (ii) polynucleotide donor molecules having a defined nucleotide sequence, wherein sequence encoded by the polynucleotide molecules is capable of being integrated into the DSBs by non-homologous end-joining (NHEJ); whereby when sequence encoded by at least some of the polynucleotide molecules is inserted into at least some of the DSBs, a genetically heterogeneous population of cells is produced; (b) selecting from the genetically heterogeneous population of cells a subset of cells that exhibit a phenotype of interest; (c) using a pool of PCR primers that bind to sequence encoded by the polynucleotide molecules to amplify from the subset of cells DNA from the locus of a DSB into which sequence encoded by one of the polynucleotide molecules has been inserted; and (d) sequencing the amplified DNA to identify the locus associated with the phenotype of interest; (Embodiment 116) the method of embodiment (115), wherein the genetically heterogeneous population of cells undergoes one or more doubling cycles; (Embodiment 117) the method of embodiment (115), wherein the genetically heterogeneous population of cells is subjected to conditions permitting expression of the phenotype of interest; (Embodiment 118) the method of embodiment (115), wherein the RNA-guided nuclease or a polynucleotide that encodes the RNA-guided nuclease is exogenously provided to the population of cells; (Embodiment 119) the method of embodiment (115), wherein each gRNA is provided as a polynucleotide composition comprising: (a) a CRISPR RNA (crRNA) that comprises the gRNA, or a polynucleotide that encodes a crRNA, or a polynucleotide that is processed into a crRNA; or (b) a single guide RNA (sgRNA) that comprises the gRNA, or a polynucleotide that encodes a sgRNA, or a polynucleotide that is processed into a sgRNA; (Embodiment 120) the method of embodiment (115), wherein each gRNA is provided as a ribonucleoprotein (RNP) comprising the RNA-guided nuclease and an sgRNA; (Embodiment 121) the method of embodiment (72), wherein: (a) the at least one DSB is two blunt-ended DSBs, resulting in deletion of genomic sequence between the two blunt-ended DSBs, and wherein the polynucleotide donor molecule is selected from the group consisting of a blunt-ended double-stranded DNA, a single-stranded DNA, a single-stranded DNA/RNA hybrid, and a blunt-ended double-stranded DNA/RNA hybrid, and wherein sequence encoded by the polynucleotide donor molecule is integrated into the genome between the two blunt-ended DSBs; (b) the at least one DSB is two DSBs, wherein the first DSB is blunt-ended and the second DSB has an overhang, resulting in deletion of genomic sequence between the two DSBs, and wherein the polynucleotide donor molecule is a double-stranded DNA or double-stranded DNA/RNA hybrid that is blunt-ended at one terminus and has an overhang on the other terminus, or is a single-stranded DNA or a single-stranded DNA/RNA hybrid, and wherein sequence encoded by the polynucleotide donor molecule is integrated into the genome between the two DSBs; (c) the at least one DSB is two DSBs, each having an overhang, resulting in deletion of genomic sequence between the two DSBs, and wherein the polynucleotide donor molecule is a double-stranded DNA or double-stranded DNA/RNA hybrid that has an overhang at each terminus or is a single-stranded DNA or a single-stranded DNA/RNA hybrid, and wherein sequence encoded by the polynucleotide donor molecule is integrated into the genome between the two DSBs; (Embodiment 122) the method of embodiment (72), wherein the at least one DSB is two DSBs, and wherein sequence encoded by the polynucleotide donor molecule comprises at least one recombinase recognition site sequence and is integrated at each of the two DSBs; (Embodiment 123) the method of embodiment (72), further comprising providing (a) the recombinase corresponding to the at least one recombinase recognition site sequence, and (b) a polynucleotide donor molecule encoding a replacement sequence and comprising at or near each terminus a recombinase recognition site sequence that is homospecific to at least one of the recombinase recognition site sequences integrated at each of the two DSBs; whereby the recombinase mediates replacement of the genomic sequence located between the two DSBs with the replacement sequence; (Embodiment 124) a modified maize cell comprising a targeted modification in a gene, wherein the targeted modification is a replacement of EPSPS exon 2, wherein the targeted modification results in increased resistance to glyphosate; (Embodiment 125) a modified maize cell comprising two targeted modifications in two different genes, wherein the targeted modifications are an insertion of a nitrogen responsive element in AMT3 gene and an insertion of an OCS homologue in Lc gene, wherein the targeted modifications result in increased nitrogen use efficiency (NUE); (Embodiment 126) a modified maize cell comprising three targeted modifications in three different genes, wherein the targeted modifications are an insertion of a nitrogen responsive element in Dof1 gene, an insertion of a nitrogen responsive element in NRT2.2 gene, and an insertion of a nitrogen responsive element in Gln1.4 gene, wherein the targeted modifications result in increased nitrogen use efficiency (NUE); (Embodiment 127) a modified maize cell comprising three targeted modifications in three different genes, wherein the targeted modifications are an insertion of a nitrogen responsive element in NRT2.2 gene, an insertion of a nitrogen responsive element in Gln1.4 gene, and an insertion of an OCS homologue in Dof1 gene, wherein the targeted modifications result in increased nitrogen use efficiency (NUE); (Embodiment 128) a modified maize cell comprising four targeted modifications in four different genes, wherein the targeted modifications are an insertion of a nitrogen responsive element in NRT2.2 gene, an insertion of a nitrogen responsive element in Gln1.4 gene, an insertion of an OCS homologue in Dof1 gene, and an insertion of an mRNA destabilizing element in FEA3 gene, wherein the targeted modifications result in increased nitrogen use efficiency (NUE) and increased kernel number; (Embodiment 129) a modified maize cell comprising six targeted modifications in six different genes, wherein the targeted modifications are an insertion of a nitrogen responsive element in NRT2.2 gene, an insertion of a nitrogen responsive element in Gln1.4 gene, an insertion of an OCS homologue in Dof1 gene, a deletion of genomic sequence in FEA3 gene, an insertion of an OCS homologue in EPSPS gene, and an insertion of an upstream ORF (uORF) in NPR1 gene, wherein the targeted modifications result in increased nitrogen use efficiency (NUE), increased kernel number, elevated glyphosate tolerance, and broad spectrum disease resistance; (Embodiment 130) a modified soybean cell comprising a targeted modification in a gene, wherein the targeted modification is an insertion of a SHAT1-5 repressor sequence in SHAT1-5 gene, wherein the targeted modification results in reduced pod shattering; (Embodiment 131) modified soybean cell comprising three targeted modifications in three different genes, wherein the targeted modifications are an insertion of a nitrogen responsive element in NRT gene, an insertion of a nitrogen responsive element in NRT2 gene, and an insertion of an OCS homologue in GS gene, wherein the targeted modifications result in increased nitrogen use efficiency (NUE); (Embodiment 132) a modified soybean cell comprising four targeted modifications in four different genes, wherein the targeted modifications are an insertion of a nitrogen responsive element in NRT gene, an insertion of a nitrogen responsive element in NRT2 gene, an insertion of an OCS homologue in GS gene, and an insertion of an auxin-responsive element 3×DR5 in FT2a gene, wherein the targeted modifications result in increased nitrogen use efficiency (NUE) and early flowering; (Embodiment 133) a modified soybean cell comprising five targeted modifications in five different genes, wherein the targeted modifications are an insertion of a nitrogen responsive element in NRT gene, an insertion of a nitrogen responsive element in NRT2 gene, an insertion of an OCS homologue in GS gene, an insertion of an auxin-responsive element 3×DR5 in FT2a gene, and an insertion of a SAUR mRNA destabilizing sequence in E1 gene, wherein the targeted modifications result in increased nitrogen use efficiency (NUE) and early flowering; (Embodiment 134) a modified tomato cell comprising three targeted modifications in three different genes, wherein the targeted modifications are an insertion of an OCS homologue in CS gene, an insertion of an OCS homologue in BCAT gene, and an insertion of an OCS homologue in KAS gene, wherein the targeted modifications result in capsaicin production; (Embodiment 135) a modified sugarcane tissue comprising a targeted modification in a gene, wherein the targeted modification is a glutamic acid (E) to leucine (L) substitution at position 149 in the protein sequence of PYL-E gene, wherein the targeted modification results in increased water use efficiency; (Embodiment 136) a modified potato tissue comprising a targeted modification in a gene, wherein the target modification is a disruption of StCESA3 gene, wherein the targeted modification results in resistance to late blight caused by *Phytophthora infestans*; (Embodiment 137) a modified potato tissue comprising a targeted modification in a gene, wherein the target modification is a disruption of Stv1NV gene, wherein the targeted modification results in decreased amount of reducing sugar; (Embodiment 138) a modified plant derived from the modified cell or tissue of any of embodiments (124) to (137).

The subject matter of this invention further includes the additional embodiments set forth in this paragraph as follows: (Embodiment 139) a method of changing expression of a sequence of interest in a genome, comprising integrating a dsDNA molecule at the site of at least one double-strand break (DSB) in a genome; (Embodiment 140) the method of embodiment (139), wherein the genome is that of a plant; (Embodiment 141) the method of embodiment (140), wherein the genome is that of a nucleus, mitochondrion, or plastid in a plant cell; (Embodiment 142) the method of embodiment (139), wherein the at least one DSB is introduced into the genome by at least one of the group consisting of: (a) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, and a meganuclease or engineered meganuclease; (b) a polynucleotide encoding one or more nucleases capable of effecting site-specific alteration of a target nucleotide sequence; and (c) a guide RNA (gRNA) for an RNA-guided nuclease, or a DNA encoding a gRNA for an RNA-guided nuclease; (Embodiment 143) the method of embodiment (139), wherein the at least one DSB is introduced into the genome by at least one treatment selected from the group consisting of: (a) bacterially mediated (e. g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection; (b) Biolistics or particle bombardment; (c) treatment with at least one chemical, enzymatic, or physical agent; and (d) application of heat or cold, ultrasonication, centrifugation, positive or negative pressure, cell wall or membrane disruption or deformation, or electroporation; (Embodiment 144) the method of embodiment (139), wherein the at least one DSB in a genome is located: (a) within the sequence of interest, (b) upstream of the sequence of interest, or (c) downstream of the sequence of interest; (Embodiment 145) the method of embodiment (139), wherein the dsDNA molecule, when integrated into the genome, is functionally or operably linked to the sequence of interest; (Embodiment 146) the method of embodiment (139), wherein the sequence of interest comprises coding sequence, non-coding sequence, or a combination of coding and non-coding sequence; (Embodiment 147) the method of embodiment (139), wherein the at least one DSB is two or more DSBs; (Embodiment 148) the method of embodiment (147), wherein the dsDNA molecule that is integrated into each of the two or more DSBs is (a) identical, or (b) different, for each of the DSBs; (Embodiment 149) the method of embodiment (139), wherein the dsDNA molecule comprises at least one of the nucleotide sequences selected from the group consisting of: (a) DNA encoding at least one stop codon, or at least one stop codon on each strand, or at least one stop codon within each reading frame on each strand; (b) heterologous primer sequence; (c) a unique identifier sequence; (d) a transcript-stabilizing sequence; (e) a transcript-destabilizing sequence; (f) a DNA aptamer or DNA encoding an RNA or amino acid aptamer; and (g) a sequence recognizable by a specific binding agent; (Embodiment 150) the method of embodiment (139), wherein the dsDNA molecule comprises a sequence recognizable by a specific binding agent, and wherein contacting the integrated dsDNA molecule with the specific binding agent results in a change of expression of the sequence of interest; (Embodiment 151) the method of embodiment (150), wherein: (a) the sequence recognizable by a specific binding agent comprises an auxin response element sequence, the specific binding agent is an auxin, and the change of expression is upregulation; (b) the sequence recognizable by a specific binding agent comprises at least one D1-4 sequence, the specific binding agent is an auxin, and the change of expression is upregulation; (c) the sequence recognizable by a specific binding agent comprises at least one DR5 sequence, the specific binding agent is an auxin, and the change of expression is upregulation; (d) the sequence recognizable by a specific binding agent comprises at least one m5-DR5 sequence, the specific binding agent is an auxin, and the change of expression is upregulation; (e) the sequence recognizable by a specific binding agent comprises at least one P3 sequence, the specific binding agent is an auxin, and the change of expression is upregulation; (f) the sequence recognizable by a specific binding agent comprises a small RNA recognition site sequence, the specific binding agent is the corresponding small RNA, and the change of expression is downregulation; (g) the sequence recognizable by a specific binding agent comprises a microRNA (miRNA) recognition site sequence, the specific binding agent is the corresponding mature miRNA, and the change of expression is downregulation; (h) the sequence recognizable by a specific binding agent comprises a microRNA (miRNA) recognition site sequence for an engineered miRNA, the specific binding agent is the corresponding engineered mature miRNA, and the change of expression is downregulation; (i) the sequence recognizable by a specific binding agent comprises a transposon recognition sequence, the specific binding agent is the corresponding transposon, and the change of expression is upregulation or downregulation; (j) the sequence recognizable by a specific binding agent comprises an ethylene-responsive element binding-factor-associated amphiphilic repression (EAR) motif sequence, the specific binding agent is ERF (ethylene-responsive element binding factor) or co-repressor, and the change of expression is downregulation; (k) the sequence recognizable by a specific binding agent comprises a splice site sequence, the specific binding agent is a spliceosome, and the change of expression is expression of a spliced transcript; (l) the sequence recognizable by a specific binding agent comprises a site-specific recombinase recognition site sequence, the specific binding agent is the corresponding site-specific recombinase, and the change of expression is upregulation or downregulation or expression of a transcript having an altered sequence; (m) the sequence recognizable by a specific binding agent comprises sequence encoding an RNA aptamer or an RNA riboswitch, the specific binding agent is the corresponding ligand, and the change in expression is upregulation or downregulation; (n) the sequence recognizable by a specific binding agent is a hormone responsive element, the specific binding agent is a hormone, and the change in expression is upregulation or downregulation; or (o) the sequence recognizable by a specific binding agent is a transcription factor binding sequence, the specific binding agent is the corresponding transcription factor, and the change in expression is upregulation or downregulation; (Embodiment 152) the method of embodiment (150), wherein the dsDNA molecule comprises a nucleotide sequence that encodes an RNA molecule or an amino acid sequence that is recognizable by a specific binding agent; (Embodiment 153) the method of embodiment (150), wherein the dsDNA molecule comprises a nucleotide sequence that encodes an RNA molecule or an amino acid sequence that binds specifically to a ligand;

(Embodiment 154) the method of embodiment (139), wherein the dsDNA molecule encodes at least one stop codon on each strand; (Embodiment 155) the method of embodiment (139), wherein the dsDNA molecule encodes at least one stop codon within each reading frame on each strand; (Embodiment 156) the method of embodiment (139), wherein the dsDNA molecule comprises at least partially self-complementary sequence, such that the dsDNA molecule encodes a transcript that is capable of forming at least partially double-stranded RNA; (Embodiment 157) the method of embodiment (139), wherein the dsDNA molecule comprises a nucleotide sequence that is responsive to a specific change in the physical environment, and wherein exposing the integrated dsDNA molecule to the specific change in the physical environment results in a change of expression of the sequence of interest; (Embodiment 158) the method of embodiment (157), wherein the specific change in the physical environment is at least one of: a change in light intensity or quality, a change in temperature, a change in pressure, a change in osmotic concentration, or a change in day length; (Embodiment 159) the method of embodiment (139), wherein the dsDNA molecule comprises a nucleotide sequence encoding an RNA molecule or an amino acid sequence that is responsive to a specific change in the physical environment; (Embodiment 160) the method of embodiment (159), wherein the dsDNA molecule encodes a Light-Oxygen-Voltage domain; (Embodiment 161) a plant cell comprising in its genome a heterologous DNA sequence that comprises: (a) nucleotide sequence of a dsDNA molecule integrated by the method of embodiment 1 at the site of a DSB in a genome; and (b) genomic nucleotide sequence adjacent to the site of the DSB; (Embodiment 162) a plant comprising the plant cell of embodiment (161); (Embodiment 163) a processed or commodity product of the plant of embodiment (162); (Embodiment 164) a heterologous nucleotide sequence comprising: (a) nucleotide sequence of a dsDNA molecule integrated by the method of embodiment 1 at the site of a DSB in a genome, and (b) genomic nucleotide sequence adjacent to the site of the DSB; (Embodiment 165) a plasmid, vector, or chromosome comprising the heterologous nucleotide sequence of embodiment (164); (Embodiment 166) a polymerase primer for amplification of the heterologous nucleotide sequence of embodiment (164); (Embodiment 167) a composition comprising: (a) a plant cell; and (b) a dsDNA molecule; (Embodiment 168) the composition of embodiment (167), wherein the plant cell is an isolated plant cell or plant protoplast; (Embodiment 169) the composition of embodiment (167), wherein the plant cell is a plant cell capable of division or differentiation; (Embodiment 170) the composition of embodiment (167), wherein the plant cell comprises a double-strand break (DSB) in its genome; (Embodiment 171) the composition of embodiment (170), wherein the DSB is induced by providing a DSB-inducing agent to the plant cell; (Embodiment 172) the composition of embodiment (171), wherein the DSB-inducing agent is at least one of the group consisting of: (a) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, and a meganuclease or engineered meganuclease; (b) a polynucleotide encoding one or more nucleases capable of effecting site-specific alteration of a target nucleotide sequence; and (c) a guide RNA (gRNA) for an RNA-guided nuclease, or a DNA encoding a gRNA for an RNA-guided nuclease; (Embodiment 173) the composition of embodiment (167), wherein the dsDNA molecule is: (a) blunt-ended; (b) contains one or more terminal overhangs; or (c) modified at one or both termini with at least one phosphorothioate bond between adjacent nucleotides; (Embodiment 174) the composition of embodiment (167), wherein the dsDNA molecule comprises: (a) a nucleotide sequence that is recognizable by a specific binding agent; (b) a nucleotide sequence encoding an RNA molecule or an amino acid sequence that is recognizable by a specific binding agent; (c) a nucleotide sequence that encodes an RNA molecule or an amino acid sequence that binds specifically to a ligand; (d) a nucleotide sequence that is responsive to a specific change in the physical environment; or (e) a nucleotide sequence encoding an RNA molecule or an amino acid sequence that is responsive to a specific change in the physical environment; (f) a nucleotide sequence encoding at least one stop codon on each strand; (g) a nucleotide sequence encoding at least one stop codon within each reading frame on each strand; or (h) at least partially self-complementary sequence, such that the dsDNA molecule encodes a transcript that is capable of forming at least partially double-stranded RNA; or (i) a combination of any of (a)-(h); (Embodiment 175) a reaction mixture comprising: (a) a plant cell having a double-strand break (DSB) at a locus in its genome; and (b) a dsDNA molecule capable of being integrated at the DSB, with a length of between about 18 to about 300 base-pairs, or between about 30 to about 100 base-pairs; wherein the dsDNA molecule, if integrated at the DSB, forms a heterologous insertion; (Embodiment 176) the reaction mixture of embodiment (175), wherein the plant cell is an isolated plant cell or plant protoplast; (Embodiment 177) the reaction mixture of embodiment (175), wherein the dsDNA molecule comprises: (a) a nucleotide sequence that is recognizable by a specific binding agent; (b) a nucleotide sequence encoding an RNA molecule or an amino acid sequence that is recognizable by a specific binding agent; (c) a nucleotide sequence that encodes an RNA molecule or an amino acid sequence that binds specifically to a ligand; (d) a nucleotide sequence that is responsive to a specific change in the physical environment; or (e) a nucleotide sequence encoding an RNA molecule or an amino acid sequence that is responsive to a specific change in the physical environment; (f) a nucleotide sequence encoding at least one stop codon on each strand; (g) a nucleotide sequence encoding at least one stop codon within each reading frame on each strand; or (h) at least partially self-complementary sequence, such that the dsDNA molecule encodes a transcript that is capable of forming at least partially double-stranded RNA; or (i) a combination of any of (a)-(h); (Embodiment 178) an oligonucleotide for disrupting gene expression, comprising a strand of at least 18 nucleotides and encoding at least one stop codon in each possible reading frame on each strand; (Embodiment 179) the oligonucleotide of embodiment (178), wherein the oligonucleotide is double-stranded DNA (dsDNA) comprising at least 18 contiguous base-pairs and encoding at least one stop codon in each possible reading frame on either strand; (Embodiment 180) the oligonucleotide of embodiment (178), wherein the dsDNA is blunt-ended; (Embodiment 181) the oligonucleotide of embodiment (178), wherein each strand of the dsDNA comprises at least 18 and fewer than 200 contiguous base-pairs, wherein the number of base-pairs is not divisible by 3, and wherein each strand encodes at least one stop codon in each possible reading frame in the 5' to 3' direction; (Embodiment 182) the oligonucleotide of embodiment (178), wherein the dsDNA comprises at least one phosphorothioate modification; (Embodiment 183) a method of identifying the locus of at least one double-stranded break (DSB) in genomic DNA in a cell comprising the genomic DNA, the method comprising (a) contacting the genomic DNA having a DSB with a dsDNA molecule, wherein the dsDNA molecule is capable of being integrated at the DSB and has a length of between about 18 to about 300 base-pairs, or between about 30 to about 100 base-pairs; wherein the dsDNA molecule, if integrated at the DSB, forms a heterologous insertion; (b) using at least part of the sequence of the dsDNA molecule as a target for PCR primers to allow amplification of DNA in the locus of the double-stranded break; (Embodiment 184) the method of embodiment (183), wherein the dsDNA molecule, when integrated at the DSB, imparts a functional trait to the cell comprising the genomic DNA, or to an organism comprising the cell; (Embodiment 185) a method of identifying the locus of double-stranded breaks (DSBs) in genomic DNA in a pool of cells, wherein the pool of cells comprises cells having genomic DNA with a dsDNA molecule inserted at the locus of the double-stranded breaks; wherein the dsDNA molecule is capable of being integrated at the DSB and has a length of between about 18 to about 300 base-pairs, or between about 30 to about 100 base-pairs; wherein the dsDNA molecule, if integrated at the DSB, forms a heterologous insertion; wherein the sequence of the dsDNA molecule is used as a target for PCR primers to allow amplification of DNA in the region of said double-stranded breaks; (Embodiment 186) the method of embodiment (185), wherein the pool of cells is a population of plant cells or plant protoplasts; (Embodiment 187) the method of embodiment (185), wherein the genomic DNA is that of a nucleus, mitochondrion, or plastid; (Embodiment 188) the method of embodiment (185), wherein the pool of cells is a population of plant cells or plant protoplasts, wherein the population of plant cells or plant protoplasts comprise multiple different DSBs in the genome; (Embodiment 189) the method of embodiment (188), wherein each of the different DSBs is introduced by a different guide RNA; (Embodiment 190) a method of identifying the nucleotide sequence of a locus in the genome that is associated with a phenotype, the method comprising: (a) providing to a population of cells having the genome: (i) multiple different guide RNAs (gRNAs) to induce multiple different double strand breaks_(DSBs) in the genome, wherein each DSB is produced by an RNA-guided nuclease guided to a locus on the genome by one of the gRNAs, and (ii) blunt-ended, double-stranded DNA (dsDNA) molecules having a defined nucleotide sequence, wherein the dsDNA molecules are capable of being integrated into the DSBs by non-homologous end-joining (NHEJ) recombination; whereby when at least some of the dsDNA molecules are inserted into at least some of the DSBs, a genetically heterogeneous population of cells is produced; (b) selecting from the genetically heterogeneous population of cells a subset of cells that exhibit a phenotype of interest; (c) using a pool of PCR primers that bind to the dsDNA molecules to amplify from the subset of cells DNA from the locus of a DSB into which one of the dsDNA molecules has been inserted; and (d) sequencing the amplified DNA to identify the locus associated with the phenotype of interest; (Embodiment 191) the method of embodiment (190), wherein the genetically heterogeneous population of cells undergoes one or more doubling cycles; (Embodiment 192) the method of embodiment (190), wherein the genetically heterogeneous population of cells is subjected to conditions permitting expression of the phenotype of interest; (Embodiment 193) the method of embodiment (190), wherein the RNA-guided nuclease or a polynucleotide that encodes the RNA-guided nuclease is exogenously provided to the population of cells; (Embodiment 194) the method of embodiment (190), wherein each gRNA is provided as a polynucleotide composition comprising: (a) a CRISPR RNA (crRNA) that comprises the gRNA, or a polynucleotide that encodes a crRNA, or a polynucleotide that is processed into a crRNA; or (b) a single guide RNA (sgRNA) that comprises the gRNA, or a polynucleotide that encodes a sgRNA, or a polynucleotide that is processed into a sgRNA; (Embodiment 194) the method of embodiment (190), wherein each gRNA is provided as a ribonucleoprotein (RNP) comprising the RNA-guided nuclease and an sgRNA; (Embodiment 196) the method of embodiment (147), wherein: (a) the at least one DSB is two blunt-ended DSBs, resulting in deletion of genomic sequence between the two blunt-ended DSBs, and wherein the dsDNA molecule is blunt-ended and is integrated into the genome between the two blunt-ended DSBs; (b) the at least one DSB is two DSBs, wherein the first DSB is blunt-ended and the second DSB has an overhang, resulting in deletion of genomic sequence between the two DSBs, and wherein the dsDNA molecule is blunt-ended at one terminus and has an overhang on the other terminus, and is integrated into the genome between the two DSBs; (c) the at least one DSB is two DSBs, each having an overhang, resulting in deletion of genomic sequence between the two DSBs, and wherein the dsDNA molecule has an overhang at each terminus and is integrated into the genome between the two DSBs.

The subject matter of this invention further includes the additional embodiments set forth in this paragraph as follows: (Embodiment 197) a method of modifying a plant cell by creating a plurality of targeted modifications in the genome of the cell, comprising: contacting the genome with one or more targeting agents, wherein the one or more agents comprise or encode predetermined peptide or nucleic acid sequences, wherein the predetermined peptide or nucleic acid sequences bind preferentially at or near predetermined target sites within the plant genome, and wherein the binding directs the generation of the plurality of targeted modifications within the genome; wherein the plurality of targeted modifications occurs without an intervening step of separately identifying an individual modification and without a step of separately selecting for the occurrence of an individual modification among the plurality of targeted modifications mediated by the targeting agents; and wherein the targeted modifications alter at least one trait of the plant cell, or at least one trait of a plant comprising the plant cell, or at least one trait of a plant grown from the plant cell, or result in a detectable phenotype in the modified plant cell; and wherein at least two of the targeted modifications are insertions of predetermined sequences encoded by one or more polynucleotide donor molecules, and wherein at least one of the polynucleotide donor molecules lacks homology to the genome sequences adjacent to the site of insertion; (Embodiment 198) the method of embodiment (197) wherein the plant cell has a ploidy of 2n, with n being a value selected from the group consisting of 0.5, 1, 1.5, 2, 2.5, 3, 3.5, 4, 5, and 6, and wherein the method generates 2n targeted modifications at 2n loci of the predetermined target sites within the genome; and wherein 2n of the targeted modifications are insertions or creations of predetermined sequences encoded by one or more polynucleotide donor molecules; (Embodiment 199) the method of embodiment (197) or (198), wherein at least one of the polynucleotide donor molecules is a single stranded DNA molecule, a single stranded RNA molecule, a single stranded DNA-RNA hybrid molecule, or a duplex RNA-DNA molecule; (Embodiment 200) the method of embodiment (197), (198), or (199), wherein at least one insertion is a non-coding regulatory element; (Embodiment 201) the method of any of embodiments (197)-(200), wherein said polynucleotide donor molecules have a length of at least 5 nucleotides; (Embodiment 202) the method of any of embodiments 197-201, (a) wherein the genome of the modified cell does not comprise a nuclease, or a selection marker, or both, stably linked integrated as a result of the targeted modifications; and/or (b) wherein the method is conducted without the use of a selection marker; and/or (c) wherein the agents employed in the method do not comprise a vector; (Embodiment 203) the method of any of embodiments (197)-(202), wherein the method results in a non-transgenic plant cell containing homozygous edits, without an intervening chromosome segregation event; (Embodiment 204) the method of any of embodiments (197)-(203), wherein at least one of the polynucleotide donor molecules is provided as a ribonucleoprotein (RNP) polynucleotide composition; (Embodiment 205) the method of any of embodiments (197)-(204), wherein said RNP comprises an RNA-guided nuclease and (a) a CRISPR RNA (crRNA) that comprises a guide RNA (gRNA), or a polynucleotide that encodes a crRNA, or a polynucleotide that is processed into a crRNA; or (b) a single guide RNA (sgRNA) that comprises the gRNA, or a polynucleotide that encodes a sgRNA, or a polynucleotide that is processed into a sgRNA; (Embodiment 206) the method of any of embodiments (197)-(205), wherein the modified plant cell is a meristematic cell, embryonic cell, or germline cell; (Embodiment 207) the method of any of embodiments (197)-(206), wherein repetition of the method results in an efficiency of at least 1%, wherein said efficiency is determined by dividing the number of successfully targeted cells by the total number of cells targeted; (Embodiment 208) the method of any of embodiments (197)-(207), wherein at least one of the targeted modifications is an insertion between at least 3 and 400 nucleotides in length; (Embodiment 209) the method of any of embodiments (197)-(208), wherein at least one of the targeted modifications is an insertion between 10 and 350 nucleotides in length; (Embodiment 210) the method of any of embodiments (197)-(209), wherein at least one double-stranded break (DSB) is introduced into the genome, and wherein (a) the at least one DSB is two blunt-ended DSBs, resulting in deletion of genomic sequence between the two blunt-ended DSBs, and wherein the polynucleotide molecule is selected from the group consisting of a blunt-ended double-stranded DNA, a single-stranded DNA, a single-stranded DNA/RNA hybrid, and a blunt-ended double-stranded DNA/RNA hybrid and is integrated into the genome between the two blunt-ended DSBs; or (b) the at least one DSB is two DSBs, wherein the first DSB is blunt-ended and the second DSB has an overhang, resulting in deletion of genomic sequence between the two DSBs, and wherein the polynucleotide molecule is a double-stranded DNA or double-stranded DNA/RNA hybrid that is blunt-ended at one terminus and has an overhang on the other terminus, or is a single-stranded DNA or a single-stranded DNA/RNA hybrid, and is integrated into the genome between the two DSBs; or (c) the at least one DSB is two DSBs, each having an overhang, resulting in deletion of genomic sequence between the two DSBs, and wherein the polynucleotide molecule is a double-stranded DNA or double-stranded DNA/RNA hybrid that has an overhang at each terminus or is a single-stranded DNA or a single-stranded DNA/RNA hybrid, and is integrated into the genome between the two DSBs; (Embodiment 211) the method of any of embodiments (205)-(210) wherein the donor polynucleotide is tethered to a crRNA by a covalent bond, a non-covalent bond, or a combination of covalent and non-covalent bonds; (Embodiment 212) the method of any of embodiments (197)-(211), wherein the genome of the modified plant cell has not more unintended changes in comparison to the genome of the original plant than $2\times10^{-9}$ mutations per bp per replication; (Embodiment 213) the method of any of embodiments (197)-(212), wherein the modified plant cell is identical to the original plant cell but for (i) the targeted insertions, and (ii) the naturally occurring mutation rate as a consequence of multiplying the cell, and, optionally (iii) any off-target mutations; (Embodiment 214) the method of any of embodiments (197)-(213), wherein at least one DSB is introduced into the genome by at least one of the group consisting of: (a) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, a meganuclease, an engineered meganuclease, a recombinase, integrase, and a transposase; (b) a polynucleotide encoding one or more nucleases capable of effecting site-specific alteration of a target nucleotide sequence; and (c) a guide RNA (gRNA) for an RNA-guided nuclease, and a DNA encoding a gRNA for an RNA-guided nuclease; (Embodiment 215) the method of any of embodiments (197)-(214), wherein at least one DSB is introduced into the genome by at least one treatment selected from the group consisting of: (a) bacterially mediated transfection; (b) biolistics or particle bombardment; (c) treatment with at least one chemical, enzymatic, or physical agent; and (d) application of heat or cold, ultrasonication, centrifugation, positive or negative pressure, cell wall or membrane disruption or deformation, or electroporation; (Embodiment 216) the method of any of embodiments (197)-(215), wherein at least one DSB is introduced in the genome: (a) within a sequence of interest, (b) upstream of a sequence of interest, or (c) downstream of a sequence of interest; (Embodiment 217) the method of any of embodiments (197)-(216), wherein a polynucleotide molecule, when integrated into the genome, is functionally or operably linked to the sequence of interest; (Embodiment 218) the method of embodiment (217), wherein the polynucleotide molecule comprises at least one of the nucleotide sequences selected from the group consisting of: (a) DNA or RNA encoding at least one stop codon, or at least one stop codon on each strand, or at least one stop codon within each reading frame on each strand; (b) DNA or RNA encoding heterologous primer sequence; (c) DNA or RNA encoding a unique identifier sequence; (d) DNA or RNA encoding a transcript-stabilizing sequence; (e) DNA or RNA encoding a transcript-destabilizing sequence; (f) a DNA or RNA aptamer, or DNA encoding an RNA aptamer, or DNA or RNA encoding an amino acid aptamer; and (g) DNA or RNA encoding a sequence recognizable by a specific binding agent; (Embodiment 219) the method of any of embodiments (197)-(218) further comprising obtaining a plant from the modified plant cell; (Embodiment 220) the method of any of embodiments (197)-(218), wherein the modified plant cell is identical to the original plant cell but for (i) the targeted insertions, (ii) mutations arising naturally during mitotic propagation, and optionally, (iii) any off-target mutations; (Embodiment 221) a method of manufacturing a commercial seed, comprising: (a) engineering a plant cell according to the method of any one of embodiments 197-220, (b) growing a modified plant from said plant cell, and optionally further multiplying or propagating said plant, and (c) using said plant to produce commercial seed; (Embodiment 222) a modified plant or plant part derived from the modified cell resulting from the method of any of embodiments (197)-(220); (Embodiment 223) a method of manufacturing a plant comprising a modified cell, wherein said modified cell is generated by the method of any of embodiments (197)-(220); (Embodiment 224) a method of manufacturing a plant comprising growing a plant from a modified cell, wherein said modified cell is generated by the method of any of embodiments (197)-(220); (Embodiment 225) a modified plant cell, wherein said plant cell comprises at least 2 separately targeted modifications in its genome, wherein the targeted modifications are determined relative to an original plant cell, and wherein the modified plant cell is genetically identical to the original plant with the exception of the targeted insertions and any changes as a consequence of multiplying said modified plant cell; (Embodiment 226) a plant, comprising modified plant cells, wherein each of said modified plant cells comprises at least 2 separately targeted modifications in its genome, wherein the modifications are determined relative to an original plant cell, and wherein the plant is genetically identical to the original plant with the exception of the targeted modifications and any changes as a consequence of regenerating or growing said plant from a plant cell of embodiment (225), and—optionally—further propagating said plant; (Embodiment 227) a plant cell of embodiment (225) or a plant of embodiment (226), wherein the changes as a consequence of multiplication or propagation are less than $2\times10^{-10}$ mutations per bp per replication.

EXAMPLES

Example 1

This example illustrates techniques for preparing a plant cell or plant protoplast useful in compositions and methods of the invention, for example, in providing a reaction mixture including a plant cell having a double-strand break (DSB) at at least one locus in its genome. More specifically this non-limiting example describes techniques for preparing isolated, viable plant protoplasts from monocot and dicot plants.

The following mesophyll protoplast preparation protocol (modified from one publicly available at molbio[dot]mgh [dot]harvard.edu/sheenweb/protocols_reg[dot]html) is generally suitable for use with monocot plants such as maize (*Zea mays*) and rice (*Oryza sativa*):

Prepare an enzyme solution containing 0.6 molar mannitol, 10 millimolar MES pH 5.7, 1.5% cellulase R10, and 0.3% macerozyme R10. Heat the enzyme solution at 50-55 degrees Celsius for 10 minutes to inactivate proteases and accelerate enzyme solution and cool it to room temperature before adding 1 millimolar $CaCl_2$, 5 millimolar β-mercaptoethanol, and 0.1% bovine serum albumin. Pass the enzyme solution through a 0.45 micrometer filter. Prepare a washing solution containing 0.6 molar mannitol, 4 millimolar MES pH 5.7, and 20 millimolar KCl.

Obtain second leaves of the monocot plant (e. g., maize or rice) and cut out the middle 6-8 centimeters. Stack ten leaf sections and cut into 0.5 millimeter-wide strips without bruising the leaves. Submerge the leaf strips completely in the enzyme solution in a petri dish, cover with aluminum foil, and apply vacuum for 30 minutes to infiltrate the leaf tissue. Transfer the dish to a platform shaker and incubate for an additional 2.5 hours' digestion with gentle shaking (40 rpm). After digestion, carefully transfer the enzyme solution (now containing protoplasts) using a serological pipette through a 35 micrometer nylon mesh into a round-bottom tube; rinse the petri with 5 milliliters of washing solution and filter this through the mesh as well. Centrifuge the protoplast suspension at 1200 rpm, 2 minutes in a swing-bucket centrifuge. Aspirate off as much of the supernatant as possible without touching the pellet; gently wash the pellet once with 20 milliliters washing buffer and remove the supernatant carefully. Gently resuspend the pellet by swirling in a small volume of washing solution, then resuspend in 10-20 milliliters of washing buffer. Place the tube upright on ice for 30 minutes-4 hours (no longer). After resting on ice, remove the supernatant by aspiration and resuspend the pellet with 2-5 milliliters of washing buffer. Measure the concentration of protoplasts using a hemocytometer and adjust the concentration to 2×10^5 protoplasts/milliliter with washing buffer.

The following mesophyll protoplast preparation protocol (modified from one described by Niu and Sheen (2012) *Methods Mol. Biol.,* 876:195-206, doi: 10.1007/978-1-61779-809-2_16) is generally suitable for use with dicot plants such as *Arabidopsis thaliana* and brassicas such as kale (*Brassica oleracea*).

Prepare an enzyme solution containing 0.4 M mannitol, 20 millimolar KCl, 20 millimolar MES pH 5.7, 1.5% cellulase R10, and 0.4% macerozyme R10. Heat the enzyme solution at 50-55 degrees Celsius for 10 minutes to inactivate proteases and accelerate enzyme solution, and then cool it to room temperature before adding 10 millimolar $CaCl_2$, 5 millimolar β-mercaptoethanol, and 0.1% bovine serum albumin. Pass the enzyme solution through a 0.45 micrometer filter. Prepare a "W5" solution containing 154 millimolar NaCl, 125 millimolar $CaCl_2$, 5 millimolar KCl, and 2 millimolar MES pH 5.7. Prepare a "MMg solution" solution containing 0.4 molar mannitol, 15 millimolar $MgCl_2$, and 4 millimolar MES pH 5.7.

Obtain second or third pair true leaves of the dicot plant (e. g., a *brassica* such as kale) and cut out the middle section. Stack 4-8 leaf sections and cut into 0.5 millimeter-wide strips without bruising the leaves. Submerge the leaf strips completely in the enzyme solution in a petri dish, cover with aluminum foil, and apply vacuum for 30 minutes to infiltrate the leaf tissue. Transfer the dish to a platform shaker and incubate for an additional 2.5 hours' digestion with gentle shaking (40 rpm). After digestion, carefully transfer the enzyme solution (now containing protoplasts) using a serological pipette through a 35 micrometer nylon mesh into a round-bottom tube; rinse the petri dish with 5 milliliters of washing solution and filter this through the mesh as well. Centrifuge the protoplast suspension at 1200 rpm, 2 minutes in a swing-bucket centrifuge. Aspirate off as much of the supernatant as possible without touching the pellet; gently wash the pellet once with 20 milliliters washing buffer and remove the supernatant carefully. Gently resuspend the pellet by swirling in a small volume of washing solution, then resuspend in 10-20 milliliters of washing buffer. Place the tube upright on ice for 30 minutes-4 hours (no longer). After resting on ice, remove the supernatant by aspiration and resuspend the pellet with 2-5 milliliters of MMg solution. Measure the concentration of protoplasts using a hemocytometer and adjust the concentration to 2×10^5 protoplasts/milliliter with MMg solution.

Example 2

This example illustrates a method of delivery of an effector molecule to a plant cell or plant protoplast to effect a genetic change, in this case introduction of a double-strand break in the genome. More specifically, this non-limiting example describes a method of delivering a guide RNA (gRNA) in the form of a ribonucleoprotein (RNP) to isolated plant protoplasts.

The following delivery protocol (modified from one publicly available at molbio[dot]mgh[dot]harvard.edu/sheenweb/protocols_reg[dot]html) is generally suitable for use with monocot plants such as maize (*Zea mays*) and rice (*Oryza sativa*):

Prepare a polyethylene glycol (PEG) solution containing 40% PEG 4000, 0.2 molar mannitol, and 0.1 molar $CaCl_2$. Prepare an incubation solution containing 170 milligram/liter $KH_2PO_4$, 440 milligram/liter $CaCl_2 \cdot 2H_2O$, 505 milligram/liter $KNO_3$, 160 milligram/liter $NH_4NO_3$, 370 milligram/liter $MgSO_4 \cdot 7H_2O$, 0.01 milligram/liter KI, 1 milligram/liter $H_3BO_3$, 0.1 milligram/liter $MnSO_4 \cdot 4H_2O$, 1 milligram/liter $ZnSO_4 \cdot 7H_2O$, 0.03 milligram/liter $CuSO_4 \cdot 5H_2O$, 1 milligram/liter nicotinic acid, 1 milligram/liter thiamine HCl, 1 milligram/liter pyridoxine HCl, 0.2 milligram/liter folic acid, 0.01 milligram/liter biotin, 1 milligram/liter D-Ca-pantothenate, 100 milligram/liter myo-inositol, 40 grams/liter glucose, 60 grams/liter mannitol, 700 milligram/liter MES, 10 microliter/liter Tween 80, 1 milligram/liter 2,4-D, and 1 milligram/liter 6-benzylaminopurine (BAP); adjust pH to 5.6.

Prepare a crRNA:tracrRNA or guide RNA (gRNA) complex by mixing equal amounts of CRISPR crRNA and tracrRNA (obtainable e. g., as custom-synthesized Alt® CRISPR crRNA and tracrRNA oligonucleotides from Integrated DNA Technologies, Coralville, IA): mix 6 microliters of 100 micromolar crRNA and 6 microliters of 100 micromolar tracrRNA, heat at 95 degrees Celsius for 5 minutes, and then cool the crRNA:tracrRNA complex to room temperature. To the cooled gRNA solution, add 10 micrograms Cas9 nuclease (Aldevron, Fargo, ND) and incubate 5 minutes at room temperature to allow the ribonucleoprotein (RNP) complex to form. Add the RNP solution to 100 microliters of monocot protoplasts (prepared as described in Example 1) in a microfuge tube; add 5 micrograms salmon sperm DNA (VWR Cat. No.: 95037-160) and an equal volume of the PEG solution. Mix gently by tapping. After 5 minutes, dilute with 880 microliters of washing buffer and mix gently by inverting the tube. Centrifuge 1 minute at 1200 rpm and then remove the supernatant. Resuspend the protoplasts in 1 milliliter incubation solution and transfer to a multi-well plate. The efficiency of genome editing is assessed by any suitable method such as heteroduplex cleavage assay or by sequencing, as described elsewhere in this disclosure.

The following delivery protocol (modified from one described by Niu and Sheen (2012) *Methods Mol. Biol.,* 876:195-206, doi: 10.1007/978-1-61779-809-2_16) is generally suitable for use with dicot plants such as *Arabidopsis thaliana* and brassicas such as kale (*Brassica oleracea*):

Prepare a polyethylene glycol (PEG) solution containing 40% PEG 4000, 0.2 molar mannitol, and 0.1 molar $CaCl_2$. Prepare an incubation solution containing 170 milligram/liter $KH_2PO_4$, 440 milligram/liter $CaCl_2 \cdot 2H_2O$, 505 milligram/liter $KNO_3$, 160 milligram/liter $NH_4NO_3$, 370 milligram/liter $MgSO_4 \cdot 7H_2O$, 0.01 milligram/liter KI, 1 milligram/liter $H_3BO_3$, 0.1 milligram/liter $MnSO_4 \cdot 4H_2O$, 1 milligram/liter $ZnSO_4 \cdot 7H_2O$, 0.03 milligram/liter $CuSO_4 \cdot 5H_2O$, 1 milligram/liter nicotinic acid, 1 milligram/liter thiamine HCl, 1 milligram/liter pyridoxine HCl, 0.2 milligram/liter folic acid, 0.01 milligram/liter biotin, 1 milligram/liter D-Ca-pantothenate, 100 milligram/liter myo-inositol, 40 grams/liter glucose, 60 grams/liter mannitol, 700 milligram/liter MES, 10 microliter/liter Tween 80, 1 milligram/liter 2,4-D, and 1 milligram/liter 6-benzylaminopurine (BAP); adjust pH to 5.6.

Prepare a crRNA:tracrRNA or guide RNA (gRNA) complex by mixing equal amounts of CRISPR crRNA and tracrRNA (obtainable e. g., as custom-synthesized Alt® CRISPR crRNA and tracrRNA oligonucleotides from Integrated DNA Technologies, Coralville, IA): mix 6 microliters of 100 micromolar crRNA and 6 microliters of 100 micromolar tracrRNA, heat at 95 degrees Celsius for 5 minutes, and then cool the crRNA:tracrRNA complex to room temperature. To the cooled gRNA solution, add 10 micrograms Cas9 nuclease (Aldevron, Fargo, ND) and incubate 5 minutes at room temperature to allow the ribonucleoprotein (RNP) complex to form. Add the RNP solution to 100 microliters of dicot protoplasts (prepared as described in Example 1) in a microfuge tube; add 5 micrograms salmon sperm DNA (VWR Cat. No.: 95037-160) and an equal volume of the PEG solution. Mix gently by tapping. After 5 minutes, dilute with 880 microliters of washing buffer and mix gently by inverting the tube. Centrifuge 1 minute at 1200 rpm and then remove the supernatant. Resuspend the protoplasts in 1 milliliter incubation solution and transfer to a multi-well plate. The efficiency of genome editing is assessed by any suitable method such as heteroduplex cleavage assay or by sequencing, as described elsewhere in this disclosure.

The above protocols for delivery of gRNAs as RNPs to plant protoplasts are adapted for delivery of guide RNAs alone to monocot or dicot protoplasts that express Cas9 nuclease by transient or stable transformation; in this case, the guide RNA complex is prepared as before and added to the protoplasts, but no Cas9 nuclease and no salmon sperm DNA is added. The remainder of the procedures are identical.

Example 3

This example illustrates a method of identifying a nucleotide sequence associated with a phenotype of interest. More specifically, this non-limiting example describes delivering a guide RNA (gRNA) in the form of a ribonucleoprotein (RNP) to isolated plant protoplasts, followed by screening to identify the protoplasts in which the target nucleotide sequence has been altered by the introduction of a double-strand break.

Rice (*Oryza sativa*) protoplasts were prepared according to the protocol described in Example 1. Multiple guide RNAs are prepared as described in Example 2 using crRNAs with the sequences provided in Table 1, complexed with a tracrRNA to form the gRNA (crRNA:tracrRNA) complex; the targetted nucleotide sequences are OsADHI (alcohol dehydrogenase 1) and OsLsi2 (a silicon or arsenic efflux exporter). Both the crRNAs and tracrRNA were purchased from Integrated DNA Technologies, Coralville, IA. Ribonucleoprotein (RNP) complexes were then prepared as described in Example 2 using the gRNAs and Cas9 nuclease (Aldevron, Fargo, ND).

TABLE 1

| crRNA | crRNA sequence | SEQ ID NO. |
|---|---|---|
| OsADH1-1 | GCACUUGAUCACCUUCCCUGGUUUUAGAGCUAUGCU | 1 |
| OsADH1-2 | UCCACCUCCUCGAUCACCAGGUUUUAGAGCUAUGCU | 2 |
| OsADH1-3 | GGCCUCCCAGAAGUAGACGUGUUUUAGAGCUAUGCU | 3 |
| OsADH1-4 | GGGAAGGUGAUCAAGUGCAAGUUUUAGAGCUAUGCU | 4 |
| OsADH1-5 | GCCACCGUCGAACCCUUUGGGUUUUAGAGCUAUGCU | 5 |
| OsADH1-6 | GUAAAUGGGCUUCCCGUUGAGUUUUAGAGCUAUGCU | 6 |
| OsADH1-7 | GACAGACUCCCGUGUUCCCUGUUUUAGAGCUAUGCU | 7 |
| OsADH1-8 | GUGAAUUCAGGAGCUGGAGGGUUUUAGAGCUAUGCU | 8 |
| OsADH1-9 | GUACUUGCUGAGAUGACCAAGUUUUAGAGCUAUGCU | 9 |
| OsADH1-10 | GCAACAUGUGUGAUCUGCUCGUUUUAGAGCUAUGCU | 10 |
| OsLsi2-1 | UGGCCGGGAGGAUUCCCAUGGUUUUAGAGCUAUGCU | 11 |
| OsLsi2-2 | AUGGUUCAUGCAGUGCACGGGUUUUAGAGCUAUGCU | 12 |
| OsLsi2-3 | GCUCGAGGACGAACUCGGUGGUUUUAGAGCUAUGCU | 13 |
| OsLsi2-4 | AUGUACUGGAGGGAGCUGGGGUUUUAGAGCUAUGCU | 14 |
| OsLsi2-5 | UAGAAUGUAUAAUUACCCGUGUUUUAGAGCUAUGCU | 15 |
| OsLsi2-6 | CGGGCCUCCCGGGAGCCAUCGUUUUAGAGCUAUGCU | 16 |
| OsLsi2-7 | CAAGCACCUGGGGCGUCUGCGUUUUAGAGCUAUGCU | 17 |
| OsLsi2-8 | GAGAUCAGAUCUUGCCGAUGGUUUUAGAGCUAUGCU | 18 |
| OsLsi2-9 | GAAGGUGAUCUUGCUAUUGAGUUUUAGAGCUAUGCU | 19 |
| OsLsi2-10 | GAAGAUGAGUGAGCUUGCGUGUUUUAGAGCUAUGCU | 20 |

Arrayed screens can be conveniently carried out with protoplasts in multi-well (e. g., 24- or 96-well) plates. In this example, the protoplasts (25 microliters/well) were distributed in a 24-well plate treated with 5 microliters/well of an individual RNP complex according to the protocols described in Example 2. An HBT-sGFP plasmid was used as a transfection control (2 wells) and Cas9 protein without a guide RNA was used as a null control (2 wells); two technical replicas were performed. Efficiency of editing was estimated to be between 20%-30% by a T7E1 endonuclease (heteroduplex cleavage) assay as described in Example 4.

In embodiments where editing of a target nucleotide sequence is expected to provide an observable phenotype, the phenotype can be used to select the plant cells or protoplasts having the edited sequence. Optionally, the plant cells or plant protoplasts are grown or cultured under conditions that permit expression of the phenotype, allowing selection of the plant cells or plant protoplasts that exhibit the phenotype. For example, rice cells or protoplasts in which the ADH1 gene is disrupted or altered by editing can be exposed to low concentrations of allyl alcohol; cells wherein one or both copies of the ADH1 gene has been disrupted will have increased susceptibility to allyl alcohol toxicity. In another example, rice cells or protoplasts in which the Lsi gene is disrupted or altered by editing are expected to have decreased arsenic content.

Pooled screens are carried out in a similar fashion, except that editing is carried out with multiple guide RNAs (e. g., in the form of multiple RNPs) provided to a complement of plant protoplasts. For example, maize (*Zea mays*, variety B73) protoplasts are treated with a mixture of RNPs for delivering different gRNAs targetting a selection of 2630 transcription factors in 5 families identified in maize (sequences publicly available at grassius[dot]org/tf_browsefamily.html?species=Maize). Those guides that are over-represented at the read-out stage are those that target genes that are identified as candidates for controlling cell division.

Example 4

This example illustrates genome editing in monocot plants and further illustrates a method of identifying a nucleotide sequence associated with a phenotype of interest. More specifically, this non-limiting example describes delivering a guide RNA (gRNA) in the form of a ribonucleoprotein (RNP) to isolated plant protoplasts, followed by screening to identify the protoplasts in which the target nucleotide sequence has been altered by introduction of a double-stranded break (DSB).

The target gene selected for editing was the maize (*Zea mays*) alcohol dehydrogenase ADH1 (see www[dot]maizegdb[dot]org/gene_center/gene/GRMZM2G442658) with the partial genomic sequence:

(SEQ ID NO: 21)

GAACAGTGCCGCAGTGGCGCTGATCTTGTATGCTATCCTGCAATCGTGGT

GAACTTATTTCTTTTATATCCTTTACTCCCATGAAAAGGCTAGTAATCTT

TCTCGATGTAACATCGTCCAGCACTGCTATTACCGTGTGGTCCATCCGAC

AGTCTGGCTGAACACATCATACGATCTATGGAGCAAAAATCTATCTTCCC

TGTTCTTTAATGAAGGACGTCATTTTCATTAGTATGATCTAGGAATGTTG

CAACTTGCAAGGAGGCGTTTCTTTCTTTGAATTTAACTAACTCGTTGAGT

GGCCCTGTTTCTCGGACGTAAGGCCTTTGCTGCTCCACACATGTCCATTC

GAATTTTACCGTGTTTAGCAAGGGCGAAAAGTTTGCATCTTGATGATTTA

GCTTGACTATGCGATTGCTTTCCTGGACCCGTGCAGCTGCGGTGGCATGG

GAGGCCGGCAAGCCACTGTCGATCGAGGAGGTGGAGGTAGCGCCTCCGCA

GGCCATGGAGGTGCGCGTCAAGATCCTCTTCACCTCGCTCTGCCACACCG

ACGTCTACTTCTGGGAGGCCAAGGTATCTAATCAGCCATCCCATTTGTGA

TCTTTGTCAGTAGATATGATACAACAACTCGCGGTTGACTTGCGCCTTCT

TGGCGGCTTATCTGTCTTAGGGGCAGACTCCCGTGTTCCCTCGGATCTTT

GGCCACGAGGCTGGAGGGTA;

the first exon (SEQ ID NO:22), located at nucleotide positions 409-571 of SEQ ID NO:21 is indicated by bold, underlined text and guide RNA (crRNA) sequences were designed to edit this exon.

Maize protoplasts were prepared as described in Example 1. A ribonucleoprotein (RNP) was prepared with Cas9 nuclease (Aldevron, Fargo, ND) and a guide RNA complex of a crRNA (ZmADH1-B) having the sequence GGCCUCCCAGAAGUAGACGUGUUUUAGAGCUAUGCU (SEQ ID NO:23) and a tracrRNA (both purchased from Integrated DNA Technologies, Coralville, IA). This was used for editing the target gene ADH1 in the maize protoplasts following the procedures described in Example 1. A T7 endonuclease (T7E1, New England Biolabs, Ipswich, MA) was used in a heteroduplex cleavage assay to detect on-target editing. In brief, genomic DNA from the protoplasts was amplified by PCR; the amplified products were denatured and re-annealed to allow heteroduplex formation between wild-type or unedited DNA and the edited DNA. T7E1, which recognizes and cleaves mismatched DNA, was used to digest the heteroduplexes, and the resulting cleaved and full-length PCR products are analysed by gel electrophoresis. The primers used for the T7E1 assay had the sequences GAACAGTGCCGCAGTGGCG (forward primer, SEQ ID NO:24) and TACCCTCCAGCCTCGTGGC (reverse primer, SEQ ID NO:25) for an expected amplicon size of 720 base-pairs (i. e., SEQ ID NO:21). Gel electrophoretic analysis demonstrated the presence of the expected cleaved products.

For quantitation of editing efficiency, next-generation sequencing (NGS) analysis was used. A second set of primers were used for CRISPR sequencing; these had the sequences ACTATGCGATTGCTTTCCTGGAC (forward primer, SEQ ID NO:26) and ACCGCGAGTTGTTGTATCATATCT (reverse primer, SEQ ID NO:27) for an expected amplicon size of 230 base-pairs which includes the ADH1 first exon (i. e., ACTATCCGATTCCITTCCTGGACCCGTGCACCTCCGGTGGCATGGGAGGCCGGCAA GCCACTGTCCATCGACCAGGTGGACGTAGCGCCTCCGCACCCCA TCGACGTGCGC GTCAAGATCCTCTTCACCTCGCTCTGCCACACCGACGTCTACTTCTGGGAGGCCAA GGTATCTAATCAGCCATCCCATTTGTGATCTTTGTCAGTAGATATGATACAACAACTCGC GGT, SEQ ID NO:28); the ADH1 first exon (SEQ ID NO:22) is indicated by bold, underlined text. The NGS sequencing results are provided in FIGS. 1A-1C. The editing efficiency was estimated to be 38%.

Another gene selected for editing was the maize (*Zea mays*) Babyboom gene BBM2 (see www[dot]maizegdb[dot]org/gene_center/gene/GRMZM2G141638) with the partial genomic sequence: AACCGGTGTAATACATACTAAGGGCTAGTTTGGGAACCCTGGTTTTCTAAGGAATTT TATTTTTCCAAAAAAAATAGTTTATTTTTCTTCGGAAATTAGG AATCTCTTATAAAA TTCGAGTTCCCAAACTATTCCTAATATATATATCATACTCTCCATCAGTCTATATATA GATTACATATAGTAAGTATAGAGTATCTCGCTATCACATAG TGCCACTAATCTTCTG GAGTGTACCAGTTGTATAAATATCTATCAGTATCAGCACTACTGTTTGCTGAATACCCC AAAACTCTCTGCTTGACTTCTCTTCCCTAACCTTTG CACTGTCCAAAATGGCTTCCTGATC CCCTCACTTCCTCGAATCATTCTAAGAAGAAACTCAAGCCGCTACCATTAGGGGCAGATT AATTGCTGCACTTTCAGATAATCTACCATGGCCACTGT GAACAACTGGCTCGCTTTCTCCC TCTCCCCGCAGGAGCTGCCGCCCTCCCAGACGACGGACTCCACGCTCATCTCGGCCGCCA CCGCCGACCATGTCTCCGGCGATGTCTGCTTCAACATCCCCCA AGGTAGCATCTATCTAT CTGGCGACATACGTG (SEQ ID NO:29); promoter sequence (SEQ ID NO:30), located at nucleotide positions 1-254 of SEQ ID NO:29 is indicated by bold, underlined text and guide RNA (crRNA) sequences were designed to edit this non-coding DNA.

Maize protoplasts were prepared as described in Example 1. A ribonucleoprotein (RNP) was prepared with Cas9 nuclease (Aldevron, Fargo, ND) and a guide RNA complex of a crRNA (ZmBBM2-2) having the sequence AAGAGAUUCCUAAUUUCCGAGUUUUAGAGCUAUGCU (SEQ ID NO:31) and a tracrRNA (both purchased from Integrated DNA Technologies, Coralville, IA). This was used for editing the target gene BBM2 in the maize protoplasts following the procedures described in Example 1.

For quantitation of editing efficiency, next-generation sequencing (NGS) analysis was used. The primers used for CRISPR sequencing had the sequences GGGAACCCTGGTTTTCTAAG (forward primer, SEQ ID NO:32) and GCAAACAGTAGTGCTGATACTG (reverse primer, SEQ ID NO:33) for an expected amplicon size of 248 base-pairs which includes the BBM2 promoter sequence (i. e., GGGAACCCTGGTTTTCTAAGGAATTTTATTTTTCCAAAAAAAAATAGTTTATTTTTCCTTCGGAAATTAGGAATCTCTTATAAAATTCGAGTTCCCAAACTATTCCTAATATATATATCATACTCTCCATCAGTCTATATATAGATTACATATAGTAAGTATAGAGTATCTCGCTATCACATAGTGCCACTAATCTTCTGGAGTGTACCAGTTGTATAAATATCTATCAGTATCAGCACTACTGTTTGC, SEQ ID NO:34); the BBM2 promoter sequence (SEQ ID NO:30) is indicated by bold, underlined text.

Example 5

This example illustrates genome editing in dicot plants and further illustrates a method of identifying a nucleotide sequence associated with a phenotype of interest. More specifically, this non-limiting example describes delivering a guide RNA (gRNA) in the form of a ribonucleoprotein (RNP) to isolated plant protoplasts, followed by screening to identify the protoplasts in which the target nucleotide sequence has been altered by introduction of a double-strand break (DSB).

The target gene selected for editing was the kale (*Brassica oleracea*) Myb-like transcription factor 2, BoMYBL2 (see www[dot]ocri-genomics[dot]org/cgi-bin/bolbase/gene_detail[dot]cgi?locus=Bol016164 #) with the partial genomic sequence:

(SEQ ID NO: 35)
GAAACCTACCAGTCTCTCCTTTGAAGAAGACATGAACAAAATTAGCCAC
GGCGCTCTATCTCGGCCTTCCGGTAACGTTTCTTGTTCAATATTGTTGT
ATTAGCTTTCATATGACCAAATTCTTCATAATTAAAGATCGGTATAGAA
GTCATAGATTACATATATGTACATTTGCACGGGTGAGTTTGCAACAAAT
GTCGTTTTACTTTGTGAAATTTAATCCCTAATCATGTTTTAGGAATGCT
GCACCGTGCC;

the first exon (SEQ ID NO:36) and part of the second exon (SEQ ID NO:37), located respectively at nucleotide positions 32-71 and 239-255 of SEQ ID NO:35, are indicated by bold, underlined text.

Kale protoplasts were prepared as described in Example 1. A ribonucleoprotein (RNP) was prepared with Cas9 nuclease (Aldevron, Fargo, ND) and a guide RNA complex of a crRNA (BoMYBL2-2) having the sequence GAACAAGAAACGUUACCGGAGUUUUAGAGCUAUGCU (SEQ ID NO:38) and a tracrRNA (both purchased from Integrated DNA Technologies, Coralville, IA). This was used for editing the target gene BoMYBL2 in the kale protoplasts following the procedures described in Example 1.

For quantitation of editing efficiency, next-generation sequencing (NGS) analysis was used. The primers used for CRISPR sequencing had the sequences GAAACCTACCAGTCTCTCCTTTG (forward primer, SEQ ID NO:39) and GGCACGGTGCAGCATTCCTA (reverse primer, SEQ ID NO:40) for an expected amplicon size of 255 base-pairs (i. e., SEQ ID NO:35). The NGS sequencing results are provided in FIGS. 2A-2F. The editing efficiency was estimated to be 21%.

Another gene selected for editing was the kale (*Brassica oleracea*) "*Gigantea*" gene BoGI, transgenic silencing of which has been reported to result in delaying flowering and leaf senescence in broccoli (*Brassica oleracea* L. var. *italica*); see Thiruvengadam et al. (2015) *Plant Mol. Biol. Rep.*, doi 10.1007/s11105-015-0852-3). The kale BoGI gene (see www[dot]ocri-genomics[dot]org/cgi-bin/bolbase/gene_ detail[dot]cgi?locus=Bol023541 #) has the partial genomic sequence:

(SEQ ID NO: 41)
CCGATGGTCTTCAGTTCTCTTCCTTGTTATGGTCTCCCCCACGAGATCC
TCAACAACATAAGGTACTTAACAATAATAAATAAAGCCTCAGATGTCTC
ATCCATGAACCGGTGCTGATTGTCTTTCTCCTTAGGATCAAGTCGTTGC
TTATGTCGAATACTTTGGTCGGTTCACATCAGAGCAATTCCCTGATGAT
ATTGCTGAGG;

part of the first exon (SEQ ID NO:42) and the second exon (SEQ ID NO:43), located respectively at nucleotide positions 1-60 and 132-203 of SEQ ID NO:41, are indicated by bold, underlined text.

Kale protoplasts were prepared as described in Example 1. A ribonucleoprotein (RNP) was prepared with Cas9 nuclease (Aldevron, Fargo, ND) and a guide RNA complex of a crRNA (BoGI-1) having the sequence UCGUGGGGGAGACCAUAACAGUUUUAGAGCUAUGCU (SEQ ID NO:44) and a tracrRNA (both purchased from Integrated DNA Technologies, Coralville, IA). This was used for editing the target gene GI in the kale protoplasts following the procedures described in Example 1.

For quantitation of editing efficiency, next-generation sequencing (NGS) analysis was used. The primers used for CRISPR sequencing had the sequences CCGATGGTCTTCAGTTCTCT (forward primer, SEQ ID NO:45) and CCTCAGCAATATCATCAGGG (reverse primer, SEQ ID NO:46) for an expected amplicon size of 206 base-pairs (i. e., SEQ ID NO:41). The NGS sequencing results are provided in FIGS. 3A-3C. The editing efficiency was estimated to be 76%.

Example 6

This example illustrates compositions and reaction mixtures useful for delivering at least one effector molecule for inducing a genetic alteration in a plant cell or plant protoplast.

Sequences of plasmids for delivery of Cas9 (Csn1) endonuclease from the *Streptococcus pyogenes* Type II CRISPR/Cas system (SEQ ID NO:136) and for delivery of a single guide RNA (sgRNA) are provided in Tables 2 and 3. In this non-limiting example, the sgRNA targets the endogenous phytoene desaturase (PDS) in soybean, *Glycine max*; one of skill would understand that other sgRNA sequences for alternative target genes could be substituted in the plasmid.

TABLE 2

| SGRNA VECTOR (SEQ ID NO: 136), 3079 BASE PAIRS DNA | | |
|---|---|---|
| Nucleotide position in SEQ ID NO: 136 | Description | Comment |
| 1-3079 | Intact plasmid | SEQ ID NO: 136 |
| 379-395 | M13 forward primer for sequencing | |
| 412-717 | *Glycine max* U6 promoter | |
| 717-736 | *Glycine max* phytoene desaturase targeting sequence (gRNA) | SEQ ID NO: 137 |
| 737-812 | guide RNA scaffold sequence for *S. pyogenes* CRISPR/Cas9 system | SEQ ID NO: 138 |
| 856-874 | M13 reverse primer for sequencing | complement |
| 882-898 | lac repressor encoded by lacI | |
| 906-936 | lac promoter for the *E. coli* lac operon | complement |
| 951-972 | *E. coli* catabolite activator protein (CAP) binding site | |
| 1260-1848 | high-copy-number ColE1/pMB1/pBR322/pUC origin of replication (left direction) | complement |
| 2019-2879 | CDS for bla, beta-lactamase, AmpR | complement; ampicillin selection |
| 2880-2984 | bla promoter | complement |

The sgRNA vector having the sequence of SEQ ID NO: 136 contains nucleotides at positions 717-812 encoding a single guide RNA having the sequence of SEQ ID NO:139, which includes both a targeting sequence (gRNA) (SEQ ID NO:137) and a guide RNA scaffold (SEQ ID NO:138) transcription of the sgRNA is driven by a *Glycine max* U6 promoter at nucleotide positions 412-717. The sgRNA vector also includes lac operon and ampicillin resistance sequences for convenient selection of the plasmid in bacterial cultures.

TABLE 3

ENDONUCLEASE VECTOR (SEQ ID NO: 140), 8569 BASE PAIRS DNA

| Nucleotide position in SEQ ID NO: 140 | Description | Comment |
|---|---|---|
| 1-8569 | Intact plasmid | SEQ ID NO: 140 |
| 379-395 | M13 forward primer for sequencing | |
| 419-1908 | *Glycine max* UbiL promoter | |
| 1917-6020 | Cas9 (Csn1) endonuclease from the *Streptococcus pyogenes* type II CRISPR/Cas system | SEQ ID NO: 141 (encodes protein with sequence of SEQ ID NO: 142) |
| 6033-6053 | nuclear localization signal of SV40 large T antigen | SEQ ID NO: 143 (encodes peptide with sequence of SEQ ID NO: 144 |
| 6065-6317 | nopaline synthase (NOS) terminator and poly(A) signal | |
| 6348-6364 | M13 reverse primer for sequencing | complement |
| 6372-6388 | lac repressor encoded by lacI | |
| 6396-6426 | lac promoter for the *E. coli* lac operon | complement |
| 6441-6462 | *E. coli* catabolite activator protein (CAP) binding site | |
| 6750-7338 | high-copy-number ColE1/pMB1/pBR322/pUC origin of replication (left direction) | complement |
| 7509-8369 | CDS for bla, beta-lactamase, AmpR | complement; ampicillin selection |
| 8370-8474 | bla promoter | complement |

The endonuclease vector having the sequence of SEQ ID NO:140 contains nucleotides at positions 1917-6020 having the sequence of SEQ ID NO:141 and encoding the Cas9 nuclease from *Streptococcus pyogenes* that has the amino acid sequence of SEQ ID NO:142, and nucleotides at positions 6033-6053 having the sequence of SEQ ID NO:143 and encoding the nuclear localization signal (NLS) of simian virus 40 (SV40) large T antigen that has the amino acid sequence of SEQ ID NO:144. Transcription of the Cas9 nuclease and adjacent SV40 nuclear localization signal is driven by a *Glycine max* UbiL promoter at nucleotide positions 419-1908; the resulting transcript including nucleotides at positions 1917-6053 having the sequence of SEQ ID NO:145 encodes a fusion protein having the sequence of SEQ ID NO:146 wherein the Cas9 nuclease is linked through a 4-residue peptide linker to the SV40 nuclear localization signal. The endonuclease vector also includes lac operon and ampicillin resistance sequences for convenient selection of the plasmid in bacterial cultures.

Similar vectors for expression of nucleases and sgRNAs are also described, e. g., in Fauser et al. (2014) *Plant J.,* 79:348-359; and described at www[dot]addgene[dot[org/crispr. It will be apparent to one skilled in the art that analogous plasmids are easily designed to encode other guide polynucleotide or nuclease sequences, optionally including different elements (e. g., different promoters, terminators, selectable or detectable markers, a cell-penetrating peptide, a nuclear localization signal, a chloroplast transit peptide, or a mitochondrial targeting peptide, etc.), and used in a similar manner. Embodiments of nuclease fusion proteins include fusions (with or without an optional peptide linking sequence) between the Cas9 nuclease from *Streptococcus pyogenes* that has the amino acid sequence of SEQ ID NO:142 and at least one of the following peptide sequences: (a) GRKKRRQRRRPPQ ("HIV-1 Tat (48-60)", SEQ ID NO:147), (b) GRKKRRQRRRPQ ("TAT", SEQ ID NO:148), (c) YGRKKRRQRRR ("TAT (47-57)", SEQ ID NO:149), (d) KLALKLALKALKAALKLA ("MAP (KLAL)", SEQ ID NO:150), (e) RQIRIWFQNRRMRWRR ("Penetratin-Arg", SEQ ID NO:151), (f) CSIPPEVKFNKPFVYLI ("antitrypsin (358-374)", SEQ ID NO:152), (g) RRRQRRKKRGGDIMGEWGNEIFGAIAGFLG ("TAT-HA2 Fusion Peptide", SEQ ID NO:153), (h) FVQWFSKFLGRIL-NH2 ("Temporin L, amide", SEQ ID NO:154), (i) LLIILRRRIRKQAHAHSK ("pVEC (Cadherin-5)", SEQ ID NO:155), (j) LGTYTQDFNKFHTFPQTAIGVGAP ("Calcitonin", SEQ ID NO:156), (k) GAAEAAARVYDLGLRRLRQRRRLRRERVRA ("Neurturin", SEQ ID NO:157), (l) MGLGLHLLVLAAALQGAWSQPKKKRKV ("Human P1", SEQ ID NO:158), (m) RQIKIWFQNRRMKWKKGG ("Penetratin", SEQ ID NO:159), poly-arginine peptides including (n) RRRRRRRR ("octo-arginine", SEQ ID NO:160) and (o) RRRRRRRRR ("nono-arginine", SEQ ID NO:161), and (p) KKLFKKILKYLKKLFKKILKYLKKKKKKKK ("(BP100×2)-K8", SEQ ID NO:162); these nuclease fusion proteins are specifically claimed herein, as are analogous fusion proteins including a nuclease selected from Cpf1, CasY, CasX, C2c1, or C2c3 and at least one of the peptides having a sequence selected from SEQ ID NOs:147-162. In other embodiments, such vectors are used to produce a guide RNA (such as one or more crRNAs or sgRNAs) or the nuclease protein; guide RNAs and nucleases can be combined to produce a specific ribonucleoprotein complex for delivery to the plant cell; in an example, a ribonucleoprotein including the sgRNA having the sequence of SEQ ID NO:139 and the Cas9-NLS fusion protein having the sequence of SEQ ID NO:146 is produced for delivery to the plant cell. Related aspects of the invention thus encompass ribonucleoprotein compositions containing the ribonucleoprotein including the sgRNA having the sequence of SEQ ID NO:139 and a Cas9 fusion protein such as the Cas9-NLS fusion protein having the sequence of SEQ ID NO:146, and polynucleotide compositions containing one or more polynucleotides including the sequences of SEQ ID NOs:139 or 145. The above sgRNA and nuclease vectors are delivered to plant cells or plant protoplasts using compositions and methods described in the specification.

A plasmid ("pCas9TPC-GmPDS") having the nucleotide sequence of SEQ ID NO:163 was designed for simultaneous delivery of Cas9 (Csn1) endonuclease from the *Streptococcus pyogenes* Type II CRISPR/Cas system and a single guide RNA (sgRNA) targeting the endogenous phytoene desaturase (PDS) in soybean, *Glycine max*. In this non-limiting example, the sgRNA targets the endogenous phytoene desaturase (PDS) in soybean, *Glycine max*; one of skill would understand that other sgRNA sequences for alternative target genes could be substituted in the plasmid. The sequences of this plasmid and specific elements contained therein are described in Table 4 below.

TABLE 4

PCAS9TPC-GMPDS VECTOR (SEQ ID NO: 163), 14548 BASE PAIRS DNA

| Nucleotide position in SEQ ID NO: 163 | Description | Comment |
|---|---|---|
| 1-14548 | Intact plasmid | SEQ ID NO: 163 |
| 1187-1816 | pVS1 StaA | stability protein from the Pseudomonas plasmid pVS1 |
| 2250-3317 | pVS1 RepA | replication protein from the Pseudomonas plasmid pVS1 |
| 3383-3577 | pVS1 oriV | origin of replication for the Pseudomonas plasmid pVS1 |
| 3921-4061 | basis of mobility region from pBR322 | |
| 4247-4835 | high-copy-number ColE1/pMB1/pBR322/pUC origin of replication (left direction) | complement |
| 5079-5870 | aminoglycoside adenylyltransferase (aadA), confers resistance to spectinomycin and streptomycin | complement |
| 6398-6422 | left border repeat from nopaline C58 T-DNA | |
| 6599-6620 | *E. coli* catabolite activator protein (CAP) binding site | |
| 6635-6665 | lac promoter for the *E. coli* lac operon | |
| 6673-6689 | lac repressor encoded by lacI | |
| 6697-6713 | M13 reverse primer for sequencing | |
| 6728-7699 | PcUbi4-2 promoter | |
| 7714-11817 | Cas9 (Csn1) endonuclease from the *Streptococcus pyogenes* type II CRISPR/Cas system | SEQ ID NO: 141 (encodes protein with sequence of SEQ ID NO: 142) |
| 11830-11850 | nuclear localization signal of SV40 large T antigen | SEQ ID NO: 143 (encodes peptide with sequence of SEQ ID NO: 144 |
| 11868-12336 | Pea3A terminator | |
| 12349-12736 | AtU6-26 promoter | |
| 12737-12756 | *Glycine max* phytoene desaturase targeting sequence (gRNA) | SEQ ID NO: 137 |
| 12757-12832 | guide RNA scaffold sequence for *S. pyogenes* CRISPR/Cas9 system | SEQ ID NO: 138 |
| 12844-12868 | attB2; recombination site for Gateway ® BP reaction | complement |
| 13549-14100 | *Streptomyces hygroscopicus* bar or pat, encodes phosphinothricin acetyltransferase, confers resistance to bialophos or phosphinothricin | |
| 14199-14215 | M13 forward primer, for sequencing | complement |
| 14411-14435 | right border repeat from nopaline C58 T-DNA | |

The pCas9TPC-GmPDS vector having the sequence of SEQ ID NO:163 contains nucleotides at positions 12737-12832 encoding a single guide RNA having the sequence of SEQ ID NO: 139, which includes both a targeting sequence (gRNA) (SEQ ID NO: 137) and a guide RNA scaffold (SEQ ID NO: 138); transcription of the single guide RNA is driven by a AtU6-26 promoter at nucleotide positions 12349-12736. This vector further contains nucleotides at positions 7714-11817 having the sequence of SEQ ID NO:141 and encoding the Cas9 nuclease from *Streptococcus pyogenes* that has the amino acid sequence of SEQ ID NO: 142, and nucleotides at positions 11830-11850 having the sequence of SEQ ID NO:143 and encoding the nuclear localization signal (NLS) of simian virus 40 (SV40) large T antigen that has the amino acid sequence of SEQ ID NO: 144. Transcription of the Cas9 nuclease and adjacent SV40 nuclear localization signal is driven by a PcUbi4-2 promoter at nucleotide positions 6728-7699; the resulting transcript including nucleotides at positions 7714-11850 having the sequence of SEQ ID NO: 145 encodes a fusion protein having the sequence of SEQ ID NO: 146 wherein the Cas9 nuclease is linked through a 4-residue peptide linker to the SV4 nuclear localization signal. The pCas9TPC-GmPDS vector also includes lac operon, aminoglycoside adenylyltransferase, and phosphinothricin acetyltransferase sequences for convenient selection of the plasmid in bacterial or plant cultures.

A plasmid ("pCas9TPC-NbPDS") having the nucleotide sequence of SEQ ID NO:164 was designed for simultaneous delivery of Cas9 (Csn1) endonuclease from the *Streptococcus pyogenes* Type II CRISPR/Cas system and a single guide RNA (sgRNA) targeting the endogenous phytoene desaturase (PDS) in *Nicotiana benthamiana*; see Nekrasov et al. (2013) *Nature Biotechnol.,* 31:691-693. In this non-limiting example, the sgRNA targets the endogenous phytoene desaturase (PDS) in *Nicotiana benthamiana* one of skill would understand that other sgRNA sequences for alternative target genes could be substituted in the plasmid. The sequences of this plasmid and specific elements contained therein are described in Table 5 below.

TABLE 5

PCAS9TPC-NBPDS VECTOR (SEQ ID NO: 164), 14548 BASE PAIRS DNA

| Nucleotide position in SEQ ID NO: 164 | Description | Comment |
|---|---|---|
| 1-14548 | Intact plasmid | SEQ ID NO: 164 |
| 1187-1816 | pVS1 StaA | stability protein from the Pseudomonas plasmid pVS1 |
| 2250-3317 | pVS1 RepA | replication protein from the Pseudomonas plasmid pVS1 |
| 3383-3577 | pVS1 oriV | origin of replication for the Pseudomonas plasmid pVS1 |
| 3921-4061 | basis of mobility region from pBR322 | |
| 4247-4835 | high-copy-number ColE1/pMB1/pBR322/pUC origin of replication (left direction) | Complement |
| 5079-5870 | aminoglycoside adenylyltransferase (aadA), confers resistance to spectinomycin and streptomycin | Complement |
| 6398-6422 | left border repeat from nopaline C58 T-DNA | |
| 6599-6620 | *E. coli* catabolite activator protein (CAP) binding site | |
| 6635-6665 | lac promoter for the *E. coli* lac operon | |
| 6673-6689 | lac repressor encoded by lacI | |
| 6697-6713 | M13 reverse primer for sequencing | |
| 6728-7699 | PcUbi4-2 promoter | |
| 7714-11817 | Cas9 (Csn1) endonuclease from the *Streptococcus pyogenes* type II CRISPR/Cas system | SEQ ID NO: 141 (encodes protein with sequence of SEQ ID NO: 142) |
| 11830-11850 | nuclear localization signal of SV40 large T antigen | SEQ ID NO: 143 (encodes peptide with sequence of SEQ ID NO: 144 |
| 11868-12336 | Pea3A terminator | |
| 12349-12736 | AtU6-26 promoter | |
| 12737-12756 | *Nicotiana benthamiana* phytoene desaturase targeting sequence | SEQ ID NO: 165 |
| 12757-12832 | guide RNA scaffold sequence for *S. pyogenes* CRISPR/Cas9 system | SEQ ID NO: 138 |
| 12844-12868 | attB2; recombination site for Gateway ® BP reaction | Complement |
| 13549-14100 | *Streptomyces hygroscopicus* bar or pat, encodes phosphinothricin acetyltransferase, confers resistance to bialophos or phosphinothricin | |
| 14199-14215 | M13 forward primer, for sequencing | Complement |
| 14411-14435 | right border repeat from nopaline C58 T-DNA | |

The pCas9TPC-NbPDS vector having the sequence of SEQ ID NO:164 contains nucleotides at positions 12737-12832 encoding a single guide RNA having the sequence of SEQ ID NO:166, which includes both a targeting sequence (gRNA) (SEQ ID NO:165) and a guide RNA scaffold (SEQ ID NO:138); transcription of the single guide RNA is driven by a AtU6-26 promoter at nucleotide positions 12349-12736. This vector further contains nucleotides at positions 7714-11817 having the sequence of SEQ ID NO:141 and encoding the Cas9 nuclease from *Streptococcus pyogenes* that has the amino acid sequence of SEQ ID NO:142, and nucleotides at positions 11830-11850 having the sequence of SEQ ID NO:143 and encoding the nuclear localization signal (NLS) of simian virus 40 (SV40) large T antigen that has the amino acid sequence of SEQ ID NO:144. Transcription of the Cas9 nuclease and adjacent SV40 nuclear localization signal is driven by a PcUbi4-2 promoter at nucleotide positions 6728-7699; the resulting transcript including nucleotides at positions 7714-11850 having the sequence of SEQ ID NO:145 encodes a fusion protein having the sequence of SEQ ID NO:146 wherein the Cas9 nuclease is linked through a 4-residue peptide linker to the SV40 nuclear localization signal. The pCas9TPC-NbPDS vector also includes lac operon, aminoglycoside adenylyltransferase, and phosphinothricin acetyltransferase sequences for convenient selection of the plasmid in bacterial or plant cultures.

Example 7

This example illustrates examples of transcription factor binding sequences that can be included in the sequence of a polynucleotide (such as a double-stranded DNA, a single-stranded DNA, a single-stranded DNA/RNA hybrid, or a double-stranded DNA/RNA hybrid) donor molecule that is integrated at the site of an at least one double-strand break (DSB) in a genome. In an embodiment, the polynucleotide donor molecule includes one or more strands containing chemically modified DNA. Embodiments include double-stranded DNA or double-stranded DNA/RNA hybrid donor molecules, and single-stranded DNA or single-stranded DNA/RNA hybrid donor molecules, the sequence of which in analogous procedures is integrated at the site of at least one DSB. In an embodiment, sequence encoded by the polynucleotide donor molecule that is integrated at the site of at least one double-stand break (DSB) in a genome includes a transcription factor binding sequence, the specific binding agent is the corresponding transcription factor (or more specifically, the DNA-binding domain of the corresponding transcription factor), and the change in expression is upregulation or downregulation (depending on the type of transcription factor involved). In an embodiment, the transcription factor is an activating transcription factor or activator, and the change in expression is upregulation or increased expression of a sequence of interest to which the transcription factor binding sequence, when integrated at a DSB in the genome, is operably linked. In another embodiment, the transcription factor is a repressing transcription factor or repressor, and the change in expression is downregulation or decreased expression of a sequence of interest to which the transcription factor binding sequence when integrated at a DSB in the genome, is operably linked.

Examples of transcription factor binding sequences useful in compositions, reaction mixtures, cells, and methods of the invention include the *Arabidopsis thaliana* sequences provided in Table 6 (publicly available at *arabidopsis*[dot]med [dot]ohio-state [dot]edu/AtcisDB/bindingsites[dot]html).

TABLE 6

| Transcription Factor Binding Site Name | Sequence or consensus motif | SEQ ID NO: |
|---|---|---|
| ABFs binding site motif | CACGTGGC | 167 |
| ABRE binding site motif | (C/T)ACGTGGC | 168 |
| ABRE-like binding site motif | (C/G/T)ACGTG(G/T)(A/C) | 169 |
| ACE promoter motif | GACACGTAGA | 170 |
| AG binding site motif | TT(A/G/T)CC(A/T)(A/T)(A/T)(A/T)(A/T)(A/T)GG (A/C/T) | 171 |
| AG binding site in AP3 | CCATTTTTAGT | 172 |
| AG binding site in SUP | CCATTTTTGG | 173 |
| AGL1 binding site motif | NTT(A/G/T)CC(A/T)(A/T)(A/T)(A/T)NNGG(A/T)AAN | 174 |
| AGL2 binding site motif | NN(A/T)NCCA(A/T)(A/T)(A/T)(A/T)T(A/G)G(A/T)(A/T) AN | 175 |
| AGL3 binding site motif | TT(A/T)C(C/T)A(A/T)(A/T)(A/T)(A/T)T(A/G)G(A/T)AA | 176 |
| AP1 binding site in AP3 | CCATTTTTAG | 177 |
| AP1 binding site in SUP | CCATTTTTGG | 178 |
| ARF binding site motif | TGTCTC | 179 |
| ARF1 binding site motif | TGTCTC | 180 |
| ATHB1 binding site motif | CAAT(A/T)ATTG | 181 |
| ATHB2 binding site motif | CAAT(C/G)ATTG | 182 |

TABLE 6-continued

| Transcription Factor Binding Site Name | Sequence or consensus motif | SEQ ID NO: |
|---|---|---|
| ATHB5 binding site motif | CAATNATTG | 183 |
| ATHB6 binding site motif | CAATTATTA | 184 |
| AtMYB2 binding site in RD22 | CTAACCA | 185 |
| AtMYC2 binding site in RD22 | CACATG | 186 |
| Box II promoter motif | GGTTAA | 187 |
| CArG promoter motif | CC(A/T)(A/T)(A/T)(A/T)(A/T)(A/T)GG | 188 |
| CArG1 motif in AP3 | GTTTACATAAATGGAAAA | 189 |
| CArG2 motif in AP3 | CTTACCTTTCATGGATTA | 190 |
| CArG3 motif in AP3 | CTTTCCATTTTTAGTAAC | 191 |
| CBF1 binding site in cor15a | TGGCCGAC | 192 |
| CBF2 binding site motif | CCACGTGG | 193 |
| CCA1 binding site motif | AA(A/C)AATCT | 194 |
| CCA1 motif1 binding site in CAB1 | AAACAATCTA | 195 |
| CCA1 motif2 binding site in CAB1 | AAAAAAAATCTATGA | 196 |
| DPBF1&2 binding site motif | ACACNNG | 197 |
| DRE promoter motif | TACCGACAT | 198 |
| DREB1&2 binding site in rd29a | TACCGACAT | 199 |
| DRE-like promoter motif | (A/G/T)(A/G)CCGACN(A/T) | 200 |
| E2F binding site motif | TTTCCCGC | 201 |
| E2F/DP binding site in AtCDC6 | TTTCCCGC | 202 |
| E2F-varient binding site motif | TCTCCCGCC | 203 |
| EIL1 binding site in ERF1 | TTCAAGGGGGCATGTATCTTGAA | 204 |
| EIL2 binding site in ERF1 | TTCAAGGGGGCATGTATCTTGAA | 205 |
| EIL3 binding site in ERF1 | TTCAAGGGGGCATGTATCTTGAA | 206 |
| EIN3 binding site in ERF1 | GGATTCAAGGGGGCATGTATCTTGAATCC | 207 |
| ERE promoter motif | TAAGAGCCGCC | 208 |
| ERF1 binding site in AtCHI-B | GCCGCC | 209 |
| EveningElement promoter motif | AAAATATCT | 210 |
| GATA promoter motif | (A/T)GATA(G/A) | 211 |
| GBF1/2/3 binding site in ADH1 | CCACGTGG | 212 |
| G-box promoter motif | CACGTG | 213 |
| GCC-box promoter motif | GCCGCC | 214 |
| GT promoter motif | TGTGTGGTTAATATG | 215 |
| Hexamer promoter motif | CCGTCG | 216 |
| HSEs binding site motif | AGAANNTTCT | 217 |
| Ibox promoter motif | GATAAG | 218 |
| JASE1 motif in OPR1 | CGTCAATGAA | 219 |

TABLE 6-continued

| Transcription Factor Binding Site Name | Sequence or consensus motif | SEQ ID NO: |
|---|---|---|
| JASE2 motif in OPR2 | CATACGTCGTCAA | 220 |
| L1-box promoter motif | TAAATG(C/T)A | 221 |
| LS5 promoter motif | ACGTCATAGA | 222 |
| LS7 promoter motif | TCTACGTCAC | 223 |
| LTRE promoter motif | ACCGACA | 224 |
| MRE motif in CHS | TCTAACCTACCA | 225 |
| MYB binding site promoter | (A/C)ACC(A/T)A(A/C)C | 226 |
| MYB1 binding site motif | (A/C)TCC(A/T)ACC | 227 |
| MYB2 binding site motif | TAACT(G/C)GTT | 228 |
| MYB3 binding site motif | TAACTAAC | 229 |
| MYB4 binding site motif | A(A/C)C(A/T)A(A/C)C | 230 |
| Nonamer promoter motif | AGATCGACG | 231 |
| OBF4,5 binding site in GST6 | ATCTTATGTCATTGATGACGACCTCC | 232 |
| OBP-1,4,5 binding site in GST6 | TACACTTTTGG | 233 |
| OCS promoter motif | TGACG(C/T)AAG(C/G)(A/G)(A/C)T(G/T)ACG(C/T)(A/C)(A/C) | 234 |
| octamer promoter motif | CGCGGATC | 235 |
| PI promoter motif | GTGATCAC | 236 |
| PII promoter motif | TTGGTTTTGATCAAAACCAA | 237 |
| PRHA binding site in PAL1 | TAATTGACTCAATTA | 238 |
| RAV1-A binding site motif | CAACA | 239 |
| RAV1-B binding site motif | CACCTG | 240 |
| RY-repeat promoter motif | CATGCATG | 241 |
| SBP-box promoter motif | TNCGTACAA | 242 |
| T-box promoter motif | ACTTTG | 243 |
| TEF-box promoter motif | AGGGGCATAATGGTAA | 244 |
| TELO-box promoter motif | AAACCCTAA | 245 |
| TGA1 binding site motif | TGACGTGG | 246 |
| W-box promoter motif | TTGAC | 247 |
| Z-box promoter motif | ATACGTGT | 248 |
| AG binding site in SPL/NOZ | AAAACAGAATAGGAAA | 249 |
| Bellringer/replumless pennywise binding site IN AG | AAATTAAA | 250 |
| Bellringer/replumless/ pennywise binding site 2 in AG | AAATTAGT | 251 |
| Bellringer/replumless/ pennywise binding site 3 in AG | ACTAATTT | 252 |
| AGL15 binding site in AtGA2ox6 | CCAATTTAATGG | 253 |

TABLE 6-continued

| Transcription Factor Binding Site Name | Sequence or consensus motif | SEQ ID NO: |
|---|---|---|
| ATB2/AtbZIP53/AtbZIP44/GBF5 binding site in ProDH | ACTCAT | 254 |
| LFY binding site in AP3 | CTTAAACCCTAGGGGTAAT | 255 |
| SORLREP1 | TT(A/T)TACTAGT | 256 |
| SORLREP2 | ATAAAACGT | 257 |
| SORLREP3 | TGTATATAT | 258 |
| SORLREP4 | CTCCTAATT | 259 |
| SORLREP5 | TTGCATGACT | 260 |
| SORLIP1 | AGCCAC | 261 |
| SORLIP2 | GGGCC | 262 |
| SORLIP3 | CTCAAGTGA | 263 |
| SORLIP4 | GTATGATGG | 264 |
| SORLIP5 | GAGTGAG | 265 |
| ABFs binding site motif | CACGTGGC | 266 |

Other transcription factors and sequences or nucleotide motifs for the corresponding transcription factor recognition sites are known in the art and can similarly be included in a polynucleotide molecule sequence to be integrated at one or more DSBs introduced into genomic sequence; see, e. g., neomorph[dot]salk[dot]edu/dap_web/pages/index[dot]php.

Example 8

This example illustrates a method of integrating sequence encoded by a polynucleotide (such as a double-stranded DNA, a single-stranded DNA, a single-stranded DNA/RNA hybrid, or a double-stranded DNA/RNA hybrid) donor molecule at the site of at least one double-strand break (DSB) in a genome. More specifically, this non-limiting example illustrates using a ribonucleoprotein (RNP) including a guide RNA (gRNA) and a nuclease to effect a DSB in the genome of a monocot plant, and integration of sequence encoded by a double-stranded DNA (dsDNA) at the site of the DSB.

Experimental details were similar to those described in Example 4. As in Example 4, the target gene selected for editing was the maize (*Zea mays*) alcohol dehydrogenase ADH1 (see www[dot]maizegdb[dot]org/gene_center/gene/GRMZM2G442658) with the partial genomic sequence of SEQ ID NO:21; the first exon (SEQ ID NO:22) is located at nucleotide positions 409-571 of SEQ ID NO:21 and guide RNA (crRNA) sequences were designed to edit this exon.

Maize protoplasts were prepared as described in Examples 1 and 4. A ribonucleoprotein (RNP) was prepared with Cas9 nuclease (Aldevron, Fargo, ND) and a guide RNA complex of a crRNA (ZmADH1-B) having the sequence GGCCUCCCAGAAGUAGACGUGUUUUAGAGC-UAUGCU (SEQ ID NO:23) and a tracrRNA (both purchased from Integrated DNA Technologies, Coralville, IA). A chemically modified double-stranded DNA (dsDNA) molecule of 34 base pairs was produced by annealing one strand having the sequence 5'-GTTTAATTGAGTTGTCATATGT-TAATAACGGTAT-3' (SEQ ID NO:267, which contains an NdeI recognition site at nucleotide positions 16-21 shown as underlined font) and a second strand having the sequence 5'-ATACCGTTATTAACATATGACAACTCAATTAAAC-3' (SEQ ID NO:268) (both purchased from Integrated DNA Technologies, Coralville, IA); each strand was phosphorylated on the 5' end and contained two phosphorothioate linkages at each terminus (i. e., the two linkages between the most distal three bases on either end of the strand). Transfection procedures for editing the target gene ADH1 in the maize protoplasts were identical to those described in Examples 1 and 4, except the dsDNA was added at a concentration of 1 nanomolar together with the RNP. (In an alternative procedure, the RNP can be added first, followed by the dsDNA.)

A T7 endonuclease (T7E1, New England Biolabs, Ipswich, MA) was used in a heteroduplex cleavage assay to detect on-target editing. In brief, genomic DNA from the protoplasts was amplified by PCR; the amplified products were denatured and re-annealed to allow heteroduplex formation between wild-type or unedited DNA and the edited DNA. T7E1, which recognizes and cleaves mismatched DNA, was used to digest the heteroduplexes, and the resulting cleaved and full-length PCR products are analysed by gel electrophoresis. The primers used for the T7E1 assay had the sequences GAACAGTGCCGCAGTGGCG (forward primer, SEQ ID NO:24) and TACCCTCCAGCCTCGTGGC (reverse primer, SEQ ID NO:25) for an expected amplicon size of 720 base-pairs (i. e., SEQ ID NO:21). In a separate endonuclease assay, NdeI restriction enzyme was used. In both the T7E1 and NdeI assays, gel electrophoretic analysis demonstrated the presence of the expected cleavage products.

For quantitation of editing efficiency, next-generation sequencing (NGS) analysis was used. A second set of primers were used for CRISPR sequencing; these had the sequences ACTATGCGATTGCTTTCCTGGAC (forward primer, SEQ ID NO:26) and ACCGCGAGTTGTTGTAT-CATATCT (reverse primer, SEQ ID NO:27) for an expected amplicon size of 230 base-pairs (SEQ ID NO:28) which includes the ADH1 first exon (SEQ ID NO:22). The NGS sequencing results are provided in FIGS. 4A-4D, depicting the alignments of the cloned sequences SEQ ID NOs:269-304. The editing efficiency (percentage of the total population of cells in which DSB is correctly induced in the genome) was estimated to be 23% and the insertion efficiency (percentage of the total population of cells in which the dsDNA molecule is successfully introduced at the DSB correctly located in the genome) was estimated to be 17%.

Additional experiments were carried out using the same procedure for editing the ADH1 maize gene, using variations of the 34-base-pair chemically modified dsDNA molecule (all purchased from Integrated DNA Technologies, Coralville, IA) provided at 1 nanomolar together with the RNP to maize protoplasts. In one set of experiments, the dsDNA molecule was provided by annealing one DNA strand having the sequence of SEQ ID NO:267 and a second DNA strand having the sequence (SEQ ID NO:268); each strand was phosphorylated on the 5' end but contained no phosphorothioate linkages. In a second set of experiments, the dsDNA molecule was provided by annealing one DNA strand having the sequence of SEQ ID NO:267 and a second DNA strand having the sequence (SEQ ID NO:268); each strand was phosphorylated on the 5' end and contained four phosphorothioate linkages at each terminus (i. e., the four linkages between the most distal five bases on either end of the strand). In a second set of experiments, the dsDNA molecule was provided by annealing one DNA strand having the sequence of SEQ ID NO:267 and that was phosphorylated on the 5' end and contained two phosphorothioate linkages at each terminus (i. e., the two linkages between the most distal three bases on either end of the strand), and a second DNA strand having the sequence (SEQ ID NO:268) and that contained two phosphorothioate linkages at each terminus (i. e., the two linkages between the most distal three bases on either end of the strand) but was not phosphorylated on the 5' end.

Example 9

This example illustrates a method of changing expression of a sequence of interest in a genome, comprising integrating sequence encoded by a polynucleotide (such as a double-stranded DNA, a single-stranded DNA, a single-stranded DNA/RNA hybrid, or a double-stranded DNA/RNA hybrid) donor molecule at the site of at least one double-strand break (DSB) in a genome. More specifically, this non-limiting example illustrates using a ribonucleoprotein (RNP) including a guide RNA (gRNA) and a nuclease to effect a DSB in the genome of a monocot plant, and integration of sequence encoded by a double-stranded DNA (dsDNA) at the site of the DSB, wherein the sequence encoded by the dsDNA molecule includes a sequence recognizable by a specific binding agent, and wherein contacting the integrated sequence encoded by the dsDNA molecule with the specific binding agent results in a change of expression of a sequence of interest. In this particular example, sequence encoded by the dsDNA molecule is integrated at a DSB located in non-coding genomic sequence (i. e., in a promoter region), the sequence recognizable by a specific binding agent includes an auxin response element (AuxRE) sequence, the specific binding agent is an auxin (e. g., an exogenously applied auxin), and the change of expression is upregulation of the sequence of interest.

Experimental details were similar to those described in Examples 4 and 8. The target gene selected for editing was non-coding sequence, in this case the partial promoter sequence (sequence upstream of the transcription start site) of the maize (*Zea mays*) Lc gene (see www[dot]maizegdb [dot]org/gene_center/gene/GRMZM5G822829) with the sequence of GGGTTGTTGTGGGTTGAACCCGTCC-CAACCATCATCAACTCGCTAGCCAAACACACGCTT AGGGGCCAAAGCAGTGCTATAATAT-GAGTGGTGGCGCTATTATATATAGCGTCAGAGAA CTTAGATCTGATATTCTGATGAAGAAAAAATGACTT-TACTGACTACGAAAGAAGAAGAA AGGAGC-TATAGAGAGAGAGAAAAAGAGGGGTCGTGTAGTG CTTAAACTGTACATGAAC AGCAGTAGTGTTA-CAGAAGCTAAACTCAACCAGAGCTCCACCAAA-GACAAAGAGGGTCT ACTTCCAT-CACCGTCTTGCTCGGTCACTTGGAGCTCTGTCCATA AATTAAACCCATCTTGG ATCCCAAGGTTCGTGG-CATATCTGTAGGCATC-TACCCCGTCTTCGTCGTCCGCTCCTCACT AGCTAC-CAAGAGGTCGCCATTATTGCCAACATAGAGTGTAC GTGGATGTCTATATATATG CCTACTTGCACC-CATATGGC (SEQ ID NO:305); and guide RNA (crRNA) sequences were designed to edit this non-coding sequence.

Maize protoplasts were prepared as described in Examples 1, 4, and 8. A ribonucleoprotein (RNP) was prepared with Cas9 nuclease (Aldevron, Fargo, ND) and a guide RNA complex of a crRNA (ZmLc Pro-1) having the sequence GCUCCUCACUAGCUACCAAGGUUUUA-GAGCUAUGCU (SEQ ID NO:306) and a tracrRNA (both purchased from Integrated DNA Technologies, Coralville, IA). Three different lengths of chemically modified double-stranded DNA (dsDNA) molecules were used in this experiment, with each dsDNA added at a concentration of 1 nanomolar together with the RNP. The transfection procedures for editing the target gene Lc in the maize protoplasts were otherwise identical to those described in Example 8.

All dsDNA molecules were purchased from Integrated DNA Technologies, Coralville, IA One dsDNA ("3×DR5") molecule of 34 base pairs was produced by annealing a first strand having the sequence 5'-ccgacaaaaggccgacaaaaggccgacaaaaggt-3' (SEQ ID NO:306) and a second strand having the sequence 5'-accttttgtcggccttttgtcggccttttgtcgg-3' (SEQ ID NO:307, which includes three concatenated copies of an auxin response element having the sequence ccttttgtcgg (SEQ ID NO:308)). A second dsDNA ("6×DR5") molecule of 68 base pairs was produced by annealing a first strand having the sequence 5'-GCCGACAAAAGGCCGACAAAAGGCCGACAAAA GGCCGACAAAAGGCCGACAAAAGGCC GACAAAAGGT-3' (SEQ ID NO:309) and a second strand having the sequence 5'-ACCTTTTGTCGGCCTTTTGTCGGCCTTTTGTCGG CCTTTTGTCGGCCTTTTGTCGGCCTTTT GTCGGC-3' (SEQ ID NO:310, which includes six concatenated copies of the auxin response element having the sequence SEQ ID NO:308). A third dsDNA ("9×DR5") molecule of 100 base pairs was produced by annealing a first strand having the sequence 5'-CCGACAAAAGGCCGACAAAAGGCCGACAAAAG GCCGACAAAAGGCCGACAAAAGGCCG ACAAAAGGCCGACAAAAGGCCGACAAAAGGCCGA CAAAAGGT-3' (SEQ ID NO:311) and a second strand having the sequence 5'-ACCTTTTGTCGGCCTTTTGTCGGCCTTTTGTCGGC CTTTTGTCGGCCTTTTGTCGGCCTTTT GTCGGCCTTTTGTCGGCCTTTTGTCGGCCTTTTGTC GG-3' (SEQ ID NO:312 which includes nine concatenated copies of the auxin response element having the sequence SEQ ID NO:308). In all cases, each strand was phosphorylated on the 5' end and contained two phosphorothioate linkages at each terminus (i. e., the two linkages between the most distal three bases on either end of the strand).

For quantitation of editing efficiency, next-generation sequencing (NGS) analysis was used. A second set of primers were used for CRISPR sequencing; these had the sequences CTCCACCAAAGACAAAGAGGG (forward primer, SEQ ID NO:313) and GCCATATGGGTGCAAGTAGGC (reverse primer, SEQ ID NO:314) for an expected amplicon size of 226 base-pairs (SEQ ID NO:315). Based on the NGS sequencing results, the editing efficiency (percentage of the total population of cells in which DSB is correctly induced in the genome) for the 3×DR5 insertion was estimated to be 34% and the insertion efficiency (percentage of the total population of cells in which the dsDNA molecule is successfully introduced at the DSB correctly located in the genome) was estimated to be 21%; for the 6×DR5 insertion, the editing efficiency was estimated to be 25% and the insertion efficiency was estimated to be 3%; and for the 9×DR5 insertion, the editing efficiency was estimated to be 11% and the insertion efficiency was estimated to be less than 1%.

All of the dsDNA molecules were designed to contain at least one sequence recognizable by a specific binding agent, in this case multiple copies of an auxin response element (SEQ ID NO:308). As the dsDNA molecules were integrated at the site of a DSB in promoter sequence operably linked to the gene of interest (the endogenous maize Lc gene), and the culture medium contained an herbicide (2, 4-dichlorophenoxyacetic acid) with auxin-like properties, expression of the gene of interest (the Lc gene) was expected to increase in cells that had the dsDNA molecule integrated into their genome, relative to that in cells that did not have the dsDNA molecule integrated into their genome. Quantitative RT-PCR was employed on three technical replicates per treatment to measure the relative expression of the Lc gene. Controls were cells that had been subjected to the transfection procedure without an RNP. Results are provided in Table 7 with Lc gene expression levels normalized to tubulin. These data demonstrate that, in each case, integration of the dsDNA molecules containing the auxin response factor sequences into the Lc promoter region resulted in very strong upregulation of Lc expression in the presence of auxin.

TABLE 7

| Treatment | Lc relative expression | standard deviation | Increase in relative expression |
|---|---|---|---|
| dsDNA = 3xDR5 | 3863.48 | 174.46 | 304-fold |
| dsDNA = 6xDR5 | 1479.15 | 74.99 | 116-fold |
| dsDNA = 9xDR5 | 1030.89 | 28.01 | 81-fold |
| RNP alone (no dsDNA) | 12.72 | 2.63 | 1 |
| no RNP | 1.02 | 0.25 | n.a. |

Example 10

This example illustrates a method of integrating sequence encoded by a polynucleotide (such as a double-stranded DNA, a single-stranded DNA, a single-stranded DNA/RNA hybrid, or a double-stranded DNA/RNA hybrid) donor molecule at the site of at least one double-strand break (DSB) in a genome. More specifically, this non-limiting example illustrates using a ribonucleoprotein (RNP) including a guide RNA (gRNA) and a nuclease to effect a DSB in the genome of a dicot plant, and integration of sequence encoded by a double-stranded DNA (dsDNA) at the site of the DSB.

Experimental details were similar to those described in Example 5. As in Example 5, the target gene selected for editing was the kale (*Brassica oleracea*) "*Gigantea*" gene BoGI with the partial genomic sequence of SEQ ID NO:41, including part of the first exon (SEQ ID NO:42) and the second exon (SEQ ID NO:43) located respectively at nucleotide positions 1-60 and 132-203 of SEQ ID NO:41.

Kale protoplasts were prepared as described in Examples 1 and 5. A ribonucleoprotein (RNP) was prepared with Cas9 nuclease (Aldevron, Fargo, ND) and a guide RNA complex of a crRNA (BoGI-1) having the sequence of SEQ ID NO:44 and a tracrRNA (both purchased from Integrated DNA Technologies, Coralville, IA). A chemically modified double-stranded DNA (dsDNA) molecule of 34 base pairs was produced by annealing one strand having the sequence of SEQ ID NO:267, containing an NdeI recognition site at nucleotide positions 16-21, and a second strand having the sequence of SEQ ID NO:268 (both purchased from Integrated DNA Technologies, Coralville, IA); each strand was phosphorylated on the 5' end and contained two phosphorothioate linkages at each terminus (i. e., the two linkages between the most distal three bases on either end of the strand).

Transfection procedures for editing the target gene BoGI in the kale protoplasts were identical to those described in Examples 1 and 5, except the dsDNA was added at a concentration of 1 nanomolar together with the RNP. (In an alternative procedure, the RNP can be added first, followed by the dsDNA.)

For quantitation of editing efficiency, next-generation sequencing (NGS) analysis was used. The primers used for CRISPR sequencing had the sequences CCGATGGTCTTCAGTTCTCT (forward primer, SEQ ID NO:45) and CCTCAGCAATATCATCAGGG (reverse primer, SEQ ID NO:46) for an expected amplicon size of 206 base-pairs (i. e., SEQ ID NO:41). The editing efficiency was estimated to be 76%.

Additional experiments were carried out using the same procedure for editing the kale BoGI gene, using variations of the 34-base-pair chemically modified dsDNA molecule (all purchased from Integrated DNA Technologies, Coralville, IA) provided at 1 nanomolar together with the RNP to maize protoplasts. In one set of experiments, the dsDNA molecule was provided by annealing one DNA strand having the sequence of SEQ ID NO:267 and a second DNA strand having the sequence (SEQ ID NO:268); each strand was phosphorylated on the 5' end but contained no phosphorothioate linkages. In a second set of experiments, the dsDNA molecule was provided by annealing one DNA strand having the sequence of SEQ ID NO:267 and a second DNA strand having the sequence (SEQ ID NO:268); each strand was phosphorylated on the 5' end and contained four phosphorothioate linkages at each terminus (i. e., the four linkages between the most distal five bases on either end of the strand). In a second set of experiments, the dsDNA molecule was provided by annealing one DNA strand having the sequence of SEQ ID NO:267 and that was phosphorylated on the 5' end and contained two phosphorothioate linkages at each terminus (i. e., the two linkages between the most distal three bases on either end of the strand), and a second DNA strand having the sequence (SEQ ID NO:268) and that contained two phosphorothioate linkages at each terminus (i. e., the two linkages between the most distal three bases on either end of the strand) but was not phosphorylated on the 5' end.

Example 11

This example illustrates a method of changing expression of a sequence of interest in a genome, comprising integrating sequence encoded by a polynucleotide (such as a double-stranded DNA, a single-stranded DNA, a single-stranded DNA/RNA hybrid, or a double-stranded DNA/RNA hybrid) donor molecule at the site of at least one double-strand break (DSB) in a genome. More specifically, this non-limiting example illustrates using a ribonucleoprotein (RNP) including a guide RNA (gRNA) and a nuclease to effect a DSB in the genome of a plant, and integration of sequence encoded by a double-stranded DNA (dsDNA) at the site of the DSB, wherein the dsDNA molecule includes a sequence recognizable by a specific binding agent, and wherein contacting the integrated sequence encoded by dsDNA molecule with the specific binding agent results in a change of expression of a sequence of interest. In this particular example, the sequence recognizable by a specific binding agent includes a recombinase recognition site sequence, the specific binding agent is a site-specific recombinase, and the change of expression is upregulation or downregulation or expression of a transcript having an altered sequence (for example, expression of a transcript that has had a region of DNA excised, inverted, or translocated by the recombinase).

The loxP ("locus of cross-over") recombinase recognition site and its corresponding recombinase Cre, were originally identified in the P1 bacteriophage. The wild-type loxP 34 base-pair sequence is (SEQ ID NO: 316)
ATAACTTCGTATAGCATACATTATACGAAGTTAT and includes two 13 base-pair palindromic sequences flanking an 8 base-pair spacer sequence; the spacer sequence, shown in underlined font, is asymmetric and provides directionality to the loxP site. Other useful loxP variants or recombinase recognition site sequence that function with Cre recombinase are provided in Table 8.

TABLE 8

| SEQ ID NO: | Cre recombinase recognition site | Sequence |
|---|---|---|
| 316 | LoxP (wild-type 1) | ATAACTTCGTATAGCATACATTATACGAAGTTAT |
| 317 | LoxP (wild-type 2) | ATAACTTCGTATAATGTATGCTATACGAAGTTAT |
| 318 | Canonical LoxP | ATAACTTCGTATANNNTANNNTATACGAAGTTAT |
| 319 | Lox 511 | ATAACTTCGTATAATGTATACTATACGAAGTTAT |
| 320 | Lox 5171 | ATAACTTCGTATAATGTGTACTATACGAAGTTAT |
| 321 | Lox 2272 | ATAACTTCGTATAAAGTATCCTATACGAAGTTAT |
| 322 | M2 | ATAACTTCGTATAAGAAACCATATACGAAGTTAT |
| 323 | M3 | ATAACTTCGTATATAATACCATATACGAAGTTAT |
| 324 | M7 | ATAACTTCGTATAAGATAGAATATACGAAGTTAT |
| 325 | M11 | ATAACTTCGTATAAGATAGAATATACGAAGTTAT |
| 326 | Lox 71 | TACCGTTCGTATANNNTANNNTATACGAAGTTAT |
| 327 | Lox 66 | ATAACTTCGTATANNNTANNNTATACGAACGGTA |

Cre recombinase catalyzes the recombination between two compatible (non-heterospecific) loxP sites, which can be located either on the same or on separate DNA molecules. Thus, in embodiments of the invention, polynucleotide (such as double-stranded DNA, single-stranded DNA, single-stranded DNA/RNA hybrid, or double-stranded DNA/RNA hybrid) molecules including compatible recombinase recognition sites sequence are integrated at the site of two or more double-strand breaks (DSBs) in a genome, which can be on the same or on separate DNA molecules (such as chromosomes). Depending on the number of recombinase recognition sites, where these are integrated, and in what orientation, various results are achieved, such as expression of a transcript that has had a region of DNA excised, inverted, or translocated by the recombinase. For example, in the case where one pair of loxP sites (or any pair of compatible recombinase recognition sites) are integrated at the site of DSBs in the genome, if the loxP sites are on the same DNA molecule and integrated in the same orientation, the genomic sequence flanked by the loxP sites is excised, resulting in a deletion of that portion of the genome. If the loxP sites are on the same DNA molecule and integrated in opposite orientation, the genomic sequence flanked by the loxP sites is inverted. If the loxP sites are on separate DNA molecules, translocation of genomic sequence adjacent to the loxP site occurs. Examples of heterologous arrangements or integration patterns of recombinase recognition sites and methods for their use, particularly in plant breeding, are disclosed in U.S. Pat. No. 8,816,153 (see, for example, the Figures and working examples), the entire specification of which is incorporated herein by reference.

One of skill in the art would recognize that the details provided here are applicable to other recombinases and their corresponding recombinase recognition site sequences, such as, but not limited to, FLP recombinase and frt recombinase recognition site sequences, R recombinase and Rs recombinase recognition site sequences, Dre recombinase and rox recombinase recognition site sequences, and Gin recombinase and gix recombinase recognition site sequences.

Example 12

This example illustrates a method of changing expression of a sequence of interest in a genome, comprising integrating sequence encoded by a polynucleotide (such as a double-stranded DNA, a single-stranded DNA, a single-stranded DNA/RNA hybrid, or a double-stranded DNA/RNA hybrid) donor molecule at the site of at least one double-strand break (DSB) in a genome. This example illustrates introducing at least two DSBs into a genome by one or more nucleases in such a way that genomic sequence is deleted between the DSBs (leaving a deletion with blunt ends, overhangs or a combination of a blunt end and an overhang), and sequence encoded by at least one polynucleotide molecule is integrated between the DSBs (i. e., sequence encoded by at least one individual polynucleotide molecule is integrated at the location of the deleted genomic sequence). In an embodiment, the polynucleotide molecule includes one or more strands containing chemically modified DNA. Embodiments include double-stranded DNA or double-stranded DNA/RNA hybrid molecules, and single-stranded DNA or single-stranded DNA/RNA hybrid molecules, the sequence of which in analogous procedures is integrated at the location of genomic sequence that has been deleted between two DSBs. More specifically, this non-limiting example illustrates using multiple different ribonucleoproteins (RNPs), wherein each RNP includes a guide RNA (gRNA) and a nuclease, to effect multiple DSBs in the genome of a monocot plant, and integration of sequence encoded by a double-stranded DNA (dsDNA) at the location of the genomic sequence that is deleted between two DSBs. In this particular example, the sequence encoded by the dsDNA molecule includes a sequence recognizable by a specific binding agent and is integrated between two DSBs that are introduced into non-coding genomic sequence (i. e., in a promoter region); the sequence recognizable by a specific binding agent includes an auxin response element (AuxRE) sequence, the specific binding agent is an auxin (e. g., an exogenously applied auxin), and contacting the integrated dsDNA molecule with the specific binding agent results in a change of expression of the sequence of interest (upregulation of the gene to which the promoter is operably linked). This example also illustrates a method to modify expression of a sequence of interest (e. g., increased or decreased levels of the sequence's transcript or of a polypeptide encoded by the sequence, a change in stability of the sequence's transcript, or a change in the expression pattern of the sequence) by modifying a region of the genome that is operably linked to the sequence of interest, i. e., modification of that operably linked genomic region results in a change the expression level or expression pattern of the sequence of interest.

Experimental details were similar to those described in Examples 4, 8, and 9. The target gene selected for editing was non-coding sequence, in this case the partial promoter sequence (sequence upstream of the transcription start site) of the maize (*Zea mays*) Lc gene (see www[dot]maizegdb [dot]org/gene_center/gene/GRMZM5G822829) with the sequence of GGGTTGTTGTGGGTTGAACCCGTCCCAACCATCATCAACTCGCTAGCCAAACACACGCTT AGGGGCCAAAGCAGTGCTATAATATGAGTGGTGGCGCTATTATATATAGCGTCAGAGAA CTTAGATCTGATATTCTGATGAAGAAAAAATGACTTTACTGACTACGAAAGAAGAAGAA AGGAGCTATAGAGAGAGAGAAAAAGAGGGGTCGTGTAGTG CTTAAACTGTACATGAAC AGCAGTAGTGTTACAGAAGCTAAACTCAACCAGAGCTCCACCAAAGACAAAGAGGGTCT ACTTCCATCACCGTCTTGCTCGGTCACTTGGAGCTCTGTCCATA AATTAAACCCATCTTGG ATCCCAAGGTTCGTGGCATATCTGTAGGCATCTACCCCGTCTTCGTCGTCCGCTCCTCACT AGCTACCAAGAGGTCGCCATTATTGCCAACATAGAGTGTAC GTGGATGTCTATATATATG CCTACTTGCACCCATATGGC (SEQ ID NO:305); and guide RNA (crRNA) sequences were designed to edit this non-coding sequence.

Maize protoplasts were prepared as described in Examples 1, 4, 8, and 9. Ribonucleoproteins (RNPs) were prepared with Cas9 nuclease (Aldevron, Fargo, ND) and guide RNA complexes. Two guide RNA complexes were made with a crRNA and a tracrRNA (crRNAs and tracrRNA were purchased from Integrated DNA Technologies, Coralville, IA); the first guide RNA complex used a crRNA (ZmLc Pro-1) having the sequence GCUCCUCACUAGCUACCAAGGUUUUAGAGCUAUGCU (SEQ ID NO:306) and the second guide RNA complex used a crRNA (ZmLc Pro-3) having the sequence CUCCAAGUGACCGAGCAAGAGUUUUAGAGCUAUGCU (SEQ ID NO:334).

Three different lengths of chemically modified double-stranded DNA (dsDNA) molecules were used in this experiment, with each dsDNA added at a concentration of 1 nanomolar together with the RNP. The transfection procedures for editing the target gene Lc in the maize protoplasts were otherwise identical to those described in Example 8 and 9. All dsDNA molecules were purchased from Integrated DNA Technologies, Coralville, IA One dsDNA ("3×DR5") molecule of 34 base pairs was produced by annealing a first strand having the sequence 5'-ccgacaaaaggccgacaaaaggccgacaaaaggt-3' (SEQ ID NO:306) and a second strand having the sequence 5'-accttttgtcggccttttgtcggccttttgtcgg-3' (SEQ ID NO:307, which includes three concatenated copies of an auxin response element having the sequence ccttttgtcgg (SEQ ID NO:308)). A second dsDNA ("6×DR5") molecule of 68 base pairs was produced by annealing a first strand having the sequence 5'-GCCGACAAAAGGCCGACAAAAGGCCGACAAAA GGCCGACAAAAGGCCGACAAAAGGCC GACAAAAGGT-3' (SEQ ID NO:309) and a second strand having the sequence 5'-ACCTTTTGTCGGCCTTTTGTCGGCCTTTTGTCGG CCTTTTGTCGGCCTTTTGTCGGCCTTTT GTCGGC-3' (SEQ ID NO:310, which includes six concatenated copies of the auxin response element having the sequence SEQ ID NO:308). A third dsDNA ("9×DR5") molecule of 100 base pairs was produced by annealing a first strand having the sequence 5'-CCGACAAAAGGCCGACAAAAGGCCGACAAAAG GCCGACAAAAGGCCGACAAAAGGCCG ACAAAAGGCCGACAAAAGGCCGACAAAAGGCCGA CAAAAGGT-3' (SEQ ID NO:311) and a second strand having the sequence 5'-ACCTTTTGTCGGCCTTTTGTCGGCCTTTTGTCGGC CTTTTGTCGGCCTTTTGTCGGCCTTTT GTCGGCCTTTTGTCGGCCTTTTGTCGGCCTTTTGTC GG-3' (SEQ ID NO:312 which includes nine concatenated copies of the auxin response element having the sequence SEQ ID NO:308). In all cases, each strand was phosphorylated on the 5' end and contained two phosphorothioate linkages at each terminus (i. e., the two linkages between the most distal three bases on either end of the strand).

For quantitation of editing efficiency, next-generation sequencing (NGS) analysis was used. A second set of primers were used for CRISPR sequencing; these had the sequences CTCCACCAAAGACAAAGAGGG (forward primer, SEQ ID NO:313) and GCCATATGGGTGCAAGTAGGC (reverse primer, SEQ ID NO:314) for an expected amplicon size of 226 base-pairs (SEQ ID NO:315).

All of the dsDNA molecules were designed to contain at least one sequence recognizable by a specific binding agent, in this case multiple copies of an auxin response element (SEQ ID NO:308). In this example, the dsDNA molecules were integrated at the site where non-coding genomic sequence was deleted (i. e., integrated between the DSBs introduced at two discrete locations in the genome, in this case in the Lc promoter). This effected replacement of part of the Lc promoter sequence with multiple copies of the auxin response element. As the culture medium contained an herbicide (2, 4-dichlorophenoxyacetic acid) with auxin-like properties, expression of the gene of interest (the endogenous maize Lc gene) operably linked to the Lc promoter sequence was expected to increase in cells that had any of the dsDNA molecules integrated into their genome, relative to that in cells that did not have a dsDNA molecule integrated into their genome.

Quantitative RT-PCR was employed on three technical replicates per treatment to measure the relative expression of the Lc gene. Results are provided in Table 9 with relative Lc gene expression levels normalized to tubulin. These data demonstrate that, in each case, integration of sequence encoded by the dsDNA molecules containing the auxin response factor sequences into the Lc promoter region resulted in very strong upregulation of Lc expression in the presence of an exogenously provided auxin. The strongest upregulation of Lc expression was observed in the treatment using both the ZmLc Pro-1 and ZmLc Pro-3 RNPs (e. g., >40-fold increase observed with the 3×DR5 dsDNA and >35-fold increase observed with the 6×DR5, relative to controls transfected without any RNP), which may indicate that introduction of two DSBs into the genome and integration of sequence encoded by the dsDNA molecule between the two DSBs provided greater efficacy than introducing either of the two DSBs individually into the genome and integrating sequence encoded by the dsDNA molecule at the site of the individual DSB.

TABLE 9

| | No oligo | | 3x | | 6x | | 9x | |
|---|---|---|---|---|---|---|---|---|
| crRNA | Average | STD | Average | STD | Average | STD | Average | STD |
| ZmLc Pro-1 | 1.0 | 0.04 | 25.5 | 0.86 | 17.8 | 0.30 | 1.1 | 0.04 |
| ZmLc Pro-3 | 1.0 | 0.05 | 32.7 | 0.91 | 27.7 | 2.43 | 1.5 | 0.48 |
| ZmLc Pro-1 + ZmLc Pro-3 | 1.0 | 0.04 | 41.4 | 0.73 | 36.7 | 1.65 | 4.3 | 0.27 |

One of skill in the art would recognize that there are alternative methods for introducing DSBs into the genome (e. g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the approach described herein include use of any of these methods for introducing two or more DSBs into a genome in such a way that genomic sequence is deleted between the DSBs, and integration of at least one polynucleotide (such as a double-stranded DNA, a single-stranded DNA, a single-stranded DNA/RNA hybrid, or a double-stranded DNA/RNA hybrid) molecule at the location of the genomic sequence that is deleted between the DSBs.

Example 13

This example illustrates a method of modifying a sequence of interest in a genome, comprising integrating sequence encoded by a polynucleotide (such as a double-stranded DNA, a single-stranded DNA, a single-stranded DNA/RNA hybrid, or a double-stranded DNA/RNA hybrid) donor molecule at the site of at least one double-strand break (DSB) in a genome. This example illustrates introducing at least two DSBs into a genome by one or more nucleases in such a way that genomic sequence is deleted between the DSBs (leaving a deletion with blunt ends, overhangs or a combination of a blunt end and an overhang), and sequence encoded by at least one polynucleotide molecule is integrated between the DSBs (i. e., sequence encoded by at least one individual polynucleotide molecule is integrated at the location of the deleted genomic sequence), thus replacing the deleted genomic sequence. More specifically, this non-limiting example illustrates using multiple different ribonucleoproteins (RNPs), wherein each RNP includes a guide RNA (gRNA) and a nuclease, to effect multiple DSBs in the genome of a monocot plant, and integration of sequence encoded by a double-stranded DNA (dsDNA) at the location of the genomic sequence that is deleted between two DSBs. In embodiments, this technique is useful, e. g., for replacing regions of genomic sequence such as one or more exons ("exon exchange") or one or more protein domains. In an example, DSBs are introduced into intronic sequence on each side of an exon, resulting in deletion of the exon, and—when sequence encoded by at least one dsDNA molecule is integrated at the location of the deleted exon—incorporation of a "replacement" exon. This technique avoids editing inaccuracies such as unintentional nucleotide changes, deletions, or additions at the nuclease cleavage sites in the resulting exon sequence or the messenger RNA encoded by the exon. In the particular example described below, this technique is used to replace a "wild-type" exon (an exon having unmodified, native sequence) of the maize EPSPS genomic sequence with a modified exon sequence that encodes an EPSPS protein having resistance to glyphosate.

Experimental details were similar to those described in Examples 4, 8, and 9. The target gene selected for editing was the maize (*Zea mays*, B73 line) enolpyruvylshikimate phosphate synthase1 (EPSPS) gene (see www[dot]maizegdb[dot]org/gene_center/gene/Zm00001d045450) with the partial genomic sequence of acaacaaaaaaaggtaacctcgctactaacataacaaaatacttgttgcttattaattatatgtttttaatctttgatcAGGGGACA ACAGT GGTTGATAACCTGTTGAACAGTGAGGATGTCCACTACATGCTCGGGGCCTTGAGGACTCTTGGTCTCTCTGTCGAAGCGGACAAAGCTGCCAAAAGAGCTGTAGTTGTTGGCTGTGGTGGAAAGTTCCCAGTTGAGGATTCTAAAGAGGAAGTGCAGCTCTTCTTGGGGAATGCTGGAACTGCAATGCGGCCATTGACAGCAGCTGTTACTGCTGCTGGTGGAAATGCAACgtatgtttcctctcttctctctacaatacttgctggagttagtatgaaacccatgggtatgtctagt (SEQ ID NO:335); a first intronic sequence (nucleotides 1-80 of SEQ ID NO:335) and a second intronic sequence (nucleotides 325-392 of SEQ ID NO:335) are given in lower-case font, exonic sequence (nucleotides 81-324 of SEQ ID NO:335) is given in upper-case font, a first crRNA (guide RNA) target site sequence (nucleotides 21-40 of SEQ ID NO:335) and a second crRNA (guide RNA) target site sequence (nucleotides 360-379 of SEQ ID NO:335) are italicized and the PAM sites (nucleotides 18-20 and nucleotides 380-382 of SEQ ID NO:335) are underlined.

Maize protoplasts were prepared as described in Examples 1, 4, 8, 9, and 12. Ribonucleoproteins (RNPs) were prepared with Cas9 nuclease (Aldevron, Fargo, ND) and guide RNA complexes. Two guide RNA complexes were made with a crRNA and a tracrRNA (crRNAs and tracrRNA were purchased from Integrated DNA Technologies, Coralville, IA); the first guide RNA complex used a crRNA (EPS-gRNA-1) having the sequence AUUUUGUUAUGUUAGUAGCGGUUUUAGAGCUAUGCU (SEQ ID NO:336) and the second guide RNA complex used a crRNA (EPS-gRNA-2) having the sequence GGAGUUAGUAUGAAACCCAUGUUUUAGAGCUAUGCU (SEQ ID NO:337).

A dsDNA molecule was prepared by PCR using primers and a template purchased from Integrated DNA Technologies, Coralville, IA. The primers were had the sequences 5'-P-T*A*CTAACATAACAAAATACTTGT (forward primer, SEQ ID NO:338) and 5'-P-G*G*TTTCATACTAACTCCAGCAAG (reverse primer, SEQ ID NO:339), where P represents a 5' phosphorylation and * indicates a phosphorothioate linkage. The template sequence is given by 5'-TACTAACATAACAAAATACTTGTTGCTTATTAATTATATGTTTTTTAATCTTTGATCAGGG GACAACAGTGGTTGATAACCTGTTGAACAGTGAGGATGTCCACTACATGCTCGGGGCCTT GAGGACTCTTGGTCTCTCTGTCGAAGCGGACAAAGCTGCCAAAAGAGCTGTAGTTGTTGG CTGTGGTGGAAAGTTCCCAGTTGAGGATTCTAAAGAGGAAGTGCAGCTCTTCTTGGGGA ATGCTGGAATTGCAATGCGGGCATTGACAGCAGCTGTTACTGCTGCTGGTGGAAATGCA ACGTATGTTTCCTCTCTTTCTCTCTACAATACTTGCTGGAGTTAGTATGAAACC-3' (SEQ ID NO:340), with nucleotide changes (relative to the wild-type sequence) at positions 250 and 261 (indicated by underlined font) of SEQ ID NO:340 to provide the amino acid mutations T102I and P106A in the mature protein, which are point mutations found in glyphosate-resistant EPSPS.

NGS sequencing data indicated that the replacement exon sequence encoded by the dsDNA molecule was correctly integrated at the location of the deleted exon. The EPSPS genomic sequence of 0.48% of the total reads included the nucleotide changes (relative to the wild-type sequence) at positions 250-261 of SEQ ID NO:340, to provide the amino acid mutations T102I and P106A in the mature protein; this was accompanied by deletion of part of the intronic sequence 3' to the modified exon.

In a related embodiment, the sequence encoding a small RNA recognition site for a small RNA (e. g., an siRNA or a miRNA) expressed only in a specific tissue (for example, miRNAs specifically expressed in male reproductive tissue or female reproductive tissue, e. g., the miRNAs disclosed in Table 6 of U.S. Pat. No. 8,334,430, incorporated herein by reference and including the sequences provided herein in Tables A and B, or the siRNAs disclosed in U.S. Pat. No. 9,139,838, incorporated herein by reference and including the sequences provided herein in Table C), encoded by a polynucleotide (such as a double-stranded DNA, a single-stranded DNA, a single-stranded DNA/RNA hybrid, or a double-stranded DNA/RNA hybrid) donor molecule, is further integrated elsewhere in the EPSPS genomic sequence, e. g., in the 3' untranslated region. This limits expression of the glyphosate-resistant EPSPS protein to tissues other than those in which the small RNA is endogenously expressed, and leaves the male reproductive tissue or female reproductive tissue susceptible to glyphosate; this approach is useful for providing male-sterile or female-sterile plants. Table A provides the RNA sequences of miRNA recognition sites recognized and cleaved by mature miRNAs specifically expressed in maize female reproductive tissue (e. g., ovule, embryo). Table B provides the RNA sequences of miRNA or siRNA recognition sites recognized and cleaved by mature miRNAs specifically expressed in maize male reproductive tissue (e. g., pollen, tassel). Table C provides DNA sequences encoding "male tissue-specific siRNA elements" (see U.S. Pat. No. 9,139,838, incorporated herein by reference) which can similarly be integrated into a maize genome so that a transcript including one or more of these male tissue-specific siRNA elements is suppressed in maize male reproductive tissue. Integration into the maize genome of one or more DNA sequences encoding these small RNA (miRNA or siRNA) recognition sites is broadly useful for placing a transcript that includes one or more of these small RNA recognition sites under regulation by the mature small RNA(s) corresponding to the recognition site, and resulting in tissue-specific suppression of the transcript in male or female reproductive tissue. In a broader context, integration of DNA encoding one or more small RNA (e. g., miRNA or siRNA) recognition site into genomic sequence encoding a transcript of interest is useful for placing that transcript under regulation of the corresponding small RNA; depending on the expression pattern of the corresponding small RNA, this allows, e. g., specific spatial or temporal or developmental expression of the transcript.

TABLE A

| SEQ ID NO: | RNA sequence of recognition site corresponding to mature miRNA expressed in maize female reproductive tissue |
|---|---|
| 467 | GUGCUCUCUCUCUUCUGUCA |
| 468 | CUGCUCUCUCUCUUCUGUCA |
| 469 | UUGCUUACUCUCUUCUGUCA |
| 470 | CCGCUCUCUCUCUUCUGUCA |
| 471 | UGGAGCUCCCUUCAUUCCAAU |
| 472 | UCGAGUUCCCUUCAUUCCAAU |
| 473 | AUGAGCUCUCUUCAAACCAAA |
| 474 | UGGAGCUCCCUUCAUUCCAAG |
| 475 | UAGAGCUUCCUUCAAACCAAA |
| 476 | UGGAGCUCCAUUCGAUCCAAA |
| 477 | AGCAGCUCCCUUCAAACCAAA |
| 478 | CAGAGCUCCCUUCACUCCAAU |
| 479 | UGGAGCUCCCUUCACUCCAAU |
| 480 | UGGAGCUCCCUUCACUCCAAG |
| 481 | UGGAGCUCCCUUUAAUCCAAU |
| 482 | UUGGGAUGAAGCCUGGUCCGG |
| 483 | CUGGGAUGAAGCCUGGUCCGG |
| 484 | CUGGAAUGAAGCCUGGUCCGG |
| 485 | CGGGAUGAAGCCUGGUCCGG |
| 486 | GAGAUCAGGCUGGCAGCUUGU |
| 487 | UAGAUCAGGCUGGCAGCUUGU |
| 488 | AAGAUCAGGCUGGCAGCUUGU |

TABLE B

| SEQ ID NO: | RNA sequence of recognition site corresponding to mature miRNA expressed in maize male reproductive tissue |
|---|---|
| 489 | GUGCUCUCUCUCUUCUGUCA |
| 490 | CUGCUCUCUCUCUUCUGUCA |
| 491 | UUGCUUACUCUCUUCUGUCA |
| 492 | CCGCUCUCUCUCUUCUGUCA |
| 493 | UGGCAUGCAGGGAGCCAGGCA |
| 494 | AGGAAUACAGGGAGCCAGGCA |
| 495 | GGGUUUACAGGGAGCCAGGCA |
| 496 | AGGCAUACAGGGAGCCAGGCA |
| 497 | AAACAAUGCGAUCCCUUUGGA |
| 498 | AGACCAUGCGAUCCCUUUGGA |
| 499 | GGUCAGAGCGAUCCCUUUGGC |
| 500 | AGACAAUGCGAUCCCUUUGGA |
| 501 | UCGUUCAAGAAAGCCUGUGGAA |
| 502 | CGUUCAAGAAAGCCUGUGGAA |
| 503 | UCGUUCAAGAAAGCAUGUGGAA |
| 504 | ACGUUCAAGAAAGCUUGUGGAA |
| 505 | CGUUCAAGAAAGCCUGUGGAA |

TABLE C

| SEQ ID NO: | DNA sequence including recognition sites corresponding to tassel-specific siRNAs expressed in maize male reproductive tissue |
|---|---|
| 506 | GGACAACAAGCACCTTCTTGCCTTGCAAGGCCTCCCTTCCCTATGGTAGC CACTTGAGTGGATGACTTCACCTTAAAGCTATTGATTCCCTAAGTGCCAG ACATAATAGGCTATACATTCTCTCTGGTGGCAACAATGAGCCATTTTGGT TGGTGTGGTAGTCTATTATTGAGTTTTTTTTGGCACCGTACTCCCATGGAG AGTAGAAGACAAACTCTTCACCGTTGTAGTCGTTGATGGTATTGGTGGTG ACGACATCCTTGGTGTGCATGCACTGGTGAGTCACTGTTGTACTCGGCG |
| 507 | GGACAACAAGCACCTTCTTGCCTTGCAAGGCCTCCCTTCCCTATGGTAGC CACTTGAGTGGATGACTTCACCTTAAAGCTATCGATTCCCTAAGTGCCAG ACAT |
| 508 | CTCTTCACCGTTGTAGTCGTTGATGGTATTGGTGGTGACGACATCCTTGGT GTGCATGCACTGGTGAGTCACTGTTGTAC |
| 509 | GGACAACAAGCACCTTCTTGCCTTGCAAGGCCTCCCTTCCCTATGGTAGC CACTTGAGTGGATGACTTCACCTTAAAGCTATCGATTCCCTAAGTGCCAG ACATCTCTTCACCGTTGTAGTCGTTGATGGTATTGGTGGTGACGACATCC TTGGTGTGCATGCACTGGTGAGTCACTGTTGTAC |

Example 14

This example illustrates a method of changing expression of a sequence of interest in a genome, comprising integrating sequence encoded by a polynucleotide (such as a double-stranded DNA, a single-stranded DNA, a single-stranded DNA/RNA hybrid, or a double-stranded DNA/RNA hybrid) donor molecule at the site of at least one double-strand break (DSB) in a genome. More specifically, this non-limiting example illustrates using a ribonucleoprotein (RNP) including a guide RNA (gRNA) and a nuclease to effect a DSB in the genome of a monocot plant, and integration of sequence encoded by a polynucleotide molecule at the site of the DSB, wherein sequence encoded by the polynucleotide molecule includes a sequence recognizable by a specific binding agent, and wherein contacting the integrated sequence encoded by polynucleotide molecule with the specific binding agent results in a change of expression of a sequence of interest. In this particular example, sequence encoded by the polynucleotide molecule is integrated at a DSB located in non-coding genomic sequence (i. e., in a promoter region), the sequence recognizable by a specific binding agent includes an endogenous maize enhancer element that was identified by homology to a bacterial enhancer element and that in maize cells demonstrated at least partial responsiveness to auxin, the specific binding agent is an auxin, and the change of expression is upregulation of the sequence of interest. Further embodiments include integration of sequence of one or more endogenous enhancer elements (see, for example, endogenous maize transcriptional enhancers described in Oka et al., (2017) *Genome Biol.,* 18:137-161, doi 10.1186/s13059-017-1273-4) into genomic sequence, resulting in a heterologous arrangement of the integrated enhancer element and genomic sequence.

The ocs enhancer element is a 16 nucleotide sequence, ACGTAAGCGCTTACGT (SEQ ID NO:341) that was originally identified from the 5' untranslated region of the octopine synthase gene of the soil bacterium *Agrobacterium* sp., and is a palindromic sequence, i. e., has a reverse complement that is the exact same nucleotide sequence. A 16 base-pair dsDNA molecule having one strand with the sequence of SEQ ID NO:341 and the other strand being the reverse complement was designed. Endogenous maize sequences having homology to the bacterial enhancer sequence were identified from *Zea mays* B73 genomic data, including the 15 nucleotide sequence, ACGTAAGCGCTTACG (SEQ ID NO:342, located on chromosome 6) and the 12 nucleotide sequence, GTAAGCGCTTAC (SEQ ID NO:343, located on chromosome 10 and is palindromic). These sequences were used to design a first chemically modified dsDNA molecule of 15 base-pairs (with one strand having the sequence of SEQ ID NO:342 and the other strand being the reverse complement) and a second dsDNA molecule of 12 base-pairs (with one strand having the sequence of SEQ ID NO:343 and the other strand being the reverse complement), respectively. For comparison, the 34 base-pair dsDNA ("3×DR5") molecule (with strands having the sequences of SEQ ID NO:306 and SEQ ID NO:307), which contains three copies of an auxin response element (SEQ ID NO:308), was used. All dsDNA molecules were purchased from Integrated DNA Technologies, Coralville, IA In all cases, each strand was phosphorylated on the 5' end and contained two phosphorothioate linkages at each terminus (i. e., the two linkages between the most distal three bases on either end of the strand).

Experimental details were similar to those described, e. g., in Examples 4, 8, and 9. The target gene selected for editing was non-coding sequence, in this case the partial promoter sequence (sequence upstream of the transcription start site) of the maize (*Zea mays*) Lc gene (see www[dot]maizegdb[dot]org/gene_center/gene/GRMZM5G822829) having the sequence of SEQ ID NO:305; and guide RNA (crRNA) sequences were designed to edit this non-coding sequence.

Maize protoplasts were prepared as described, e. g., in Examples 1, 4, 8, and 9. A ribonucleoprotein (RNP) was prepared with Cas9 nuclease (Aldevron, Fargo, ND) and a guide RNA complex of a crRNA (ZmLc Pro-1) having the sequence of SEQ ID NO:306 and a tracrRNA (both purchased from Integrated DNA Technologies, Coralville, IA). Each dsDNA molecule was added at a concentration of 1 nanomolar together with the RNP. The transfection procedures for editing the target gene Lc in the maize protoplasts were otherwise identical to those described in Example 8 and 9.

An experiment was designed similar to that described in Example 9; sequences encoded by dsDNA molecules were integrated at the site of a DSB in promoter sequence operably linked to the gene of interest (the endogenous maize Lc gene). If the dsDNA molecule contained an auxin-responsive sequence, in the presence of an exogenously provided auxin (2, 4-dichlorophenoxyacetic acid) in the culture medium, expression of the gene of interest (the Lc gene) was expected to increase in cells that had the dsDNA molecule integrated into their genome, relative to that in cells that did not have the dsDNA molecule integrated into their genome. Quantitative RT-PCR was employed on three technical replicates per treatment to measure the relative expression of the Lc gene. Controls were cells that had been subjected to the transfection procedure without an RNP. Results are provided in Table 10 with Lc gene expression levels normalized to tubulin. As previously demonstrated in Example 9, integration of the 3×DR5 dsDNA sequence into the Lc promoter region resulted in very strong upregulation of Lc expression in the presence of auxin. The 16-nucleotide *Agrobacterium* ocs enhancer sequence (SEQ ID NO:341) increased expression of the Lc gene relative to the control by about 6-fold in the absence of auxin, and by about 11-fold in the presence of auxin. In spite of its considerably truncated length, the 12-nucleotide endogenous maize sequence SEQ ID NO:343 similarly increased expression of the Lc gene relative to the control by about 4-fold in the absence of auxin, and by about 6-fold in the presence of auxin. In contrast, in the absence of auxin, the 15-nucleotide endogenous maize sequence SEQ ID NO:342 did not increase expression of the Lc gene relative to the control whether or not auxin was present. These data demonstrate sequence encoded by that a dsDNA molecule only 12 base-pairs in length and including a strand with the sequence of an endogenous maize nucleotide sequence (SEQ ID NO:343), could be integrated at a DSB introduced into the 5' untranslated (promoter) region of a gene of interest (target gene) and was capable of enhancing expression of the gene of interest by several fold in a partially auxin-dependent manner.

TABLE 10

| Treatment | dsDNA (SEQ ID NO:) | WITHOUT AUXIN Lc relative expression | WITHOUT AUXIN standard deviation | WITH AUXIN Lc relative expression | WITH AUXIN standard deviation |
|---|---|---|---|---|---|
| No RNP | — | 1.0 | 0.05 | 1.0 | 0.7 |
| No dsDNA | — | 0.6 | 0.12 | 0.7 | 0.01 |
| 3xDR5 | 306, 307 | 0.7 | 0.25 | 20.2 | 6.2 |
| 16 nt OCS | 341 | 6.0 | 0.62 | 10.6 | 1.25 |
| 15 nt OCS | 342 | 0.5 | 0.14 | 1.8 | 0.11 |
| 12 nt OCS | 343 | 4.4 | 0.30 | 6.2 | 0.33 |

Example 15

This example illustrates a method of modulating expression of a sequence of interest in a genome, comprising introducing at least one double-strand break (DSB) into the 5' untranslated or promoter region and integrating sequence encoded by a polynucleotide (such as a double-stranded DNA, a single-stranded DNA, a single-stranded DNA/RNA hybrid, or a double-stranded DNA/RNA hybrid) donor molecule at the site of the DSB. More specifically, this non-limiting example illustrates a method to upregulate the expression level of a sequence of interest by integrating an expression-enhancing element at the site of a DSB in the 5' untranslated or promoter region of a sequence of interest, whereby the expression level of the sequence of interest is increased, relative to a reference expression level (e. g., the expression level of the sequence of interest without the expression-enhancing element integrated into the 5' untranslated or promoter region of the sequence of interest). By "expression-enhancing element" is meant at least one contiguous sequence of nucleotides that is capable of activating or increasing transcription of a gene or sequence of interest (which can be coding, non-coding, or a combination of coding and non-coding sequence). Embodiments of expression-enhancing elements include those that are located cis to the sequence of interest, and that can be located upstream (5' to) or downstream (3' of) the sequence of interest; if located upstream of the sequence of interest, an expression-enhancing element can be located within a promoter region, or outside of (even several hundred or thousand nucleotides upstream from) the promoter region. In some embodiments, the expression-enhancing element is one that provides a constitutive increase in expression levels of the sequence of interest. In other embodiments, the expression-enhancing element is one that provides a non-constitutive (e. g., tissue-specific, temporally specific, developmentally specific, inducible by or responsive to a physical influence such as light intensity or quality, day length, temperature levels, small molecules or ligands or hormones, transcription factors, water availability, or nutrient availability) change in expression levels of the sequence of interest. The expression level of the sequence of interest is estimated by any suitable technique, such as by measuring transcript abundance (e. g., by quantitative PCR) or (for sequences of interest that encode a protein) by measuring protein abundance (e. g., by Western blots). The method further provides the ability to adjust the expression of an endogenous gene or sequence of interest to a desired level under given conditions, by selecting a particular expression-enhancing element and the location of its integration upstream of (5' to) the TSS of the endogenous gene or sequence of interest. In embodiments, the degree of increase in expression level is selected by the proximity of the DSB (and of the integrated expression-enhancing element) to the transcription start site (TSS) of the sequence of interest. The more proximal the integrated expression-enhancing element is to the TSS, the greater is the increase in expression level; an expression-enhancing element integrated at locations more distal to the TSS provides a correspondingly lowered increase in expression level.

The following non-limiting example illustrates using a ribonucleoprotein (RNP) including a guide RNA (gRNA) and a nuclease to introduce a DSB in the promoter region of a protein-coding gene, integration of at least one expression-enhancing element (using a chemically modified double-stranded DNA encoding multiple copies of the auxin response element DR5) at the site of the DSB, wherein the at least one expression-enhancing element provides a non-constitutive increase in expression of the gene—in this case an increase in expression that is responsive to the presence of a hormone (auxin).

Experimental details were similar to those described in Examples 4, 8, 9, and 12. The target gene selected for editing was non-coding sequence, in this case the partial promoter sequence (sequence directly upstream of the transcription start site) of the maize (*Zea mays*) Lc gene (see www[dot]maizegdb[dot]org/gene_center/gene/GRMZM5G822829) with the sequence of SEQ ID NO:305; and guide RNA (crRNA) sequences were designed to edit this non-coding sequence.

Maize A188 protoplasts were prepared as described in Examples 1, 4, 8, 9, and 12. Ribonucleoproteins (RNPs) were prepared with Cas9 nuclease (Aldevron, Fargo, ND) and guide RNA complexes. Three guide RNA complexes were made with a crRNA and a tracrRNA (crRNAs and tracrRNA were purchased from Integrated DNA Technologies, Coralville, IA); the first guide RNA complex used a crRNA (ZmLc Pro-1) having the sequence GCUCCUCACUAGCUACCAAGGUUUUAGAGCUAUGCU (SEQ ID NO:306); the second guide RNA complex used a crRNA (ZmLc Pro-2) having the sequence AUAGAGAGAGAGAAAAAGAGGUUUUAGAGCUAUGCU (SEQ ID NO:344) and the third guide RNA complex used a crRNA (ZmLc Pro-3) having the sequence CUCCAAGUGACCGAGCAAGAGUUUUAGAGCUAUGCU (SEQ ID NO:334). These guides were designed to respectively effect a DSB at 173 (ZmLc Pro-1), 272 (ZmLc Pro-3), or 415 (ZmLc Pro-2) nucleotides upstream of (5' to) the TSS of the Lc coding sequence.

The transfection procedures for editing the target gene Lc in the maize protoplasts were similar to those described in Example 8, 9, and 12. Three different expression-enhancing elements (each including a different copy number of the auxin response element DR5 having the sequence cctttgtcgg (SEQ ID NO:308)) were integrated at the site of a DSB introduced into the Lc promoter region at one of three specific locations upstream of (5' to) the Lc TSS. The three dsDNA molecules ("3×DR5", ("6×DR5", and ("9×DR5") described in Example 9 and encoding different copy numbers of DR5 were used, with each dsDNA added together with the RNP. All dsDNA molecules were purchased from Integrated DNA Technologies, Coralville, IA In all cases, each strand was phosphorylated on the 5' end and contained two phosphorothioate linkages at each terminus (i. e., the two linkages between the most distal three bases on either end of the strand). Experimental controls including no dsDNA samples (i. e., no expression-enhancing element integrated) including the RNP only (Cas9 and guide RNA complex but no dsDNA molecule), as well as controls consisting of samples treated with Cas9 nuclease only (no guide RNA, no dsDNA) and null samples (no nuclease, guide RNA, or dsDNA). As the culture medium contained an herbicide (2, 4-dichlorophenoxyacetic acid) having auxin-like properties, expression of the endogenous maize Lc gene was expected to increase in cells that had any of the expression-enhancing elements integrated into the endogenous Lc promoter region, relative to that in cells that did not have an expression-enhancing element integrated into the endogenous Lc promoter region.

Quantitative RT-PCR was employed on three technical replicates per treatment to measure the relative expression of the Lc gene. Results (mean of triplicates, standard deviation) are provided in Table 11 with relative Lc gene expression levels normalized to tubulin. The data indicate that integration of the expression-enhancing elements (including multiple copies of the auxin response element DR5) upstream of (5' to) the transcription start site of the Lc gene resulted in an increased expression of the Lc transcript in the presence of an exogenously provided auxin (included in the medium); this increase was greatest for the 3×DR5 element. The degree of increase in expression was also observed to lessen as the integration location of the expression-enhancing element was moved further from (more distal to) the TSS; for example, the 3×DR5 element provided an increase in expression of 3863-fold, 2420-fold, or 1314-fold relative to the Cas9 nuclease control (no guide RNA and no dsDNA) when located at 173, 272, or 415 nucleotide positions upstream of the TSS, respectively. In combination, the data indicate that the degree of increase in expression can be optimized by selecting the type of expression-enhancing element as well as the location where the expression-enhancing element(s) is (are) integrated, relative to the location of the sequence of interest.

TABLE 11

| | ZmLc-Pro1 (173 nt from TSS) | | ZmLc-Pro3 (272 nt from TSS) | | ZmLc-Pro2 (415 nt from TSS) | | | |
|---|---|---|---|---|---|---|---|---|
| dsDNA | Relative expression | SD | Relative expression | SD | Relative expression | SD | Relative expression | SD |
| 3xDR5 | 3863 | 174 | 2420 | 41 | 1314 | 77 | — | — |
| 6xDR5 | 1479 | 75 | 1496 | 90 | 273 | 12 | — | — |
| 9xDR5 | 1031 | 28 | 823 | 9.0 | 101 | 2.8 | — | — |
| RNP only | 12.7 | 2.6 | 9.0 | 1.4 | 11.2 | 1.2 | — | — |
| Cas9 nuclease only | — | — | — | — | — | — | 1.0 | 0.25 |
| Null | — | — | — | — | — | — | 0.8 | 0.4 |

Samples from the treatments with the guide complexes ZmLc-Pro1I and ZmLc-Pro3 were subjected to next-generation sequencing analysis to quantify editing efficiency. The primers for sequencing included the forward primer having SEQ ID NO:313 and the reverse primer having SEQ ID NO:314) for an expected amplicon size of 226 base-pairs (SEQ ID NO:315). Results are provided in Table 12.

TABLE 12

| Guide RNA complex | dsDNA | Editing efficiency at 173 nt from TSS | Editing efficiency at 272 nt from TSS | dsDNA insertion efficiency |
|---|---|---|---|---|
| ZmLc-Pro1 (173 nt from TSS) | 3xDR5 | 34% | 0% | 21% |
| | 6xDR5 | 25% | 0% | 3% |
| | 9xDR5 | 11% | 0% | 0% |
| | none | 41% | 0% | 0% |
| ZmLc-Pro3 (272 nt from TSS) | 3xDR5 | 1% | 17% | 11% |
| | 6xDR5 | 1% | 15% | 0% |
| | 9xDR5 | 2% | 10% | 0% |
| | RNP | 0% | 23% | 0% |
| Cas9 nuclease only | — | 9% | 0% | 5% |
| Null | — | 7% | 0% | 3% |

In a second experiment following the same general procedures described above, maize A188 protoplasts were transfected with the guide RNA complex including the "ZmLc Pro-3" crRNA (SEQ ID NO:334) complexed with a tracrRNA (Integrated DNA Technologies, Coralville, IA); this guide complex was designed to effect a DSB at 272 nucleotides upstream of (5' to) the TSS of the Lc coding sequence. In one set of samples, an expression-enhancing element in the form of the 34 base-pair dsDNA molecule "3×DR5" (with strands having the sequences of SEQ ID NO:306 and SEQ ID NO:307), which contains three copies of an auxin response element (SEQ ID NO:308), as described in Example 9, was integrated at this DSB. The "3×DR5" dsDNA was purchased from Integrated DNA Technologies, Coralville, IA; each strand was phosphorylated on the 5' end and contained two phosphorothioate linkages at each terminus (i. e., the two linkages between the most distal three bases on either end of the strand). Maize protoplasts treated with no nuclease, no guide RNA complex, and no dsDNA served as a null control. The transformed protoplasts were then incubated in a maize incubation buffer including the herbicides 2, 4-dichlorophenoxyacetic acid ("2,4-D") or 3,6-dichloro-2-methoxybenzoic acid ("dicamba"), both of which have auxin-like properties, each at 1 milligram/liter, or including no herbicide as a control. Quantitative RT-PCR was employed on three technical replicates per treatment to measure the relative expression of the Lc gene. Results (mean of triplicates, standard deviation) are provided in Table 13 with relative Lc gene expression levels normalized to tubulin. The data indicate that, without any modification of the Lc promoter, or with only treatment with the RNP to effect a DSB but without integration of the 3×DR5 expression-enhancing element, no difference was seen in Lc transcript expression in the presence or absence of either herbicide. In contrast, integrating the 3×DR5 expression-enhancing element into a DSB in the promoter region of the endogenous Lc gene resulted in an over 200-fold increase in expression of the Lc transcript in the presence of either herbicide, in comparison to expression in the absence of either herbicide.

TABLE 13

| Transfection | dsDNA | Incubation medium | Relative expression | SD |
|---|---|---|---|---|
| Null control | none | No added herbicide | 1.0 | 0.22 |
| Null control | none | 2,4-D | 1.0 | 0.14 |
| Null control | none | Dicamba | 1.0 | 0.019 |
| ZmLc-Pro3 | 3xDR5 | No added herbicide | 9.0 | 0.84 |
| ZmLc-Pro3 | 3xDR5 | 2,4-D | 290 | 31 |
| ZmLc-Pro3 | 3xDR5 | Dicamba | 236 | 47 |
| ZmLc-Pro3 | none | No added herbicide | 1.6 | 0.22 |
| ZmLc-Pro3 | none | 2,4-D | 1.5 | 0.36 |
| ZmLc-Pro3 | none | Dicamba | 1.3 | 0.11 |

Details of editing the Lc gene at whole plant level in maize by biolistic delivery can be found in Example 49.

A third experiment demonstrated the use of an expression-enhancing element to provide inducible upregulation of expression for a sequence of interest. Following the same general procedures described above, protoplasts were harvested from leaves of B73 maize plants that had been grown in nitrate-free medium for 13 days. The sequence of interest was an endogenous maize ammonium transporter AMT3 gene (GRMZM2G118950, see www[dot]maizegdb[dot]org/gbrowse?name=GRMZM2G118950), having a promoter sequence of CGATAAACGCCACTAAAAATGGTTT-TACGACCGCCAGTATATATCTTCTCTGTACTAGTG TGATACTATCAGGCCGCATGCAGATTCCTTTCGAT-TGTTTATAGGGTTTTTTTTTTTATAA AGACTGCTGGTTTTCAAGCCTT-GAATCTTGTAGCTAGGTAGCCA-GACCGGTCCCGGCCGG GTCGAGGAA-GACGCAAAACTCAGCAAGCACAGTTGTGCTAGCC TGCTAGGCACGGTGTG TAGCAAGA-GACAGAAACGAGCGTATAACCATGGCGATTAACT-GATAGCTGTGGAATTTT GAGCACATAGTCCTC-CAAACATTTGCATTTGTATTGTACTATTGTTTATGTA GCGAAGTTT AAAATGCAGTTTGGTAGGCCTAACCCG-CATGCGAGGGCACCGCACAGTGAGGCTGAGGA ACGGAACCACTCCAGCTAAGAT-TCCGCACCGCAGCAACCCTGG-GATCCTGCTGTCAGCG CGGGCCGCGGGAGGG-GAGATTCACTGGCAGCAGGGCCCCACACCCCTTCC CAGGCTTCC CATCTCAGAAAACAGAAGCC-GATCTGTTTTGTTCTGCCGAATCAAAAGTGCGATAT-GATC GTCATCTCTTCGACAGCACCCGCCCAAC-CATCTCCTATAAATCCGATCGCCGCCACTGGC CGTTCGTCCCCCATC (SEQ ID NO:345). The nitrate-starved maize protoplasts were transfected with ribonucleoproteins (RNPs) prepared with Cas9 nuclease (Aldevron, Fargo, ND) and guide RNA complexes. Guide RNA complexes were made with three different crRNAs and a tracrRNA (all purchased from Integrated DNA Technologies, Coralville, IA); the first guide RNA complex used a crRNA (AMT3Pro-1) having the sequence CCAGUGAAU-CUCCCCUCCCGGUUUUAGAGCUAUGCU (SEQ ID NO:346); the second guide RNA complex used a crRNA (AMT3Pro-2) having the sequence CGUUCCUCAGCCU-CACUGUGGUUUUAGAGCUAUGCU (SEQ ID NO:347) and the third guide RNA complex used a crRNA (AMT3Pro-3) having the sequence CAGAAACGAGCGUAUAACCAGUUUUAGAGC-UAUGCU (SEQ ID NO:348). These guides were designed to respectively effect a DSB at 147 (AMT3Pro-1), 230 (AMT3Pro-2), and 382 (AMT3Pro-3) nucleotides upstream of (5' to) the TSS of the AMT3 coding sequence. An inducible expression-enhancing element based on a nitrogen responsive element from *Arabidopsis thaliana*, AtNRE, was used to design a 43 base-pair dsDNA (purchased from Integrated DNA Technologies, Coralville, IA) having one strand with the sequence (AAGAGATGAGCTCTT-GAGCAATGTAAAGGGTCAAGTTGTTTCT, SEQ ID NO:349), annealed to a second strand with the sequence (AGAAACAACTTGACCCTTTACATTGCT-CAAGAGCTCATCTCTT, SEQ ID NO:350); each strand was phosphorylated on the 5' end and contained two phosphorothioate linkages at each terminus (i. e., the two linkages between the most distal three bases on either end of the strand). The NRE dsDNA was integrated at the site of the DSBs introduced into the AMT3 promoter region.

After approximately 48 hours, samples of the transfected maize cells were treated with either 0.5 millimolar $KNO_3$ or 0.5 millimolar KCl, incubated for 1 hour, and then harvested for analysis. Quantitative RT-PCR was employed on three technical replicates per treatment to measure the relative expression of the AMT3 gene. Results (mean of triplicates, standard deviation) are provided in Table 14 with relative AMT3 gene expression levels normalized to tubulin. The data indicate that integrating the NRE expression-enhancing element into the promoter region of the endogenous AMT3 gene resulted in an inducible response to nitrate; in the presence of nitrate, expression of the AMT3 transcript was increased by about 25-fold, about 17-fold, or about 8-fold, where the NRE expression-enhancing element was inserted at 147, 230, or 382 nucleotides, respectively, from the TSS of the AMT3 gene. While the endogenous AMT3 gene shows moderate upregulation of expression in the presence of nitrate, integration of the NRE element into the AMT3 promoter region provided a much stronger response induced by nitrate.

TABLE 14

| crRNA | AtNRE insert | Treatment | Relative Expression | SD |
|---|---|---|---|---|
| AMT3Pro-1 | Y | KNO3 | 24.6 | 0.11 |
| AMT3Pro-2 | Y | KNO3 | 17.3 | 0.17 |
| AMT3Pro-3 | Y | KNO3 | 8.03 | 0.32 |
| AMT3Pro-1 | N | KNO3 | 7.95 | 0.26 |
| AMT3Pro-2 | N | KNO3 | 5.54 | 0.28 |
| AMT3Pro-3 | N | KNO3 | 5.49 | 0.23 |
| AMT3Pro-1 | Y | KCl | 0.94 | 0.064 |
| AMT3Pro-2 | Y | KCl | 1.03 | 0.20 |
| AMT3Pro-3 | Y | KCl | 1.29 | 0.079 |
| AMT3Pro-1 | N | KCl | 1.00 | 0.026 |
| AMT3Pro-2 | N | KCl | 1.02 | 0.25 |
| AMT3Pro-3 | N | KCl | 1.00 | 0.036 |

The data from these various experiments all indicate that the degree of increase in expression of a sequence or gene of interest can be set at a specific level by selecting the type (or copy number) of an expression-enhancing element as well as the location where the expression-enhancing element(s) is (are) integrated, relative to the location of the sequence of interest (e. g., relative to the location of the transcription start site of a sequence of interest). In these non-limiting examples, the expression-enhancing elements were selected for responsiveness to an exogenously provided stimulus (e. g., auxin or nitrate), and further control of expression can thus be achieved by controlling the amount of the stimulus provided. Other embodiments include the use of expression-enhancing elements that are responsive to other stimuli, e. g., transcription factors, signaling molecules such as salicylic acid or jasmonic acid, hormones, metal ions, small molecules or ligands, heat, temperature, and light or light quality; such expression-enhancing elements can be provided, e. g., in the form of sequences encoded by polynucleotide donor molecules (such as those described above under the heading "Polynucleotide Molecules") that are integrated at the site of one or more DSBs.

One of skill in the art would recognize that there are alternative methods for introducing DSBs into the genome (e. g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the approach described herein include use of any of these methods for introducing at least one DSB into a genome, and integration of at least one expression-enhancing element at the location of the at least one DSB.

Example 16

This example illustrates a method of simultaneously effecting multiple modifications in a genome (i. e., multiple modifications of at least one sequence of interest in a genome), comprising introducing at least two DSBs into a genome by one or more nucleases, and, optionally, integrating sequence encoded by at least one polynucleotide (such as a double-stranded DNA, a single-stranded DNA, a single-stranded DNA/RNA hybrid, or a double-stranded DNA/RNA hybrid) donor molecule at one or more DSBs. In embodiments, the modifications are effected in two or more sequences or genes of interest. In embodiments, individual DSBs have blunt ends, overhangs or a combination of a blunt end and an overhang. In embodiments, sequences encoded by two or more different polynucleotide donor molecules are integrated at one or more DSBs. In an embodiment, sequences encoded by at least two different polynucleotide donor molecules are integrated at different DSBs. In an embodiment, the polynucleotide donor molecule includes one or more strands containing chemically modified DNA. Embodiments include double-stranded DNA or double-stranded DNA/RNA hybrid molecules, and single-stranded DNA or single-stranded DNA/RNA hybrid donor molecules, the sequence of which in analogous procedures is integrated at the site of at least two DSBs. More specifically, this non-limiting example illustrates using multiple different ribonucleoproteins (RNPs), wherein each RNP includes a guide RNA (gRNA) and a nuclease, to effect multiple DSBs in the genome of a monocot plant, and integration of sequence encoded by a double-stranded DNA (dsDNA) at the location of the multiple DSBs. In this example, two endogenous maize (*Zea mays*) sequences or genes of interest, Lc (see Examples 9, 12, 14, and 15) and BBM2 (see Example 4), were selected for modification by insertion of an expression-enhancing element at a DSB located in the promoter region of each gene.

Maize B73 protoplasts were prepared as described in Examples 1, 4, 8, 9, 12, and 15. Ribonucleoproteins (RNPs) were prepared with Cas9 nuclease (Aldevron, Fargo, ND) and guide RNA complexes. Guide RNA complexes were made with crRNAs and a tracrRNA purchased from Integrated DNA Technologies, Coralville, IA For modifying the promoter of the endogenous maize Lc gene, the crRNA "ZmLc Pro-1" (SEQ ID NO:306, see Example 9) was used; this was designed to effect a DSB 173 nucleotides upstream of (5' to) the transcription start site (TSS) of the Lc coding sequence. For modifying the promoter of the endogenous maize BBM2 gene, the crRNA "ZmBBM2-2" (SEQ ID NO:31, see Example 4) was used; this was designed to effect a DSB 342 nucleotides upstream of (5' to) the TSS of the BBM2 coding sequence. An expression-enhancing element in the form of the 34 base-pair dsDNA molecule "3×DR5" (with strands having the sequences of SEQ ID NO:306 and SEQ ID NO:307), which contains three copies of an auxin response element (SEQ ID NO:308), as described in Example 9, was purchased from Integrated DNA Technologies, Coralville, IA; each strand was phosphorylated on the 5' end and contained two phosphorothioate linkages at each terminus (i. e., the two linkages between the most distal three bases on either end of the strand).

Following the same general procedures described above (e. g., Examples 4, 8, 9, 12, and 15) the protoplasts were transfected with the RNPs (including the guide RNA complexes), with or without the dsDNA molecule "3×DR5" (see Example 9). Transfections were carried out to deliver the same molar quantity of RNP for each genomic locus targetted for modification. Samples transfected with both the RNP containing the ZmLc Pro-1 guide RNA complex and the RNP containing the ZmBBM2-2 guide complex were thus transfected with twice the amount of nuclease (provided as RNP) as the samples that were transfected with only a single RNP (containing either the ZmLc Pro-1 guide RNA complex or the ZmBBM2-2 guide complex). Maize protoplasts treated with no nuclease, no guide RNA complex, and no dsDNA served as a null control. The transformed protoplasts were then incubated for about 48 hours in a maize incubation buffer including the herbicide 2, 4-dichlorophenoxyacetic acid ("2,4-D"), which has auxin-like properties. Quantitative RT-PCR was employed on three technical replicates per treatment to measure the relative expression of the Lc and BBM2 genes. Results (mean of triplicates, standard deviation) are provided in Table 15 with relative Lc or BBM2 gene expression levels normalized to tubulin. The data indicate that integrating the 3×DR5 expression-enhancing element into the promoter region of either the endogenous Lc gene or the BBM2 gene resulted in an increased expression of that gene in the presence of exogenous auxin, relative to the expression of either gene lacking the promoter modification (integration of the expression-enhancing element). The data also indicate that simultaneous multiple modifications (integration of a dsDNA at a DSB in the promoter region of two different genes) in the maize protoplasts' genome was effected at about the same efficiency as a single modification, as the relative expression of the individual genes in these protoplasts was approximately the same expression level as observed for the same gene in the protoplasts that had only that one gene modified.

TABLE 15

| | | Lc | | BBM2 | |
|---|---|---|---|---|---|
| crRNA(s) | dsRNA | Relative Expression | SD | Relative Expression | SD |
| none (null control) | none | 1.01 | 0.16 | 1.01 | 0.13 |
| ZmBBM2-2 | 3xDR5 | 1.03 | 0.12 | 4.62 | 0.52 |
| ZmLc Pro-1 | 3xDR5 | 8.16 | 1.51 | 0.77 | 0.046 |
| ZmBBM2-2 and ZmLc Pro-1 | none | 1.18 | 0.14 | 0.70 | 0.064 |
| ZmBBM2-2 and ZmLc Pro-1 | 3xDR5 | 6.61 | 0.22 | 4.99 | 0.17 |

One of skill in the art would recognize that simultaneously effecting multiple DSBs in a genome (e. g., effecting multiple DSBs in a sequence of interest or effecting at least one DSB in each of two or more sequences of interest) can be achieved with alternative methods (e. g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the approach described herein include use of any of these methods for simultaneously effecting multiple DSBs in a genome, and, optionally, integrating at least one polynucleotide molecule at one or more DSBs.

Additional experiments can be carried out with the same editing reagents in a plant/plant tissue, e. g., using microinjection or biolistics as described in Examples 49-51 and 54. A one-step delivery method can be used to achieve multiplexed edits (multiple modifications) with the same polynucleotide donor to target different genes. For insertion of different polynucleotide donor sequences using the same nuclease (e. g. Cas9 or Cpf1), sequential steps for delivery of different combinations of reagents with a 30 min to 48 h gap between the steps can be used. For insertion of different polynucleotide donor sequences using different nucleases (e. g. Cas9 and Cpf1), a one-step delivery method can be used, for example, with a blunt-ended double-stranded polynucleotide donor for Cas9 and a double-stranded polynucleotide donor containing overhangs for Cpf1.

Example 17

This example illustrates a method of changing expression of a sequence of interest in a genome, comprising integrating sequence encoded by a polynucleotide (such as a double-stranded DNA, a single-stranded DNA, a single-stranded DNA/RNA hybrid, or a double-stranded DNA/RNA hybrid) donor molecule, at the site of at least one double-strand break (DSB) in a genome. This example further demonstrates integration of sequences encoded by polynucleotide (such as a double-stranded DNA, a single-stranded DNA, a single-stranded DNA/RNA hybrid, or a double-stranded DNA/RNA hybrid) donor molecules at a DSB in genomic sequence. More specifically, this non-limiting example illustrates using a ribonucleoprotein (RNP) including a guide RNA (gRNA) and a nuclease to effect a DSB in the genome of a monocot plant, and integration of sequence encoded by a polynucleotide donor molecule including a sequence recognizable by a specific binding agent, and wherein contacting the integrated sequence encoded by the polynucleotide donor molecule with the specific binding agent results in a change of expression of a sequence of interest. In this particular example, sequence encoded by the polynucleotide is integrated at a DSB located in non-coding genomic sequence (i. e., in a promoter region), the sequence recognizable by a specific binding agent includes an enhancer element that is responsive to auxin, the specific binding agent is an auxin, and the change of expression is upregulation of the sequence of interest.

Maize B73 protoplasts were prepared as described in Examples 1, 4, 8, 9, 12, 15, and 16. Ribonucleoproteins (RNPs) were prepared with Cas9 nuclease (Aldevron, Fargo, ND) and a guide RNA complex including the "ZmLc Pro-3" crRNA (SEQ ID NO:334) complexed with a tracrRNA (Integrated DNA Technologies, Coralville, IA); this guide complex was designed to effect a DSB at 272 nucleotides upstream of (5' to) the TSS of the Lc coding sequence. Three polynucleotides including a sequence recognizable by a specific binding agent were tested for integration at the site of the DSB: (a) a 34 base-pair dsDNA molecule "3×DR5" (with strands having the sequences of SEQ ID NO:306 and SEQ ID NO:307), which contains three copies of an auxin response element (SEQ ID NO:308) (see Example 9); (b) a 34 nucleotide single-stranded DNA (ssDNA) molecule having the sequence 5'-ccgacaaaaggccgacaaaaggccgacaaaaggt-3' (SEQ ID NO:306) (i. e., equivalent to only a single strand of the "3×DR5" dsDNA molecule); and a 34 base-pair blunt-ended double-stranded DNA/RNA hybrid (analogous to the dsDNA molecule "3×DR5") formed by annealing a DNA strand having the sequence of SEQ ID NO:306 and an RNA strand having the sequence of 5'-ACCUUUUGUCGGCCUUUUGUCGGCCUUUUGUCGG-3' (SEQ ID NO:351). All polynucleotides tested for integration at the DSB were purchased from Integrated DNA Technologies, Coralville, IA; each DNA or RNA strand was phosphorylated on the 5' end and contained two phosphorothioate linkages at each terminus (i. e., the two linkages between the most distal three bases on either end of the strand).

Following the same general procedures described above (e. g., Examples 4, 8, 9, 12, and 15) the protoplasts were transfected with the RNPs (including the guide RNA complexes), with or without a dsDNA, ssDNA, or DNA/RNA hybrid polynucleotide for integration. Transfections were carried out to deliver the same molar quantity of polynucleotide for integration. Maize protoplasts treated with no nuclease, no guide RNA complex, and no dsDNA served as a null control. The transformed protoplasts were then incubated for about 48 hours in a maize incubation buffer including the herbicide 2, 4-dichlorophenoxyacetic acid ("2,4-D"), which has auxin-like properties. Quantitative RT-PCR was employed on three technical replicates per treatment to measure the relative expression of the Lc gene.

Results (mean of triplicates, standard deviation) are provided in Table 16 with relative Lc gene expression levels normalized to tubulin.

TABLE 16

| Conditions | Lc relative expression | standard deviation |
|---|---|---|
| Null (no RNP, no polynucleotide) | 1.00 | 0.11 |
| RNP only | 2.39 | 0.19 |
| RNP + dsDNA | 61.1 | 2.71 |
| RNP + ssDNA | 107.5 | 2.28 |
| RNP + DNA/RNA hybrid | 6.79 | 0.30 |

As in previous Examples, the data indicate that integration of sequence encoded by a dsDNA including the 3×DR5 expression-enhancing element into the promoter region of the endogenous Lc gene resulted in increased expression in the presence of exogenous auxin, about sixty-fold increased expression relative to the expression of the Lc gene lacking the promoter modification (integration of an expression-enhancing element). Surprisingly, the data also indicate that integration of sequence encoded by a ssDNA polynucleotide containing the 3×DR5 expression-enhancing element appeared to provide an even greater increase in relative expression of the Lc gene in the presence of endogenous auxin, well over 100-fold increased relative expression, or nearly twice the increase in relative expression observed with that obtained with the dsDNA 3×DR5 polynucleotide. Furthermore, the data also indicate that integration of sequence encoded by a double-stranded DNA/RNA hybrid polynucleotide containing the 3×DR5 expression-enhancing element also increased relative expression of the Lc gene in the presence of endogenous auxin by at least a few fold relative to the expression of the Lc gene lacking the promoter modification (integration of an expression-enhancing element).

A second experiment to compare the effects of dsDNA and ssDNA polynucleotides was performed using essentially the same procedures as above, using maize B73 protoplasts and ribonucleoproteins (RNPs) prepared with Cas9 nuclease (Aldevron, Fargo, ND) and a guide RNA complex including the "ZmLc Pro-3" crRNA (SEQ ID NO:334) complexed with a tracrRNA (Integrated DNA Technologies, Coralville, IA). This experiment included longer ssDNA polynucleotides encoding the 6×DR5 or 9×DR5 sequences (see Examples 9, 12, and 15). Maize protoplasts treated with no nuclease, no guide RNA complex, and no dsDNA served as a null control. The transformed protoplasts were then incubated for about 48 hours in a maize incubation buffer including the herbicide 2, 4-dichlorophenoxyacetic acid ("2,4-D"), which has auxin-like properties. Quantitative RT-PCR was employed on three technical replicates per treatment to measure the relative expression of the Lc gene. Results (mean of triplicates, standard deviation) are provided in Table 17 with relative Lc gene expression levels normalized to tubulin. The results indicated that, in each case, the integration of sequence encoded by the ssDNA polynucleotide into the Lc promoter region resulted in greater upregulation of Lc relative expression; in this experiment, the increased upregulation of Lc expression was most marked in the 3×DR5 and 9×DR5 cases (an approximately 2-fold increase in upregulation effected by the ssDNA polynucleotides, compared to that observed with the dsDNA equivalents). This suggests that ssDNA polynucleotides are especially of use when integrating longer nucleotide sequences (e. g., of more than 100 contiguous nucleotides).

TABLE 17

| Conditions | Lc relative expression | standard deviation |
|---|---|---|
| Null | 1.00 | 0.07 |
| RNP only | 1.52 | 0.05 |
| 3xDR5, ssDNA | 61.0 | 2.6 |
| 3xDR5, dsDNA | 34.7 | 3.0 |
| 6xDR5, ssDNA | 46.8 | 1.8 |
| 6xDR5, dsDNA | 43.3 | 2.2 |
| 9xDR5, ssDNA | 19.6 | 0.6 |
| 9xDR5, dsDNA | 8.9 | 0.9 |

Example 18

This example illustrates a method of changing expression of a sequence of interest in a genome, comprising integrating sequence encoded by a polynucleotide (such as a double-stranded DNA, a single-stranded DNA, a single-stranded DNA/RNA hybrid, or a double-stranded DNA/RNA hybrid) donor molecule at the site of at least one double-strand break (DSB) in a genome. More specifically, this non-limiting example illustrates using a ribonucleoprotein (RNP) including a guide RNA (gRNA, in this case a Cpf1 crRNA without a tracrRNA) and a Cpf1 nuclease to effect a DSB in the genome of a plant, and integration of sequence encoded by a polynucleotide donor molecule including a sequence recognizable by a specific binding agent, wherein contacting the integrated sequence encoded by polynucleotide with the specific binding agent results in a change of expression of a sequence of interest. In this particular example, sequences encoded by dsDNAs either with blunt ends or with overhangs, and encoding an auxin-responsive enhancer element, were integrated at a DSB located in non-coding genomic sequence (i. e., in the promoter region of a sequence of interest); in the presence of auxin, expression of the sequence of interest was increased.

Maize B73 protoplasts were prepared as described in Examples 1, 4, 8, 9, 12, 15, 16, and 17. Ribonucleoproteins (RNPs) were prepared with Cpf1 nuclease (Aldevron, Fargo, ND) and a "Cpf1 LcPro3" crRNA with the sequence 5'-UGGACAGAGCUCCAAGUGACC-3' (SEQ ID NO:352). Two polynucleotides including a sequence recognizable by a specific binding agent were tested for integration at the site of the Cpf1-effected DSB. The first polynucleotide was a 34 base-pair blunt-ended dsDNA molecule "3×DR5" (with strands having the sequences of SEQ ID NO:306 and SEQ ID NO:307), which contains three copies of an auxin response element (SEQ ID NO:308) (see Example 9); each DNA strand was phosphorylated on the 5' end and contained two phosphorothioate linkages at each terminus (i. e., the two linkages between the most distal three bases on either end of the strand). The second polynucleotide was a "sticky-ended" dsDNA molecule with overhangs at each terminus, produced by annealing (a) a forward DNA strand having the sequence 5'-TCGGTCCGACAAAAGGCCGACAAAAGGCGGACAAAAGG-3' (SEQ ID NO:353) and containing four phosphorothioate linkages at the 5' end (i. e., the four linkages between the five most 5' bases of the strand) and two phosphorothioate linkages at the 3' end (i. e., the two linkages between the three most 3' bases of the strand) and (b) a reverse DNA strand having the sequence 5'-ACCGACCTTTTGTCGGCCTTTTGTCGGCCTTTTGTCGG-3' (SEQ ID NO:354) and containing five phosphorothioate linkages at the 5' end (i. e., the five linkages between the six most 5' bases of the strand) and two phosphorothioate linkages at the 3' end (i. e., the two linkages between the three most 3' bases of the strand); each DNA strand was phosphorylated on the 5' end and. All polynucleotides tested for integration at the DSB were purchased from Integrated DNA Technologies, Coralville, IA.

Following the same general procedures described above (e. g., Examples 4, 8, 9, 12, 15, 16, and 17) the protoplasts were transfected with the RNPs (including the guide RNA complexes), with or without a blunt-ended or a "sticky-ended" dsDNA polynucleotide for integration. Maize protoplasts treated with no nuclease, no guide RNA complex, and no dsDNA served as a null control. The transformed protoplasts were pelleted by centrifugation at 1200 rpm, resuspended in 1 milliliter maize incubation buffer (see Example 2) including the herbicide 2, 4-dichlorophenoxyacetic acid ("2,4-D") with 50 millimolar $CaCl_2$ added), and plated in 6-well plates. The plates were incubated 1 hour at 37 degrees Celsius, and then incubated for about 48 hours at 26 degrees Celsius in the dark. Results are provided in Table 18. The data indicate that the sticky-ended dsDNA was inserted at a higher percentage than was the blunt-ended dsDNA. NGS sequencing results showed that the stick-ended dsDNA was inserted in the correct orientation to a much greater degree than was the blunt-ended dsDNA. This observation suggests that using a nuclease (such as Cpf1) that effects a double-strand break with overhangs (or, alternatively, using two nucleases to effect two DSBs between which genomic sequence is excised, wherein at least one of the nucleases effects a DSB with overhangs) results in an asymmetry at the locus for insertion of a nucleotide sequence encoded by a polynucleotide donor molecule that provides an opportunity for insertion of the nucleotide sequence in the correct orientation.

TABLE 18

| Conditions | % correct editing | % correct insertion | + Orientation (% of Insertion) |
|---|---|---|---|
| Null (no RNP, no polynucleotide) | 0 | 0 | |
| RNP only | 72 | — | |
| RNP + blunt-ended dsDNA | 72 | 9 | 38.9 |
| RNP + sticky-ended dsDNA | 68 | 15 | 97.1 |

Example 19

This example illustrates a method of changing expression of a sequence of interest in a genome, comprising integrating sequence encoded by a polynucleotide (such as a double-stranded DNA, a single-stranded DNA, a single-stranded DNA/RNA hybrid, or a double-stranded DNA/RNA hybrid) donor molecule, at the site of at least one double-strand break (DSB) in a genome. This example further demonstrates integration of sequence encoded by double-stranded DNA, single-stranded DNA, and double-stranded DNA/RNA hybrid polynucleotides at a DSB in genomic sequence. More specifically, this non-limiting example illustrates using a ribonucleoprotein (RNP) including a guide RNA (gRNA) and a nuclease to effect a DSB in the genome of a monocot plant, and integration of sequence encoded by a polynucleotide donor molecule including a sequence recognizable by a specific binding agent, and wherein contacting the integrated sequence encoded by the polynucleotide donor molecule with the specific binding agent results in a change of expression of a sequence of interest. In this particular example, sequence encoded by a polynucleotide encoding an upstream open reading frame ("uORF", a small open reading frame (ORF) located in the 5' untranslated region upstream of, and controlling translation of, the main open reading frame of an mRNA) is integrated at a DSB upstream of (5' to) the coding sequence of the reporter gene luciferase. Translation of the uORF typically inhibits downstream translation of the main ORF, possibly by blocking ribosome access to the main ORF; in the presence of a microbe-associated molecular pattern (MAMP) molecule, inhibition by the uORF is lifted and the main ORF is translated.

The TBF1 transcription factor (TL1 binding factor, which binds to the TL1 cis element) is a key gene in plant defense systems, and both the transcription and translation of TBF1 is tightly controlled. Plants lacking a functional TBF1 have a compromised immune response to salicylic acid and to the microbe-associated molecular pattern (MAMP), elf18. Two uORFs are located 5' to the translation initiation codon of TBF1; both have an inhibitory effect on TBF1 translation which is alleviated with immune induction (induction of a defense response to pathogens), with the effect of uORF2 epistatic to that of uORF1; see Pajerowska-Mukhtar et al. (2012) *Current Biol.,* 22:103-112. Both uORFs are highly enriched in aromatic amino acids, especially phenylalanine; uORF2 (At4g36988) is well-conserved among TBF1 homologues in other plant species. In addition to uORFs, another genetic element identified as important in translational control of TBF1 is a "R-motif", an mRNA consensus sequence consisting largely of purines, which interacts with poly-A-binding proteins; see Xu et al. (2017) *Nature,* 545:487-490, doi:10.1038/nature22371. Genes containing R-motifs and uORFS located upstream of the main ORF, show increased translation of the endogenous gene's main ORF in the presence of pathogen signals. Heterologous insertion of one or more of these immune-responsive elements (R-motifs and uORFs) upstream of an endogenous gene's main ORF provides a way to "tune" the translation level of an endogenous gene (even in the absence of pathogen signals (where translation is expected to be repressed). This approach can be employed in modifying endogenous genes to provide plants having enhanced expression of a gene when pathogen signals are present, without the growth or yield penalty potential in constitutive translation of the endogenous gene in question.

The following procedures are carried out to investigate the translational regulation potential of uORF sequences heterologously integrated upstream of a gene's main open reading frame. The rice (*Oryza sativa*) TBF1 gene (Os09g28354, see signal[dot]salk[dot]edu/cgi-bin/RiceGE?GENE=Os09g28340) contains a uORF similar to AtTBF1 (Xu et al. (2017) *Nature,* 545:491-494, doi:10.1038/nature22372) but does not have an obvious purine-rich R-motif A5' UTR region of the rice (Os) TBF1 gene is provided in SEQ ID NO:355; this region includes: an upstream ORF (OsTBF1 uORF2, SEQ ID NO:356, located at nucleotide positions 113-229 of SEQ ID NO:355), Cas9 nuclease PAM motifs at nucleotide positions 69-71 and 126-128 of SEQ ID NO:355, with the corresponding gRNA-specific target sequences at nucleotide positions 72-91 and 106-125 of SEQ ID NO:355.

The rice (*Oryza sativa*) NPR1 gene (Os01g0194300, see, e. g., ensemble[dot]gramene[dot]org/*Oryza_sativa*/Gene/Summary?g=OS01G0194300; r=1:5060605-5065209; t=OS01T0194300-01) and its orthologues are involved in salicylic acid-induced broad-spectrum pathogen resistance in plants. A 5' region of the rice (Os) NPR1 gene is provided in SEQ ID NO:357; this region includes a Cas9 nuclease PAM motif at nucleotide positions 51-53 of SEQ ID NO:357, with a corresponding gRNA-specific target sequence at nucleotide positions 54-73 of SEQ ID NO:357. In the presence of MAMP signals (e. g., the bacterial flagellin peptide fragment "flg22"), the OsTBF1 uORF2 sequence heterologously integrated upstream (e. g., at a double-strand break effected by Cas9 nuclease and a gRNA targetting nucleotide positions 54-73 of SEQ ID NO:357) of the main NPR1 ORF is expected to induce NPR1-mediated broad-spectrum resistance to pathogens. Similar strategies to provide plants having improved resistance to pathogens includes integration of a uORF sequence upstream of the main ORF of other defense-related genes, such as the R genes (e. g., NB-LRR genes).

Various experiments investigating the ability of the OsTBF1 5' UTR sequence (SEQ ID NO:355, including the uORF2 sequence SEQ ID NO:356) to regulate translation are performed. In a first experiment, the OsTBF1 5' UTR sequence (SEQ ID NO:355, including the uORF2 sequence SEQ ID NO:356) is inserted 3' to a 35S promoter and 5' to a luciferase (LUC) reporter gene. A control construct comprises the 35S promoter driving expression of LUC. The two constructs are individually transfected into rice protoplasts using techniques similar to those described elsewhere in this specification. The luciferase activity of the 35S-OsTBF1-5'UTR-LUC construct is predicted to be lower than the luciferase activity of the control 35S-LUC construct.

Another experiment is designed to delete the functional OsTBF1 uORF2, to test its effects on translation. Two guide RNAs designed to target the sequences at nucleotide positions 72-91 and 106-125 of SEQ ID NO:355 are delivered to the 35S-OsTBF1-5'UTR-LUC-transformed cells (e. g., by Cas9 nuclease RNPs). This results in deletion of the genomic region (which includes the start codon of the uORF2's sequence) flanked by the double-stranded breaks effected by the two gRNAs; an increase in luciferase translation is expected with removal of the uORF's repressive effect.

Another experiment is designed to evaluate the OsTBF1 uORF2's responsiveness to MAMP signals and the effects of this on translation of an ORF downstream of the uORF. The 355-OsTBF1-5'UTR-LUC-transformed cells are treated with 10 micromolar bacterial flg22 (e. g., catalogue number AS-62633, AnaSpec, Fremont, CA) as an elicitor signal, which is expected to lower the uORF's translational inhibition and result in increased luciferase translation.

A 15-nucleotide consensus sequence for purine-rich R-motifs is described in FIG. 2*a* of Xu et al. (2017) *Nature,* 545:487-490, doi:10.1038/nature22371. The ability of added R-motifs to regulate translation is tested by inserting an R-motif consisting of a 15-nucleotide poly(A) sequence (SEQ ID NO:358) or an AtTBF1 R-motif with the 25-nucleotide sequence CACATA-CACACAAAAATAAAAAAGA (SEQ ID NO:359) 3' to the 35S promoter and 5' to the OsTBF1 uORF2 in the construct 35S-OsTBF1-5'UTR-LUC. Luciferase translation is compared in the 35S-R-motif-OsTBF1-5'UTR-LUC-transformed cells, with or without 10 micromolar bacterial flg22.

In one method to improve a plant's general immunity to pathogens, sequence encoded by a polynucleotide (such as a double-stranded DNA, a single-stranded DNA, a single-stranded DNA/RNA hybrid, or a double-stranded DNA/RNA hybrid) donor molecule including nucleotides having the sequence of or encoding an uORF is integrated at the site of at least one double-strand break (DSB) in a genome, wherein the DSB is located upstream of the transcription start site (TSS) of a plant defense gene main ORF. In embodiments, the polynucleotide is: (a) a double-stranded DNA molecule having at least one strand including an uORF, such as the OsTBF1 uORF2 sequence (SEQ ID NO:356); (b) a single-stranded DNA molecule including an uORF, such as the OsTBF1 uORF2 sequence (SEQ ID NO:356) or its complement; (c) a single-stranded polynucleotide that is a DNA/RNA hybrid and that includes an uORF, such as the OsTBF1 uORF2 sequence (SEQ ID NO:356); or (d) a double-stranded DNA/RNA molecule including a DNA strand and an RNA strand capable of forming a double-stranded duplex, wherein at least one strand of the duplex includes an uORF, such as the OsTBF1 uORF2 sequence (SEQ ID NO:356). In a non-limiting example, sequence encoded by a polynucleotide including nucleotides having the sequence of a uORF is integrated at the site of at least one DSB located upstream of the transcription start site (TSS) of the main ORF of the endogenous rice chitinase 8 gene (Os10g0542900; see, e. g., ensemble[dot]gramene[dot]org/*Oryza_sativa*/Gene/Summary?g=OS10G0542900; r=10:21205700-21207611; t=OS10T0542900-01). A 5' region of the rice chitinase 8 gene is provided in SEQ ID NO:360; this region includes a Cas9 nuclease PAM motif at nucleotide positions 319-321 of SEQ ID NO: 360, with a corresponding gRNA-specific target sequence at nucleotide positions 299-318 of SEQ ID NO: 360. A single-stranded DNA molecule including the OsTBF1 uORF2 sequence (SEQ ID NO:356) is delivered to rice protoplasts together with an RNP including the Cas9 nuclease and a guide RNA designed to effect a DSB at the gRNA-specific target sequence at nucleotide positions 299-318 of SEQ ID NO: 360, which is located upstream of the transcription start site (TSS) of the chitinase ORF. The effect of the uORF2 sequence on chitinase 8 translation is measured by Western blot analysis with an anti-chitinase 8 antibody (catalogue number AS15 2889, Agrisera, Vannas, Sweden).

Example 20

This example illustrates a method of providing a plant cell having a modified phenotype, the method including introducing multiple double-strand breaks (DSBs) into the genome, in this case into non-translated genomic sequence (the 5' untranslated or promoter region) of multiple genes, and integrating at the site of the DSBs a nucleotide sequence encoded by a polynucleotide (such as a double-stranded DNA, a single-stranded DNA, a single-stranded DNA/RNA hybrid, or a double-stranded DNA/RNA hybrid) donor molecule. In this non-limiting example, multiple genomic modifications ("multiplexed edits") are effected in a maize cell by using multiple ribonucleoproteins (RNPs), each including a nuclease and a guide RNA (gRNA), to introduce a DSB at a predetermined site in the promoter region of each of three different maize genes involved in nitrogen uptake and utilization, and integrating a nitrate-responsive element sequence (encoded by a chemically modified double-stranded DNA) at the site of each DSB. The effects of the resulting multiple genomic modifications include both a non-constitutive (nitrate-responsive) increase in expression of each of the three modified genes as well as an increase in expression of an unmodified gene, AMT3.

The three endogenous maize genes selected for modification were a maize transcription factor, Dof1 (see, e. g., www[dot]uniprot[dot]org/uniprot/Q1HFQ1; Kurai et al. (2001) *Plant Biotechnol. J.,* 9:826-837); a maize nitrogen transporter, NRT2.2 (see, e. g., www[dot]uniprot[dot]org/uniprot/Q53CL7); and a maize glutamine synthetase, Gln1.4 (see, e. g., www[dot]uniprot[dot]org/uniprot/B9TSW5). The nitrate-responsive maize ammonium transporter AMT3 gene (GRMZM2G118950, see www[dot]maizegdb[dot]org/gbrowse?name=GRMZM2G118950) was chosen as an unmodified read-out gene.

Maize B73 protoplasts were harvested from leaves of B73 maize plants that had been grown in nitrate-free medium for 13 days (see Example 15). Three different ribonucleoproteins (RNPs) were prepared with Cas9 nuclease (Aldevron, Fargo, ND) and one of three guide RNA complexes, each including a different crRNA complexed with a tracrRNA (Integrated DNA Technologies, Coralville, IA). The three crRNAs were "NRT2.2_Pro1" with the sequence CAAACAAAAAAGAAUGCAUGGUUUUAGAGC-UAUGCU (SEQ ID NO:361), "Gln1-4_Pro-1" with the sequence UGUAUCCGUAUUUAUACGUGGUUUUA-GAGCUAUGCU (SEQ ID NO:362), and "Dof1_Pro-1" with the sequence GACGCGAGUGGGGGCCCACG-GUUUUAGAGCUAUGCU (SEQ ID NO:363). A nitrogen responsive element (AtNRE, see Example 15) encoded by a polynucleotide donor molecule was provided as a 43 base-pair chemically modified dsDNA (purchased from Integrated DNA Technologies, Coralville, IA) having a first strand with the sequence of SEQ ID NO:349 annealed to a second strand with the sequence of SEQ ID NO:350); each strand was phosphorylated on the 5' end and contained two phosphorothioate linkages at each terminus (i. e., the two linkages between the most distal three bases on either end of the strand).

Following the same general procedures described above (e. g., Examples 4, 8, 9, 12, 15, and 17) the protoplasts were transfected with the RNPs. Maize protoplasts treated with no nuclease, no guide RNA complex, no salmon sperm DNA, and no polynucleotide donor molecule served as a null control. The different guide RNA (gRNA) complexes were prepared by mixing equal amounts of tracrRNA and the gene-specific CRISPR crRNA: 30 microliters of 100 micromolar crRNA were mixed with 30 microliters of 100 micromolar tracrRNA, heated at 95 degrees Celsius for 5 minutes, and then cooled to room temperature. To the cooled gRNA solution, 100 micrograms Cas9 nuclease (Aldevron, Fargo, ND) was added and the mixture incubated 5 minutes at room temperature to allow the ribonucleoprotein (RNP) complex to form. For three reactions, 35 microliters of an individual ("NRT2.2_Pro1", "Gln1-4_Pro-1", or "ˆ5 Dof1_Pro-1") RNP solution were added to 1000 microliters of maize protoplasts (prepared as described in Example 1) in a microfuge tube; in one "multiplexed editing" reaction, 35 microliters of each individual ("NRT2.2_Pro1", "Gln1-4_Pro-1", or "Dof1_Pro-1") RNP solution were added to 1000 microliters of maize protoplasts in a microfuge tube. All tubes except for the null control also received 50 microliters (50 micromolar) of the AtNRE polynucleotide donor molecule. Two microliters (20 micrograms) salmon sperm DNA (VWR Cat. No.: 95037-160) and 1.2 milliliters of 40% PEG were added to each tube. The reaction mixtures were mixed gently by tapping and incubated 5 minutes at room temperature. The reactions were stopped by adding 5 milliliters of washing buffer (0.6 molar mannitol, 4 millimolar MES pH 5.7, and 20 millimolar KCl; see Example 1) to each tube and mixed gently by inverting the tube. The tubes were centrifuged 2 minutes at 1200 rpm and the supernatant was then removed. The protoplasts were resuspended in 10 milliliters incubation solution and transferred to 10×10 cm dishes pre-coated with 5% calf serum; the dishes were sealed with Parafilm M® film (Bemis, Oshkosh, WI), incubated 1 hour at 37 degrees Celsius, and then incubated an additional 47 hours at 26 degrees Celsius in the dark. Forty-eight hours after transfection, half of the cells were treated with 0.5 millimolar $KNO_3$ and half with 0.5 millimolar KCl; cells were incubated 1 hour, and then harvested for analysis.

Quantitative RT-PCR was employed on three technical replicates per treatment to measure the relative expression of each gene. Results (mean of triplicates, standard deviation) are provided in Table 19 and illustrated in FIG. 5, panels A and B, with relative gene expression levels normalized to tubulin. The data indicate that, without any modifications, the Dof1, NRT2.2, and Gln1.4 genes individually responded to nitrate exposure with an increase in relative expression of about 3- to about 5-fold (Table 19; FIG. 5, panel A). Integrating a nitrogen responsive element (AtNRE) sequence into the promoter region of the Dof1, NRT2.2, and Gln1.4 strongly increased the responsiveness of these genes to nitrate; the NRE-modified genes responded to nitrate exposure with an increase in relative expression of about 12- to about 16-fold (Table 19; FIG. 5, panel A). When the Dof1, NRT2.2, and Gln1.4 genes were modified by multiplexed editing of all three genes together, the result was an additional increase in nitrate response, especially marked in NRT2.2, which responded to nitrate exposure by about 26-fold, or nearly twice the increase in expression observed when NRT2.2 was modified alone (Table 19; FIG. 5, panel A).

The relative expression of the unmodified, endogenous AMT3 gene was also measured. In cells where the Dof1, NRT2.2, and Gln1.4 genes had not been modified, AMT3 relative expression increased in the presence of nitrate by about 4-fold (Table 19; FIG. 5, panel B). In cells where the Dof1, NRT2.2, and Gln1.4 genes were individually modified, AMT3 relative expression increased in the presence of nitrate by about 12-, about 11-, and about 9-fold, respectively (Table 19; FIG. 5, panel B). In cells where the Dof1, NRT2.2, and Gln1.4 genes were modified by multiplexed editing of all three genes together, AMT3 relative expression increased in the presence of nitrate by about 25-fold (Table 19; FIG. 5, panel B).

TABLE 19

| | | KCl | | $KNO_3$ | |
|---|---|---|---|---|---|
| RNP used | Gene | Relative Expression | SD | Relative Expression | SD |
| Null control (no RNP) | Dof1 | 1.00 | 0.09 | 3.11 | 0.09 |
| | NRT2.2 | 1.00 | 0.05 | 3.76 | 0.10 |
| | Gln1.4 | 1.00 | 0.02 | 5.06 | 0.21 |
| | AMT3 | 1.01 | 0.14 | 3.72 | 0.43 |
| Dof1 | Dof1 | 0.81 | 0.04 | 16.08 | 0.28 |
| | NRT2.2 | 0.52 | 0.06 | 5.70 | 0.38 |
| | Gln1.4 | 0.86 | 0.03 | 7.24 | 0.38 |
| | AMT3 | 1.06 | 0.09 | 12.32 | 0.20 |
| NRT2.2 | Dof1 | 0.88 | 0.12 | 6.86 | 0.42 |
| | NRT2.2 | 0.83 | 0.04 | 13.28 | 0.58 |
| | Gln1.4 | 0.56 | 0.02 | 6.02 | 0.23 |
| | AMT3 | 0.50 | 0.00 | 11.25 | 0.04 |
| Gln1.4 | Dof1 | 1.21 | 0.07 | 5.67 | 0.33 |
| | NRT2.2 | 0.91 | 0.07 | 6.52 | 0.46 |
| | Gln1.4 | 0.89 | 0.02 | 12.04 | 0.11 |
| | AMT3 | 1.38 | 0.16 | 8.70 | 0.14 |
| Multiplexed edits (Dof1, NRT2.2, and Gln1.4) | Dof1 | 0.66 | 0.06 | 17.62 | 1.08 |
| | NRT2.2 | 0.49 | 0.03 | 25.74 | 2.88 |
| | Gln1.4 | 0.60 | 0.29 | 14.05 | 0.53 |
| | AMT3 | 1.12 | 0.19 | 25.01 | 2.03 |

Additional experiments can be carried out with the same editing reagents in a plant/plant tissue, e. g., using microinjection or biolistics as described in Examples 49-51 and 54. A one-step delivery method can be used to achieve multiplexed edits (multiple modifications) with the same polynucleotide donor to target different genes. For insertion of different polynucleotide donor sequences using the same nuclease (e. g. Cas9 or Cpf1), sequential steps for delivery of different combinations of reagents with a 30 min to 48 h gap between the steps can be used. For insertion of different polynucleotide donor sequences using different nucleases (e. g. Cas9 and Cpf1), a one-step delivery method can be used, for example, with a blunt-ended double-stranded polynucleotide donor for Cas9 and a double-stranded polynucleotide donor containing overhangs for Cpf1.

Example 21

This example illustrates a method of providing a plant cell having a modified phenotype, the method including integrating at a predetermined genomic locus a nucleotide sequence encoded by a polynucleotide (such as a double-stranded DNA, a single-stranded DNA, a single-stranded DNA/RNA hybrid, or a double-stranded DNA/RNA hybrid) donor molecule. More specifically, this non-limiting example illustrates incorporation of an insulator element in the 5' untranslated or promoter region of the maize nitrate-responsive gene, AMT3.

Two different crRNAs and a tracrRNA were purchased from Integrated DNA Technologies, Coralville, IA. The first crRNA (AMT3-Pro1) had the sequence CCAGUGAAUCUCCCCUCCCGGUUUUAGAGCUAUGCU (SEQ ID NO:346), and the second crRNA (AMT3-Pro2) had the sequence CGUUCCUCAGCCUCACUGUGGUUUUAGAGCUAUGCU (SEQ ID NO:347). Guide RNAs made with these crRNAs were designed to respectively effect a DSB at 147 (AMT3Pro-1) or 230 (AMT3Pro-2) nucleotides upstream of (5' to) the transcription start site of the AMT3 coding sequence. Guide RNA complexes were made by mixing 70 microliters of 100 micromolar tracrRNA and 70 microliters of 100 micromolar crRNA, heating the mixture to 95 degrees Celsius for 5 minutes, removing from the heating block, and allowing the tubes to cool to room temperature on the benchtop.

The palindromic nucleotide sequence of the insulator was 5'-GAATATATATATATTC-3' (SEQ ID NO:364, see U.S. Pat. No. 7,605,300, which is incorporated herein by reference) which was encoded on a chemically modified, single-stranded DNA donor molecule that was phosphorylated on the 5' end and contained two phosphorothioate linkages at each terminus (i. e., the two linkages between the most distal three bases on either end of the strand). One hundred microliters (100 micromolar) of the insulator solution was heated to 95 degrees Celsius for 5 minutes, then the heat was turned off and the solution allowed to slowly cool to room temperature in the block.

Maize B73 protoplasts were harvested from leaves of B73 maize plants that had been grown in nitrate-free medium for 13 days (see Examples 15 and 20). One milliliter of protoplasts (2×10^5 cells per milliliter) was added to each of five reaction tubes. Ribonucleoproteins (RNPs) were prepared by mixing 200 micrograms Cas9 nuclease (Aldevron, Fargo, ND) and 120 microliters of one of the two guide RNA complexes (AMT3Pro-1 crRNA/tracrRNA or AMT3Pro-2 crRNA/tracrRNA), incubating the mixtures for 5 minutes at room temperature. To each RNP solution was added 2 microliters (20 micrograms) of salmon sperm DNA (VWR Cat. No.: 95037-160). Editing experiments were carried out in the five reaction tubes with 70 microliters of an RNP solution, with or without 50 microliters of insulator solution, and sufficient buffer added if necessary to make up a total volume of 120 microliters. Maize protoplasts treated with no nuclease, no guide RNA complex, no salmon sperm DNA, and no polynucleotide donor molecule served as a null control. To each tube was added 1.2 milliliters of 40% PEG; the reaction mixtures were mixed gently by tapping and incubated 5 minutes at room temperature. The reactions were stopped by adding 5 milliliters of washing buffer (0.6 molar mannitol, 4 millimolar MES pH 5.7, and 20 millimolar KCl; see Example 1) to each tube and mixed gently by inverting the tube. The tubes were centrifuged 2 minutes at 1200 rpm and the supernatant was then removed. The protoplasts were resuspended in 6 milliliters incubation solution and transferred to 10×10 cm dishes pre-coated with 5% calf serum; the dishes were sealed with Parafilm M® film (Bemis, Oshkosh, WI), incubated 1 hour at 37 degrees Celsius, and then incubated an additional 47 hours at 26 degrees Celsius in the dark. Forty-eight hours after transfection, half of the plates were treated with 10 millimolar (final concentration) $KNO_3$ and half with 10 millimolar (final concentration) KCl; cells were incubated 1 hour, and then harvested for analysis.

Quantitative RT-PCR was employed on three technical replicates per treatment to measure the relative expression of the AMT3 gene. Results (mean of triplicates, standard deviation) are provided in Table 20, with relative AMT3 expression levels normalized to tubulin. The unmodified (native) maize AMT gene is responsive to high nitrate, with an increase in relative expression of about 15-fold, compared to relative expression under low nitrate conditions. Editing with only an RNP (nuclease and guide RNA complex) resulted in decreasing this response to high nitrate to about 10-fold with the AMT3-Pro1 RNP and about 12-fold with the AMT3-Pro2 RNP; this could be attributed to possible disruption of the promoter sequence and consequently possible interference with normal transcription or translation. Integration of the insulator sequence at the AMT3Pro-1-mediated DSB located 147 nucleotides upstream of the TSS of the AMT3 coding region resulted in only about 2-fold increase in relative expression under high nitrate. Integration of the insulator sequence at the AMT3Pro-2-mediated DSB located 230 nucleotides upstream of the TSS of the AMT3 coding region resulted in only about 7-fold increase in relative expression under high nitrate. Thus, integrating the relatively small insulator sequence upstream of the AMT3 TSS reduced the AMT3 gene's induction by nitrate. These results demonstrate the ability of an integrated sequence encoded by a polynucleotide donor molecule to efficiently moderate or decrease a gene's expression, for example, by "insulating" the gene's promoter from upstream enhancer sequences. This approach may also be useful, e. g., in insulating an actively transcribed gene from an epigenetically silenced gene.

TABLE 20

| | KCl | | $KNO_3$ | |
|---|---|---|---|---|
| Editing treatment | Relative Expression | SD | Relative Expression | SD |
| Null control (no RNP) | 1.00 | 0.12 | 15.55 | 1.18 |
| AMT3-Pro1 | 1.08 | 0.10 | 10.16 | 0.46 |
| AMT3-Pro1 + Insulator | 1.61 | 0.10 | 2.58 | 0.03 |
| AMT3-Pro2 | 1.69 | 0.21 | 12.33 | 0.60 |
| AMT3-Pro2 + Insulator | 1.71 | 0.06 | 7.15 | 0.26 |

Example 22

This example illustrates a method of providing a plant cell having a modified phenotype, the method including effecting a double-strand break (DSB) at a predetermined genomic locus. More specifically, this non-limiting example illustrates effecting a double-strand break (DSB) at one or at multiple predetermined loci within a first gene (FEA3), thereby reducing that gene's expression; this further results in increasing expression of a second gene (WUS), which is normally repressed by the first gene.

The transcription factor WUSCHL (WUS) is expressed in the organizing center cells below the stem cells in a plant's shoot meristem; WUS expression prevents differentiation of stem cells. WUS activates expression of *CLAVATA* (CLV) and the CLV signalling pathway, which then controls stem cell proliferation and differentiation. The balance between WUS and CLV is maintained by feedback signalling between the organizing center cells and stem cells. The CLV3 peptide is secreted from stem cells at the tip of the shoot apical meristem, and is bound by CLV1, is a leucine-rich-repeat (LRR) receptor kinase; this results in negative regulation of shoot and floral meristem. Another LRR receptor reported to respond to the CLV3 peptide is FASCIATED EAR3 (FEA3); weak alleles of fea3 have been reported to enhance yield in hybrid maize; see: Je et al. (2016) *Nature Genetics,* 48:785-791; DOI: 10.1038/ng.3567. Reducing expression of FEA3 is predicted to increase expression of WUS.

These experiments were carried out to observe the effects of down-regulating or knocking-out expression of FEA3 in maize cells. Two different crRNAs and a tracrRNA were purchased from Integrated DNA Technologies, Coralville, IA. The first crRNA (ZmFea3-1) had the sequence GCGCUCCUUCUCCUCCAUGGGUUUUAGAGCUAUGCU (SEQ ID NO:365), and the second crRNA (ZmFea3-2) had the sequence CCUCGGCGUGGCGCUCUCGGGUUUUAGAGCUAUGCU (SEQ ID NO:366). Guide RNA complexes were made by mixing 60 microliters of 100 micromolar tracrRNA and 60 microliters of 100 micromolar crRNA, heating the mixture to 95 degrees Celsius for 5 minutes, removing from the heating block, and allowing the tubes to cool to room temperature on the benchtop.

Maize B73 protoplasts were harvested from leaves of B73 maize plants. One milliliter of protoplasts (2×10^5 cells per milliliter) was added to each of four reaction tubes. Ribonucleoproteins (RNPs) were prepared by mixing 24 microliters (240 micrograms) Cas9 nuclease (Aldevron, Fargo, ND) and 120 microliters of one of the two guide RNA complexes (AMT3Pro-1 crRNA/tracrRNA or AMT3Pro-2 crRNA/tracrRNA), incubating the mixtures for 5 minutes at room temperature. Editing experiments were carried out in the four reaction tubes with either 72 microliters of one of the two RNP solutions or 72 microliters of both RNP solutions, with sufficient buffer added if necessary to make up a total volume of 144 microliters; 2 microliters (20 micrograms) of salmon sperm DNA (VWR Cat. No.: 95037-160) was added to each tube except for the null control. Maize protoplasts treated with no nuclease, no guide RNA complex, no salmon sperm DNA, and no polynucleotide donor molecule served as a null control. To each tube was added 1.2 milliliters of 40% PEG; the reaction mixtures were mixed gently by tapping and incubated 5 minutes at room temperature. The reactions were stopped by adding 5 milliliters of washing buffer (0.6 molar mannitol, 4 millimolar MES pH 5.7, and 20 millimolar KCl) to each tube and mixed gently by inverting the tube. The tubes were centrifuged 2 minutes at 1200 rpm and the supernatant was then removed. The protoplasts were resuspended in 4 milliliters incubation buffer (see Example 2) including the herbicide 2,4-dichlorophenoxyacetic acid ("2,4-D") with 50 millimolar $CaCl_2$ added) solution. One milliliter of cells from each tube was transferred to a well in a 6-well plate; the remaining 3 milliliters of cells from each tube were plated in four 10×10 cm dishes (all pre-coated with 5% calf serum), with another 3 milliliters of incubation buffer added per dish (for an optimal cell density for incubation). The plate and dishes were sealed with Parafilm M® film (Bemis, Oshkosh, WI), incubated 1 hour at 37 degrees Celsius, and then incubated an additional 47 hours at 26 degrees Celsius in the dark. Forty-eight hours after transfection, cells were harvested for analysis.

Quantitative RT-PCR was employed on three technical replicates per treatment to measure the relative expression of the FEA3 and WUS1 genes. Results (mean of triplicates, standard deviation) are provided in Table 21, with relative gene expression levels normalized to tubulin. The data show that use of a single RNP (i. e., providing a DSB at a single precise locus in the FEA3 gene), either Fea3-1 or Fea3-2, was sufficient to knock down FEA3 expression by about two-thirds; this further resulted in about a 2-fold increase in WUS expression. Use of both RNPs (i. e., providing a DSB at two precise loci in the FEA3 gene) knocked down FEA3 expression by about four-fifths, and further resulted in strong (about 15-fold) upregulation of WUS expression.

TABLE 21

| | FEA3 | | WUS | |
|---|---|---|---|---|
| Treatment | Relative expression | SD | Relative expression | SD |
| Null control | 1.00 | 0.04 | 1.00 | 0.09 |
| Fea3-1 | 0.27 | 0.03 | 2.81 | 0.24 |
| Fea3-2 | 0.31 | 0.02 | 2.10 | 0.20 |
| Fea3 1 + 2 | 0.19 | 0.01 | 15.15 | 2.01 |

Example 23

This example illustrates a method of providing a plant cell having a modified phenotype, the method including introducing double-strand breaks (DSBs) into multiple loci or into multiple genes, and integrating at the DSBs at least two different nucleotide sequences encoded by a polynucleotide (such as a double-stranded DNA, a single-stranded DNA, a single-stranded DNA/RNA hybrid, or a double-stranded DNA/RNA hybrid) donor molecule. In this non-limiting example, multiple genomic modifications ("multiplexed edits") were effected in a maize cell by using multiple ribonucleoproteins (RNPs), each including a nuclease and a guide RNA (gRNA), to introduce a DSB at a predetermined site in the promoter region of each of two different maize genes involved in nitrogen uptake and utilization; a nitrate-responsive element sequence is then integrated at the site of the DSB in the first gene (AMT3), and a palindromic 12-nucleotide endogenous maize sequence having homology to the bacterial OCS enhancer is integrated at the site of the DSB in the second gene (Lc). In this example, a first round of editing to effect a first DSB and integration of a sequence encoded by a first polynucleotide donor molecule was carried out, followed by a second round of editing to effect a second DSB and integration of a sequence encoded by a second polynucleotide donor molecule; no selection or screening was performed between the editing rounds. The time between editing rounds was 3 hours or 18 hours.

Two crRNAs, a tracrRNA, and the polynucleotide donor molecules were purchased from Integrated DNA Technologies, Coralville, IA. The first crRNA (AMT3-Pro1) had the sequence of SEQ ID NO:346 (see Example 21) and the second crRNA (ZmLc-Pro3) had the sequence of SEQ ID NO:334 (see Example 15). The first polynucleotide donor molecule was a nitrogen responsive element (AtNRE, see Examples 15 and 20) encoded by a 43 base-pair chemically modified dsDNA having a first strand with the sequence of SEQ ID NO:349 annealed to a second strand with the sequence of SEQ ID NO:350, and the second polynucleotide donor molecule was the maize OCS homologue (see Example 14) encoded by a chemically modified single-stranded DNA with the sequence of SEQ ID NO:343. For both polynucleotide donor molecules, whether dsDNA or ssDNA, each strand was phosphorylated on the 5' end and contained two phosphorothioate linkages at each terminus (i. e., the two linkages between the most distal three bases on either end of the strand). Individual guide RNA complexes were made by mixing 60 microliters of 100 micromolar tracrRNA and 60 microliters of the 100 micromolar crRNA (AMT3-Pro1 or ZmLc-Pro3), heating the mixture to 95 degrees Celsius for 5 minutes, removing from the heating block, and allowing the tubes to cool to room temperature on the benchtop. To prepare the donor polynucleotide molecules, 150 microliters (100 micromolar) of the first AtNRE strand (SEQ ID NO:349) and 150 microliters (100 micromolar) of the second AtNRE strand (SEQ ID NO:350) were mixed together in a tube; to another tube was added 150 microliters (100 micromolar) of the palindromic OCS homologue ssDNA (SEQ ID NO:343). The tubes were heated to 95 degrees Celsius for 5 minutes, then the heat was turned off and the solution allowed to slowly cool to room temperature in the block.

Maize B73 protoplasts were harvested from leaves of B73 maize plants that had been grown in nitrate-free medium for 13 days (see Examples 15, 20, and 21). The protoplasts underwent a first editing reaction to integrate a nitrogen-responsive element sequence in the promoter region of the AMT3 gene, and then underwent a second editing reaction to integrate an auxin-responsive element in the promoter region of the Lc gene. Maize protoplasts treated with no nuclease, no guide RNA complex, no salmon sperm DNA, and no polynucleotide donor molecule served as a null control. One milliliter of protoplasts (2×10^5 cells per milliliter) was added to each of six reaction tubes. Then, to each of four tubes were added 5 microliters (50 micrograms) Cas9 nuclease (Aldevron, Fargo, ND) and 30 microliters of the AMT3-Pro1 guide RNA complex (AMT3-Pro1 crRNA/tracrRNA), and to the remaining two tubes (null controls) were added 90 microliters buffer. All tubes were incubated 5 minutes at room temperature. To each of the first four tubes (treated with the Cas9/AMT3-Pro1 guide RNA) were added 50 microliters of the AtNRE polynucleotide donor solution and 2 microliters (20 micrograms) salmon sperm DNA (VWR Cat. No.: 95037-160). To each tube was added 1.1 milliliters of 40% PEG; the reaction mixtures were mixed gently by tapping and incubated 5 minutes at room temperature. The reactions were stopped by adding 5 milliliters of washing buffer (0.6 molar mannitol, 4 millimolar MES pH 5.7, and 20 millimolar KCl) to each tube and mixed gently by inverting the tube. The tubes were centrifuged 2 minutes at 1200 rpm and the supernatant was then removed. The protoplasts were resuspended in 5 milliliters incubation solution (see Example 2, but without any nitrate and with 50 millimolar $CaCl_2$ added) and transferred to 10×10 cm dishes pre-coated with 5% calf serum; the dishes were sealed with Parafilm M® film (Bemis, Oshkosh, WI), incubated 30 minutes at 37 degrees Celsius, and then incubated at 26 degrees Celsius in the dark.

After 3 hours incubation at 26 degrees Celsius, two of the plates containing protoplasts treated with the Cas9/AMT3-Pro1 guide RNA and AtNRE polynucleotide donor molecule were subjected to the second editing reaction as follows. Ten microliters (100 micrograms) Cas9 and 60 microliters of the ZmLc-Pro3 guide RNA were mixed gently in a tube and incubated 5 minutes at room temperature; 50 microliters of the palindromic OCS homologue ssDNA (SEQ ID NO:343) solution and 2 microliters (20 micrograms) salmon sperm DNA (VWR Cat. No.: 95037-160) were then added and mixed gently in the tube. Two of the plates containing protoplasts treated with the Cas9/AMT3-Pro1 guide RNA and AtNRE polynucleotide donor molecule were harvested by centrifugation 2 minutes at 1200 rpm and the supernatant removed. The protoplasts from an individual plate were resuspended in two tubes each containing 1 milliliter washing buffer. Each tube received half of the prepared RNP (Cas9/ZmLc-Pro3)/OCS ssDNA/salmon sperm DNA mixture, and tapped gently to mix. To each tube was added 1.1 milliliters of 40% PEG; the reaction mixtures were mixed gently by tapping and incubated 5 minutes at room temperature. The reactions were stopped by adding 5 milliliters of washing buffer to each tube and mixed gently by inverting the tube. The tubes were centrifuged 2 minutes at 1200 rpm and the supernatant was then removed. The protoplasts were resuspended in 5 milliliters incubation solution (see Example 2, but without any nitrate and with 50 millimolar $CaCl_2$ added) and transferred to 10×10 cm dishes pre-coated with 5% calf serum; the dishes were sealed with Parafilm M® film (Bemis, Oshkosh, WI), incubated 30 minutes at 37 degrees Celsius, and then incubated at 26 degrees Celsius in the dark.

After 18 hours incubation at 26 degrees Celsius, the remaining two of the plates containing protoplasts treated with the Cas9/AMT3-Pro1 guide RNA and AtNRE polynucleotide donor molecule were subjected in a similar manner to the second editing reaction. All treatment steps were identical to those carried out at the 3-hour timepoint as described in the immediately preceding paragraph.

Twenty-four additional hours after the 18-hour transfection (editing reaction), half of the plates were treated with 0.5 millimolar $KNO_3$ and half with 0.5 millimolar KCl; cells were incubated 1 hour, and then harvested for analysis.

Quantitative RT-PCR was employed on three technical replicates per treatment to measure the relative expression of the AMT3 and Lc genes. Results (mean of triplicates, standard deviation) are provided in Table 21 and illustrated in FIG. 6, with relative gene expression levels normalized to tubulin. The data show that the endogenous (non-edited) AMT3 and Lc genes both show a moderate (about 4- to 5-fold, relative to KCl controls), nitrate-induced increase in expression. In the cells that underwent a second (ZmLc-Pro3/OCS homologue) transfection or editing reaction 3 hours after the first (AMT3-Pro1/AtNRE) transfection, there is a nitrate-induced increase in Lc expression that may be due to excess AtNRE polynucleotide donor, resulting in the AtNRE sequence being incorporated into the DSB effected by the later-provided Lc-Pro3 guide. In the cells that underwent a second (ZmLc-Pro3/OCS homologue) transfection or editing reaction 18 hours after the first (AMT3-Pro1/AtNRE) transfection, nitrate-induced increase is not observed in Lc expression, indicating that excess AtNRE polynucleotide has degraded and that it is the sequence encoded by the OCS homologue that is incorporated into the DSB effected by the Lc-Pro3 guide. There is increased relative expression of AMT3 even in the absence of nitrate induction, which suggests the possibility of some Cas9 remaining bound to the AMT3-Pro1 site at the time of the second (ZmLc-Pro3/OCS homologue) editing reaction, which might have resulted in unintentional incorporation of some OCS homologue sequence into the AMT3-Pro1 site; this effect is more evident at 3 hours than at 18 hours, indicating that there is less Cas9 remaining bound to the AMT3-Pro1 at 18 hours than at 3 hours. NGS sequencing is performed to verify and quantify correct integration of the polynucleotide donor molecules at the intended loci in the genome.

TABLE 22

| | | AMT3 | | Lc | |
|---|---|---|---|---|---|
| Genome editing treatment | Nutrient treatment | Relative Expression | SD | Relative Expression | SD |
| Null | KCl | 1.02 | 0.25 | 1.00 | 0.10 |
| | $KNO_3$ | 3.76 | 0.17 | 5.10 | 1.06 |
| AMT3-Pro1 + AtRNE; at 3 hours Lc-Pro3 + OCS | KCl | 5.74 | 0.30 | 17.66 | 1.00 |
| | $KNO_3$ | 14.45 | 1.18 | 23.67 | 0.98 |
| AMT3-Pro1 + AtRNE; at 18 hours Lc-Pro3 + OCS | KCl | 3.37 | 0.06 | 20.34 | 1.51 |
| | $KNO_3$ | 15.22 | 1.97 | 20.04 | 0.51 |

One of skill in the art would recognize that effecting multiple DSBs in a genome (e. g., effecting multiple DSBs in a sequence of interest or effecting at least one DSB in each of two or more sequences of interest) can be achieved by successive rounds of editing reactions in the same plant cell (or whole plant, plant part or tissue, embryo, or seed) in a manner such as that illustrated by this example. Any of these DSBs can be effected through alternative methods (e. g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the approach described herein include use of any of these methods and effector molecules for simultaneously effecting multiple DSBs in a genome, and, optionally, integrating at least one polynucleotide molecule at one or more DSBs.

Additional experiments can be carried out with the same editing reagents in a plant/plant tissue, e. g., using microinjection or biolistics as described in Examples 49-51 and 54. A one-step delivery method can be used to achieve multiplexed edits (multiple modifications) with the same polynucleotide donor to target different genes. For insertion of different polynucleotide donor sequences using the same nuclease (e. g. Cas9 or Cpf1), sequential steps for delivery of different combinations of reagents with a 30 min to 48 h gap between the steps can be used. For insertion of different polynucleotide donor sequences using different nucleases (e. g. Cas9 and Cpf1), a one-step delivery method can be used, for example, with a blunt-ended double-stranded polynucleotide donor for Cas9 and a double-stranded polynucleotide donor containing overhangs for Cpf1.

Example 24

This example illustrates a method of modifying a sequence of interest in a genome, comprising integrating a polynucleotide (such as a double-stranded DNA, a single-stranded DNA, a single-stranded DNA/RNA hybrid, or a double-stranded DNA/RNA hybrid) molecule at the site of at least one double-strand break (DSB) in a genome. More specifically, this example illustrates integrating a sequence encoded by a polynucleotide into one or more double-strand breaks in a genome, wherein at least one of the DSBs is asymmetric (e. g., has at least a one-nucleotide overhang), and wherein the sequence encoded by the polynucleotide is integrated at the asymmetric DSB in a specific orientation. This approach is useful for integrating a specifically oriented recombinase recognition site sequence at each of two DSBs effected in a genome, allowing use of a sequence-specific recombinase to mediate deletion, exchange, inversion, or translocation of genomic sequence flanked by the recombinase recognition sites thus integrated.

In this example, the nuclease Cpf1 is used to effect a DSB containing overhangs at two loci in a genome, for example, in each of the two introns flanking an exon. A first recombinase recognition site sequence is integrated into one DSB and a second recombinase recognition site sequence is integrated into the other DSB; the two recombinase recognition site sequences are heterospecific relative to each other, i. e., each will not recombine together but each will recombine only with another recombination site of its own type. Subsequent to the genomic integration of the heterospecific recombinase recognition site sequences, a polynucleotide donor molecule is provided for recombinase-mediated genomic sequence replacement, for example, replacement of an exon. This polynucleotide donor molecule includes a replacement genomic sequence (for example, a replacement exon sequence) and further includes on each terminus a recombinase recognition site sequence that is homospecific to (i. e., will recombine with) one of the genomically integrated recombinase recognition site sequences. The appropriate recombinase is also provided, resulting in the exchange of the endogenous exon sequence for the replacement exon sequence. This technique avoids introducing editing inaccuracies such as unintentional nucleotide changes, deletions, or additions in the integrated replacement exon sequence or the messenger RNA encoded by the replacement exon. In the particular example described below, this technique is used to replace a "wild-type" maize EPSPS exon 2 (an exon having unmodified, native genomic sequence) with a replacement exon 2 sequence that encodes a modified EPSPS protein having resistance to glyphosate.

The target gene selected for editing is the maize (*Zea mays*, B73 line) enolpyruvylshikimate phosphate synthase1 (EPSPS) gene (see www[dot]maizegdb[dot]org/gene_center/gene/Zm00001d045450) with the partial genomic sequence of gtgaacaaccttatgaaatgggcgcaaagaactcgccct-caagggttgatcttatgccatcgtcatgataaacagtggagcacggacgatccttta egttgtttttaacaaaetttgtcagaaaactagcatcattaaettettaatgacgattt-cacaacaaaaaaaggtaacetegetactaacataacaaaatac ttgttgcttat-taattatatgtttttaatctttgatcAGGGGACAACAGTGGTTGA-TAACCTGTTGAACAGTGAGGA TGTCCACTACATGCTCGGGGCCTT-GAGGACTCTTGGTCTCTCTGTCGAAGCGGACAAAG C TGCCAAAAGAGCTGTAGTTGTTGGCTGTGGTG-GAAAGTTCCCAGTTGAGGATTCTAAAGA GGAAGTGCAGCTCTTCTTGGGGAATGCTG-GAACTGCAATGCGGCCATTGACAGCAGCTG TTACTGCTGCTGGTG-GAAATGCAACgtatgtttcctctctttctctctacaatacttgctggagt-tagtatgaaacccatgggtat gtctagt (SEQ ID NO:367); a first intronic sequence (nucleotides 1-238 of SEQ ID NO:367) and a second intronic sequence (nucleotides 483-550 of SEQ ID NO:367) are given in lower-case font, exonic sequence (nucleotides 239-482 of SEQ ID NO:367) is given in upper-case font, a first crRNA (guide RNA) target site sequence (nucleotides 23-43 of SEQ ID NO:367) and a second crRNA (guide RNA) target site sequence (nucleotides 508-528 of SEQ ID NO:367) are italicized and the PAM sites (nucleotides 19-22 and nucleotides 529-532 of SEQ ID NO:367) are underlined.

Maize B73 protoplasts are prepared as described in Examples 1, 4, 8, 9, 12, 15, 16, and 17. Ribonucleoproteins (RNPs) are prepared with Cpf1 nuclease (Aldevron, Fargo, ND) and either of two guide RNAs (purchased from Integrated DNA Technologies, Coralville, IA); the first guide RNA ("EPS-Cpf1-g1") has the sequence UAAUUUCUACUCUUGUAGAUGGCGCAAAGAACUCGCCCUCA (SEQ ID NO:368) and the second guide RNA ("EPS-Cpf1-g2") has the sequence UAAUUUCUACUCUUGUAGAUAUACUAACUCCAGCAAGUAUU (SEQ ID NO:369).

Two different, chemically modified, double-stranded DNA (dsDNA) donor molecules, each encoding one of a pair of heterospecific recombinase recognition site sequences (in this case, loxP and lox2272), are used in this experiment. The first dsDNA ("loxP") donor molecule, containing 40 base pairs and 5-nucleotide overhangs, is produced by annealing a first strand having the sequence (SEQ ID NO: 370)
5'-P-T*C*AAGGGTATAACTTCGTATAGCATACATTATACGAAGTTAT

TCA-3' and a second strand having the sequence (SEQ ID NO: 371)
5'-P-C*T*TGATGAATAACTTCGTATAATGTATGCTATACGAAGTTAT

ACC-3';

the loxP sequences are underlined. The second dsDNA ("lox2272") donor molecule, containing 40 base pairs and 5-nucleotide overhangs, is produced by annealing a first strand having the sequence (SEQ ID NO: 372)
5'-P-A*C*AATGGTATAACTTCGTATAAAGTATCCTATACGAAGTTAT

TCA-3' and a second strand having the sequence (SEQ ID NO: 373)
5'-P-A*T*TGTTGAATAACTTCGTATAGgATACtTTATACGAAGTTAT

ACC-3';

the lox2272 sequences are underlined.

This polynucleotide molecule including a replacement genomic sequence (for example, a replacement exon sequence) and further includes on each terminus a recombinase recognition site sequence that is homospecific to (i. e., will recombine with) one of the genomically integrated recombinase recognition site sequences.

A dsDNA molecule, including a replacement EPSPS exon sequence and further including a loxP recombinase recognition sequence 5' to the EPSPS exon sequence and a lox2272 recombinase recognition sequence 3' to the EPSPS exon sequence, was prepared by PCR using primers and a template purchased from Integrated DNA Technologies, Coralville, IA. The primers were had the sequences 5'-P-G*T*GAACAACCTTATGAAATTTGGG (forward primer, SEQ ID NO:374) and 5'-P-A*C*TAGACATACCCATGGGTTTCAT (reverse primer, SEQ ID NO:375), where P represents a 5' phosphorylation and * indicates a phosphorothioate linkage. The template sequence is given by (SEQ ID NO: 376)
5'-GTGAACAACCTTATGAAATTTGGGCGCATAACTTCGTATAGCATAC

ATTATACGAAGTTATAAAGAACTCGCCCTCAAGGGTTGATCTTATGCCA

TCGTCATGATAAACAGTGGAGCACGGACGATCCTTTACGTTGTTTTTAA

CAAACTTTGTCAGAAAACTAGCATCATTAACTTCTTAATGACGATTTCA

CAACAAAAAAAGGTAACCTCGCTACTAACATAACAAAATACTTGTTGCT

TATTAATTATATGTTTTTTAATCTTTGATCAGGGGACAACAGTGGTTGA

TAACCTGTTGAACAGTGAGGATGTCCACTACATGCTCGGGGCCTTGAGG

ACTCTTGGTCTCTCTGTCGAAGCGGACAAAGCTGCCAAAAGAGCTGTAG

TTGTTGGCTGTGGTGGAAAGTTCCCAGTTGAGGATTCTAAAGAGGAAGT

GCAGCTCTTCTTGGGGAATGCTGGAATTGCAATGCGGGCATTGACAGCA

GCTGTTACTGCTGCTGGTGGAAATGCAACGTATGTTTCCTCTCTTTCTC

TCTACAATACTTGCATAACTTCGTATAAAGTATCCTATACGAAGTTATT

GGAGTTAGTATGAAACCCATGGGTATGTCTAGT-3';

this contains a loxP recombinase site sequence at positions 28-61 (underlined) of SEQ ID NO:376 and a lox2272 recombinase site sequence at positions 551-584 (underlined single nucleotides) of SEQ ID NO:376, and further contains nucleotide changes (relative to the wild-type sequence) at positions 465 and 476 of SEQ ID NO:376 to provide the amino acid mutations T102I and P106A in the mature protein, which are point mutations found in glyphosate-resistant EPSPS; see also Example 13.

A plant-codon-optimized Cre recombinase sequence is synthesized (Integrated DNA Technologies, Coralville, IA). The Cre recombinase sequence is cloned into a vector including a heat shock-inducible promoter for driving the expression of Cre. Alternatively, Cre protein is delivered directly into the cells. A Cre fusion protein useful for this recombinase reaction is a recombinant cell-permeant fusion including Cre-recombinase and a TAT sequence (a nuclear localization sequence, NLS); see, e. g., Millipore Sigma catalogue number SCR508 (EMD Millipore Corporation, Billerica, MA).

The maize protoplasts are subjected to a first editing reaction to integrate a loxP recombinase site sequence in the first intronic region of the EPSPS sequence given by SEQ ID NO:367, followed by a second editing reaction to integrate a lox2272 recombinase site sequence in the first intronic region of the EPSPS sequence given by SEQ ID NO:367. Maize protoplasts treated with no nuclease, no guide RNA complex, no salmon sperm DNA, and no polynucleotide donor molecule serve as a null control. The multiplexed editing steps are carried out essentially as described in Example 23, with the second editing reaction carried out 3 hours after the first editing reaction. The protoplasts are then incubated overnight. In a final step, the protoplasts are subjected to a Cre recombinase-mediated recombination reaction in which a replacement EPSPS exon sequence replaces the endogenous EPSPS exon sequence, guided by the respective pairing of the homospecific loxP and homospecific lox2272 recombinase recognition site sequence pairs. The protoplasts are transfected with the dsDNA molecule including a replacement EPSPS exon sequence (provided, e. g., as a circular plasmid or as linearized dsDNA) and with the plant-codon-optimized Cre recombinase (provided, e. g., as the recombinase protein or via an expression vector). Twenty-four additional hours after the Cre-mediated recombination reaction, cells are harvested for analysis.

One of skill in the art would recognize that there are many other possible applications of this approach, which combines (a) integrating at least one recombinase recognition site sequence encoded by a polynucleotide donor molecule at one or more DSBs effected by a sequence-specific nuclease, and (b) treatment with a recombinase, and optionally with a polynucleotide molecule that includes at least one recombinase recognition site sequence. Various combinations of homospecific and heterospecific recombinase recognition sites and recombinases can be used. The genomic outcome of such applications include recombinase-mediated deletion, exchange, inversion, or translocation of genomic sequence. Any of these approaches can be combined with other editing techniques. For example, the edited herbicide-tolerant EPSPS enzyme provided by the methods described in this Example can be combined with integration at a DSB effected in the 3' untranslated region of the edited herbicide-tolerant EPSPS gene of at least one recognition site sequence for an siRNA or a miRNA specifically expressed in male reproductive tissue or female reproductive tissue (e. g., the miRNAs disclosed in Table 6 of U.S. Pat. No. 8,334,430 or the siRNAs disclosed in U.S. Pat. No. 9,139,838, both incorporated herein by reference); this results in expression of the edited herbicide-tolerant enzyme being restricted to tissues other than those in which the siRNA or miRNA is endogenously expressed, and those tissues in which the siRNA or miRNA is expressed will not be resistant to herbicide application; this approach is useful, e. g., to provide male-sterile or female-sterile plants. Although the details provided here are specific to Cre recombinase and loxP (and lox variant) sites, the methods and compositions described herein are generally applicable to other recombinases and their corresponding recombinase recognition site sequences, such as, but not limited to, FLP recombinase and frt recombinase recognition site sequences, R recombinase and Rs recombinase recognition site sequences, Dre recombinase and rox recombinase recognition site sequences, and Gin recombinase and gix recombinase recognition site sequences.

Example 25

This example describes the preparation of reagents to create novel diversity in a region of the genome where low recombination frequency has prevented plant breeders from being able to select for novel alleles.

The gene selected is SHAT1-5 (see www.uniprot.org/uniprot/W8E7P1), a major domestication gene in soybean responsible for the reduced pod shattering that is required for harvestability (DOI: 10.1038/ncomms4352). The selective sweep and apparent low rate of recombination at this locus has resulted in no detectable genetic diversity across a 116 kb region of *Glycine max* chromosome 16 including 5 genes. As such, breeders have not been able to select different alleles of SHAT1-5 or diverse alleles for the surrounding 5 genes.

Soybean hypocotyl protoplasts were isolated as described in Example 1. One milliliter of protoplasts ($2\times10^5$ cells per milliliter) was added to each reaction tube. Ribonucleoproteins (RNPs) were prepared by mixing 5 microliters (50 micrograms) Cas9 nuclease (Aldevron, Fargo, ND) and 30 microliters of one of the three guide RNA complexes, incubating the mixtures for 5 minutes at room temperature. Editing experiments were carried out with either RNP solutions or RNP solutions and 50 microliters of SHAT1-repressor double-stranded DNA donor molecule, with sufficient buffer added if necessary to make up a total volume of 86 microliters; 2 microliters (20 micrograms) of salmon sperm DNA (VWR Cat. No.: 95037-160) was added to each tube except for the null control. Soybean protoplasts treated with no nuclease, no guide RNA complex, no salmon sperm DNA, and no polynucleotide donor molecule served as a null control. To each tube was added 1.1 milliliters of 40% PEG; the reaction mixtures were mixed gently by tapping and incubated 5 minutes at room temperature. The reactions were stopped by adding 5 milliliters of washing buffer (0.6 molar mannitol, 4 millimolar MES pH 5.7, and 20 millimolar KCl) to each tube and mixed gently by inverting the tube. The tubes were centrifuged 2 minutes at 1200 rpm and the supernatant was then removed. The protoplasts were resuspended in 6 milliliters incubation buffer (see Example 2) including the herbicide 2, 4-dichlorophenoxyacetic acid ("2,4-D") with 50 millimolar $CaCl_2$ added) solution. Cells from each tube were plated in 10×10 cm dishes (all precoated with 5% calf serum). The plate and dishes were sealed with Parafilm M® film (Bemis, Oshkosh, WI), incubated 1 hour at 37 degrees Celsius, and then incubated an additional 47 hours at 26 degrees Celsius in the dark. Forty-eight hours after transfection, cells were harvested for analysis.

A partial genomic sequence of SHAT1-5 is provided as SEQ ID NO:391. A SHAT1-repressor nucleotide sequence encoded by a polynucleotide (such as a double-stranded DNA, a single-stranded DNA, a single-stranded DNA/RNA hybrid, or a double-stranded DNA/RNA hybrid) donor molecule having the sequence ATTAAAAAAATAAATAAGATATTATTAAAAAAATAAATAAGATATTATTAAAAAAATAAATAAGATATTATTAAAAAAATAAATAAGATATT (SEQ ID NO:377) is designed for insertion at a double-strand break effected between nucleotides at positions 103/104, 274/275, or 359/360 of SEQ ID NO:391 (see Table 23; insertion is in between the underlined nucleotides) in order to reduce the expression of SHAT1-5 gene. The nucleotides targeted by each of the three different SHAT1-5 crRNAs are shown in bold italic in SEQ ID NO:391 (Table 23); the crRNA sequences are provided as SEQ ID NOs:421, 422, 423 (see Table 24). The three different guide RNAs were prepared as described in Example 2 using crRNAs with the sequences provided in Table 24 complexed with a tracrRNA to form the gRNA (crRNA:tracrRNA) complex; the targetted nucleotide sequence is SHAT1-5 (SEQ ID NO:391). Integration of the SHAT1-5 repressor sequence was carried out using procedures similar to those described in Examples 5 and 10. Both the crRNAs and tracrRNA were purchased from Integrated DNA Technologies, Coralville, IA. Ribonucleoprotein (RNP) complexes were then prepared as described in Example 2 using the gRNAs and Cas9 nuclease (Aldevron, Fargo, ND).

Quantitative RT-PCR was employed on three technical replicates per treatment to measure the relative expression of the SHAT1-5 gene. Results (mean of triplicates, standard deviation) are provided in Table D, with relative gene expression levels normalized to tubulin. The data show that use of a single RNP with repressor oligo donor molecule (i. e., providing a DSB at a single precise locus in the SHAT1-5 gene), either SEQ ID NO:421 or SEQ ID NO:423, was sufficient to knock down SHAT1-5 expression by about 77% to 88%.

TABLE D

| Treatment | SHAT1-5 | |
|---|---|---|
| | Relative expression | SD |
| Null control (no RNP) | 1 | 0.01 |
| SHAT1-5_Guide 1 (SEQ ID NO: 421) | 1.11 | 0.05 |
| SHAT1-5_Guide 1 + Repressor | 0.23 | 0.03 |
| SHAT1-5_Guide 2 (SEQ ID NO: 422) | 0.92 | 0.05 |
| SHAT1-5_Guide 2 + Repressor | 0.85 | 0.06 |
| SHAT1-5_Guide 3 (SEQ ID NO: 423) | 1.1 | 0.08 |
| SHAT1-5_Guide 3 + Repressor | 0.12 | 0.05 |

Example 26

This example describes the modification of three genes in a maize plant cell to provide increased nitrogen use efficiency (NUE).

Maize protoplasts are prepared as described in Example 1. Preparation of reagents, gene editing procedures, and detection of gene modifications are carried out using procedures similar to those described in Examples 20-23.

An increase in expression of NRT2.2 (Zm00001d054060) is predicted to increase nitrogen use efficiency. A partial genomic sequence of NRT2.2 is provided as SEQ ID NO:381. A nitrogen responsive element sequence encoded by a polynucleotide (such as a double-stranded DNA, a single-stranded DNA, a single-stranded DNA/RNA hybrid, or a double-stranded DNA/RNA hybrid) is inserted upstream of the transcription start site (TSS) of the NRT2.2 coding region at a double-strand break effected between nucleotides at positions 101/102 of SEQ ID NO:381 in order to enhance the expression of NRT2.2. The nitrogen responsive element (AtNRE, see Examples 15, 20, and 23) is encoded by a 43 base-pair chemically modified dsDNA (Integrated DNA Technologies, Coralville, IA) having a first strand with the sequence of SEQ ID NO:349 annealed to a second strand with the sequence of SEQ ID NO:350; each strand was phosphorylated on the 5' end and contained two phosphorothioate linkages at each terminus (i. e., the two linkages between the most distal three bases on either end of the strand). A NRT2.2 crRNA with the sequence of SEQ ID NO:397 is designed to target the nucleotides shown in bold italic in SEQ ID NO:381 (Table 23); the crRNA and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the NRE sequence into the NRT2.2 gene is carried out using procedures similar to those described in Examples 20-23.

An increase in expression of NRT2.2 and GLN1.4 (Zm00001d051804) simultaneously is predicted to further increase nitrogen use efficiency. A partial genomic sequence of GLN1.4 is provided as SEQ ID NO:382. A nitrogen responsive element sequence encoded by a polynucleotide (such as a double-stranded DNA, a single-stranded DNA, a single-stranded DNA/RNA hybrid, or a double-stranded DNA/RNA hybrid) donor molecule is inserted upstream of the transcription start site (TSS) of the GLN1.4 coding region at a double-strand break effected between nucleotides at positions 115/116 of SEQ ID NO:382 in order to enhance the expression of GLN1.4. The NRE is provided as a 43 base-pair chemically modified dsDNA (Integrated DNA Technologies, Coralville, IA) having a first strand with the sequence of SEQ ID NO:349 annealed to a second strand with the sequence of SEQ ID NO:350; each strand was phosphorylated on the 5' end and contained two phosphorothioate linkages at each terminus (i. e., the two linkages between the most distal three bases on either end of the strand). A GLN1.4 crRNA with the sequence of SEQ ID NO:398 is designed to target the nucleotide shown in bold italic in SEQ ID NO:382 (Table 23); the crRNA and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the NRE sequence into the GLN1.4 gene is carried out using procedures similar to those described in Examples 20-23.

An increase in expression of NRT2.2, GLN1.4, and Dof1 (Zm00001d031278) simultaneously is predicted to even further increase nitrogen use efficiency. A partial genomic sequence of Dof1 is provided as SEQ ID NO:383. Constitutive overexpression of Dof1 has been shown to result in increased photosynthesis under low nitrate conditions in rice (DOI: 10.1111/j.1467-7652.2011.00592.x). In this embodiment the expression of Dof1 is modified to be constitutively expressed by inserting a constitutive enhancer sequence. A maize OCS homologue (see Examples 14 and 23) encoded by a chemically modified single-stranded DNA with the sequence of SEQ ID NO:343 (Integrated DNA Technologies, Coralville, IA), phosphorylated on the 5' end and containing two phosphorothioate linkages at each terminus (i. e., the two linkages between the most distal three bases on either end of the strand), is designed for insertion upstream of the transcription start site (TSS) of the Dof1 coding region at a double-strand break effected between nucleotides at positions 101/102 of SEQ ID NO:383 in order to enhance the expression of Dof1. A Dof1 crRNA with the sequence of SEQ ID NO:399 is designed to target the nucleotides shown in bold italic in SEQ ID NO:383 (Table 23); crRNA and tracrRNA are purchased from Integrated DNA Technologies, Coralville, IA. Ribonucleoprotein (RNP) complexes are prepared using gRNA (crRNA: tracrRNA) and Cas9 nuclease (Aldevron, Fargo, ND). Integration of the maize OCS homologue sequence into the Dof1 gene is carried out using procedures similar to those described in Examples 20-23.

Additional experiments can be carried out with the same editing reagents in a plant/plant tissue, e. g., using microinjection or biolistics as described in Examples 49-51 and 54. A one-step delivery method can be used to achieve multiplexed edits (multiple modifications) with the same polynucleotide donor to target different genes. For insertion of different polynucleotide donor sequences using the same nuclease (e. g. Cas9 or Cpf1), sequential steps for delivery of different combinations of reagents with a 30 min to 48 h gap between the steps can be used. For insertion of different polynucleotide donor sequences using different nucleases (e. g. Cas9 and Cpf1), a one-step delivery method can be used, for example, with a blunt-ended double-stranded polynucleotide donor for Cas9 and a double-stranded polynucleotide donor containing overhangs for Cpf1.

Example 27

This example describes the modification of four genes in a maize plant cell to provide increased NUE and to create higher yield through increased kernel number. In this example the proxy assay for increased kernel number is increased expression of the gene Wuschel, which has been shown to be connected to kernel row number (see, e. g., doi:10.1038/ng.3567).

An increase in expression of NRT2.2 (Zm00001d054060) is predicted to increase nitrogen use efficiency. A partial genomic sequence of NRT2.2 is provided as SEQ ID NO:381. A nitrogen responsive element sequence encoded by a polynucleotide (such as a double-stranded DNA, a single-stranded DNA, a single-stranded DNA/RNA hybrid, or a double-stranded DNA/RNA hybrid) is inserted at a double-strand break effected between nucleotides at positions 101/102 of SEQ ID NO:381 in order to enhance the expression of NRT2.2. The nitrogen responsive element (AtNRE, see Examples 15, 20, and 23) is encoded by a 43 base-pair chemically modified dsDNA (Integrated DNA Technologies, Coralville, IA) having a first strand with the sequence of SEQ ID NO:349 annealed to a second strand with the sequence of SEQ ID NO:350; each strand was phosphorylated on the 5' end and contained two phosphorothioate linkages at each terminus (i. e., the two linkages between the most distal three bases on either end of the strand). A NRT2.2 crRNA with the sequence of SEQ ID NO:397 is designed to target the nucleotides shown in bold italic in SEQ ID NO:381 (Table 23); the crRNA and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the NRE sequence into the NRT2.2 gene is carried out using procedures similar to those described in Examples 20-23.

An increase in expression of NRT2.2 and GLN1.4 (Zm00001d051804) simultaneously is predicted to further increase nitrogen use efficiency. A partial genomic sequence of GLN1.4 is provided as SEQ ID NO:382. A nitrogen responsive element sequence encoded by a polynucleotide (such as a double-stranded DNA, a single-stranded DNA, a single-stranded DNA/RNA hybrid, or a double-stranded DNA/RNA hybrid) donor molecule is inserted at a double-strand break effected between nucleotides at positions 115/116 of SEQ ID NO:382 in order to enhance the expression of GLN1.4. The NRE is provided as a 43 base-pair chemically modified dsDNA (Integrated DNA Technologies, Coralville, IA) having a first strand with the sequence of SEQ ID NO:349 annealed to a second strand with the sequence of SEQ ID NO:350; each strand was phosphorylated on the 5' end and contained two phosphorothioate linkages at each terminus (i. e., the two linkages between the most distal three bases on either end of the strand). A GLN1.4 crRNA with the sequence of SEQ ID NO:398 is designed to target the nucleotide shown in bold italic in SEQ ID NO:382 (Table 23); the crRNA and tracrRNA are purchased from Integrated DNA Technologies, Coralville, IA. Ribonucleoprotein (RNP) complexes are prepared using gRNA (crRNA: tracrRNA) and Cas9 nuclease (Aldevron, Fargo, ND). Integration of the NRE sequence into the GLN1.4 gene is carried out using procedures similar to those described in Examples 20-23.

An increase in expression of NRT2.2, GLN1.4, and Dof1 (Zm00001d031278) simultaneously is predicted to even further increase nitrogen use efficiency. A partial genomic sequence of Dof1 is provided as SEQ ID NO:383. Constitutive overexpression of Dof1 has been shown to result in increased photosynthesis under low nitrate conditions in rice (see, e. g., DOI: 10.1111/j.1467-7652.2011.00592.x). In this embodiment the expression of Dof1 is modified to be constitutively expressed by inserting a constitutive enhancer sequence. A maize OCS homologue (see Examples 14 and 23) encoded by a chemically modified single-stranded DNA with the sequence of SEQ ID NO:343 (Integrated DNA Technologies, Coralville, IA), phosphorylated on the 5' end and containing two phosphorothioate linkages at each terminus (i. e., the two linkages between the most distal three bases on either end of the strand), is designed for insertion at a double-strand break effected between nucleotides at positions 101/102 of SEQ ID NO:383 in order to enhance the expression of Dof1. A Dof1 crRNA with the sequence of SEQ ID NO:399 is designed to target the nucleotides shown in bold italic in SEQ ID NO:383 (Table 23); crRNA and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the maize OCS homologue sequence into the Dof1 gene is carried out using procedures similar to those described in Examples 20-23.

An increase in expression of NRT2.2, GLN1.4, and Dof1 and a decrease in expression of FEA3 (Zm00001d040130), a putative Leucine Rich Repeat (LRR) Receptor-like protein, is predicted to provide an increase in the expression of Wuschel and other meristem-promoting genes, resulting in an overall increase in meristem size and ultimately in increased yield (see, e. g., doi:10.1038/ng.3567). A partial genomic sequence of FEA3 including 3' untranslated region (3' UTR) is provided as SEQ ID NO:386. An mRNA destabilizing element oligonucleotide having the sequence TTATTTATTTTATTTATTTATTTATTTATTTATTTATT (SEQ ID NO:378) and encoded by a polynucleotide (such as a double-stranded DNA, a single-stranded DNA, a single-stranded DNA/RNA hybrid, or a double-stranded DNA/RNA hybrid) donor molecule is designed for insertion in the 3' UTR of FEA3 at a double-strand break effected between nucleotides at positions 25/26, 143/144, or 263/264 of SEQ ID NO:386 (see Table 23) in order to reduce the expression of FEA3 gene. The nucleotides targeted by each of the three different FEA3 crRNAs are shown in bold italic in SEQ ID NO:386 in Table 23; the crRNA sequences are provided as SEQ ID NOs:402, 403, 404 (see Table 24). All crRNAs and tracrRNA are purchased from Integrated DNA Technologies, Coralville, IA. Ribonucleoprotein (RNP) complexes are prepared using guide RNAs (crRNA:tracrRNA) and Cas9 nuclease (Aldevron, Fargo, ND). Insertion of the mRNA destabilizing element into the 3' untranslated region of the FEA3 gene is carried out using procedures similar to those described in Examples 20-23.

Maize B73 nitrate-free protoplasts were prepared as described in Example 20. Preparation of reagents, gene editing procedures, and detection of gene modifications are carried out using procedures similar to those described in Examples 20-23.

The protoplasts were transfected with two ribonucleoproteins (RNPs) targeting NRT2.2 and GLN1.4 and the double-stranded DNA AtNRE donor molecule on Day One. On Day Two (18 hours after initial transfection), the plated cells were harvested and transfected with the RNP targeting Dof1 and the double-stranded DNA OCS donor molecule. The transfected cells were suspended in 6 milliliters of nitrate free medium and incubated 1 hour at 37 degrees Celsius, and then incubated an additional 6 hours at 26 degrees Celsius in the dark. The cells were then harvested and transfected with RNP (crRNA: FEA3-3'UTR-1 SEQ ID NO:402) targeting FEA3 and the double-stranded DNA Destabilizer donor molecule. The transfected cells were suspended in 6 milliliters of nitrate-free medium and incubated 1 hour at 37 degrees Celsius, and then incubated at 26 degrees Celsius in the dark. The cells were collected after a total of 48 hours post initial transfection and split to two sets for treatments with 10 mM $KNO_3$ or 10 mM KCl for 30 minutes. The cells were then harvested for analysis.

Quantitative RT-PCR was employed on three technical replicates per treatment to measure the relative expression of the NRT2.2, GLN1.4, Dof1, FEA3 and FEA3 targeting gene WUS genes. Results (mean of triplicates, standard deviation) are provided in Tables E, F, G, H, and I respectively, with relative gene expression levels normalized to actin.

TABLE E

Relative Expression of NRT2.2

| Editing treatment | KCl Relative Expression | KCl SD | $KNO_3$ Relative Expression | $KNO_3$ SD |
|---|---|---|---|---|
| Null control (no RNP) | 1.01 | 0.15 | 4.06 | 0.27 |
| RNPs (NRT2.2, GLN1.4, Dof1 and FEA3) | 1.73 | 0.03 | 3.4 | 0.2 |
| RNPs + Donor oligos (AtNRE, OCS and Destabilizer) | 1.25 | 0.24 | 9.55 | 0.37 |

TABLE F

Relative Expression of GLN1.4

| Editing treatment | KCl Relative Expression | KCl SD | $KNO_3$ Relative Expression | $KNO_3$ SD |
|---|---|---|---|---|
| Null control (no RNP) | 1 | 0.03 | 3.57 | 0.22 |
| RNPs (NRT2.2, GLN1.4, Dof1 and FEA3) | 1.9 | 0.1 | 3.66 | 0.03 |
| RNPs + Donor oligos (AtNRE, OCS and Destabilizer) | 1.33 | 0.06 | 9.18 | 0.63 |

TABLE G

Relative Expression of Dof1

| Editing treatment | KCl Relative Expression | KCl SD | $KNO_3$ Relative Expression | $KNO_3$ SD |
|---|---|---|---|---|
| Null control (no RNP) | 1 | 0.01 | 3.68 | 0.54 |
| RNPs (NRT2.2, GLN1.4, Dof1 and FEA3) | 2.2 | 0.12 | 2.51 | 0.4 |
| RNPs + Donor oligos (AtNRE, OCS and Destabilizer) | 1.61 | 0.3 | 13.9 | 1.39 |

TABLE H

Relative Expression of FEA3

| Editing treatment | KCl Relative Expression | KCl SD | $KNO_3$ Relative Expression | $KNO_3$ SD |
|---|---|---|---|---|
| Null control (no RNP) | 1 | 0.07 | 1.37 | 0.05 |
| RNPs (NRT2.2, GLN1.4, Dof1 and FEA3) | 2.13 | 0.32 | 1.81 | 0.04 |
| RNPs + Donor oligos (AtNRE, OCS and Destabilizer) | 0.68 | 0.01 | 0.67 | 0.04 |

TABLE I

| Relative Expression of WUS | | | | |
|---|---|---|---|---|
| | KCl | | $KNO_3$ | |
| Editing treatment | Relative Expression | SD | Relative Expression | SD |
| Null control (no RNP) | 1.16 | 0.67 | 1.66 | 0.13 |
| RNPs (NRT2.2, GLN1.4, Dof1 and FEA3) | 1.36 | 0.18 | 1.33 | 0.09 |
| RNPs + Donor oligos (AtNRE, OCS and Destabilizer) | 6 | 0.09 | 6.63 | 0.12 |

In a non-limiting embodiment, donor polynucleotide sequences were designed forPG-9T integration at a double-strand break (DSB) in the 3' untranslated region (3' UTR) of the maize Fea3 gene (GRMZM2G166524_Fea3 (see www [dot]maize gdb[dot]org/gene_center/gene/ GRMZM2G166524): an *Arabidopsis* destabilizer having the sequence AATTTTAATTTTAATTTTAATTTTAATTT-TAATTTT (SEQ ID NO:510, provided as ssDNA), a mammalian mRNA destabilizer having the sequence TTATTT-ATTTTATTTATTTATTTATTTATTTATTTATT (SEQ ID NO:511, provided as a dsDNA), and a stabilizer having the sequence TCTCTTTCTCTTTCTCTTTCTCTTTCTCTTTCTCTT (SEQ ID NO:512, provided as ssDNA). Guide RNAs designed to effect a DSB in the 3' UTR of the maize Fea3 gene had the sequences UGGAUAGGGUAGCUUCUCCG-GUUUUAGAGCUAUGCU (guide Fea3-1, SEQ ID NO:513), CCAUCGUCAGAUGGUGACGGGUUUUA-GAGCUAUGCU (guide Fea3-2, SEQ ID NO:514), and GCAGGUUCAGAAGAAGAACAGUUUUAGAGC-UAUGCU (guide Fea3-3, SEQ ID NO:515).

Integration of either the 3×DR5 donor polynucleotide sequence (as dsDNA or as ssDNA) or the G-box donor polynucleotide sequence at the DSB located 272 nucleotides 5' to the ZmLc gene's TSS was performed using protocols similar to those described in other Examples (e. g., Example 57). After the PEG-mediated transfection and wash steps, the protoplast pellet was resuspended in 4 milliliters of PIM containing 50 mM calcium chloride. For gDNA isolation for T7 and qPCR assays, 1 milliliter of the suspension was plated on a 6-well plate coated with 5% calf serum; for RNA analysis, 3 milliliters of the suspension were plated onto a 10-centimeter plate coated with 5% calf serum containing 3 milliliters of PIM containing 50 mM calcium chloride. The dishes were sealed with Parafilm M® film (Bemis, Oshkosh, WI), incubated 30 minutes at 37 degrees Celsius, and then incubated an additional 47 hours at 26 degrees Celsius in the dark, after which the cells were harvested for analysis. Analysis employed a T7E1 assay to confirm the predicted cleavage and qPCR analysis of both maize Fea3 and WUS1 (GRMZM2G047448_Wus1) genes (normalized to tubulin) to quantify editing efficiency as described in the preceding Examples. The qPCR results for the destabilizer elements are provided in Table J; data were not collected for the stabilizer element. These results demonstrate that integration of either of the destabilizer sequences into the Fea3 3' UTR results in a decrease in Fea3 expression, and a corresponding increase in Wus1 expression. Thus, incorporation of at least one donor polynucleotide sequence at a DSB located within one target gene (Zm-Fea3) effected a change in expression in both that target gene and in a second, different gene (Zm-Wus1) that interacts with the target gene.

TABLE J

| | Donor | Fea3 | | Wus1 | |
|---|---|---|---|---|---|
| Guide | polynucleotide | Expression | SD | Expression | SD |
| Fea3-1 | *Arabidopsis* destabilizer | 0.15 | 0.03 | 3.52 | 0.41 |
| Fea3-1 | Mammalian destabilizer | 0.39 | 0.02 | 2.27 | 0.26 |
| Fea3-1 | none | 1.22 | 0.07 | 0.66 | 0.06 |
| Fea3-2 | *Arabidopsis* destabilizer | 0.81 | 0.11 | 1.20 | 0.09 |
| Fea3-2 | Mammalian destabilizer | 1.43 | 0.05 | 1.07 | 0.10 |
| Fea3-2 | none | 1.10 | 0.07 | 1.47 | 0.09 |
| Fea3-3 | *Arabidopsis* destabilizer | 0.68 | 0.05 | 1.02 | 0.11 |
| Fea3-3 | Mammalian destabilizer | 0.60 | 0.17 | 1.60 | 0.17 |
| Fea3-3 | Nothing | 1.11 | 0.13 | 1.12 | 0.27 |
| none | Null control (no RNP) | 1.01 | 0.19 | 1.01 | 0.19 |

Additional experiments can be carried out with the same editing reagents in a plant/plant tissue, e. g., using microinjection or biolistics as described in Examples 49-51 and 54. A one-step delivery method can be used to achieve multiplexed edits (multiple modifications) with the same polynucleotide donor to target different genes. For insertion of different polynucleotide donor sequences using the same nuclease (e. g. Cas9 or Cpf1), sequential steps for delivery of different combinations of reagents with a 30 min to 48 h gap between the steps can be used. For insertion of different polynucleotide donor sequences using different nucleases (e. g. Cas9 and Cpf1), a one-step delivery method can be used, for example, with a blunt-ended double-stranded polynucleotide donor for Cas9 and a double-stranded polynucleotide donor containing overhangs for Cpf1.

Example 28

This example illustrates a method of providing a plant cell having a modified phenotype, the method including introducing double-strand breaks (DSBs) into multiple loci or into multiple genes, and integrating at the DSBs at least three different nucleotide sequences encoded by a polynucleotide (such as a double-stranded DNA, a single-stranded DNA, a single-stranded DNA/RNA hybrid, or a double-stranded DNA/RNA hybrid) donor molecule, and generating loss-of-function alleles by deletion of genome sequences between at least two DSBs. In this non-limiting example, multiple genomic modifications ("multiplexed edits") are effected in a maize cell by using multiple ribonucleoproteins (RNPs), each including a nuclease and a guide RNA (gRNA) and three different nucleotide sequences.

This example describes the modification of six genes in maize protoplast cells to provide increased nitrogen use efficiency, increased kernel number, elevated glyphosate tolerance in the plant cell, and broad spectrum disease resistance.

Maize protoplasts are prepared as described in Example 1. Preparation of reagents, gene editing procedures, and detection of gene modifications are carried out using procedures similar to those described in Examples 20-23.

An increase in expression of NRT2.2 (Zm00001d054060) is predicted to increase nitrogen use efficiency. A partial genomic sequence of NRT2.2 is provided as SEQ ID NO:381. A nitrogen responsive element sequence encoded by a polynucleotide (such as a double-stranded DNA, a single-stranded DNA, a single-stranded DNA/RNA hybrid, or a double-stranded DNA/RNA hybrid) is inserted at a double-strand break effected between nucleotides at positions 101/102 of SEQ ID NO:381 in order to enhance the expression of NRT2.2. The nitrogen responsive element (AtNRE, see Examples 15, 20, and 23) is encoded by a 43 base-pair chemically modified dsDNA (Integrated DNA Technologies, Coralville, IA) having a first strand with the sequence of SEQ ID NO:349 annealed to a second strand with the sequence of SEQ ID NO:350; each strand was phosphorylated on the 5' end and contained two phosphorothioate linkages at each terminus (i. e., the two linkages between the most distal three bases on either end of the strand). A NRT2.2 crRNA with the sequence of SEQ ID NO:397 is designed to target the nucleotides shown in bold italic in SEQ ID NO:381 (Table 23); the crRNA and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the NRE sequence into the NRT2.2 gene is carried out using procedures similar to those described in Examples 20-23.

An increase in expression of NRT2.2 and GLN1.4 (Zm00001d051804) simultaneously is predicted to further increase nitrogen use efficiency. A partial genomic sequence of GLN1.4 is provided as SEQ ID NO:382. A nitrogen responsive element sequence encoded by a polynucleotide (such as a double-stranded DNA, a single-stranded DNA, a single-stranded DNA/RNA hybrid, or a double-stranded DNA/RNA hybrid) donor molecule is inserted at a double-strand break effected between nucleotides at positions 115/116 of SEQ ID NO:382 in order to enhance the expression of GLN1.4. The NRE is provided as a 43 base-pair chemically modified dsDNA (Integrated DNA Technologies, Coralville, IA) having a first strand with the sequence of SEQ ID NO:349 annealed to a second strand with the sequence of SEQ ID NO:350; each strand was phosphorylated on the 5' end and contained two phosphorothioate linkages at each terminus (i. e., the two linkages between the most distal three bases on either end of the strand). A GLN1.4 crRNA with the sequence of SEQ ID NO:398 is designed to target the nucleotide shown in bold italic in SEQ ID NO:382 (Table 23); the crRNA and tracrRNA are purchased from Integrated DNA Technologies, Coralville, IA. Ribonucleoprotein (RNP) complexes are prepared using gRNA (crRNA: tracrRNA) and Cas9 nuclease (Aldevron, Fargo, ND). Integration of the NRE sequence into the GLN1.4 gene is carried out using procedures similar to those described in Examples 20-23.

An increase in expression of NRT2.2, GLN1.4, and Dof1 (Zm00001d031278) simultaneously is predicted to even further increase nitrogen use efficiency. A partial genomic sequence of Dof1 is provided as SEQ ID NO:383. Constitutive overexpression of Dof1 has been shown to result in increased photosynthesis under low nitrate conditions in rice (see, e. g., DOI: 10.1111/j.1467-7652.2011.00592.x). In this embodiment the expression of Dof1 is modified to be constitutively expressed by inserting a constitutive enhancer sequence. A maize OCS homologue (see Examples 14 and 23) encoded by a chemically modified single-stranded DNA with the sequence of SEQ ID NO:343 (Integrated DNA Technologies, Coralville, IA), phosphorylated on the 5' end and containing two phosphorothioate linkages at each terminus (i. e., the two linkages between the most distal three bases on either end of the strand) is designed for insertion at a double-strand break effected between nucleotides at positions 101/102 of SEQ ID NO:383 in order to enhance the expression of Dof1. A Dof1 crRNA with sequence of SEQ ID NO:399 is designed to target the nucleotides shown in bold italic in SEQ ID NO:383 (Table 23); crRNA and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the maize OCS homologue sequence into the Dof1 gene is carried out using procedures similar to those described in Examples 20-23.

An increase in expression of NRT2.2, GLN1.4, and Dof1 and a loss of function allele of FEA3 (Zm00001d040130), a putative Leucine Rich Repeat (LRR) Receptor-like protein, is expected to provide an increase in the expression of Wuschel and other meristem-promoting genes, resulting in an overall increase in meristem size and ultimately in increased kernel row numbers (see, e. g., doi:10.1038/ng.3567). A partial genomic sequence of FEA3 is provided as SEQ ID NO:387. Two ribonucleoproteins (RNPs), each including a nuclease and a guide RNA (gRNA) are designed to effect double-strand breaks between nucleotides at positions 115/116 and 207/208 of SEQ ID NO:387 (see Table 23), resulting in deletion of genomic sequence of FEA3 gene between the two guide targeting regions and effectively knocking out expression of a functional FEA3 protein. The nucleotides targeted by each of the two FEA3 crRNAs are shown in bold italic in SEQ ID NO:387 in Table 23; the crRNA sequences are provided as SEQ ID NOs:405 and 406 (see Table 24). All crRNAs and tracrRNA are purchased from Integrated DNA Technologies, Coralville, IA. Ribonucleoprotein (RNP) complexes are prepared using guide RNAs (crRNA:tracrRNA) and Cas9 nuclease (Aldevron, Fargo, ND). Functional knock-out by partial sequence deletion of the FEA3 gene is carried out using procedures similar to those described in Examples 20-23.

An increase in the expression of the maize enolpyruvylshikimate phosphate synthase 1 (EPSPS, Zm00001d045450) is predicted to be required in order to deliver a plant with commercial-level glyphosate tolerance with no growth or performance drag. A partial genomic sequence of EPSPS is provided as SEQ ID NO:384. In this embodiment, the expression of the endogenous EPSPS is modified to be constitutively expressed by inserting a constitutive enhancer sequence. A maize OCS homologue (see Examples 14 and 23) encoded by a chemically modified single-stranded DNA with the sequence of SEQ ID NO:343 (Integrated DNA Technologies, Coralville, IA), phosphorylated on the 5' end and containing two phosphorothioate linkages at each terminus (i. e., the two linkages between the most distal three bases on either end of the strand) is designed for insertion at a double-strand break effected between nucleotides at positions 101/102 of SEQ ID NO:384 in order to provide constitutively increased expression of EPSPS. An EPSPS crRNA with sequence of SEQ ID NO:400 is designed to target the nucleotides shown in bold italic in SEQ ID NO:384 (Table 23); crRNA and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the maize OCS homologue sequence into the EPSPS gene is carried out using procedures similar to those described in Examples 20-23.

An increase in the expression of NPR1 (Zm00001d012660) is predicted to increase disease resistance (see, e. g., doi: 10.1094/MPMI-21-9-1215). However, constitutive overexpression results in a significant fitness cost (see, e. g., doi.org/10.1016/j.plantsci.2016.06.005). It is predicted that this undesirable fitness drag will be mitigated by modifying the endogenous NPR1 gene by inserting an upstream ORF (uORF) into the 5'UTR, which will reduce the translation efficiency of the target gene (and hence the fitness drag) in the absence of a pathogen. A partial sequence of NPR1 is provided as SEQ ID NO:385. A uORF sequence encoded by a chemically modified single-stranded DNA with the sequence of SEQ ID NO:379, phosphorylated on the 5' end and containing two phosphorothioate linkages at each terminus (i. e., the two linkages between the most distal three bases on either end of the strand), is designed for insertion at a double-strand break effected between nucleotides at positions 101/102 of SEQ ID NO:385 (see Table 23) in order to modulate the expression of NPR1. The nucleotides targeted by the NPR1 crRNA are shown in bold italic in Table 23. The crRNA sequence is provided as SEQ ID NO:401 (see Table 24). All crRNA and tracrRNA are purchased from Integrated DNA Technologies, Coralville, IA. Ribonucleoprotein (RNP) complexes are prepared using guide RNAs (crRNA:tracrRNA) and Cas9 nuclease (Aldevron, Fargo, ND). Integration of the uORF sequence into the NPR1 gene is carried out using procedures similar to those described in Examples 20-23.

Additional experiments can be carried out with the same editing reagents in a plant/plant tissue, e. g., using microinjection or biolistics as described in Examples 49-51 and 54. A one-step delivery method can be used to achieve multiplexed edits (multiple modifications) with the same polynucleotide donor to target different genes. For insertion of different polynucleotide donor sequences using the same nuclease (e. g. Cas9 or Cpf1), sequential steps for delivery of different combinations of reagents with a 30 min to 48 h gap between the steps can be used. For insertion of different polynucleotide donor sequences using different nucleases (e. g. Cas9 and Cpf1), a one-step delivery method can be used, for example, with a blunt-ended double-stranded polynucleotide donor for Cas9 and a double-stranded polynucleotide donor containing overhangs for Cpf1.

Example 29

This example describes the preparation of reagents for the modification of three genes in a soybean plant cell to provide increased nitrogen use efficiency.

Soybean protoplasts are prepared as described in Example 1. Preparation of reagents, gene editing procedures, and detection of gene modifications are carried out using procedures similar to those described in Examples 5 and 10.

An increase in expression of NRT (GLYMA_12G078900) is predicted to increase nitrogen use efficiency (NUE). The sequence of NRT is shown as SEQ ID NO:388. Similar to the previous examples, a nitrogen-responsive element (NRE) sequence having the sequence of SEQ ID NO:350 and encoded by a polynucleotide (such as a double-stranded DNA, a single-stranded DNA, a single-stranded DNA/RNA hybrid, or a double-stranded DNA/RNA hybrid) donor molecule is designed for insertion at a double-strand break effected between nucleotides at positions 101/102, 303/304, and 446/447 of SEQ ID NO:388 in order to enhance the expression of NRT. Three NRT crRNAs are designed to target the nucleotides shown in bold italic in SEQ ID NO:388 (see Table 23) and have the sequences of SEQ ID NOs:407, 408, and 409 (see Table 24). All crRNAs and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the NRE sequence in the NRT gene is carried out using procedures similar to those described in Examples 5 and 10.

An increase in expression of NRT and NRT2 (Glyma13g39850.1) simultaneously is predicted to further increase nitrogen use efficiency (NUE). A partial genomic sequence of NRT2 is provided as SEQ ID NO:389, a nitrogen-responsive element (NRE) sequence having the sequence of SEQ ID NO:350 and encoded by a polynucleotide (such as a double-stranded DNA, a single-stranded DNA, a single-stranded DNA/RNA hybrid, or a double-stranded DNA/RNA hybrid) donor molecule is designed for insertion at a double-strand break effected between nucleotides at positions 101/102, 195/196, and 374/375 of SEQ ID NO:389 in order to enhance the expression of NRT2. Three NRT2 crRNAs are designed to target the nucleotides shown in bold italic in SEQ ID NO:389 (see Table 23) and have the sequences of SEQ ID NOs:410, 411, and 412 (see Table 24). All crRNAs and tracrRNA are purchased from Integrated DNA Technologies, Coralville, IA. Ribonucleoprotein (RNP) complexes are prepared using gRNA (crRNA: tracrRNA) and Cas9 nuclease (Aldevron, Fargo, ND). Integration of the NRE sequence in the NRT gene is carried out using procedures similar to those described in Examples 5 and 10.

An increase in expression of NRT, NRT2 and glutamine synthase (GS, Glyma.07G104500) simultaneously can even further increase nitrogen use efficiency (NUE). Constitutive overexpression of GS has been shown to result in increased photosynthesis under low nitrate conditions (see, e. g., doi: 10.1104/pp. 020013). In this example, the expression of GS is constitutively increased by inserting a constitutive enhancer sequence. A partial genomic sequence of GS is provided as SEQ ID NO:395. A maize OCS homologue (see Examples 14 and 23) encoded by a chemically modified single-stranded DNA with the sequence of SEQ ID NO:343 (Integrated DNA Technologies, Coralville, IA), phosphorylated on the 5' end and containing two phosphorothioate linkages at each terminus (i.e., the two linkages between the most distal three bases on either end of the strand) is designed for insertion at a double-strand break effected between nucleotides at positions 103/104, 193/194, and 331/332 of SEQ ID NO: 395 in order to provide constitutively increased expression of GS. A GS crRNA is designed to target the nucleotides shown in bold italic in SEQ ID NO:395 (Table 23) and has the sequences of SEQ ID NO:413, 414, and 415. The crRNA and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the OCS homologue sequence in the GS gene is carried out using procedures similar to those described in Examples 5 and 10.

Additional experiments can be carried out with the same editing reagents in a plant/plant tissue, e. g., using microinjection or biolistics as described in Examples 49-51 and 54. A one-step delivery method can be used to achieve multiplexed edits (multiple modifications) with the same polynucleotide donor to target different genes. For insertion of different polynucleotide donor sequences using the same nuclease (e. g. Cas9 or Cpf1), sequential steps for delivery of different combinations of reagents with a 30 min to 48 h gap between the steps can be used. For insertion of different polynucleotide donor sequences using different nucleases (e. g. Cas9 and Cpf1), a one-step delivery method can be used, for example, with a blunt-ended double-stranded polynucleotide donor for Cas9 and a double-stranded polynucleotide donor containing overhangs for Cpf1.

Example 30

It is predicted that modification of NRT, NRT2, and GS in soybean will result in soybean cells with increased nitrogen use efficiency (NUE), and, further that the additional modification of FT2a will result in early flowering, higher yielding soybean plants (see, e. g., U.S. Patent Application Publication 20160304891 A1, incorporated herein by reference).

Soybean protoplasts are prepared as described in Example 1. Preparation of reagents and detection of gene modifications are completed essentially as described in Examples 5 and 10.

An increase in expression of NRT (GLYMA_12G078900) is predicted to increase nitrogen use efficiency (NUE). The sequence of NRT is shown as SEQ ID NO:388. Similar to the previous examples, a nitrogen-responsive element (NRE) sequence having the sequence of SEQ ID NO:350 and encoded by a polynucleotide (such as a double-stranded DNA, a single-stranded DNA, a single-stranded DNA/RNA hybrid, or a double-stranded DNA/RNA hybrid) donor molecule is designed for insertion at a double-strand break effected between nucleotides at positions 101/102, 303/304, and 446/447 of SEQ ID NO:388 in order to enhance the expression of NRT. Three NRT crRNAs are designed to target the nucleotides shown in bold italic in SEQ ID NO:388 (see Table 23) and have the sequences of SEQ ID NOs:407, 408, and 409 (see Table 24). All crRNAs and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the NRE sequence in the NRT gene is carried out using procedures similar to those described in Examples 5 and 10.

An increase in expression of NRT and NRT2 (Glyma13g39850.1) simultaneously is predicted to further increase nitrogen use efficiency (NUE). A partial genomic sequence of NRT2 is provided as SEQ ID NO:389, a nitrogen-responsive element (NRE) sequence having the sequence of SEQ ID NO:350 and encoded by a polynucleotide (such as a double-stranded DNA, a single-stranded DNA, a single-stranded DNA/RNA hybrid, or a double-stranded DNA/RNA hybrid) donor molecule is designed for insertion at a double-strand break effected between nucleotides at positions 101/102, 195/196, and 374/375 of SEQ ID NO:389 in order to enhance the expression of NRT2. Three NRT2 crRNAs are designed to target the nucleotides shown in bold italic in SEQ ID NO:389 (see Table 23) and have the sequences of SEQ ID NOs: 410, 411, and 412 (see Table 24). All crRNAs and tracrRNA are purchased from Integrated DNA Technologies, Coralville, IA. Ribonucleoprotein (RNP) complexes are prepared using gRNA (crRNA: tracrRNA) and Cas9 nuclease (Aldevron, Fargo, ND). Integration of the NRE sequence in the NRT gene is carried out using procedures similar to those described in Examples 5 and 10.

An increase in expression of NRT, NRT2 and glutamine synthase (GS, Glyma.07G104500) simultaneously can even further increase nitrogen use efficiency (NUE). Constitutive overexpression of GS has been shown to result in increased photosynthesis under low nitrate conditions (see, e. g., doi: 10.1104/pp. 020013). In this example, the expression of GS is constitutively increased by inserting a constitutive enhancer sequence. A partial genomic sequence of GS is provided as SEQ ID NO:395. A maize OCS homologue (see Examples 14 and 23) encoded by a chemically modified single-stranded DNA with the sequence of SEQ ID NO:343 (Integrated DNA Technologies, Coralville, IA), phosphorylated on the 5' end and containing two phosphorothioate linkages at each terminus (i. e., the two linkages between the most distal three bases on either end of the strand) is designed for insertion at a double-strand break effected between nucleotides at positions 103/104, 193/194, and 331/332 of SEQ ID NO: 395 in order to provide constitutively increased expression of GS. A GS crRNA is designed to target the nucleotides shown in bold italic in SEQ ID NO:395 (Table 23) and has the sequences of SEQ ID NO: ID NO:413, 414, and 415. The crRNA and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the OCS homologue sequence in the GS gene is carried out using procedures similar to those described in Examples 5 and 10.

FT2a (Glyma.16G150700) is the mobile flowering trigger in soybean and an increase in expression of FT2a is anticipated to trigger flowering. Early flowering is not normally a desirable phenotype as early-flowering plants do not maintain high vegetative growth rates, resulting in overall lower yields. It is predicted that a short burst of FT2a expression will be sufficient to trigger flowering while allowing the plants to maintain vegetative growth, resulting in an ever-bearing and high-yielding phenotype. Thus, in addition to the increased nitrogen utilization efficiency achieved by modification of NRT, NTR2, and GS, an auxin-inducible element is integrated in the promoter of the FT2a gene. A partial genomic sequence of FT2a is provided as SEQ ID NO:390. The auxin-responsive element 3×DR5 with the sequence of SEQ ID NO:306 is provided as a polynucleotide (e. g., as a double-stranded DNA, a single-stranded DNA, a single-stranded DNA/RNA hybrid, or a double-stranded DNA/RNA hybrid) donor molecule for insertion at a double-strand break effected between nucleotides at positions 115/116, 334/335, and 428/429 of SEQ ID NO:390. A FT2a crRNA is designed to target the nucleotides shown in bold italic in SEQ ID NO: 390 (Table 23) and has the sequences of SEQ ID NO:416, 417 and 418. The crRNA and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the OCS homologue sequence in the GS gene is carried out using procedures similar to those described in Examples 5 and 10.

Additional experiments can be carried out with the same editing reagents in a plant/plant tissue, e. g., using microinjection or biolistics as described in Examples 49-51 and 54. A one-step delivery method can be used to achieve multiplexed edits (multiple modifications) with the same polynucleotide donor to target different genes. For insertion of different polynucleotide donor sequences using the same nuclease (e. g. Cas9 or Cpf1), sequential steps for delivery of different combinations of reagents with a 30 min to 48 h gap between the steps can be used. For insertion of different polynucleotide donor sequences using different nucleases (e. g. Cas9 and Cpf1), a one-step delivery method can be used, for example, with a blunt-ended double-stranded polynucleotide donor for Cas9 and a double-stranded polynucleotide donor containing overhangs for Cpf1.

Example 31

This example describes additional genomic modifications that further enhance the effects of the modifications of soybean genes described in Example 30. E1

(Glyma.06G207800.1) is a large effect flowering time gene in soybean and has been reported to be a repressor of two genes involved in the induction of flowering, FT2a and FT5a (see, e. g., DOI: 10.1104/pp. 15.00763). It is predicted that by stacking the inducible increased expression of FT2a described in Example 30 with a modest decrease in expression of E1 will result in early flowering with increased yield outcomes. In this example, a SAUR mRNA destabilizing sequence is integrated in the 3' untranslated region (3' UTR) of the E1 gene. SAUR destabilizing sequences result in reduced expression due to increased mRNA degradation (see, e. g., DOI 10.1105/tpc.5.6.701, and U.S. Patent Application Publication 2007/0011761, incorporated herein by reference). A partial genomic sequence of E1 is provided as SEQ ID NO:396. A SAUR mRNA destabilizing element with the sequence of SEQ ID NO:380 is designed for insertion at a double-strand break effected between nucleotides at positions 117/118 or 152/153 of SEQ ID NO:396. The SAUR destabilizing element in the form of a single-stranded DNA molecule, phosphorylated on the 5' end and containing two phosphorothioate linkages at each terminus (i. e., the two linkages between the most distal three bases on either end of the strand) is purchased from Integrated DNA Technologies, Coralville, IA. A E1 crRNA is designed to target the nucleotides shown in bold italic in SEQ ID NO: 396 (Table 23) and has the sequences of SEQ ID NO:419 and 420. The E1 crRNA and tracrRNA are purchased from Integrated DNA Technologies, Coralville, IA. Ribonucleoprotein (RNP) complexes are prepared using gRNA (crRNA: tracrRNA) and Cas9 nuclease (Aldevron, Fargo, ND). Integration of the SAUR destabilizing element sequence in the 3' UTR of the E1 gene is carried out using procedures similar to those described in Examples 5 and 10.

Additional experiments can be carried out with the same editing reagents in a plant/plant tissue, e. g., using microinjection or biolistics as described in Examples 49-51 and 54. A one-step delivery method can be used to achieve multiplexed edits (multiple modifications) with the same polynucleotide donor to target different genes. For insertion of different polynucleotide donor sequences using the same nuclease (e. g. Cas9 or Cpf1), sequential steps for delivery of different combinations of reagents with a 30 min to 48 h gap between the steps can be used. For insertion of different polynucleotide donor sequences using different nucleases (e. g. Cas9 and Cpf1), a one-step delivery method can be used, for example, with a blunt-ended double-stranded polynucleotide donor for Cas9 and a double-stranded polynucleotide donor containing overhangs for Cpf1.

Example 32

This example describes the preparation of reagents for the modification of three genes in tomato. It is predicted that the activation of these three genes will result in a tomato that produces capsaicin, the molecule that gives peppers their spicy taste. Peppers and tomatoes are closely related and share many genes. The genes involved in the biosynthesis of capsaicin in pepper were used to identify the homologous genes in tomato. Based on the pepper genome (see: doi: 10.1038/ng.2877) three genes were selected for modification and enhanced expression: capsaicin synthase (CS), BCAT, and KAS. Putative tomato homologues were identified by BLAST analysis and manual annotation.

A partial genomic sequence of the tomato capsaicin synthase (CS) gene (Solyc02g081740.1.1) is provided as SEQ ID NO:392. CS is the last step in the synthesis of capsaicin. The expression of CS is constitutively increased by inserting an expression enhancing oligonucleotide in the 5' region of the gene. A maize OCS homologue (see Examples 14 and 23) encoded by a chemically modified single-stranded DNA with the sequence of SEQ ID NO:343 (Integrated DNA Technologies, Coralville, IA), phosphorylated on the 5' end and containing two phosphorothioate linkages at each terminus (i. e., the two linkages between the most distal three bases on either end of the strand) is designed for insertion at a double-strand break effected between nucleotides at positions 46/47, 216/217, and 333/334 of SEQ ID NO:392 in order to provide constitutively increased expression of CS. A CS crRNA is designed to target the nucleotides shown in bold italic in SEQ ID NO: 392 (Table 23) and has the sequences of SEQ ID NO:424, 425, and 426. The crRNA and tracrRNA are purchased from Integrated DNA Technologies, Coralville, IA. Ribonucleoprotein (RNP) complexes are prepared using gRNA (crRNA: tracrRNA) and Cas9 nuclease (Aldevron, Fargo, ND). Integration of the OCS homologue sequence in the CS gene is carried out using procedures similar to those described in Examples 5 and 10.

The tomato BCAT gene (Solyc07g021630.2.1) has the partial genomic sequence of SEQ ID NO:393. Expression of BCAT is constitutively increased by inserting an expression enhancing oligonucleotide in the 5' region of the gene. A maize OCS homologue (see Examples 14 and 23) encoded by a chemically modified single-stranded DNA with the sequence of SEQ ID NO:343 (Integrated DNA Technologies, Coralville, IA), phosphorylated on the 5' end and containing two phosphorothioate linkages at each terminus (i. e., the two linkages between the most distal three bases on either end of the strand) is designed for insertion at a double-strand break effected between nucleotides at positions 103/104, 330/331, or 362/363 of SEQ ID NO:393 in order to provide constitutively increased expression of BCAT. Three BCAT crRNAs are designed to target the nucleotides shown in bold italic in SEQ ID NO: 393 (Table 23) and have the sequences of SEQ ID NO:427, 428, and 429. The crRNAs and tracrRNA are purchased from Integrated DNA Technologies, Coralville, IA. Ribonucleoprotein (RNP) complexes are prepared using gRNA (crRNA: tracrRNA) and Cas9 nuclease (Aldevron, Fargo, ND). Integration of the OCS homologue sequence in the BCAT gene is carried out using procedures similar to those described in Examples 5 and 10.

The tomato KAS gene (Solyc08g082620.2.1) has the partial genomic sequence of SEQ ID NO:394. Expression of KAS is constitutively increased by inserting an expression enhancing oligonucleotide in the 5' region of the gene. A maize OCS homologue (see Examples 14 and 23) encoded by a chemically modified single-stranded DNA with the sequence of SEQ ID NO:343 (Integrated DNA Technologies, Coralville, IA), phosphorylated on the 5' end and containing two phosphorothioate linkages at each terminus (i. e., the two linkages between the most distal three bases on either end of the strand) is designed for insertion at a double-strand break effected between nucleotides at positions 103/104, 168/169 or 259/260 of SEQ ID NO:394 in order to provide constitutively increased expression of KAS. Three BCAT crRNAs are designed to target the nucleotides shown in bold italic in SEQ ID NO: 394 (Table 23) and have the sequences of SEQ ID NO:430, 431, and 432. The crRNAs and tracrRNA are purchased from Integrated DNA Technologies, Coralville, IA. Ribonucleoprotein (RNP) complexes are prepared using gRNA (crRNA:tracrRNA) and Cas9 nuclease (Aldevron, Fargo, ND). Integration of the OCS homologue sequence in the KAS gene is carried out using procedures similar to those described in Examples 5 and 10.

In one embodiment, one or more genomic changes are made in the plant's genome during vegetative development; this is useful especially in plants that can be vegetatively propagated (e. g., from cuttings), such as tomato and tobacco. Such plants are conveniently grown in soil or in tissue culture media.

In this example, tomato meristem microinjection and meristem cell preparation are described. The apical or axillary meristem of a young plant is surgically exposed and genome editing reagents are introduced just below the L1 layer, into the L2 layer, of the meristem using a microinjection apparatus. The injected tissue is allowed to recover, and the resulting newly formed tissue is examined for the presence of the intended genomic edits. This cycle can be repeated many times, facilitated by propagating cuttings of the edited plant material from time to time. Modifications to the plant genome can be monitored by one or more molecular assays. Once the intended changes are complete, the plant is permitted to flower, is selfed or crossed, and produces seed. The next generation is examined for the presence and activity of all intended edits.

The genome editing reagents for this work are selected from DNA, RNA, protein, or a combination thereof (such as the ribonucleoproteins described elsewhere in this application). The reagents are delivered using an appropriate microinjection apparatus in a volume of about 2 to about 20 nanoliters per cell. The editing reagents can be delivered alone or as part of a formulation to aid in uptake by the targeted meristematic cells. These reagents can include saponin (e.g., Sigma Cat. No. 47036-50g-F), pectinase, DMSO, Silwet-77, Tween-20, or any other agent that permeabilizes or otherwise makes penetrable the plant cell wall without compromising the cell's activity or interfering with the activity of the editing reagents.

To introduce editing reagents, the newly formed leaf tissue in the target plant is carefully removed to expose the meristem without damaging it. The stem is gently, but firmly supported to counteract the pressure of the microinjection needle. A dissecting or compound microscope with appropriate optics is used to ensure that the microinjection needle accurately contacts the meristematic cells (specifically, the L2 cell layer, which gives rise to the germline). Once the meristem cells are treated, the stem is marked and the plant allowed to recover for several days. It is possible that more than one meristem per plant can be treated with identical or distinct editing reagents. The recovery period is long enough for the plant to grow 3-5 new leaves from the treated meristem. When sufficient new leaf tissue is present, a small piece of a newly formed leaf is excised for molecular analysis.

Molecular analysis encompasses a variety of assays or tests designed to detect the presence of the intended genomic modifications. For example, mRNA from the targeted gene(s) can be amplified by RT-PCR and sequenced to determine if genomic edits are present. Genomic DNA can be examined by targeted sequence analysis for the presence of the intended genomic modifications. Leaf tissue can be examined for visual or physical evidence (i. e., a detectable phenotype) of an intended genomic modification. The time required for evaluation of genomic modifications allows the plant to further recover from the microinjection and makes it competent for further genomic editing, if necessary.

If more genomic edits are required prior to flowering, tissue segments representing edited material can be vegetatively propagated. Excised plantlets are rooted in fresh soil or tissue culture media prior to the next editing step. Care is taken to insure the propagated plant is actively growing (e. g., displays evidence of robust root growth and new leaf formation) before initiating the next microinjection.

When genomic editing activities are complete, the plants are grown to reproductive maturity. If desired further vegetative propagation can be done to produce multiple clones of the edited plant prior to flowering. This may be desirable to ensure adequate seed production. Plants can be selfed or crossed as appropriate to produce seed. The resulting seeds are planted and the germinated seedlings are tested for the presence of the intended edits.

TABLE 23

| Name | Sequence | SEQ ID NO | Category |
| --- | --- | --- | --- |
| Zm00001d054060 NRT2.2 | TCCATCCTCGCTCTACCTGCCTGCTGCCAGTTTCAACTCTCCAAGGTCAACGCCAGCCCTCGCGCGCTTGGTGTACTCTAGTTTAGTACACCAATCCG***CATGCATTCTTTTTTGTTTG***TTTGTTTGTTTGTTTGTTTTGATTGACAAATATATGCGGCAGAGTTAAGAACGAATCGACTCCGTCGTCTCGGCTAGTCGACC | SEQ ID NO: 381 | DNA; *Zea mays* |
| Zm00001d051804 GLN1.4 | AGGGGCTTGACGCCTTACCAGTACGCGGTGCTCCCTCTTCTCGCACCTACCGCACGGAGGATATGACCTAATACAATTAATTTACGCGGAACTCGAAA***TGTATCCGTATTTATACGTG***TGGAACGTACAAGTATACGTATTTTGTTGGTTTTTTTTTTACTTTTTACCCGGCTGGACGCCAACCAACTGGTTTCCCGTCCT | SEQ ID NO: 382 | DNA; *Zea mays* |
| Zm00001d031278 Dof1 | CGGGCCCACGGGAGGTCGCGTCGATTCGCAGCAGCGCGCCGCCCCCCTCCCCACCACCACGTCAAGCGGCGTGGGCTTCCGCCCCTCCCTGCCCGCCG***CGTGGGCCCCCACTCGCGTC***CTGTAACCGGGATAGCGTGAGCACGTCGCTATCGTCCGTAACGGCGACCGCGACCATAAGAGAGGAGGCAAAGCCAGCCCCCG | SEQ ID NO: 383 | DNA; *Zea mays* |

TABLE 23-continued

| Name | Sequence | SEQ ID NO | Category |
|---|---|---|---|
| Zm00001d045450 EPSPS | AGCACGGACGATCCTTTACGTTGTTTTTAACAAACTTTGTCAGAAAACTAGCATCATTAACTTCTTAATGACGATTTCACAACAAAAAAAGGTAACCT***CGCTACTAACATAACAAAAT***ACTTGTTGCTTATTAATTATATGTTTTTTAATCTTTGATCAGGGGACAACAGTGGTTGATAACCTGTTGAACAGTGAGGATGT | SEQ ID NO: 384 | DNA; *Zea mays* |
| Zm00001d012660 NPR1 | ATTCCGTTGGACCCCTACCGCTCCTCAGTCAGTCCTCGCCCCTCCCAGCACCGGCCAACAATCCCTCACGTTATTCCCTGTAGCTACTATGCTGCCCT***CTTGGATCCCTTTTTCACTT***GTCTGAGATTTAGCCACCGCCCGGTAGGAAGAAGAAGGGGAAGCACCATATTTTCTGTTCCTGGCCTGACGCAGCGCCGGTGA | SEQ ID NO: 385 | DNA; *Zea mays* |
| Zm00001d040130 FEA3 (3'-UTR) | CAAGCAA***GCAGGTTCAGAAGAAGAACAC***GGAGAAACTTGAAGTAATGCTAGGTAGGTTAGCACGAAGTAGTTTCTGCGCGTTCTCTGTGATCTTTTGGCATTTGTTTTTGGCTGCTGGTGGCTTA***CCATCGTCAGATGGTGACGG***AGGAAGGAGGGAACATGGATCTGGATGGTGTGAGCCACAGATTACATTACAGTAGTAGAGTAAACTATGAGAGTTCTTGTGGACTGAAGGTGTGTAGTGG***TGGATAGGGTAGCTTCTCCG***GGGTTCTTTTGTGTG | SEQ ID NO: 386 | DNA; *Zea mays* |
| Zm00001d040130 FEA3 | GACTTCTGAGCGAGGAGTGGACGAGTGGTGTGCCGTCGTCCGGTTCCCGTTGGTTTGGCGATGAGGCGCGCTCGCGGTCGCCGCGGGCTGCTGCTTCT***CCTCGGCGTGGCGCTCTCG***GCGGCTGCGCTGCTCCGTGGCTGCGCGGGGCAGCAAGGGGAGGACGGCTCGGACGCCCCTGCGGCGGCGGCGGCGGAGACGGCCCCC***ATGGAGGAGAAGGAGCGC***AGGGCGCTGTACGCCGCCATCGAGAGCTTCGTCGGCAAGGGGTGGAACGGCTCCGGGCTCTACCCAGACCCCTGCGGCTGGTCTC | SEQ ID NO: 387 | DNA; *Zea mays* |
| GLYMA_12G078900 NRT | AATTTAATCTAATGGTAGATAATGTGTTCAAAGGAACGCTTGATAACATTTCTCGTGATAAATACGTATTTATGAGACTATTTAGTTATGATCATCCA***TGTCAATTAATTTCCAACCC***AAAGTAATGATCATGTGCCAAGTTGCCACCCATAATTTATCTCAAAATTAATGAAACCCAAATAAAGGCGTTGAATAATACCACCATACAAAAGTGTGTTATTTAGCAGCATATGTAACTAGGCATATATCTATCTGTATATATGAGAGTTGATTATGTGTCACATAT***GAACCTTTGAGACATACCAT***GGGTTCTTTTTGGCATACGCGGCGAAATGGATTACGTCAAATACAGCTTTTGTTTAATGCTTAAAGCTTTGGCAGCCGATGGAAATTTCATTGGCATTGTCAACGCCTTCCCCTACTATAAGTACAATCACACTCCT***TGTCTCTCCCTCACAACACT***AGGCCTTCAATTTGGTTTTGTTTCATCAGTTTTCCAGATACAGCACATTGATTGTTAAGGCGAAATGGCTGATATTGAGGGTT | SEQ ID NO: 388 | DNA; *Glycine max* |
| Glyma13g39850.1 NRT2 | TTGTTTACTCCTAGTTATTATCTTAAAAAAATTGAATCATATAATTATATATTAAGTTTTGAATATGTGTTTCCATCTTATAGTTTATGAGATTACCA***TGTGTTTAACAGATTGGGAT***CTACAAACTTTAAAAGTAAGCAGTAGATACATAATAGTTTTATAGGCCTGGTTGGTTAGC***TGAAATTTACAGCTACTACG***CGGATAATGAACCCCAATGATGAAAACATGCAGACGCATGTTGCAGCATGGAAGTATTTTATTTAATAAGAATAATAATAAGGTAAGTGGTAGTAATTAAATTCCATATTCAGTATCATGGGAAATGAGATTCTTTGCCTTTGGGATACACCATTAGGCTTTTAGCCGTTCCA***CTGTGTATATGCGGCGAAAT***GCATTACTCC | SEQ ID NO: 389 | DNA; *Glycine max* |

TABLE 23-continued

| Name | Sequence | SEQ ID NO | Category |
|---|---|---|---|
| | ATGGCCCTTGGGAATCCACTTGCCTCCTA<br>TCAGACTCTTACGTAGTCAACGCCTTCGC<br>CTACTATAAAAACAC | | |
| Glyma.16G150700<br>FT2a | AAAGAAGCTATGAGGTGCAAGAACCGAT<br>CACATGGAGAAGGCAATGAAAGACAAG<br>GAGGAGCAATGGAAGAGAGAAAATGAG<br>AAGATGGAAGGGATGT***GAAAATGTTTGA***<br>***AAAAAACG***AGGTGATCAGTTTTAAAATA<br>CGAATTTAGTATTTTCTTTTTAAGAAAAT<br>TCTTTCGGAAAGTCGTGTTTTAAAACATG<br>ACTTTTATTTATTTGAAGTCGTGTTCTAA<br>AACATGACTTTATTTCATATCCTTTAATA<br>TTTTATATCCTTAATATTTTTAAAATTTAT<br>CCATTTGTAATATTTTTTAAAAATTGACC<br>CATATATGTAAAATACCC***GTCAAGATCTC***<br>***TTTATTATT***TTGAAAGCGAAAGCATATCA<br>CTTCAAACACAATGGAATCGAGGCTATT<br>GACTAAGTATAA***ATAGAGAAGACTTCATA***<br>***TCG***GGGTTCATAATTCATAACAAAGCAA<br>ACGAGTATATAAGAAAGCATAAGCCAAA<br>TTTTGAGTAAACTAGTGTGCACACTATCC<br>C | SEQ ID NO: 390 | DNA; *Glycine max* |
| Glyma.16g019400<br>SHAT1-5 | CACGTGGCCCCACACACATTTTTTTTCCC<br>TCAACAGTTAAACTCTCTTCCTCCATCTT<br>TCTTGGTAGGTGGCACTTCTCGGAGCAT<br>AGTAAAACTAACCC***CACATTTTTCTTTTT***<br>***CATTT***TCATTTTCATTATATTATAAACCT<br>ATATATATACCCAATTGGTTATTGGTGTC<br>TGGTGTCCCTTCAACCTTTAAAACAAAC<br>AAATCCATTTTCTTTTTCTTTTTTTTTTCA<br>TTTTATTTTTTCCATTATTTTATCAACACA<br>ATTAATTCCA***TGTGTATCCTTTGGTCCTT***<br>***T***CTGTCCCACAGCACATATATATAGTCTC<br>GCTTTACATACTCATTCCATGGCCAGTAC<br>ACACACCA***CACCTCATTATATCTTTCTT***T<br>CAATTCCTATCCTCTTCCTTGTAGTGTAC<br>CCATTTTGAATGTGTTCTCTCTCTCTCT<br>CTTTCTTTAGGTCCCTGGTGAATATCTAG<br>AACCACTCTCT | SEQ ID NO: 391 | DNA; *Glycine max* |
| SOLYC02g081740<br>CS | ATAAGTATGTGCGTAAAAGTCTAAGTGG<br>***AGTCACGTGTGTATGATATG***AGGTCACAT<br>TAGAATTGTTACTAGAAAAGATATGAAG<br>GAATCTTTTCATTTTTATTTTATTTTCTTT<br>TTACATAGAGTAAACAAAAAAAATTGAC<br>TGGAATTGAAGTGGTAAGCCAAAAAATG<br>TGAGAATACATGAAAAAGTGTGAGAGA***A***<br>***GTCACGTGTGTATGGTATG***AGGTCACATG<br>AATATTATTGCCGAAAATGATATGAGAG<br>AATCTTTTCATTTTTATTTTATTTTCTTTT<br>TTAAACAGAGTAAAAAAAATTAAGTGTG<br>T***ATATATATATATGAGAAATG***GGGAAACA<br>AATTATCAAACATAATTACCATTG | SEQ ID NO: 392 | DNA; *Solanum lycopersicum* |
| SOLYC07G021630.2<br>BCAT | ATTACATAAAGATACAACTATAATCTGA<br>CCTAGCTTATAAAGGATGTGAAATCTAA<br>AATGATGATATATACCTTGATAAAAAAA<br>TTTTGCTACATCGCC***TTTTGCAATTATTTC***<br>***ATTTTG***AAAGTATTCATATTTGTTTATAA<br>AAAATTTTCAAATATTTTAATAAATAAAT<br>AAATAAAATTATATTTTATTTATGATTTT<br>CAAATATGTCAATGATATAAATGATTAG<br>CTATAAATCTCATAAATTTCTATATAGAC<br>TTATTAAAATAAAGTATAAAAAGATTTT<br>ATTTTATTTTTGAAATACGAAAAATATGC<br>GTGCTTGAGCCT***CTAACTACCTCCTATAT***<br>***AAATGATGAAAGAAAAATGTT***AGGTGTGAG<br>AAGTATATATCCTTATCCCAACTTTGGAA<br>TTTCAAATCGTTTGATTATTAAGTTATTT<br>GTTTGTTGTGGAAATTAAATATGATTCAA<br>AGGG | SEQ ID NO: 393 | DNA; *Solanum lycopersicum* |
| SOLC08G082620.2<br>KAS | CAACCCTTTAATGTCACATTTCTTGTTTG<br>GTCTTGTGAATTTAAGTCTGCAACTGTCA<br>CAAAAATCATACTACTATATTAATGTGTT | SEQ ID NO: 394 | DNA; *Solanum lycopersicum* |

TABLE 23-continued

| Name | Sequence | SEQ ID NO | Category |
|---|---|---|---|
| | GCATTTATCGCCA***TTTTTTTAATACTGTTTTCT***TGCTTAGCAAATATTACTATACTTGGGCGGATTCTCCAAATCCCA***TGTGCAATTAAAATTACAAA***CTTTGTTATTTACTCCATTTTCTTGGATCTCTCTATGACTTGTCTTTTTCTAATTTTCTATATATTTACCA***ACATGTTATGTTGAATTAAA***AGAAGAAAAAAAAACAAGAAGATTTAGTTTTTTTATTTTTGTGTGTGTGTGTTTGAGAAAATGAGTAGTATTACTTATTCTAATTTGATATTGAAGAGGA | | |
| Glyma07G104500 GS | CAAAAATTAATTCTTTTAGTAATGATAGAATCTAATATCTTAATTCAATGATTAATTATAACTTAAGTCTTCCTTTAAAATAAATCTCATCTCATCTCCT***TCTTCCTTTTTTGAGAGAGA***ATCTCATCTCATTCTTCGGTGATCAAATCTAGTGCCAGTACCGTACTTGGTACGCTACCTTCACTTGCCT***ATGTGCTTATCAGCTATCAC***CTACCTTTCATAATTTAATATAAAAAATAAATAAACAATGTCGCTGCAAAGCATGTTCATGTTCATTAATTCATTTTTATTATTAAAAAAAAAACACCCCTTTA***TTAGGCGGCGGAAAAACTCA***CGGTATCTTTCCACCACTTTCTTTATCTTTAGAGATCTTCTTTTATATATATATATATATATAGATAGATAGATAGATAGATACAGAGATGAAAAATACT | SEQ ID NO: 395 | DNA; *Glycine max* |
| Glyma06G207800.1 E1 | ATCGGATTTCATTGGGATCCATATAATTGCGTTTTCAATTTCTGTGTCCTTAAACAAGCTATGCCAGAGAATTAATTTAATTTTAAGTGTTAGCTTTATT***ATTTTACTTTCAAATCATTG***AGGAAAACAATGGCCTATATATTATTCCT***ATATGTAACATACAATAATG***TTATTGCAATAGCGTGTACTTCAACCTAATTATTTAATACCAAGTTTCTATATTAATGTTGTATCTTATGAAATCCTTCTATTTTCCATTCTATAAATTA | SEQ ID NO: 396 | DNA; *Glycine max* |

TABLE 24

| Gene | Guide (crRNA) | Orientation (relative to gene sequence) | Cut site | SEQ ID NO | Category |
|---|---|---|---|---|---|
| NRT2.2 ZM00001D054060 | CAAACAAAAAAGAAUGCAUGGUUUUAGAGCUAUGCU | reverse | 101 | SEQ ID NO: 397 | RNA; artificial |
| GLN1.4 ZM00001D051804 | UGUAUCCGUAUUUAUACGUGGUUUUAGAGCUAUGCU | forward | 115 | SEQ ID NO: 398 | RNA; artificial |
| Dof1 ZM00001D031278 | GACGCGAGUGGGGGCCCACGGUUUUAGAGCUAUGCU | reverse | 101 | SEQ ID NO: 399 | RNA; artificial |
| EPSPS ZM00001D045450 | AUUUUGUUAUGUUAGUAGCGGUUUUAGAGCUAUGCU | reverse | 101 | SEQ ID NO: 400 | RNA; artificial |
| NPR1 ZM00001D012660 | AAGUGAAAAAGGGAUCCAAGGUUUUAGAGCUAUGCU | reverse | 101 | SEQ ID NO: 401 | RNA; artificial |
| FEA3 ZM00001D040130 | GCAGGUUCAGAAGAAGAACAGUUUUAGAGCUAUGCU | forward | 25 | SEQ ID NO: 402 | RNA; artificial |
| FEA3 ZM00001D040130 | CCAUGUCAGAUGGUGACGGGUUUUAGAGCUAUGCU | Forward | 143 | SEQ ID NO: 403 | RNA; artificial |
| FEA3 ZM00001D040130 | UGGAUAGGGUAGCUUCUCCGGUUUUAGAGCUAUGCU | forward | 263 | SEQ ID NO: 404 | RNA; artificial |
| FEA3 ZM00001D040130 | GCGCUCCUUCUCCUCCAUGUUUUAGAGCUAUGCU | reverse | 207 | SEQ ID NO: 405 | RNA; artificial |

TABLE 24-continued

| Gene | Guide (crRNA) | Orientation (relative to gene sequence) | Cut site | SEQ ID NO | Category |
|---|---|---|---|---|---|
| FEA3 ZM00001D040130 | CCUCGGCGUGGCGCUCUCGGG UUUUAGAGCUAUGCU | forward | 115 | SEQ ID NO: 406 | RNA; artificial |
| NRT GLYMA12G078900 | AGUGUUGUGAGGGAGAGACA GUUUUAGAGCUAUGCU | reverse | 446 | SEQ ID NO: 407 | RNA; artificial |
| NRT GLYMA12G078900 | GAACCUUUGAGACAUACCAU GUUUUAGAGCUAUGCU | forward | 303 | SEQ ID NO: 408 | RNA; artificial |
| NRT GLYMA12G078900 | GGGUUGGAAAUUAAUUGACA GUUUUAGAGCUAUGCU | reverse | 101 | SEQ ID NO: 409 | RNA; artificial |
| NRT2 GLYMA13G39850.1 | AUUUCGCCGCAUAUACACAG GUUUUAGAGCUAUGCU | reverse | 374 | SEQ ID NO: 410 | RNA; artificial |
| NRT2 GLYMA13G39850.1 | UGAAAUUUACAGCUACUACG GUUUUAGAGCUAUGCU | forward | 195 | SEQ ID NO: 411 | RNA; artificial |
| NRT2 GLYMA13G39850.1 | AUCCCAAUCUGUUAAACACA GUUUUAGAGCUAUGCU | reverse | 101 | SEQ ID NO: 412 | RNA; artificial |
| GS GLYMA07G104500 | GUGAUAGCUGAUAAGCACAU GUUUUAGAGCUAUGCU | reverse | 193 | SEQ ID NO: 413 | RNA; artificial |
| GS GLYMA07G104500 | UUAGGCGGCGGAAAAACUCA GUUUUAGAGCUAUGCU | forward | 331 | SEQ ID NO: 414 | RNA; artificial |
| GS GLYMA07G104500 | UCUCUCUCAAAAAAGGAAGA GUUUUAGAGCUAUGCU | reverse | 103 | SEQ ID NO: 415 | RNA; artificial |
| FT2a GLYMA16G150700 | GAAAAUGUUUGAAAAAAACG GUUUUAGAGCUAUGCU | forward | 115 | SEQ ID NO: 416 | RNA; artificial |
| FT2a GLYMA16G150700 | AUAGAGAAGACUUCAUAUCG GUUUUAGAGCUAUGCU | forward | 428 | SEQ ID NO: 417 | RNA; artificial |
| FT2a GLYMA16G150700 | AAUAAUAAAGAGAUCUUGAC GUUUUAGAGCUAUGCU | reverse | 334 | SEQ ID NO: 418 | RNA; artificial |
| E1 GLYMA06G207800.1 | AUUUUACUUUCAAAUCAUUG GUUUUAGAGCUAUGCU | forward | 117 | SEQ ID NO: 419 | RNA; artificial |
| E1 GLYMA06G207800.1 | CAUUAUUGUAUGUUACAUAU GUUUUAGAGCUAUGCU | reverse | 152 | SEQ ID NO: 420 | RNA; artificial |
| SHAT1-5 GLYMA16G019400 | AAAUGAAAAAGAAAAAUGUG GUUUUAGAGCUAUGCU | reverse | 103 | SEQ ID NO: 421 | RNA; artificial |
| SHAT1-5 GLYMA16G019400 | AAAGGACCAAAGGAUACACA GUUUUAGAGCUAUGCU | reverse | 274 | SEQ ID NO: 422 | RNA; artificial |
| SHAT1-5 GLYMA16G019400 | AAGAAAGAUAUAAUGAGGUG GUUUUAGAGCUAUGCU | reverse | 359 | SEQ ID NO: 423 | RNA; artificial |
| CS SOLYC02G081740.1 | AGUCACGUGUGUAUGAUAUG GUUUUAGAGCUAUGCU | forward | 46 | SEQ ID NO: 424 | RNA; artificial |
| CS SOLYC02G081740.1 | AGUCACGUGUGUAUGGUAUG GUUUUAGAGCUAUGCU | forward | 216 | SEQ ID NO: 425 | RNA; artificial |
| CS SOLYC02G081740.1 | AUAUAUAUAUAUGAGAAAUG GUUUUAGAGCUAUGCU | forward | 333 | SEQ ID NO: 426 | RNA; artificial |
| BCAT SOLYC07G021630.2 | UUUAUAUAGGAGGUAGUUAG GUUUUAGAGCUAUGCU | reverse | 330 | SEQ ID NO: 427 | RNA; artificial |
| BCAT SOLYC07G021630.2 | CAAAAUGAAAUAAUUGCAAA GUUUUAGAGCUAUGCU | reverse | 103 | SEQ ID NO: 428 | RNA; artificial |
| BCAT SOLYC07G021630.2 | AAAUGAUGAAAGAAAAUGUU GUUUUAGAGCUAUGCU | forward | 361 | SEQ ID NO: 429 | RNA; artificial |
| KAS SOLYC08G082620.2 | UUUGUAAUUUUAAUUGCACA GUUUUAGAGCUAUGCU | reverse | 168 | SEQ ID NO: 430 | RNA; artificial |

TABLE 24-continued

| Gene | Guide (crRNA) | Orientation (relative to gene sequence) | Cut site | SEQ ID NO | Category |
|---|---|---|---|---|---|
| KAS SOLYC08G082620.2 | UUUAAUUCAACAUAACAUGU GUUUUAGAGCUAUGCU | reverse | 259 | SEQ ID NO: 431 | RNA; artificial |
| KAS SOLYC08G082620.2 | AGAAAACAGUAUUAAAAAAA GUUUUAGAGCUAUGCU | reverse | 103 | SEQ ID NO: 432 | RNA; artificial |

Example 33

This example illustrates techniques for preparing a plant cell or plant protoplast useful in compositions and methods of the invention. More specifically this non-limiting example describes techniques for preparing isolated, viable plant protoplasts from monocot and dicot plants.

The following mesophyll protoplast preparation protocol (modified from one publicly available at molbio[dot]mgh [dot]harvard.edu/sheenweb/protocols_reg[dot]html) is generally suitable for use with monocot plants such as maize (*Zea mays*) and rice (*Oryza sativa*):

Prepare an enzyme solution containing 0.6 molar mannitol, 10 millimolar MES pH 5.7, 1.5% cellulase R10, and 0.3% macerozyme R10. Heat the enzyme solution at 50-55 degrees Celsius for 10 minutes to inactivate proteases and accelerate enzyme solution and cool it to room temperature before adding 1 millimolar CaCl2), 5 millimolar β-mercaptoethanol, and 0.1% bovine serum albumin. Pass the enzyme solution through a 0.45 micrometer filter. Prepare a washing solution containing 0.6 molar mannitol, 4 millimolar MES pH 5.7, and 20 millimolar KCl.

Obtain second leaves of the monocot plant (e. g., maize or rice) and cut out the middle 6-8 centimeters. Stack ten leaf sections and cut into 0.5 millimeter-wide strips without bruising the leaves. Submerge the leaf strips completely in the enzyme solution in a petri dish, cover with aluminum foil, and apply vacuum for 30 minutes to infiltrate the leaf tissue. Transfer the dish to a platform shaker and incubate for an additional 2.5 hours' digestion with gentle shaking (40 rpm). After digestion, carefully transfer the enzyme solution (now containing protoplasts) using a serological pipette through a 35 micrometer nylon mesh into a round-bottom tube; rinse the petri with 5 milliliters of washing solution and filter this through the mesh as well. Centrifuge the protoplast suspension at 1200 rpm, 2 minutes in a swing-bucket centrifuge. Aspirate off as much of the supernatant as possible without touching the pellet; gently wash the pellet once with 20 milliliters washing buffer and remove the supernatant carefully. Gently resuspend the pellet by swirling in a small volume of washing solution, then resuspend in 10-20 milliliters of washing buffer. Place the tube upright on ice for 30 minutes-4 hours (no longer). After resting on ice, remove the supernatant by aspiration and resuspend the pellet with 2-5 milliliters of washing buffer. Measure the concentration of protoplasts using a hemocytometer and adjust the concentration to 2×10^5 protoplasts/milliliter with washing buffer.

The following mesophyll protoplast preparation protocol (modified from one described by Niu and Sheen (2012) *Methods Mol. Biol.,* 876:195-206, doi: 10.1007/978-1-61779-809-2_16) is generally suitable for use with dicot plants such as *Arabidopsis thaliana* and brassicas such as kale (*Brassica oleracea*).

Prepare an enzyme solution containing 0.4 M mannitol, 20 millimolar KCl, 20 millimolar MES pH 5.7, 1.5% cellulase R10, and 0.4% macerozyme R10. Heat the enzyme solution at 50-55 degrees Celsius for 10 minutes to inactivate proteases and accelerate enzyme solution, and then cool it to room temperature before adding 10 millimolar CaCl2), 5 millimolar β-mercaptoethanol, and 0.1% bovine serum albumin. Pass the enzyme solution through a 0.45 micrometer filter. Prepare a "W5" solution containing 154 millimolar NaCl, 125 millimolar CaCl2), 5 millimolar KCl, and 2 millimolar MES pH 5.7. Prepare a "MMg solution" solution containing 0.4 molar mannitol, 15 millimolar MgCl2, and 4 millimolar MES pH 5.7.

Obtain second or third pair true leaves of the dicot plant (e. g., a *brassica* such as kale) and cut out the middle section. Stack 4-8 leaf sections and cut into 0.5 millimeter-wide strips without bruising the leaves. Submerge the leaf strips completely in the enzyme solution in a petri dish, cover with aluminum foil, and apply vacuum for 30 minutes to infiltrate the leaf tissue. Transfer the dish to a platform shaker and incubate for an additional 2.5 hours' digestion with gentle shaking (40 rpm). After digestion, carefully transfer the enzyme solution (now containing protoplasts) using a serological pipette through a 35 micrometer nylon mesh into a round-bottom tube; rinse the petri dish with 5 milliliters of washing solution and filter this through the mesh as well. Centrifuge the protoplast suspension at 1200 rpm, 2 minutes in a swing-bucket centrifuge. Aspirate off as much of the supernatant as possible without touching the pellet; gently wash the pellet once with 20 milliliters washing buffer and remove the supernatant carefully. Gently resuspend the pellet by swirling in a small volume of washing solution, then resuspend in 10-20 milliliters of washing buffer. Place the tube upright on ice for 30 minutes-4 hours (no longer). After resting on ice, remove the supernatant by aspiration and resuspend the pellet with 2-5 milliliters of MMg solution. Measure the concentration of protoplasts using a hemocytometer and adjust the concentration to 2×10^5 protoplasts/milliliter with MMg solution.

Example 34

This example illustrates culture conditions effective in improving viability of plant cells or plant protoplasts. More specifically, this non-limiting example describes media and culture conditions for improving viability of isolated plant protoplasts.

Table 25 provides the compositions of different liquid basal media suitable for culturing plant cells or plant protoplasts; final pH of all media was adjusted to 5.8 if necessary.

TABLE 25

| | Concentration (mg/L unless otherwise noted) | | | | |
|---|---|---|---|---|---|
| Component | SH | 8p | PIM | P2 | YPIM B− |
| Casamino acids | | 250 | | | |
| Coconut water | | 20000 | | | |
| Ascorbic acid | | 2 | | | |
| biotin | | 0.01 | 0.01 | | |
| Cholicalciferol (Vitamin D-3) | | 0.01 | | | |
| choline chloride | | 1 | | | |
| Citric acid | | 40 | | | |
| Cyanocobalamin (Vitamin B-12) | | 0.02 | | | |
| D-calcium pantothenate | | 1 | 1 | | |
| D-Cellobiose | | 250 | | | |
| D-Fructose | | 250 | | | |
| D-Mannose | | 250 | | | |
| D-Ribose | | 250 | | | |
| D-Sorbitol | | 250 | | | |
| D-Xylose | | 250 | | | |
| folic acid | | 0.4 | 0.2 | | |
| Fumaric acid | | 40 | | | |
| L-Malic acid | | 40 | | | |
| L-Rhamnose | | 250 | | | |
| p-Aminobenzoic acid | | 0.02 | | | |
| Retinol (Vitamin A) | | 0.01 | | | |
| Riboflavin | | 0.2 | | | |
| Sodium pyruvate | | 20 | | | |
| 2,4-D | 0.5 | 0.2 | 1 | 5 | 1 |
| 6-benzylaminopurine (BAP) | | | | | 1 |
| Indole-3-butyric acid (IBA) | | | | 2.5 | |
| Kinetin | 0.1 | | | | |
| Naphthaleneacetic acid (NAA) | | 1 | | | |
| parachlorophenoxyacetate (pCPA) | 2 | | | | |
| Thidiazuron | | | 0.022 | | |
| Zeatin | | 0.5 | | | |
| AlCl3 | | | 0.03 | | |
| Bromocresol purple | | | 8 | | |
| $CaCl_2$•$2H_2O$ | 200 | 600 | 440 | 200 | 440 |
| $CoCl_2$•$6H_2O$ | 0.1 | 0.025 | | 0.1 | |
| $CuSO_4$•$5H_2O$ | 0.2 | 0.025 | 0.03 | 0.2 | 0.03 |
| D-Glucose | | 68400 | 40000 | | 40000 |
| D-Mannitol | 52000 | 250 | 60000 | 52000 | 60000 |
| $FeSO_4$•$7H_2O$ | 15 | 27.8 | 15 | 15 | 15 |
| $H_3BO_3$ | 5 | 3 | 1 | 5 | 1 |
| KCl | | 300 | | | |
| $KH_2PO_4$ | | 170 | 170 | | 170 |
| KI | 1 | 0.75 | 0.01 | 1 | 0.01 |
| $KNO_3$ | 2500 | 1900 | 505 | 2500 | 505 |
| MES pH 5.8 (mM) | | | 3.586 | 25 | 25 |
| $MgSO_4$•$7H_2O$ | 400 | 300 | 370 | 400 | 370 |
| $MnSO_4$•$H_2O$ | 10 | 10 | 0.1 | 10 | 0.1 |
| $Na_2EDTA$ | 20 | 37.3 | 20 | 20 | 20 |
| $Na_2MoO_4$•$2H_2O$ | 0.1 | 0.25 | | 0.1 | |
| $NH_4H_2PO_4$ | 300 | | | 300 | |
| $NH_4NO_3$ | | 600 | 160 | | 160 |
| $NiCl_2$•$6H_2O$ | | | 0.03 | | |
| Sucrose | 30000 | 2500 | | 30000 | |
| $ZnSO_4$•$7H_2O$ | 1 | 2 | 1 | 1 | 1 |
| Tween-80 (microliter/L) | 10 | 10 | | | |
| Inositol | 1000 | 100 | 100 | 1000 | 100 |
| Nicotinamide | | 1 | | | |
| Nicotinic acid | 5 | | 1 | 5 | 1 |
| Pyridoxine•HCl | 0.5 | 1 | 1 | 0.5 | 1 |
| Thiamine•HCl | 5 | 1 | 1 | 5 | 1 |

* Sources for basal media:
SH—Schenk and Hildebrandt, *Can. J. Bot.* 50: 199 (1971).
8p—Kao and Michayluk, *Planta* 126: 105 (1975).
P2—SH but with hormones from Potrykus et al., *Mol. Gen. Genet.* 156: 347 (1977).
PIM—Chupeau et al., *The Plant Cell* 25: 2444 (2013).

Example 35

This example illustrates culture conditions effective in improving viability of plant cells or plant protoplasts. More specifically, this non-limiting example describes methods for encapsulating isolated plant protoplasts.

When protoplasts are encapsulated in alginate or pectin, they remain intact far longer than they would in an equivalent liquid medium. In order to encapsulate protoplasts, a liquid medium ("calcium base") is prepared that is in all other respects identical to the final desired recipe with the exception that the calcium (usually CaCl2·2H2O) is increased to 80 millimolar. A second medium ("encapsulation base") is prepared that has no added calcium but contains 10 g/L of the encapsulation agent, e. g., by making a 20 g/L solution of the encapsulation agent and adjusting its pH with KOH or NaOH until it is about 5.8, making a 2× solution of the final medium (with no calcium), then combining these two solutions in a 1:1 ratio. Encapsulation agents include alginate (e. g., alginic acid from brown algae, catalogue number A0682, Sigma-Aldrich, St. Louis, MO) and pectin (e. g., pectin from citrus peel, catalogue number P9136, Sigma-Aldrich, St. Louis, MO; various pectins including non-amidated low-methoxyl pectin, catalogue number 1120-50 from Modernist Pantry, Portsmouth, NH). The solutions, including the encapsulation base solution, is filter-sterilized through a series of filters, with the final filter being a 0.2-micrometer filter. Protoplasts are pelleted by gentle centrifugation and resuspended in the encapsulation base; the resulting suspension is added dropwise to the calcium base, upon which the protoplasts are immediately encapsulated in solid beads.

Example 36

This example illustrates culture conditions effective in improving viability of plant cells or plant protoplasts. More specifically, this non-limiting example describes observations of effects on protoplast viability obtained by adding non-conventionally high levels of divalent cations to culture media.

Typical plant cell or plant protoplast media contain between about 2 to about 4 millimolar calcium cations and between about 1-1.5 millimolar magnesium cations. In the course of experiments varying and adding components to media, it was discovered that the addition of non-conventionally high levels of divalent cations had a surprisingly beneficial effect on plant cell or plant protoplast viability. Beneficial effects on plant protoplast viability begin to be seen when the culture medium contains about 30 millimolar calcium cations (e. g., as calcium chloride) or about 30 millimolar magnesium cations (e. g., as magnesium chloride). Even higher levels of plant protoplast viability were observed with increasing concentrations of calcium or magnesium cations, i. e., at about 40 millimolar or about 50 millimolar calcium or magnesium cations. The result of several titration experiments indicated that greatest improvement in protoplast viability was seen using media containing between about 50 to about 100 millimolar calcium cations or 50 to about 100 millimolar magnesium cations; no negative effects on protoplast viability or physical appearance was observed at these high cation levels. This was observed in multiple experiments using protoplasts obtained from several plant species including maize (multiple germplasms, e. g., B73, A188, B104, HiIIA, HiIIB, BMS), rice, wheat, soy, kale, and strawberry; improved protoplast viability was observed in both encapsulated protoplasts and non-encapsulated protoplasts. Addition of potassium chloride at the same levels had no effect on protoplast viability. It is possible that inclusion of slightly lower (but still non-conventionally high) levels of divalent cations (e. g., about 10 millimolar, about 15 millimolar, about 20 millimolar, or about 25 millimolar calcium cations or magnesium cations) in media is beneficial for plant cells or plant protoplasts of additional plant species.

Example 37

This example illustrates culture conditions effective in improving viability of plant cells or plant protoplasts. More specifically, this non-limiting example describes observations of effects on maize protoplast viability obtained by adding non-conventionally high levels of divalent cations to culture media.

Separate suspensions of maize B73 and A188 protoplasts (2×10^5 cells per milliliter) were prepared in YPIM B-liquid medium containing various combinations of the added salts calcium chloride, potassium ascorbate, and magnesium chloride or magnesium sulfate. One-half milliliter aliquots of the suspensions were dispensed into a 24-well microtiter plate in the arrangement shown in Table 26, which lists the concentrations of calcium chloride ("Ca"), potassium ascorbate ("A"), and magnesium chloride ("MgCl2") or magnesium sulfate ("MgSO4") in millimolar values.

TABLE 26

| | | | | | |
|---|---|---|---|---|---|
| YPIM B− | Ca = 0, A = 0.1 | Ca = 0, A = 0.2 | Ca = 0, A = 0.5 | Ca = 0, A = 1 | YPIM B− |
| Ca = 50, A = 0 | Ca = 50, A = 0.1 | Ca = 50, A = 0.2 | Ca = 50, A = 0.5 | Ca = 50, A = 1 | YPIM B− |
| Ca = 100, A = 0 | Ca = 100, A = 0.1 | Ca = 100, A = 0.2 | Ca = 100, A = 0.5 | Ca = 100, A = 1 | YPIM B− |
| YPIM B− | $MgCl_2$ = 50 | $MgCl_2$ = 100 | $MgSO_4$ = 50 | $MgSO_4$ = 100 | YPIM B− |

Viability was judged by Evans blue staining and visualization under a light microscope. After 96 hours, both maize species were still highly viable in all wells. After 288 hours, there were clear differences at various calcium and magnesium concentrations, but only slight effects at various ascorbate concentrations.

The observations at 288 hours were recorded as follows: Maize B73: protoplasts in all Ca=0 wells appeared small and dead; protoplasts in Ca=50 wells appeared larger but were now also almost all dead; protoplasts in Ca=100 wells still appeared larger and had a viability of between 10-20%. Protoplasts in MgCl2=50 wells were similar to those in Ca=100 wells, and protoplasts in MgCl2=100 wells had much higher viability than any well. Wells with MgSO4=50 or 100 showed only a modest improvement in protoplast viability. Maize A188: protoplasts in all Ca=0 wells appeared small and dead; protoplasts in Ca=50 wells appeared and had about 20% viability; protoplasts in Ca=100 wells had about 70% viability and were visibly healthier. Addition of ascorbate at 0.2 millimolar and above to the wells with added calcium appeared to slightly decrease viability. Wells with MgSO4=50 had about 30-40% viability, and wells with MgCl2=100 had about 70% viability. Wells with MgSO4=50 or 100 showed only a modest improvement in protoplast viability. These results demonstrate that calcium chloride or magnesium chloride added at non-conventionally high levels improved maize protoplast viability over a culture time of ~12 days.

Example 38

This example illustrates culture conditions effective in improving viability of plant cells or plant protoplasts. More specifically, this non-limiting example describes observations of effects on maize, soybean, and strawberry protoplast viability obtained by adding non-conventionally high levels of divalent cations to culture media.

Separate suspensions of maize B73, winter wheat, soy, and strawberry protoplasts (2×10^5 cells per milliliter) were prepared in YPIM B-liquid medium containing calcium chloride at 0, 50, or 100 millimolar. One-half milliliter aliquots of the suspensions were dispensed into a 24-well microtiter plate.

Viability at day 8 of culture was judged by visualization under a light microscope. At this point, the viability of the maize protoplasts in the 0, 50, and 100 millimolar calcium conditions was 10%, 30%, and 80%, respectively. There were no large differences observed at this time point for protoplasts of the other species.

Viability at day 13 was judged by Evans blue staining and visualization under a light microscope. At this point, the viability of the maize protoplasts in the 0, 50, and 100 millimolar calcium conditions was 0%, 0%, and 10%, respectively; viability of the soybean protoplasts in the 0, 50, and 100 millimolar calcium conditions was 0%, 50%, and 50%, respectively; and viability of the maize protoplasts in the 0 and 50 millimolar calcium conditions was 0% and 50%, respectively (viability was not measured for the 100 millimolar condition). These results demonstrate that culture conditions including calcium cations at 50 or 100 millimolar improved viability of both monocot and dicot protoplasts over a culture time of ~13 days.

Example 39

This example illustrates culture conditions effective in improving viability of plant cells or plant protoplasts. More specifically, this non-limiting example describes observations of effects on maize protoplast viability obtained by adding non-conventionally high levels of divalent cations to culture media.

Separate suspensions of maize A188 protoplasts (2×10^5 cells per milliliter) were prepared in YPIM B-liquid medium containing calcium chloride at 0 or 50 millimolar. One-half milliliter aliquots of the suspensions were dispensed into a 24-well microtiter plate.

Viability was judged by visualization under a light microscope. At 96 hours, protoplasts grown with 50 millimolar calcium cations appeared healthier than those grown with no added calcium. At 168 hours (7 days), wells with 50 millimolar calcium cations still contained very many large, healthy-looking protoplasts, whereas protoplasts in the wells with no added calcium were nearly all dead. This experiment was carried on to day 20, at which point the protoplasts in the wells with 50 millimolar calcium had generated cell walls and undergone at least some cell division. These results demonstrate that culture conditions including calcium cations at 50 millimolar improved viability, cell wall regeneration, and cell division of maize protoplasts over a culture time of at least 7 to 20 days.

Example 40

This example illustrates culture conditions effective in improving viability of plant cells or plant protoplasts. More specifically, this non-limiting example describes observations of effects on maize protoplast viability obtained by adding non-conventionally high levels of divalent cations to culture media.

Separate suspensions of maize B73 protoplasts (2×10^5 cells per milliliter) were prepared in PIM B-liquid medium (identical to YPIM B-medium except with the 6-benzylaminopurine substituted with 0.022 milligrams/L thidiazuron) containing calcium chloride added at 0, 5, 20, 40, 70, or 100 millimolar. One-half milliliter aliquots of the suspensions were dispensed into a 24-well microtiter plate.

Viability was judged by visualization under a light microscope at day 7 and at day 14 of culture. In this experiment, by day 7 the maize protoplasts were dead in the wells containing less than 40 millimolar calcium; the maize protoplasts in the wells containing 40, 70, or 100 millimolar calcium formed clusters of viable, healthy cells with cell division occurring, with the strongest enhanced viability and cell division observed at 100 millimolar calcium. These results demonstrate that culture conditions including calcium cations at 40, 70, or 100 improved viability, cell wall regeneration, and cell division of maize protoplasts over a culture time of at least 7 to 14 days.

Example 41

This example illustrates culture conditions effective in improving viability of plant cells or plant protoplasts. More specifically, this non-limiting example describes observations of effects on maize protoplast viability obtained by adding non-conventionally high levels of divalent cations to culture media.

Separate suspensions of maize B73 and A188 protoplasts (2×10^5 cells per milliliter) were prepared in PIM B-liquid medium (identical to YPIM B-medium except with the 6-benzylaminopurine substituted with 0.022 milligrams/L thidiazuron) containing calcium chloride added at 0 or 50 millimolar. One-half milliliter aliquots of the suspensions were dispensed into a 24-well microtiter plate.

Viability was judged by visualization under a light microscope. In this experiment, by day 6 the maize A188 protoplasts were about 40% viable in the wells containing no added calcium but showed much higher viability in the wells containing 50 millimolar calcium, where several wells showed 100% viability. The maize B73 protoplasts in the wells containing no added calcium had all died, but wells containing 50 millimolar calcium still contained viable cells.

Example 42

This example illustrates culture conditions effective in improving viability of plant cells or plant protoplasts. More specifically, this non-limiting example describes observations of effects on maize protoplast viability obtained by adding non-conventionally high levels of divalent cations or a low-molecular-weight antioxidant to culture media.

Separate suspensions of maize B73 and A188 protoplasts (2×10^5 cells per milliliter) were prepared in YPIM B-liquid medium containing (a) calcium chloride added at 100 millimolar, or (b) 1 millimolar glutathione, or (c) no added calcium or glutathione. One-milliliter aliquots of the suspensions were dispensed into a 24-well microtiter plate. At 16, 40, 64, and 136 hours of culture, 50-microliter samples were taken for hemocytometer analysis from each well; for the plates containing maize A188 protoplasts, parallel 50-microliter samples were taken from a replicate well at 16, 40, and 64 hours of culture for quantification using a Cellometer cell counter (Nexcelom Bioscience LLC, Lawrence, MA).

Viability was determined by Evans blue staining and quantification using a hemocytometer. Under conditions with high concentrations of calcium, Evans blue can create precipitates that interfere with cell counting; to prevent this, 5 microliters of an EDTA solution was added to the samples from the wells containing 100 millimolar calcium chloride immediately prior to staining. Results from the hemocytometer analysis are provided in Table 27 (results from the Cellometer analysis were very similar); "Control"=YPIM B-medium with no added calcium or glutathione. These results demonstrate that inclusion in the medium of either non-conventionally high (100 millimolar) calcium cations or the low-molecular-weight thiol antioxidant glutathione resulted in increasing protoplast viability of both maize lines by (a) at least 10% higher after 30 hours (in this example, about 10-34% higher at 40 hours) culture; (b) at least 10% higher after 48 hours' culture hours (in this example, between 17-53% higher at 64 hours); or (c) at least 10% higher after 72 hours' culture hours or at least 10% higher after 96 hours' culture hours (in this example, about 12-at least 46% higher at 138 hours).

TABLE 27

| Cell | | Viability (%) | | |
|---|---|---|---|---|
| Type | Hours | Control | 100 mM Ca | 1 mM GSH |
| B73 | 0 | 90 | 90 | 90 |
| | 16 | 65 | 65 | 77 |
| | 40 | 38 | 57 | 72 |
| | 64 | 31 | 58 | 48 |
| | 136 | 12 | 30 | 24 |
| A188 | 0 | 90 | 90 | 90 |
| | 16 | 60 | 67 | 69 |
| | 40 | 40 | 57 | 50 |
| | 64 | 6 | 59 | 50 |
| | 136 | 0 | 46 | 42 |

Example 43

This example illustrates culture conditions effective in improving viability of plant cells or plant protoplasts. More specifically, this non-limiting example describes observations of effects on maize protoplast viability obtained by adding non-conventionally high levels of divalent cations to culture media.

Separate suspensions of maize protoplasts from five different germplasm lines (A188, B73, B104, HiIIA, HiIIB) (2×10^5 cells per milliliter) were prepared in YPIM B-liquid medium containing calcium chloride added at 0, 50, or 100 millimolar. One-half milliliter aliquots of the suspensions were dispensed into a 24-well microtiter plate.

Viability was judged by visualization under a light microscope. At 19 hours, protoplasts of all five maize lines grown under the different conditions appeared healthy, with large proportions of round, green cells; slightly more debris was observed in the 0 calcium conditions. At 34 hours, protoplasts of all five maize lines showed a response to the increased calcium conditions similar to what had been previously observed; across the five maize lines, viability of protoplasts grown without added calcium was about 40%, while those grown with 50 millimolar calcium was about 55%, and those grown with 100 millimolar calcium was about 70%. These results demonstrate that culture conditions including calcium cations at 50 or 100 millimolar improved viability of protoplasts from various maize germplasm over a culture time of 34 hours.

Example 44

This example illustrates genome editing in plants and further illustrates a method of delivering gene-editing effector molecules into a plant cell. This example describes introducing at least one double-strand break (DSB) in a genome in a plant cell or plant protoplast, by delivering at least one effector molecules to the plant cell or plant protoplast using at least one physical agent, such as a particulate, microparticulate, or nanoparticulate. More specifically, this non-limiting example illustrates introducing at least one double-strand break (DSB) in a genome in a plant cell or plant protoplast by contacting the plant cell or plant protoplast with a composition including at least one sequence-specific nuclease and at least one physical agent, such as at least one nanocarrier. Embodiments include those wherein the nanocarrier comprises metals (e. g., gold, silver, tungsten, iron, cerium), ceramics (e. g., aluminum oxide, silicon carbide, silicon nitride, tungsten carbide), polymers (e. g., polystyrene, polydiacetylene, and poly(3,4-ethylenedioxythiophene) hydrate), semiconductors (e. g., quantum dots), silicon (e. g., silicon carbide), carbon (e. g., graphite, graphene, graphene oxide, or carbon nanosheets, nanocomplexes, or nanotubes), composites (e. g., polyvinylcarbazole/graphene, polystyrene/graphene, platinum/graphene, palladium/graphene nanocomposites), a polynucleotide, a poly (AT), a polysaccharide (e. g., dextran, chitosan, pectin, hyaluronic acid, and hydroxyethylcellulose), a polypeptide, or a combination of these. In embodiments, such particulates and nanoparticulates are further covalently or non-covalently functionalized, or further include modifiers or cross-linked materials such as polymers (e. g., linear or branched polyethylenimine, poly-lysine), polynucleotides (e. g., DNA or RNA), polysaccharides, lipids, polyglycols (e. g., polyethylene glycol, thiolated polyethylene glycol), polypeptides or proteins, and detectable labels (e. g., a fluorophore, an antigen, an antibody, or a quantum dot). Embodiments include those wherein the nanocarrier is a nanotube, a carbon nanotube, a multi-walled carbon nanotube, or a single-walled carbon nanotube. Specific nanocarrier embodiments contemplated herein include the single-walled carbon nanotubes, cerium oxide nanoparticles ("nanoceria"), and modifications thereof (e. g., with cationic, anionic, or lipid coatings) described in Giraldo et al. (2014) *Nature Materials,* 13:400-409; the single-walled carbon nanotubes and heteropolymer complexes thereof described in Zhang et al. (2013) *Nature Nanotechnol.,* 8:959-968 (doi:10.1038/NNANO.2013.236); the single-walled carbon nanotubes and heteropolymer complexes thereof described in Wong et al. (2016) *Nano Lett.,* 16:1161-1172; and the various carbon nanotube preparations described in US Patent Application Publication US 2015/0047074 and International Patent Application PCT/US2015/050885 (published as WO 2016/044698 and claiming priority to U.S. Provisional Patent Application 62/052,767), all of which patent applications are incorporated in their entirety by reference herein. See also, for example, the various types of particles and nanoparticles, their preparation, and methods for their use, e. g., in delivering polynucleotides and polypeptides to cells, disclosed in US Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety.

In these examples, single-walled carbon nanotubes (SWCNT) and modifications thereof are prepared as described in Giraldo et al. (2014) *Nature Materials,* 13:400-409; Zhang et al. (2013) *Nature Nanotechnol.,* 8:959-968; Wong et al. (2016) *Nano Lett.,* 16:1161-1172; US Patent Application Publication US 2015/0047074; and International Patent Application PCT/US2015/050885 (published as WO 2016/044698). In an initial experiment, a DNA plasmid encoding green fluorescent protein (GFP) as a reporter is non-covalently complexed with a SWCNT preparation and tested on various plant cell preparations including plant cells in suspension culture, plant callus, plant embryos, intact or half seeds, and shoot apical meristem. Delivery to the plant callus, embryos, seeds, and meristem is by treatment with pressure, centrifugation, bombardment, microinjection, infiltration (e. g., with a syringe), or by direct application to the surface of the plant tissue. Efficiency of the SWCNT delivery of GFP across the plant cell wall and the cellular localization of the GFP signal is evaluated by microscopy.

In another experiment, plasmids encoding Cas9 and at least one guide RNA (gRNA), such as those described in Example 6, are non-covalently complexed with a SWCNT preparation and tested on various plant cell preparations including plant cells in suspension culture, plant callus, plant embryos, intact or half seeds, and shoot apical meristem. Delivery to the plant callus, embryos, seeds, and meristem is by treatment with pressure, centrifugation, bombardment, microinjection, infiltration (e. g., with a syringe), or by direct application to the surface of the plant tissue. The gRNA is designed to target the endogenous plant gene phytoene desaturase (PDS) for silencing, where PDS silencing produces a visible phenotype (bleaching, or low/no chlorophyll).

In another experiment, RNA encoding Cas9 and at least one guide RNA (gRNA), such as those described in Example 6, are non-covalently complexed with a SWCNT preparation and tested on various plant cell preparations including plant cells in suspension culture, plant callus, plant embryos, intact or half seeds, and shoot apical meristem. Delivery to the plant callus, embryos, seeds, and meristem is by treatment with pressure, centrifugation, bombardment, microinjection, infiltration (e. g., with a syringe), or by direct application to the surface of the plant tissue. The gRNA is designed to target the endogenous plant gene phytoene desaturase (PDS) for silencing, where PDS silencing produces a visible phenotype (bleaching, or low/no chlorophyll).

In another experiment, a ribonucleoprotein (RNP), prepared by complexation of Cas9 nuclease and at least one guide RNA (gRNA), is non-covalently complexed with a SWCNT preparation and tested on various plant cell preparations including plant cells in suspension culture, plant callus, plant embryos, intact or half seeds, and shoot apical meristem. Delivery to the plant callus, embryos, seeds, and meristem is by treatment with pressure, centrifugation, bombardment, microinjection, infiltration (e. g., with a syringe), or by direct application to the surface of the plant tissue. The gRNA is designed to target the endogenous plant gene phytoene desaturase (PDS) for silencing, where PDS silencing produces a visible phenotype (bleaching, or low/no chlorophyll).

One of skill in the art would recognize that the above general compositions and procedures can be modified or combined with other reagents and treatments, such as those described in detail in the paragraphs following the heading "Delivery Methods and Delivery Agents". In addition, the single-walled carbon nanotubes (SWCNT) and modifications thereof prepared as described in Giraldo et al. (2014) *Nature Materials,* 13:400-409; Zhang et al. (2013) *Nature Nanotechnol.,* 8:959-968; Wong et al. (2016) *Nano Lett.,* 16:1161-1172; US Patent Application Publication US 2015/0047074; and International Patent Application PCT/US2015/050885 (published as WO 2016/044698) can be used to prepare complexes with other polypeptides or polynucleotides or a combination of polypeptides and polynucleotides (e. g., with one or more polypeptides or ribonucleoproteins including at least one functional domain selected from the group consisting of: transposase domains, integrase domains, recombinase domains, resolvase domains, invertase domains, protease domains, DNA methyltransferase domains, DNA hydroxylmethylase domains, DNA demethylase domains, histone acetylase domains, histone deacetylase domains, nuclease domains, repressor domains, activator domains, nuclear-localization signal domains, transcription-regulatory protein (or transcription complex recruiting) domains, cellular uptake activity associated domains, nucleic acid binding domains, antibody presentation domains, histone modifying enzymes, recruiter of histone modifying enzymes, inhibitor of histone modifying enzymes, histone methyltransferases, histone demethylases, histone kinases, histone phosphatases, histone ribosylases, histone deribosylases, histone ubiquitinases, histone deubiquitinases, histone biotinases, and histone tail proteases).

Example 45

This example illustrates genome editing in plants and further illustrates a method of delivering gene-editing effector molecules into a plant cell. More specifically, this non-limiting example describes introducing at least one double-strand break (DSB) in a genome in a plant cell or plant protoplast, by contacting the plant cell or plant protoplast with a composition including a sequence-specific nuclease complexed with a gold nanoparticle.

In embodiments, at least one double-strand break (DSB) is introduced in a genome in a plant cell or plant protoplast, by contacting the plant cell or plant protoplast with a composition that includes a charge-modified sequence-specific nuclease complexed to a charge-modified gold nanoparticle, wherein the complexation is non-covalent, e. g., through ionic or electrostatic interactions. In an embodiment, a sequence-specific nuclease having at least one region bearing a positive charge forms a complex with a negatively-charged gold particle; in another embodiment, a sequence-specific nuclease having at least one region bearing a negative charge forms a complex with a positively-charged gold particle. Any suitable method can be used for modifying the charge of the nuclease or the nanoparticle, for instance, through covalent modification to add functional groups, or non-covalent modification (e. g., by coating a nanoparticle with a cationic, anionic, or lipid coating). In embodiments, the sequence-specific nuclease is a type II Cas nuclease having at least one modification selected from the group consisting of: (a) modification at the N-terminus with at least one negatively charged moiety; (b) modification at the N-terminus with at least one moiety carrying a carboxylate functional group; (c) modification at the N-terminus with at least one glutamate residue, at least one aspartate residue, or a combination of glutamate and aspartate residues; (d) modification at the C-terminus with a localization signal, transit, or targeting peptide; (e) modification at the C-terminus with a nuclear localization signal (NLS), a chloroplast transit peptide (CTP), or a mitochondrial targeting peptide (MTP). In embodiments, the type II Cas nuclease is a Cas9 from *Streptococcus pyogenes* wherein the Cas9 is modified at the N-terminus with at least one negatively charged moiety and modified at the C-terminus with a nuclear localization signal (NLS), a chloroplast transit peptide (CTP), or a mitochondrial targeting peptide (MTP). In embodiments, the type II Cas nuclease is a Cas9 from

*Streptococcus pyogenes* wherein the Cas9 is modified at the N-terminus with a polyglutamate peptide and modified at the C-terminus with a nuclear localization signal (NLS). In embodiments, the gold nanoparticle has at least one modification selected from the group consisting of: (a) modification with positively charged moieties; (b) modification with at least one moiety carrying a positively charged amine; (c) modification with at least one polyamine; (d) modification with at least one lysine residue, at least one histidine residue, at least one arginine residue, at least one guanidine, or a combination thereof. Specific embodiments include those wherein: (a) the sequence-specific nuclease is a type II Cas nuclease modified at the N-terminus with at least one negatively charged moiety and modified at the C-terminus with a nuclear localization signal (NLS), a chloroplast transit peptide (CTP), or a mitochondrial targeting peptide (MTP); and the gold nanoparticle is modified with at least one positively charged moiety; (b) the type II Cas nuclease is a Cas9 from *Streptococcus pyogenes* modified at the N-terminus with a polyglutamate peptide and modified at the C-terminus with a nuclear localization signal (NLS); and the gold nanoparticle is modified with at least one at least one lysine residue, at least one histidine residue, at least one arginine residue, at least one guanidine, or a combination thereof; (c) the type II Cas nuclease is a Cas9 from *Streptococcus pyogenes* modified at the N-terminus with a polyglutamate peptide that includes at least 15 glutamate residues and modified at the C-terminus with a nuclear localization signal (NLS); and wherein the gold nanoparticle is modified with at least one at least one lysine residue, at least one histidine residue, at least one arginine residue, at least one guanidine, or a combination thereof. In a specific embodiment, at least one double-strand break (DSB) is introduced in a genome in a plant cell or plant protoplast, by contacting the plant cell or plant protoplast with a composition including a sequence-specific nuclease complexed with a gold nanoparticle, wherein the sequence-specific nuclease is a Cas9 from *Streptococcus pyogenes* modified at the N-terminus with a polyglutamate peptide that includes at least 15 glutamate residues and modified at the C-terminus with a nuclear localization signal (NLS); and wherein the gold nanoparticle is in the form of cationic arginine gold nanoparticles (ArgNPs), and wherein when the modified Cas9 and the ArgNPs are mixed, self-assembled nanoassemblies are formed as described in Mout et al. (2017) *ACS Nano*, doi:10.1021/acsnano.6b07600. Other embodiments contemplated herein include the various nanoparticle-protein complexes (e. g., amine-bearing nanoparticles complexed with carboxylate-bearing proteins) described in International Patent Application PCT/US2016/015711, published as International Patent Application Publication WO2016/123514, which claims priority to U.S. Provisional Patent Applications 62/109,389, 62/132,798, and 62/169,805, all of which patent applications are incorporated in their entirety by reference herein.

In embodiments, the sequence-specific nuclease is an RNA-guided DNA endonuclease, such as a type II Cas nuclease, and the composition further includes at least one guide RNA (gRNA) for an RNA-guided nuclease, or a DNA encoding a gRNA for an RNA-guided nuclease. The method effects the introduction of at least one double-strand break (DSB) in a genome in a plant cell or plant protoplast; in embodiments, the genome is that of the plant cell or plant protoplast; in embodiments, the genome is that of a nucleus, mitochondrion, plastid, or endosymbiont in the plant cell or plant protoplast. In embodiments, the at least one double-strand break (DSB) is introduced into coding sequence, non-coding sequence, or a combination of coding and non-coding sequence. In embodiments, the plant cell or plant protoplast is a plant cell in an intact plant or seedling or plantlet, a plant tissue, seed, embryo, meristem, germline cells, callus, or a suspension of plant cells or plant protoplasts.

In embodiments, at least one dsDNA molecule is also provided to the plant cell or plant protoplast, and is integrated at the site of at least one DSB or at the location where genomic sequence is deleted between two DSBs. Embodiments include those wherein: (a) the at least one DSB is two blunt-ended DSBs, resulting in deletion of genomic sequence between the two blunt-ended DSBs, and wherein the dsDNA molecule is blunt-ended and is integrated into the genome between the two blunt-ended DSBs; (b) the at least one DSB is two DSBs, wherein the first DSB is blunt-ended and the second DSB has an overhang, resulting in deletion of genomic sequence between the two DSBs, and wherein the dsDNA molecule is blunt-ended at one terminus and has an overhang on the other terminus, and is integrated into the genome between the two DSBs; (c) the at least one DSB is two DSBs, each having an overhang, resulting in deletion of genomic sequence between the two DSBs, and wherein the dsDNA molecule has an overhang at each terminus and is integrated into the genome between the two DSBs.

In a non-limiting example, self-assembled green fluorescent protein (GFP)/cationic arginine gold nanoparticles (ArgNPs), nanoassemblies are prepared as described in International Patent Application Publication WO2016/123514. The GFP/ArgNP nanoassemblies are delivered to maize protoplasts and to kale protoplasts prepared as described in Example 1, and to protoplasts prepared from the Black Mexican Sweet (BMS) maize cell line. Efficiency of transfection or delivery is assessed by fluorescence microscopy at time points after transfection (30 minutes, 1 hour, 3 hours, 6 hours, and overnight).

In a non-limiting example, self-assembled GFP/cationic arginine gold nanoparticles (ArgNPs), nanoassemblies are prepared as described in International Patent Application Publication WO2016/123514. The GFP/ArgNP nanoassemblies are co-incubated with plant cells in suspension culture. Efficiency of transfection or delivery across the plant cell wall is assessed by fluorescence microscopy at time points after transfection (30 minutes, 1 hour, 3 hours, 6 hours, and overnight).

In a non-limiting example, self-assembled GFP/cationic arginine gold nanoparticles (ArgNPs), nanoassemblies are prepared as described in International Patent Application Publication WO2016/123514. The GFP/ArgNP nanoassemblies are further prepared for Biolistics or particle bombardment and thus delivered to plant cells from suspension cultures transferred to semi-solid or solid media, as well as to rice embryogenic callus. Efficiency of transfection or delivery across the plant cell wall is assessed by fluorescence microscopy at time points after transfection (30 minutes, 1 hour, 3 hours, 6 hours, and overnight).

In a non-limiting example, self-assembled GFP/cationic arginine gold nanoparticles (ArgNPs), nanoassemblies are prepared as described in International Patent Application Publication WO2016/123514. The GFP/ArgNP nanoassemblies are delivered by infiltration (e. g., using mild positive pressure or negative pressure) into leaves of *Arabidopsis thaliana* plants. Efficiency of transfection or delivery across the plant cell wall is assessed by fluorescence microscopy at time points after transfection (30 minutes, 1 hour, 3 hours, 6 hours, and overnight).

In a non-limiting example, self-assembled Cas9/ArgNP nanoassemblies are prepared as described in Mout et al. (2017) *ACS Nano*, doi:10.1021/acsnano.6b07600 or alternatively as described in International Patent Application Publication WO2016/123514, by mixing a Cas9 from *Streptococcus pyogenes* modified at the N-terminus with a polyglutamate peptide that includes at least 15 glutamate residues and modified at the C-terminus with a nuclear localization signal (NLS) with cationic arginine gold nanoparticles (ArgNPs). The Cas9/ArgNP nanoassemblies are delivered to maize protoplasts or to kale protoplasts prepared as described in Example 1, and to protoplasts prepared from the Black Mexican Sweet (BMS) maize cell line. In one variation of the procedure, the Cas9/ArgNP nanoassemblies are co-delivered with at least one guide RNA (such as those described in Examples, 4, 5, 8, 9, 10, 12, and 13) to the protoplasts. In other variations of the procedure, the self-assembled Cas9/ArgNP nanoassemblies are prepared with at least one guide RNA to allow the modified Cas9 to form a ribonucleoprotein (RNP) either prior to or after formation of the nanoassemblies; the self-assembled RNP/ArgNP nanoassemblies are then delivered to the protoplasts. Efficiency of editing is assessed by any suitable method such as a heteroduplex cleavage assay or by sequencing, as described elsewhere in this disclosure.

In a non-limiting example, self-assembled Cas9/ArgNP nanoassemblies are prepared as described in Mout et al. (2017) *ACS Nano*, doi:10.1021/acsnano.6b07600 or alternatively as described in International Patent Application Publication WO2016/123514, by mixing a Cas9 from *Streptococcus pyogenes* modified at the N-terminus with a polyglutamate peptide that includes at least 15 glutamate residues and modified at the C-terminus with a nuclear localization signal (NLS) with cationic arginine gold nanoparticles (ArgNPs). The Cas9/ArgNP nanoassemblies are co-incubated with plant cells in suspension culture. In one variation of the procedure, the Cas9/ArgNP nanoassemblies are co-delivered with at least one guide RNA (such as those described in Examples, 4, 5, 8, 9, 10, 12, and 13) to the plant cells in suspension culture. In other variations of the procedure, the self-assembled Cas9/ArgNP nanoassemblies are prepared with at least one guide RNA to allow the modified Cas9 to form a ribonucleoprotein (RNP) either prior to or after formation of the nanoassemblies; the self-assembled RNP/ArgNP nanoassemblies are then delivered to the plant cells in suspension culture. Efficiency of editing is assessed by any suitable method such as a heteroduplex cleavage assay or by sequencing, as described elsewhere in this disclosure.

In a non-limiting example, self-assembled Cas9/ArgNP nanoassemblies are prepared as described in Mout et al. (2017) *ACS Nano*, doi:10.1021/acsnano.6b07600 or alternatively as described in International Patent Application Publication WO2016/123514, by mixing a Cas9 from *Streptococcus pyogenes* modified at the N-terminus with a polyglutamate peptide that includes at least 15 glutamate residues and modified at the C-terminus with a nuclear localization signal (NLS) with cationic arginine gold nanoparticles (ArgNPs). The Cas9/ArgNP nanoassemblies are further prepared for Biolistics or particle bombardment and thus delivered to plant cells from suspension cultures transferred to semi-solid or solid media, as well as to rice embryogenic callus. In one variation of the procedure, the Cas9/ArgNP nanoassemblies are co-delivered with at least one guide RNA (such as those described in Examples, 4, 5, 8, 9, 10, 12, and 13) to the plant cells or callus. In other variations of the procedure, the self-assembled Cas9/ArgNP nanoassemblies are prepared with at least one guide RNA to allow the modified Cas9 to form a ribonucleoprotein (RNP) either prior to or after formation of the nanoassemblies; the self-assembled RNP/ArgNP nanoassemblies are then delivered to the plant cells or callus. Efficiency of editing is assessed by any suitable method such as a heteroduplex cleavage assay or by sequencing, as described elsewhere in this disclosure.

In a non-limiting example, self-assembled Cas9/ArgNP nanoassemblies are prepared as described in Mout et al. (2017) *ACS Nano*, doi:10.1021/acsnano.6b07600 or alternatively as described in International Patent Application Publication WO2016/123514, by mixing a Cas9 from *Streptococcus pyogenes* modified at the N-terminus with a polyglutamate peptide that includes at least 15 glutamate residues and modified at the C-terminus with a nuclear localization signal (NLS) with cationic arginine gold nanoparticles (ArgNPs). The Cas9/ArgNP nanoassemblies are delivered by infiltration (e. g., using mild positive pressure or negative pressure) into leaves of *Arabidopsis thaliana* plants. In one variation of the procedure, the Cas9/ArgNP nanoassemblies are co-delivered with at least one guide RNA (such as those described in Examples, 4, 5, 8, 9, 10, 12, and 13) to the *Arabidopsis* leaves. In other variations of the procedure, the self-assembled Cas9/ArgNP nanoassemblies are prepared with at least one guide RNA to allow the modified Cas9 to form a ribonucleoprotein (RNP) either prior to or after formation of the nanoassemblies; the self-assembled RNP/ArgNP nanoassemblies are then delivered to the *Arabidopsis* leaves. Efficiency of editing is assessed by any suitable method such as a heteroduplex cleavage assay or by sequencing, as described elsewhere in this disclosure.

One of skill in the art would recognize that alternatives to the above compositions and procedures can be used to edit plant cells and intact plants, tissues, seeds, and callus. In embodiments, nanoassemblies are made using other sequence-specific nucleases (e. g., zinc-finger nucleases (ZFNs), transcription activator-like effector nucleases (TAL-effector nucleases or TALENs), Argonaute proteins, or a meganuclease or engineered meganuclease) which can be similarly charge-modified. In embodiments, nanoassemblies are made using other nanoparticles (e. g., nanoparticles made of materials such as carbon, silicon, silicon carbide, gold, tungsten, polymers, ceramics, iron oxide, or cobalt ferrite) which can be similarly charge-modified in order to form non-covalent complexes with the charge-modified sequence-specific nuclease. Similar nanoassemblies including other polypeptides (e. g., phosphatases, hydrolases, oxidoreductases, transferases, lyases, recombinases, polymerases, ligases, and isomerases) or polynucleotides or a combination of polypeptides and polynucleotides are made using similar charge modification methods to enable non-covalent complexation with charge-modified nanoparticles. For example, similar nanoassemblies are made by complexing charge-modified nanoparticles with one or more polypeptides or ribonucleoproteins including at least one functional domain selected from the group consisting of: transposase domains, integrase domains, recombinase domains, resolvase domains, invertase domains, protease domains, DNA methyltransferase domains, DNA hydroxylmethylase domains, DNA demethylase domains, histone acetylase domains, histone deacetylase domains, nuclease domains, repressor domains, activator domains, nuclear-localization signal domains, transcription-regulatory protein (or transcription complex recruiting) domains, cellular uptake activity associated domains, nucleic acid binding domains, antibody presentation domains, histone modifying enzymes, recruiter of histone modifying enzymes, inhibitor of histone modifying enzymes, histone methyltransferases, histone demethylases, histone kinases, histone phosphatases, histone ribosylases, histone deribosylases, histone ubiquitinases, histone deubiquitinases, histone biotinases, and histone tail proteases.

Example 46

This example illustrates a method of simultaneously effecting multiple modifications in a genome (i. e., multiple modifications of at least one sequence of interest in a genome), comprising introducing at least two DSBs into a genome by one or more nucleases, and, optionally, integrating at least one sequence encoded by a polynucleotide (such as a double-stranded DNA, a single-stranded DNA, a single-stranded DNA/RNA hybrid, or a double-stranded DNA/RNA hybrid) molecule at one or more DSBs. In embodiments, the modifications are effected in two or more sequences or genes of interest. More specifically, this non-limiting example illustrates using multiple different ribonucleoproteins (RNPs), wherein each RNP includes a guide RNA (gRNA) and a nuclease, to effect multiple DSBs in the genome of a monocot plant, and integration of a sequence encoded by a double-stranded DNA (dsDNA) donor molecule at the location of the multiple DSBs. In this example, two endogenous maize (*Zea mays*) sequences or genes of interest, Lc (see Examples 9, 12, 14, and 15) and ADH1 (see Example 4), were selected for modification by insertion of an expression-enhancing element at a DSB located in the promoter region of each gene.

The target genes selected for editing were the maize (*Zea mays*) alcohol dehydrogenase ADH1 (see www[dot]maizegdb[dot]org/gene_center/gene/GRMZM2G442658) with the partial genomic sequence of SEQ ID NO:21 (see Example 4), and the maize (*Zea mays*) Lc gene (see www[dot]maizegdb[dot]org/gene_center/gene/GRMZM5G822829) with the partial promoter sequence of SEQ ID NO:305 (see Example 9).

Ribonucleoproteins (RNPs) were prepared with Cas9 nuclease (Aldevron, Fargo, ND) and guide RNA complexes. Two guide RNA complexes were made with a crRNA and a tracrRNA (crRNAs and tracrRNA were purchased from Integrated DNA Technologies, Coralville, IA); the first guide RNA complex used a crRNA (ZmADH1-B) having the sequence of SEQ ID NO:23 (see Example 4) and the second guide RNA complex used a crRNA (ZmLc-Pro3) having the sequence of SEQ ID NO:334 (see Example 12). An expression-enhancing element in the form of the 34 base-pair dsDNA molecule "3×DR5" (with strands having the sequences of SEQ ID NO:306 and SEQ ID NO:307), which contains three copies of an auxin response element (SEQ ID NO:308), as described in Example 9, was purchased from Integrated DNA Technologies, Coralville, IA; each strand was phosphorylated on the 5' end and contained two phosphorothioate linkages at each terminus (i. e., the two linkages between the most distal three bases on either end of the strand).

Maize B73 protoplasts were prepared as described in, e. g., Examples 1, 4, 8, 9, 12, 15, and 16. Following the same general procedures described above (e. g., Examples 4, 8, 9, 12, 15, 16, and 20-23), the protoplasts were transfected with the RNPs (including the guide RNA complexes), with or without the dsDNA molecule "3×DR5". Transfections were carried out to deliver the same molar quantity of RNP for each genomic locus targetted for modification. Samples transfected with both the RNP containing the ZmADH1-B guide RNA complex and the RNP containing the ZmLc-Pro3 guide complex were thus transfected with twice the amount of nuclease (provided as RNP) as the samples that were transfected with only a single RNP (containing either the ZmADH1-B guide RNA complex or the ZmLc-Pro3 guide complex). Maize protoplasts treated with no nuclease, no guide RNA complex, and no dsDNA served as a null control. The transformed protoplasts were then incubated for about 48 hours in a maize incubation buffer including the herbicide 2, 4-dichlorophenoxyacetic acid ("2,4-D"), which has auxin-like properties. Next-generation sequencing (NGS) analysis was used for quantitation of editing efficiency and efficiency of integration of the "3×DR5" sequence into the maize genome. Results are provided in Table 28. Editing efficiency is expressed as the percentage of the total population of cells in which a DSB is correctly induced in the genome, i. e., wherein the DSB is correctly effected at the locus targeted by the crRNA. Insertion efficiency is expressed as the percentage of the total population of cells in which the "3×DR5" sequence is inserted at the correct locus in the genome, i. e., inserted at the locus targeted by the crRNA. Based on the NGS sequencing results, editing efficiency was nearly 60% (i. e., nearly 60% of the total cell population subjected to the editing treatment) for either of the RNPs used, whether or not the polynucleotide donor molecule was provided. Insertion efficiency was about 21% of the total cell population treated with the single ADH1-B RNP and the "3×DR5" donor (i. e., about 37% of the cells that contained a DSB at the correct locus also contained the "3×DR5" sequence), and about 25% of the total cell population treated with the single Lc-Pro3 RNP and the "3×DR5" donor (i. e., about 44% of the cells that contained a DSB at the correct locus also contained the "3×DR5" sequence). In the case of cells treated with both RNPs and the "3×DR5" donor, insertion efficiency was about 27% at the ADH1 locus and about 29% at the Lc locus. These data demonstrate a consistent over-all editing efficiency of approximately 60% of the total cell population and a consistent over-all insertion efficiency of approximately 25% of the total cell population (which is equivalent to approximately 40% of the cells that contained a DSB at the correct locus). The data indicate that simultaneous multiple modifications (integration of a dsDNA at a DSB in two different genes) in the maize protoplasts' genome was effected at about the same efficiency as a modification in one of the genes individually, as the editing and insertion efficiencies were approximately the same as those observed for modification carried out in an individual gene.

TABLE 28

| Treatment | | ADH1 | | | $L_c$ | | |
|---|---|---|---|---|---|---|---|
| RNP | Polynucleotide donor molecule | Editing efficiency | Insertion efficiency | DSB with 3xDR5 insertion | Editing efficiency | Insertion efficiency | DSB with 3xDR5 insertion |
| Null | none | 0 | 0 | 0 | 0 | 0 | 0 |
| ADH1-B | 3xDR5 | 57.17 | 20.94 | 36.6% | 0 | 0 | 0 |
| Lc-Pro3 | 3xDR5 | 0 | 0 | 0 | 59.74 | 24.83 | 41.6% |
| ADH1-B + Lc-Pro3 | none | 55.83 | 0 | 0 | 65.24 | 0 | 0 |
| ADH1-B + Lc-Pro3 | 3xDR5 | 61.58 | 27.13 | 44.1% | 67.73 | 29.31 | 43.3% |

One of skill in the art would recognize that simultaneously effecting multiple DSBs in a genome (e. g., effecting multiple DSBs in a sequence of interest or effecting at least one DSB in each of two or more sequences of interest) can be achieved with alternative methods (e. g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the approach described herein include use of any of these methods for simultaneously effecting multiple DSBs in a genome, and, optionally, integrating a sequence encoded by at least one polynucleotide molecule at one or more DSBs.

Additional experiments can be carried out with the same editing reagents in a plant/plant tissue, e. g., using microinjection or biolistics as described in Examples 49-51 and 54. A one-step delivery method can be used to achieve multiplexed edits (multiple modifications) with the same polynucleotide donor to target different genes. For insertion of different polynucleotide donor sequences using the same nuclease (e. g. Cas9 or Cpf1), sequential steps for delivery of different combinations of reagents with a 30 min to 48 h gap between the steps can be used. For insertion of different polynucleotide donor sequences using different nucleases (e. g. Cas9 and Cpf1), a one-step delivery method can be used, for example, with a blunt-ended double-stranded polynucleotide donor for Cas9 and a double-stranded polynucleotide donor containing overhangs for Cpf1.

Example 47

As described herein, microinjection techniques can be used as an alternative to the methods for delivering effector molecules or targeting agents to protoplasts as described, e.g., in certain Examples above. Microinjection is typically used to target specific cells in isolated embryo sacs or the shoot apical meristem. See, e.g., U.S. Pat. No. 6,300,543, incorporated by reference herein. For example, an injector attached to a Narashige manipulator on a dissecting microscope is adequate because the cells to be microinjected are relatively large (e.g., the egg/synergids/zygote and the central cell). For smaller cells, such as those of the embryo, a compound, inverted microscope with an attached Narashige manipulator is used. Injection pipette diameter and bevel are also important. Use a high quality pipette puller and beveler to prepare needles with adequate strength, flexibility and pore diameter. These will vary depending on the cargo being delivered to cells. The volume of fluid to be microinjected must be exceedingly small and must be carefully controlled. An Eppendorf Transjector yields consistent results (Laurie et al., 1999).

The genetic cargo can be RNA, DNA, protein or a combination thereof. The cargo can be designed to change one aspect of the target genome or many. The concentration of each cargo component will vary depending on the nature of the manipulation. Typical cargo volumes can vary from 2-20 nanoliters. After microinjection the embryos are maintained on an appropriate media alone (e.g., sterile MS medium with 10% sucrose) or supplemented with a feeder culture. Plantlets are transferred to fresh MS media every two weeks and to larger containers as they grow. Plantlets with a well-developed root system are transferred to soil and maintained in high-humidity for 5 days to acclimate. Plants are gradually exposed to the air and cultivated to reproductive maturity.

Microinjection of corn embryos: The cobs and tassels are immediately bagged when they appear to prevent pollination. To obtain zygote-containing maize embryo sacs, hand pollination of silks is performed when the silks are 6-10 cm long, the pollinated ears are bagged and tassels removed, and then ears are harvested at 16 hours later. After removing husks and silks, the cobs are cut transversely into 3 cm segments. The segments are surface sterilized in 70% ethanol and then rinsed in sterile distilled, deionized water. Ovaries are then removed and prepared for sectioning. The initial preparation may include mechanical removal of the ovarian wall, but this may not be required.

Once the ovaries have been removed, they are attached to a Vibratome sectioning block, an instrument designed to produce histological sections without chemical fixation or embedment. The critical attachment step is accomplished using a commercial adhesive such as Locktite cement. Normally 2-3 pairs of ovaries are attached on each sterile sectioning block with the adaxial ovarian surface facing upwards and perpendicular to the longitudinal axis of the rectangular sectioning block (Laurie et al., *In Vitro Cell Dev Biol.,* 35: 320-325, 1999). Ovarian sections (or "nucellar slabs") are obtained at a thickness of 200 to 400 micrometers. Ideal section thickness is 200 micrometers. The embryo sac will remain viable if it is not cut. The sections are collected with fine forceps and evaluated on a dissecting microscope with basal illumination. Sections with an intact embryo sac are placed on semi-solid Murashige-Skoog (MS) culture medium (Campenot et al., 1992) containing 15% sucrose and 0.1 mg/L benzylaminopurine. Sterile Petriplates containing semi-solid MS medium and nucellar slabs are then placed in an incubator maintained at 26° C. These can be monitored visually by removing plates from the incubator and examining the nucellar slabs with a dissecting microscope in a laminar flow hood.

Microinjection of soy embryonic axes: Mature soybean seeds are surface sterilized using chlorine gas. The gas is cleared by air flow in a sterile, laminar flow hood. Seeds are wetted with 70% ethanol for 30 seconds and rinsed with sterile distilled, deionized water then incubated in sterile distilled, deionized water for 30 minutes to 12 hours. The embryonic axes are carefully removed from the cotyledons and placed in MS media with the radicle oriented downwards and the apex exposed to air. The embryonic leaves are carefully removed with fine tweezers to expose the shoot apical meristem.

Example 48

This example illustrates increasing gene expression by integration of a transcription factor binding site. More specifically, this example illustrates insertion of the E2F binding site in the Lc (Gene ID: GRMZM5G822829) promoter.

The ZmE2F donor polynucleotide included four copies of an E2F binding site. The sequence of the E2F binding site monomer is TTTCCCGC (SEQ ID NO:201). The ZmE2F donor polynucleotide dsDNA had a first strand sequence of TTTCCCGCTTTCCCGCTTTCCCGCTTTCCCGC (SEQ ID NO:433) and a second strand with the sequence GCGGGAAAGCGGGAAAGCGGGAAAGCGGGAAA (SEQ ID NO:434); each strand was phosphorylated on the 5' end and contained two phosphorothioate linkages at the 5' terminus (i. e., the two linkages between the most distal three bases at the 5' end of the strand). The crRNA of LcPro-3 had a sequence of CUCCAAGUGACCGAGCAAGAGUUUUAGAGCUAUGCU (SEQ ID NO: 334). In some conditions, we also overexpressed ZmE2F4 by co-transfection of HBT-ZmE2F4 (a vector containing the coding sequence of ZmE2F4 (see www[dot]maizegdb[dot]org/gene_center/gene/Zm00001d016737) driven by the 35S promoter). The coding sequence of ZmE2F4 is provided as SEQ ID NO:435.

Maize protoplasts were prepared as described as in Example 1. Preparation of reagents, gene editing procedures, and detection of gene modifications were carried out using procedures similar to those described in Examples 20-23.

Four 10 cm plates were pre-coated with 5% calf serum. The gRNA-tracrRNA duplex was prepared by mixing 45 μL of ZmLcPro3 with 45 μL of tracrRNA and heating the mixture to 95° C. for 5 minutes. The mixture was then allowed to cool to room temperature. The E2F binding site was prepared by mixing 100 μL of ZmE2F_BS-F and 100 μL ZmE2F_BS-R and heating the mixture to 95° C. for 5 minutes. The mixture was then allowed to cool to room temperature. Before transfection 15 μL Cas9 protein was added to the duplexing mix and incubated at room temperature for 5 minutes. The setup of reagents is shown in Table 29.

TABLE 29

| # | Name | RNP | Salmon Sperm | E2F BS | ZmE2F | Buffer |
|---|---|---|---|---|---|---|
| 1 | RNP only | 35 | 2 | 0 | 0 | 100 |
| 2 | RNP + binding site | 35 | 2 | 50 | 0 | 50 |
| 3 | RNP + binding site + E2F | 35 | 2 | 50 | 50 | 0 |
| 4 | Empty | 0 | 0 | 0 | 0 | 137 |

Maize B73 protoplasts were prepared from etiolated leaves. 1 mL of cells each and the reagents as prepared in Table 29 were added to four 15 mL round bottom tubes. 1.2 mL of PEG was added each tube. The content in each tube was mixed and incubated at RT for 5 minutes. The reaction was stopped with 5 mL of maize washing buffer. The cells were washed by centrifugation and resuspension. The maize protoplast cells resuspended in 6 mL of maize washing buffer were plated onto 10 cm plate pre-coated with calf serum and was incubated at 37° C. for 30 min to 1 hour. The extended incubation of cells was under 27° C. The cells were harvested 48 hours after transfection for qPCR readout.

The relative expression of Lc gene in maize protoplasts transfected with different reaction mixtures is show in Table 30.

TABLE 30

| Sample # | Sample Name | Avg Relative Expression | STDEV |
|---|---|---|---|
| 1 | RNP only | 1.60 | 0.11 |
| 2 | RNP + binding site | 3.54 | 0.04 |
| 3 | RNP + binding site + E2F | 8.78 | 0.13 |
| 4 | Empty | 1.00 | 0.05 |

Induction of Lc expression was observed with the insertion of the E2F binding site only. However, co-transfection of the transcription factor E2F4 led to additional increase of the expression of Lc gene.

To confirm E2F transcription factors were expressed in leaf protoplast cells and the expression of ZmE2F4 from transfected plasmid HBT-ZmE2F4, qPCR was conducted with the primers specifically amplifying ZmE2F4. The relative expression levels of ZmE2F4 are listed in Table 31.

TABLE 31

| | Sample | Relative expression* | SD |
|---|---|---|---|
| 1 | Empty | 0.18 | 0.01 |
| 2 | RNP only | 0.16 | 0.01 |
| 3 | RNP + binding site | 0.15 | 0.01 |
| 4 | RNP + binding site + E2F4 | 0.61 | 0.08 |

*Comparison of the transcripts level of E2F4 to that of the house keeping gene Actin.

This further indicates that the induction of Lc with E2F binding site insertion in the promoter region was due to the existence of E2F transcription factors in protoplast cells and overexpression of ZmE2F4 enhanced the expression of Lc by binding to the E2F binding sites inserted in the promoter.

Example 49

This example illustrates biolistic delivery of effector molecules into the maize embryo. More specifically, this example illustrates biolistic delivery of anthocyanin regulatory Lc editing reagents to the maize B73 inbred.

RNA guided nuclease (SpCas9), gene specific guide RNA (gRNA), ZmLc Pro-3 (SEQ ID NO:334) and double-stranded oligonucleotide 3×DR5 (with strands having the sequences of SEQ ID NO:306 and SEQ ID NO:307) were used as editing reagents for oligo insertion to increase the expression of the maize Lc gene which is responsible for tissue specific anthocyanin biosynthesis. Reagents were delivered to immature (11DAP) zygotic embryo scutellum cells of maize inbred B73. The gRNA used was previously validated in vivo in protoplasts.

Sample preparation: Immature (11 days after pollination) ears of maize inbred B73 were surface sterilized in a laminar flow cabinet with 6% sodium hypochlorite and one drop of Tween-20® for 20 minutes and rinsed 3 times with sterile water. To excise an immature zygotic embryo (IZE), a scalpel blade was used to trim off about 3 mm from the tip of the kernel crown. Next, a micro spatula was inserted between the endosperm and pericarp to pop the endosperm out of the seed coat and gently nudge the IZE (nested in the endosperm) onto the spatula tip. The embryo (approximately 1.8-2.0 mm long) was immediately transferred to filter paper placed on embryo pre-culture medium and incubated at 26° C.±2° C. in a dark growth incubator for 2-3 days prior to bombardment.

Gold microparticle coating with RNP: Complexed RNP (Cas9 and sgRNA ZmLc Pro-3) were co-delivered with a double-stranded oligonucleotides (3×DR5) to scutella cells in maize B73 inbred immature zygotic embryos using 1 μm gold microparticle carriers. Pre-sterilized (100% ethanol wash for 20 minutes followed by ice cold sterile-water wash) 1 μm gold microparticles stored at −20° C. in 1× aliquot were thawed at 4° C. and sonicated for 30 seconds. The gold coating reaction was performed by adding 10 μL RNP complex comprising 7 μL CRISPR gRNA duplex (crRNA and tracrRNA) to 3 μL Cas9 (Aldevron) and 8 μL (100 uM) double-stranded donor oligonucleotides (3×DR5) and allowed to incubate for 6 minutes at room temperature. The reagents were added to a single 50 μL1× gold suspension and mixed gently by pipetting up and down. Next, 50 μL Calcium Chloride (2.5M) and 20 μL Spermidine (0.2M) were added to the gold-RNP mixture and immediately placed on a shaking vortex at a speed of 1000 rpm for at least 5 minutes. The mixture was allowed to settle for 5-10 minutes, then centrifuged briefly for 30 seconds at 2900 rpm and followed by removal of supernatant and resuspension of RNP coated gold pellet in 250 μL ice cold 100% ethanol. The gold particle mixture was allowed to settle for 5 minutes and centrifuged as described above. The supernatant was carefully removed, and the pellet was resuspended in 80 μL ice cold ethanol. The RNP coated gold suspension was placed on a vortex shaker at a low speed (300 rpm) to prevent aggregation of the gold particles prior to loading onto the microcarrier.

RNP Bombardment: The microcarrier was soaked in 70% ethanol for 10 minutes and air-dried for at least 3 hours or until completely dried for sterilization. The RNP coated gold coated particles were loaded (10 μL/shot) onto a sterilized microcarrier and allowed to dry for about 5-10 minutes. The macrocarrier assembly, rupture disk holder and sample plates were loaded into the gun chamber, and secured according to the manufactures instructions for the PDS 1000/He Biolistic® particle delivery system (Bio-Rad, Hercules, CA). To prepare the cells for bombardment, immature embryos were transferred to an osmotic medium (with the scutellum side up) containing 37 g/L each of mannitol and sorbitol for a duration of 4 hours prior to bombardment. The following gene gun settings were used for gold particle delivery: sample target distance: 6 cm, vacuum pressure: 29 mmHg, rupture disc: 900 psi. Bombarded samples were transferred to embryo pre-culture media and placed in a dark incubator. Bombarded embryos were sampled to for genotype the edited sites 10 days after bombardment.

DNA extraction and T7E1 assay: Genomic DNA was extracted from bombarded B73 immature embryos using a modified CTAB DNA miniprep method. DNA concentration and quality were assessed using a nanodrop spectrophotometer and gel electrophoresis on 1% TAE agarose. The genomic DNA was analyzed by T7E1 assay and amplicon sequencing. The details of the T7E1 assay and amplicon sequencing are as described in the preceding Examples.

35.2% of whole reads were edited and 12.5% of whole reads showed an insertion, with 6.7% in forward direction and 5.8% in reverse direction. 0.87% of whole reads showed a perfect insertion in forward direction without unintended changes around the cut site and 1.81% of whole reads showed a perfect insertion in the reverse direction without unintended change around the cut site.

Example 50

The following describes direct delivery by microinjection of effector molecules (e. g., at least one crRNA or sgRNA or a polynucleotide encoding at least one crRNA or sgRNA or an RNA-guided nuclease or a polynucleotide that encodes the RNA-guided nuclease) directly into maize (*Zea mays*) zygotes; the embryos are isolated and allowed to shoot, and the resulting maize plants containing the desired genomic edit or alteration of the target nucleotide sequence are subsequently identified. The methods described do not employ the common techniques of bacterially mediated transformation (e. g., by *Agrobacterium* sp.) or biolistics.

A non-limiting example of a microinjection protocol utilizes maize B73 fertilized cobs (ears) (collected 1 day after pollination). All steps of this protocol are performed under a laminal flow hood. Husks and silks are removed from the cobs. The cobs are transversely cut into approximately 3-centimeter segments with the top and bottom two centimeters of each cob discarded. The segments are surface-sterilized for 10 minutes with 70% ethanol followed by three one minute washes in distilled, sterile water.

Ethanol-sterilized fifty-milliliter tube caps are used as specimen mounting blocks, to which two rows of 4-5 ovaries each cut from the prepared cob slices are glued with a thin layer of fast-acting adhesive (e. g., Loctite Control Gel Premium Super Glue); one row of ovaries is mounted facing the other pair's basal end. The mounted ovaries are attached to a modified specimen tray of a Vibratome (PELCO easiSlicer™, Ted Pella, Inc.) with the stylar ends facing the blade. Two-hundred twenty micrometer sections are sliced from the ovary surface. Sections that contain embryo sacs are collected for microinjection on MMIM (modified maize induction medium). To prepare MMIM, 2.2 g Murashige and Skoog (MS) medium, 50 g sucrose, 10 g mannitol, and 2.5 g Phytagel are dissolved in 500 milliliters water and adjusted to pH 5.8; after autoclaving, indole acetic acid or 1-naphthaleneacetic acid (0.1 milligrams/liter final concentration), 6-benzylaminopurine (0.5 milligrams/liter final concentration), and vitamins (1× final concentration) are added just prior to polymerization.

A ribonucleoprotein (RNP) complex is prepared with Cas9 nuclease and crRNA/tracrRNA or sgRNA as described elsewhere in this application. For delivery by microinjection, a microinjection mixture containing the RNP complex is prepared by taking a volume (e. g., 30 microliters) of the RNP solution and adding sufficient 10×Cas9 reaction buffer (20 millimolar HEPES, 1 molar NaCl, 50 millimolar MgCl2, 1 millimolar EDTA) to yield a 1× buffer concentration in the final mixture. The microinjection mixture is centrifuged through a Millipore filter (UFC30VV25) at 13,000 rpm for 10 minutes at room temperature.

For microinjection of the maize zygotes, 2.5 microliters of the filtered injection mix are loaded into a borosilicate needle (catalogue number G100F-4, Warner Instruments, Hamden, CT), previously pulled with a P1000 micropipette puller (Sutter Instrument, Novato, CA) with the following settings: Heat: Ramp-20; Pull: 140; Velocity: 70; Delay: 200; Pressure: 510; Ramp: 499. The needle is opened with a micropipette beveller (BV-10, Sutter Instrument, Novato, CA) with an angle of 35 degrees. The egg apparatus is visualized with basal illumination using a fluorescence stereoscope (model SMZ18, Nikon, Tokyo, Japan). The injection mix is injected into the egg apparatus using a FemtoJet 4i with a PatchMan micromanipulator (both from Eppendorf, Hauppauge, NY). Embryo sacs are recovered in MMIM medium. The embryos are kept in the dark at 26 degrees Celsius until shoots form, and then kept in the light at 26 degrees Celsius. Shoots thus produced are optionally grown under selection conditions if selection by expression of the predicted phenotype (e. g., resistance to selection pressure) is desired. Surviving maize seedlings are grown to maturity and the presence of the intended genome modification is determined by molecular analysis of the resulting seeds and seedlings.

One of skill in the art would recognize that there are alternative reagents and compositions including such reagents that are useful for introducing alterations or edits into the genome (e. g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the microinjection technique described herein include use of any of these reagents. Similarly, the microinjection technique described herein is generally applicable to any plant cell of sufficient size to permit microinjection (e. g., germline cells or cells that develop into germline cells, egg cells, zygote cells, embryo cells, meristematic cells), and of any plant species (e. g., alfalfa (*Medicago sativa*), almonds (*Prunus dulcis*), apples (*Malus* x *domestica*), apricots (*Prunus armeniaca, P. brigantine, P. mandshurica, P. mume, P. sibirica*), *asparagus* (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (Cider *arietinum*), chicory (*Cichorium intybus*), chili peppers and other *capsicum* peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), *eucalyptus* (*Eucalyptus* spp.), flax (*Linum usitatissumum* L.), geraniums (*Pelargonium* spp.), grapefruit (*Citrus* x *paradisi*), grapes (*Vitus* spp.) including wine grapes (*Vitus vinifera*), guava (*Psidium guajava*), hemp and *cannabis* (*Cannabis sativa* and *Cannabis* spp.), hops (*Humulus lupulus*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), *papaya* (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria* x *ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), and yams (*Discorea* spp.)). Non-limiting embodiments include microinjection delivery of DNA or RNP editing reagents to egg cells, zygote cells, embryo cells, and meristematic cells of maize, rice, wheat, barley, rye, millet, sorghum, soybean, cotton, brassicas (including oilseed brassicas and sugar beet), solanaceous plants (including tomato, pepper, potato, and eggplant), strawberry, banana, plantain, citrus fruits, coffee, cacao, and sugarcanes.

Example 51

The following describes direct delivery of effector molecules (e. g., at least one crRNA or sgRNA or a polynucleotide encoding at least one crRNA or sgRNA or an RNA-guided nuclease or a polynucleotide that encodes the RNA-guided nuclease) by gold microparticle bombardment directly into germline cells of excised soybean (*Glycine max*) embryos.

In a non-limiting protocol, sgRNA and nuclease vectors are delivered by gold microparticle bombardment to non-epidermal cells in soybean embryonic axes. Mature, dry soybean seeds (cv. Williams 82) are surface-sterilized by holding overnight in an enclosed chamber with a beaker containing 100 milliliters 5% sodium hypochlorite solution to which 4 milliliters concentrated (12N) hydrochloric acid were freshly added. The sterilized seeds are imbibed in sterile water for 2-20 hours. Seeds are splitted by inserting a razor blade into the hilum leaving the embryonic axes intact. The pericarp is removed and the tip of the radicle excised. The leaf primordia and a thin layer of the shoot apical meristems are excised with a scalpel with the aid of a dissecting microscope. Prepared explants are placed on pre-bombardment medium ("Recipe X" with the addition of 2 milligrams/liter 6-benzylaminopurine) for 2-3 days in the dark at 26 (plus or minus 2) degrees Celsius. In an alternative protocol, explants are placed on osmoticum medium ("Recipe X" modified by the addition of 36.8 grams/liter sorbitol and 36.8 grams/liter mannitol) for four hours prior to bombardment. To make a 1-liter quantity of "Recipe X" medium, mix 4.43 g MS salts with B5 vitamins, 10 milliliter 0.2 molar MES hydrate stock solution, 100 milligrams myo-inositol, 30 grams sucrose, 8 grams Oxoid agar (Remel, Inc. Lenexa, KS) and bring volume to 1 liter with water. Adjust pH to 5.8 before adding agar and autoclaving. Add 6-benzylaminopurine (BA) after cooling to about 50 degrees Celsius.

Gold microparticles are prepared as follows. In the following non-limiting embodiment, 1.0 micrometer gold microparticles are used (Bio-Rad, Hercules, CA). (In other protocols, gold microparticles of other sizes (e. g., 0.6 or 1.6 micrometer) are also useful.) Approximately 15-20 milligrams of gold microparticles are transferred to sterile 1.5 milliliter microcentrifuge tubes. Cold absolute ethanol (500 microliters) is added to each tube, and the tubes are placed in the ultrasonicating water bath for 15 seconds. Gold microparticles are allowed to settle ~10-30 minutes followed by pelleting by centrifugation for 1 minute at 3000 rpm. The supernatant is removed and the pellet is carefully rinsed with 1 milliliter ice-cold sterile water. The tubes are tapped gently to disturb the pellets, which are then allowed to settle again. The rinse step is repeated two more times. After the third rinse, the microparticles are pelleted 15 seconds at 5000 rpm, and the final supernatant removed. The pellet is resuspended in 500 microliters sterile water to form a "IX" concentration, placed in the ultrasonicating water bath for 15 seconds, and immediately after is vortexed. Aliquots of 50 microliters are transferred to 1.5-milliliter microcentrifuge tubes, with the original preparation continually vortexed during the transfers. The 1× aliquots are stored at −20 degrees Celsius.

Prior to precipitation of DNA on gold microparticles, soy explants are embedded in pre-bombardment medium with the shoot apical meristem arranged parallel with the medium's surface and directly facing the trajectory of the coated microparticles. Approximately, 20-40 explants are placed in the center of the plate, corresponding to the ~3.5-centimeter diameter circle of the tissue platform (Bio-Rad, Hercules, CA). A tube of 1× prepared gold is used for bombardment of three media plates of soy explants. Prepared 1× tubes are thawed on ice, placed in the ultrasonicating water bath for 15 seconds, and then centrifuged at 2000 rpm for 2 minutes. The supernatant is removed and the gold microparticles are resuspended in either 25 microliters DNA (1 microgram/microliter) solution or 25 microliters sterile water as a control. The following is added in order, vortexing between each addition: 220 microliters sterile water, 250 microliters 2.5 molar calcium chloride, and 50 microliters 0.1 molar spermidine. The tubes are placed on ice for 5 minutes, vortexed for ~2 minutes at room temperature, and then centrifuged at 500 rpm for 5 minutes. The supernatant is removed and the pellet is resuspended in 600 microliters absolute ethanol. The tubes are centrifuged for 1 minute at 14000 rpm. The supernatant is removed and the pellet is resuspended in 36 microliters absolute ethanol. (To conserve the amount of gold used, the pellet can be resuspended in about 90 microliters absolute ethanol, and about 10 microliters or about 444 nanograms gold used for each shot for 9 shots.) DNA-coated gold (11 microliters) is placed in the center of autoclaved macrocarriers (Bio-Rad, Hercules, CA) and allowed to dry for approximately 5-10 minutes. The PDS-1000/He Biolistic® particle delivery system (Bio-Rad, Hercules, CA) is assembled. The rupture discs (1,100 psi rupture discs, Bio-Rad, Hercules, CA; 900 or 650 psi rupture discs can also be used) are dipped in 70% ethanol to sterilize, placed in the retaining cap, and tightened with the manufacturer's supplied wrench. The autoclaved stopping screen is placed in the macrocarrier assembly followed by the DNA-coated gold macrocarrier. The system is assembled as directed in the manual. The distance used from stopping screen to soy explants is 6 centimeters. The gun is fired when the vacuum in the chamber reaches 27-28 inches of Hg.

After bombardment, explants are transferred to Recipe X medium containing 0.5 milligrams/liter 6-benzylaminopurine. Plates with bombarded explants are placed in the dark for 2-4 days at 26 (plus or minus 2) degrees Celsius, then moved to a 16-hour light (75 micromoles)/8-hour dark light regime at 26 (plus or minus 2) degrees Celsius for several days to weeks depending on assay performed. For non-destructive assays, soybean shoots are sampled and explants moved to fresh Recipe X medium containing 0.5 milligrams/liter 6-benzylaminopurine. When shoots reach about 2-3 centimeters in length, explants are transferred to shoot elongation media ("Recipe Y"). To make 1 liter of "Recipe Y" medium, mix 4.43 grams MS salts with B5 vitamins, 0.59 grams MES hydrate, and 30 grams sucrose in 1 liter water, adjust pH to 5.7, and add 3 grams Phytagel. Autoclave 35 minutes on liquid cycle and cool to 50 degrees Celsius. In a laminar flow hood, add to 1 liter of cooled medium 0.5 milligrams gibberellic acid (as a premade stock, G362, PhytoTechnologies Laboratories, Shawnee Mission, KS), 500 microliters 50 milligrams/milliliter asparagine stock solution, 5 milligrams glutamine, 400 microliters indole acetic acid (as a 1 milligram/milliliter stock), and 1 milligram trans-zeatin riboside. Pour 100 milliliters per phytatray and allow to cool; store at room temperature. After approximately two weeks of shoot elongation, shoots are of sufficient size to transfer to Jiffy peat pellets, and are later transplanted to soilless mix in pots for maturation, observation of phenotype, and analysis.

In another non-limiting protocol, a ribonucleoprotein (RNP) complex is delivered by gold microparticle bombardment to shoot apical meristem cells. A ribonucleoprotein (RNP) complex is prepared with Cas9 nuclease and crRNA/tracrRNA or sgRNA as described elsewhere in this application. In an example, an RNP preparation is made with 6 microliters of 100 micromolar crRNA annealed with 6 microliters of 100 micromolar tracrRNA, and complexed with 20 micrograms Cas9 nuclease. The RNP preparation was added to a tube of 1× gold microparticles in 50 microliters water, mixed gently, and used at a rate of 14 microliters RNP-coated gold per macrocarrier. Sixty microliters 2.5 molar calcium chloride and 20 microliters 0.1 molar spermidine are optionally added, with vortexing, to this preparation. (To conserve the amount of gold used, one tube of ~1.5 mg gold coated with 5 micrograms Cas9 complexed with 2.5 micrograms crRNA-tracrRNA complex is sufficient for 9 shots.) The samples are dried in Petri dishes with Drierite desiccant (W. A. Hammond DRIERITE Co., LTD, Xenia, OH) for 1-2 hours. The rest of the bombardment procedure is similar to that described above for the DNA-coated gold microparticles. The shoot apical meristems of 48 soybean embryonic axes were sampled 5 days after bombardment and analysed for the presence of edits of the target gene by any of various molecular assays, including, e. g., T7E1 assay, fragment analyzer assay, Sanger sequencing, and enrichment of edited amplicons by restriction digest and NGS amplicon sequencing.

One of skill in the art would recognize that there are alternative reagents and compositions (e. g., DNA encoding a nuclease or RNPs including a nuclease) including such reagents that are useful for introducing alterations or edits into the genome (e. g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the bombardment technique described herein include use of any of these reagents or compositions. Similarly, the bombardment technique described herein is generally applicable to any plant part, plant tissue, or whole plant, seed, seedling, or embryo (e. g., excised embryos, callus, leaf or other plant part, meristematic tissue), and of any plant species (e. g., alfalfa (*Medicago sativa*), almonds (*Prunus dulcis*), apples (*Malus* x *domestica*), apricots (*Prunus armeniaca, P. brigantine, P. mandshurica, P. mume, P. sibirica*), *asparagus* (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other *capsicum* peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), *eucalyptus* (*Eucalyptus* spp.), flax (*Linum usitatissumum* L.), geraniums (*Pelargonium* spp.), grapefruit (*Citrus* x *paradisi*), grapes (*Vitus* spp.) including wine grapes (*Vitus vinfera*), guava (*Psidium guajava*), hemp and *cannabis* (*Cannabis sativa* and *Cannabis* spp.), hops (*Humulus lupulus*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), *papaya* (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria* x *ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), and yams (*Discorea* spp.)). Non-limiting embodiments include microinjection delivery of DNA or RNP editing reagents to egg cells, zygote cells, embryo cells, and meristematic cells of maize, rice, wheat, barley, rye, millet, sorghum, soybean, cotton, brassicas (including oilseed brassicas and sugar beet), solanaceous plants (including tomato, pepper, potato, and eggplant), strawberry, banana, plantain, citrus fruits, coffee, cacao, and sugarcanes.

Example 52

This example demonstrates improving clonally propagated monocots. Sugarcane is used as an exemplary plant.

Source of plant material: The preparation of plant material essentially follows Ramgareeb et al (2010) *Plant Cell Tiss Organ Cult,* 100:175-181. Stalk material is cut into single budded nodes (SBN) and incubated in a hot water bath (50° C.) containing the fungicide Eria (0.5 mL $L^{-1}$; Syngenta) for 40 minutes. Following hot water treatment (HWT), the SBN are planted in seedling trays (L×W×H: 47×34×6 cm) filled with potting soil mix (3 parts commercial potting soil, 1 part river sand, 1 part vermiculite). Trays are incubated in a greenhouse for 6-8 weeks (25:20° C.; 16:8 hour day:night). Plants are watered twice daily. Shoots resulting from the development of SBN are referred to as node shoots. These shoots are harvested for meristem excision when the first node is observed.

Apical meristem preparation: Apical meristem excision is from either mature field grown stalks or the node shoot. The leaf roll and stem consisting of at least the first visible node are cut from source material. Stalks are surface sterilized with 99% (v/v) ethanol, outer leaves are removed and the leaf roll shortened to contain the first node above which the shoot apical meristem is situated (~4 cm). Broad tipped, long forceps are used to hold below the first node while outer whorls of the leaf roll are aseptically removed using a No. 23 surgical blade in a Petri dish containing 1 mL of liquid nutrient medium (MS salts and vitamins (Murashige and Skoog (1962) *Physiol Plant,* 15:473-497), 20 g $L^{-1}$ sucrose). When the leaf roll is ~5 mm in diameter, a No. 10 surgical blade is used to dissect away the outer leaves under a stereo microscope (e.g. Nikon SMZ1500). Meristems of different lengths (0.5-10 mm) are dissected from both explant sources.

Excised meristems are cultured on an initiation medium for 1 week (MS salts and vitamins (Murashige and Skoog (1962) *Physiol Plant,* 15:473-497), 0.1 mg $L^{-1}$ benzyl aminopurine (BAP), 0.015 mg $L^{-1}$ kinetin (KIN), 4 g $L^{-1}$ activated charcoal, 20 g $L^{-1}$ sucrose (from Sigma-Aldrich*, St Louis, MO) all added pre-sterilization, then adjusted to pH 4.5 (with 1 M KOH or 1 M HCl) and mixed with 8 g $L^{-1}$ agar (Plant Tissue Culture Agar, Lab M Ltd., Lancashire, UK) then autoclaved at 121° C. for 20 minutes) in the dark at 28° C. This is followed by culturing on semi-solid shoot multiplication medium (same as initiation medium but with 1 mg $L^{-1}$ methylene blue and without activated charcoal) in a growth room at 28° C. with a 16 hour photoperiod. After 4-6 weeks, once shoot clusters are established, these are subcultured every 2 weeks in Magenta™ vessels (GA-7, Sigma-Aldrich® or equivalent) containing 60-100 mL of liquid shoot multiplication medium (as above but at pH 5.3). All cultures are maintained in a growth room at 28° C. and 16 hour photoperiod at a photon flux density of 160 μM $m^{-2}$ $s^{-1}$ (Biolux®, Osram Licht AG, Munich, Germany or equivalent). The outer leaf covering of the meristem which turns brown is dissected away. This facilitates new shoots which were transferred to glass jars (100 mL) containing liquid shoot multiplication medium, pH 5.3. Meristems are subcultured every two weeks for no longer than 8 weeks.

Meristem microinjection: This method introduces one or more edits to the sugarcane genome during vegetative development. This is done using cultured 0.5-2 mm meristems. The editing reagents are introduced just below the L1 layer, into the L2 layer, of the meristem using a microinjection apparatus. The injected tissue recovers and the resulting, newly formed tissue is examined for the presence of the intended edits. This cycle can be repeated up to four times, facilitated by subculturing the edited plant material every two weeks. Modifications to the sugarcane genome can be monitored by one or more molecular assays.

The genome editing tools for this work can be DNA, RNA, protein or a combination thereof. Components to introduce these reagents are combined and delivered using an appropriate microinjection apparatus. The editing reagents can be delivered to the cell in a volume of about 2 to about 20 nanoliters. The editing reagents can be delivered alone or as part of a formulation to aid in uptake by the targeted meristematic cells. These reagents can include saponin, pectinase, DMSO, Silwet®-77, Tween®-20 or any other agent that loosens the plant cell wall without compromising the cell's activity or interferes with the activity of the editing reagents.

To introduce editing reagents, the meristem is gently, but firmly supported to counteract the pressure of the microinjection needle. A dissecting or compound microscope with appropriate optics may be required to insure the microinjection needle targets the intended meristematic cells. To ensure that edits are heritable, it is critical that the L2 cell layer is the targeted plant tissue. Once the meristem cells are treated, the tissue is transferred to fresh semi-solid shoot multiplication medium to recover for several days. When sufficient new leaf tissue is present, a small piece of a newly formed leaf is excised for molecular analysis.

Molecular analysis encompasses a variety of assays or tests designed to detect the presence of the intended edits. For example, mRNA from the targeted gene(s) can be amplified by RT-PCR and sequenced to determine if edits are present. Also, genomic DNA can be examined by targeted sequence analysis for the presence of the intended edits. Leaf tissue can be examined for visual or physical evidence (a phenotype) of an intended edit. The time required for evaluation of edits allows the plant to further recover from the microinjection and makes it competent for further editing, if necessary. If more edits are required, the propagated meristems representing edited material can be used for the next iteration. Once the intended changes are complete, the treated meristem is induced to shoot then root and is then transferred to soil. The developing tillers are examined for the presence and activity of all intended edits.

Meristem biolistics: Meristems can also be prepped to receive editing reagents delivered using a gene gun. Methods describing the preparation of editing reagents for delivery using gene gun technology can be found in Yadava et al. (2017) *Frontiers in Plant Science,* 7: 1949; Kikkert et al. (2005) *Methods in Molecular Biology,* 286:61-78; Taylor and Fauquet (2002) *DNA and Cell Biology,* 21:963-977; and Casas et al. (1995) *Plant Breeding Reviews,* 13:235-264, or as described elsewhere in this disclosure. Methods describing applying gene gun technology to introduce genetic information into sugarcane can be found it Gambley et al. (1993) *Plant Cell Reports,* 12:343-346; Gallo-Meagher and Irvine (1993) *Plant Cell Reports,* 12:666-670; Jackson et al. (2013) *Transgenic Research,* 22:143-151; and Basnayake et. al. (2011) *Plant Cell Reports* 30:439-48.

Meristems are prepared as above. Briefly, shoots are removed using a sterile scalpel to expose the meristematic tissues. The exposed tissue is placed on 0.8% (w/v) agar in 100 mm diameter polystyrene Petri dishes for use as a target. Preparation of 1.0 μm gold particles and coating with editing reagents can be as described in Martin-Ortigosa and Wang (2014) *Transgenic Research,* 23:743-756 for RNPs or in Yadava et al. (2017) *Frontiers in Plant Science,* 7: 1949 or as described elsewhere in this disclosure for DNA. Each bombardment treatment involves two bombarded plates from each of four precipitation reactions (n=8). Bombarded meristems are returned to shoot multiplication media for recovery and selection.

Shoot induction: Shoots are subcultured every two weeks until there are ~20 shoots (~4 cm in height). Clusters are divided in groups of two and transferred to Magenta™ vessels where they are further divided and placed in fresh shoot multiplication medium, pH 5.3 every two weeks for a total of 11 weeks.

Root induction: All shoots (~4 cm) are rooted in media containing half strength MS; 5 g $L^{-1}$ sucrose; 8 g $L^{-1}$ agar; 0.25 g $L^{-1}$ casein hydrolysate (pH 5.6-5.8). In vitro rooting is achieved in 2-3 weeks. Plants with a well-formed root system are transferred into a 98-well polystyrene seedling tray (or equivalent) containing potting soil and placed in a mist box (a perspex box designed to enclose the seedling tray and apply a mist of water for 2 minutes three times a day) within a greenhouse for 2 weeks. Thereafter plants were transferred to a greenhouse chamber (25:20° C.; 16:8 hour day:night), watered twice daily (for 2 minutes) and fertilized (0.2 g of N:P:K; 2:3:2) monthly. If desired, further vegetative propagation can be done to produce multiple clones of the edited plant.

Example 53

This example illustrates the method of creating a hypersensitive SoPYL-E allele in sugarcane through genome editing.

Abscisic acid (ABA) is the primary plant hormone involved in regulating plant water status and plant response to changes in internal and external water potential. ABA receptors are at the top of the ABA signal transduction cascade (See Cutler et al. (2010) *Annual Review of Plant Biology,* 61:651-79) that regulates plant water status. U.S. Patent Publication US20160194653 describes several changes in conserved abscisic acid (ABA) receptor amino acids that render the receptor hypersensitive the ABA and how to apply this discovery to almost any ABA receptor using a CRISPR-Cas9 mediated homology-dependent repair (HDR) approach. However, the HDR approach described relies on traditional plant transformation technology to introduce Cas9 and the sgRNA targeting ABA receptors, which is inefficient.

Here we disclose a unique allele substitution strategy for plant applications that greatly improves HDR outcomes because it does not require plant regeneration from callus. Our method delivers the HDR template directly to the intended DNA cut site as a component of the Cas9 complex and uses a non-heritable form of the Cas9 complex. This method can be applied to any plant tissue, preferably tissues that give rise to the germline to ensure heritability of the intended DNA modifications.

The following describes allele substitutions in an ABA receptor, PYL-E gene (with genomic DNA sequence of SEQ ID NO:436 and protein sequence of SEQ ID NO:437) in sugarcane (*Saccharum officinarum*) using this approach. A single amino acid substitution from a glutamic acid (E) to a leucine (L) at position 149 is generated to make a hypersensitive SoPYL-E gene in the sugarcane genome. Several possible nucleotide changes can alter the codon for this amino acid substitution. Here we illustrate how genome editing can be used to change GAG to CTG. The sgRNA targeting sequence (5'-CCTTGTGATC<u>GAG</u>TCGTTCG-3' (SEQ ID NO:438)) is used to target Cas9 to SoPYL-E and make a double strand break very close to the edit site (the edit site is shown as underlined font). A second sgRNA targeting sequence (5'-CCACGAACGA<u>CTC</u>GATCACA-3' (SEQ ID NO:439)) which is complementary to a nearby sequence on the opposite strand can also be used.

The sgRNA can include a 33 bp extension at the 3'-end of a portion of the pBlueScript SK(+) multiple cloning sequence with a sequence of 5'-GUCGACG-GUAUCGAUAAGCUUGAUAUCGAAUUC-3' (SEQ ID NO:440). This acts as a tether to carry donor template to the Cas9-mediated double strand break in SoPYL-E. This RNA extension will form a highly stable RNA:DNA duplex with complementary DNA. This enables the Cas9 complex to carry HDR template directly to the intended double strand break. The full sgRNA has the sequence of 5'-CCUU-GUGAUCGAGUCGUUCGGUUUUAGAGCUA-GAAAUAGCAAGUUAAAAUAAGGCUA GUCCGUUAUCAACUUGAAAAAGUGGCACCGAGU-CGGUGCUUUUUUGUCGACGGUAUC GAUAAGC-UUGAUAUCGAAUUC-3' (SEQ ID NO:441). The donor template (5'-CCCGGAGAGCATTGACGG-GAGGCCAGGTACCCTTGT-GATCCTGTCGTTCGTCGTCGATGT GCCT-GATGGCAACACAAAGGATGAGACATG-3', SEQ ID NO:442) carries both the new codon information and a mutation in Valine 152 codon changing GTG to GTA, GTC, or GTT, which destroys the PAM site and prevents further cleavage by Cas9. The full donor template including the tether complement (5'-GAATTCGATATCAAGCTTATC-GATACCGTCGAC-3', SEQ ID NO:443) has a sequence of 5'-CCCGGAGAGCATTGACGG-GAGGCCAGGTACCCTTGT-GATCCTGTCGTTCGTCGTCGATGT GCCT-GATGGCAACACAAAGGATGAGACATGGAATTCGAT ATCAAGCTTATCGATACCGT CGAC-3' (SEQ ID NO:444).

The tether carries donor template in one of several forms including single- or double-stranded RNA or DNA. The donor length can vary from about 30-200 nucleotides. To assemble the complex, equal-molar amounts of sgRNA and donor are mixed and heated to 95° C. for 5 minutes, then removed from the heat and naturally cooled to room temperature. The appropriate amount of Cas9 is then added to sgRNA:donor complex and incubated at room temperature for 5 minutes.

The Cas9 complex can be delivered to sugarcane meristem cells by microinjection or biolistics as detailed in Example 52. The modified PYL-E gene has a coding sequence of SEQ ID NO:445.

Several methods can be used to assay successful introduction of the SoPYL-E hypersensitive allele. Firstly, the maize Rab17 gene is well characterized with respect to ABA-induction (See Buchanan et al. (2004) *Genetics* 168: 1639-1654). Secondly, a close sugarcane homolog is A0A059Q184 with a CDS of SEQ ID NO:446 and a protein sequence of SEQ ID NO:447. The A0A059Q184 steady state transcript level in plants possessing a hypersensitive SoPYL-E allele will be higher than plants lacking this allele. Thirdly, sugarcane with a SoPYL-E hypersensitive allele will exhibit increased water use efficiency, that is more biomass produced per unit water transpired (See Medrano et al. (2015) *The Crop Journal,* 3:220-328) when compared to plants that lack this allele.

Example 54

This example illustrates genetic modification to a plant genome during vegetative development. Specifically, the method introduces one or more edits to the plant genome by microinjection or biolistics. It applies to potato plants that can be vegetatively propagated by cutting or by tuber eyes. A basic discussion of these methods can be found at www [dot]ndsu[dot]edu/pubweb/chiwonlee/plsc368/student/papers06/carina %20de %20luca/carinadel uca.htm. It can be done using plants grown in soil or in tissue culture media. The apical or axillary meristem of a young plant is exposed and editing reagents are introduced just below the L1 layer, into the L2 layer, of the meristem using a microinjection or biolistic apparatus. The treated tissue recovers and the resulting, newly formed tissue is examined for the presence of the intended edits. This cycle can be repeated many times, facilitated by propagating cuttings of the edited plant material from time to time. Modifications to the plant genome can be monitored by one or more molecular assays. Once the intended changes are complete, the plant can be clonally propagated by cutting (the basic unit is a stem segment with at least one axillary leaf or the stem segment comprising the shoot apical meristem) or by tuber eyes. The next generation is examined for the presence and activity of all intended edits.

The genome editing tools for this work can be DNA, RNA, protein or a combination thereof. Components to introduce these reagents are combined and delivered using an appropriate microinjection apparatus or biolistics (Craig et al. (2005) *Plant Cell Reports,* 24:603-611) or as describe elsewhere in this disclosure. For microinjection the editing reagents can be delivered to the cell in a volume of about 2 to about 20 nanoliters. The editing reagents can be delivered alone or as part of a formulation to aid in uptake by the targeted meristematic cells. These reagents can include saponin, pectinase, DMSO, Silwet®-77, Tween®-20 or any other agent that loosens the plant cell wall without compromising the cell's activity or interferes with the activity of the editing reagents.

To introduce editing reagents, the newly formed leaf tissue in the target plant is carefully removed to expose the meristem without damaging it. The stem is gently, but firmly supported to counteract the pressure of the microinjection needle. A dissecting or compound microscope with appropriate optics may be required to insure the microinjection needle targets the intended meristematic cells. To insure that edits are heritable, it is critical that the L2 cell layer, which gives rise to the germline, is the targeted plant tissue. Once the meristem cells are treated, the stem is marked and the plant recovers for several days. The recovery period is long enough for the plant to grow 3-5 new leaves from the treated meristem. When sufficient new leaf tissue is present, a small piece of a newly formed leaf is excised for molecular analysis.

An alternative approach is to introduce editing reagents into potato leaf protoplasts (Craig et al. (2005) *Plant Cell Reports,* 24:603-611) together with a reporter gene such as fluorescent protein. Transfected protoplasts can then be collected using a cell sorting apparatus and transferred to callus induction media to regenerate edited plant candidates. Each candidate is subjected to molecular analysis to determine which contain the intended edits.

Molecular analysis encompasses a variety of assays or tests designed to detect the presence of the intended edits. For example, mRNA from the targeted gene(s) can be amplified by RT-PCR and sequenced to determine if edits are present. Also, genomic DNA can be examined by targeted sequence analysis for the presence of the intended edits. Leaf tissue can be examined for visual or physical evidence (a phenotype) of an intended edit. The time required for evaluation of edits allows the plant to further recover from the microinjection and makes it competent for further editing, if necessary.

If more edits are required prior to flowering, the segments representing edited material can be vegetatively propagated by cutting an appropriate segment to start a new plant. Excised plantlets are rooted in fresh soil or tissue culture media prior to the next editing step. Care should be taken to insure the propagated plant is actively growing before initiating the next microinjection. Plants are healthy when there is evidence of robust root growth and new leaves have formed.

When editing activities are complete plants there are several possible ways to maintain/propagate the edited plant. First, the plants can be grown to reproductive maturity, and selfed or crossed as appropriate to produce seed. The resulting seed are planted and the subsequent germinated seedlings are tested for the presence of the intended edits. Second, further vegetative propagation can be done to produce multiple clones of the edited plant. Third, potato seed from tubers can be collected and used to propagate the plant. The resulting vegetatively propagated plants are planted and tested for the presence of the intended edits.

Disease free plantlets are grown in test tubes on a nutrient media. Each plantlet is cut into 3 to 10 nodal sections after 18-60 days. Each new cutting is planted in a new test tube. This can be repeated until the desired number of plantlets is obtained. Plantlets are then removed from the tubes and grown in sterile soil to complete their entire growth cycle. Tubers produced are collected and stored to later be sold to growers. This is also the process followed to obtain certified seeds. This first seed lot would be called nuclear seed and then after harvesting the product of this seed you get Generation 1 (GI) and so forth.

One skilled in the art would recognize that the microinjection or biolistics or technique described herein is generally applicable to any plants that are commonly propagated through asexual or vegetative methods, e. g., cloning, grafting. The plants that are propagated through asexual or vegetative methods include apples (*Malus* x *domestica*), apricots (*Prunus armeniaca, P. brigantine, P. mandshurica, P. mume, P. sibirica*), avocado (*Persea americana*), bananas (*Musa* spp.), cherry (*Prunus avium*), grapefruit (*Citrus* x *paradisi*), grapes (*Vitus* spp.) including wine grapes (*Vitus vinifera*), irises (*Iris* spp.), lemon (*Citrus limon*), limes (*Citrus* spp.), orange (*Citrus sinensis*), peaches and nectarines (*Prunus persica*), pear (*Pyrus* spp.), pineapple (*Ananas comosus*), plantains (*Musa* spp.), plum (*Prunus domestica*), poinsettia (*Euphorbia pulcherrima*), potato (*Solanum tuberosum*), roses (*Rosa* spp.), strawberries (*Fragaria* spp., *Fragaria* x *ananassa*), sugarcanes (*Saccharum* spp.), sweet potato (*Ipomoea batatas*), tangerine (*Citrus tangerina*), tea (*Camellia sinensis*), yams (*Discorea* spp.), hops (*Humulus lupulus*), and hemp and *cannabis* (*Cannabis sativa* and *Cannabis* spp.).

Example 55

Genome editing can be applied to control disease and damage in potato (See Sun et al. (2016) *Transgenic Research* 25:731-42; Sun et al. (2017) *BMC Plant Biology* 17:235; Wiel et al. (2017) *Plant Biotechnology Reports* 11:1-8). In this example, we demonstrate a method of inactivating all alleles of the susceptibility gene StCESA3, a negative regulator of cellulose synthesis, by genome editing.

StCESA (Sotub01g026250) has a genomic DNA sequence of SEQ ID NO:448, a protein sequence of SEQ ID NO:449, and a CDS sequence of SEQ ID NO:450. This gene can be disrupted using targeted endonuclease technology, such as the CRISPR-Cas9 system. The Cas9 complex can be delivered to potato meristem cells by microinjection or biolistics as detailed in Example 54. The guide RNAs are designed to specifically target the StCESA gene. StCESA gRNA-1 (TCTGTGCCTTCCCTGTTTGT, SEQ ID NO:451), gRNA-2 (TTGAGCTGGCACGCGACTTA, SEQ ID NO:452), and gRNA-3 (ATGGCATCTCCTGGACCTGC, SEQ ID NO:453) target exons 3, 4 and 5 of the StCESA gene, respectively.

Successful disruption of StCESA3 will produce robust resistance to potato late blight due to *Phytophthora infestans*. This can be assessed using a leaf assay as described in Sun et al. (2016) *Transgenic Research* 25:731-42, incorporated by reference in its entirety.

Example 56

Potatoes are typically subject to cold storage for long periods before they are consumed. A consequence of prolonged storage is the breakdown of sucrose to glucose and fructose, increasing the concentration of reducing sugars. This presents problems for potatoes that are processed into fried products such as potato chips and French fries because high temperatures induce the Maillard reaction which produces acrylamide when reducing sugars and amino acids like asparagine are present. Acrylamide is a known carcinogen (See Ye et al. 2010 *Journal of Agricultural and Food Chemistry* 58:12162-12167). Down regulating vacuolar invertase (StvINV) (Clasen et al. (2016) *Plant Biotechnology Journal* 14:169-76; Ye et al. 2010 *Journal of Agricultural and Food Chemistry* 58:12162-12167; Zhu et al. (2014) *PloS One* 9: e93381) and asparagine synthase (Zhu et al. (2016) *Plant Biotechnology Journal* 14:709-718) can reduce acrylamide formation in fried potato products.

In this example, we illustrate a way to disrupt the potato vacuolar invertase (GenBank ID: DQ478950.1) using gene editing. StvINV has a genomic DNA sequence of SEQ ID NO:454, a protein sequence of SEQ ID NO:455, and a CDS sequence of SEQ ID NO:456. Disruption of StvINV can be done by targeting conserved sequences of first exon as identified in FIG. 1 of Clasen et al. 2016 *Plant Biotechnology Journal* 14:169-76. Three guide RNAs StvINV gRNA-1 (TTTAAGGGACTTCCGGTGGC, SEQ ID NO:457), gRNA-2 (CGGAATCGGGTTGATCCGGG, SEQ ID NO:458) and gRNA-3 (GTTGTTGAGGATCGGAAAGA, SEQ ID NO:459) are designed to direct the Cas 9 enzyme to create double strand breaks in each StvINV allele. The Cas9 complex can be delivered to potato meristem cells by microinjection or biolistics as detailed in Example 54. DNA repair via the NHEJ pathway will create indels at the break site, some of which will eliminate the gene activity.

Molecular assays can be used to identify edited plants with the StvINV disruption. Tubers produced by the appropriately edited plants contain significantly less reducing sugar (glucose and fructose) and produce less acrylamide. Methods to perform these assays are available in Ye et al. (2010) *Journal of Agricultural and Food Chemistry* 58:12162-12167, which is incorporated by reference in its entirety.

Example 57

This example illustrates a method of effecting a modification in a genome in a plant cell and thereby providing a plant cell having a modified phenotype, the method including integrating, at a predetermined genomic locus, a nucleotide sequence encoded by a polynucleotide (such as a double-stranded DNA, a single-stranded DNA, a single-stranded DNA/RNA hybrid, or a double-stranded DNA/RNA hybrid) donor molecule. More specifically, this non-limiting example illustrates incorporation of a miniature inverted-repeat transposable element ("MITE"; see, e. g., Fattash et al. (2013) *Genome,* 56:475-486, dx.doi.org/10.1139/gen-2012-0174) in the 5' untranslated or promoter region of the endogenous maize nitrate-responsive gene, AMT3.

An experiment comparing the effects of incorporating an insulator element or a MITE element in the 5' untranslated or promoter region of a sequence of interest in a genome was performed using protocols similar to those described in Example 21. A crRNA (AMT3-Pro1) with the sequence of SEQ ID NO:346, designed to effect a DSB at 147 nucleotides upstream of (5' to) the transcription start site of the endogenous maize ammonium transporter AMT3 (GRMZM2G118950, see www[dot]maizegdb[dot]org/gbrowse?name=GRMZM2G118950) gene's coding sequence, and a tracrRNA were purchased from Integrated DNA Technologies, Coralville, IA A AMT3-Pro1 guide RNA complex was made by mixing 45 microliters of 100 micromolar tracrRNA and 45 microliters of 100 micromolar AMT3-Pro1 crRNA, heating the mixture to 95 degrees Celsius for 5 minutes, removing from the heating block, and allowing the tube to cool to room temperature on the benchtop.

The palindromic nucleotide sequence of the insulator was 5'-GAATATATATATATTC-3' (SEQ ID NO:364, see U.S. Pat. No. 7,605,300, which is incorporated herein by reference) which was encoded on a chemically modified, single-stranded DNA donor molecule that was phosphorylated on the 5' end and contained two phosphorothioate linkages at each terminus (i. e., the two linkages between the most distal three bases on either end of the strand). One hundred microliters (100 micromolar) of the insulator solution was heated to 95 degrees Celsius for 5 minutes, then the heat was turned off and the solution allowed to slowly cool to room temperature in the block. The MITE was provided as a double-stranded DNA (Integrated DNA Technologies, Coralville, IA) including a forward DNA strand having the nucleotide sequence of TACTCCCTCCGTTTCTTTTTATTAGTCGCTGGATAGTGCAATTTTGCACTATCCAGCGACT AATAAAAAGAAACGGAGGGAGTA (SEQ ID NO:460) and a reverse DNA strand having the nucleotide sequence of TACTCCCTCCGTTTCTTTTTATTAGTCGCTGGATAGTGCAAAATTGCACTATCCAGCGACT AATAAAAAGAAACGGAGGGAGTA (SEQ ID NO:461); each strand was phosphorylated on the 5' end and contained two phosphorothioate linkages at the 5' terminus (i. e., the two linkages between the most distal three bases on the 5' end of the strand).

Maize B73 protoplasts were harvested from leaves of B73 maize plants that had been grown in nitrate-free medium for 13 days (see Examples 15, 20, and 21). One milliliter of protoplasts (2×10^5 cells per milliliter) was added to each of four reaction tubes. Ribonucleoproteins (RNPs) were prepared by mixing 15 microliters (150 micrograms) Cas9 nuclease (Aldevron, Fargo, ND) with the AMT3-Prolguide RNA complex, and incubating the mixture for 5 minutes at room temperature. To the RNP solution was added 2 microliters (20 micrograms) of salmon sperm DNA (VWR Cat. No.: 95037-160). Editing experiments were carried out in three of the four protoplast-containing reaction tubes with 35 microliters of an RNP solution, with 50 microliters of insulator solution, MITE solution, or buffer; the fourth reaction tube received only 85 microliters buffer and served as the null control. To each tube was added 1.1 milliliters of 40% PEG; the reaction mixtures were mixed gently by tapping and incubated 5 minutes at room temperature. The reactions were stopped by adding 5 milliliters of washing buffer (0.6 molar mannitol, 4 millimolar MES pH 5.7, and 20 millimolar KCl; see Example 1) to each tube and mixed gently by inverting the tube. The tubes were centrifuged 5 minutes at 1200 rpm and the supernatant was then removed. The protoplasts were resuspended in 6 milliliters incubation solution and the protoplasts from each treatment were divided between two 10×10 cm dishes pre-coated with 5% calf serum; the dishes were sealed with Parafilm M® film (Bemis, Oshkosh, WI), incubated 1 hour at 37 degrees Celsius, and then incubated an additional 47 hours at 26 degrees Celsius in the dark. Forty-eight hours after transfection, half of the plates were treated with 10 millimolar (final concentration) $KNO_3$ and half with 10 millimolar (final concentration) KCl; cells were incubated 1 hour, and then harvested for analysis.

Quantitative RT-PCR was employed on three technical replicates per treatment to measure the relative expression of the AMT3 gene. The qPCR primer used included an AMT3 forward primer TCGCCACTTTGGAGTCGCAATC (SEQ ID NO:462), an AMT3 reverse primer ACACACATACGTTCGTGCTTCG (SEQ ID NO:463), a tubulin forward primer AAGGGATGAGATGACCTGGGACAC (SEQ ID NO:464), and a tubulin reverse primer TGCTGGACAATGAGGCCATCTAC (SEQ ID NO:465). Results (mean of triplicates, standard deviation) are provided in Table 32, with relative AMT3 expression levels normalized to tubulin. The unmodified (null control) maize AMT gene is responsive to high nitrate, with an increase in relative expression of about 21-fold, compared to relative expression under low nitrate conditions. Editing with only an RNP (nuclease and AMT3-Pro1 guide RNA complex) resulted in decreasing this response to high nitrate to about 14-fold; this could be attributed to possible disruption of the promoter sequence and consequently possible interference with normal transcription or translation. Integration of the MITE sequence at the AMT3Pro-1-mediated DSB resulted in about 9-fold increase in relative expression under high nitrate. Integration of the insulator sequence at the AMT3Pro-1-mediated DSB resulted in only about 4.5-fold increase in relative expression under high nitrate. This demonstrates the ability to select the degree of reduction of expression of a gene (or sequence of interest) by integration of an appropriate sequence (e. g., such as a MITE sequence or an insulator sequence) in the regulatory region of the gene.

TABLE 32

| | KCl | | $KNO_3$ | |
|---|---|---|---|---|
| Genome editing treatment | Relative Expression | SD | Relative Expression | SD |
| Null | 1.00 | 0.04 | 21.4 | 0.60 |
| AMT3-Pro1 only | 1.27 | 0.09 | 17.9 | 1.02 |
| AMT3-Pro1 + MITE | 1.17 | 0.03 | 10.2 | 0.37 |
| AMT3-Pro1 + insulator | 1.22 | 0.20 | 5.49 | 0.21 |

Example 58

This example illustrates a method of effecting a modification in a genome in a plant cell and thereby providing a plant cell having a modified phenotype, the method including integrating, at a predetermined genomic locus, a nucleotide sequence encoded by a polynucleotide (such as a double-stranded DNA, a single-stranded DNA, a single-stranded DNA/RNA hybrid, or a double-stranded DNA/RNA hybrid) donor molecule. More specifically, this non-limiting example illustrates integration of a G-box element (see, e. g., Williams et al. (1992) *Plant Cell,* 4:485-496; Ishige et al. (1999) *Plant J.,* 18:443-448) in the 5' untranslated or promoter region of the endogenous maize (*Zea mays*) Lc gene (see www[dot]maizegdb[dot]org/gene_center/gene/GRMZM5G822829). A G-box sequence (G-box 10) has been reported to effect strong constitutive expression in both monocot and dicot plants; see, e. g., Ishige et al. (1999) *Plant J.,* 18:443-448.

A crRNA (ZmLc Pro-3) having the sequence of SEQ ID NO:334, designed to effect a DSB at 272 nucleotides upstream of (5' to) the transcription start site of the endogenous maize (*Zea mays*) Lc gene's coding sequence, and a tracrRNA were purchased from Integrated DNA Technologies, Coralville, IA A ZmLc Pro-3 guide RNA complex was made by mixing 48 microliters of 100 micromolar tracrRNA and 48 microliters of 100 micromolar ZmLc Pro-3 crRNA, heating the mixture to 95 degrees Celsius for 5 minutes, removing from the heating block, and allowing the tube to cool to room temperature on the benchtop. A ribonucleoprotein (RNP) was made with this guide RNA complex and Cas9 nuclease.

All dsDNA molecules were purchased from Integrated DNA Technologies, Coralville, IA. One dsDNA ("3×DR5") molecule of 34 base pairs was produced by annealing a first strand having the sequence 5'-ccgacaaaaggccgacaaaaggccgacaaaaggt-3' (SEQ ID NO:306) and a second strand having the sequence 5'-accttttgtcggccttttgtcggccttttgtcgg-3' (SEQ ID NO:307, which includes three concatenated copies of an auxin response element having the sequence ccttttgtcgg (SEQ ID NO:308)). A 34-nucleotide single-stranded DNA (ssDNA) molecule having the sequence 5'-ccgacaaaaggccgacaaaaggccgacaaaaggt-3' (SEQ ID NO:306) (i. e., equivalent to only a single strand of the "3×DR5" dsDNA molecule) was also used. A single-stranded DNA molecule encoding a self-hybridizing (forming partially double-stranded DNA), near-palindromic G-box sequence ACACGTGACACGTGACACGTGACACGTG (SEQ ID NO:466) was also produced. In all cases, each strand was phosphorylated on the 5' end and contained two phosphorothioate linkages at the 5' terminus (i. e., the two linkages between the most distal three bases on the 5' end of the strand).

Integration of either the 3×DR5 donor polynucleotide sequence (as dsDNA or as ssDNA) or the G-box donor polynucleotide sequence at the DSB located 272 nucleotides 5' to the ZmLc gene's TSS was performed using protocols similar to those described in the preceding Examples (e. g., Example 57). After the PEG-mediated transfection and wash steps, the protoplast pellet was resuspended in 4 milliliters of PIM containing 50 mM calcium chloride. For gDNA isolation for T7 and qPCR assays, 1 milliliter of the suspension was plated on a 6-well plate coated with 5% calf serum; for RNA analysis, 3 milliliters of the suspension were plated onto a 10-centimeter plate coated with 5% calf serum containing 3 milliliters of PIM containing 50 mM calcium chloride. The dishes were sealed with Parafilm M® film (Bemis, Oshkosh, WI), incubated 1 hour at 37 degrees Celsius, and then incubated an additional 47 hours at 26 degrees Celsius in the dark. Analysis employed a T7E1 assay to confirm the predicted cleavage and qPCR (normalized to tubulin) to quantify editing efficiency as described in the preceding Examples. The qPRT results are provided in Table 33. The results confirm the predicted strong upregulation of the Lc gene by insertion of the G-box sequence in the 5' UTR of the Lc gene as well as again demonstrating strong upregulation by insertion of the 3×DR5 sequence in the 5' UTR of the Lc gene.

TABLE 33

| Treatment | Lc expression | SD |
|---|---|---|
| 3xDR5/dsDNA | 13.99 | 0.69 |
| 3xDR5/ssDNA | 17.93 | 1.18 |
| G-box | 6.68 | 0.37 |
| No Insert | 0.98 | 0.14 |
| Null control (no RNP) | 1.00 | 0.08 |

All cited patents and patent publications referred to in this application are incorporated herein by reference in their entirety. All of the materials and methods disclosed and claimed herein can be made and used without undue experimentation as instructed by the above disclosure and illustrated by the examples. Although the materials and methods of this invention have been described in terms of embodiments and illustrative examples, it will be apparent to those of skill in the art that substitutions and variations can be applied to the materials and methods described herein without departing from the concept, spirit, and scope of the invention. For instance, while the particular examples provided illustrate the methods and embodiments described herein using a specific plant, the principles in these examples are applicable to any plant of interest; similarly, while the particular examples provided illustrate the methods and embodiments described herein using a particular sequence-specific nuclease such as Cas9, one of skill in the art would recognize that alternative sequence-specific nucleases (e. g., CRISPR nucleases other than Cas9, such as CasX, CasY, and Cpf1, zinc-finger nucleases, transcription activator-like effector nucleases, Argonaute proteins, and meganucleases) are useful in various embodiments. All such similar substitutes and modifications apparent to those skilled in the art are deemed to be within the spirit, scope, and concept of the invention as encompassed by the embodiments of the inventions recited herein and the specification and appended claims.

What is claimed is:

1. A modified plant cell comprising a targeted modification in a first gene and a targeted modification in a second gene, wherein the targeted modifications result in an increase in expression of the first gene and the second gene relative to a plant cell lacking the modifications, wherein the targeted modifications comprise an insertion of an enhancer element consisting of SEQ ID NO: 343.

2. The modified plant cell of claim 1, wherein the targeted modifications comprise an insertion of the enhancer element in the promoter region of the first gene and the second gene.

3. The modified plant cell of claim 1, wherein the targeted modifications comprise an insertion of the enhancer element at about 50 to about 500 nucleotides upstream of the start codon of the first gene and the second gene.

4. The modified plant cell of claim 1, wherein the plant cell is a maize plant cell.

5. The modified plant cell of claim 1, wherein the plant cell is a soybean plant cell.

6. A plant comprising the modified plant cell of claim 1.

7. The plant of claim 6, wherein the plant is an inbred line or an F1 hybrid.

8. A plant part comprising the modified plant cell of claim 1, optionally wherein the plant part is a seed.

9. A method of manufacturing commercial seed comprising growing the plant of claim 6, and optionally further multiplying or propagating the plant, and using the plant to produce commercial seed.

10. A method of manufacturing a processed plant product comprising processing the plant of claim 6 or a part thereof into the product.

11. The method of claim 10, wherein the product is seed meal, starch, sugar, silage, or oil.

12. A processed plant product comprising the modified plant cell of claim 1.

13. The processed plant product of claim 12, wherein the product is seed meal.

* * * * *